US008529911B2

(12) United States Patent
Meinke et al.

(10) Patent No.: US 8,529,911 B2
(45) Date of Patent: Sep. 10, 2013

(54) **SMALL *STREPTOCOCCUS PYOGENES* ANTIGENS AND THEIR USE**

(75) Inventors: Andreas Meinke, Pressbaum (AT); Eszter Nagy, Vienna (AT); Alexander von Gabain, Vienna (AT); Manfred Berger, Wr. Neustadt (AT); Beatrice Senn, Vienna (AT); Michael Schunn, Vienna (AT)

(73) Assignee: Intercell Austria AG, Vienna (AT)

( * ) Notice: Subject to any disclaimer, the term of this patent is extended or adjusted under 35 U.S.C. 154(b) by 216 days.

(21) Appl. No.: 12/304,981

(22) PCT Filed: Jul. 6, 2007

(86) PCT No.: PCT/EP2007/006027
§ 371 (c)(1), (2), (4) Date: May 20, 2009

(87) PCT Pub. No.: WO2008/003515
PCT Pub. Date: Jan. 10, 2008

(65) Prior Publication Data
US 2010/0166732 A1 Jul. 1, 2010

(30) Foreign Application Priority Data
Jul. 7, 2006 (EP) .................................... 06014166

(51) Int. Cl.
*A61K 39/09* (2006.01)
*C07K 14/315* (2006.01)

(52) U.S. Cl.
USPC .................. 424/244.1; 424/190.1; 424/192.1; 530/300; 530/350

(58) Field of Classification Search
None
See application file for complete search history.

(56) References Cited

U.S. PATENT DOCUMENTS

| | | | | |
|---|---|---|---|---|
| 4,946,778 | A | 8/1990 | Ladner et al. | |
| 7,838,010 | B2 * | 11/2010 | Bensi et al. | 424/237.1 |

FOREIGN PATENT DOCUMENTS

| | | | |
|---|---|---|---|
| GB | 2188638 | | 10/1987 |
| WO | WO 86/01533 | | 3/1986 |
| WO | WO 90/07861 | | 7/1990 |
| WO | WO 91/18088 | | 11/1991 |
| WO | WO 96/02555 | | 2/1996 |
| WO | WO 01/24822 | | 4/2001 |
| WO | WO 01/54720 | | 8/2001 |
| WO | WO 01/78767 | | 10/2001 |
| WO | WO 01/93903 | | 12/2001 |
| WO | WO 01/93905 | | 12/2001 |
| WO | WO 02/13857 | | 2/2002 |
| WO | WO 02/32451 | | 4/2002 |
| WO | WO 02/34771 | | 5/2002 |
| WO | WO 02/077183 | A2 | 10/2002 |
| WO | WO0277183 | A2 * | 10/2002 |
| WO | WO 02/092818 | A2 | 11/2002 |
| WO | WO 02/095027 | | 11/2002 |
| WO | WO 03/047602 | | 6/2003 |
| WO | WO 03/093306 | A2 | 11/2003 |
| WO | WO 2004/078907 | | 9/2004 |
| WO | WO 2004/009924 | A2 | 11/2004 |
| WO | WO 2005/032582 | | 4/2005 |
| WO | WO2005032582 | A2 * | 4/2005 |
| WO | WO 2006/042027 | A2 | 4/2006 |

OTHER PUBLICATIONS

Accession No. Q1J872, Jun. 13, 2006.*
Altschul et al., "Basic Local Alignment Search Tool," *J. Mol. Biol.* 215:403-410 (1990).
Amit et al., "Three-Dimensional Structure of an Antigen-Antibody Complex at 2.8 A Resolution," *Science* 233:747-753 (1986).
Bessen et al., "Influence of Intranasal Immunization with Synthetic Peptides Corresponding to Conserved Epitopes of M Protein on Mucosal Colonization by Group A Streptococci," *Infect. Immun.* 56:2666-2672 (1988).
Bisno et al., "M Proteins of Group G Streptococci Isolated from Bacteremic Human Infections," *Infect. Immun.* 55:753-757 (1987).
Bronze et al., "Protective Immunity Evoked by Locally Administered Group A Streptococcal Vaccines in Mice," *J. Immunol.* 141:2767-2770 (1988).
Carter et al., "Improved Oligonucleotide Site-Directed Mutagenesis Using M13 Vectors," *Nucl. Acids Res.* 13:4431-4443 (1985).
Cohen et al., "Naked DNA Points Way to Vaccines," *Science* 259:1691-1692 (1993).
Cone et al., "Clinical and Bacteriologic Observations of a Toxic Shock-Like Syndrome Due to *Streptococcus pyogenes*," *N. Engl. J. Med.* 317:146-149 (1987).
Cunningham et al., "Pathogenesis of Group A Streptococcal Infections," *Clin. Microbiol. Rev.* 13:470-511 (2000).
Dale et al., "Recombinant Tetravalent Group A Streptococcal M Protein Vaccine," *J. Immunol.* 151:2188-2194 (1993).
Enright et al., "Multilocus Sequence Typing of *Streptococcus pyogenes* and the Relationships Between emm Type and Clone," *Infect. Immun.* 69:2416-2427 (2001).

(Continued)

*Primary Examiner* — Padma V Baskar
(74) *Attorney, Agent, or Firm* — Wolf, Greenfield & Sacks, P.C.

(57) ABSTRACT

The present invention relates to a peptide consisting of one antigen of *Streptococcus pyogenes* (*S. pyogenes*) of any of the SEQ ID NOS: 1 to 7 or a functional active variant thereof, optionally further consisting of additional amino acid residue(s); a nucleic acid coding for the same; a pharmaceutical composition, especially a vaccine, comprising said peptide or said nucleic acid; an antibody or functional active fragment thereof specifically binding to the antigen; a hybridoma cell line which produces said antibody; a method for producing said antibody; a pharmaceutical composition comprising said antibody; the use of said peptide or said nucleic acid for the manufacture of a medicament for the immunization or treatment of a subject; the use of said antibody or functional fragment thereof for the manufacture of a medicament for the treatment of an infection; a method of diagnosing a *S. pyogenes* infection; a method for identifying a ligand capable of binding to said peptide; and the use of said peptide for the isolation and/or purification and/or identification of an interaction partner of the peptide.

18 Claims, 4 Drawing Sheets

(56) References Cited

OTHER PUBLICATIONS

Facklam et al., "emm Typing and Validation of Provisional M Types for Group A Streptococci," *Emerg. Infect. Dis.* 5:247-253 (1999).
Fenderson et al., "Tropomyosin Shares Immunologic Epitopes with Group A Streptococcal M Proteins," *J. Immunol.* 142:2475-2481 (1989).
Fischetti et al., "Streptococcal M Protein: Molecular Design and Biological Behavior," *Clin. Microbiol. Rev.* 2:285-314 (1989).
Guzman et al., "Protective Immune Response Against *Streptococcus pyogenes* in Mice After Intranasal Vaccination with the Fibronectin-Binding Protein Sfbl," *J. Infect. Dis.* 179:901-906 (1999).
Hoe et al., "Distribution of Streptococcal Inhibitor of Complement Variants in Pharyngitis and Invasive Isolates in an Epidemic of Serotype M1 Group A *Streptococcus* Infection," *J. Infect. Dis.* 183:633-639 (2001).
Hope-Simpson et al., "*Streptococcus pyogenes* in the Throat: A Study in a Small Population, 1962-1975," *J. Hyg.* (*Lond*). 87:109-129 (1981).
Huse et al., "Generation of a Large Combinatorial Library of the Immunoglobulin Repertoire in Phage Lambda," *Science* 246:1275-1281 (1989).
Ishibashi et al., "Hypercholesterolemia in Low Density Lipoprotein Receptor Knockout Mice and its Reversal by Adenovirus-Mediated Gene Delivery," *J. Clin. Invest.* 92:883-893 (1993).
Ji et al., "Intranasal Immunization with C5a Peptidase Prevents Nasopharyngeal Colonization of Mice by the Group A *Streptococcus,*" *Infect. Immun.* 65:2080-2087 (1997).
Kay et al., "In Vivo Hepatic Gene Therapy: Complete Albeit Transient Correction of Factor IX Deficiency in Hemophilia B Dogs," *Proc. Natl. Acad. Sci. USA* 91:2353-2357 (1994).
Lee et al, "Quantification and Toxicity of Group A Streptococcal Pyrogenic Exotoxins in an Animal Model of Toxic Shock Syndrome-Like Illness," *J. Clin. Microbiol.* 27:1890-1892 (1989).
Pearson et al., "Improved Tools for Biological Sequence Comparison," *Proc. Natl. Acad. Sci. USA* 85:2444-2448 (1988).
Queen et al., "A Humanized Antibody That Binds to the Interleukin 2 Receptor," *Proc. Natl. Acad. Sci. USA* 86:10029-10033 (1989).
Rammensee et al., "SYFPEITHI: Database for MHC Ligands and Peptide Motifs," *Immunogenetics* 50:213-219 (1999).
Riechmann et al., "Reshaping Human Antibodies for Therapy," *Nature* 332:323-327 (1988).
Smith et al., "Comparison of Biosequences," *Adv. Appl. Math.* 2:482-489 (1981).
Stalhammar-Carlemalm et al., "The R28 Protein of *Streptococcus pyogenes* is Related to Several Group B Streptococcal Surface Proteins, Confers Protective Immunity and Promotes Binding to Human Epithelial Cells," *Mol. Microbiol.* 33:208-219 (1999).
Stevens et al., "Invasive Group A *Streptococcus* Infections," *Clin. Infect. Dis.* 14:2-11 (1992).
Vitali et al., "PCR M Typing: A New Method for Rapid Typing of Group A Streptococci," *J. Clin. Microbiol.* 40:679-681 (2002).
Wells et al., "Cassette Mutagenesis: An Efficient Method for Generation of Multiple Mutations at Defined Sites," *Gene* 34:315-323 (1985).
Wells et al., "Importance of Hydrogen-Bond Formation in Stabilizing the Transition State of Subtilisin," *Philos. Trans. R. Soc. Lond. A* 317:415-423 (1986).
Zoller et al., "Oligonucleotide-Directed Mutagenesis Using M13-Derived Vectors: An Efficient and General Procedure for the Production of Point Mutations in any Fragment of DNA," *Nucl Acids. Res.* 10:6487-6500 (1982).
Beres et al., "Molecular Genetic Anatomy of Inter- and Intraserotype Variation in the Human acterial pathogen Group A *Streptococcus,*" *PNAS* 103(18): 7059-7064 (2006).
Podbielski et al., "Molecular Characterization of Group A Streptococcal (GAS) Oligopeptide Permease (Opp) and its Effect on Cysteine Protease Production," *Molecular Microbiology* 21(5): 1087-1099 (1996).
Banks, et al.; "Progress toward Characterization of the Group A *Streptococcus* Metagenome: Complete Genome Sequence of a Macrolide-Resistant Serotype M6 Strain"; JID (2004); 190: 727-738.
Beres, et al.; "Genome sequence of a serotype M3 strain of group A *Streptococcus*: Phage-encoded toxins, the high-virulence phenotype, and clone emergence"; PNAS (2002); 99(15): 10-78-10083.
Ferretti, et al.; "Complete genome sequence of an M1 strain of *Streptococcus pyogenes*"; PNAS (2001); 98(8): 4658-4663.
Green, et al.; "Genome Sequence of a Serotype M28 Strain of Group A *Streptococcus*: Potential New Insights into Puerperal Sepsis and Bacterial Disease Specifity"; JID (2005); 192: 760-770.
Holden, et al.; "Complete Genome of Acute Pheumatic Fevere-Associated Serotype M5 *Streptococcus pyrogenes* Strain Manfredo"; J. Bacteriol (2007); 189(4): 1473-1477.
Nakagawa, et al.; "Genome Sequence of an M3 Strain of *Streptococcus pyrogenes* Reveal a Large-Scale Genomic Rearrangement in Invasive Strains and New Insights into Phage Evolution"; Genome Research (2003); 13: 1042-1055.
Smoot, et al.; "Genome sequence and comparative microarray analysis of serotype M18 group A *Streptococcus* strains associated with acute rheumatic fever outbreaks"; PNAS (2002); 99(7): 4668-4673.
European Search Report for Application No. EP 10 01 0868 dated Apr. 5, 2011.
Search Opinion for Application No. EP 10 01 0868.
European Search Report for Application No. EP 10 01 0869 dated Mar. 25, 2011.
Search Opinion for Application No. EP 10 01 0869.
European Search Report for Application No. EP 10 01 0870 dated Apr. 27, 2011.
Search Opinion for Application No. EP 10 01 0870.
European Search Report for Application No. EP 10 01 0871 dated Dec. 23, 2010.
Search Opinion for Application No. EP 10 01 0871.
European Search Report for Application No. EP 10 01 0872 dated Dec. 23, 2010.
Search Opinion for Application No. EP 10 01 0872.
European Search Report for Application No. EP 10 01 1208 dated Apr. 29, 2011.
Search Opinion for Application No. EP 10 01 1208.
European Search Report for Application No. EP 10 01 1209 dated Apr. 29, 2011.
Search Opinion for Application No. EP 10 01 1209.
European Search Report for Application No. EP 10 01 0865 dated Mar. 31, 2011.
Search Opinion for Application No. EP 10 01 0865.

* cited by examiner

CFA/IFA model

CFA/IFA model

ALUM model

IC31 i.n. model

SEQUENCE LISTING

<160> NUMBER OF SEQ ID NOS: 244

<210> SEQ ID NO 1
<211> LENGTH: 452
<212> TYPE: PRT
<213> ORGANISM: Artificial Sequence
<220> FEATURE:
<223> OTHER INFORMATION: Protein SPY0269-1

<400> SEQUENCE: 1

```
Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
            20                  25                  30

Ala Val Glu Lys Thr Leu Ser Gln Gln Lys Ala Glu Leu Thr Glu Leu
        35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65                  70                  75                  80
```

```
Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys His Asn Pro
        435                 440                 445

Asn Ala Pro Val
    450
```

<210> SEQ ID NO 2
<211> LENGTH: 162
<212> TYPE: PRT
<213> ORGANISM: Artificial Sequence
<220> FEATURE:
<223> OTHER INFORMATION: Protein SPY0292-1

<400> SEQUENCE: 2

Glu Glu Tyr Ser Val Thr Ala Lys His Ala Ile Ala Val Asp Leu Glu
1 5 10 15

Ser Gly Lys Val Leu Tyr Glu Lys Asp Ala Lys Glu Val Val Pro Val
20 25 30

Ala Ser Val Ser Lys Leu Leu Thr Thr Tyr Leu Val Tyr Lys Glu Val
35 40 45

Ser Lys Gly Lys Leu Asn Trp Asp Ser Pro Val Thr Ile Ser Asn Tyr
50 55 60

Pro Tyr Glu Leu Thr Thr Asn Tyr Thr Ile Ser Asn Val Pro Leu Asp
65 70 75 80

Lys Arg Lys Tyr Thr Val Lys Glu Leu Leu Ser Ala Leu Val Val Asn
85 90 95

Asn Ala Asn Ser Pro Ala Ile Ala Leu Ala Glu Lys Ile Gly Gly Thr
100 105 110

Glu Pro Lys Phe Val Asp Lys Met Lys Lys Gln Leu Arg Gln Trp Gly
115 120 125

Ile Ser Asp Ala Lys Val Val Asn Ser Thr Gly Leu Thr Asn His Phe
130 135 140

Leu Gly Ala Asn Thr Tyr Pro Asn Thr Glu Pro Asp Asp Glu Asn Cys
145 150 155 160

Phe Cys

<210> SEQ ID NO 3
<211> LENGTH: 278
<212> TYPE: PRT
<213> ORGANISM: Artificial Sequence
<220> FEATURE:
<223> OTHER INFORMATION: Protein SPY0292-3

<400> SEQUENCE: 3

Glu Glu Tyr Ser Val Thr Ala Lys His Ala Ile Ala Val Asp Leu Glu
1 5 10 15

Ser Gly Lys Val Leu Tyr Glu Lys Asp Ala Lys Glu Val Val Pro Val
20 25 30

Ala Ser Val Ser Lys Leu Leu Thr Thr Tyr Leu Val Tyr Lys Glu Val
35 40 45

Ser Lys Gly Lys Leu Asn Trp Asp Ser Pro Val Thr Ile Ser Asn Tyr
50 55 60

Pro Tyr Glu Leu Thr Thr Asn Tyr Thr Ile Ser Asn Val Pro Leu Asp
65 70 75 80

Lys Arg Lys Tyr Thr Val Lys Glu Leu Leu Ser Ala Leu Val Val Asn
85 90 95

Asn Ala Asn Ser Pro Ala Ile Ala Leu Ala Glu Lys Ile Gly Gly Thr
100 105 110

Glu Pro Lys Phe Val Asp Lys Met Lys Lys Gln Leu Arg Gln Trp Gly
115 120 125

Ile Ser Asp Ala Lys Val Val Asn Ser Thr Gly Leu Thr Asn His Phe
130 135 140

Leu Gly Ala Asn Thr Tyr Pro Asn Thr Glu Pro Asp Asp Glu Asn Cys
145 150 155 160

Phe Cys Ala Thr Asp Leu Ala Ile Ile Ala Arg His Leu Leu Leu Glu
165 170 175

Phe Pro Glu Val Leu Lys Leu Ser Ser Lys Ser Ser Thr Ile Phe Ala
180 185 190

```
Gly Gln Thr Ile Tyr Ser Tyr Asn Tyr Met Leu Lys Gly Met Pro Cys
        195                 200                 205

Tyr Arg Glu Gly Val Asp Gly Leu Phe Val Gly Tyr Ser Lys Lys Ala
    210                 215                 220

Gly Ala Ser Phe Val Ala Thr Ser Val Glu Asn Gln Met Arg Val Ile
225                 230                 235                 240

Thr Val Val Leu Asn Ala Asp Gln Ser His Glu Asp Asp Leu Ala Ile
                245                 250                 255

Phe Lys Thr Thr Asn Gln Leu Leu Gln Tyr Leu Leu Ile Asn Phe Gln
            260                 265                 270

Lys Val Gln Leu Ile Glu
        275


<210> SEQ ID NO 4
<211> LENGTH: 644
<212> TYPE: PRT
<213> ORGANISM: Artificial Sequence
<220> FEATURE:
<223> OTHER INFORMATION: Protein SPY0416A-1

<400> SEQUENCE: 4

Ala Asp Glu Leu Ser Thr Met Ser Glu Pro Thr Ile Thr Asn His Ala
1               5                   10                  15

Gln Gln Gln Ala Gln His Leu Thr Asn Thr Glu Leu Ser Ser Ala Glu
            20                  25                  30

Ser Lys Ser Gln Asp Thr Ser Gln Ile Thr Leu Lys Thr Asn Arg Glu
        35                  40                  45

Lys Glu Gln Ser Gln Asp Leu Val Ser Glu Pro Thr Thr Thr Glu Leu
    50                  55                  60

Ala Asp Thr Asp Ala Ala Ser Met Ala Asn Thr Gly Ser Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Glu Ala Glu Pro Lys Ala Ile Lys Lys His Lys Ile Tyr
        195                 200                 205

Arg Pro Gln Ser Thr Gln Ala Pro Lys Glu Thr Val Ile Lys Thr Glu
    210                 215                 220

Glu Thr Asp Gly Ser His Asp Ile Asp Trp Thr Gln Thr Asp Asp Asp
225                 230                 235                 240

Thr Lys Tyr Glu Ser His Gly Met His Val Thr Gly Ile Val Ala Gly
                245                 250                 255

Asn Ser Lys Glu Ala Ala Ala Thr Gly Glu Arg Phe Leu Gly Ile Ala
            260                 265                 270
```

-continued

```
Pro Glu Ala Gln Val Met Phe Met Arg Val Phe Ala Asn Asp Ile Met
        275                 280                 285

Gly Ser Ala Glu Ser Leu Phe Ile Lys Ala Ile Glu Asp Ala Val Ala
    290                 295                 300

Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
    370                 375                 380

Asn Ser Lys Trp Val Ile Gln Arg Leu Met Thr Val Lys Glu Leu Glu
385                 390                 395                 400

Asn Arg Ala Asp Leu Asn His Gly Lys Ala Ile Tyr Ser Glu Ser Val
                405                 410                 415

Asp Phe Lys Asp Ile Lys Asp Ser Leu Gly Tyr Asp Lys Ser His Gln
            420                 425                 430

Phe Ala Tyr Val Lys Glu Ser Thr Asp Ala Gly Tyr Asn Ala Gln Asp
        435                 440                 445

Val Lys Gly Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Val Leu
465                 470                 475                 480

Ile Phe Asn Asn Lys Pro Gly Gln Ser Asn Arg Ser Met Arg Leu Thr
                485                 490                 495

Ala Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
        515                 520                 525

Asp Ser Val Val Ser Lys Ala Pro Ser Gln Lys Gly Asn Glu Met Asn
    530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
    610                 615                 620

Ala Gln Ile His Val Asn Pro Glu Thr Lys Thr Thr Thr Ser Pro Arg
625                 630                 635                 640

Gln Gln Gly Ala
```

```
<210> SEQ ID NO 5
<211> LENGTH: 311
<212> TYPE: PRT
<213> ORGANISM: Artificial Sequence
<220> FEATURE:
<223> OTHER INFORMATION: Protein SPY0416A-6

<400> SEQUENCE: 5
```

```
Ala Val Ile Asp Thr Gly Ile Asp Pro Ala His Gln Ser Met Arg Ile
1               5                   10                  15

Ser Asp Val Ser Thr Ala Lys Val Lys Ser Lys Glu Asp Met Leu Ala
            20                  25                  30

Arg Gln Lys Ala Ala Gly Ile Asn Tyr Gly Ser Trp Ile Asn Asp Lys
        35                  40                  45

Val Val Phe Ala His Asn Tyr Val Glu Asn Ser Asp Asn Ile Lys Glu
    50                  55                  60

Asn Gln Phe Glu Asp Phe Asp Glu Asp Trp Glu Asn Phe Glu Phe Asp
65                  70                  75                  80

Ala Glu Ala Glu Pro Lys Ala Ile Lys Lys His Lys Ile Tyr Arg Pro
                85                  90                  95

Gln Ser Thr Gln Ala Pro Lys Glu Thr Val Ile Lys Thr Glu Glu Thr
            100                 105                 110

Asp Gly Ser His Asp Ile Asp Trp Thr Gln Thr Asp Asp Asp Thr Lys
        115                 120                 125

Tyr Glu Ser His Gly Met His Val Thr Gly Ile Val Ala Gly Asn Ser
    130                 135                 140

Lys Glu Ala Ala Ala Thr Gly Glu Arg Phe Leu Gly Ile Ala Pro Glu
145                 150                 155                 160

Ala Gln Val Met Phe Met Arg Val Phe Ala Asn Asp Ile Met Gly Ser
                165                 170                 175

Ala Glu Ser Leu Phe Ile Lys Ala Ile Glu Asp Ala Val Ala Leu Gly
            180                 185                 190

Ala Asp Val Ile Asn Leu Ser Leu Gly Thr Ala Asn Gly Ala Gln Leu
        195                 200                 205

Ser Gly Ser Lys Pro Leu Met Glu Ala Ile Glu Lys Ala Lys Lys Ala
    210                 215                 220

Gly Val Ser Val Val Val Ala Ala Gly Asn Glu Arg Val Tyr Gly Ser
225                 230                 235                 240

Asp His Asp Asp Pro Leu Ala Thr Asn Pro Asp Tyr Gly Leu Val Gly
                245                 250                 255

Ser Pro Ser Thr Gly Arg Thr Pro Thr Ser Val Ala Ala Ile Asn Ser
            260                 265                 270

Lys Trp Val Ile Gln Arg Leu Met Thr Val Lys Glu Leu Glu Asn Arg
        275                 280                 285

Ala Asp Leu Asn His Gly Lys Ala Ile Tyr Ser Glu Ser Val Asp Phe
    290                 295                 300

Lys Asp Ile Lys Asp Ser Leu
305                 310
```

```
<210> SEQ ID NO 6
<211> LENGTH: 487
<212> TYPE: PRT
<213> ORGANISM: Artificial Sequence
<220> FEATURE:
<223> OTHER INFORMATION: Protein SPY0416A-7

<400> SEQUENCE: 6

Ser Gln Ile Thr Leu Lys Thr Asn Arg Glu Lys Glu Gln Ser Gln Asp
1               5                   10                  15

Leu Val Ser Glu Pro Thr Thr Thr Glu Leu Ala Asp Thr Asp Ala Ala
            20                  25                  30

Ser Met Ala Asn Thr Gly Ser Asp Ala Thr Gln Lys Ser Ala Ser Leu
        35                  40                  45
```

-continued

```
Pro Pro Val Asn Thr Asp Val His Asp Trp Val Lys Thr Lys Gly Ala
    50                  55                  60

Trp Asp Lys Gly Tyr Lys Gly Gln Gly Lys Val Val Ala Val Ile Asp
65                  70                  75                  80

Thr Gly Ile Asp Pro Ala His Gln Ser Met Arg Ile Ser Asp Val Ser
                85                  90                  95

Thr Ala Lys Val Lys Ser Lys Glu Asp Met Leu Ala Arg Gln Lys Ala
            100                 105                 110

Ala Gly Ile Asn Tyr Gly Ser Trp Ile Asn Asp Lys Val Val Phe Ala
        115                 120                 125

His Asn Tyr Val Glu Asn Ser Asp Asn Ile Lys Glu Asn Gln Phe Glu
    130                 135                 140

Asp Phe Asp Glu Asp Trp Glu Asn Phe Glu Phe Asp Ala Glu Ala Glu
145                 150                 155                 160

Pro Lys Ala Ile Lys Lys His Lys Ile Tyr Arg Pro Gln Ser Thr Gln
                165                 170                 175

Ala Pro Lys Glu Thr Val Ile Lys Thr Glu Glu Thr Asp Gly Ser His
            180                 185                 190

Asp Ile Asp Trp Thr Gln Thr Asp Asp Asp Thr Lys Tyr Glu Ser His
        195                 200                 205

Gly Met His Val Thr Gly Ile Val Ala Gly Asn Ser Lys Glu Ala Ala
    210                 215                 220

Ala Thr Gly Glu Arg Phe Leu Gly Ile Ala Pro Glu Ala Gln Val Met
225                 230                 235                 240

Phe Met Arg Val Phe Ala Asn Asp Ile Met Gly Ser Ala Glu Ser Leu
                245                 250                 255

Phe Ile Lys Ala Ile Glu Asp Ala Val Ala Leu Gly Ala Asp Val Ile
            260                 265                 270

Asn Leu Ser Leu Gly Thr Ala Asn Gly Ala Gln Leu Ser Gly Ser Lys
        275                 280                 285

Pro Leu Met Glu Ala Ile Glu Lys Ala Lys Lys Ala Gly Val Ser Val
    290                 295                 300

Val Val Ala Ala Gly Asn Glu Arg Val Tyr Gly Ser Asp His Asp Asp
305                 310                 315                 320

Pro Leu Ala Thr Asn Pro Asp Tyr Gly Leu Val Gly Ser Pro Ser Thr
                325                 330                 335

Gly Arg Thr Pro Thr Ser Val Ala Ala Ile Asn Ser Lys Trp Val Ile
            340                 345                 350

Gln Arg Leu Met Thr Val Lys Glu Leu Glu Asn Arg Ala Asp Leu Asn
        355                 360                 365

His Gly Lys Ala Ile Tyr Ser Glu Ser Val Asp Phe Lys Asp Ile Lys
    370                 375                 380

Asp Ser Leu Gly Tyr Asp Lys Ser His Gln Phe Ala Tyr Val Lys Glu
385                 390                 395                 400

Ser Thr Asp Ala Gly Tyr Asn Ala Gln Asp Val Lys Gly Lys Ile Ala
                405                 410                 415

Leu Ile Glu Arg Asp Pro Asn Lys Thr Tyr Asp Glu Met Ile Ala Leu
            420                 425                 430

Ala Lys Lys His Gly Ala Leu Gly Val Leu Ile Phe Asn Asn Lys Pro
        435                 440                 445

Gly Gln Ser Asn Arg Ser Met Arg Leu Thr Ala Asn Gly Met Gly Ile
    450                 455                 460

Pro Ser Ala Phe Ile Ser His Glu Phe Gly Lys Ala Met Ser Gln Leu
465                 470                 475                 480
```

```
Asn Gly Asn Gly Thr Gly Ser
                485


<210> SEQ ID NO 7
<211> LENGTH: 290
<212> TYPE: PRT
<213> ORGANISM: Artificial Sequence
<220> FEATURE:
<223> OTHER INFORMATION: Protein SPY0872-2

<400> SEQUENCE: 7

Ala Ile Ile Asn His Ala Asn Asp Ile Val Lys Thr Val Thr Glu Arg
1               5                   10                  15

Lys Ile Gly Thr Ala Thr Asn Ser Ser Thr Ile Ser Lys Thr Glu Asn
            20                  25                  30

Ile Asp Lys Glu Ser Pro Val Gly Asn Leu Ala Thr Thr Ala Gln Leu
        35                  40                  45

Thr Ile Ala Lys Lys Thr Phe Pro Thr Val Asp Phe Ala Met Thr Asn
    50                  55                  60

Asn Gly Gly Ile Arg Ser Asp Leu Val Val Lys Asn Asp Arg Thr Ile
65                  70                  75                  80

Thr Trp Gly Ala Ala Gln Ala Val Gln Pro Phe Gly Asn Ile Leu Gln
                85                  90                  95

Val Ile Gln Met Thr Gly Gln His Ile Tyr Asp Val Leu Asn Gln Gln
            100                 105                 110

Tyr Asp Glu Asn Gln Thr Tyr Phe Leu Gln Met Ser Gly Leu Thr Tyr
        115                 120                 125

Thr Tyr Thr Asp Asn Asp Pro Lys Asn Ser Asp Thr Pro Phe Lys Ile
    130                 135                 140

Val Lys Val Tyr Lys Asp Asn Gly Glu Glu Ile Asn Leu Thr Thr Thr
145                 150                 155                 160

Tyr Thr Val Val Val Asn Asp Phe Leu Tyr Gly Gly Gly Asp Gly Phe
                165                 170                 175

Ser Ala Phe Lys Lys Ala Lys Leu Ile Gly Ala Ile Asn Thr Asp Thr
            180                 185                 190

Glu Ala Phe Ile Thr Tyr Ile Thr Asn Leu Glu Ala Ser Gly Lys Thr
        195                 200                 205

Val Asn Ala Thr Ile Lys Gly Val Lys Asn Tyr Val Thr Ser Asn Leu
    210                 215                 220

Glu Ser Ser Thr Lys Val Asn Ser Ala Gly Lys His Ser Ile Ile Ser
225                 230                 235                 240

Lys Val Phe Arg Asn Arg Asp Gly Asn Thr Val Ser Ser Glu Val Ile
                245                 250                 255

Ser Asp Leu Leu Thr Ser Thr Glu Asn Thr Asn Asn Ser Leu Gly Lys
            260                 265                 270

Lys Glu Thr Thr Thr Asn Lys Asn Thr Ile Ser Ser Ser Thr Leu Pro
        275                 280                 285

Ile Thr
    290


<210> SEQ ID NO 8
<211> LENGTH: 331
<212> TYPE: PRT
<213> ORGANISM: Streptococcus pyogenes

<400> SEQUENCE: 8

Leu Arg Gln Ile Gln Ser Ile Arg Leu Ile Asp Val Leu Glu Leu Ala
```

-continued

```
1               5                   10                  15

Phe Gly Val Gly Tyr Lys Glu Glu Thr Thr Ser Gln Phe Ser Ser Asp
            20                  25                  30

Gln Pro Ser Gln Val Val Leu Tyr Arg Gly Glu Ala Asn Thr Val Arg
        35                  40                  45

Phe Ala Tyr Thr Asn Gln Met Ser Leu Met Lys Asp Ile Arg Ile Ala
    50                  55                  60

Leu Asp Gly Ser Asp Lys Ser Leu Thr Ala Gln Ile Val Pro Gly Met
65                  70                  75                  80

Gly His Val Tyr Glu Gly Phe Gln Thr Ser Ala Arg Gly Ile Phe Thr
                85                  90                  95

Met Ser Gly Val Pro Glu Ser Thr Val Pro Val Ala Asn Pro Asn Val
            100                 105                 110

Gln Thr Lys Tyr Ile Arg Tyr Phe Lys Val Ile Asp Asp Met His Asn
        115                 120                 125

Thr Met Tyr Lys Gly Thr Val Phe Leu Val Gln Pro Gln Ala Trp Lys
    130                 135                 140

Tyr Thr Met Lys Ser Val Asp Gln Leu Pro Val Asp Asp Leu Asn His
145                 150                 155                 160

Ile Gly Val Ala Gly Ile Glu Arg Met Thr Thr Leu Ile Lys Asn Ala
                165                 170                 175

Gly Ala Leu Leu Thr Thr Gly Gly Ser Gly Ala Phe Pro Asp Asn Ile
            180                 185                 190

Lys Val Ser Ile Asn Pro Lys Gly Arg Gln Ala Thr Ile Thr Tyr Gly
        195                 200                 205

Asp Gly Ser Thr Asp Ile Ile Pro Pro Ala Val Leu Trp Lys Lys Gly
    210                 215                 220

Ser Val Lys Glu Pro Thr Glu Ala Asp Gln Ser Val Gly Thr Pro Thr
225                 230                 235                 240

Pro Gly Ile Pro Gly Lys Phe Lys Arg Asp Gln Ser Leu Asn Glu His
                245                 250                 255

Glu Ala Met Val Asn Val Glu Pro Leu Ser His Val Val Lys Asp Asn
            260                 265                 270

Ile Lys Val Ile Asp Glu Lys Ser Thr Gly Arg Phe Glu Pro Phe Arg
        275                 280                 285

Pro Asn Glu Asp Glu Lys Glu Lys Pro Ala Ser Asp Val Lys Val Arg
    290                 295                 300

Pro Ala Glu Val Gly Ser Trp Leu Glu Pro Ala Thr Ala Leu Pro Ser
305                 310                 315                 320

Val Glu Met Ser Ala Glu Asp Arg Leu Lys Ser
                325                 330
```

<210> SEQ ID NO 9
<211> LENGTH: 261
<212> TYPE: PRT
<213> ORGANISM: Streptococcus pyogenes

<400> SEQUENCE: 9

```
Thr Asn Asn Gln Thr Leu Asp Ile Leu Leu Asp Val Tyr Ala Tyr Asn
1               5                   10                  15

His Ala Phe Arg Ile Ala Lys Ala Leu Pro Asn Ile Pro Lys Thr Ala
            20                  25                  30

Leu Tyr Leu Leu Glu Met Leu Lys Glu Arg Arg Glu Leu Asn Leu Ala
        35                  40                  45

Phe Leu Ala Glu His Ala Ala Glu Asn Arg Thr Ile Glu Asp Gln Tyr
```

```
    50                  55                  60

His Cys Ser Leu Trp Leu Asn Gln Ser Leu Glu Asp Glu Gln Ile Ala
65                  70                  75                  80

Asn Tyr Ile Leu Asp Leu Glu Val Lys Val Lys Asn Gly Ala Ile Ile
                85                  90                  95

Asp Phe Val Arg Ser Val Ser Pro Ile Leu Tyr Arg Leu Phe Leu Arg
            100                 105                 110

Leu Ile Thr Ser Glu Ile Pro Asn Phe Lys Ala Tyr Ile Phe Asp Thr
        115                 120                 125

Lys Asn Asp Gln Tyr Asp Thr Trp His Phe Gln Ala Met Leu Glu Ser
    130                 135                 140

Asp His Glu Val Phe Lys Ala Tyr Leu Ser Gln Lys Gln Ser Arg Asn
145                 150                 155                 160

Val Thr Thr Lys Ser Leu Ala Asp Met Leu Thr Leu Thr Ser Leu Pro
                165                 170                 175

Gln Glu Ile Lys Asp Leu Val Phe Leu Leu Arg His Phe Glu Lys Ala
            180                 185                 190

Val Arg Asn Pro Leu Ala His Leu Ile Lys Pro Phe Asp Glu Glu Glu
        195                 200                 205

Leu His Arg Thr Thr His Phe Ser Ser Gln Ala Phe Leu Glu Asn Ile
    210                 215                 220

Ile Thr Leu Ala Thr Phe Ser Gly Val Ile Tyr Arg Arg Glu Pro Phe
225                 230                 235                 240

Tyr Phe Asp Asp Met Asn Ala Ile Ile Lys Lys Glu Leu Ser Leu Trp
                245                 250                 255

Arg Gln Ser Ile Val
            260


<210> SEQ ID NO 10
<211> LENGTH: 263
<212> TYPE: PRT
<213> ORGANISM: Streptococcus pyogenes

<400> SEQUENCE: 10

Val Thr Thr Thr Glu Gln Glu Leu Thr Leu Thr Pro Leu Arg Gly Lys
1               5                   10                  15

Ser Gly Lys Ala Tyr Lys Gly Thr Tyr Pro Asn Gly Glu Cys Val Phe
            20                  25                  30

Ile Lys Leu Asn Thr Thr Pro Ile Leu Pro Ala Leu Ala Lys Glu Gln
        35                  40                  45

Ile Ala Pro Gln Leu Leu Trp Ala Lys Arg Met Gly Asn Gly Asp Met
    50                  55                  60

Met Ser Ala Gln Glu Trp Leu Asn Gly Arg Thr Leu Thr Lys Glu Asp
65                  70                  75                  80

Met Asn Ser Lys Gln Ile Ile His Ile Leu Leu Arg Leu His Lys Ser
                85                  90                  95

Lys Lys Leu Val Asn Gln Leu Leu Gln Leu Asn Tyr Lys Ile Glu Asn
            100                 105                 110

Pro Tyr Asp Leu Leu Val Asp Phe Glu Gln Asn Ala Pro Leu Gln Ile
        115                 120                 125

Gln Gln Asn Ser Tyr Leu Gln Ala Ile Val Lys Glu Leu Lys Arg Ser
    130                 135                 140

Leu Pro Glu Phe Lys Ser Glu Val Ala Thr Ile Val His Gly Asp Ile
145                 150                 155                 160

Lys His Ser Asn Trp Val Ile Thr Thr Ser Gly Met Ile Phe Leu Val
```

-continued

```
            165                 170                 175

Asp Trp Asp Ser Val Arg Leu Thr Asp Arg Met Tyr Asp Val Ala Tyr
        180                 185                 190

Leu Leu Ser His Tyr Ile Pro Arg Ser Arg Trp Ser Glu Trp Leu Ser
    195                 200                 205

Tyr Tyr Gly Tyr Lys Asn Asn Asp Lys Val Met Gln Lys Ile Ile Trp
210                 215                 220

Tyr Gly Gln Phe Ser His Leu Thr Gln Ile Leu Lys Cys Phe Asp Lys
225                 230                 235                 240

Arg Asp Met Glu His Val Asn Gln Glu Ile Tyr Ala Leu Arg Lys Phe
            245                 250                 255

Arg Glu Ile Phe Arg Lys Lys
        260
```

```
<210> SEQ ID NO 11
<211> LENGTH: 1356
<212> TYPE: DNA
<213> ORGANISM: Artificial Sequence
<220> FEATURE:
<223> OTHER INFORMATION: DNA SPY0269-1

<400> SEQUENCE: 11

gatgatagag cctcaggaga aacgaaggcg agtaatactc acgacgatag tttaccaaaa     60

ccagaaacaa ttcaagaggc aaaggcaact attgatgcag ttgaaaaaac tctcagtcaa    120

caaaaagcag aactgacaga gcttgctacc gctctgacaa aaactactgc tgaaatcaac    180

cacttaaaag agcagcaaga taatgaacaa aaagctttaa cctctgcaca agaaatttac    240

actaatactc ttgcaagtag tgaggagacg ctattagccc aaggagccga acatcaaaga    300

gagttaacag ctactgaaac agagcttcat aatgctcaag cagatcaaca ttcaaaagag    360

actgcattgt cagaacaaaa agctagcatt tcagcagaaa ctactcgagc tcaagattta    420

gtggaacaag tcaaaacgtc tgaacaaaat attgctaagc tcaatgctat gattagcaat    480

cctgatgcta tcactaaagc agctcaaacg gctaatgata atacaaaagc attaagctca    540

gaattggaga aggctaaagc tgacttagaa aatcaaaaag ctaaagttaa aaagcaattg    600

actgaagagt tggcagctca gaaagctgct ctagcagaaa aagaggcaga acttagtcgt    660

cttaaatcct cagctccgtc tactcaagat agcattgtgg gtaataatac catgaaagca    720

ccgcaaggct atcctcttga agaacttaaa aaattagaag ctagtggtta tattggatca    780

gctagttaca ataattatta caaagagcat gcagatcaaa ttattgccaa agctagtcca    840

ggtaatcaat taaatcaata ccaagatatt ccagcagatc gtaatcgctt tgttgatccc    900

gataatttga caccagaagt gcaaaatgag ctagcgcagt ttgcagctca catgattaat    960

agtgtaagaa gacaattagg tctaccacca gttactgtta cagcaggatc acaagaattt   1020

gcaagattac ttagtaccag ctataagaaa actcatggta atacaagacc atcatttgtc   1080

tacggacagc caggggtatc agggcattat ggtgttgggc ctcatgataa aactattatt   1140

gaagactctg ccggagcgtc agggctcatt cgaaatgatg ataacatgta cgagaatatc   1200

ggtgctttta acgatgtgca tactgtgaat ggtattaaac gtggtattta tgacagtatc   1260

aagtatatgc tctttacaga tcatttacac ggaaatacat acggccatgc tattaacttt   1320

ttacgtgtag ataaacataa ccctaatgcg cctgtt                             1356

<210> SEQ ID NO 12
<211> LENGTH: 486
<212> TYPE: DNA
```

<213> ORGANISM: Artificial Sequence
<220> FEATURE:
<223> OTHER INFORMATION: DNA SPY0292-1

<400> SEQUENCE: 12
gaagagtatt cggtaactgc taagcatgcg attgccgttg accttgaaag tggcaaagtt 60
ttatacgaaa aagatgctaa agaagttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgc 486

<210> SEQ ID NO 13
<211> LENGTH: 834
<212> TYPE: DNA
<213> ORGANISM: Artificial Sequence
<220> FEATURE:
<223> OTHER INFORMATION: DNA SPY0292-3

<400> SEQUENCE: 13
gaagagtatt cggtaactgc taagcatgcg attgccgttg accttgaaag tggcaaagtt 60
ttatacgaaa aagatgctaa agaagttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgcgcca ctgatttagc tattattgcc aggcatctct tattagaatt tccagaagta 540
ctgaaattat ctagcaaatc ctccactatt tttgctggac aaaccattta cagttataat 600
tacatgctta aaggcatgcc ttgttatcga gaaggcgtgg atggtctttt tgttggttat 660
tctaaaaaag ccggtgcttc ttttgtagct actagtgtcg aaaatcaaat gagggttatt 720
acagtagttt taaatgctga tcaaagccac gaggatgatt tagctatatt taaaacaacc 780
aatcaattgt tgcagtacct tttaattaat tttcaaaaag tccagttaat tgaa 834

<210> SEQ ID NO 14
<211> LENGTH: 1932
<212> TYPE: DNA
<213> ORGANISM: Artificial Sequence
<220> FEATURE:
<223> OTHER INFORMATION: DNA SPY0416A-1

<400> SEQUENCE: 14
gcagatgagc taagcacaat gagcgaacca acaatcacga atcacgctca acaacaagcg 60
caacatctca ccaatacaga gttgagctca gctgaatcaa aatctcaaga cacatcacaa 120
atcactctca agacaaatcg tgaaaaagag caatcacaag atctagtctc tgagccaacc 180
acaactgagc tagctgacac agatgcagca tcaatggcta atacaggttc tgatgcgact 240

-continued

```
caaaaaagcg cttctttacc gccagtcaat acagatgttc acgattgggt aaaaaccaaa    300

ggagcttggg acaagggata caaaggacaa ggcaaggttg tcgcagttat tgacacaggg    360

atcgatccgg cccatcaaag catgcgcatc agtgatgtat caactgctaa agtaaaatca    420

aaagaagaca tgctagcacg ccaaaaagcc gccggtatta attatgggag ttggataaat    480

gataaagttg tttttgcaca taattatgtg gaaaatagcg ataatatcaa agaaaatcaa    540

ttcgaggatt ttgatgagga ctgggaaaac tttgagtttg atgcagaggc agagccaaaa    600

gccatcaaaa aacacaagat ctatcgtccc caatcaaccc aggcaccgaa agaaactgtt    660

atcaaaacag aagaaacaga tggttcacat gatattgact ggacacaaac agacgatgac    720

accaaatacg agtcacacgg tatgcatgtg acaggtattg tagccggtaa tagcaaagaa    780

gccgctgcta ctggagaacg ctttttagga attgcaccag aggcccaagt catgttcatg    840

cgtgtttttg ccaacgacat catgggatca gctgaatcac tctttatcaa agctatcgaa    900

gatgccgtgg ctttaggagc agatgtgatc aacctgagtc ttggaaccgc taatggggca    960

cagcttagtg gcagcaagcc tctaatggaa gcaattgaaa aagctaaaaa agccggtgta   1020

tcagttgttg tagcagcagg aaatgagcgc gtctatggat ctgaccatga tgatccattg   1080

gcgacaaatc cagactatgg tttggtcggt tctccctcaa caggtcgaac accaacatca   1140

gtggcagcta taaacagtaa gtgggtgatt caacgtctaa tgacggtcaa agaattagaa   1200

aaccgtgccg atttaaacca tggtaaagcc atctattcag agtctgtcga ctttaaagac   1260

ataaaagata gcctaggtta tgataaatcg catcaatttg cttatgtcaa agagtcaact   1320

gatgcgggtt ataacgcaca agacgttaaa ggtaaaattg ctttaattga acgtgatccc   1380

aataaaacct atgacgaaat gattgctttg gctaagaaac atggagctct gggagtactt   1440

atttttaata acaagcctgg tcaatcaaac cgctcaatgc gtctaacagc taatgggatg   1500

gggataccat ctgctttcat atcgcacgaa tttggtaagg ccatgtccca attaaatggc   1560

aatggtacag gaagtttaga gtttgacagt gtggtctcaa aagcaccgag tcaaaaaggc   1620

aatgaaatga atcatttttc aaattggggc ctaacttctg atggctattt aaaacctgac   1680

attactgcac caggtggcga tatctattct acctataacg ataaccacta tggtagccaa   1740

acaggaacaa gtatggcctc tcctcagatt gctggcgcca gccttttggt caaacaatac   1800

ctagaaaaga ctcagccaaa cttgccaaaa gaaaaaattg ctgatatcgt taagaaccta   1860

ttgatgagca atgctcaaat tcatgttaat ccagagacaa aaacgaccac ctcaccgcgt   1920

cagcaagggg ca                                                       1932
```

<210> SEQ ID NO 15
<211> LENGTH: 933
<212> TYPE: DNA
<213> ORGANISM: Artificial Sequence
<220> FEATURE:
<223> OTHER INFORMATION: DNA SPY0416A-6

<400> SEQUENCE: 15

```
gcagttattg acacagggat cgatccggcc catcaaagca tgcgcatcag tgatgtatca     60

actgctaaag taaaatcaaa agaagacatg ctagcacgcc aaaaagccgc cggtattaat    120

tatgggagtt ggataaatga taaagttgtt tttgcacata attatgtgga aaatagcgat    180

aatatcaaag aaaatcaatt cgaggatttt gatgaggact gggaaaactt tgagtttgat    240

gcagaggcag agccaaaagc catcaaaaaa cacaagatct atcgtcccca atcaacccag    300

gcaccgaaag aaactgttat caaaacagaa gaaacagatg gttcacatga tattgactgg    360
```

-continued

```
acacaaacag acgatgacac caaatacgag tcacacggta tgcatgtgac aggtattgta    420

gccggtaata gcaaagaagc cgctgctact ggagaacgct tttaggaat tgcaccagag     480

gcccaagtca tgttcatgcg tgtttttgcc aacgacatca tgggatcagc tgaatcactc    540

tttatcaaag ctatcgaaga tgccgtggct ttaggagcag atgtgatcaa cctgagtctt    600

ggaaccgcta atggggcaca gcttagtggc agcaagcctc taatggaagc aattgaaaaa    660

gctaaaaaag ccggtgtatc agttgttgta gcagcaggaa atgagcgcgt ctatggatct    720

gaccatgatg atccattggc gacaaatcca gactatggtt tggtcggttc tccctcaaca    780

ggtcgaacac caacatcagt ggcagctata aacagtaagt gggtgattca acgtctaatg    840

acggtcaaag aattagaaaa ccgtgccgat ttaaaccatg gtaaagccat ctattcagag    900

tctgtcgact ttaaagacat aaaagatagc cta                                 933
```

<210> SEQ ID NO 16
<211> LENGTH: 1461
<212> TYPE: DNA
<213> ORGANISM: Artificial Sequence
<220> FEATURE:
<223> OTHER INFORMATION: DNA SPY0416A-7

<400> SEQUENCE: 16

```
tcacaaatca ctctcaagac aaatcgtgaa aaagagcaat cacaagatct agtctctgag     60

ccaaccacaa ctgagctagc tgacacagat gcagcatcaa tggctaatac aggttctgat    120

gcgactcaaa aaagcgcttc tttaccgcca gtcaatacag atgttcacga ttgggtaaaa    180

accaaaggag cttgggacaa gggatacaaa ggacaaggca aggttgtcgc agttattgac    240

acagggatcg atccggccca tcaaagcatg cgcatcagtg atgtatcaac tgctaaagta    300

aaatcaaaag aagacatgct agcacgccaa aaagccgccg gtattaatta tgggagttgg    360

ataaatgata aagttgtttt tgcacataat tatgtggaaa atagcgataa tatcaaagaa    420

aatcaattcg aggattttga tgaggactgg gaaaactttg agtttgatgc agaggcagag    480

ccaaaagcca tcaaaaaaca caagatctat cgtccccaat caacccaggc accgaaagaa    540

actgttatca aaacagaaga aacagatggt tcacatgata ttgactggac acaaacagac    600

gatgacacca aatacgagtc acacggtatg catgtgacag gtattgtagc cggtaatagc    660

aaagaagccg ctgctactgg agaacgcttt ttaggaattg caccagaggc ccaagtcatg    720

ttcatgcgtg tttttgccaa cgacatcatg ggatcagctg aatcactctt tatcaaagct    780

atcgaagatg ccgtggcttt aggagcagat gtgatcaacc tgagtcttgg aaccgctaat    840

ggggcacagc ttagtggcag caagcctcta atggaagcaa ttgaaaaagc taaaaaagcc    900

ggtgtatcag ttgttgtagc agcaggaaat gagcgcgtct atggatctga ccatgatgat    960

ccattggcga caaatccaga ctatggtttg gtcggttctc cctcaacagg tcgaacacca   1020

acatcagtgg cagctataaa cagtaagtgg gtgattcaac gtctaatgac ggtcaaagaa   1080

ttagaaaacc gtgccgattt aaaccatggt aaagccatct attcagagtc tgtcgacttt   1140

aaagacataa aagatagcct aggttatgat aaatcgcatc aatttgctta tgtcaaagag   1200

tcaactgatg cgggttataa cgcacaagac gttaaaggta aaattgcttt aattgaacgt   1260

gatcccaata aaacctatga cgaaatgatt gctttggcta agaaacatgg agctctggga   1320

gtacttattt ttaataacaa gcctggtcaa tcaaaccgct caatgcgtct aacagctaat   1380

gggatgggga taccatctgc tttcatatcg cacgaatttg gtaaggccat gtcccaatta   1440

aatggcaatg gtacaggaag t                                             1461
```

<210> SEQ ID NO 17
<211> LENGTH: 870
<212> TYPE: DNA
<213> ORGANISM: Artificial Sequence
<220> FEATURE:
<223> OTHER INFORMATION: DNA SPY0872-2

<400> SEQUENCE: 17
gctataataa atcatgctaa tgatattgtt aaaacagtta ctgaacgaaa aatcggaact 60
gcaactaatt cttcaactat ttctaaaaca gaaaatattg ataaagaatc tcctgtcggt 120
aacttagcaa caacggctca gcttactatt gctaagaaaa cttttccaac tgttgacttt 180
gctatgacca ataatggtgg tattcgaagt gacctagttg tcaaaaatga ccggaccatc 240
acctggggag ctgcacaggc tgtacaacca tttggtaata tccttcaagt cattcaaatg 300
actggtcaac acatttacga tgtcctaaat cagcaatacg atgaaaacca gacctatttt 360
cttcaaatgt caggtttaac atacacttat acagataatg atcctaagaa ctctgatacc 420
cccttcaaga tagttaaggt ttataaagac aatggtgaag aaattaactt aacaactact 480
tacaccgttg ttgtcaacga ctttctttat ggtggtggtg atggcttttc agcatttaaa 540
aaagctaaat taatcggagc tattaacaca gatactgaag ctttcatcac atatatcaca 600
aatttagaag catcaggtaa aactgttaat gctactataa aaggggttaa aaattatgta 660
acttcaaacc ttgaaagttc gacaaaagtt aatagtgctg gtaaacacag tatcattagt 720
aaggttttta gaaatcgtga tggcaataca gtgtctagtg aagtcatttc agaccttttg 780
acttctactg aaaacactaa taacagcctt ggcaaaaaag aaacaacaac aaacaaaaat 840
actatctcta gttccactct tccaataaca 870

<210> SEQ ID NO 18
<211> LENGTH: 993
<212> TYPE: DNA
<213> ORGANISM: Streptococcus pyogenes

<400> SEQUENCE: 18
ttgcggcaga ttcagtccat tcgtctgata gacgttttgg agttggcttt tggagttggc 60
tataaggaag aaacaacctc tcagttttct tcggatcagc cctcccaagt ggttttgtat 120
cgaggtgagg ctaacacggt taggtttgcc tataccaatc agatgtctct gatgaaagat 180
attcgcattg ctttggatgg ttctgataag tctttgaccg ctcagattgt tcctggtatg 240
ggtcatgttt atgagggctt tcaaacttct gctagaggga tttttacgat gtcaggagtt 300
cctgaaagca ctgttcccgt tgctaaccct aatgtacaaa ccaaatatat aaggtatttc 360
aaagtcattg atgatatgca taacacaatg tataaaggaa ctgtttttct tgttcaaccg 420
caagcttgga aatacaccat gaaatctgtt gatcagttac cagtagatga cttgaaccat 480
attggcgttg ctggtattga acgaatgaca actctcatta aaaatgcggg tgccctttta 540
accacaggag gtagtggggc tttcccagac aatattaaag tatctattaa tccaaagggg 600
aggcaggcca cgattactta tggggacggc tctacggata ttattcctcc agcagtttta 660
tggaaaaaag gctccgtaaa agagcctact gaagccgatc aatctgtcgg aacaccgact 720
cctggtattc ctggtaaatt caaacgagac cagagcctta acgagcatga agctatggta 780
aatgtcgaac cactgtctca tgtagtaaaa gacaatataa aggtcataga tgaaaaatca 840
acagggcggt ttgagccttt tagacctaat gaagatgaga aggagaagcc tgccagcgat 900
gttaaggtaa gaccagcaga agttggtagc tggctagaac cagcgacagc tcttcctagt 960
gttgaaatga gcgctgagga caggttaaaa agt 993

<210> SEQ ID NO 19
<211> LENGTH: 783
<212> TYPE: DNA
<213> ORGANISM: Streptococcus pyogenes

<400> SEQUENCE: 19
actaataatc aaacactaga catccttttg gatgtctatg cttataatca cgcctttaga 60
attgctaaag ccttgccaaa tatccctaaa actgccctct atttactaga gatgttaaaa 120
gagcgcagag aattgaacct tgcctttcta gcggaacatg cagcagagaa tcggaccatt 180
gaagaccagt atcactgttc attatggctt aaccaatcgc ttgaagatga gcagattgcc 240
aattacattt tggatttaga agttaaagta aaaaacggtg ctattattga tttcgtcagg 300
tcagtgtcgc ctattcttta ccgacttttt ctcagactaa tcacgtcaga aattccaaac 360
ttcaaggctt atatttttga tacaaagaat gaccaatatg atacctggca ttttcaggcc 420
atgttggaat ctgatcacga ggttttcaag gcttacctgt ctcaaaagca gtctcgcaat 480
gtgacgacca aaagcttagc agacatgttg acgttgacct ccttacctca ggaaatcaag 540
gacttggttt ttttgttacg acattttgaa aaggctgtcc gtaatcctct ggctcatttg 600
attaagcctt ttgatgaaga ggaactgcat cgcaccactc atttttcttc tcaggctttt 660
ttggaaaaca ttatcacctt ggcgactttt tctggtgtaa tctaccgacg tgagcctttt 720
tactttgatg acatgaatgc cattattaaa aaggagttga gcctttggag acaatctatt 780
gtc 783

<210> SEQ ID NO 20
<211> LENGTH: 789
<212> TYPE: DNA
<213> ORGANISM: Streptococcus pyogenes

<400> SEQUENCE: 20
gtgacaacga cggaacaaga acttaccttg actcccttac gtgggaaaag tggcaaagct 60
tataaaggca cttatccaaa tggggaatgt gtctttataa aattaaatac gacccctatt 120
ctacctgcct tagcaaaaga acagattgcg ccacagttac tttgggccaa acgcatgggc 180
aatggtgata tgatgagtgc ccaagaatgg cttaacggcc gtacattgac caaagaagat 240
atgaacagta agcaaatcat tcatattcta ttgcgccttc acaaatctaa aaaattagtc 300
aatcaactgc ttcagctcaa ttataagatt gaaaacccat acgatttatt ggttgatttt 360
gagcaaaatg caccccttgca aattcagcaa aattcatact tacaagctat cgttaaagaa 420
ttaaaacgga gcttaccaga gttcaaatca gaagtagcaa cgattgtgca tggagatatt 480
aaacatagca attgggtgat tactactagt ggtatgattt ttttagtaga ttgggattct 540
gttcgtctaa ctgatcggat gtatgatgtt gcttacctgt tgagccacta tattccacgg 600
tctcgttggt cagaatggct gtcttattat ggctataaaa ataatgacaa ggttatgcaa 660
aaaattattt ggtatggtca attttctcac ctgacacaaa ttctcaagtg ttttgacaag 720
cgtgacatgg agcatgtgaa tcaggagatt tatgccctca gaaaatttag agaaatattt 780
agaaagaaa 789

<210> SEQ ID NO 21
<211> LENGTH: 32
<212> TYPE: DNA
<213> ORGANISM: Artificial sequence
<220> FEATURE:

<223> OTHER INFORMATION: Primer

<400> SEQUENCE: 21
tagtagccat gggcgatgat agagcctcag ga 32

<210> SEQ ID NO 22
<211> LENGTH: 35
<212> TYPE: DNA
<213> ORGANISM: Artificial sequence
<220> FEATURE:
<223> OTHER INFORMATION: Primer

<400> SEQUENCE: 22
tagtaggcgg ccgccttaga ttccttacgg aacct 35

<210> SEQ ID NO 23
<211> LENGTH: 32
<212> TYPE: DNA
<213> ORGANISM: Artificial sequence
<220> FEATURE:
<223> OTHER INFORMATION: Primer

<400> SEQUENCE: 23
tagtagccat gggcgatgat agagcctcag ga 32

<210> SEQ ID NO 24
<211> LENGTH: 30
<212> TYPE: DNA
<213> ORGANISM: Artificial sequence
<220> FEATURE:
<223> OTHER INFORMATION: Primer

<400> SEQUENCE: 24
tagtaggcgg ccgcaacagg cgcattaggg 30

<210> SEQ ID NO 25
<211> LENGTH: 34
<212> TYPE: DNA
<213> ORGANISM: Artificial sequence
<220> FEATURE:
<223> OTHER INFORMATION: Primer

<400> SEQUENCE: 25
tagtagccat gggcgaagag tattcggtaa ctgc 34

<210> SEQ ID NO 26
<211> LENGTH: 35
<212> TYPE: DNA
<213> ORGANISM: Artificial sequence
<220> FEATURE:
<223> OTHER INFORMATION: Primer

<400> SEQUENCE: 26
tagtaggcgg ccgctaaaga ggtattgaca tacct 35

<210> SEQ ID NO 27
<211> LENGTH: 34
<212> TYPE: DNA
<213> ORGANISM: Artificial sequence
<220> FEATURE:
<223> OTHER INFORMATION: Primer

<400> SEQUENCE: 27
tagtagccat gggcgaagag tattcggtaa ctgc 34

<210> SEQ ID NO 28

<211> LENGTH: 35
<212> TYPE: DNA
<213> ORGANISM: Artificial sequence
<220> FEATURE:
<223> OTHER INFORMATION: Primer

<400> SEQUENCE: 28
tagtaggcgg ccgcgcaaaa acaattttca tcatc 35

<210> SEQ ID NO 29
<211> LENGTH: 34
<212> TYPE: DNA
<213> ORGANISM: Artificial sequence
<220> FEATURE:
<223> OTHER INFORMATION: Primer

<400> SEQUENCE: 29
tagtagccat gggcgaagag tattcggtaa ctgc 34

<210> SEQ ID NO 30
<211> LENGTH: 35
<212> TYPE: DNA
<213> ORGANISM: Artificial sequence
<220> FEATURE:
<223> OTHER INFORMATION: Primer

<400> SEQUENCE: 30
tagtaggcgg ccgcttcaat taactggact ttttg 35

<210> SEQ ID NO 31
<211> LENGTH: 34
<212> TYPE: DNA
<213> ORGANISM: Artificial sequence
<220> FEATURE:
<223> OTHER INFORMATION: Primer

<400> SEQUENCE: 31
tagtaggaat tcggcagatg agctaagcac aatg 34

<210> SEQ ID NO 32
<211> LENGTH: 33
<212> TYPE: DNA
<213> ORGANISM: Artificial sequence
<220> FEATURE:
<223> OTHER INFORMATION: Primer

<400> SEQUENCE: 32
tagtagctcg agctctgaac caagagtgac aag 33

<210> SEQ ID NO 33
<211> LENGTH: 34
<212> TYPE: DNA
<213> ORGANISM: Artificial sequence
<220> FEATURE:
<223> OTHER INFORMATION: Primer

<400> SEQUENCE: 33
tagtaggaat tcggcagatg agctaagcac aatg 34

<210> SEQ ID NO 34
<211> LENGTH: 32
<212> TYPE: DNA
<213> ORGANISM: Artificial sequence
<220> FEATURE:
<223> OTHER INFORMATION: Primer

<400> SEQUENCE: 34
tagtagctcg agtgcccctt gctgacgcgg tg 32

<210> SEQ ID NO 35
<211> LENGTH: 31
<212> TYPE: DNA
<213> ORGANISM: Artificial sequence
<220> FEATURE:
<223> OTHER INFORMATION: Primer

<400> SEQUENCE: 35
tagtaggaat tcggcagtta ttgacacagg g 31

<210> SEQ ID NO 36
<211> LENGTH: 30
<212> TYPE: DNA
<213> ORGANISM: Artificial sequence
<220> FEATURE:
<223> OTHER INFORMATION: Primer

<400> SEQUENCE: 36
tagtagctcg agtaggctat cttttatgtc 30

<210> SEQ ID NO 37
<211> LENGTH: 31
<212> TYPE: DNA
<213> ORGANISM: Artificial sequence
<220> FEATURE:
<223> OTHER INFORMATION: Primer

<400> SEQUENCE: 37
tagtaggaat tcgtcacaaa tcactctcaa g 31

<210> SEQ ID NO 38
<211> LENGTH: 30
<212> TYPE: DNA
<213> ORGANISM: Artificial sequence
<220> FEATURE:
<223> OTHER INFORMATION: Primer

<400> SEQUENCE: 38
tagtagctcg agacttcctg taccattgcc 30

<210> SEQ ID NO 39
<211> LENGTH: 34
<212> TYPE: DNA
<213> ORGANISM: Artificial sequence
<220> FEATURE:
<223> OTHER INFORMATION: Primer

<400> SEQUENCE: 39
tagtaggaat tcgcatgtag acccacaaaa gggc 34

<210> SEQ ID NO 40
<211> LENGTH: 33
<212> TYPE: DNA
<213> ORGANISM: Artificial sequence
<220> FEATURE:
<223> OTHER INFORMATION: Primer

<400> SEQUENCE: 40
tagtagctcg agcgttgatg gtagggcttt tgc 33

<210> SEQ ID NO 41
<211> LENGTH: 35
<212> TYPE: DNA
<213> ORGANISM: Artificial sequence
<220> FEATURE:

<223> OTHER INFORMATION: Primer

<400> SEQUENCE: 41
tagtagccat gggcttgcgg cagattcagt ccatt 35

<210> SEQ ID NO 42
<211> LENGTH: 35
<212> TYPE: DNA
<213> ORGANISM: Artificial sequence
<220> FEATURE:
<223> OTHER INFORMATION: Primer

<400> SEQUENCE: 42
tagtaggcgg ccgcactttt taacctgtcc tcagc 35

<210> SEQ ID NO 43
<211> LENGTH: 35
<212> TYPE: DNA
<213> ORGANISM: Artificial sequence
<220> FEATURE:
<223> OTHER INFORMATION: Primer

<400> SEQUENCE: 43
tagtagccat gggcgatcaa gttgatgtgc aattc 35

<210> SEQ ID NO 44
<211> LENGTH: 35
<212> TYPE: DNA
<213> ORGANISM: Artificial sequence
<220> FEATURE:
<223> OTHER INFORMATION: Primer

<400> SEQUENCE: 44
tagtaggcgg ccgctgttat tggaagagtg gaact 35

<210> SEQ ID NO 45
<211> LENGTH: 32
<212> TYPE: DNA
<213> ORGANISM: Artificial sequence
<220> FEATURE:
<223> OTHER INFORMATION: Primer

<400> SEQUENCE: 45
tagtagccat gggcgctata ataaatcatg ct 32

<210> SEQ ID NO 46
<211> LENGTH: 35
<212> TYPE: DNA
<213> ORGANISM: Artificial sequence
<220> FEATURE:
<223> OTHER INFORMATION: Primer

<400> SEQUENCE: 46
tagtaggcgg ccgctgttat tggaagagtg gaact 35

<210> SEQ ID NO 47
<211> LENGTH: 32
<212> TYPE: DNA
<213> ORGANISM: Artificial sequence
<220> FEATURE:
<223> OTHER INFORMATION: Primer

<400> SEQUENCE: 47
tagtagccat gggcactaat aatcaaacac ta 32

<210> SEQ ID NO 48

<211> LENGTH: 35
<212> TYPE: DNA
<213> ORGANISM: Artificial sequence
<220> FEATURE:
<223> OTHER INFORMATION: Primer

<400> SEQUENCE: 48
tagtaggcgg ccgcgacaat agattgtctc caaag 35

<210> SEQ ID NO 49
<211> LENGTH: 33
<212> TYPE: DNA
<213> ORGANISM: Artificial sequence
<220> FEATURE:
<223> OTHER INFORMATION: Primer

<400> SEQUENCE: 49
tagtagccat gggcattgaa atgcctggag gcg 33

<210> SEQ ID NO 50
<211> LENGTH: 35
<212> TYPE: DNA
<213> ORGANISM: Artificial sequence
<220> FEATURE:
<223> OTHER INFORMATION: Primer

<400> SEQUENCE: 50
tagtaggcgg ccgctttgcg aagataaacc agtgc 35

<210> SEQ ID NO 51
<211> LENGTH: 35
<212> TYPE: DNA
<213> ORGANISM: Artificial sequence
<220> FEATURE:
<223> OTHER INFORMATION: Primer

<400> SEQUENCE: 51
tagtagccat gggcacaaaa gaatttcatc acgtg 35

<210> SEQ ID NO 52
<211> LENGTH: 35
<212> TYPE: DNA
<213> ORGANISM: Artificial sequence
<220> FEATURE:
<223> OTHER INFORMATION: Primer

<400> SEQUENCE: 52
tagtaggcgg ccgctttccg aattttttg gcaac 35

<210> SEQ ID NO 53
<211> LENGTH: 33
<212> TYPE: DNA
<213> ORGANISM: Artificial sequence
<220> FEATURE:
<223> OTHER INFORMATION: Primer

<400> SEQUENCE: 53
tagtagccat gggcgtgaca acgacggaac aag 33

<210> SEQ ID NO 54
<211> LENGTH: 35
<212> TYPE: DNA
<213> ORGANISM: Artificial sequence
<220> FEATURE:
<223> OTHER INFORMATION: Primer

<400> SEQUENCE: 54
tagtaggcgg ccgctttctt tctaaatatt tctct 35

<210> SEQ ID NO 55
<211> LENGTH: 11
<212> TYPE: PRT
<213> ORGANISM: Artificial sequence
<220> FEATURE:
<223> OTHER INFORMATION: KLKLLLLLKLK

<400> SEQUENCE: 55

```
Lys Leu Lys Leu Leu Leu Leu Leu Lys Leu Lys
1               5                   10
```

<210> SEQ ID NO 56
<211> LENGTH: 882
<212> TYPE: PRT
<213> ORGANISM: Streptococcus pyogenes

<400> SEQUENCE: 56

```
His Val Asp Pro Gln Lys Gly Arg Phe Thr Leu Thr Ser His Ser Leu
1               5                   10                  15

Lys Thr Tyr Gln Gly Gly Glu Val Thr Val Pro Ala Asn Gly Lys Val
            20                  25                  30

Thr Val Arg Val Thr Met Asp Val Ser Gln Phe Thr Lys Glu Leu Thr
        35                  40                  45

Lys Gln Met Pro Asn Gly Tyr Tyr Leu Glu Gly Phe Val Arg Phe Arg
    50                  55                  60

Asp Ser Gln Asp Asp Gln Leu Asn Arg Val Asn Ile Pro Phe Val Gly
65                  70                  75                  80

Phe Lys Gly Gln Phe Glu Asn Leu Ala Val Ala Glu Glu Ser Ile Tyr
                85                  90                  95

Arg Leu Lys Ser Gln Gly Lys Thr Gly Phe Tyr Phe Asp Glu Ser Gly
            100                 105                 110

Pro Lys Asp Asp Ile Tyr Val Gly Lys His Phe Thr Gly Leu Val Thr
        115                 120                 125

Leu Gly Ser Glu Thr Asn Val Ser Thr Lys Thr Ile Ser Asp Asn Gly
    130                 135                 140

Leu His Thr Leu Gly Thr Phe Lys Asn Ala Asp Gly Lys Phe Ile Leu
145                 150                 155                 160

Glu Lys Asn Ala Gln Gly Asn Pro Val Leu Ala Ile Ser Pro Asn Gly
                165                 170                 175

Asp Asn Asn Gln Asp Phe Ala Ala Phe Lys Gly Val Phe Leu Arg Lys
            180                 185                 190

Tyr Gln Gly Leu Lys Ala Ser Val Tyr His Ala Ser Asp Lys Glu His
        195                 200                 205

Lys Asn Pro Leu Trp Val Ser Pro Glu Ser Phe Lys Gly Asp Lys Asn
    210                 215                 220

Phe Asn Ser Asp Ile Arg Phe Ala Lys Ser Thr Thr Leu Leu Gly Thr
225                 230                 235                 240

Ala Phe Ser Gly Lys Ser Leu Thr Gly Ala Glu Leu Pro Asp Gly His
                245                 250                 255

Tyr His Tyr Val Val Ser Tyr Tyr Pro Asp Val Val Gly Ala Lys Arg
            260                 265                 270

Gln Glu Met Thr Phe Asp Met Ile Leu Asp Arg Gln Lys Pro Val Leu
        275                 280                 285

Ser Gln Ala Thr Phe Asp Pro Glu Thr Asn Arg Phe Lys Pro Glu Pro
    290                 295                 300
```

```
Leu Lys Asp Arg Gly Leu Ala Gly Val Arg Lys Asp Ser Val Phe Tyr
305                 310                 315                 320

Leu Glu Arg Lys Asp Asn Lys Pro Tyr Thr Val Thr Ile Asn Asp Ser
                325                 330                 335

Tyr Lys Tyr Val Ser Val Glu Asp Asn Lys Thr Phe Val Glu Arg Gln
            340                 345                 350

Ala Asp Gly Ser Phe Ile Leu Pro Leu Asp Lys Ala Lys Leu Gly Asp
        355                 360                 365

Phe Tyr Tyr Met Val Glu Asp Phe Ala Gly Asn Val Ala Ile Ala Lys
    370                 375                 380

Leu Gly Asp His Leu Pro Gln Thr Leu Gly Lys Thr Pro Ile Lys Leu
385                 390                 395                 400

Lys Leu Thr Asp Gly Asn Tyr Gln Thr Lys Glu Thr Leu Lys Asp Asn
                405                 410                 415

Leu Glu Met Thr Gln Ser Asp Thr Gly Leu Val Thr Asn Gln Ala Gln
            420                 425                 430

Leu Ala Val Val His Arg Asn Gln Pro Gln Ser Gln Leu Thr Lys Met
        435                 440                 445

Asn Gln Asp Phe Phe Ile Ser Pro Asn Glu Asp Gly Asn Lys Asp Phe
    450                 455                 460

Val Ala Phe Lys Gly Leu Lys Asn Asn Val Tyr Asn Asp Leu Thr Val
465                 470                 475                 480

Asn Val Tyr Ala Lys Asp Asp His Gln Lys Gln Thr Pro Ile Trp Ser
                485                 490                 495

Ser Gln Ala Gly Ala Ser Val Ser Ala Ile Glu Ser Thr Ala Trp Tyr
            500                 505                 510

Gly Ile Thr Ala Arg Gly Ser Lys Val Met Pro Gly Asp Tyr Gln Tyr
        515                 520                 525

Val Val Thr Tyr Arg Asp Glu His Gly Lys Glu His Gln Lys Gln Tyr
    530                 535                 540

Thr Ile Ser Val Asn Asp Lys Lys Pro Met Ile Thr Gln Gly Arg Phe
545                 550                 555                 560

Asp Thr Ile Asn Gly Val Asp His Phe Thr Pro Asp Lys Thr Lys Ala
                565                 570                 575

Leu Asp Ser Ser Gly Ile Val Arg Glu Glu Val Phe Tyr Leu Ala Lys
            580                 585                 590

Lys Asn Gly Arg Lys Phe Asp Val Thr Glu Gly Lys Asp Gly Ile Thr
        595                 600                 605

Val Ser Asp Asn Lys Val Tyr Ile Pro Lys Asn Pro Asp Gly Ser Tyr
    610                 615                 620

Thr Ile Ser Lys Arg Asp Gly Val Thr Leu Ser Asp Tyr Tyr Tyr Leu
625                 630                 635                 640

Val Glu Asp Arg Ala Gly Asn Val Ser Phe Ala Thr Leu Arg Asp Leu
                645                 650                 655

Lys Ala Val Gly Lys Asp Lys Ala Val Val Asn Phe Gly Leu Asp Leu
            660                 665                 670

Pro Val Pro Glu Asp Lys Gln Ile Val Asn Phe Thr Tyr Leu Val Arg
        675                 680                 685

Asp Ala Asp Gly Lys Pro Ile Glu Asn Leu Glu Tyr Tyr Asn Asn Ser
    690                 695                 700

Gly Asn Ser Leu Ile Leu Pro Tyr Gly Lys Tyr Thr Val Glu Leu Leu
705                 710                 715                 720

Thr Tyr Asp Thr Asn Ala Ala Lys Leu Glu Ser Asp Lys Ile Val Ser
                725                 730                 735
```

```
Phe Thr Leu Ser Ala Asp Asn Asn Phe Gln Gln Val Thr Phe Lys Ile
            740                 745                 750

Thr Met Leu Ala Thr Ser Gln Ile Thr Ala His Phe Asp His Leu Leu
        755                 760                 765

Pro Glu Gly Ser Arg Val Ser Leu Lys Thr Ala Gln Asp Gln Leu Ile
    770                 775                 780

Pro Leu Glu Gln Ser Leu Tyr Val Pro Lys Ala Tyr Gly Lys Thr Val
785                 790                 795                 800

Gln Glu Gly Thr Tyr Glu Val Val Val Ser Leu Pro Lys Gly Tyr Arg
                805                 810                 815

Ile Glu Gly Asn Thr Lys Val Asn Thr Leu Pro Asn Glu Val His Glu
            820                 825                 830

Leu Ser Leu Arg Leu Val Lys Val Gly Asp Ala Ser Asp Ser Thr Gly
        835                 840                 845

Asp His Lys Val Met Ser Lys Asn Asn Ser Gln Ala Leu Thr Ala Ser
    850                 855                 860

Ala Thr Pro Thr Lys Ser Thr Thr Ser Ala Thr Ala Lys Ala Leu Pro
865                 870                 875                 880

Ser Thr


<210> SEQ ID NO 57
<211> LENGTH: 873
<212> TYPE: PRT
<213> ORGANISM: Streptococcus pyogenes

<400> SEQUENCE: 57

Met Asp Leu Glu Gln Thr Lys Pro Asn Gln Val Lys Gln Lys Ile Ala
1               5                   10                  15

Leu Thr Ser Thr Ile Ala Leu Leu Ser Ala Ser Val Gly Val Ser His
            20                  25                  30

Gln Val Lys Ala Asp Asp Arg Ala Ser Gly Glu Thr Lys Ala Ser Asn
        35                  40                  45

Thr His Asp Asp Ser Leu Pro Lys Pro Glu Thr Ile Gln Glu Ala Lys
    50                  55                  60

Ala Thr Ile Asp Ala Val Glu Lys Thr Leu Ser Gln Gln Lys Ala Glu
65                  70                  75                  80

Leu Thr Glu Leu Ala Thr Ala Leu Thr Lys Thr Thr Ala Glu Ile Asn
                85                  90                  95

His Leu Lys Glu Gln Gln Asp Asn Glu Gln Lys Ala Leu Thr Ser Ala
            100                 105                 110

Gln Glu Ile Tyr Thr Asn Thr Leu Ala Ser Ser Glu Glu Thr Leu Leu
        115                 120                 125

Ala Gln Gly Ala Glu His Gln Arg Glu Leu Thr Ala Thr Glu Thr Glu
    130                 135                 140

Leu His Asn Ala Gln Ala Asp Gln His Ser Lys Glu Thr Ala Leu Ser
145                 150                 155                 160

Glu Gln Lys Ala Ser Ile Ser Ala Glu Thr Thr Arg Ala Gln Asp Leu
                165                 170                 175

Val Glu Gln Val Lys Thr Ser Glu Gln Asn Ile Ala Lys Leu Asn Ala
            180                 185                 190

Met Ile Ser Asn Pro Asp Ala Ile Thr Lys Ala Ala Gln Thr Ala Asn
        195                 200                 205

Asp Asn Thr Lys Ala Leu Ser Ser Glu Leu Glu Lys Ala Lys Ala Asp
    210                 215                 220
```

```
Leu Glu Asn Gln Lys Ala Lys Val Lys Lys Gln Leu Thr Glu Glu Leu
225                 230                 235                 240

Ala Ala Gln Lys Ala Ala Leu Ala Glu Lys Glu Ala Glu Leu Ser Arg
                245                 250                 255

Leu Lys Ser Ser Ala Pro Ser Thr Gln Asp Ser Ile Val Gly Asn Asn
            260                 265                 270

Thr Met Lys Ala Pro Gln Gly Tyr Pro Leu Glu Glu Leu Lys Lys Leu
        275                 280                 285

Glu Ala Ser Gly Tyr Ile Gly Ser Ala Ser Tyr Asn Asn Tyr Tyr Lys
    290                 295                 300

Glu His Ala Asp Gln Ile Ile Ala Lys Ala Ser Pro Gly Asn Gln Leu
305                 310                 315                 320

Asn Gln Tyr Gln Asp Ile Pro Ala Asp Arg Asn Arg Phe Val Asp Pro
                325                 330                 335

Asp Asn Leu Thr Pro Glu Val Gln Asn Glu Leu Ala Gln Phe Ala Ala
            340                 345                 350

His Met Ile Asn Ser Val Arg Arg Gln Leu Gly Leu Pro Pro Val Thr
        355                 360                 365

Val Thr Ala Gly Ser Gln Glu Phe Ala Arg Leu Leu Ser Thr Ser Tyr
    370                 375                 380

Lys Lys Thr His Gly Asn Thr Arg Pro Ser Phe Val Tyr Gly Gln Pro
385                 390                 395                 400

Gly Val Ser Gly His Tyr Gly Val Gly Pro His Asp Lys Thr Ile Ile
                405                 410                 415

Glu Asp Ser Ala Gly Ala Ser Gly Leu Ile Arg Asn Asp Asp Asn Met
            420                 425                 430

Tyr Glu Asn Ile Gly Ala Phe Asn Asp Val His Thr Val Asn Gly Ile
        435                 440                 445

Lys Arg Gly Ile Tyr Asp Ser Ile Lys Tyr Met Leu Phe Thr Asp His
    450                 455                 460

Leu His Gly Asn Thr Tyr Gly His Ala Ile Asn Phe Leu Arg Val Asp
465                 470                 475                 480

Lys His Asn Pro Asn Ala Pro Val Tyr Leu Gly Phe Ser Thr Ser Asn
                485                 490                 495

Val Gly Ser Leu Asn Glu His Phe Val Met Phe Pro Glu Ser Asn Ile
            500                 505                 510

Ala Asn His Gln Arg Phe Asn Lys Thr Pro Ile Lys Ala Val Gly Ser
        515                 520                 525

Thr Lys Asp Tyr Ala Gln Arg Val Gly Thr Val Ser Asp Thr Ile Ala
    530                 535                 540

Ala Ile Lys Gly Lys Val Ser Ser Leu Glu Asn Arg Leu Ser Ala Ile
545                 550                 555                 560

His Gln Glu Ala Asp Ile Met Ala Ala Gln Ala Lys Val Ser Gln Leu
                565                 570                 575

Gln Gly Lys Leu Ala Ser Thr Leu Lys Gln Ser Asp Ser Leu Asn Leu
            580                 585                 590

Gln Val Arg Gln Leu Asn Asp Thr Lys Gly Ser Leu Arg Thr Glu Leu
        595                 600                 605

Leu Ala Ala Lys Ala Lys Gln Ala Gln Leu Glu Ala Thr Arg Asp Gln
    610                 615                 620

Ser Leu Ala Lys Leu Ala Ser Leu Lys Ala Ala Leu His Gln Thr Glu
625                 630                 635                 640

Ala Leu Ala Glu Gln Ala Ala Ala Arg Val Thr Ala Leu Val Ala Lys
                645                 650                 655
```

```
Lys Ala His Leu Gln Tyr Leu Arg Asp Phe Lys Leu Asn Pro Asn Arg
            660                 665                 670

Leu Gln Val Ile Arg Glu Arg Ile Asp Asn Thr Lys Gln Asp Leu Ala
        675                 680                 685

Lys Thr Thr Ser Ser Leu Leu Asn Ala Gln Glu Ala Leu Ala Ala Leu
    690                 695                 700

Gln Ala Lys Gln Ser Ser Leu Glu Ala Thr Ile Ala Thr Thr Glu His
705                 710                 715                 720

Gln Leu Thr Leu Leu Lys Thr Leu Ala Asn Glu Lys Glu Tyr Arg His
                725                 730                 735

Leu Asp Glu Asp Ile Ala Thr Val Pro Asp Leu Gln Val Ala Pro Pro
            740                 745                 750

Leu Thr Gly Val Lys Pro Leu Ser Tyr Ser Lys Ile Asp Thr Thr Pro
        755                 760                 765

Leu Val Gln Glu Met Val Lys Glu Thr Lys Gln Leu Leu Glu Ala Ser
    770                 775                 780

Ala Arg Leu Ala Ala Glu Asn Thr Ser Leu Val Ala Glu Ala Leu Val
785                 790                 795                 800

Gly Gln Thr Ser Glu Met Val Ala Ser Asn Ala Ile Val Ser Lys Ile
                805                 810                 815

Thr Ser Ser Ile Thr Gln Pro Ser Ser Lys Thr Ser Tyr Gly Ser Gly
            820                 825                 830

Ser Ser Thr Thr Ser Asn Leu Ile Ser Asp Val Asp Glu Ser Thr Gln
        835                 840                 845

Arg Ala Leu Lys Ala Gly Val Val Met Leu Ala Ala Val Gly Leu Thr
    850                 855                 860

Gly Phe Arg Phe Arg Lys Glu Ser Lys
865                 870


<210> SEQ ID NO 58
<211> LENGTH: 452
<212> TYPE: PRT
<213> ORGANISM: Streptococcus pyogenes

<400> SEQUENCE: 58

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
            20                  25                  30

Ala Val Glu Lys Thr Leu Ser Gln Gln Lys Ala Glu Leu Thr Glu Leu
        35                  40                  45

Ala Thr Ala Leu Thr Lys Thr Thr Ala Glu Ile Asn Asn Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160
```

```
Pro Asp Ala Ile Thr Lys Ala Ala Gln Thr Ala Asn Asp Asn Thr Lys
            165                 170                 175

Ala Leu Ser Ser Glu Leu Glu Lys Ala Lys Ala Asp Leu Glu Asn Gln
        180                 185                 190

Lys Ala Lys Val Lys Lys Gln Leu Thr Glu Glu Leu Ala Ala Gln Lys
    195                 200                 205

Ala Ala Leu Ala Glu Lys Glu Ala Glu Leu Ser Arg Leu Lys Ser Ser
210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
        435                 440                 445

Asn Ala Pro Val
    450


<210> SEQ ID NO 59
<211> LENGTH: 452
<212> TYPE: PRT
<213> ORGANISM: Streptococcus pyogenes

<400> SEQUENCE: 59

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
            20                  25                  30

Ala Val Glu Lys Thr Leu Ser Gln Gln Lys Ala Glu Leu Thr Glu Leu
        35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65                  70                  75                  80
```

```
Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys His Asn Pro
        435                 440                 445

Lys Ala Pro Val
    450
```

<210> SEQ ID NO 60
<211> LENGTH: 438
<212> TYPE: PRT
<213> ORGANISM: Streptococcus pyogenes

<400> SEQUENCE: 60

```
Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
            20                  25                  30

Ala Val Glu Lys Thr Leu Ser Gln Gln Lys Ala Glu Leu Thr Lys Leu
        35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
```

```
            420                 425                 430

Thr Tyr Gly His Ala Ile
        435


<210> SEQ ID NO 61
<211> LENGTH: 452
<212> TYPE: PRT
<213> ORGANISM: Streptococcus pyogenes

<400> SEQUENCE: 61

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Glu
            20                  25                  30

Ala Val Glu Lys Ala Leu Ser Gln Gln Lys Ala Glu Leu Thr Glu Leu
        35                  40                  45

Ala Thr Ala Leu Thr Lys Thr Thr Ala Lys Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
```

```
        355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
        435                 440                 445

Asn Ala Pro Val
    450


<210> SEQ ID NO 62
<211> LENGTH: 452
<212> TYPE: PRT
<213> ORGANISM: Streptococcus pyogenes

<400> SEQUENCE: 62

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Glu
            20                  25                  30

Ala Val Glu Lys Ala Leu Ser Gln Gln Lys Ala Glu Leu Thr Glu Leu
        35                  40                  45

Ala Thr Ala Leu Thr Lys Thr Thr Ala Lys Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
```

275 280 285

Asp Ile Pro Ala Asp Arg Asn Arg Phe Val Asp Pro Asp Asn Leu Thr
290 295 300

Pro Glu Val Gln Asn Glu Leu Ala Gln Phe Ala Ala His Met Ile Asn
305 310 315 320

Ser Val Arg Arg Gln Leu Gly Leu Pro Pro Val Thr Val Thr Ala Gly
325 330 335

Ser Gln Glu Phe Ala Arg Leu Leu Ser Thr Ser Tyr Lys Lys Thr His
340 345 350

Gly Asn Thr Arg Pro Ser Phe Val Tyr Gly Gln Pro Gly Val Ser Gly
355 360 365

His Tyr Gly Val Gly Pro His Asp Lys Thr Ile Ile Glu Asp Ser Ala
370 375 380

Gly Ala Ser Gly Leu Ile Arg Asn Asp Asp Asn Met Tyr Glu Asn Ile
385 390 395 400

Gly Ala Phe Asn Asp Val His Thr Val Asn Gly Ile Lys Arg Gly Ile
405 410 415

Tyr Asp Ser Ile Lys Tyr Met Leu Phe Thr Asp His Leu His Gly Asn
420 425 430

Thr Tyr Gly His Ala Ile Asn Phe Leu Arg Val Asp Lys Arg Asn Pro
435 440 445

Asn Ala Pro Val
450

<210> SEQ ID NO 63
<211> LENGTH: 452
<212> TYPE: PRT
<213> ORGANISM: Streptococcus pyogenes

<400> SEQUENCE: 63

Asp Asp Arg Ala Ser Gly Glu Thr Lys Ala Ser Asn Thr His Asp Asp
1 5 10 15

Ser Leu Pro Lys Pro Glu Thr Ile Gln Glu Ala Lys Ala Thr Ile Asp
20 25 30

Ala Val Glu Lys Thr Leu Ser Gln Gln Lys Ala Glu Leu Thr Glu Leu
35 40 45

Ala Thr Ala Leu Thr Lys Thr Thr Ala Glu Ile Asn His Leu Lys Glu
50 55 60

Gln Gln Asp Asn Glu Gln Lys Ala Leu Thr Ser Ala Gln Glu Ile Tyr
65 70 75 80

Thr Asn Thr Leu Ala Ser Ser Glu Glu Thr Leu Leu Ala Gln Gly Ala
85 90 95

Glu His Gln Arg Glu Leu Thr Ala Thr Glu Thr Glu Leu His Asn Ala
100 105 110

Gln Ala Asp Gln His Ser Lys Glu Thr Ala Leu Ser Glu Gln Lys Ala
115 120 125

Ser Ile Ser Ala Glu Thr Thr Arg Ala Gln Asp Leu Val Glu Gln Val
130 135 140

Lys Thr Ser Glu Gln Asn Ile Ala Lys Leu Asn Ala Met Ile Ser Asn
145 150 155 160

Pro Asp Ala Ile Thr Lys Ala Ala Gln Thr Ala Asn Asp Asn Thr Lys
165 170 175

Ala Leu Ser Ser Glu Leu Glu Lys Ala Lys Ala Asp Leu Glu Asn Gln
180 185 190

Lys Ala Lys Val Lys Lys Gln Leu Thr Glu Glu Leu Ala Ala Gln Lys

```
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
        435                 440                 445

Asn Ala Pro Val
    450


<210> SEQ ID NO 64
<211> LENGTH: 452
<212> TYPE: PRT
<213> ORGANISM: Streptococcus pyogenes

<400> SEQUENCE: 64

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
            20                  25                  30

Ala Val Glu Lys Thr Leu Ser Gln Gln Lys Ala Glu Leu Thr Glu Leu
        35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
```

```
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys His Asn Pro
        435                 440                 445

Asn Ala Pro Val
    450


<210> SEQ ID NO 65
<211> LENGTH: 452
<212> TYPE: PRT
<213> ORGANISM: Streptococcus pyogenes

<400> SEQUENCE: 65

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
            20                  25                  30

Ala Val Glu Lys Thr Leu Ser Gln Gln Lys Ala Glu Leu Thr Glu Leu
```

-continued

```
        35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Val Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
        435                 440                 445

Asn Ala Pro Val
    450
```

<210> SEQ ID NO 66
<211> LENGTH: 452
<212> TYPE: PRT
<213> ORGANISM: Streptococcus pyogenes

<400> SEQUENCE: 66

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Asp
            20                  25                  30

Ala Val Glu Lys Thr Leu Ser Gln Gln Lys Ala Glu Leu Thr Glu Leu
        35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300

Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
    370                 375                 380

```
Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
        435                 440                 445

Asn Ala Pro Val
    450


<210> SEQ ID NO 67
<211> LENGTH: 452
<212> TYPE: PRT
<213> ORGANISM: Streptococcus pyogenes

<400> SEQUENCE: 67

Asp Asp Arg Ala Ser Gly Glu Thr Lys Ala Ser Asn Thr His Asp Asp
1               5                   10                  15

Ser Leu Pro Lys Pro Glu Thr Ile Gln Glu Ala Lys Ala Thr Ile Glu
            20                  25                  30

Ala Val Glu Lys Thr Leu Ser Gln Gln Lys Ala Glu Leu Thr Glu Leu
        35                  40                  45

Ala Thr Ala Leu Thr Lys Thr Thr Ala Glu Ile Asn His Leu Lys Glu
    50                  55                  60

Gln Gln Asp Asn Glu Gln Lys Ala Leu Thr Ser Ala Gln Glu Ile Tyr
65                  70                  75                  80

Thr Asn Thr Leu Ala Ser Ser Glu Glu Thr Leu Leu Ala Gln Gly Ala
                85                  90                  95

Glu His Gln Arg Glu Leu Thr Ala Thr Glu Thr Glu Leu His Asn Ala
            100                 105                 110

Gln Ala Asp Gln His Ser Lys Glu Thr Ala Leu Ser Glu Gln Lys Ala
        115                 120                 125

Ser Ile Ser Ala Glu Thr Thr Arg Ala Gln Asp Leu Val Glu Gln Val
    130                 135                 140

Lys Thr Ser Glu Gln Asn Ile Ala Lys Leu Asn Ala Met Ile Ser Asn
145                 150                 155                 160

Pro Asp Ala Ile Thr Lys Ala Ala Gln Thr Ala Asn Asp Asn Thr Lys
                165                 170                 175

Ala Leu Ser Ser Glu Leu Glu Lys Ala Lys Ala Asp Leu Glu Asn Gln
            180                 185                 190

Lys Ala Lys Val Lys Lys Gln Leu Thr Glu Glu Leu Ala Ala Gln Lys
        195                 200                 205

Ala Ala Leu Ala Glu Lys Glu Ala Glu Leu Ser Arg Leu Lys Ser Ser
    210                 215                 220

Ala Pro Ser Thr Gln Asp Ser Ile Val Gly Asn Asn Thr Met Lys Ala
225                 230                 235                 240

Pro Gln Gly Tyr Pro Leu Glu Glu Leu Lys Lys Leu Glu Ala Ser Gly
                245                 250                 255

Tyr Ile Gly Ser Ala Ser Tyr Asn Asn Tyr Tyr Lys Glu His Ala Asp
            260                 265                 270

Gln Ile Ile Ala Lys Ala Ser Pro Gly Asn Gln Leu Asn Gln Tyr Gln
        275                 280                 285

Asp Ile Pro Ala Asp Arg Asn Arg Phe Val Asp Pro Asp Asn Leu Thr
    290                 295                 300
```

```
Pro Glu Val Gln Asn Glu Leu Ala Gln Phe Ala Ala His Met Ile Asn
305                 310                 315                 320

Ser Val Arg Arg Gln Leu Gly Leu Pro Pro Val Thr Val Thr Ala Gly
                325                 330                 335

Ser Gln Glu Phe Ala Arg Leu Leu Ser Thr Ser Tyr Lys Lys Thr His
            340                 345                 350

Gly Asn Thr Arg Pro Ser Phe Val Tyr Gly Gln Pro Gly Val Ser Gly
        355                 360                 365

His Tyr Gly Val Gly Pro His Asp Lys Thr Ile Ile Glu Asp Ser Ala
    370                 375                 380

Gly Ala Ser Gly Leu Ile Arg Asn Asp Asp Asn Met Tyr Glu Asn Ile
385                 390                 395                 400

Gly Ala Phe Asn Asp Val His Thr Val Asn Gly Ile Lys Arg Gly Ile
                405                 410                 415

Tyr Asp Ser Ile Lys Tyr Met Leu Phe Thr Asp His Leu His Gly Asn
            420                 425                 430

Thr Tyr Gly His Ala Ile Asn Phe Leu Arg Val Asp Lys Arg Asn Pro
        435                 440                 445

Asn Ala Pro Val
    450


<210> SEQ ID NO 68
<211> LENGTH: 410
<212> TYPE: PRT
<213> ORGANISM: Streptococcus pyogenes

<400> SEQUENCE: 68

Met Ile Lys Arg Leu Ile Ser Leu Val Val Ile Ala Leu Phe Phe Ala
1               5                   10                  15

Ala Ser Thr Val Ser Gly Glu Glu Tyr Ser Val Thr Ala Lys His Ala
            20                  25                  30

Ile Ala Val Asp Leu Glu Ser Gly Lys Val Leu Tyr Glu Lys Asp Ala
        35                  40                  45

Lys Glu Val Val Pro Val Ala Ser Val Ser Lys Leu Leu Thr Thr Tyr
    50                  55                  60

Leu Val Tyr Lys Glu Val Ser Lys Gly Lys Leu Asn Trp Asp Ser Pro
65                  70                  75                  80

Val Thr Ile Ser Asn Tyr Pro Tyr Glu Leu Thr Thr Asn Tyr Thr Ile
                85                  90                  95

Ser Asn Val Pro Leu Asp Lys Arg Lys Tyr Thr Val Lys Glu Leu Leu
            100                 105                 110

Ser Ala Leu Val Val Asn Asn Ala Asn Ser Pro Ala Ile Ala Leu Ala
        115                 120                 125

Glu Lys Ile Gly Gly Thr Glu Pro Lys Phe Val Asp Lys Met Lys Lys
    130                 135                 140

Gln Leu Arg Gln Trp Gly Ile Ser Asp Ala Lys Val Val Asn Ser Thr
145                 150                 155                 160

Gly Leu Thr Asn His Phe Leu Gly Ala Asn Thr Tyr Pro Asn Thr Glu
                165                 170                 175

Pro Asp Asp Glu Asn Cys Phe Cys Ala Thr Asp Leu Ala Ile Ile Ala
            180                 185                 190

Arg His Leu Leu Leu Glu Phe Pro Glu Val Leu Lys Leu Ser Ser Lys
        195                 200                 205

Ser Ser Thr Ile Phe Ala Gly Gln Thr Ile Tyr Ser Tyr Asn Tyr Met
    210                 215                 220
```

```
Leu Lys Gly Met Pro Cys Tyr Arg Glu Gly Val Asp Gly Leu Phe Val
225                 230                 235                 240

Gly Tyr Ser Lys Lys Ala Gly Ala Ser Phe Val Ala Thr Ser Val Glu
                245                 250                 255

Asn Gln Met Arg Val Ile Thr Val Val Leu Asn Ala Asp Gln Ser His
            260                 265                 270

Glu Asp Asp Leu Ala Ile Phe Lys Thr Thr Asn Gln Leu Leu Gln Tyr
        275                 280                 285

Leu Leu Ile Asn Phe Gln Lys Val Gln Leu Ile Glu Asn Asn Lys Pro
    290                 295                 300

Val Lys Thr Leu Tyr Val Leu Asp Ser Pro Glu Lys Thr Val Lys Leu
305                 310                 315                 320

Val Ala Gln Asn Ser Leu Phe Phe Ile Lys Pro Ile His Thr Lys Thr
                325                 330                 335

Lys Asn Thr Val His Ile Thr Lys Lys Ser Ser Thr Met Ile Ala Pro
            340                 345                 350

Leu Ser Lys Gly Gln Val Leu Gly Arg Ala Thr Leu Gln Asp Lys His
        355                 360                 365

Leu Ile Gly Gln Gly Tyr Leu Asp Thr Pro Pro Ser Ile Asn Leu Ile
    370                 375                 380

Leu Gln Lys Asn Ile Ser Lys Ser Phe Phe Leu Lys Val Trp Trp Asn
385                 390                 395                 400

Arg Phe Val Arg Tyr Val Asn Thr Ser Leu
                405                 410
```

<210> SEQ ID NO 69
<211> LENGTH: 162
<212> TYPE: PRT
<213> ORGANISM: Streptococcus pyogenes

<400> SEQUENCE: 69

```
Glu Glu Tyr Ser Val Thr Ala Lys His Ala Ile Ala Val Asp Leu Glu
1               5                   10                  15

Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys
```

<210> SEQ ID NO 70
<211> LENGTH: 162
<212> TYPE: PRT

<213> ORGANISM: Streptococcus pyogenes

<400> SEQUENCE: 70

```
Glu Glu Tyr Ser Val Thr Ala Lys His Ala Ile Ala Val Asp Leu Glu
1               5                   10                  15

Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Thr Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys
```

<210> SEQ ID NO 71
<211> LENGTH: 162
<212> TYPE: PRT
<213> ORGANISM: Streptococcus pyogenes

<400> SEQUENCE: 71

```
Glu Glu Tyr Ser Val Thr Ala Lys His Ala Ile Ala Val Asp Leu Glu
1               5                   10                  15

Ser Gly Lys Val Leu Tyr Glu Lys Asp Thr Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys
```

<210> SEQ ID NO 72
<211> LENGTH: 162
<212> TYPE: PRT

<213> ORGANISM: Streptococcus pyogenes

<400> SEQUENCE: 72

Glu Glu Tyr Ser Val Thr Ala Lys His Ala Ile Ala Val Asp Leu Glu
1               5                   10                  15

Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys

<210> SEQ ID NO 73
<211> LENGTH: 162
<212> TYPE: PRT
<213> ORGANISM: Streptococcus pyogenes

<400> SEQUENCE: 73

Glu Glu Tyr Ser Val Thr Ala Lys His Ala Ile Ala Val Asp Leu Glu
1               5                   10                  15

Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys

<210> SEQ ID NO 74
<211> LENGTH: 162
<212> TYPE: PRT

<213> ORGANISM: Streptococcus pyogenes

<400> SEQUENCE: 74

Glu Glu Tyr Ser Val Thr Ala Lys His Ala Ile Ala Val Asp Leu Glu
1 5 10 15

Ser Gly Lys Val Leu Tyr Glu Lys Asp Ala Lys Glu Val Val Pro Val
20 25 30

Ala Ser Val Ser Lys Leu Leu Thr Thr Tyr Leu Val Tyr Lys Glu Val
35 40 45

Ser Lys Gly Lys Leu Asn Trp Asp Ser Pro Val Thr Ile Ser Asn Tyr
50 55 60

Pro Tyr Glu Leu Thr Thr Asn Tyr Thr Ile Ser Asn Val Pro Leu Asp
65 70 75 80

Lys Arg Lys Tyr Thr Val Lys Glu Leu Leu Ser Ala Leu Val Val Asn
85 90 95

Asn Ala Asn Ser Pro Ala Ile Ala Leu Ala Glu Lys Ile Gly Gly Thr
100 105 110

Glu Pro Lys Phe Val Asp Lys Met Lys Lys Gln Leu Arg Gln Trp Gly
115 120 125

Ile Ser Asp Ala Lys Val Val Asn Ser Thr Gly Leu Thr Asn His Phe
130 135 140

Leu Gly Ala Asn Thr Tyr Pro Asn Thr Glu Pro Asp Asp Glu Asn Cys
145 150 155 160

Phe Cys

<210> SEQ ID NO 75
<211> LENGTH: 162
<212> TYPE: PRT
<213> ORGANISM: Streptococcus pyogenes

<400> SEQUENCE: 75

Glu Glu Tyr Ser Val Thr Ala Lys His Ala Ile Ala Val Asp Leu Glu
1 5 10 15

Ser Gly Lys Val Leu Tyr Glu Lys Asp Ala Lys Glu Val Val Pro Val
20 25 30

Ala Ser Val Ser Lys Leu Leu Thr Thr Tyr Leu Val Tyr Lys Glu Val
35 40 45

Ser Lys Gly Lys Leu Asn Trp Asp Ser Pro Val Thr Ile Ser Asn Tyr
50 55 60

Pro Tyr Glu Leu Thr Thr Asn Tyr Thr Ile Ser Asn Val Pro Leu Asp
65 70 75 80

Lys Arg Lys Tyr Thr Val Lys Glu Leu Leu Ser Ala Leu Val Val Asn
85 90 95

Asn Ala Asn Ser Pro Ala Ile Ala Leu Ala Glu Lys Ile Gly Gly Thr
100 105 110

Glu Pro Lys Phe Val Asp Lys Met Lys Lys Gln Leu Arg Gln Trp Gly
115 120 125

Ile Ser Asp Ala Lys Val Val Asn Ser Thr Gly Leu Thr Asn His Phe
130 135 140

Leu Gly Ala Asn Thr Tyr Pro Asn Thr Glu Pro Asp Asp Glu Asn Cys
145 150 155 160

Phe Cys

<210> SEQ ID NO 76
<211> LENGTH: 162
<212> TYPE: PRT

<213> ORGANISM: Streptococcus pyogenes

<400> SEQUENCE: 76

Glu Glu Tyr Ser Val Thr Ala Lys His Ala Ile Ala Val Asp Leu Glu
1 5 10 15

Ser Gly Lys Val Leu Tyr Glu Lys Asp Ala Lys Glu Val Val Pro Val
20 25 30

Ala Ser Val Ser Lys Leu Leu Thr Thr Tyr Leu Val Tyr Lys Glu Val
35 40 45

Ser Lys Gly Lys Leu Asn Trp Asp Ser Pro Val Thr Ile Ser Asn Tyr
50 55 60

Pro Tyr Glu Leu Thr Thr Asn Tyr Thr Ile Ser Asn Val Pro Leu Asp
65 70 75 80

Lys Arg Lys Tyr Thr Val Lys Glu Leu Leu Ser Ala Leu Val Val Asn
85 90 95

Asn Ala Asn Ser Pro Ala Ile Ala Leu Ala Glu Lys Ile Gly Gly Thr
100 105 110

Glu Pro Lys Phe Val Asp Lys Met Lys Lys Gln Leu Arg Gln Trp Gly
115 120 125

Ile Ser Asp Ala Lys Val Val Asn Ser Thr Gly Leu Thr Asn His Phe
130 135 140

Leu Gly Ala Asn Thr Tyr Pro Asn Thr Glu Pro Asp Asp Glu Asn Cys
145 150 155 160

Phe Cys

<210> SEQ ID NO 77
<211> LENGTH: 162
<212> TYPE: PRT
<213> ORGANISM: Streptococcus pyogenes

<400> SEQUENCE: 77

Glu Glu Tyr Ser Val Thr Ala Lys His Ala Ile Ala Val Asp Leu Glu
1 5 10 15

Ser Gly Lys Val Leu Tyr Glu Lys Asp Ala Lys Glu Val Val Pro Val
20 25 30

Ala Ser Val Ser Lys Leu Leu Thr Thr Tyr Leu Val Tyr Lys Glu Val
35 40 45

Ser Lys Gly Lys Leu Asn Trp Asp Ser Pro Val Thr Ile Ser Asn Tyr
50 55 60

Pro Tyr Glu Leu Thr Thr Asn Tyr Thr Ile Ser Asn Val Pro Leu Asp
65 70 75 80

Lys Arg Lys Tyr Thr Val Lys Glu Leu Leu Ser Ala Leu Val Val Asn
85 90 95

Asn Ala Asn Ser Pro Ala Ile Ala Leu Ala Glu Lys Ile Gly Gly Thr
100 105 110

Glu Pro Lys Phe Val Asp Lys Met Lys Lys Gln Leu Arg Gln Trp Gly
115 120 125

Ile Ser Asp Ala Lys Val Val Asn Ser Thr Gly Leu Thr Asn His Phe
130 135 140

Leu Gly Ala Asn Thr Tyr Pro Asn Thr Glu Pro Asp Asp Glu Asn Cys
145 150 155 160

Phe Cys

<210> SEQ ID NO 78
<211> LENGTH: 162
<212> TYPE: PRT

<213> ORGANISM: Streptococcus pyogenes

<400> SEQUENCE: 78

Glu Glu Tyr Ser Val Thr Ala Lys His Ala Ile Ala Val Asp Leu Glu
1 5 10 15

Ser Gly Lys Val Leu Tyr Glu Lys Asp Ala Lys Glu Val Val Pro Val
20 25 30

Ala Ser Val Ser Lys Leu Leu Thr Thr Tyr Leu Val Tyr Lys Glu Val
35 40 45

Ser Lys Gly Lys Leu Asn Trp Asp Ser Pro Val Thr Ile Ser Asn Tyr
50 55 60

Pro Tyr Glu Leu Thr Thr Asn Tyr Thr Ile Ser Asn Val Pro Leu Asp
65 70 75 80

Lys Arg Lys Tyr Thr Val Lys Glu Leu Leu Ser Ala Leu Val Val Asn
85 90 95

Asn Ala Asn Ser Pro Ala Ile Ala Leu Ala Glu Lys Ile Gly Gly Thr
100 105 110

Glu Pro Lys Phe Val Asp Lys Met Lys Lys Gln Leu Arg Gln Trp Gly
115 120 125

Ile Ser Asp Ala Lys Val Val Asn Ser Thr Gly Leu Thr Asn His Phe
130 135 140

Leu Gly Ala Asn Thr Tyr Pro Asn Thr Glu Pro Asp Asp Glu Asn Cys
145 150 155 160

Phe Cys

<210> SEQ ID NO 79
<211> LENGTH: 278
<212> TYPE: PRT
<213> ORGANISM: Streptococcus pyogenes

<400> SEQUENCE: 79

Glu Glu Tyr Ser Val Thr Ala Lys His Ala Ile Ala Val Asp Leu Glu
1 5 10 15

Ser Gly Lys Val Leu Tyr Glu Lys Asp Ala Lys Glu Val Val Pro Val
20 25 30

Ala Ser Val Ser Lys Leu Leu Thr Thr Tyr Leu Val Tyr Lys Glu Val
35 40 45

Ser Lys Gly Lys Leu Asn Trp Asp Ser Pro Val Thr Ile Ser Asn Tyr
50 55 60

Pro Tyr Glu Leu Thr Thr Asn Tyr Thr Ile Ser Asn Val Pro Leu Asp
65 70 75 80

Lys Arg Lys Tyr Thr Val Lys Glu Leu Leu Ser Ala Leu Val Val Asn
85 90 95

Asn Ala Asn Ser Pro Ala Ile Ala Leu Ala Glu Lys Ile Gly Gly Thr
100 105 110

Glu Pro Lys Phe Val Asp Lys Met Lys Lys Gln Leu Arg Gln Trp Gly
115 120 125

Ile Ser Asp Ala Lys Val Val Asn Ser Thr Gly Leu Thr Asn His Phe
130 135 140

Leu Gly Ala Asn Thr Tyr Pro Asn Thr Glu Pro Asp Asp Glu Asn Cys
145 150 155 160

Phe Cys Ala Thr Asp Leu Ala Ile Ile Ala Arg His Leu Leu Leu Glu
165 170 175

Phe Pro Glu Val Leu Lys Leu Ser Ser Lys Ser Ser Thr Ile Phe Asp
180 185 190

```
Gly Gln Thr Ile Tyr Ser Tyr Asn Tyr Met Leu Lys Gly Met Pro Cys
        195                 200                 205

Tyr Arg Glu Gly Val Asp Gly Leu Phe Val Gly Tyr Ser Lys Lys Ala
    210                 215                 220

Gly Ala Ser Phe Val Ala Thr Ser Val Glu Asn Gln Met Arg Val Ile
225                 230                 235                 240

Thr Val Val Leu Asn Ala Asp Gln Ser His Glu Asp Asp Leu Ala Ile
                245                 250                 255

Phe Lys Thr Thr Asn Gln Leu Leu Gln Tyr Leu Leu Ile Asn Phe Gln
            260                 265                 270

Lys Val Gln Leu Ile Glu
        275


<210> SEQ ID NO 80
<211> LENGTH: 278
<212> TYPE: PRT
<213> ORGANISM: Streptococcus pyogenes

<400> SEQUENCE: 80

Glu Glu Tyr Ser Val Thr Ala Lys His Ala Ile Ala Val Asp Leu Glu
1               5                   10                  15

Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Thr Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys Ala Thr Asp Leu Ala Ile Ile Ala Arg His Leu Leu Leu Glu
                165                 170                 175

Phe Pro Glu Val Leu Lys Leu Ser Ser Lys Ser Ser Thr Ile Phe Asp
            180                 185                 190

Gly Gln Thr Ile Tyr Ser Tyr Asn Tyr Met Leu Lys Gly Met Pro Cys
        195                 200                 205

Tyr Arg Glu Gly Val Asp Gly Leu Phe Val Gly Tyr Ser Lys Lys Ala
    210                 215                 220

Gly Ala Ser Phe Val Ala Thr Ser Val Glu Asn Gln Met Arg Val Ile
225                 230                 235                 240

Thr Val Val Leu Asn Ala Asp Gln Ser His Glu Asp Asp Leu Ala Ile
                245                 250                 255

Phe Lys Thr Thr Asn Gln Leu Leu Gln Tyr Leu Leu Ile Asn Phe Gln
            260                 265                 270

Lys Val Gln Leu Ile Glu
        275
```

<210> SEQ ID NO 81
<211> LENGTH: 278
<212> TYPE: PRT
<213> ORGANISM: Streptococcus pyogenes

<400> SEQUENCE: 81

Glu Glu Tyr Ser Val Thr Ala Lys His Ala Ile Ala Val Asp Leu Glu
1 5 10 15

Ser Gly Lys Val Leu Tyr Glu Lys Asp Thr Lys Glu Val Val Pro Val
20 25 30

Ala Ser Val Ser Lys Leu Leu Thr Thr Tyr Leu Val Tyr Lys Glu Val
35 40 45

Ser Lys Gly Lys Leu Asn Trp Asp Ser Pro Val Thr Ile Ser Asn Tyr
50 55 60

Pro Tyr Glu Leu Thr Thr Asn Tyr Thr Ile Ser Asn Val Pro Leu Asp
65 70 75 80

Lys Arg Lys Tyr Thr Val Lys Glu Leu Leu Ser Ala Leu Val Val Asn
85 90 95

Asn Ala Asn Ser Pro Ala Ile Ala Leu Ala Glu Lys Ile Gly Gly Thr
100 105 110

Glu Pro Lys Phe Val Asp Lys Met Lys Lys Gln Leu Arg Gln Trp Gly
115 120 125

Ile Ser Asp Ala Lys Val Val Asn Ser Thr Gly Leu Thr Asn His Phe
130 135 140

Leu Gly Ala Asn Thr Tyr Pro Asn Thr Glu Pro Asp Asp Glu Asn Cys
145 150 155 160

Phe Cys Ala Thr Asp Leu Ala Ile Ile Ala Arg His Leu Leu Leu Glu
165 170 175

Phe Pro Glu Val Leu Lys Leu Ser Ser Lys Ser Ser Thr Ile Phe Asp
180 185 190

Gly Gln Thr Ile Tyr Ser Tyr Asn Tyr Met Leu Lys Gly Met Pro Cys
195 200 205

Tyr Arg Glu Gly Val Asp Gly Leu Phe Val Gly Tyr Ser Lys Lys Ala
210 215 220

Gly Ala Ser Phe Val Ala Thr Ser Val Glu Asn Gln Met Arg Val Ile
225 230 235 240

Thr Val Val Leu Asn Ala Asp Gln Ser His Glu Asp Asp Leu Ala Ile
245 250 255

Phe Lys Thr Thr Asn Gln Leu Leu Gln Tyr Leu Leu Ile Asn Phe Gln
260 265 270

Lys Val Gln Leu Ile Glu
275

<210> SEQ ID NO 82
<211> LENGTH: 278
<212> TYPE: PRT
<213> ORGANISM: Streptococcus pyogenes

<400> SEQUENCE: 82

Glu Glu Tyr Ser Val Thr Ala Lys His Ala Ile Ala Val Asp Leu Glu
1 5 10 15

Ser Gly Lys Val Leu Tyr Glu Lys Asp Ala Lys Glu Val Val Pro Val
20 25 30

Ala Ser Val Ser Lys Leu Leu Thr Thr Tyr Leu Val Tyr Lys Glu Val
35 40 45

Ser Lys Gly Lys Leu Asn Trp Asp Ser Pro Val Thr Ile Ser Asn Tyr

```
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys Ala Thr Asp Leu Ala Ile Ile Ala Arg His Leu Leu Leu Glu
                165                 170                 175

Phe Pro Glu Val Leu Lys Leu Ser Ser Lys Ser Ser Thr Ile Phe Ala
            180                 185                 190

Gly Gln Thr Ile Tyr Ser Tyr Asn Tyr Met Leu Lys Gly Met Pro Cys
        195                 200                 205

Tyr Arg Glu Gly Val Asp Gly Leu Phe Val Gly Tyr Ser Lys Lys Ala
    210                 215                 220

Gly Ala Ser Phe Val Ala Thr Ser Val Glu Asn Gln Met Arg Val Ile
225                 230                 235                 240

Thr Val Val Leu Asn Ala Asp Gln Ser His Glu Asp Asp Leu Ala Ile
                245                 250                 255

Phe Lys Thr Thr Asn Gln Leu Leu Gln Tyr Leu Leu Ile Asn Phe Gln
            260                 265                 270

Lys Val Gln Leu Ile Glu
        275


<210> SEQ ID NO 83
<211> LENGTH: 278
<212> TYPE: PRT
<213> ORGANISM: Streptococcus pyogenes

<400> SEQUENCE: 83

Glu Glu Tyr Ser Val Thr Ala Lys His Ala Ile Ala Val Asp Leu Glu
1               5                   10                  15

Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
```

```
145                 150                 155                 160

Phe Cys Ala Thr Asp Leu Ala Ile Ile Ala Arg His Leu Leu Leu Glu
                165                 170                 175

Phe Pro Glu Val Leu Lys Leu Ser Ser Lys Ser Ser Thr Ile Phe Asp
            180                 185                 190

Gly Gln Thr Ile Tyr Ser Tyr Asn Tyr Met Leu Lys Gly Met Pro Cys
        195                 200                 205

Tyr Arg Glu Gly Val Asp Gly Leu Phe Val Gly Tyr Ser Lys Lys Ala
    210                 215                 220

Gly Ala Ser Phe Val Ala Thr Ser Val Glu Asn Gln Met Arg Val Ile
225                 230                 235                 240

Thr Val Val Leu Asn Ala Asp Gln Ser His Glu Asp Asp Leu Ala Ile
                245                 250                 255

Phe Lys Thr Thr Asn Gln Leu Leu Gln Tyr Leu Leu Ile Asn Phe Gln
            260                 265                 270

Lys Val Gln Leu Ile Glu
        275


<210> SEQ ID NO 84
<211> LENGTH: 278
<212> TYPE: PRT
<213> ORGANISM: Streptococcus pyogenes

<400> SEQUENCE: 84

Glu Glu Tyr Ser Val Thr Ala Lys His Ala Ile Ala Val Asp Leu Glu
1               5                   10                  15

Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys Ala Thr Asp Leu Ala Ile Ile Ala Arg His Leu Leu Leu Glu
                165                 170                 175

Phe Pro Glu Val Leu Lys Leu Ser Ser Lys Ser Ser Thr Ile Phe Asp
            180                 185                 190

Gly Gln Thr Ile Tyr Ser Tyr Asn Tyr Met Leu Lys Gly Met Pro Cys
        195                 200                 205

Tyr Arg Glu Gly Val Asp Gly Leu Phe Ile Gly Tyr Ser Lys Lys Ala
    210                 215                 220

Gly Ala Ser Phe Val Ala Thr Ser Val Glu Asn Gln Met Arg Val Ile
225                 230                 235                 240

Thr Val Val Leu Asn Ala Asp Gln Ser His Glu Asp Asp Leu Ala Ile
```

-continued

```
                245                 250                 255

Phe Lys Thr Thr Asn Gln Leu Leu Gln Tyr Leu Leu Ile Asn Phe Gln
            260                 265                 270

Lys Val Gln Leu Ile Glu
        275


<210> SEQ ID NO 85
<211> LENGTH: 278
<212> TYPE: PRT
<213> ORGANISM: Streptococcus pyogenes

<400> SEQUENCE: 85

Glu Glu Tyr Ser Val Thr Ala Lys His Ala Ile Ala Val Asp Leu Glu
1               5                   10                  15

Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys Ala Thr Asp Leu Ala Ile Ile Ala Arg His Leu Leu Leu Glu
                165                 170                 175

Phe Pro Glu Val Leu Lys Leu Ser Ser Lys Ser Ser Thr Ile Phe Ala
            180                 185                 190

Gly Gln Thr Ile Tyr Ser Tyr Asn Tyr Met Leu Lys Gly Met Pro Cys
        195                 200                 205

Tyr Arg Glu Gly Val Asp Gly Leu Phe Val Gly Tyr Ser Lys Lys Ala
    210                 215                 220

Gly Ala Ser Phe Val Ala Thr Ser Val Glu Asn Gln Met Arg Val Ile
225                 230                 235                 240

Thr Val Val Leu Asn Ala Asp Gln Ser His Glu Asp Asp Leu Ala Ile
                245                 250                 255

Phe Lys Thr Thr Asn Gln Leu Leu Gln Tyr Leu Leu Ile Asn Phe Gln
            260                 265                 270

Lys Val Gln Leu Ile Glu
        275


<210> SEQ ID NO 86
<211> LENGTH: 278
<212> TYPE: PRT
<213> ORGANISM: Streptococcus pyogenes

<400> SEQUENCE: 86

Glu Glu Tyr Ser Val Thr Ala Lys His Ala Ile Ala Val Asp Leu Glu
1               5                   10                  15
```

```
Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys Ala Thr Asp Leu Ala Ile Ile Ala Arg His Leu Leu Leu Glu
                165                 170                 175

Phe Pro Glu Val Leu Lys Leu Ser Ser Lys Ser Ser Thr Ile Phe Asp
            180                 185                 190

Gly Gln Thr Ile Tyr Ser Tyr Asn Tyr Met Leu Lys Gly Met Pro Cys
        195                 200                 205

Tyr Arg Glu Gly Val Asp Gly Leu Phe Val Gly Tyr Ser Lys Lys Ala
    210                 215                 220

Gly Ala Ser Phe Val Ala Thr Ser Val Glu Asn Gln Met Arg Val Ile
225                 230                 235                 240

Thr Val Val Leu Asn Ala Asp Gln Ser His Glu Asp Asp Leu Ala Ile
                245                 250                 255

Phe Lys Thr Thr Asn Gln Leu Leu Gln Tyr Leu Leu Ile Asn Phe Gln
            260                 265                 270

Lys Val Gln Leu Ile Glu
        275


<210> SEQ ID NO 87
<211> LENGTH: 278
<212> TYPE: PRT
<213> ORGANISM: Streptococcus pyogenes

<400> SEQUENCE: 87

Glu Glu Tyr Ser Val Thr Ala Lys His Ala Ile Ala Val Asp Leu Glu
1               5                   10                  15

Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110
```

```
Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys Ala Thr Asp Leu Ala Ile Ile Ala Arg His Leu Leu Leu Glu
                165                 170                 175

Phe Pro Glu Val Leu Lys Leu Ser Ser Lys Ser Ser Thr Ile Phe Asp
            180                 185                 190

Gly Gln Thr Ile Tyr Ser Tyr Asn Tyr Met Leu Lys Gly Met Pro Cys
        195                 200                 205

Tyr Arg Glu Gly Val Asp Gly Leu Phe Val Gly Tyr Ser Lys Lys Ala
    210                 215                 220

Gly Ala Ser Phe Val Ala Thr Ser Val Glu Asn Gln Met Arg Val Ile
225                 230                 235                 240

Thr Val Val Ile Asn Ala Asp Gln Ser His Glu Asp Asp Leu Ala Ile
                245                 250                 255

Phe Lys Thr Thr Asn Gln Leu Leu Gln Tyr Leu Leu Ile Asn Phe Gln
            260                 265                 270

Lys Val Gln Leu Ile Glu
        275


<210> SEQ ID NO 88
<211> LENGTH: 278
<212> TYPE: PRT
<213> ORGANISM: Streptococcus pyogenes

<400> SEQUENCE: 88

Glu Glu Tyr Ser Val Thr Ala Lys His Ala Ile Ala Val Asp Leu Glu
1               5                   10                  15

Ser Gly Lys Val Leu Tyr Glu Lys Asp Ala Lys Glu Val Val Pro Val
            20                  25                  30

Ala Ser Val Ser Lys Leu Leu Thr Thr Tyr Leu Val Tyr Lys Glu Val
        35                  40                  45

Ser Lys Gly Lys Leu Asn Trp Asp Ser Pro Val Thr Ile Ser Asn Tyr
    50                  55                  60

Pro Tyr Glu Leu Thr Thr Asn Tyr Thr Ile Ser Asn Val Pro Leu Asp
65                  70                  75                  80

Lys Arg Lys Tyr Thr Val Lys Glu Leu Leu Ser Ala Leu Val Val Asn
                85                  90                  95

Asn Ala Asn Ser Pro Ala Ile Ala Leu Ala Glu Lys Ile Gly Gly Thr
            100                 105                 110

Glu Pro Lys Phe Val Asp Lys Met Lys Lys Gln Leu Arg Gln Trp Gly
        115                 120                 125

Ile Ser Asp Ala Lys Val Val Asn Ser Thr Gly Leu Thr Asn His Phe
    130                 135                 140

Leu Gly Ala Asn Thr Tyr Pro Asn Thr Glu Pro Asp Asp Glu Asn Cys
145                 150                 155                 160

Phe Cys Ala Thr Asp Leu Ala Ile Ile Ala Arg His Leu Leu Leu Glu
                165                 170                 175

Phe Pro Glu Val Leu Lys Leu Ser Ser Lys Ser Ser Thr Ile Phe Ala
            180                 185                 190

Gly Gln Thr Ile Tyr Ser Tyr Asn Tyr Met Leu Lys Gly Met Pro Cys
        195                 200                 205
```

```
Tyr Arg Glu Gly Val Asp Gly Leu Phe Val Gly Tyr Ser Lys Lys Ala
    210                 215                 220

Gly Ala Ser Phe Val Ala Thr Ser Val Glu Asn Gln Met Arg Val Ile
225                 230                 235                 240

Thr Val Val Leu Asn Ala Asp Gln Ser His Glu Asp Asp Leu Ala Ile
                245                 250                 255

Phe Lys Thr Thr Asn Gln Leu Leu Gln Tyr Leu Leu Ile Asn Phe Gln
            260                 265                 270

Lys Val Gln Leu Ile Glu
        275


<210> SEQ ID NO 89
<211> LENGTH: 834
<212> TYPE: PRT
<213> ORGANISM: Streptococcus pyogenes

<400> SEQUENCE: 89

Ala Asp Glu Leu Ser Thr Met Ser Glu Pro Thr Ile Thr Asn His Ala
1               5                   10                  15

Gln Gln Gln Ala Gln His Leu Thr Asn Thr Glu Leu Ser Ser Ala Glu
            20                  25                  30

Ser Lys Ser Gln Asp Thr Ser Gln Ile Thr Leu Lys Thr Asn Arg Glu
        35                  40                  45

Lys Glu Gln Ser Gln Asp Leu Val Ser Glu Pro Thr Thr Thr Glu Leu
    50                  55                  60

Ala Asp Thr Asp Ala Ala Ser Met Ala Asn Thr Gly Ser Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Glu Ala Glu Pro Lys Ala Ile Lys Lys His Lys Ile Tyr
        195                 200                 205

Arg Pro Gln Ser Thr Gln Ala Pro Lys Glu Thr Val Ile Lys Thr Glu
    210                 215                 220

Glu Thr Asp Gly Ser His Asp Ile Asp Trp Thr Gln Thr Asp Asp Asp
225                 230                 235                 240

Thr Lys Tyr Glu Ser His Gly Met His Val Thr Gly Ile Val Ala Gly
                245                 250                 255

Asn Ser Lys Glu Ala Ala Ala Thr Gly Glu Arg Phe Leu Gly Ile Ala
            260                 265                 270

Pro Glu Ala Gln Val Met Phe Met Arg Val Phe Ala Asn Asp Ile Met
        275                 280                 285

Gly Ser Ala Glu Ser Leu Phe Ile Lys Ala Ile Glu Asp Ala Val Ala
    290                 295                 300
```

```
Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
    370                 375                 380

Asn Ser Lys Trp Val Ile Gln Arg Leu Met Thr Val Lys Glu Leu Glu
385                 390                 395                 400

Asn Arg Ala Asp Leu Asn His Gly Lys Ala Ile Tyr Ser Glu Ser Val
                405                 410                 415

Asp Phe Lys Asp Ile Lys Asp Ser Leu Gly Tyr Asp Lys Ser His Gln
            420                 425                 430

Phe Ala Tyr Val Lys Glu Ser Thr Asp Ala Gly Tyr Asn Ala Gln Asp
        435                 440                 445

Val Lys Gly Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Val Leu
465                 470                 475                 480

Ile Phe Asn Asn Lys Pro Gly Gln Ser Asn Arg Ser Met Arg Leu Thr
                485                 490                 495

Ala Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
        515                 520                 525

Asp Ser Val Val Ser Lys Ala Pro Ser Gln Lys Gly Asn Glu Met Asn
    530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
    610                 615                 620

Ala Gln Ile His Val Asn Pro Glu Thr Lys Thr Thr Thr Ser Pro Arg
625                 630                 635                 640

Gln Gln Gly Ala Gly Leu Leu Asn Ile Asp Gly Ala Val Thr Ser Gly
                645                 650                 655

Leu Tyr Val Thr Gly Lys Asp Asn Tyr Gly Ser Ile Ser Leu Gly Asn
            660                 665                 670

Ile Thr Asp Thr Met Thr Phe Asp Val Thr Val His Asn Leu Ser Asn
        675                 680                 685

Lys Asp Lys Thr Leu Arg Tyr Asp Thr Glu Leu Leu Thr Asp His Val
    690                 695                 700

Asp Pro Gln Lys Gly Arg Phe Thr Leu Thr Ser His Ser Leu Lys Thr
705                 710                 715                 720

Tyr Gln Gly Gly Glu Val Thr Val Pro Ala Asn Gly Lys Val Thr Val
```

```
                725                 730                 735

Arg Val Thr Met Asp Val Ser Gln Phe Thr Lys Glu Leu Thr Lys Gln
            740                 745                 750

Met Pro Asn Gly Tyr Tyr Leu Glu Gly Phe Val Arg Phe Arg Asp Ser
        755                 760                 765

Gln Asp Asp Gln Leu Asn Arg Val Asn Ile Pro Phe Val Gly Phe Lys
    770                 775                 780

Gly Gln Phe Glu Asn Leu Ala Val Ala Glu Glu Ser Ile Tyr Arg Leu
785                 790                 795                 800

Lys Ser Gln Gly Lys Thr Gly Phe Tyr Phe Asp Glu Ser Gly Pro Lys
                805                 810                 815

Asp Asp Ile Tyr Val Gly Lys His Phe Thr Gly Leu Val Thr Leu Gly
            820                 825                 830

Ser Glu


<210> SEQ ID NO 90
<211> LENGTH: 642
<212> TYPE: PRT
<213> ORGANISM: Streptococcus pyogenes

<400> SEQUENCE: 90

Ala Asp Glu Leu Thr Thr Thr Ser Glu Pro Thr Ile Thr Asn His Ala
1               5                   10                  15

Gln Gln Gln Ala Gln His Leu Thr Asn Thr Glu Leu Ser Ser Ala Glu
            20                  25                  30

Ser Gln Ser Pro Asp Thr Ser Gln Ile Thr Pro Lys Thr Asn Arg Glu
        35                  40                  45

Lys Glu Gln Pro Gln Gly Leu Val Ser Glu Pro Thr Thr Thr Glu Leu
    50                  55                  60

Ala Asp Thr Asp Ala Ala Ser Met Ala Asn Thr Gly Pro Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Gly Asp Phe Asp Glu Asp Trp Glu Asn Phe Glu
            180                 185                 190

Phe Asp Ala Glu Pro Lys Ala Ile Lys Lys Asn Lys Ile Tyr Arg Pro
        195                 200                 205

Gln Ser Thr Gln Ala Pro Lys Glu Thr Val Ile Lys Thr Glu Glu Thr
    210                 215                 220

Asp Gly Ser His Asp Ile Asp Trp Thr Gln Thr Asp Asp Asp Thr Lys
225                 230                 235                 240

Tyr Glu Ser His Gly Met His Val Thr Gly Ile Val Ala Gly Asn Ser
                245                 250                 255

Lys Glu Ala Ala Ala Thr Gly Glu Arg Phe Leu Gly Ile Ala Pro Glu
            260                 265                 270
```

-continued

Ala Gln Val Met Phe Met Arg Val Phe Ala Asn Asp Val Met Gly Ser
275 280 285

Ala Glu Ser Leu Phe Ile Lys Ala Ile Glu Asp Ala Val Ala Leu Gly
290 295 300

Ala Asp Val Ile Asn Leu Ser Leu Gly Thr Ala Asn Gly Ala Gln Leu
305 310 315 320

Ser Gly Ser Lys Pro Leu Met Glu Ala Ile Glu Lys Ala Lys Lys Ala
325 330 335

Gly Val Ser Val Val Val Ala Ala Gly Asn Glu Arg Val Tyr Gly Ser
340 345 350

Asp His Asp Asp Pro Leu Ala Thr Asn Pro Asp Tyr Gly Leu Val Gly
355 360 365

Ser Pro Ser Thr Gly Arg Thr Pro Thr Ser Val Ala Ala Ile Asn Ser
370 375 380

Lys Trp Val Ile Gln Arg Leu Met Thr Ala Lys Glu Leu Glu Asn Arg
385 390 395 400

Ala Asp Leu Asn His Gly Lys Ala Ile Tyr Ser Glu Ser Val Asp Phe
405 410 415

Lys Asp Ile Lys Asp Ser Leu Gly Tyr Asp Lys Ser His Gln Phe Ala
420 425 430

Tyr Val Lys Glu Ser Thr Asp Ala Gly Tyr Lys Ala Gln Asp Val Lys
435 440 445

Asp Lys Ile Ala Leu Ile Glu Arg Asp Pro Asn Lys Thr Tyr Asp Glu
450 455 460

Met Ile Ala Leu Ala Lys Lys His Gly Ala Leu Gly Val Leu Ile Phe
465 470 475 480

Asn Asn Lys Pro Gly Gln Ser Asn Arg Ser Met Arg Leu Thr Ala Asn
485 490 495

Gly Met Gly Ile Pro Ser Ala Phe Ile Ser His Glu Phe Gly Lys Ala
500 505 510

Met Ser Gln Leu Asn Gly Asn Gly Thr Gly Ser Leu Glu Phe Asp Ser
515 520 525

Val Val Ser Lys Ala Pro Ser Gln Lys Gly Asn Glu Met Asn His Phe
530 535 540

Ser Asn Trp Gly Leu Thr Ser Asp Gly Tyr Leu Lys Pro Asp Ile Thr
545 550 555 560

Ala Pro Gly Gly Asp Ile Tyr Ser Thr Tyr Asn Asp Asn His Tyr Gly
565 570 575

Ser Gln Thr Gly Thr Ser Met Ala Ser Pro Gln Ile Ala Gly Ala Ser
580 585 590

Leu Leu Val Lys Gln Tyr Leu Glu Lys Thr Gln Pro Asn Leu Pro Lys
595 600 605

Glu Lys Ile Ala Asp Ile Val Lys Asn Leu Leu Met Ser Asn Ala Gln
610 615 620

Ile His Val Asn Pro Glu Thr Lys Thr Thr Thr Ser Pro Arg Gln Gln
625 630 635 640

Gly Ala

<210> SEQ ID NO 91
<211> LENGTH: 644
<212> TYPE: PRT
<213> ORGANISM: Streptococcus pyogenes

<400> SEQUENCE: 91

-continued

```
Ala Asp Glu Leu Thr Thr Thr Ser Glu Pro Thr Ile Thr Asn His Thr
1               5                   10                  15

Gln Gln Gln Ala Gln His Leu Thr Asn Thr Glu Leu Ser Ser Ala Glu
            20                  25                  30

Ser Lys Pro Gln Asp Thr Ser Gln Ile Thr Leu Lys Thr Asn Arg Glu
        35                  40                  45

Lys Glu Gln Pro Gln Gly Leu Val Ser Glu Pro Thr Thr Thr Glu Leu
    50                  55                  60

Ala Asp Thr Asp Ala Ala Pro Met Ala Asn Thr Gly Pro Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Glu Ala Glu Pro Lys Ala Ile Lys Lys His Lys Ile Tyr
        195                 200                 205

Arg Pro Gln Ser Thr Gln Ala Pro Lys Glu Thr Val Ile Lys Thr Glu
    210                 215                 220

Glu Thr Asp Gly Ser His Asp Ile Asp Trp Thr Gln Thr Asp Asp Asp
225                 230                 235                 240

Thr Lys Tyr Glu Ser His Gly Met His Val Thr Gly Ile Val Ala Gly
                245                 250                 255

Asn Ser Lys Glu Ala Ala Ala Thr Gly Glu Arg Phe Leu Gly Ile Ala
            260                 265                 270

Pro Glu Ala Gln Val Met Phe Met Arg Val Phe Ala Asn Asp Val Met
        275                 280                 285

Gly Ser Ala Glu Ser Leu Phe Ile Lys Ala Ile Glu Asp Ala Val Ala
    290                 295                 300

Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
    370                 375                 380

Asn Ser Lys Trp Val Ile Gln Arg Leu Met Thr Val Lys Glu Leu Glu
385                 390                 395                 400

Asn Arg Ala Asp Leu Asn His Gly Lys Ala Ile Tyr Ser Glu Ser Val
                405                 410                 415

Asp Phe Lys Asp Ile Lys Asp Ser Leu Gly Tyr Asp Lys Ser His Gln
            420                 425                 430
```

```
Phe Ala Tyr Val Lys Glu Ser Thr Asp Ala Gly Tyr Asn Ala Gln Asp
        435                 440                 445

Val Lys Gly Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Val Leu
465                 470                 475                 480

Ile Phe Asn Asn Lys Pro Gly Gln Ser Asn Arg Ser Met Arg Leu Thr
                485                 490                 495

Ala Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
        515                 520                 525

Asp Ser Val Val Ser Lys Ala Pro Ser Gln Lys Gly Asn Glu Met Asn
    530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
    610                 615                 620

Ala Gln Ile His Val Asn Pro Glu Thr Lys Thr Thr Thr Ser Pro Arg
625                 630                 635                 640

Gln Gln Gly Ala


<210> SEQ ID NO 92
<211> LENGTH: 644
<212> TYPE: PRT
<213> ORGANISM: Streptococcus pyogenes

<400> SEQUENCE: 92

Ala Asp Glu Leu Thr Thr Thr Ser Glu Pro Thr Ile Thr Asn His Ala
1               5                   10                  15

Gln Gln Gln Ala Pro Pro Leu Thr Asn Thr Glu Leu Ser Ser Ala Glu
            20                  25                  30

Ser Gln Pro Gln Asp Thr Ser Gln Val Thr Pro Glu Thr Asn Arg Glu
        35                  40                  45

Lys Glu Gln Pro Gln Gly Leu Val Ser Glu Pro Thr Thr Thr Glu Leu
    50                  55                  60

Ala Asp Thr Asp Ala Ala Pro Met Ala Asn Thr Gly Ser Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160
```

-continued

```
Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Glu Ala Glu Pro Lys Ala Ile Lys Lys His Lys Ile Tyr
        195                 200                 205

Arg Pro Gln Ser Thr Gln Ala Pro Lys Glu Thr Val Ile Lys Thr Glu
    210                 215                 220

Glu Thr Asp Gly Ser His Asp Ile Asp Trp Thr Gln Thr Asp Asp Asp
225                 230                 235                 240

Thr Lys Tyr Glu Ser His Gly Met His Val Thr Gly Ile Val Ala Gly
                245                 250                 255

Asn Ser Lys Glu Ala Ala Ala Thr Gly Glu Arg Phe Leu Gly Ile Ala
            260                 265                 270

Pro Glu Ala Gln Val Met Phe Met Arg Val Phe Ala Asn Asp Val Met
        275                 280                 285

Gly Ser Ala Glu Ser Leu Phe Ile Lys Ala Ile Glu Asp Ala Val Ala
    290                 295                 300

Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
    370                 375                 380

Asn Ser Lys Trp Val Ile Gln Arg Leu Met Thr Val Lys Glu Leu Glu
385                 390                 395                 400

Asn Arg Ala Asp Leu Asn His Gly Lys Ala Ile Tyr Ser Glu Ser Val
                405                 410                 415

Asp Phe Lys Asp Ile Lys Asp Ser Leu Gly Tyr Asp Lys Ser His Gln
            420                 425                 430

Phe Ala Tyr Val Lys Glu Ser Thr Asp Ala Gly Tyr Asn Ala Gln Asn
        435                 440                 445

Val Lys Gly Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Val Leu
465                 470                 475                 480

Ile Phe Asn Asn Lys Pro Gly Gln Ser Asn Arg Ser Met Arg Leu Thr
                485                 490                 495

Ala Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
        515                 520                 525

Asp Ser Val Val Ser Lys Ala Pro Ser Gln Lys Gly Asn Glu Met Asn
    530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590
```

Ala Ser Leu Leu Val Lys Gln Tyr Leu Glu Lys Thr Gln Pro Asn Leu
595 600 605

Pro Lys Glu Lys Ile Ala Asp Ile Val Lys Asn Leu Leu Met Ser Asn
610 615 620

Ala Gln Ile His Val Asn Pro Glu Thr Lys Thr Thr Thr Ser Pro Arg
625 630 635 640

Gln Gln Gly Ala

<210> SEQ ID NO 93
<211> LENGTH: 644
<212> TYPE: PRT
<213> ORGANISM: Streptococcus pyogenes

<400> SEQUENCE: 93

Ala Asp Glu Leu Thr Thr Thr Ser Glu Pro Thr Ile Thr Asn His Ala
1 5 10 15

Gln Gln Gln Ala Pro Pro Leu Thr Asn Thr Glu Leu Ser Ser Ala Glu
20 25 30

Ser Gln Pro Gln Asp Thr Ser Gln Val Thr Pro Glu Thr Asn Arg Glu
35 40 45

Lys Glu Gln Pro Gln Gly Leu Val Ser Glu Pro Thr Thr Thr Glu Leu
50 55 60

Ala Asp Thr Asp Ala Ala Pro Met Ala Asn Thr Gly Ser Asp Ala Thr
65 70 75 80

Gln Lys Ser Ala Ser Leu Pro Pro Val Asn Thr Asp Val His Asp Trp
85 90 95

Val Lys Thr Lys Gly Ala Trp Asp Lys Gly Tyr Lys Gly Gln Gly Lys
100 105 110

Val Val Ala Val Ile Asp Thr Gly Ile Asp Pro Ala His Gln Ser Met
115 120 125

Arg Ile Ser Asp Val Ser Thr Ala Lys Val Lys Ser Lys Glu Asp Met
130 135 140

Leu Ala Arg Gln Lys Ala Ala Gly Ile Asn Tyr Gly Ser Trp Ile Asn
145 150 155 160

Asp Lys Val Val Phe Ala His Asn Tyr Val Glu Asn Ser Asp Asn Ile
165 170 175

Lys Glu Asn Gln Phe Glu Asp Phe Asp Glu Asp Trp Glu Asn Phe Glu
180 185 190

Phe Asp Ala Glu Ala Glu Pro Lys Ala Ile Lys Lys His Lys Ile Tyr
195 200 205

Arg Pro Gln Ser Thr Gln Ala Pro Lys Glu Thr Val Ile Lys Thr Glu
210 215 220

Glu Thr Asp Gly Ser His Asp Ile Asp Trp Thr Gln Thr Asp Asp Asp
225 230 235 240

Thr Lys Tyr Glu Ser His Gly Met His Val Thr Gly Ile Val Ala Gly
245 250 255

Asn Ser Lys Glu Ala Ala Ala Thr Gly Glu Arg Phe Leu Gly Ile Ala
260 265 270

Pro Glu Ala Gln Val Met Phe Met Arg Val Phe Ala Asn Asp Val Met
275 280 285

Gly Ser Ala Glu Ser Leu Phe Ile Lys Ala Ile Glu Asp Ala Val Ala
290 295 300

Leu Gly Ala Asp Val Ile Asn Leu Ser Leu Gly Thr Ala Asn Gly Ala
305 310 315 320

Gln Leu Ser Gly Ser Lys Pro Leu Met Glu Ala Ile Glu Lys Ala Lys
325 330 335

Lys Ala Gly Val Ser Val Val Val Ala Ala Gly Asn Glu Arg Val Tyr
340 345 350

Gly Ser Asp His Asp Asp Pro Leu Ala Thr Asn Pro Asp Tyr Gly Leu
355 360 365

Val Gly Ser Pro Ser Thr Gly Arg Thr Pro Thr Ser Val Ala Ala Ile
370 375 380

Asn Ser Lys Trp Val Ile Gln Arg Leu Met Thr Val Lys Glu Leu Glu
385 390 395 400

Asn Arg Ala Asp Leu Asn His Gly Lys Ala Ile Tyr Ser Glu Ser Val
405 410 415

Asp Phe Lys Asp Ile Lys Asp Ser Leu Gly Tyr Asp Lys Ser His Gln
420 425 430

Phe Ala Tyr Val Lys Glu Ser Thr Asp Ala Gly Tyr Asn Ala Gln Asn
435 440 445

Val Lys Gly Lys Ile Ala Leu Ile Glu Arg Asp Pro Asn Lys Thr Tyr
450 455 460

Asp Glu Met Ile Ala Leu Ala Lys Lys His Gly Ala Leu Gly Val Leu
465 470 475 480

Ile Phe Asn Asn Lys Pro Gly Gln Ser Asn Arg Ser Met Arg Leu Thr
485 490 495

Ala Asn Gly Met Gly Ile Pro Ser Ala Phe Ile Ser His Glu Phe Gly
500 505 510

Lys Ala Met Ser Gln Leu Asn Gly Asn Gly Thr Gly Ser Leu Glu Phe
515 520 525

Asp Ser Val Val Ser Lys Ala Pro Ser Gln Lys Gly Asn Glu Met Asn
530 535 540

His Phe Ser Asn Trp Gly Leu Thr Ser Asp Gly Tyr Leu Lys Pro Asp
545 550 555 560

Ile Thr Ala Pro Gly Gly Asp Ile Tyr Ser Thr Tyr Asn Asp Asn His
565 570 575

Tyr Gly Ser Gln Thr Gly Thr Ser Met Ala Ser Pro Gln Ile Ala Gly
580 585 590

Ala Ser Leu Leu Val Lys Gln Tyr Leu Glu Lys Thr Gln Pro Asn Leu
595 600 605

Pro Lys Glu Lys Ile Ala Asp Ile Val Lys Asn Leu Leu Met Ser Asn
610 615 620

Ala Gln Ile His Val Asn Pro Glu Thr Lys Thr Thr Thr Ser Pro Arg
625 630 635 640

Gln Gln Gly Ala

<210> SEQ ID NO 94
<211> LENGTH: 644
<212> TYPE: PRT
<213> ORGANISM: Streptococcus pyogenes

<400> SEQUENCE: 94

Ala Asp Glu Leu Ser Thr Met Ser Glu Pro Thr Ile Thr Asn His Ala
1 5 10 15

Gln Gln Gln Ala Gln His Leu Thr Asn Thr Glu Leu Ser Ser Ala Glu
20 25 30

Ser Lys Ser Gln Asp Thr Ser Gln Ile Thr Leu Lys Thr Asn Arg Glu
35 40 45

Lys Glu Gln Ser Gln Asp Leu Val Ser Glu Pro Thr Thr Thr Glu Leu

```
    50                  55                  60

Ala Asp Thr Asp Ala Ala Ser Met Ala Asn Thr Gly Ser Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Glu Ala Glu Pro Lys Ala Ile Lys Lys His Lys Ile Tyr
        195                 200                 205

Arg Pro Gln Ser Thr Gln Ala Pro Lys Glu Thr Val Ile Lys Thr Glu
    210                 215                 220

Glu Thr Asp Gly Ser His Asp Ile Asp Trp Thr Gln Thr Asp Asp Asp
225                 230                 235                 240

Thr Lys Tyr Glu Ser His Gly Met His Val Thr Gly Ile Val Ala Gly
                245                 250                 255

Asn Ser Lys Glu Ala Ala Ala Thr Gly Glu Arg Phe Leu Gly Ile Ala
            260                 265                 270

Pro Glu Ala Gln Val Met Phe Met Arg Val Phe Ala Asn Asp Ile Met
        275                 280                 285

Gly Ser Ala Glu Ser Leu Phe Ile Lys Ala Ile Glu Asp Ala Val Ala
    290                 295                 300

Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
    370                 375                 380

Asn Ser Lys Trp Val Ile Gln Arg Leu Met Thr Val Lys Glu Leu Glu
385                 390                 395                 400

Asn Arg Ala Asp Leu Asn His Gly Lys Ala Ile Tyr Ser Glu Ser Val
                405                 410                 415

Asp Phe Lys Asp Ile Lys Asp Ser Leu Gly Tyr Asp Lys Ser His Gln
            420                 425                 430

Phe Ala Tyr Val Lys Glu Ser Thr Asp Ala Gly Tyr Asn Ala Gln Asp
        435                 440                 445

Val Lys Gly Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Val Leu
465                 470                 475                 480
```

```
Ile Phe Asn Asn Lys Pro Gly Gln Ser Asn Arg Ser Met Arg Leu Thr
                485                 490                 495

Ala Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
        515                 520                 525

Asp Ser Val Val Ser Lys Ala Pro Ser Gln Lys Gly Asn Glu Met Asn
    530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
    610                 615                 620

Ala Gln Ile His Val Asn Pro Glu Thr Lys Thr Thr Thr Ser Pro Arg
625                 630                 635                 640

Gln Gln Gly Ala


<210> SEQ ID NO 95
<211> LENGTH: 644
<212> TYPE: PRT
<213> ORGANISM: Streptococcus pyogenes

<400> SEQUENCE: 95

Ala Asp Glu Leu Thr Thr Thr Ser Glu Pro Thr Ile Thr Asn His Ala
1               5                   10                  15

Gln Gln Gln Ala Gln Pro Leu Thr Asn Thr Glu Leu Ser Ser Ala Glu
            20                  25                  30

Ser Gln Ser Pro Asp Ile Ser Gln Val Thr Pro Glu Thr Asn Arg Glu
        35                  40                  45

Lys Glu Gln Pro Gln Gly Leu Val Ser Glu Pro Thr Thr Thr Glu Leu
    50                  55                  60

Ala Asp Thr Asp Ala Ala Pro Met Ala Asn Thr Gly Pro Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Asp Ala Glu Pro Lys Ala Ile Lys Lys His Lys Ile Tyr
        195                 200                 205

Arg Pro Gln Ser Thr Gln Ala Pro Lys Glu Thr Val Ile Lys Thr Glu
```

```
    210                 215                 220

Glu Thr Asp Gly Ser His Asp Ile Asp Trp Thr Gln Thr Asp Asp Asp
225                 230                 235                 240

Thr Lys Tyr Glu Ser His Gly Met His Val Thr Gly Ile Val Ala Gly
                245                 250                 255

Asn Ser Lys Glu Ala Ala Ala Thr Gly Glu Arg Phe Leu Gly Ile Ala
            260                 265                 270

Pro Glu Ala Gln Val Met Phe Met Arg Val Phe Ala Asn Asp Val Met
        275                 280                 285

Gly Ser Ala Glu Ser Leu Phe Ile Lys Ala Ile Glu Asp Ala Val Ala
    290                 295                 300

Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
    370                 375                 380

Asn Ser Lys Trp Val Ile Gln Arg Leu Met Thr Val Lys Gly Leu Glu
385                 390                 395                 400

Asn Arg Ala Asp Leu Asn His Gly Lys Ala Ile Tyr Ser Glu Ser Val
                405                 410                 415

Asp Phe Lys Asp Ile Lys Asp Ser Leu Gly Tyr Asp Lys Ser His Gln
            420                 425                 430

Phe Ala Tyr Val Lys Glu Ser Thr Asp Ala Gly Tyr Asn Ala Gln Asp
        435                 440                 445

Val Lys Gly Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Leu Leu
465                 470                 475                 480

Ile Phe Asn Asn Lys Ser Gly Gln Ser Asn Arg Ser Met Arg Leu Thr
                485                 490                 495

Ala Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
        515                 520                 525

Asp Ser Val Val Ser Lys Ala Pro Ser Gln Lys Gly Asn Glu Met Asn
    530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
    610                 615                 620

Ala Gln Ile His Val Asn Pro Glu Thr Lys Thr Thr Thr Ser Pro Arg
625                 630                 635                 640
```

Gln Gln Gly Ala

<210> SEQ ID NO 96
<211> LENGTH: 644
<212> TYPE: PRT
<213> ORGANISM: Streptococcus pyogenes

<400> SEQUENCE: 96

```
Ala Asp Glu Leu Thr Thr Thr Ser Glu Pro Thr Ile Thr Asn His Ala
1               5                   10                  15

Gln Gln Gln Ala Gln His Leu Thr Asn Thr Glu Leu Ser Ser Ala Glu
            20                  25                  30

Ser Lys Pro Gln Asp Thr Ser Gln Ile Thr Pro Lys Thr Asn Arg Glu
        35                  40                  45

Lys Glu Gln Ser Gln Asp Leu Val Ser Glu Pro Thr Thr Thr Glu Leu
    50                  55                  60

Ala Asp Thr Asp Ala Ala Ser Met Ala Asn Thr Gly Pro Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Glu Ala Glu Pro Lys Ala Ile Lys Lys His Lys Ile Tyr
        195                 200                 205

Arg Pro Gln Ser Thr Gln Ala Pro Lys Glu Thr Val Ile Lys Thr Glu
    210                 215                 220

Glu Thr Asp Gly Ser His Asp Ile Asp Trp Thr Gln Thr Asp Asp Asp
225                 230                 235                 240

Thr Lys Tyr Glu Ser His Gly Met His Val Thr Gly Ile Val Ala Gly
                245                 250                 255

Asn Ser Lys Glu Ala Ala Ala Thr Gly Glu Arg Phe Leu Gly Ile Ala
            260                 265                 270

Pro Glu Ala Gln Val Met Phe Met Arg Val Phe Ala Asn Asp Val Met
        275                 280                 285

Gly Ser Ala Glu Ser Leu Phe Ile Lys Ala Ile Glu Asp Ala Val Ala
    290                 295                 300

Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
```

```
    370                 375                 380

Asn Ser Lys Trp Val Ile Gln Arg Leu Met Thr Val Lys Glu Leu Glu
385                 390                 395                 400

Asn Arg Ala Asp Leu Asn His Gly Lys Ala Ile Tyr Ser Glu Ser Val
                405                 410                 415

Asp Phe Lys Asn Ile Lys Asp Ser Leu Gly Tyr Asp Lys Ser His Gln
            420                 425                 430

Phe Ala Tyr Val Lys Glu Ser Thr Asp Ala Gly Tyr Asn Ala Gln Asp
        435                 440                 445

Val Lys Gly Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Val Leu
465                 470                 475                 480

Ile Phe Asn Asn Lys Pro Gly Gln Ser Asn Arg Ser Met Arg Leu Thr
                485                 490                 495

Ser Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
        515                 520                 525

Asp Ser Val Val Ser Lys Ala Pro Ser Gln Lys Gly Asn Glu Met Asn
    530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
    610                 615                 620

Ala Gln Ile His Val Asn Pro Glu Thr Lys Thr Thr Thr Ser Pro Arg
625                 630                 635                 640

Gln Gln Gly Ala


<210> SEQ ID NO 97
<211> LENGTH: 644
<212> TYPE: PRT
<213> ORGANISM: Streptococcus pyogenes

<400> SEQUENCE: 97

Ala Asp Glu Leu Thr Thr Thr Ser Glu Pro Thr Ile Thr Asn His Thr
1               5                   10                  15

Gln Gln Gln Ala Gln His Leu Thr Asn Thr Glu Leu Ser Ser Ala Glu
            20                  25                  30

Ser Lys Pro Gln Asp Thr Ser Gln Ile Thr Leu Lys Thr Asn Arg Glu
        35                  40                  45

Lys Glu Gln Pro Gln Gly Leu Val Ser Glu Pro Thr Thr Thr Glu Leu
    50                  55                  60

Ala Asp Thr Asp Ala Ala Pro Met Ala Asn Thr Gly Pro Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110
```

```
Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Glu Ala Glu Pro Lys Ala Ile Lys Lys His Lys Ile Tyr
        195                 200                 205

Arg Pro Gln Ser Thr Gln Ala Pro Lys Glu Thr Val Ile Lys Thr Glu
    210                 215                 220

Glu Thr Asp Gly Ser His Asp Ile Asp Trp Thr Gln Thr Asp Asp Asp
225                 230                 235                 240

Thr Lys Tyr Glu Ser His Gly Met His Val Thr Gly Ile Val Ala Gly
                245                 250                 255

Asn Ser Lys Glu Ala Ala Ala Thr Gly Glu Arg Phe Leu Gly Ile Ala
            260                 265                 270

Pro Glu Ala Gln Val Met Phe Met Arg Val Phe Ala Asn Asp Val Met
        275                 280                 285

Gly Ser Ala Glu Ser Leu Phe Ile Lys Ala Ile Glu Asp Ala Val Ala
    290                 295                 300

Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
    370                 375                 380

Asn Ser Lys Trp Val Ile Gln Arg Leu Met Thr Val Lys Glu Leu Glu
385                 390                 395                 400

Asn Arg Ala Asp Leu Asn His Gly Lys Ala Ile Tyr Ser Glu Ser Val
                405                 410                 415

Asp Phe Lys Asn Ile Lys Asp Ser Leu Gly Tyr Asp Lys Ser His Gln
            420                 425                 430

Phe Ala Tyr Val Lys Glu Ser Thr Asp Ala Gly Tyr Lys Ala Gln Asp
        435                 440                 445

Val Lys Gly Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Val Leu
465                 470                 475                 480

Ile Phe Asn Asn Lys Pro Gly Gln Ser Asn Arg Ser Met Arg Leu Thr
                485                 490                 495

Ala Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
        515                 520                 525

Asp Ser Val Val Ser Lys Ala Pro Ser Gln Lys Gly Asn Glu Met Asn
```

```
    530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
    610                 615                 620

Ala Gln Ile His Val Asn Pro Glu Thr Lys Thr Thr Thr Ser Pro Arg
625                 630                 635                 640

Gln Gln Gly Ala


<210> SEQ ID NO 98
<211> LENGTH: 644
<212> TYPE: PRT
<213> ORGANISM: Streptococcus pyogenes

<400> SEQUENCE: 98

Ala Asp Glu Leu Ser Thr Met Ser Glu Pro Thr Ile Thr Asn His Ala
1               5                   10                  15

Gln Gln Gln Ala Gln His Leu Thr Asn Thr Glu Leu Ser Ser Ala Glu
            20                  25                  30

Ser Lys Ser Gln Asp Thr Ser Gln Ile Thr Pro Lys Thr Asn Arg Glu
        35                  40                  45

Lys Glu Gln Ser Gln Asp Leu Val Ser Glu Pro Thr Thr Thr Glu Leu
    50                  55                  60

Ala Asp Thr Asp Ala Ala Ser Met Ala Asn Thr Gly Ser Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Glu Asp Phe Asp Glu Asp Trp Glu Asn Phe Glu
            180                 185                 190

Phe Asp Ala Asp Ala Glu Pro Lys Ala Ile Lys Lys His Lys Ile Tyr
        195                 200                 205

Arg Pro Gln Ser Thr Gln Ala Pro Lys Glu Thr Val Ile Lys Thr Glu
    210                 215                 220

Glu Thr Asp Gly Ser His Asp Ile Asp Trp Thr Gln Thr Asp Asp Asp
225                 230                 235                 240

Thr Lys Tyr Glu Ser His Gly Met His Val Thr Gly Ile Val Ala Gly
                245                 250                 255

Asn Ser Lys Glu Ala Ala Ala Thr Gly Glu Arg Phe Leu Gly Ile Ala
            260                 265                 270
```

```
Pro Glu Ala Gln Val Met Phe Met Arg Val Phe Ala Asn Asp Val Met
        275                 280                 285

Gly Ser Ala Glu Ser Leu Phe Ile Lys Ala Ile Glu Asp Ala Val Ala
    290                 295                 300

Leu Gly Ala Asp Val Ile Asn Leu Ser Leu Gly Thr Ala Asn Gly Ala
305                 310                 315                 320

Gln Leu Ser Gly Ser Lys Pro Leu Met Glu Ala Ile Glu Lys Ala Lys
                325                 330                 335

Lys Ala Gly Val Ser Val Val Val Ala Ala Gly Asn Glu Arg Val Tyr
            340                 345                 350

Gly Ser Asp His Asp Asp Pro Leu Ala Thr Asn Pro Asp Tyr Gly Leu
        355                 360                 365

Val Gly Ser Pro Ser Thr Gly Arg Thr Pro Thr Ser Val Ala Ala Ile
    370                 375                 380

Asn Ser Lys Trp Val Ile Gln Arg Leu Met Thr Val Lys Glu Leu Glu
385                 390                 395                 400

Asn Arg Ala Asp Leu Asn His Gly Lys Ala Ile Tyr Ser Glu Ser Val
                405                 410                 415

Asp Phe Lys Asp Ile Lys Asp Ser Leu Gly Tyr Asp Lys Ser His Gln
            420                 425                 430

Phe Ala Tyr Val Lys Glu Ser Thr Asp Ala Gly Tyr Lys Ala Gln Asp
        435                 440                 445

Val Lys Asp Lys Ile Ala Leu Ile Glu Arg Asp Pro Asn Lys Thr Tyr
    450                 455                 460

Asp Glu Met Ile Ala Leu Ala Lys Lys His Gly Ala Leu Gly Val Leu
465                 470                 475                 480

Ile Phe Asn Asn Lys Pro Gly Gln Ser Asn Arg Ser Met Arg Leu Thr
                485                 490                 495

Ala Asn Gly Met Gly Ile Pro Ser Ala Phe Ile Ser His Glu Phe Gly
            500                 505                 510

Lys Ala Met Ser Gln Leu Asn Gly Asn Gly Thr Gly Ser Leu Glu Phe
        515                 520                 525

Asp Ser Val Val Ser Lys Ala Pro Ser Gln Lys Gly Asn Glu Met Asn
    530                 535                 540

His Phe Ser Asn Trp Gly Leu Thr Ser Asp Gly Tyr Leu Lys Pro Asp
545                 550                 555                 560

Ile Thr Ala Pro Gly Gly Asp Ile Tyr Ser Thr Tyr Asn Asp Asn His
                565                 570                 575

Tyr Gly Ser Gln Thr Gly Thr Ser Met Ala Ser Pro Gln Ile Ala Gly
            580                 585                 590

Ala Ser Leu Leu Val Lys Gln Tyr Leu Glu Lys Thr Gln Pro Asn Leu
        595                 600                 605

Pro Lys Glu Lys Ile Ala Asp Ile Val Lys Asn Leu Leu Met Ser Asn
    610                 615                 620

Ala Gln Ile His Val Asn Pro Glu Thr Lys Thr Thr Thr Ser Pro Arg
625                 630                 635                 640

Gln Gln Gly Ala

<210> SEQ ID NO 99
<211> LENGTH: 642
<212> TYPE: PRT
<213> ORGANISM: Streptococcus pyogenes

<400> SEQUENCE: 99
```

-continued

```
Ala Asp Glu Leu Thr Thr Thr Ser Glu Pro Thr Ile Thr Asn His Ala
1               5                   10                  15

Gln Gln Gln Ala Gln His Leu Thr Asn Thr Glu Leu Ser Ser Ala Glu
            20                  25                  30

Ser Gln Ser Pro Asp Thr Ser Gln Ile Thr Pro Lys Thr Asn Arg Glu
        35                  40                  45

Lys Glu Gln Pro Gln Gly Leu Val Ser Glu Pro Thr Thr Thr Glu Leu
    50                  55                  60

Ala Asp Thr Asp Ala Ala Ser Met Ala Asn Thr Gly Pro Asp Ala Thr
65                  70                  75                  80

Gln Lys Ser Ala Ser Leu Pro Pro Val Asn Thr Asp Val His Asp Trp
                85                  90                  95

Val Lys Thr Lys Gly Ala Trp Asp Lys Gly Tyr Lys Gly Gln Gly Lys
            100                 105                 110

Val Val Ala Val Ile Asp Thr Gly Ile Asp Pro Ala His Gln Ser Met
        115                 120                 125

Arg Ile Ser Asp Val Ser Thr Ala Lys Val Lys Ser Lys Glu Asp Met
    130                 135                 140

Leu Ala Arg Gln Lys Ala Ala Gly Ile Asn Tyr Gly Ser Trp Ile Asn
145                 150                 155                 160

Asp Lys Val Val Phe Ala His Asn Tyr Val Glu Asn Ser Asp Asn Ile
                165                 170                 175

Lys Glu Asn Gln Phe Gly Asp Phe Asp Glu Asp Trp Glu Asn Phe Glu
            180                 185                 190

Phe Asp Ala Glu Pro Lys Ala Ile Lys Lys Asn Lys Ile Tyr Arg Pro
        195                 200                 205

Gln Ser Thr Gln Ala Pro Lys Glu Thr Val Ile Lys Thr Glu Glu Thr
    210                 215                 220

Asp Gly Ser His Asp Ile Asp Trp Thr Gln Thr Asp Asp Asp Thr Lys
225                 230                 235                 240

Tyr Glu Ser His Gly Met His Val Thr Gly Ile Val Ala Gly Asn Ser
                245                 250                 255

Lys Glu Ala Ala Ala Thr Gly Glu Arg Phe Leu Gly Ile Ala Pro Glu
            260                 265                 270

Ala Gln Val Met Phe Met Arg Val Phe Ala Asn Asp Val Met Gly Ser
        275                 280                 285

Ala Glu Ser Leu Phe Ile Lys Ala Ile Glu Asp Ala Val Ala Leu Gly
    290                 295                 300

Ala Asp Val Ile Asn Leu Ser Leu Gly Thr Ala Asn Gly Ala Gln Leu
305                 310                 315                 320

Ser Gly Ser Lys Pro Leu Met Glu Ala Ile Glu Lys Ala Lys Lys Ala
                325                 330                 335

Gly Val Ser Val Val Val Ala Ala Gly Asn Glu Arg Val Tyr Gly Ser
            340                 345                 350

Asp His Asp Asp Pro Leu Ala Thr Asn Pro Asp Tyr Gly Leu Val Gly
        355                 360                 365

Ser Pro Ser Thr Gly Arg Thr Pro Thr Ser Val Ala Ala Ile Asn Ser
    370                 375                 380

Lys Trp Val Ile Gln Arg Leu Met Thr Ala Lys Glu Leu Glu Asn Arg
385                 390                 395                 400

Ala Asp Leu Asn His Gly Lys Ala Ile Tyr Ser Glu Ser Val Asp Phe
                405                 410                 415

Lys Asp Ile Lys Asp Ser Leu Gly Tyr Asp Lys Ser His Gln Phe Ala
            420                 425                 430
```

Tyr Val Lys Glu Ser Thr Asp Ala Gly Tyr Lys Ala Gln Asp Val Lys
435 440 445

Asp Lys Ile Ala Leu Ile Glu Arg Asp Pro Asn Lys Thr Tyr Asp Glu
450 455 460

Met Ile Ala Leu Ala Lys Lys His Gly Ala Leu Gly Val Leu Ile Phe
465 470 475 480

Asn Asn Lys Pro Gly Gln Ser Asn Arg Ser Met Arg Leu Thr Ala Asn
485 490 495

Gly Met Gly Ile Pro Ser Ala Phe Ile Ser His Glu Phe Gly Lys Ala
500 505 510

Met Ser Gln Leu Asn Gly Asn Gly Thr Gly Ser Leu Glu Phe Asp Ser
515 520 525

Val Val Ser Lys Ala Pro Ser Gln Lys Gly Asn Glu Met Asn His Phe
530 535 540

Ser Asn Trp Gly Leu Thr Ser Asp Gly Tyr Leu Lys Pro Asp Ile Thr
545 550 555 560

Ala Pro Gly Gly Asp Ile Tyr Ser Thr Tyr Asn Asp Asn His Tyr Gly
565 570 575

Ser Gln Thr Gly Thr Ser Met Ala Ser Pro Gln Ile Ala Gly Ala Ser
580 585 590

Leu Leu Val Lys Gln Tyr Leu Glu Lys Thr Gln Pro Asn Leu Pro Lys
595 600 605

Glu Lys Ile Ala Asp Ile Val Lys Asn Leu Leu Met Ser Asn Ala Gln
610 615 620

Ile His Val Asn Pro Glu Thr Lys Thr Thr Thr Ser Pro Arg Gln Gln
625 630 635 640

Gly Ala

<210> SEQ ID NO 100
<211> LENGTH: 309
<212> TYPE: PRT
<213> ORGANISM: Streptococcus pyogenes

<400> SEQUENCE: 100

Ala Val Ile Asp Thr Gly Ile Asp Pro Ala His Gln Ser Met Arg Ile
1 5 10 15

Ser Asp Val Ser Thr Ala Lys Val Lys Ser Lys Glu Asp Met Leu Ala
20 25 30

Arg Gln Lys Ala Ala Gly Ile Asn Tyr Gly Ser Trp Ile Asn Asp Lys
35 40 45

Val Val Phe Ala His Asn Tyr Val Glu Asn Ser Asp Asn Ile Lys Glu
50 55 60

Asn Gln Phe Gly Asp Phe Asp Glu Asp Trp Glu Asn Phe Glu Phe Asp
65 70 75 80

Ala Glu Pro Lys Ala Ile Lys Lys Asn Lys Ile Tyr Arg Pro Gln Ser
85 90 95

Thr Gln Ala Pro Lys Glu Thr Val Ile Lys Thr Glu Glu Thr Asp Gly
100 105 110

Ser His Asp Ile Asp Trp Thr Gln Thr Asp Asp Asp Thr Lys Tyr Glu
115 120 125

Ser His Gly Met His Val Thr Gly Ile Val Ala Gly Asn Ser Lys Glu
130 135 140

Ala Ala Ala Thr Gly Glu Arg Phe Leu Gly Ile Ala Pro Glu Ala Gln
145 150 155 160

```
Val Met Phe Met Arg Val Phe Ala Asn Asp Val Met Gly Ser Ala Glu
                165                 170                 175

Ser Leu Phe Ile Lys Ala Ile Glu Asp Ala Val Ala Leu Gly Ala Asp
            180                 185                 190

Val Ile Asn Leu Ser Leu Gly Thr Ala Asn Gly Ala Gln Leu Ser Gly
        195                 200                 205

Ser Lys Pro Leu Met Glu Ala Ile Glu Lys Ala Lys Lys Ala Gly Val
    210                 215                 220

Ser Val Val Val Ala Ala Gly Asn Glu Arg Val Tyr Gly Ser Asp His
225                 230                 235                 240

Asp Asp Pro Leu Ala Thr Asn Pro Asp Tyr Gly Leu Val Gly Ser Pro
                245                 250                 255

Ser Thr Gly Arg Thr Pro Thr Ser Val Ala Ala Ile Asn Ser Lys Trp
            260                 265                 270

Val Ile Gln Arg Leu Met Thr Ala Lys Glu Leu Glu Asn Arg Ala Asp
        275                 280                 285

Leu Asn His Gly Lys Ala Ile Tyr Ser Glu Ser Val Asp Phe Lys Asp
    290                 295                 300

Ile Lys Asp Ser Leu
305
```

<210> SEQ ID NO 101
<211> LENGTH: 311
<212> TYPE: PRT
<213> ORGANISM: Streptococcus pyogenes

<400> SEQUENCE: 101

```
Ala Val Ile Asp Thr Gly Ile Asp Pro Ala His Gln Ser Met Arg Ile
1               5                   10                  15

Ser Asp Val Ser Thr Ala Lys Val Lys Ser Lys Glu Asp Met Leu Ala
            20                  25                  30

Arg Gln Lys Ala Ala Gly Ile Asn Tyr Gly Ser Trp Ile Asn Asp Lys
        35                  40                  45

Val Val Phe Ala His Asn Tyr Val Glu Asn Ser Asp Asn Ile Lys Glu
    50                  55                  60

Asn Gln Phe Glu Asp Phe Asp Glu Asp Trp Glu Asn Phe Glu Phe Asp
65                  70                  75                  80

Ala Glu Ala Glu Pro Lys Ala Ile Lys Lys His Lys Ile Tyr Arg Pro
                85                  90                  95

Gln Ser Thr Gln Ala Pro Lys Glu Thr Val Ile Lys Thr Glu Glu Thr
            100                 105                 110

Asp Gly Ser His Asp Ile Asp Trp Thr Gln Thr Asp Asp Asp Thr Lys
        115                 120                 125

Tyr Glu Ser His Gly Met His Val Thr Gly Ile Val Ala Gly Asn Ser
    130                 135                 140

Lys Glu Ala Ala Ala Thr Gly Glu Arg Phe Leu Gly Ile Ala Pro Glu
145                 150                 155                 160

Ala Gln Val Met Phe Met Arg Val Phe Ala Asn Asp Val Met Gly Ser
                165                 170                 175

Ala Glu Ser Leu Phe Ile Lys Ala Ile Glu Asp Ala Val Ala Leu Gly
            180                 185                 190

Ala Asp Val Ile Asn Leu Ser Leu Gly Thr Ala Asn Gly Ala Gln Leu
        195                 200                 205

Ser Gly Ser Lys Pro Leu Met Glu Ala Ile Glu Lys Ala Lys Lys Ala
    210                 215                 220
```

Gly Val Ser Val Val Val Ala Ala Gly Asn Glu Arg Val Tyr Gly Ser
225 230 235 240

Asp His Asp Asp Pro Leu Ala Thr Asn Pro Asp Tyr Gly Leu Val Gly
245 250 255

Ser Pro Ser Thr Gly Arg Thr Pro Thr Ser Val Ala Ala Ile Asn Ser
260 265 270

Lys Trp Val Ile Gln Arg Leu Met Thr Val Lys Glu Leu Glu Asn Arg
275 280 285

Ala Asp Leu Asn His Gly Lys Ala Ile Tyr Ser Glu Ser Val Asp Phe
290 295 300

Lys Asp Ile Lys Asp Ser Leu
305 310

<210> SEQ ID NO 102
<211> LENGTH: 311
<212> TYPE: PRT
<213> ORGANISM: Streptococcus pyogenes

<400> SEQUENCE: 102

Ala Val Ile Asp Thr Gly Ile Asp Pro Ala His Gln Ser Met Arg Ile
1 5 10 15

Ser Asp Val Ser Thr Ala Lys Val Lys Ser Lys Glu Asp Met Leu Ala
20 25 30

Arg Gln Lys Ala Ala Gly Ile Asn Tyr Gly Ser Trp Ile Asn Asp Lys
35 40 45

Val Val Phe Ala His Asn Tyr Val Glu Asn Ser Asp Asn Ile Lys Glu
50 55 60

Asn Gln Phe Glu Asp Phe Asp Glu Asp Trp Glu Asn Phe Glu Phe Asp
65 70 75 80

Ala Glu Ala Glu Pro Lys Ala Ile Lys Lys His Lys Ile Tyr Arg Pro
85 90 95

Gln Ser Thr Gln Ala Pro Lys Glu Thr Val Ile Lys Thr Glu Glu Thr
100 105 110

Asp Gly Ser His Asp Ile Asp Trp Thr Gln Thr Asp Asp Thr Lys
115 120 125

Tyr Glu Ser His Gly Met His Val Thr Gly Ile Val Ala Gly Asn Ser
130 135 140

Lys Glu Ala Ala Ala Thr Gly Glu Arg Phe Leu Gly Ile Ala Pro Glu
145 150 155 160

Ala Gln Val Met Phe Met Arg Val Phe Ala Asn Asp Val Met Gly Ser
165 170 175

Ala Glu Ser Leu Phe Ile Lys Ala Ile Glu Asp Ala Val Ala Leu Gly
180 185 190

Ala Asp Val Ile Asn Leu Ser Leu Gly Thr Ala Asn Gly Ala Gln Leu
195 200 205

Ser Gly Ser Lys Pro Leu Met Glu Ala Ile Glu Lys Ala Lys Lys Ala
210 215 220

Gly Val Ser Val Val Val Ala Ala Gly Asn Glu Arg Val Tyr Gly Ser
225 230 235 240

Asp His Asp Asp Pro Leu Ala Thr Asn Pro Asp Tyr Gly Leu Val Gly
245 250 255

Ser Pro Ser Thr Gly Arg Thr Pro Thr Ser Val Ala Ala Ile Asn Ser
260 265 270

Lys Trp Val Ile Gln Arg Leu Met Thr Val Lys Glu Leu Glu Asn Arg
275 280 285

```
Ala Asp Leu Asn His Gly Lys Ala Ile Tyr Ser Glu Ser Val Asp Phe
    290                 295                 300

Lys Asp Ile Lys Asp Ser Leu
305                 310


<210> SEQ ID NO 103
<211> LENGTH: 309
<212> TYPE: PRT
<213> ORGANISM: Streptococcus pyogenes

<400> SEQUENCE: 103

Ala Val Ile Asp Thr Gly Ile Asp Pro Ala His Gln Ser Met Arg Ile
1               5                   10                  15

Ser Asp Val Ser Thr Ala Lys Val Lys Ser Lys Glu Asp Met Leu Ala
            20                  25                  30

Arg Gln Lys Ala Ala Gly Ile Asn Tyr Gly Ser Trp Ile Asn Asp Lys
        35                  40                  45

Val Val Phe Ala His Asn Tyr Val Glu Asn Ser Asp Asn Ile Lys Glu
    50                  55                  60

Asn Gln Phe Glu Asp Phe Asp Glu Asp Trp Glu Asn Phe Glu Phe Asp
65                  70                  75                  80

Ala Glu Pro Lys Ala Ile Lys Lys His Lys Ile Tyr Arg Pro Gln Ser
                85                  90                  95

Thr Gln Ala Pro Lys Glu Thr Val Ile Lys Thr Glu Glu Thr Asp Gly
            100                 105                 110

Ser His Asp Ile Asp Trp Thr Gln Thr Asp Asp Asp Thr Lys Tyr Glu
        115                 120                 125

Ser His Gly Met His Val Thr Gly Ile Val Ala Gly Asn Ser Lys Glu
    130                 135                 140

Ala Ala Ala Thr Gly Glu Arg Phe Leu Gly Ile Ala Pro Glu Thr Gln
145                 150                 155                 160

Val Met Phe Met Arg Val Phe Ala Asn Asp Val Met Gly Ser Ala Glu
                165                 170                 175

Ser Leu Phe Ile Lys Ala Ile Glu Asp Ala Val Ala Leu Gly Ala Asp
            180                 185                 190

Val Ile Asn Leu Ser Leu Gly Thr Ala Asn Gly Ala Gln Leu Ser Gly
        195                 200                 205

Ser Lys Pro Leu Met Glu Ala Ile Glu Lys Ala Lys Lys Ala Gly Val
    210                 215                 220

Ser Val Val Val Ala Ala Gly Asn Glu Arg Val Tyr Gly Ser Asp His
225                 230                 235                 240

Asp Asp Pro Leu Ala Thr Asn Pro Asp Tyr Gly Leu Val Gly Ser Pro
                245                 250                 255

Ser Thr Gly Arg Thr Pro Thr Ser Val Ala Ala Ile Asn Ser Lys Trp
            260                 265                 270

Val Ile Gln Arg Leu Met Thr Val Lys Glu Leu Glu Asn Arg Ala Asp
        275                 280                 285

Leu Asn His Gly Lys Ala Ile Tyr Ser Glu Ser Val Asp Phe Lys Asp
    290                 295                 300

Ile Lys Asp Ser Leu
305


<210> SEQ ID NO 104
<211> LENGTH: 311
<212> TYPE: PRT
<213> ORGANISM: Streptococcus pyogenes
```

<400> SEQUENCE: 104

```
Ala Val Ile Asp Thr Gly Ile Asp Pro Ala His Gln Ser Met Arg Ile
1               5                   10                  15

Ser Asp Val Ser Thr Ala Lys Val Lys Ser Lys Glu Asp Met Leu Ala
            20                  25                  30

Arg Gln Lys Ala Ala Gly Ile Asn Tyr Gly Ser Trp Ile Asn Asp Lys
        35                  40                  45

Val Val Phe Ala His Asn Tyr Val Glu Asn Ser Asp Asn Ile Lys Glu
    50                  55                  60

Asn Gln Phe Glu Asp Phe Asp Glu Asp Trp Glu Asn Phe Glu Phe Asp
65                  70                  75                  80

Ala Glu Ala Glu Pro Lys Ala Ile Lys Lys His Lys Ile Tyr Arg Pro
                85                  90                  95

Gln Ser Thr Gln Ala Pro Lys Glu Thr Val Ile Lys Thr Glu Glu Thr
            100                 105                 110

Asp Gly Ser His Asp Ile Asp Trp Thr Gln Thr Asp Asp Asp Thr Lys
        115                 120                 125

Tyr Glu Ser His Gly Met His Val Thr Gly Ile Val Ala Gly Asn Ser
    130                 135                 140

Lys Glu Ala Ala Ala Thr Gly Glu Arg Phe Leu Gly Ile Ala Pro Glu
145                 150                 155                 160

Ala Gln Val Met Phe Met Arg Val Phe Ala Asn Asp Ile Met Gly Ser
                165                 170                 175

Ala Glu Ser Leu Phe Ile Lys Ala Ile Glu Asp Ala Val Ala Leu Gly
            180                 185                 190

Ala Asp Val Ile Asn Leu Ser Leu Gly Thr Ala Asn Gly Ala Gln Leu
        195                 200                 205

Ser Gly Ser Lys Pro Leu Met Glu Ala Ile Glu Lys Ala Lys Lys Ala
    210                 215                 220

Gly Val Ser Val Val Val Ala Ala Gly Asn Glu Arg Val Tyr Gly Ser
225                 230                 235                 240

Asp His Asp Asp Pro Leu Ala Thr Asn Pro Asp Tyr Gly Leu Val Gly
                245                 250                 255

Ser Pro Ser Thr Gly Arg Thr Pro Thr Ser Val Ala Ala Ile Asn Ser
            260                 265                 270

Lys Trp Val Ile Gln Arg Leu Met Thr Val Lys Glu Leu Glu Asn Arg
        275                 280                 285

Ala Asp Leu Asn His Gly Lys Ala Ile Tyr Ser Glu Ser Val Asp Phe
    290                 295                 300

Lys Asp Ile Lys Asp Ser Leu
305                 310
```

<210> SEQ ID NO 105
<211> LENGTH: 311
<212> TYPE: PRT
<213> ORGANISM: Streptococcus pyogenes

<400> SEQUENCE: 105

```
Ala Val Ile Asp Thr Gly Ile Asp Pro Ala His Gln Ser Met Arg Ile
1               5                   10                  15

Ser Asp Val Ser Thr Ala Lys Val Lys Ser Lys Glu Asp Met Leu Ala
            20                  25                  30

Arg Gln Lys Ala Ala Gly Ile Asn Tyr Gly Ser Trp Ile Asn Asp Lys
        35                  40                  45

Val Val Phe Ala His Asn Tyr Val Glu Asn Ser Asp Asn Ile Lys Glu
```

-continued

```
    50                  55                  60

Asn Gln Phe Glu Asp Phe Asp Glu Asp Trp Glu Asn Phe Glu Phe Asp
65                  70                  75                  80

Ala Asp Ala Glu Pro Lys Ala Ile Lys Lys His Lys Ile Tyr Arg Pro
                85                  90                  95

Gln Ser Thr Gln Ala Pro Lys Glu Thr Val Ile Lys Thr Glu Glu Thr
            100                 105                 110

Asp Gly Ser His Asp Ile Asp Trp Thr Gln Thr Asp Asp Asp Thr Lys
        115                 120                 125

Tyr Glu Ser His Gly Met His Val Thr Gly Ile Val Ala Gly Asn Ser
    130                 135                 140

Lys Glu Ala Ala Ala Thr Gly Glu Arg Phe Leu Gly Ile Ala Pro Glu
145                 150                 155                 160

Ala Gln Val Met Phe Met Arg Val Phe Ala Asn Asp Val Met Gly Ser
                165                 170                 175

Ala Glu Ser Leu Phe Ile Lys Ala Ile Glu Asp Ala Val Ala Leu Gly
            180                 185                 190

Ala Asp Val Ile Asn Leu Ser Leu Gly Thr Ala Asn Gly Ala Gln Leu
        195                 200                 205

Ser Gly Ser Lys Pro Leu Met Glu Ala Ile Glu Lys Ala Lys Lys Ala
    210                 215                 220

Gly Val Ser Val Val Val Ala Ala Gly Asn Glu Arg Val Tyr Gly Ser
225                 230                 235                 240

Asp His Asp Asp Pro Leu Ala Thr Asn Pro Asp Tyr Gly Leu Val Gly
                245                 250                 255

Ser Pro Ser Thr Gly Arg Thr Pro Thr Ser Val Ala Ala Ile Asn Ser
            260                 265                 270

Lys Trp Val Ile Gln Arg Leu Met Thr Val Lys Gly Leu Glu Asn Arg
        275                 280                 285

Ala Asp Leu Asn His Gly Lys Ala Ile Tyr Ser Glu Ser Val Asp Phe
    290                 295                 300

Lys Asp Ile Lys Asp Ser Leu
305                 310


<210> SEQ ID NO 106
<211> LENGTH: 311
<212> TYPE: PRT
<213> ORGANISM: Streptococcus pyogenes

<400> SEQUENCE: 106

Ala Val Ile Asp Thr Gly Ile Asp Pro Ala His Gln Ser Met Arg Ile
1               5                   10                  15

Ser Asp Val Ser Thr Ala Lys Val Lys Ser Lys Glu Asp Met Leu Ala
            20                  25                  30

Arg Gln Lys Ala Ala Gly Ile Asn Tyr Gly Ser Trp Ile Asn Asp Lys
        35                  40                  45

Val Val Phe Ala His Asn Tyr Val Glu Asn Ser Asp Asn Ile Lys Glu
    50                  55                  60

Asn Gln Phe Glu Asp Phe Asp Glu Asp Trp Glu Asn Phe Glu Phe Asp
65                  70                  75                  80

Ala Glu Ala Glu Pro Lys Ala Ile Lys Lys His Lys Ile Tyr Arg Pro
                85                  90                  95

Gln Ser Thr Gln Ala Pro Lys Glu Thr Val Ile Lys Thr Glu Glu Thr
            100                 105                 110

Asp Gly Ser His Asp Ile Asp Trp Thr Gln Thr Asp Asp Asp Thr Lys
```

```
        115                 120                 125

Tyr Glu Ser His Gly Met His Val Thr Gly Ile Val Ala Gly Asn Ser
    130                 135                 140

Lys Glu Ala Ala Ala Thr Gly Glu Arg Phe Leu Gly Ile Ala Pro Glu
145                 150                 155                 160

Ala Gln Val Met Phe Met Arg Val Phe Ala Asn Asp Val Met Gly Ser
                165                 170                 175

Ala Glu Ser Leu Phe Ile Lys Ala Ile Glu Asp Ala Val Ala Leu Gly
            180                 185                 190

Ala Asp Val Ile Asn Leu Ser Leu Gly Thr Ala Asn Gly Ala Gln Leu
        195                 200                 205

Ser Gly Ser Lys Pro Leu Met Glu Ala Ile Glu Lys Ala Lys Lys Ala
    210                 215                 220

Gly Val Ser Val Val Val Ala Ala Gly Asn Glu Arg Val Tyr Gly Ser
225                 230                 235                 240

Asp His Asp Asp Pro Leu Ala Thr Asn Pro Asp Tyr Gly Leu Val Gly
                245                 250                 255

Ser Pro Ser Thr Gly Arg Thr Pro Thr Ser Val Ala Ala Ile Asn Ser
            260                 265                 270

Lys Trp Val Ile Gln Arg Leu Met Thr Val Lys Glu Leu Glu Asn Arg
        275                 280                 285

Ala Asp Leu Asn His Gly Lys Ala Ile Tyr Ser Glu Ser Val Asp Phe
    290                 295                 300

Lys Asn Ile Lys Asp Ser Leu
305                 310


<210> SEQ ID NO 107
<211> LENGTH: 311
<212> TYPE: PRT
<213> ORGANISM: Streptococcus pyogenes

<400> SEQUENCE: 107

Ala Val Ile Asp Thr Gly Ile Asp Pro Ala His Gln Ser Met Arg Ile
1               5                   10                  15

Ser Asp Val Ser Thr Ala Lys Val Lys Ser Lys Glu Asp Met Leu Ala
            20                  25                  30

Arg Gln Lys Ala Ala Gly Ile Asn Tyr Gly Ser Trp Ile Asn Asp Lys
        35                  40                  45

Val Val Phe Ala His Asn Tyr Val Glu Asn Ser Asp Asn Ile Lys Glu
    50                  55                  60

Asn Gln Phe Glu Asp Phe Asp Glu Asp Trp Glu Asn Phe Glu Phe Asp
65                  70                  75                  80

Ala Glu Ala Glu Pro Lys Ala Ile Lys Lys His Lys Ile Tyr Arg Pro
                85                  90                  95

Gln Ser Thr Gln Ala Pro Lys Glu Thr Val Ile Lys Thr Glu Glu Thr
            100                 105                 110

Asp Gly Ser His Asp Ile Asp Trp Thr Gln Thr Asp Asp Asp Thr Lys
        115                 120                 125

Tyr Glu Ser His Gly Met His Val Thr Gly Ile Val Ala Gly Asn Ser
    130                 135                 140

Lys Glu Ala Ala Ala Thr Gly Glu Arg Phe Leu Gly Ile Ala Pro Glu
145                 150                 155                 160

Ala Gln Val Met Phe Met Arg Val Phe Ala Asn Asp Val Met Gly Ser
                165                 170                 175

Ala Glu Ser Leu Phe Ile Lys Ala Ile Glu Asp Ala Val Ala Leu Gly
```

```
            180                 185                 190

Ala Asp Val Ile Asn Leu Ser Leu Gly Thr Ala Asn Gly Ala Gln Leu
        195                 200                 205

Ser Gly Ser Lys Pro Leu Met Glu Ala Ile Glu Lys Ala Lys Lys Ala
    210                 215                 220

Gly Val Ser Val Val Val Ala Ala Gly Asn Glu Arg Val Tyr Gly Ser
225                 230                 235                 240

Asp His Asp Asp Pro Leu Ala Thr Asn Pro Asp Tyr Gly Leu Val Gly
                245                 250                 255

Ser Pro Ser Thr Gly Arg Thr Pro Thr Ser Val Ala Ala Ile Asn Ser
            260                 265                 270

Lys Trp Val Ile Gln Arg Leu Met Thr Val Lys Glu Leu Glu Asn Arg
        275                 280                 285

Ala Asp Leu Asn His Gly Lys Ala Ile Tyr Ser Glu Ser Val Asp Phe
    290                 295                 300

Lys Asn Ile Lys Asp Ser Leu
305                 310


<210> SEQ ID NO 108
<211> LENGTH: 311
<212> TYPE: PRT
<213> ORGANISM: Streptococcus pyogenes

<400> SEQUENCE: 108

Ala Val Ile Asp Thr Gly Ile Asp Pro Ala His Gln Ser Met Arg Ile
1               5                   10                  15

Ser Asp Val Ser Thr Ala Lys Val Lys Ser Lys Glu Asp Met Leu Ala
            20                  25                  30

Arg Gln Lys Ala Ala Gly Ile Asn Tyr Gly Ser Trp Ile Asn Asp Lys
        35                  40                  45

Val Val Phe Ala His Asn Tyr Val Glu Asn Ser Asp Asn Ile Lys Glu
    50                  55                  60

Asn Gln Phe Glu Asp Phe Asp Glu Asp Trp Glu Asn Phe Glu Phe Asp
65                  70                  75                  80

Ala Asp Ala Glu Pro Lys Ala Ile Lys Lys His Lys Ile Tyr Arg Pro
                85                  90                  95

Gln Ser Thr Gln Ala Pro Lys Glu Thr Val Ile Lys Thr Glu Glu Thr
            100                 105                 110

Asp Gly Ser His Asp Ile Asp Trp Thr Gln Thr Asp Asp Asp Thr Lys
        115                 120                 125

Tyr Glu Ser His Gly Met His Val Thr Gly Ile Val Ala Gly Asn Ser
    130                 135                 140

Lys Glu Ala Ala Ala Thr Gly Glu Arg Phe Leu Gly Ile Ala Pro Glu
145                 150                 155                 160

Ala Gln Val Met Phe Met Arg Val Phe Ala Asn Asp Val Met Gly Ser
                165                 170                 175

Ala Glu Ser Leu Phe Ile Lys Ala Ile Glu Asp Ala Val Ala Leu Gly
            180                 185                 190

Ala Asp Val Ile Asn Leu Ser Leu Gly Thr Ala Asn Gly Ala Gln Leu
        195                 200                 205

Ser Gly Ser Lys Pro Leu Met Glu Ala Ile Glu Lys Ala Lys Lys Ala
    210                 215                 220

Gly Val Ser Val Val Val Ala Ala Gly Asn Glu Arg Val Tyr Gly Ser
225                 230                 235                 240

Asp His Asp Asp Pro Leu Ala Thr Asn Pro Asp Tyr Gly Leu Val Gly
```

```
                245                 250                 255

Ser Pro Ser Thr Gly Arg Thr Pro Thr Ser Val Ala Ala Ile Asn Ser
            260                 265                 270

Lys Trp Val Ile Gln Arg Leu Met Thr Val Lys Glu Leu Glu Asn Arg
        275                 280                 285

Ala Asp Leu Asn His Gly Lys Ala Ile Tyr Ser Glu Ser Val Asp Phe
    290                 295                 300

Lys Asp Ile Lys Asp Ser Leu
305                 310


<210> SEQ ID NO 109
<211> LENGTH: 309
<212> TYPE: PRT
<213> ORGANISM: Streptococcus pyogenes

<400> SEQUENCE: 109

Ala Val Ile Asp Thr Gly Ile Asp Pro Ala His Gln Ser Met Arg Ile
1               5                   10                  15

Ser Asp Val Ser Thr Ala Lys Val Lys Ser Lys Glu Asp Met Leu Ala
            20                  25                  30

Arg Gln Lys Ala Ala Gly Ile Asn Tyr Gly Ser Trp Ile Asn Asp Lys
        35                  40                  45

Val Val Phe Ala His Asn Tyr Val Glu Asn Ser Asp Asn Ile Lys Glu
    50                  55                  60

Asn Gln Phe Gly Asp Phe Asp Glu Asp Trp Glu Asn Phe Glu Phe Asp
65                  70                  75                  80

Ala Glu Pro Lys Ala Ile Lys Lys Asn Lys Ile Tyr Arg Pro Gln Ser
                85                  90                  95

Thr Gln Ala Pro Lys Glu Thr Val Ile Lys Thr Glu Glu Thr Asp Gly
            100                 105                 110

Ser His Asp Ile Asp Trp Thr Gln Thr Asp Asp Asp Thr Lys Tyr Glu
        115                 120                 125

Ser His Gly Met His Val Thr Gly Ile Val Ala Gly Asn Ser Lys Glu
    130                 135                 140

Ala Ala Ala Thr Gly Glu Arg Phe Leu Gly Ile Ala Pro Glu Ala Gln
145                 150                 155                 160

Val Met Phe Met Arg Val Phe Ala Asn Asp Val Met Gly Ser Ala Glu
                165                 170                 175

Ser Leu Phe Ile Lys Ala Ile Glu Asp Ala Val Ala Leu Gly Ala Asp
            180                 185                 190

Val Ile Asn Leu Ser Leu Gly Thr Ala Asn Gly Ala Gln Leu Ser Gly
        195                 200                 205

Ser Lys Pro Leu Met Glu Ala Ile Glu Lys Ala Lys Lys Ala Gly Val
    210                 215                 220

Ser Val Val Val Ala Ala Gly Asn Glu Arg Val Tyr Gly Ser Asp His
225                 230                 235                 240

Asp Asp Pro Leu Ala Thr Asn Pro Asp Tyr Gly Leu Val Gly Ser Pro
                245                 250                 255

Ser Thr Gly Arg Thr Pro Thr Ser Val Ala Ala Ile Asn Ser Lys Trp
            260                 265                 270

Val Ile Gln Arg Leu Met Thr Ala Lys Glu Leu Glu Asn Arg Ala Asp
        275                 280                 285

Leu Asn His Gly Lys Ala Ile Tyr Ser Glu Ser Val Asp Phe Lys Asp
    290                 295                 300

Ile Lys Asp Ser Leu
```

305

<210> SEQ ID NO 110
<211> LENGTH: 485
<212> TYPE: PRT
<213> ORGANISM: Streptococcus pyogenes

<400> SEQUENCE: 110

```
Ser Gln Ile Thr Pro Lys Thr Asn Arg Glu Lys Glu Gln Pro Gln Gly
1               5                   10                  15

Leu Val Ser Glu Pro Thr Thr Thr Glu Leu Ala Asp Thr Asp Ala Ala
            20                  25                  30

Ser Met Ala Asn Thr Gly Pro Asp Ala Thr Gln Lys Ser Ala Ser Leu
        35                  40                  45

Pro Pro Val Asn Thr Asp Val His Asp Trp Val Lys Thr Lys Gly Ala
    50                  55                  60

Trp Asp Lys Gly Tyr Lys Gly Gln Gly Lys Val Val Ala Val Ile Asp
65                  70                  75                  80

Thr Gly Ile Asp Pro Ala His Gln Ser Met Arg Ile Ser Asp Val Ser
                85                  90                  95

Thr Ala Lys Val Lys Ser Lys Glu Asp Met Leu Ala Arg Gln Lys Ala
            100                 105                 110

Ala Gly Ile Asn Tyr Gly Ser Trp Ile Asn Asp Lys Val Val Phe Ala
        115                 120                 125

His Asn Tyr Val Glu Asn Ser Asp Asn Ile Lys Glu Asn Gln Phe Gly
    130                 135                 140

Asp Phe Asp Glu Asp Trp Glu Asn Phe Glu Phe Asp Ala Glu Pro Lys
145                 150                 155                 160

Ala Ile Lys Lys Asn Lys Ile Tyr Arg Pro Gln Ser Thr Gln Ala Pro
                165                 170                 175

Lys Glu Thr Val Ile Lys Thr Glu Glu Thr Asp Gly Ser His Asp Ile
            180                 185                 190

Asp Trp Thr Gln Thr Asp Asp Asp Thr Lys Tyr Glu Ser His Gly Met
        195                 200                 205

His Val Thr Gly Ile Val Ala Gly Asn Ser Lys Glu Ala Ala Ala Thr
    210                 215                 220

Gly Glu Arg Phe Leu Gly Ile Ala Pro Glu Ala Gln Val Met Phe Met
225                 230                 235                 240

Arg Val Phe Ala Asn Asp Val Met Gly Ser Ala Glu Ser Leu Phe Ile
                245                 250                 255

Lys Ala Ile Glu Asp Ala Val Ala Leu Gly Ala Asp Val Ile Asn Leu
            260                 265                 270

Ser Leu Gly Thr Ala Asn Gly Ala Gln Leu Ser Gly Ser Lys Pro Leu
        275                 280                 285

Met Glu Ala Ile Glu Lys Ala Lys Lys Ala Gly Val Ser Val Val Val
    290                 295                 300

Ala Ala Gly Asn Glu Arg Val Tyr Gly Ser Asp His Asp Asp Pro Leu
305                 310                 315                 320

Ala Thr Asn Pro Asp Tyr Gly Leu Val Gly Ser Pro Ser Thr Gly Arg
                325                 330                 335

Thr Pro Thr Ser Val Ala Ala Ile Asn Ser Lys Trp Val Ile Gln Arg
            340                 345                 350

Leu Met Thr Ala Lys Glu Leu Glu Asn Arg Ala Asp Leu Asn His Gly
        355                 360                 365

Lys Ala Ile Tyr Ser Glu Ser Val Asp Phe Lys Asp Ile Lys Asp Ser
```

```
    370                 375                 380

Leu Gly Tyr Asp Lys Ser His Gln Phe Ala Tyr Val Lys Glu Ser Thr
385                 390                 395                 400

Asp Ala Gly Tyr Lys Ala Gln Asp Val Lys Asp Lys Ile Ala Leu Ile
                405                 410                 415

Glu Arg Asp Pro Asn Lys Thr Tyr Asp Glu Met Ile Ala Leu Ala Lys
            420                 425                 430

Lys His Gly Ala Leu Gly Val Leu Ile Phe Asn Asn Lys Pro Gly Gln
        435                 440                 445

Ser Asn Arg Ser Met Arg Leu Thr Ala Asn Gly Met Gly Ile Pro Ser
    450                 455                 460

Ala Phe Ile Ser His Glu Phe Gly Lys Ala Met Ser Gln Leu Asn Gly
465                 470                 475                 480

Asn Gly Thr Gly Ser
                485


<210> SEQ ID NO 111
<211> LENGTH: 487
<212> TYPE: PRT
<213> ORGANISM: Streptococcus pyogenes

<400> SEQUENCE: 111

Ser Gln Ile Thr Leu Lys Thr Asn Arg Glu Lys Glu Gln Pro Gln Gly
1               5                   10                  15

Leu Val Ser Glu Pro Thr Thr Thr Glu Leu Ala Asp Thr Asp Ala Ala
            20                  25                  30

Pro Met Ala Asn Thr Gly Pro Asp Ala Thr Gln Lys Ser Ala Ser Leu
        35                  40                  45

Pro Pro Val Asn Thr Asp Val His Asp Trp Val Lys Thr Lys Gly Ala
    50                  55                  60

Trp Asp Lys Gly Tyr Lys Gly Gln Gly Lys Val Val Ala Val Ile Asp
65                  70                  75                  80

Thr Gly Ile Asp Pro Ala His Gln Ser Met Arg Ile Ser Asp Val Ser
                85                  90                  95

Thr Ala Lys Val Lys Ser Lys Glu Asp Met Leu Ala Arg Gln Lys Ala
            100                 105                 110

Ala Gly Ile Asn Tyr Gly Ser Trp Ile Asn Asp Lys Val Val Phe Ala
        115                 120                 125

His Asn Tyr Val Glu Asn Ser Asp Asn Ile Lys Glu Asn Gln Phe Glu
    130                 135                 140

Asp Phe Asp Glu Asp Trp Glu Asn Phe Glu Phe Asp Ala Glu Ala Glu
145                 150                 155                 160

Pro Lys Ala Ile Lys Lys His Lys Ile Tyr Arg Pro Gln Ser Thr Gln
                165                 170                 175

Ala Pro Lys Glu Thr Val Ile Lys Thr Glu Glu Thr Asp Gly Ser His
            180                 185                 190

Asp Ile Asp Trp Thr Gln Thr Asp Asp Asp Thr Lys Tyr Glu Ser His
        195                 200                 205

Gly Met His Val Thr Gly Ile Val Ala Gly Asn Ser Lys Glu Ala Ala
    210                 215                 220

Ala Thr Gly Glu Arg Phe Leu Gly Ile Ala Pro Glu Ala Gln Val Met
225                 230                 235                 240

Phe Met Arg Val Phe Ala Asn Asp Val Met Gly Ser Ala Glu Ser Leu
                245                 250                 255

Phe Ile Lys Ala Ile Glu Asp Ala Val Ala Leu Gly Ala Asp Val Ile
```

```
            260                 265                 270

Asn Leu Ser Leu Gly Thr Ala Asn Gly Ala Gln Leu Ser Gly Ser Lys
        275                 280                 285

Pro Leu Met Glu Ala Ile Glu Lys Ala Lys Lys Ala Gly Val Ser Val
    290                 295                 300

Val Val Ala Ala Gly Asn Glu Arg Val Tyr Gly Ser Asp His Asp Asp
305                 310                 315                 320

Pro Leu Ala Thr Asn Pro Asp Tyr Gly Leu Val Gly Ser Pro Ser Thr
                325                 330                 335

Gly Arg Thr Pro Thr Ser Val Ala Ala Ile Asn Ser Lys Trp Val Ile
            340                 345                 350

Gln Arg Leu Met Thr Val Lys Glu Leu Glu Asn Arg Ala Asp Leu Asn
        355                 360                 365

His Gly Lys Ala Ile Tyr Ser Glu Ser Val Asp Phe Lys Asp Ile Lys
    370                 375                 380

Asp Ser Leu Gly Tyr Asp Lys Ser His Gln Phe Ala Tyr Val Lys Glu
385                 390                 395                 400

Ser Thr Asp Ala Gly Tyr Asn Ala Gln Asp Val Lys Gly Lys Ile Ala
                405                 410                 415

Leu Ile Glu Arg Asp Pro Asn Lys Thr Tyr Asp Glu Met Ile Ala Leu
            420                 425                 430

Ala Lys Lys His Gly Ala Leu Gly Val Leu Ile Phe Asn Asn Lys Pro
        435                 440                 445

Gly Gln Ser Asn Arg Ser Met Arg Leu Thr Ala Asn Gly Met Gly Ile
    450                 455                 460

Pro Ser Ala Phe Ile Ser His Glu Phe Gly Lys Ala Met Ser Gln Leu
465                 470                 475                 480

Asn Gly Asn Gly Thr Gly Ser
                485


<210> SEQ ID NO 112
<211> LENGTH: 487
<212> TYPE: PRT
<213> ORGANISM: Streptococcus pyogenes

<400> SEQUENCE: 112

Ser Gln Val Thr Pro Glu Thr Asn Arg Glu Lys Glu Gln Pro Gln Gly
1               5                   10                  15

Leu Val Ser Glu Pro Thr Thr Thr Glu Leu Ala Asp Thr Asp Ala Ala
            20                  25                  30

Pro Met Ala Asn Thr Gly Ser Asp Ala Thr Gln Lys Ser Ala Ser Leu
        35                  40                  45

Pro Pro Val Asn Thr Asp Val His Asp Trp Val Lys Thr Lys Gly Ala
    50                  55                  60

Trp Asp Lys Gly Tyr Lys Gly Gln Gly Lys Val Val Ala Val Ile Asp
65                  70                  75                  80

Thr Gly Ile Asp Pro Ala His Gln Ser Met Arg Ile Ser Asp Val Ser
                85                  90                  95

Thr Ala Lys Val Lys Ser Lys Glu Asp Met Leu Ala Arg Gln Lys Ala
            100                 105                 110

Ala Gly Ile Asn Tyr Gly Ser Trp Ile Asn Asp Lys Val Val Phe Ala
        115                 120                 125

His Asn Tyr Val Glu Asn Ser Asp Asn Ile Lys Glu Asn Gln Phe Glu
    130                 135                 140

Asp Phe Asp Glu Asp Trp Glu Asn Phe Glu Phe Asp Ala Glu Ala Glu
```

```
145                 150                 155                 160

Pro Lys Ala Ile Lys Lys His Lys Ile Tyr Arg Pro Gln Ser Thr Gln
                165                 170                 175

Ala Pro Lys Glu Thr Val Ile Lys Thr Glu Glu Thr Asp Gly Ser His
            180                 185                 190

Asp Ile Asp Trp Thr Gln Thr Asp Asp Asp Thr Lys Tyr Glu Ser His
        195                 200                 205

Gly Met His Val Thr Gly Ile Val Ala Gly Asn Ser Lys Glu Ala Ala
    210                 215                 220

Ala Thr Gly Glu Arg Phe Leu Gly Ile Ala Pro Glu Ala Gln Val Met
225                 230                 235                 240

Phe Met Arg Val Phe Ala Asn Asp Val Met Gly Ser Ala Glu Ser Leu
                245                 250                 255

Phe Ile Lys Ala Ile Glu Asp Ala Val Ala Leu Gly Ala Asp Val Ile
            260                 265                 270

Asn Leu Ser Leu Gly Thr Ala Asn Gly Ala Gln Leu Ser Gly Ser Lys
        275                 280                 285

Pro Leu Met Glu Ala Ile Glu Lys Ala Lys Lys Ala Gly Val Ser Val
    290                 295                 300

Val Val Ala Ala Gly Asn Glu Arg Val Tyr Gly Ser Asp His Asp Asp
305                 310                 315                 320

Pro Leu Ala Thr Asn Pro Asp Tyr Gly Leu Val Gly Ser Pro Ser Thr
                325                 330                 335

Gly Arg Thr Pro Thr Ser Val Ala Ala Ile Asn Ser Lys Trp Val Ile
            340                 345                 350

Gln Arg Leu Met Thr Val Lys Glu Leu Glu Asn Arg Ala Asp Leu Asn
        355                 360                 365

His Gly Lys Ala Ile Tyr Ser Glu Ser Val Asp Phe Lys Asp Ile Lys
    370                 375                 380

Asp Ser Leu Gly Tyr Asp Lys Ser His Gln Phe Ala Tyr Val Lys Glu
385                 390                 395                 400

Ser Thr Asp Ala Gly Tyr Asn Ala Gln Asn Val Lys Gly Lys Ile Ala
                405                 410                 415

Leu Ile Glu Arg Asp Pro Asn Lys Thr Tyr Asp Glu Met Ile Ala Leu
            420                 425                 430

Ala Lys Lys His Gly Ala Leu Gly Val Leu Ile Phe Asn Asn Lys Pro
        435                 440                 445

Gly Gln Ser Asn Arg Ser Met Arg Leu Thr Ala Asn Gly Met Gly Ile
    450                 455                 460

Pro Ser Ala Phe Ile Ser His Glu Phe Gly Lys Ala Met Ser Gln Leu
465                 470                 475                 480

Asn Gly Asn Gly Thr Gly Ser
                485


<210> SEQ ID NO 113
<211> LENGTH: 485
<212> TYPE: PRT
<213> ORGANISM: Streptococcus pyogenes

<400> SEQUENCE: 113

Ser Gln Ile Thr Pro Lys Ile Asn Arg Glu Lys Glu Gln Pro Gln Gly
1               5                   10                  15

Leu Val Ser Glu Pro Thr Thr Thr Glu Leu Ala Asp Thr Asp Ala Ala
            20                  25                  30

Pro Met Ala Asn Thr Gly Pro Asp Ala Thr Gln Lys Ser Ala Ser Leu
```

-continued

```
        35                  40                  45

Pro Pro Val Asn Thr Asp Val His Asp Trp Val Lys Thr Lys Gly Ala
    50                  55                  60

Trp Asp Lys Gly Tyr Lys Gly Gln Gly Lys Val Val Ala Val Ile Asp
65                  70                  75                  80

Thr Gly Ile Asp Pro Ala His Gln Ser Met Arg Ile Ser Asp Val Ser
                85                  90                  95

Thr Ala Lys Val Lys Ser Lys Glu Asp Met Leu Ala Arg Gln Lys Ala
            100                 105                 110

Ala Gly Ile Asn Tyr Gly Ser Trp Ile Asn Asp Lys Val Val Phe Ala
        115                 120                 125

His Asn Tyr Val Glu Asn Ser Asp Asn Ile Lys Glu Asn Gln Phe Glu
    130                 135                 140

Asp Phe Asp Glu Asp Trp Glu Asn Phe Glu Phe Asp Ala Glu Pro Lys
145                 150                 155                 160

Ala Ile Lys Lys His Lys Ile Tyr Arg Pro Gln Ser Thr Gln Ala Pro
                165                 170                 175

Lys Glu Thr Val Ile Lys Thr Glu Glu Thr Asp Gly Ser His Asp Ile
            180                 185                 190

Asp Trp Thr Gln Thr Asp Asp Asp Thr Lys Tyr Glu Ser His Gly Met
        195                 200                 205

His Val Thr Gly Ile Val Ala Gly Asn Ser Lys Glu Ala Ala Ala Thr
    210                 215                 220

Gly Glu Arg Phe Leu Gly Ile Ala Pro Glu Thr Gln Val Met Phe Met
225                 230                 235                 240

Arg Val Phe Ala Asn Asp Val Met Gly Ser Ala Glu Ser Leu Phe Ile
                245                 250                 255

Lys Ala Ile Glu Asp Ala Val Ala Leu Gly Ala Asp Val Ile Asn Leu
            260                 265                 270

Ser Leu Gly Thr Ala Asn Gly Ala Gln Leu Ser Gly Ser Lys Pro Leu
        275                 280                 285

Met Glu Ala Ile Glu Lys Ala Lys Lys Ala Gly Val Ser Val Val Val
    290                 295                 300

Ala Ala Gly Asn Glu Arg Val Tyr Gly Ser Asp His Asp Asp Pro Leu
305                 310                 315                 320

Ala Thr Asn Pro Asp Tyr Gly Leu Val Gly Ser Pro Ser Thr Gly Arg
                325                 330                 335

Thr Pro Thr Ser Val Ala Ala Ile Asn Ser Lys Trp Val Ile Gln Arg
            340                 345                 350

Leu Met Thr Val Lys Glu Leu Glu Asn Arg Ala Asp Leu Asn His Gly
        355                 360                 365

Lys Ala Ile Tyr Ser Glu Ser Val Asp Phe Lys Asp Ile Lys Asp Ser
    370                 375                 380

Leu Gly Tyr Asp Lys Ser His Gln Phe Ala Tyr Val Lys Glu Ser Thr
385                 390                 395                 400

Asp Ala Gly Tyr Asn Ala Gln Asp Val Lys Gly Lys Ile Ala Leu Ile
                405                 410                 415

Glu Arg Asp Pro Asn Lys Thr Tyr Asp Glu Met Ile Ala Leu Ala Lys
            420                 425                 430

Lys His Gly Ala Leu Gly Val Leu Ile Phe Asn Asn Lys Pro Gly Gln
        435                 440                 445

Ser Asn Arg Ser Met Arg Leu Thr Ala Asn Gly Met Gly Ile Pro Ser
    450                 455                 460
```

```
Ala Phe Ile Ser His Glu Phe Gly Lys Ala Met Ser Gln Leu Asn Gly
465                 470                 475                 480

Asn Gly Thr Gly Ser
                485


<210> SEQ ID NO 114
<211> LENGTH: 487
<212> TYPE: PRT
<213> ORGANISM: Streptococcus pyogenes

<400> SEQUENCE: 114

Ser Gln Ile Thr Leu Lys Thr Asn Arg Glu Lys Glu Gln Ser Gln Asp
1               5                   10                  15

Leu Val Ser Glu Pro Thr Thr Thr Glu Leu Ala Asp Thr Asp Ala Ala
            20                  25                  30

Ser Met Ala Asn Thr Gly Ser Asp Ala Thr Gln Lys Ser Ala Ser Leu
        35                  40                  45

Pro Pro Val Asn Thr Asp Val His Asp Trp Val Lys Thr Lys Gly Ala
    50                  55                  60

Trp Asp Lys Gly Tyr Lys Gly Gln Gly Lys Val Val Ala Val Ile Asp
65                  70                  75                  80

Thr Gly Ile Asp Pro Ala His Gln Ser Met Arg Ile Ser Asp Val Ser
                85                  90                  95

Thr Ala Lys Val Lys Ser Lys Glu Asp Met Leu Ala Arg Gln Lys Ala
            100                 105                 110

Ala Gly Ile Asn Tyr Gly Ser Trp Ile Asn Asp Lys Val Val Phe Ala
        115                 120                 125

His Asn Tyr Val Glu Asn Ser Asp Asn Ile Lys Glu Asn Gln Phe Glu
    130                 135                 140

Asp Phe Asp Glu Asp Trp Glu Asn Phe Glu Phe Asp Ala Glu Ala Glu
145                 150                 155                 160

Pro Lys Ala Ile Lys Lys His Lys Ile Tyr Arg Pro Gln Ser Thr Gln
                165                 170                 175

Ala Pro Lys Glu Thr Val Ile Lys Thr Glu Glu Thr Asp Gly Ser His
            180                 185                 190

Asp Ile Asp Trp Thr Gln Thr Asp Asp Asp Thr Lys Tyr Glu Ser His
        195                 200                 205

Gly Met His Val Thr Gly Ile Val Ala Gly Asn Ser Lys Glu Ala Ala
    210                 215                 220

Ala Thr Gly Glu Arg Phe Leu Gly Ile Ala Pro Glu Ala Gln Val Met
225                 230                 235                 240

Phe Met Arg Val Phe Ala Asn Asp Ile Met Gly Ser Ala Glu Ser Leu
                245                 250                 255

Phe Ile Lys Ala Ile Glu Asp Ala Val Ala Leu Gly Ala Asp Val Ile
            260                 265                 270

Asn Leu Ser Leu Gly Thr Ala Asn Gly Ala Gln Leu Ser Gly Ser Lys
        275                 280                 285

Pro Leu Met Glu Ala Ile Glu Lys Ala Lys Lys Ala Gly Val Ser Val
    290                 295                 300

Val Val Ala Ala Gly Asn Glu Arg Val Tyr Gly Ser Asp His Asp Asp
305                 310                 315                 320

Pro Leu Ala Thr Asn Pro Asp Tyr Gly Leu Val Gly Ser Pro Ser Thr
                325                 330                 335

Gly Arg Thr Pro Thr Ser Val Ala Ala Ile Asn Ser Lys Trp Val Ile
            340                 345                 350
```

```
Gln Arg Leu Met Thr Val Lys Glu Leu Glu Asn Arg Ala Asp Leu Asn
        355                 360                 365

His Gly Lys Ala Ile Tyr Ser Glu Ser Val Asp Phe Lys Asp Ile Lys
    370                 375                 380

Asp Ser Leu Gly Tyr Asp Lys Ser His Gln Phe Ala Tyr Val Lys Glu
385                 390                 395                 400

Ser Thr Asp Ala Gly Tyr Asn Ala Gln Asp Val Lys Gly Lys Ile Ala
                405                 410                 415

Leu Ile Glu Arg Asp Pro Asn Lys Thr Tyr Asp Glu Met Ile Ala Leu
            420                 425                 430

Ala Lys Lys His Gly Ala Leu Gly Val Leu Ile Phe Asn Asn Lys Pro
        435                 440                 445

Gly Gln Ser Asn Arg Ser Met Arg Leu Thr Ala Asn Gly Met Gly Ile
    450                 455                 460

Pro Ser Ala Phe Ile Ser His Glu Phe Gly Lys Ala Met Ser Gln Leu
465                 470                 475                 480

Asn Gly Asn Gly Thr Gly Ser
                485


<210> SEQ ID NO 115
<211> LENGTH: 487
<212> TYPE: PRT
<213> ORGANISM: Streptococcus pyogenes

<400> SEQUENCE: 115

Ser Gln Val Thr Pro Glu Thr Asn Arg Glu Lys Glu Gln Pro Gln Gly
1               5                   10                  15

Leu Val Ser Glu Pro Thr Thr Thr Glu Leu Ala Asp Thr Asp Ala Ala
            20                  25                  30

Pro Met Ala Asn Thr Gly Pro Asp Ala Thr Gln Lys Ser Ala Ser Leu
        35                  40                  45

Pro Pro Val Asn Thr Asp Val His Asp Trp Val Lys Thr Lys Gly Ala
    50                  55                  60

Trp Asp Lys Gly Tyr Lys Gly Gln Gly Lys Val Val Ala Val Ile Asp
65                  70                  75                  80

Thr Gly Ile Asp Pro Ala His Gln Ser Met Arg Ile Ser Asp Val Ser
                85                  90                  95

Thr Ala Lys Val Lys Ser Lys Glu Asp Met Leu Ala Arg Gln Lys Ala
            100                 105                 110

Ala Gly Ile Asn Tyr Gly Ser Trp Ile Asn Asp Lys Val Val Phe Ala
        115                 120                 125

His Asn Tyr Val Glu Asn Ser Asp Asn Ile Lys Glu Asn Gln Phe Glu
    130                 135                 140

Asp Phe Asp Glu Asp Trp Glu Asn Phe Glu Phe Asp Ala Asp Ala Glu
145                 150                 155                 160

Pro Lys Ala Ile Lys Lys His Lys Ile Tyr Arg Pro Gln Ser Thr Gln
                165                 170                 175

Ala Pro Lys Glu Thr Val Ile Lys Thr Glu Glu Thr Asp Gly Ser His
            180                 185                 190

Asp Ile Asp Trp Thr Gln Thr Asp Asp Asp Thr Lys Tyr Glu Ser His
        195                 200                 205

Gly Met His Val Thr Gly Ile Val Ala Gly Asn Ser Lys Glu Ala Ala
    210                 215                 220

Ala Thr Gly Glu Arg Phe Leu Gly Ile Ala Pro Glu Ala Gln Val Met
225                 230                 235                 240
```

Phe Met Arg Val Phe Ala Asn Asp Val Met Gly Ser Ala Glu Ser Leu
245 250 255

Phe Ile Lys Ala Ile Glu Asp Ala Val Ala Leu Gly Ala Asp Val Ile
260 265 270

Asn Leu Ser Leu Gly Thr Ala Asn Gly Ala Gln Leu Ser Gly Ser Lys
275 280 285

Pro Leu Met Glu Ala Ile Glu Lys Ala Lys Lys Ala Gly Val Ser Val
290 295 300

Val Val Ala Ala Gly Asn Glu Arg Val Tyr Gly Ser Asp His Asp Asp
305 310 315 320

Pro Leu Ala Thr Asn Pro Asp Tyr Gly Leu Val Gly Ser Pro Ser Thr
325 330 335

Gly Arg Thr Pro Thr Ser Val Ala Ala Ile Asn Ser Lys Trp Val Ile
340 345 350

Gln Arg Leu Met Thr Val Lys Gly Leu Glu Asn Arg Ala Asp Leu Asn
355 360 365

His Gly Lys Ala Ile Tyr Ser Glu Ser Val Asp Phe Lys Asp Ile Lys
370 375 380

Asp Ser Leu Gly Tyr Asp Lys Ser His Gln Phe Ala Tyr Val Lys Glu
385 390 395 400

Ser Thr Asp Ala Gly Tyr Asn Ala Gln Asp Val Lys Gly Lys Ile Ala
405 410 415

Leu Ile Glu Arg Asp Pro Asn Lys Thr Tyr Asp Glu Met Ile Ala Leu
420 425 430

Ala Lys Lys His Gly Ala Leu Gly Leu Leu Ile Phe Asn Asn Lys Ser
435 440 445

Gly Gln Ser Asn Arg Ser Met Arg Leu Thr Ala Asn Gly Met Gly Ile
450 455 460

Pro Ser Ala Phe Ile Ser His Glu Phe Gly Lys Ala Met Ser Gln Leu
465 470 475 480

Asn Gly Asn Gly Thr Gly Ser
485

<210> SEQ ID NO 116
<211> LENGTH: 487
<212> TYPE: PRT
<213> ORGANISM: Streptococcus pyogenes

<400> SEQUENCE: 116

Ser Gln Ile Thr Pro Lys Thr Asn Arg Glu Lys Glu Gln Ser Gln Asp
1 5 10 15

Leu Val Ser Glu Pro Thr Thr Thr Glu Leu Ala Asp Thr Asp Ala Ala
20 25 30

Ser Met Ala Asn Thr Gly Pro Asp Ala Thr Gln Lys Ser Ala Ser Leu
35 40 45

Pro Pro Val Asn Thr Asp Val His Asp Trp Val Lys Thr Lys Gly Ala
50 55 60

Trp Asp Lys Gly Tyr Lys Gly Gln Gly Lys Val Val Ala Val Ile Asp
65 70 75 80

Thr Gly Ile Asp Pro Ala His Gln Ser Met Arg Ile Ser Asp Val Ser
85 90 95

Thr Ala Lys Val Lys Ser Lys Glu Asp Met Leu Ala Arg Gln Lys Ala
100 105 110

Ala Gly Ile Asn Tyr Gly Ser Trp Ile Asn Asp Lys Val Val Phe Ala
115 120 125

```
His Asn Tyr Val Glu Asn Ser Asp Asn Ile Lys Glu Asn Gln Phe Glu
    130                 135                 140

Asp Phe Asp Glu Asp Trp Glu Asn Phe Glu Phe Asp Ala Glu Ala Glu
145                 150                 155                 160

Pro Lys Ala Ile Lys Lys His Lys Ile Tyr Arg Pro Gln Ser Thr Gln
                165                 170                 175

Ala Pro Lys Glu Thr Val Ile Lys Thr Glu Glu Thr Asp Gly Ser His
            180                 185                 190

Asp Ile Asp Trp Thr Gln Thr Asp Asp Asp Thr Lys Tyr Glu Ser His
        195                 200                 205

Gly Met His Val Thr Gly Ile Val Ala Gly Asn Ser Lys Glu Ala Ala
    210                 215                 220

Ala Thr Gly Glu Arg Phe Leu Gly Ile Ala Pro Glu Ala Gln Val Met
225                 230                 235                 240

Phe Met Arg Val Phe Ala Asn Asp Val Met Gly Ser Ala Glu Ser Leu
                245                 250                 255

Phe Ile Lys Ala Ile Glu Asp Ala Val Ala Leu Gly Ala Asp Val Ile
            260                 265                 270

Asn Leu Ser Leu Gly Thr Ala Asn Gly Ala Gln Leu Ser Gly Ser Lys
        275                 280                 285

Pro Leu Met Glu Ala Ile Glu Lys Ala Lys Lys Ala Gly Val Ser Val
    290                 295                 300

Val Val Ala Ala Gly Asn Glu Arg Val Tyr Gly Ser Asp His Asp Asp
305                 310                 315                 320

Pro Leu Ala Thr Asn Pro Asp Tyr Gly Leu Val Gly Ser Pro Ser Thr
                325                 330                 335

Gly Arg Thr Pro Thr Ser Val Ala Ala Ile Asn Ser Lys Trp Val Ile
            340                 345                 350

Gln Arg Leu Met Thr Val Lys Glu Leu Glu Asn Arg Ala Asp Leu Asn
        355                 360                 365

His Gly Lys Ala Ile Tyr Ser Glu Ser Val Asp Phe Lys Asn Ile Lys
    370                 375                 380

Asp Ser Leu Gly Tyr Asp Lys Ser His Gln Phe Ala Tyr Val Lys Glu
385                 390                 395                 400

Ser Thr Asp Ala Gly Tyr Asn Ala Gln Asp Val Lys Gly Lys Ile Ala
                405                 410                 415

Leu Ile Glu Arg Asp Pro Asn Lys Thr Tyr Asp Glu Met Ile Ala Leu
            420                 425                 430

Ala Lys Lys His Gly Ala Leu Gly Val Leu Ile Phe Asn Asn Lys Pro
        435                 440                 445

Gly Gln Ser Asn Arg Ser Met Arg Leu Thr Ser Asn Gly Met Gly Ile
    450                 455                 460

Pro Ser Ala Phe Ile Ser His Glu Phe Gly Lys Ala Met Ser Gln Leu
465                 470                 475                 480

Asn Gly Asn Gly Thr Gly Ser
                485


<210> SEQ ID NO 117
<211> LENGTH: 487
<212> TYPE: PRT
<213> ORGANISM: Streptococcus pyogenes

<400> SEQUENCE: 117

Ser Gln Ile Thr Leu Lys Thr Asn Arg Glu Lys Glu Gln Pro Gln Gly
1               5                   10                  15
```

-continued

```
Leu Val Ser Glu Pro Thr Thr Thr Glu Leu Ala Asp Thr Asp Ala Ala
            20                  25                  30

Pro Met Ala Asn Thr Gly Pro Asp Ala Thr Gln Lys Ser Ala Ser Leu
        35                  40                  45

Pro Pro Val Asn Thr Asp Val His Asp Trp Val Lys Thr Lys Gly Ala
    50                  55                  60

Trp Asp Lys Gly Tyr Lys Gly Gln Gly Lys Val Val Ala Val Ile Asp
65                  70                  75                  80

Thr Gly Ile Asp Pro Ala His Gln Ser Met Arg Ile Ser Asp Val Ser
                85                  90                  95

Thr Ala Lys Val Lys Ser Lys Glu Asp Met Leu Ala Arg Gln Lys Ala
            100                 105                 110

Ala Gly Ile Asn Tyr Gly Ser Trp Ile Asn Asp Lys Val Val Phe Ala
        115                 120                 125

His Asn Tyr Val Glu Asn Ser Asp Asn Ile Lys Glu Asn Gln Phe Glu
    130                 135                 140

Asp Phe Asp Glu Asp Trp Glu Asn Phe Glu Phe Asp Ala Glu Ala Glu
145                 150                 155                 160

Pro Lys Ala Ile Lys Lys His Lys Ile Tyr Arg Pro Gln Ser Thr Gln
                165                 170                 175

Ala Pro Lys Glu Thr Val Ile Lys Thr Glu Glu Thr Asp Gly Ser His
            180                 185                 190

Asp Ile Asp Trp Thr Gln Thr Asp Asp Asp Thr Lys Tyr Glu Ser His
        195                 200                 205

Gly Met His Val Thr Gly Ile Val Ala Gly Asn Ser Lys Glu Ala Ala
    210                 215                 220

Ala Thr Gly Glu Arg Phe Leu Gly Ile Ala Pro Glu Ala Gln Val Met
225                 230                 235                 240

Phe Met Arg Val Phe Ala Asn Asp Val Met Gly Ser Ala Glu Ser Leu
                245                 250                 255

Phe Ile Lys Ala Ile Glu Asp Ala Val Ala Leu Gly Ala Asp Val Ile
            260                 265                 270

Asn Leu Ser Leu Gly Thr Ala Asn Gly Ala Gln Leu Ser Gly Ser Lys
        275                 280                 285

Pro Leu Met Glu Ala Ile Glu Lys Ala Lys Lys Ala Gly Val Ser Val
    290                 295                 300

Val Val Ala Ala Gly Asn Glu Arg Val Tyr Gly Ser Asp His Asp Asp
305                 310                 315                 320

Pro Leu Ala Thr Asn Pro Asp Tyr Gly Leu Val Gly Ser Pro Ser Thr
                325                 330                 335

Gly Arg Thr Pro Thr Ser Val Ala Ala Ile Asn Ser Lys Trp Val Ile
            340                 345                 350

Gln Arg Leu Met Thr Val Lys Glu Leu Glu Asn Arg Ala Asp Leu Asn
        355                 360                 365

His Gly Lys Ala Ile Tyr Ser Glu Ser Val Asp Phe Lys Asn Ile Lys
    370                 375                 380

Asp Ser Leu Gly Tyr Asp Lys Ser His Gln Phe Ala Tyr Val Lys Glu
385                 390                 395                 400

Ser Thr Asp Ala Gly Tyr Lys Ala Gln Asp Val Lys Gly Lys Ile Ala
                405                 410                 415

Leu Ile Glu Arg Asp Pro Asn Lys Thr Tyr Asp Glu Met Ile Ala Leu
            420                 425                 430

Ala Lys Lys His Gly Ala Leu Gly Val Leu Ile Phe Asn Asn Lys Pro
        435                 440                 445
```

Gly Gln Ser Asn Arg Ser Met Arg Leu Thr Ala Asn Gly Met Gly Ile
    450                 455                 460

Pro Ser Ala Phe Ile Ser His Glu Phe Gly Lys Ala Met Ser Gln Leu
465                 470                 475                 480

Asn Gly Asn Gly Thr Gly Ser
                485

<210> SEQ ID NO 118
<211> LENGTH: 487
<212> TYPE: PRT
<213> ORGANISM: Streptococcus pyogenes

<400> SEQUENCE: 118

Ser Gln Ile Thr Pro Lys Thr Asn Arg Glu Lys Glu Gln Ser Gln Asp
1               5                   10                  15

Leu Val Ser Glu Pro Thr Thr Thr Glu Leu Ala Asp Thr Asp Ala Ala
            20                  25                  30

Ser Met Ala Asn Thr Gly Ser Asp Ala Thr Gln Lys Ser Ala Ser Leu
        35                  40                  45

Pro Pro Val Asn Thr Asp Val His Asp Trp Val Lys Thr Lys Gly Ala
    50                  55                  60

Trp Asp Lys Gly Tyr Lys Gly Gln Gly Lys Val Val Ala Val Ile Asp
65                  70                  75                  80

Thr Gly Ile Asp Pro Ala His Gln Ser Met Arg Ile Ser Asp Val Ser
                85                  90                  95

Thr Ala Lys Val Lys Ser Lys Glu Asp Met Leu Ala Arg Gln Lys Ala
            100                 105                 110

Ala Gly Ile Asn Tyr Gly Ser Trp Ile Asn Asp Lys Val Val Phe Ala
        115                 120                 125

His Asn Tyr Val Glu Asn Ser Asp Asn Ile Lys Glu Asn Gln Phe Glu
    130                 135                 140

Asp Phe Asp Glu Asp Trp Glu Asn Phe Glu Phe Asp Ala Asp Ala Glu
145                 150                 155                 160

Pro Lys Ala Ile Lys Lys His Lys Ile Tyr Arg Pro Gln Ser Thr Gln
                165                 170                 175

Ala Pro Lys Glu Thr Val Ile Lys Thr Glu Glu Thr Asp Gly Ser His
            180                 185                 190

Asp Ile Asp Trp Thr Gln Thr Asp Asp Asp Thr Lys Tyr Glu Ser His
        195                 200                 205

Gly Met His Val Thr Gly Ile Val Ala Gly Asn Ser Lys Glu Ala Ala
    210                 215                 220

Ala Thr Gly Glu Arg Phe Leu Gly Ile Ala Pro Glu Ala Gln Val Met
225                 230                 235                 240

Phe Met Arg Val Phe Ala Asn Asp Val Met Gly Ser Ala Glu Ser Leu
                245                 250                 255

Phe Ile Lys Ala Ile Glu Asp Ala Val Ala Leu Gly Ala Asp Val Ile
            260                 265                 270

Asn Leu Ser Leu Gly Thr Ala Asn Gly Ala Gln Leu Ser Gly Ser Lys
        275                 280                 285

Pro Leu Met Glu Ala Ile Glu Lys Ala Lys Lys Ala Gly Val Ser Val
    290                 295                 300

Val Val Ala Ala Gly Asn Glu Arg Val Tyr Gly Ser Asp His Asp Asp
305                 310                 315                 320

Pro Leu Ala Thr Asn Pro Asp Tyr Gly Leu Val Gly Ser Pro Ser Thr
                325                 330                 335

```
Gly Arg Thr Pro Thr Ser Val Ala Ala Ile Asn Ser Lys Trp Val Ile
            340                 345                 350

Gln Arg Leu Met Thr Val Lys Glu Leu Glu Asn Arg Ala Asp Leu Asn
        355                 360                 365

His Gly Lys Ala Ile Tyr Ser Glu Ser Val Asp Phe Lys Asp Ile Lys
    370                 375                 380

Asp Ser Leu Gly Tyr Asp Lys Ser His Gln Phe Ala Tyr Val Lys Glu
385                 390                 395                 400

Ser Thr Asp Ala Gly Tyr Lys Ala Gln Asp Val Lys Asp Lys Ile Ala
                405                 410                 415

Leu Ile Glu Arg Asp Pro Asn Lys Thr Tyr Asp Glu Met Ile Ala Leu
            420                 425                 430

Ala Lys Lys His Gly Ala Leu Gly Val Leu Ile Phe Asn Asn Lys Pro
        435                 440                 445

Gly Gln Ser Asn Arg Ser Met Arg Leu Thr Ala Asn Gly Met Gly Ile
    450                 455                 460

Pro Ser Ala Phe Ile Ser His Glu Phe Gly Lys Ala Met Ser Gln Leu
465                 470                 475                 480

Asn Gly Asn Gly Thr Gly Ser
                485


<210> SEQ ID NO 119
<211> LENGTH: 485
<212> TYPE: PRT
<213> ORGANISM: Streptococcus pyogenes

<400> SEQUENCE: 119

Ser Gln Ile Thr Pro Lys Thr Asn Arg Glu Lys Glu Gln Pro Gln Gly
1               5                   10                  15

Leu Val Ser Glu Pro Thr Thr Thr Glu Leu Ala Asp Thr Asp Ala Ala
            20                  25                  30

Ser Met Ala Asn Thr Gly Pro Asp Ala Thr Gln Lys Ser Ala Ser Leu
        35                  40                  45

Pro Pro Val Asn Thr Asp Val His Asp Trp Val Lys Thr Lys Gly Ala
    50                  55                  60

Trp Asp Lys Gly Tyr Lys Gly Gln Gly Lys Val Val Ala Val Ile Asp
65                  70                  75                  80

Thr Gly Ile Asp Pro Ala His Gln Ser Met Arg Ile Ser Asp Val Ser
                85                  90                  95

Thr Ala Lys Val Lys Ser Lys Glu Asp Met Leu Ala Arg Gln Lys Ala
            100                 105                 110

Ala Gly Ile Asn Tyr Gly Ser Trp Ile Asn Asp Lys Val Val Phe Ala
        115                 120                 125

His Asn Tyr Val Glu Asn Ser Asp Asn Ile Lys Glu Asn Gln Phe Gly
    130                 135                 140

Asp Phe Asp Glu Asp Trp Glu Asn Phe Glu Phe Asp Ala Glu Pro Lys
145                 150                 155                 160

Ala Ile Lys Lys Asn Lys Ile Tyr Arg Pro Gln Ser Thr Gln Ala Pro
                165                 170                 175

Lys Glu Thr Val Ile Lys Thr Glu Glu Thr Asp Gly Ser His Asp Ile
            180                 185                 190

Asp Trp Thr Gln Thr Asp Asp Asp Thr Lys Tyr Glu Ser His Gly Met
        195                 200                 205

His Val Thr Gly Ile Val Ala Gly Asn Ser Lys Glu Ala Ala Ala Thr
    210                 215                 220
```

```
Gly Glu Arg Phe Leu Gly Ile Ala Pro Glu Ala Gln Val Met Phe Met
225                 230                 235                 240

Arg Val Phe Ala Asn Asp Val Met Gly Ser Ala Glu Ser Leu Phe Ile
                245                 250                 255

Lys Ala Ile Glu Asp Ala Val Ala Leu Gly Ala Asp Val Ile Asn Leu
            260                 265                 270

Ser Leu Gly Thr Ala Asn Gly Ala Gln Leu Ser Gly Ser Lys Pro Leu
        275                 280                 285

Met Glu Ala Ile Glu Lys Ala Lys Lys Ala Gly Val Ser Val Val Val
    290                 295                 300

Ala Ala Gly Asn Glu Arg Val Tyr Gly Ser Asp His Asp Asp Pro Leu
305                 310                 315                 320

Ala Thr Asn Pro Asp Tyr Gly Leu Val Gly Ser Pro Ser Thr Gly Arg
                325                 330                 335

Thr Pro Thr Ser Val Ala Ala Ile Asn Ser Lys Trp Val Ile Gln Arg
            340                 345                 350

Leu Met Thr Ala Lys Glu Leu Glu Asn Arg Ala Asp Leu Asn His Gly
        355                 360                 365

Lys Ala Ile Tyr Ser Glu Ser Val Asp Phe Lys Asp Ile Lys Asp Ser
    370                 375                 380

Leu Gly Tyr Asp Lys Ser His Gln Phe Ala Tyr Val Lys Glu Ser Thr
385                 390                 395                 400

Asp Ala Gly Tyr Lys Ala Gln Asp Val Lys Asp Lys Ile Ala Leu Ile
                405                 410                 415

Glu Arg Asp Pro Asn Lys Thr Tyr Asp Glu Met Ile Ala Leu Ala Lys
            420                 425                 430

Lys His Gly Ala Leu Gly Val Leu Ile Phe Asn Asn Lys Pro Gly Gln
        435                 440                 445

Ser Asn Arg Ser Met Arg Leu Thr Ala Asn Gly Met Gly Ile Pro Ser
    450                 455                 460

Ala Phe Ile Ser His Glu Phe Gly Lys Ala Met Ser Gln Leu Asn Gly
465                 470                 475                 480

Asn Gly Thr Gly Ser
                485
```

<210> SEQ ID NO 120
<211> LENGTH: 613
<212> TYPE: PRT
<213> ORGANISM: Streptococcus pyogenes

<400> SEQUENCE: 120

```
Asp Gln Val Asp Val Gln Phe Leu Gly Val Asn Asp Phe His Gly Ala
1               5                   10                  15

Leu Asp Asn Thr Gly Thr Ala Tyr Thr Pro Ser Gly Lys Ile Pro Asn
            20                  25                  30

Ala Gly Thr Ala Ala Gln Leu Gly Ala Tyr Met Asp Asp Ala Glu Ile
        35                  40                  45

Asp Phe Lys Gln Ala Asn Gln Asp Gly Thr Ser Ile Arg Val Gln Ala
    50                  55                  60

Gly Asp Met Val Gly Ala Ser Pro Ala Asn Ser Ala Leu Leu Gln Asp
65                  70                  75                  80

Glu Pro Thr Val Lys Val Phe Asn Lys Met Lys Phe Glu Tyr Gly Thr
                85                  90                  95

Leu Gly Asn His Glu Phe Asp Glu Gly Leu Asp Glu Phe Asn Arg Ile
            100                 105                 110
```

```
Met Thr Gly Gln Ala Pro Asp Pro Glu Ser Thr Ile Asn Asp Ile Thr
        115                 120                 125

Lys Gln Tyr Glu His Glu Ala Ser His Gln Thr Ile Val Ile Ala Asn
    130                 135                 140

Val Ile Asp Lys Lys Thr Lys Asp Ile Pro Tyr Gly Trp Lys Pro Tyr
145                 150                 155                 160

Ala Ile Lys Asp Ile Ala Ile Asn Asp Lys Ile Val Lys Ile Gly Phe
                165                 170                 175

Ile Gly Val Val Thr Thr Glu Ile Pro Asn Leu Val Leu Lys Gln Asn
            180                 185                 190

Tyr Glu His Tyr Gln Phe Leu Asp Val Ala Glu Thr Ile Ala Lys Tyr
        195                 200                 205

Ala Lys Glu Leu Gln Glu Gln His Val His Ala Ile Val Val Leu Ala
    210                 215                 220

His Val Pro Ala Thr Ser Lys Asp Gly Val Val Asp His Glu Met Ala
225                 230                 235                 240

Thr Val Met Glu Lys Val Asn Gln Ile Tyr Pro Glu His Ser Ile Asp
                245                 250                 255

Ile Ile Phe Ala Gly His Asn His Gln Tyr Thr Asn Gly Thr Ile Gly
            260                 265                 270

Lys Thr Arg Ile Val Gln Ala Leu Ser Gln Gly Lys Ala Tyr Ala Asp
        275                 280                 285

Val Arg Gly Thr Leu Asp Thr Asp Thr Asn Asp Phe Ile Lys Thr Pro
    290                 295                 300

Ser Ala Asn Val Val Ala Val Ala Pro Gly Ile Lys Thr Glu Asn Ser
305                 310                 315                 320

Asp Ile Lys Ala Ile Ile Asn His Ala Asn Asp Ile Val Lys Thr Val
                325                 330                 335

Thr Glu Arg Lys Ile Gly Thr Ala Thr Asn Ser Ser Thr Ile Ser Lys
            340                 345                 350

Thr Glu Asn Ile Asp Lys Glu Ser Pro Val Gly Asn Leu Ala Thr Thr
        355                 360                 365

Ala Gln Leu Thr Ile Ala Lys Lys Thr Phe Pro Thr Val Asp Phe Ala
    370                 375                 380

Met Thr Asn Asn Gly Gly Ile Arg Ser Asp Leu Val Val Lys Asn Asp
385                 390                 395                 400

Arg Thr Ile Thr Trp Gly Ala Ala Gln Ala Val Gln Pro Phe Gly Asn
                405                 410                 415

Ile Leu Gln Val Ile Gln Met Thr Gly Gln His Ile Tyr Asp Val Leu
            420                 425                 430

Asn Gln Gln Tyr Asp Glu Asn Gln Thr Tyr Phe Leu Gln Met Ser Gly
        435                 440                 445

Leu Thr Tyr Thr Tyr Thr Asp Asn Asp Pro Lys Asn Ser Asp Thr Pro
    450                 455                 460

Phe Lys Ile Val Lys Val Tyr Lys Asp Asn Gly Glu Glu Ile Asn Leu
465                 470                 475                 480

Thr Thr Thr Tyr Thr Val Val Val Asn Asp Phe Leu Tyr Gly Gly Gly
                485                 490                 495

Asp Gly Phe Ser Ala Phe Lys Lys Ala Lys Leu Ile Gly Ala Ile Asn
            500                 505                 510

Thr Asp Thr Glu Ala Phe Ile Thr Tyr Ile Thr Asn Leu Glu Ala Ser
        515                 520                 525

Gly Lys Thr Val Asn Ala Thr Ile Lys Gly Val Lys Asn Tyr Val Thr
```

```
    530                 535                 540

Ser Asn Leu Glu Ser Ser Thr Lys Val Asn Ser Ala Gly Lys His Ser
545                 550                 555                 560

Ile Ile Ser Lys Val Phe Arg Asn Arg Asp Gly Asn Thr Val Ser Ser
                565                 570                 575

Glu Val Ile Ser Asp Leu Leu Thr Ser Thr Glu Asn Thr Asn Asn Ser
            580                 585                 590

Leu Gly Lys Lys Glu Thr Thr Thr Asn Lys Asn Thr Ile Ser Ser Ser
        595                 600                 605

Thr Leu Pro Ile Thr
    610


<210> SEQ ID NO 121
<211> LENGTH: 292
<212> TYPE: PRT
<213> ORGANISM: Streptococcus pyogenes

<400> SEQUENCE: 121

Ala Ile Ile Asn His Ala Asn Asp Ile Val Lys Thr Val Thr Glu Arg
1               5                   10                  15

Lys Ile Gly Thr Ala Thr Asn Ser Ser Thr Ile Ser Lys Thr Glu Asn
            20                  25                  30

Ile Asp Lys Glu Ser Pro Val Gly Asn Leu Val Thr Thr Ala Gln Leu
        35                  40                  45

Thr Ile Ala Lys Lys Thr Phe Pro Thr Val Asp Phe Ala Met Thr Asn
    50                  55                  60

Asn Gly Gly Ile Arg Ser Asp Leu Val Val Lys Asn Asp Arg Thr Ile
65                  70                  75                  80

Thr Trp Glu Ala Ala Gln Ala Val Gln Pro Phe Gly Asn Ile Leu Gln
                85                  90                  95

Val Ile Gln Met Thr Gly Gln His Ile Tyr Asp Val Leu Asn Gln Gln
            100                 105                 110

Tyr Asp Glu Asn Gln Thr Tyr Phe Leu Gln Met Ser Gly Leu Thr Tyr
        115                 120                 125

Thr Tyr Thr Asp Asn Asp Pro Lys Asn Ser Asp Thr Pro Phe Lys Ile
    130                 135                 140

Val Lys Val Tyr Lys Asp Asn Gly Glu Glu Ile Asn Leu Thr Thr Thr
145                 150                 155                 160

Tyr Thr Val Val Val Asn Asp Phe Leu Tyr Gly Gly Gly Asp Gly Phe
                165                 170                 175

Ser Ala Phe Lys Lys Ala Lys Leu Ile Gly Ala Ile Asn Thr Asp Thr
            180                 185                 190

Glu Ala Phe Ile Thr Tyr Ile Thr Asn Leu Glu Ala Ser Gly Lys Thr
        195                 200                 205

Val Asn Ala Thr Ile Lys Gly Val Lys Asn Tyr Val Thr Ser Asn Leu
    210                 215                 220

Glu Ser Ser Thr Lys Val Asn Ser Ala Gly Lys His Ser Ile Ile Ile
225                 230                 235                 240

Ile Ser Lys Val Phe Arg Asn Arg Asp Gly Asn Ile Val Ser Ser Glu
                245                 250                 255

Ile Ile Ser Asp Leu Leu Thr Ser Thr Glu Asn Thr Asn Asn Ser Phe
            260                 265                 270

Gly Lys Lys Glu Ile Thr Thr Asn Lys Asn Thr Ile Ser Asn Ser Thr
        275                 280                 285

Leu Pro Ile Thr
```

290

<210> SEQ ID NO 122
<211> LENGTH: 290
<212> TYPE: PRT
<213> ORGANISM: Streptococcus pyogenes

<400> SEQUENCE: 122

Ala Ile Ile Asn His Ala Asn Asp Ile Val Lys Thr Val Thr Glu Arg
1 5 10 15

Lys Ile Gly Thr Ala Thr Asn Ser Ser Thr Ile Ser Lys Thr Glu Asn
20 25 30

Ile Asp Lys Glu Ser Pro Val Gly Asn Leu Val Thr Thr Ala Gln Leu
35 40 45

Thr Ile Ala Lys Lys Thr Phe Pro Thr Val Asp Phe Ala Met Thr Asn
50 55 60

Asn Gly Gly Ile Arg Ser Asp Leu Val Val Lys Asn Asp Arg Thr Ile
65 70 75 80

Thr Trp Gly Ala Ala Gln Ala Val Gln Pro Phe Gly Asn Ile Leu Gln
85 90 95

Val Ile Gln Met Thr Gly Gln His Ile Tyr Asp Val Leu Asn Gln Gln
100 105 110

Tyr Asp Glu Asn Gln Thr Tyr Phe Leu Gln Met Ser Gly Leu Thr Tyr
115 120 125

Thr Tyr Thr Asp Asn Asp Pro Lys Asn Ser Asp Thr Pro Phe Lys Ile
130 135 140

Val Lys Val Tyr Lys Asp Asn Gly Glu Glu Ile Asn Leu Thr Thr Thr
145 150 155 160

Tyr Thr Val Val Val Asn Asp Phe Leu Tyr Gly Gly Gly Asp Gly Phe
165 170 175

Ser Ala Phe Lys Lys Ala Lys Leu Ile Gly Ala Ile Asn Thr Asp Thr
180 185 190

Glu Ala Phe Ile Thr Tyr Ile Thr Asn Leu Glu Ala Ser Gly Lys Thr
195 200 205

Val Asn Ala Thr Ile Lys Gly Val Lys Asn Tyr Val Thr Ser Asn Leu
210 215 220

Glu Ser Ser Thr Lys Val Asn Ser Ala Gly Lys His Ser Ile Ile Ser
225 230 235 240

Lys Val Phe Arg Asn Arg Asp Gly Asn Ile Val Ser Ser Glu Ile Ile
245 250 255

Ser Asp Leu Leu Thr Ser Thr Glu Asn Thr Asn Asn Ser Leu Gly Lys
260 265 270

Lys Glu Thr Thr Thr Asn Lys Asn Thr Ile Ser Ser Ser Thr Leu Pro
275 280 285

Ile Thr
290

<210> SEQ ID NO 123
<211> LENGTH: 290
<212> TYPE: PRT
<213> ORGANISM: Streptococcus pyogenes

<400> SEQUENCE: 123

Ala Ile Ile Asn His Ala Asn Asp Ile Val Lys Thr Val Thr Glu Arg
1 5 10 15

Lys Ile Gly Thr Ala Thr Asn Ser Ser Thr Ile Ser Lys Thr Glu Asn
20 25 30

```
Ile Asp Lys Glu Ser Pro Val Gly Asn Leu Val Thr Thr Ala Gln Leu
        35                  40                  45

Thr Ile Ala Lys Lys Thr Phe Pro Thr Val Asp Phe Ala Met Thr Asn
    50                  55                  60

Asn Gly Gly Ile Arg Ser Asp Leu Val Val Lys Asn Asp Arg Thr Ile
65                  70                  75                  80

Thr Trp Gly Ala Ala Gln Ala Val Gln Pro Phe Gly Asn Ile Leu Gln
                85                  90                  95

Val Ile Gln Met Thr Gly Gln His Ile Tyr Asp Val Leu Asn Gln Gln
            100                 105                 110

Tyr Asp Glu Asn Gln Thr Tyr Phe Leu Gln Met Ser Gly Leu Thr Tyr
        115                 120                 125

Thr Tyr Thr Asp Asn Asp Pro Lys Asn Ser Asp Ile Pro Phe Lys Ile
    130                 135                 140

Val Lys Val Tyr Lys Asp Asn Gly Glu Glu Ile Asn Leu Thr Thr Thr
145                 150                 155                 160

Tyr Thr Val Val Val Asn Asp Phe Leu Tyr Gly Gly Gly Asp Gly Phe
                165                 170                 175

Ser Ala Phe Lys Lys Ala Lys Leu Ile Gly Ala Ile Asn Thr Asp Thr
            180                 185                 190

Glu Ala Phe Ile Thr Tyr Ile Thr Asn Leu Glu Ala Ser Gly Lys Thr
        195                 200                 205

Val Asn Ala Thr Ile Lys Gly Val Lys Asn Tyr Val Thr Ser Asn Leu
    210                 215                 220

Glu Ser Ser Thr Lys Val Asn Ser Ala Gly Lys His Ser Ile Ile Ser
225                 230                 235                 240

Lys Val Phe Arg Asn Arg Asp Gly Asn Ile Val Ser Ser Glu Val Ile
                245                 250                 255

Ser Asp Leu Leu Thr Ser Thr Glu Asn Thr Asn Asn Ser Leu Gly Lys
            260                 265                 270

Lys Glu Thr Thr Thr Asn Lys Asn Thr Ile Ser Ser Ser Thr Leu Pro
        275                 280                 285

Ile Thr
    290


<210> SEQ ID NO 124
<211> LENGTH: 290
<212> TYPE: PRT
<213> ORGANISM: Streptococcus pyogenes

<400> SEQUENCE: 124

Ala Ile Ile Asn His Ala Asn Asp Ile Val Lys Thr Val Thr Glu Arg
1               5                   10                  15

Lys Ile Gly Thr Ala Thr Asn Ser Ser Thr Ile Ser Lys Thr Glu Asn
            20                  25                  30

Ile Asp Lys Glu Ser Pro Val Gly Asn Leu Val Thr Thr Ala Gln Leu
        35                  40                  45

Thr Ile Ala Lys Lys Thr Phe Pro Thr Val Asp Phe Ala Met Thr Asn
    50                  55                  60

Asn Gly Gly Ile Arg Ser Asp Leu Val Val Lys Asn Asp Arg Thr Ile
65                  70                  75                  80

Thr Trp Gly Ala Ala Gln Ala Val Gln Pro Phe Gly Asn Ile Leu Gln
                85                  90                  95

Val Ile Gln Met Thr Gly Gln His Ile Tyr Asp Val Leu Asn Gln Gln
            100                 105                 110
```

```
Tyr Asp Glu Asn Gln Thr Tyr Phe Leu Gln Met Ser Gly Leu Thr Tyr
        115                 120                 125

Thr Tyr Thr Asp Asn Asp Pro Lys Asn Ser Asp Thr Pro Phe Lys Ile
    130                 135                 140

Val Lys Val Tyr Lys Asp Asn Gly Glu Glu Ile Asn Leu Thr Thr Thr
145                 150                 155                 160

Tyr Thr Val Val Val Asn Asp Phe Leu Tyr Gly Gly Gly Asp Gly Phe
                165                 170                 175

Ser Ala Phe Lys Lys Ala Lys Leu Ile Gly Ala Ile Asn Thr Asp Thr
            180                 185                 190

Glu Ala Phe Ile Thr Tyr Ile Thr Asn Leu Glu Ala Ser Gly Lys Thr
        195                 200                 205

Val Asn Ala Thr Ile Lys Gly Val Lys Asn Tyr Val Thr Ser Asn Leu
    210                 215                 220

Glu Ser Ser Thr Lys Val Asn Ser Ala Gly Lys His Ser Ile Ile Ser
225                 230                 235                 240

Lys Val Phe Arg Asn Arg Asp Gly Asn Ile Val Ser Ser Glu Ile Ile
                245                 250                 255

Ser Asp Leu Leu Thr Ser Thr Glu Asn Thr Asn Asn Ser Leu Gly Lys
            260                 265                 270

Lys Glu Thr Thr Thr Asn Lys Asn Thr Ile Ser Ser Ser Thr Leu Pro
        275                 280                 285

Ile Thr
    290


<210> SEQ ID NO 125
<211> LENGTH: 290
<212> TYPE: PRT
<213> ORGANISM: Streptococcus pyogenes

<400> SEQUENCE: 125

Ala Ile Ile Asn His Ala Asn Asp Ile Val Lys Thr Val Thr Glu Arg
1               5                   10                  15

Lys Ile Gly Thr Ala Thr Asn Ser Ser Thr Ile Ser Lys Thr Glu Asn
            20                  25                  30

Ile Asp Lys Glu Ser Pro Val Gly Asn Leu Ala Thr Thr Ala Gln Leu
        35                  40                  45

Thr Ile Ala Lys Lys Thr Phe Pro Thr Val Asp Phe Ala Met Thr Asn
    50                  55                  60

Asn Gly Gly Ile Arg Ser Asp Leu Val Val Lys Asn Asp Arg Thr Ile
65                  70                  75                  80

Thr Trp Gly Ala Ala Gln Ala Val Gln Pro Phe Gly Asn Ile Leu Gln
                85                  90                  95

Val Ile Gln Met Thr Gly Gln His Ile Tyr Asp Val Leu Asn Gln Gln
            100                 105                 110

Tyr Asp Glu Asn Gln Thr Tyr Phe Leu Gln Met Ser Gly Leu Thr Tyr
        115                 120                 125

Thr Tyr Thr Asp Asn Asp Pro Lys Asn Ser Asp Thr Pro Phe Lys Ile
    130                 135                 140

Val Lys Val Tyr Lys Asp Asn Gly Glu Glu Ile Asn Leu Thr Thr Thr
145                 150                 155                 160

Tyr Thr Val Val Val Asn Asp Phe Leu Tyr Gly Gly Gly Asp Gly Phe
                165                 170                 175

Ser Ala Phe Lys Lys Ala Lys Leu Ile Gly Ala Ile Asn Thr Asp Thr
            180                 185                 190
```

```
Glu Ala Phe Ile Thr Tyr Ile Thr Asn Leu Glu Ala Ser Gly Lys Thr
        195                 200                 205

Val Asn Ala Thr Ile Lys Gly Val Lys Asn Tyr Val Thr Ser Asn Leu
    210                 215                 220

Glu Ser Ser Thr Lys Val Asn Ser Ala Gly Lys His Ser Ile Ile Ser
225                 230                 235                 240

Lys Val Phe Arg Asn Arg Asp Gly Asn Thr Val Ser Ser Glu Val Ile
                245                 250                 255

Ser Asp Leu Leu Thr Ser Thr Glu Asn Thr Asn Asn Ser Leu Gly Lys
            260                 265                 270

Lys Glu Thr Thr Thr Asn Lys Asn Thr Ile Ser Ser Ser Thr Leu Pro
        275                 280                 285

Ile Thr
    290


<210> SEQ ID NO 126
<211> LENGTH: 290
<212> TYPE: PRT
<213> ORGANISM: Streptococcus pyogenes

<400> SEQUENCE: 126

Ala Ile Ile Asn His Ala Asn Asp Ile Val Lys Thr Val Thr Glu Arg
1               5                   10                  15

Lys Ile Gly Thr Ala Thr Asn Ser Ser Thr Ile Ser Lys Thr Glu Asn
            20                  25                  30

Ile Asp Lys Glu Ser Pro Val Gly Asn Leu Val Thr Thr Ala Gln Leu
        35                  40                  45

Thr Ile Ala Lys Lys Thr Phe Pro Thr Val Asp Phe Ala Met Thr Asn
    50                  55                  60

Asn Gly Gly Ile Arg Ser Asp Leu Val Val Lys Asn Asp Arg Thr Ile
65                  70                  75                  80

Thr Trp Gly Ala Ala Gln Ala Val Gln Pro Phe Gly Asn Ile Leu Gln
                85                  90                  95

Val Ile Gln Met Thr Gly Gln His Ile Tyr Asp Val Leu Asn Gln Gln
            100                 105                 110

Tyr Asp Glu Asn Gln Thr Tyr Phe Leu Gln Met Ser Gly Leu Thr Phe
        115                 120                 125

Thr Tyr Thr Asp Asn Asp Pro Lys Asn Ser Asp Thr Pro Phe Lys Ile
    130                 135                 140

Val Lys Val Tyr Lys Asp Asn Gly Glu Glu Ile Asn Leu Thr Thr Thr
145                 150                 155                 160

Tyr Thr Val Val Val Asn Asp Phe Leu Tyr Gly Gly Gly Asp Gly Phe
                165                 170                 175

Ser Ala Phe Lys Lys Ala Lys Leu Ile Gly Ala Ile Asn Thr Asp Thr
            180                 185                 190

Glu Ala Phe Ile Thr Tyr Ile Thr Asn Leu Glu Ala Ser Gly Lys Thr
        195                 200                 205

Val Asn Ala Thr Ile Lys Gly Val Lys Asn Tyr Val Thr Ser Asn Leu
    210                 215                 220

Glu Ser Ser Thr Lys Val Asn Ser Ala Gly Lys His Ser Ile Ile Ser
225                 230                 235                 240

Lys Val Phe Arg Asn Arg Asp Gly Asn Ile Val Ser Ser Glu Ile Ile
                245                 250                 255

Ser Asp Leu Leu Thr Ser Thr Glu Asn Thr Asn Asn Ser Leu Gly Lys
            260                 265                 270
```

```
Lys Glu Thr Thr Thr Asn Lys Asn Thr Ile Ser Ser Ser Thr Leu Pro
        275                 280                 285

Ile Thr
    290


<210> SEQ ID NO 127
<211> LENGTH: 290
<212> TYPE: PRT
<213> ORGANISM: Streptococcus pyogenes

<400> SEQUENCE: 127

Ala Ile Ile Asn His Ala Asn Asp Ile Val Lys Thr Val Thr Glu Arg
1               5                   10                  15

Lys Ile Gly Thr Ala Thr Asn Ser Ser Thr Ile Ser Lys Thr Glu Asn
            20                  25                  30

Ile Asp Lys Glu Ser Pro Val Gly Asn Leu Val Thr Thr Ala Gln Leu
        35                  40                  45

Thr Ile Ala Lys Lys Thr Phe Pro Thr Val Asp Phe Ala Met Thr Asn
    50                  55                  60

Asn Gly Gly Ile Arg Ser Asp Leu Val Val Lys Asn Asp Arg Thr Ile
65                  70                  75                  80

Thr Trp Gly Ala Ala Gln Ala Val Gln Pro Phe Gly Asn Ile Leu Gln
                85                  90                  95

Val Ile Gln Met Thr Gly Gln His Ile Tyr Asp Val Leu Asn Gln Gln
            100                 105                 110

Tyr Asp Glu Asn Gln Thr Tyr Phe Leu Gln Met Ser Gly Leu Thr Tyr
        115                 120                 125

Thr Tyr Thr Asp Asn Asp Pro Lys Asn Ser Asp Thr Pro Phe Lys Ile
    130                 135                 140

Val Lys Val Tyr Lys Asp Asn Gly Glu Glu Ile Asn Leu Thr Thr Thr
145                 150                 155                 160

Tyr Thr Val Val Val Asn Asp Phe Leu Tyr Gly Gly Gly Asp Gly Phe
                165                 170                 175

Ser Ala Phe Lys Lys Ala Lys Leu Val Gly Ala Ile Asn Thr Asp Thr
            180                 185                 190

Glu Ala Phe Ile Thr Tyr Ile Thr Asn Leu Gln Ala Ser Gly Lys Thr
        195                 200                 205

Val Asn Ala Thr Ile Lys Gly Val Lys Asn Tyr Val Thr Ser Asn Leu
    210                 215                 220

Glu Arg Ser Thr Lys Ile Asn Ser Ala Gly Lys His Ser Ile Ile Ser
225                 230                 235                 240

Lys Val Phe Arg Asn Arg Asp Gly Asn Ile Val Ser Ser Glu Val Ile
                245                 250                 255

Ser Asp Leu Leu Thr Ser Thr Glu Asn Thr Asn Asn Ser Phe Gly Lys
            260                 265                 270

Lys Glu Thr Thr Thr Asn Lys Asn Thr Ile Ser Asn Ser Thr Leu Pro
        275                 280                 285

Ile Thr
    290


<210> SEQ ID NO 128
<211> LENGTH: 290
<212> TYPE: PRT
<213> ORGANISM: Streptococcus pyogenes

<400> SEQUENCE: 128
```

```
Ala Ile Ile Asn His Ala Asn Asp Ile Val Lys Thr Val Thr Glu Arg
1               5                   10                  15

Lys Ile Gly Thr Ala Thr Asn Ser Ser Thr Ile Ser Lys Thr Glu Asn
            20                  25                  30

Ile Asp Lys Glu Ser Pro Val Gly Asn Leu Val Thr Thr Ala Gln Leu
        35                  40                  45

Thr Ile Ala Lys Lys Thr Phe Pro Thr Val Asp Phe Ala Met Thr Asn
    50                  55                  60

Asn Gly Gly Ile Arg Ser Asp Leu Val Val Lys Asn Asp Arg Thr Ile
65                  70                  75                  80

Thr Trp Gly Ala Ala Gln Ala Val Gln Pro Phe Gly Asn Ile Leu Gln
                85                  90                  95

Val Ile Gln Met Thr Gly Gln His Ile Tyr Asp Val Leu Asn Gln Gln
            100                 105                 110

Tyr Asp Glu Asn Gln Thr Tyr Phe Leu Gln Met Ser Gly Leu Thr Tyr
        115                 120                 125

Thr Tyr Thr Asp Asn Asp Pro Lys Asn Ser Asp Thr Pro Phe Lys Ile
    130                 135                 140

Val Lys Val Tyr Lys Asp Asn Gly Glu Glu Ile Asn Leu Thr Thr Thr
145                 150                 155                 160

Tyr Thr Val Val Val Asn Asp Phe Leu Tyr Gly Gly Gly Asp Gly Phe
                165                 170                 175

Ser Ala Phe Lys Lys Ala Lys Leu Ile Gly Ala Ile Asn Thr Asp Thr
            180                 185                 190

Glu Ala Phe Ile Thr Tyr Ile Thr Asn Leu Glu Ala Ser Gly Lys Thr
        195                 200                 205

Val Asn Ala Thr Ile Lys Gly Val Lys Asn Tyr Val Thr Ser Asn Leu
    210                 215                 220

Glu Ser Ser Thr Lys Val Asn Ser Ala Gly Lys His Ser Ile Ile Ser
225                 230                 235                 240

Lys Val Phe Arg Asn Arg Asp Gly Asn Ile Val Ser Ser Glu Ile Ile
                245                 250                 255

Ser Asp Leu Leu Thr Ser Thr Glu Asn Thr Asn Asn Ser Leu Gly Lys
            260                 265                 270

Lys Glu Thr Thr Thr Asn Lys Asn Thr Ile Ser Ser Ser Thr Leu Pro
        275                 280                 285

Ile Thr
    290


<210> SEQ ID NO 129
<211> LENGTH: 290
<212> TYPE: PRT
<213> ORGANISM: Streptococcus pyogenes

<400> SEQUENCE: 129

Ala Ile Ile Asn His Ala Asn Asp Ile Val Lys Thr Val Thr Glu Arg
1               5                   10                  15

Lys Ile Gly Thr Ala Thr Asn Ser Ser Thr Ile Ser Lys Thr Glu Asn
            20                  25                  30

Ile Asp Lys Glu Ser Pro Val Gly Asn Leu Val Thr Thr Ala Gln Leu
        35                  40                  45

Thr Ile Ala Lys Lys Thr Phe Pro Thr Val Asp Phe Ala Met Thr Asn
    50                  55                  60

Asn Gly Gly Ile Arg Ser Asp Leu Val Val Lys Asn Asp Arg Thr Ile
65                  70                  75                  80
```

```
Thr Trp Gly Ala Ala Gln Ala Val Gln Pro Phe Gly Asn Ile Leu Gln
                85                  90                  95

Val Ile Gln Met Thr Gly Gln His Ile Tyr Asp Val Leu Asn Gln Gln
            100                 105                 110

Tyr Asp Glu Asn Gln Thr Tyr Phe Leu Gln Met Ser Gly Leu Thr Tyr
        115                 120                 125

Thr Tyr Thr Asp Asn Asp Pro Lys Asn Ser Asp Thr Pro Phe Lys Ile
    130                 135                 140

Val Lys Val Tyr Lys Asp Asn Gly Glu Glu Ile Asn Leu Thr Thr Thr
145                 150                 155                 160

Tyr Thr Val Val Val Asn Asp Phe Leu Tyr Gly Gly Gly Asp Gly Phe
                165                 170                 175

Ser Ala Phe Lys Lys Thr Lys Leu Ile Gly Ala Ile Asn Thr Asp Thr
            180                 185                 190

Glu Ala Phe Ile Thr Tyr Ile Thr Asn Leu Glu Ala Ser Gly Lys Thr
        195                 200                 205

Val Asn Ala Thr Ile Lys Gly Val Lys Asn Tyr Val Thr Ser Asn Leu
    210                 215                 220

Glu Ser Ser Thr Lys Val Asn Ser Ala Gly Lys His Ser Ile Ile Ser
225                 230                 235                 240

Lys Val Phe Arg Asn Arg Asp Gly Asn Ile Val Ser Ser Glu Ile Ile
                245                 250                 255

Ser Asp Leu Leu Thr Ser Thr Glu Asn Thr Asn Asn Ser Leu Gly Lys
            260                 265                 270

Lys Glu Thr Thr Thr Asn Lys Asn Thr Ile Ser Ser Ser Thr Leu Pro
        275                 280                 285

Ile Thr
    290


<210> SEQ ID NO 130
<211> LENGTH: 292
<212> TYPE: PRT
<213> ORGANISM: Streptococcus pyogenes

<400> SEQUENCE: 130

Ala Ile Ile Asn His Ala Asn Asp Ile Val Lys Thr Val Thr Glu Arg
1               5                   10                  15

Lys Ile Gly Thr Ala Thr Asn Ser Ser Thr Ile Ser Lys Thr Glu Asn
            20                  25                  30

Ile Asp Lys Glu Ser Pro Val Gly Asn Leu Val Thr Thr Ala Gln Leu
        35                  40                  45

Thr Ile Ala Lys Lys Thr Phe Pro Thr Val Asp Phe Ala Met Thr Asn
    50                  55                  60

Asn Gly Gly Ile Arg Ser Asp Leu Val Val Lys Asn Asp Arg Thr Ile
65                  70                  75                  80

Thr Trp Glu Ala Ala Gln Ala Val Gln Pro Phe Gly Asn Ile Leu Gln
                85                  90                  95

Val Ile Gln Met Thr Gly Gln His Ile Tyr Asp Val Leu Asn Gln Gln
            100                 105                 110

Tyr Asp Glu Asn Gln Thr Tyr Phe Leu Gln Met Ser Gly Leu Thr Tyr
        115                 120                 125

Thr Tyr Thr Asp Asn Asp Pro Lys Asn Ser Asp Thr Pro Phe Lys Ile
    130                 135                 140

Val Lys Val Tyr Lys Asp Asn Gly Glu Glu Ile Asn Leu Thr Thr Thr
145                 150                 155                 160
```

```
Tyr Thr Val Val Val Asn Asp Phe Leu Tyr Gly Gly Gly Asp Gly Phe
                165                 170                 175

Ser Ala Phe Lys Lys Ala Lys Leu Ile Gly Ala Ile Asn Thr Asp Thr
            180                 185                 190

Glu Ala Phe Ile Thr Tyr Ile Thr Asn Leu Glu Ala Ser Gly Lys Thr
        195                 200                 205

Val Asn Ala Thr Ile Lys Gly Val Lys Asn Tyr Val Thr Ser Asn Leu
    210                 215                 220

Glu Ser Ser Thr Lys Val Asn Ser Ala Gly Lys His Ser Ile Ile Ile
225                 230                 235                 240

Ile Ser Lys Val Phe Arg Asn Arg Asp Gly Asn Ile Val Ser Ser Glu
                245                 250                 255

Ile Ile Ser Asp Leu Leu Thr Ser Thr Glu Asn Thr Asn Asn Ser Phe
            260                 265                 270

Gly Lys Lys Glu Ile Thr Thr Asn Lys Asn Thr Ile Ser Asn Ser Thr
        275                 280                 285

Leu Pro Ile Thr
    290
```

<210> SEQ ID NO 131
<211> LENGTH: 314
<212> TYPE: PRT
<213> ORGANISM: Streptococcus pyogenes

<400> SEQUENCE: 131

```
Ile Glu Met Pro Gly Gly Ala Tyr Asp Ile Arg Thr Val Leu Gln Val
1               5                   10                  15

Asn Gly Lys Glu Asp Lys Arg Lys Gly Ala Tyr Gln Phe Val Ala Val
            20                  25                  30

Gly Ile Ser Arg Ala Ser Leu Ala Gln Leu Leu Tyr Ala Trp Leu Thr
        35                  40                  45

Pro Phe Thr Glu Ile Ser Thr Ala Glu Asp Thr Thr Gly Gly Tyr Ser
    50                  55                  60

Asp Ala Asp Phe Leu Arg Ile Asn Gln Phe Tyr Met Glu Thr Ser Gln
65                  70                  75                  80

Asn Ala Ala Ile Tyr Gln Ala Leu Ser Leu Ala Gly Lys Pro Val Thr
                85                  90                  95

Leu Asp Tyr Lys Gly Val Tyr Val Leu Asp Val Asn Asn Glu Ser Thr
            100                 105                 110

Phe Lys Gly Thr Leu His Leu Ala Asp Thr Val Thr Gly Val Asn Gly
        115                 120                 125

Lys Gln Phe Thr Ser Ser Ala Glu Leu Ile Asp Tyr Val Ser His Leu
    130                 135                 140

Lys Leu Gly Asp Glu Val Thr Val Gln Phe Thr Ser Asp Asn Lys Pro
145                 150                 155                 160

Lys Lys Gly Val Gly Arg Ile Ile Lys Leu Lys Asn Gly Lys Asn Gly
                165                 170                 175

Ile Gly Ile Ala Leu Thr Asp His Thr Ser Val Asn Ser Glu Asp Thr
            180                 185                 190

Val Ile Phe Ser Thr Lys Gly Val Gly Gly Pro Ser Ala Gly Leu Met
        195                 200                 205

Phe Thr Leu Asp Ile Tyr Asp Gln Ile Thr Lys Glu Asp Leu Arg Lys
    210                 215                 220

Gly Arg Thr Ile Ala Gly Thr Gly Thr Ile Gly Lys Asp Gly Glu Val
225                 230                 235                 240
```

```
Gly Asp Ile Gly Gly Ala Gly Leu Lys Val Val Ala Ala Ala Glu Ala
                245                 250                 255

Gly Ala Asp Ile Phe Phe Val Pro Asn Asn Pro Val Asp Lys Glu Ile
            260                 265                 270

Lys Lys Val Asn Pro Asn Ala Ile Ser Asn Tyr Glu Glu Ala Lys Arg
        275                 280                 285

Ala Ala Lys Arg Leu Lys Thr Lys Met Lys Ile Val Pro Val Thr Thr
    290                 295                 300

Val Gln Glu Ala Leu Val Tyr Leu Arg Lys
305                 310


<210> SEQ ID NO 132
<211> LENGTH: 315
<212> TYPE: PRT
<213> ORGANISM: Streptococcus pyogenes

<400> SEQUENCE: 132

Thr Lys Glu Phe His His Val Thr Val Leu Leu His Glu Thr Val Asp
1               5                   10                  15

Met Leu Asp Ile Lys Pro Asp Gly Ile Tyr Val Asp Ala Thr Leu Gly
            20                  25                  30

Gly Ser Gly His Ser Ala Tyr Leu Leu Ser Lys Leu Gly Glu Glu Gly
        35                  40                  45

His Leu Tyr Cys Phe Asp Gln Asp Gln Lys Ala Ile Asp Asn Ala Gln
    50                  55                  60

Val Thr Leu Lys Ser Tyr Ile Asp Lys Gly Gln Val Thr Phe Ile Lys
65                  70                  75                  80

Asp Asn Phe Arg His Leu Lys Ala Arg Leu Thr Ala Leu Gly Val Asp
                85                  90                  95

Glu Ile Asp Gly Ile Leu Tyr Asp Leu Gly Val Ser Ser Pro Gln Leu
            100                 105                 110

Asp Glu Arg Glu Arg Gly Phe Ser Tyr Lys Gln Asp Ala Pro Leu Asp
        115                 120                 125

Met Arg Met Asp Arg Gln Ser Leu Leu Thr Ala Tyr Glu Val Val Asn
    130                 135                 140

Thr Tyr Pro Phe Asn Asp Leu Val Lys Ile Phe Phe Lys Tyr Gly Glu
145                 150                 155                 160

Asp Lys Phe Ser Lys Gln Ile Ala Arg Lys Ile Glu Gln Ala Arg Ala
                165                 170                 175

Ile Lys Pro Ile Glu Thr Thr Thr Glu Leu Ala Glu Leu Ile Lys Ala
            180                 185                 190

Ala Lys Pro Ala Lys Glu Leu Lys Lys Lys Gly His Pro Ala Lys Gln
        195                 200                 205

Ile Phe Gln Ala Ile Arg Ile Glu Val Asn Asp Glu Leu Gly Ala Ala
    210                 215                 220

Asp Glu Ser Ile Gln Asp Ala Met Glu Leu Leu Ala Leu Asp Gly Arg
225                 230                 235                 240

Ile Ser Val Ile Thr Phe His Ser Leu Glu Asp Arg Leu Thr Lys Gln
                245                 250                 255

Leu Phe Lys Glu Ala Ser Thr Val Asp Val Pro Lys Gly Leu Pro Leu
            260                 265                 270

Ile Pro Glu Asp Met Lys Pro Lys Phe Glu Leu Val Ser Arg Lys Pro
        275                 280                 285

Ile Leu Pro Ser His Ser Glu Leu Thr Ala Asn Lys Arg Ala His Ser
    290                 295                 300
```

Ala Lys Leu Arg Val Ala Lys Lys Ile Arg Lys
305 310 315

<210> SEQ ID NO 133
<211> LENGTH: 2622
<212> TYPE: DNA
<213> ORGANISM: Streptococcus pyogenes

<400> SEQUENCE: 133
atggacttag aacaaacgaa gccaaaccaa gttaagcaga aaattgcttt aacctcaaca 60
attgctttat tgagtgccag tgtaggcgta tctcaccaag tcaaagcaga tgatagagcc 120
tcaggagaaa cgaaggcgag taatactcac gacgatagtt taccaaaacc agaaacaatt 180
caagaggcaa aggcaactat tgatgcagtt gaaaaaactc tcagtcaaca aaaagcagaa 240
ctgacagagc ttgctaccgc tctgacaaaa actactgctg aaatcaacca cttaaaagag 300
cagcaagata atgaacaaaa agctttaacc tctgcacaag aaatttacac taatactctt 360
gcaagtagtg aggagacgct attagcccaa ggagccgaac atcaaagaga gttaacagct 420
actgaaacag agcttcataa tgctcaagca gatcaacatt caaaagagac tgcattgtca 480
gaacaaaaag ctagcatttc agcagaaact actcgagctc aagatttagt ggaacaagtc 540
aaaacgtctg aacaaaatat tgctaagctc aatgctatga ttagcaatcc tgatgctatc 600
actaaagcag ctcaaacggc taatgataat acaaaagcat taagctcaga attggagaag 660
gctaaagctg acttagaaaa tcaaaaagct aaagttaaaa agcaattgac tgaagagttg 720
gcagctcaga aagctgctct agcagaaaaa gaggcagaac ttagtcgtct taaatcctca 780
gctccgtcta ctcaagatag cattgtgggt aataatacca tgaaagcacc gcaaggctat 840
cctcttgaag aacttaaaaa attagaagct agtggttata ttggatcagc tagttacaat 900
aattattaca aagagcatgc agatcaaatt attgccaaag ctagtccagg taatcaatta 960
aatcaatacc aagatattcc agcagatcgt aatcgctttg ttgatcccga taatttgaca 1020
ccagaagtgc aaaatgagct agcgcagttt gcagctcaca tgattaatag tgtaagaaga 1080
caattaggtc taccaccagt tactgttaca gcaggatcac aagaatttgc aagattactt 1140
agtaccagct ataagaaaac tcatggtaat acaagaccat catttgtcta cggacagcca 1200
ggggtatcag ggcattatgg tgttgggcct catgataaaa ctattattga agactctgcc 1260
ggagcgtcag ggctcattcg aaatgatgat aacatgtacg agaatatcgg tgcttttaac 1320
gatgtgcata ctgtgaatgg tattaaacgt ggtatttatg acagtatcaa gtatatgctc 1380
tttacagatc atttacacgg aaatacatac ggccatgcta ttaacttttt acgtgtagat 1440
aaacataacc ctaatgcgcc tgtttacctt ggattttcaa ccagcaatgt aggatctttg 1500
aatgaacact ttgtaatgtt tccagagtct aacattgcta accatcaacg ctttaataag 1560
acccctataa aagccgttgg aagtacaaaa gattatgccc aaagagtagg cactgtatct 1620
gatactattg cagcgatcaa aggaaaagta agctcattag aaaatcgttt gtcggctatt 1680
catcaagaag ctgatattat ggcagcccaa gctaaagtaa gtcaacttca aggtaaatta 1740
gcaagcacac ttaagcagtc agacagctta aatctccaag tgagacaatt aaatgatact 1800
aaaggttctt tgagaacaga attactagca gctaaagcaa aacaagcaca actcgaagct 1860
actcgtgatc aatcattagc taagctagca tcgttgaaag ccgcactgca ccagacagaa 1920
gccttagcag agcaagccgc agccagagtg acagcactgg tggctaaaaa agctcatttg 1980
caatatctaa gggactttaa attgaatcct aaccgccttc aagtgatacg tgagcgcatt 2040
gataatacta agcaagattt ggctaaaact acctcatctt tgttaaatgc acaagaagct 2100

```
ttagcagcct tacaagctaa acaaagcagt ctagaagcta ctattgctac cacagaacac   2160

cagttgactt tgcttaaaac cttagctaac gaaaaggaat atcgccactt agacgaagat   2220

atagctactg tgcctgattt gcaagtagct ccacctctta cgggcgtaaa accgctatca   2280

tatagtaaga tagatactac tccgcttgtt caagaaatgg ttaaagaaac gaaacaacta   2340

ttagaagctt cagcaagatt agctgctgaa aatacaagtc ttgtagcaga agcgcttgtt   2400

ggccaaacct ctgaaatggt agcaagtaat gccattgtgt ctaaaatcac atcttcgatt   2460

actcagccct catctaagac atcttatggc tcaggatctt ctacaacgag caatctcatt   2520

tctgatgttg atgaaagtac tcaaagagct cttaaagcag gagtcgtcat gttggcagct   2580

gtcggcctca caggatttag gttccgtaag gaatctaagt ga                      2622
```

<210> SEQ ID NO 134
<211> LENGTH: 1356
<212> TYPE: DNA
<213> ORGANISM: Streptococcus pyogenes

<400> SEQUENCE: 134

```
gatgatagag cctcaggaga aacgaaggcg agtaatactc acgacgatag tttaccaaaa     60

ccagaaacaa ttcaagaggc aaaggcaact attgatgcag ttgaaaaaac tctcagtcaa    120

caaaaagcag aactgacaga gcttgctacc gctctgacaa aaactactgc tgaaatcaac    180

aacttaaaag agcagcaaga taatgaacaa aaagctttaa cctctgcaca agaaatttac    240

actaatactc ttgcaagtag tgaggagacg ctattagccc aaggagccga acatcaaaga    300

gagttaacag ctactgaaac agagcttcat aatgctcaag cagatcaaca ttcaaaagag    360

actgcattgt cagaacaaaa agctagcatt tcagcagaaa ctactcgagc tcaagattta    420

gtggaacaag tcaaaacgtc tgaacaaaat attgctaagc tcaatgctat gattagcaat    480

cctgatgcta tcactaaagc agctcaaacg gctaatgata atacaaaagc attaagctca    540

gaattggaga aggctaaagc tgacttagaa aatcaaaaag ctaaagttaa aaagcaattg    600

actgaagagt tggcagctca gaaagctgct ctagcagaaa aagaggcaga acttagtcgt    660

cttaaatcct cagctccgtc tactcaagat agcattgtgg gtaataatac catgaaagca    720

ccgcaaggct atcctcttga agaacttaaa aaattagaag ctagtggtta tattggatca    780

gctagttaca ataattatta caaagagcat gcagatcaaa ttattgccaa agctagtcca    840

ggtaatcaat taaatcaata ccaagatatt ccagcagatc gtaatcgctt tgttgatccc    900

gataatttga caccagaagt gcaaaatgag ctagcgcagt ttgcagctca catgattaat    960

agtgtaagaa gacaattagg tctaccacca gttactgtta cagcaggatc acaagaattt   1020

gcaagattac ttagtaccag ctataagaaa actcatggta atacaagacc atcatttgtc   1080

tacggacagc caggggtatc agggcattat ggtgttgggc ctcatgataa aactattatt   1140

gaagactctg ccggagcgtc agggctcatt cgaaatgatg ataacatgta cgagaatatc   1200

ggtgctttta acgatgtgca tactgtgaat ggtattaaac gtggtattta tgacagtatc   1260

aagtatatgc tctttacaga tcatttacac ggaaatacat acggccatgc tattaacttt   1320

ttacgtgtag ataaacgtaa ccctaatgcg cctgtt                             1356
```

<210> SEQ ID NO 135
<211> LENGTH: 1356
<212> TYPE: DNA
<213> ORGANISM: Streptococcus pyogenes

<400> SEQUENCE: 135
gatgatagag cctcaggaga aacgaaggcg agtaatactc acgacgatag tttaccaaaa 60
ccagaaacaa ttcaagaggc aaaggcaact attgatgcag ttgaaaaaac tctcagtcaa 120
caaaaagcag aactgacaga gcttgctacc gctctgacaa aaactactgc tgaaatcaac 180
cacttaaaag agcagcaaga taatgaacaa aaagctttaa cctctgcaca agaaatttac 240
actaatactc ttgcaagtag tgaggagacg ctattagccc aaggagccga acatcaaaga 300
gagttaacag ctactgaaac agagcttcat aatgctcaag cagatcaaca ttcaaaagag 360
actgcattgt cagaacaaaa agctagcatt tcagcagaaa ctactcgagc tcaagattta 420
gtggaacaag tcaaaacgtc tgaacaaaat attgctaagc tcaatgctat gattagcaat 480
cctgatgcta tcactaaagc agctcaaacg gctaatgata atacaaaagc attaagctca 540
gaattggaga aggctaaagc tgacttagaa aatcaaaaag ctaaagttaa aaagcaattg 600
actgaagagt tggcagctca gaaagctgct ctagcagaaa aagaggcaga acttagtcgt 660
cttaaatcct cagctccgtc tactcaagat agcattgtgg gtaataatac catgaaagca 720
ccgcaaggct atcctcttga agaacttaaa aaattagaag ctagtggtta tattggatca 780
gctagttaca ataattatta caaagagcat gcagatcaaa ttattgccaa agctagtcca 840
ggtaatcaat taaatcaata ccaagatatt ccagcagatc gtaatcgctt tgttgatccc 900
gataatttga caccagaagt gcaaaatgag ctagcgcagt ttgcagctca catgattaat 960
agtgtaagga gacaattagg tctaccacca gttactgtca cagcaggatc acaagaattt 1020
gcaagattac ttagtaccag ctataagaaa actcatggta atacaagacc atcatttgtc 1080
tacggacagc caggggtatc agggcattat ggtgttgggc ctcatgataa aactattatt 1140
gaagactctg ccggagcgtc agggctcatt cgaaatgatg ataacatgta cgagaatatc 1200
ggtgctttta acgatgtgca tactgtgaat ggtattaaac gtggtattta tgacagtatc 1260
aagtatatgc tctttacaga tcatttacac ggaaatacat atggtcatgc tattaacttt 1320
ttacgtgtag ataaacataa ccctaaggcg cctgtt 1356

<210> SEQ ID NO 136
<211> LENGTH: 1356
<212> TYPE: DNA
<213> ORGANISM: Streptococcus pyogenes

<400> SEQUENCE: 136
gatgatagag cctcaggaga aacgaaggcg agtaatactc acgacgatag tttaccaaaa 60
ccagaaacaa ttcaagaggc aaaggcaact attgatgcag ttgaaaaaac tctcagtcaa 120
caaaaagcag aactgacaaa gcttgctacc gctctgacaa aaactactgc tgaaatcaac 180
cacttaaaag agcagcaaga taatgaacaa aaagctttaa cctctgcaca agaaatttac 240
actaatactc ttgcaagtag tgaggagacg ctattagccc aaggagccga acatcaaaga 300
gagttaacag ctactgaaac agagcttcat aatgctcaag cagatcaaca ttcaaaagag 360
actgcattgt cagaacaaaa agctagcatt tcagcagaaa ctactcgagc tcaagattta 420
gtggaacaag tcaaaacgtc tgaacaaaat attgctaagc tcaatgctat gattagcaat 480
cctgatgcta tcactaaagc agctcaaacg gctaatgata atacaaaagc attaagctca 540
gaattggaga aggctaaagc tgacttagaa aatcaaaaag ctaaagttaa aaagcaattg 600
actgaagagt tggcagctca gaaagctgct ctagcagaaa aagaggcaga acttagtcgt 660
cttaaatcct cagctccgtc tactcaagat agcattgtgg gtaataatac catgaaagca 720
ccgcaaggct atcctcttga agaacttaaa aaattagaag ctagtggtta tattggatca 780
gctagttaca ataattatta caaagagcat gcagatcaaa ttattgccaa agctagtcca 840
ggtaatcaat taaatcaata ccaagatatt ccagcagatc gtaatcgctt tgttgatccc 900
gataatttga caccagaagt gcaaaatgag ctagcgcagt ttgcagctca catgattaat 960
agtgtaagaa gacaattagg tctaccacca gttactgtta cagcaggatc acaagaattt 1020
gcaagattac ttagtaccag ctataagaaa actcatggta atacaagacc atcatttgtc 1080
tacggacagc caggggtatc agggcattat ggtgttgggc ctcatgataa aactattatt 1140
gaagactctg ccggagcgtc agggctcatt cgaaatgatg ataacatgta cgagaatatc 1200
ggtgctttta acgatgtgca tactgtgaat ggtattaaac gtggtattta tgacagtatc 1260
aagtatatgc tctttacaga tcatttacac ggaaatacat acggccatgc tattaacttt 1320
ttacgtgtag ataaacgtaa ccctaatgcg cctgtt 1356

<210> SEQ ID NO 137
<211> LENGTH: 1356
<212> TYPE: DNA
<213> ORGANISM: Streptococcus pyogenes

<400> SEQUENCE: 137
gatgatagag cctcaggaga aacgaaggcg agtaatactc acgacgatag tttaccaaaa 60
ccagaaacaa ttcaagaggc aaaggcaact attgaagcag ttgaaaaagc tctcagtcaa 120
caaaaagcag aactgacaga gcttgctacc gctctgacaa aaactactgc taaaatcaac 180
cacttaaaag agcagcaaga taatgaacaa aaagctttaa cctctgcaca agaaatttac 240
actaatactc ttgcaagtag tgaggagacg ctattagccc aaggagccga acatcaaaga 300
gagttaacag ctactgaaac agagcttcat aatgctcaag cagatcaaca ttcaaaagag 360
actgcattgt cagaacaaaa agctagcatt tcagcagaaa ctactcgagc tcaagattta 420
gtggaacaag tcaaaacgtc tgaacaaaat attgctaagc tcaatgctat gattagtaat 480
cctgatgcta tcactaaagc agctcaaacg gctaatgata atacaaaagc attaagctca 540
gaattggaga aggctaaagc tgacttagaa aatcaaaaag ctaaagttaa aaagcaattg 600
actgaagagt tggcagctca gaaagctgct ctagcagaaa aagaggcaga acttagtcgt 660
cttaaatcct cagctccgtc tactcaagat agcattgtgg gtaataatac catgaaagca 720
ccgcaaggct atcctcttga agaacttaaa aaattagaag ctagtggtta tattggatca 780
gctagttaca ataattatta caaagagcat gcagatcaaa ttattgccaa agctagtcca 840
ggtaatcaat taaatcaata ccaagatatt ccagcagatc gtaatcgctt tgttgatccc 900
gataatttga caccagaagt gcaaaatgag ctagcgcagt ttgcagctca catgattaat 960
agtgtaagaa gacaattagg tctaccacca gttactgtca cagcaggatc acaagaattt 1020
gcaagattac ttagtaccag ctataagaaa actcatggta atacaagacc atcatttgtc 1080
tacggacagc caggggtatc agggcattat ggtgttgggc ctcatgataa aactattatt 1140
gaagactctg ccggagcgtc agggctcatt cgaaatgatg ataacatgta cgagaatatc 1200
ggtgctttta acgatgtgca tactgtgaat ggtattaaac gtggtattta tgacagtatc 1260
aagtatatgc tctttacaga tcatttacac ggaaatacat atggccatgc tattaacttt 1320
ttacgtgtag ataaacgtaa ccctaatgcg cctgtt 1356

<210> SEQ ID NO 138
<211> LENGTH: 1356
<212> TYPE: DNA
<213> ORGANISM: Streptococcus pyogenes

<400> SEQUENCE: 138
gatgatagag cctcaggaga aacgaaggcg agtaatactc acgacgatag tttaccaaaa 60
ccagaaacaa ttcaagaggc aaaggcaact attgaagcag ttgaaaaagc tctcagtcaa 120
caaaaagcag aactgacaga gcttgctacc gctctgacaa aaactactgc taaaatcaac 180
cacttaaaag agcagcaaga taatgaacaa aaagctttaa cctctgcaca agaaatttac 240
actaatactc ttgcaagtag tgaggagacg ctattagccc aaggagccga acatcaaaga 300
gagttaacag ctactgaaac agagcttcat aatgctcaag cagatcaaca ttcaaaagag 360
actgcattgt cagaacaaaa agctagcatt tcagcagaaa ctactcgagc tcaagattta 420
gtggaacaag tcaaaacgtc tgaacaaaat attgctaagc tcaatgctat gattagtaat 480
cctgatgcta tcactaaagc agctcaaacg gctaatgata atacaaaagc attaagctca 540
gaattggaga aggctaaagc tgacttagaa aatcaaaaag ctaaagttaa aaagcaattg 600
actgaagagt tggcagctca gaaagctgct ctagcagaaa aagaggcaga acttagtcgt 660
cttaaatcct cagctccgtc tactcaagat agcattgtgg gtaataatac catgaaagca 720
ccgcaaggct atcctcttga agaacttaaa aaattagaag ctagtggtta tattggatca 780
gctagttaca ataattatta caaagagcat gcagatcaaa ttattgccaa agctagtcca 840
ggtaatcaat taaatcaata ccaagatatt ccagcagatc gtaatcgctt tgttgatccc 900
gataatttga caccagaagt gcaaaatgag ctagcgcagt ttgcagctca catgattaat 960
agtgtaagaa gacaattagg tctaccacca gttactgtca cagcaggatc acaagaattt 1020
gcaagattac ttagtaccag ctataagaaa actcatggta atacaagacc atcatttgtc 1080
tacggacagc caggggtatc agggcattat ggtgttgggc ctcatgataa aactattatt 1140
gaagactctg ccggagcgtc agggctcatt cgaaatgatg ataacatgta cgagaatatc 1200
ggtgctttta acgatgtgca tactgtgaat ggtattaaac gtggtattta tgacagtatc 1260
aagtatatgc tctttacaga tcatttacac ggaaatacat atggccatgc tattaacttt 1320
ttacgtgtag ataaacgtaa ccctaatgcg cctgtt 1356

<210> SEQ ID NO 139
<211> LENGTH: 1356
<212> TYPE: DNA
<213> ORGANISM: Streptococcus pyogenes

<400> SEQUENCE: 139
gatgatagag cctcaggaga aacgaaggcg agtaatactc acgacgatag tttaccaaaa 60
ccagaaacaa ttcaagaggc aaaggcaact attgatgcag ttgaaaaaac tctcagtcaa 120
caaaaagcag aactgacaga gcttgctacc gctctgacaa aaactactgc tgaaatcaac 180
cacttaaaag agcagcaaga taatgaacaa aaagctttaa cctctgcaca agaaatttac 240
actaatactc ttgcaagtag tgaggagacg ctattagccc aaggagccga acatcaaaga 300
gagttaacag ctactgaaac agagcttcat aatgctcaag cagatcaaca ttcaaaagag 360
actgcattgt cagaacaaaa agctagcatt tcagcagaaa ctactcgagc tcaagattta 420
gtggaacaag tcaaaacgtc tgaacaaaat attgctaagc tcaatgctat gattagcaat 480
cctgatgcta tcactaaagc agctcaaacg gctaatgata atacaaaagc attaagctca 540
gaattggaga aggctaaagc tgacttagaa aatcaaaaag ctaaagttaa aaagcaattg 600
actgaagagt tggcagctca gaaagctgct ctagcagaaa aagaggcaga acttagtcgt 660
cttaaatcct cagctccgtc tactcaagat agcattgtgg gtaataatac catgaaagca 720
ccgcaaggct atcctcttga agaacttaaa aaattagaag ctagtggtta tattggatca 780
gctagttaca ataattatta caaagagcat gcagatcaaa ttattgccaa agctagtcca 840
ggtaatcaat taaatcaata ccaagatatt ccagcagatc gtaatcgctt tgttgatccc 900
gataatttga caccagaagt gcaaaatgag ctagcgcagt ttgcagctca catgattaat 960
agtgtaagaa gacaattagg tctaccacca gttactgtta cagcaggatc acaagaattt 1020
gcaagattac ttagtaccag ctataagaaa actcatggta atacaagacc atcatttgtc 1080
tacggacagc caggggtatc agggcattat ggtgttgggc ctcatgataa aactattatt 1140
gaagactctg ccggagcgtc agggctcatt cgaaatgatg ataacatgta cgagaatatc 1200
ggtgctttta acgatgtgca tactgtgaat ggtattaaac gtggtattta tgacagtatc 1260
aagtatatgc tctttacaga tcatttacac ggaaatacat acggccatgc tattaacttt 1320
ttacgtgtag ataaacgtaa ccctaatgcg cctgtt 1356

<210> SEQ ID NO 140
<211> LENGTH: 1356
<212> TYPE: DNA
<213> ORGANISM: Streptococcus pyogenes

<400> SEQUENCE: 140
gatgatagag cctcaggaga aacgaaggcg agtaatactc acgacgatag tttaccaaaa 60
ccagaaacaa ttcaagaggc aaaggcaact attgatgcag ttgaaaaaac tctcagtcaa 120
caaaaagcag aactgacaga gcttgctacc gctctgacaa aaactactgc tgaaatcaac 180
cacttaaaag agcagcaaga taatgaacaa aaagctttaa cctctgcaca agaaatttac 240
actaatactc ttgcaagtag tgaggagacg ctattagccc aaggagccga acatcaaaga 300
gagttaacag ctactgaaac agagcttcat aatgctcaag cagatcaaca ttcaaaagag 360
actgcattgt cagaacaaaa agctagcatt tcagcagaaa ctactcgagc tcaagattta 420
gtggaacaag tcaaaacgtc tgaacaaaat attgctaagc tcaatgctat gattagcaat 480
cctgatgcta tcactaaagc agctcaaacg gctaatgata atacaaaagc attaagctca 540
gaattggaga aggctaaagc tgacttagaa aatcaaaaag ctaaagttaa aaagcaattg 600
actgaagagt tggcagctca gaaagctgct ctagcagaaa aagaggcaga acttagtcgt 660
cttaaatcct cagctccgtc tactcaagat agcattgtgg gtaataatac catgaaagca 720
ccgcaaggct atcctcttga agaacttaaa aaattagaag ctagtggtta tattggatca 780
gctagttaca ataattatta caaagagcat gcagatcaaa ttattgccaa agctagtcca 840
ggtaatcaat taaatcaata ccaagatatt ccagcagatc gtaatcgctt tgttgatccc 900
gataatttga caccagaagt gcaaaatgag ctagcgcagt ttgcagctca catgattaat 960
agtgtaagaa gacaattagg tctaccacca gttactgtta cagcaggatc acaagaattt 1020
gcaagattac ttagtaccag ctataagaaa actcatggta atacaagacc atcatttgtc 1080
tacggacagc caggggtatc agggcattat ggtgttgggc ctcatgataa aactattatt 1140
gaagactctg ccggagcgtc agggctcatt cgaaatgatg ataacatgta cgagaatatc 1200
ggtgctttta acgatgtgca tactgtgaat ggtattaaac gtggtattta tgacagtatc 1260
aagtatatgc tctttacaga tcatttacac ggaaatacat acggccatgc tattaacttt 1320
ttacgtgtag ataaacataa ccctaatgcg cctgtt 1356

<210> SEQ ID NO 141
<211> LENGTH: 1356

<212> TYPE: DNA
<213> ORGANISM: Streptococcus pyogenes

<400> SEQUENCE: 141

```
gatgatagag cctcaggaga aacgaaggcg agtaatactc acgacgatag tttaccaaaa     60
ccagaaacaa ttcaagaggc aaaggcaact attgatgcag ttgaaaaaac tctcagtcaa    120
caaaaagcag aactgacaga gcttgctacc gctctgacaa aaactactgc tgaaatcaac    180
cacttaaaag agcagcaaga taatgaacaa aaagctttaa cctctgcaca agaaatttac    240
actaatactc ttgcaagtag tgaggagacg ctattagccc aaggagccga acatcaaaga    300
gagttaacag ctactgaaac agagcttcat aatgctcaag tagatcaaca ttcaaaagag    360
actgcattgt cagaacaaaa agctagcatt tcagcagaaa ctactcgagc tcaagattta    420
gtggaacaag tcaaaacgtc tgaacaaaat attgctaagc tcaatgctat gattagcaat    480
cctgatgcta tcactaaagc agctcaaacg gctaatgata atacaaaagc attaagctca    540
gaattggaga aggctaaagc tgacttagaa aatcaaaaag ctaaagttaa aaagcaattg    600
actgaagagt tggcagctca gaaagctgct ctagcagaaa aagaggcaga acttagtcgt    660
cttaaatcct cagctccgtc tactcaagat agcattgtgg gtaataatac catgaaagca    720
ccgcaaggct atcctcttga agaacttaaa aaattagaag ctagtggtta tattggatca    780
gctagttaca ataattatta caaagagcat gcagatcaaa ttattgccaa agctagtcca    840
ggtaatcaat taaatcaata ccaagatatt ccagcagatc gtaatcgctt tgttgatccc    900
gataatttga caccagaagt gcaaaatgag ctagcgcagt ttgcagctca catgattaat    960
agtgtaagaa gacaattagg tctaccacca gttactgtta cagcaggatc acaagaattt   1020
gcaagattac ttagtaccag ctataagaag actcatggta atacaagacc atcatttgtc   1080
tacggacagc caggggtatc agggcattat ggtgttgggc ctcatgataa aactattatt   1140
gaagactctg ccggagcgtc agggctcatt cgaaatgatg ataacatgta cgagaatatc   1200
ggtgctttta acgatgtgca tactgtgaat ggtattaaac gtggtattta tgacagtatc   1260
aagtatatgc tctttacaga tcatttacac ggaaatacat acggccatgc tattaacttt   1320
ttacgtgtag ataaacgtaa ccctaatgcg cctgtt                             1356
```

<210> SEQ ID NO 142
<211> LENGTH: 1356
<212> TYPE: DNA
<213> ORGANISM: Streptococcus pyogenes

<400> SEQUENCE: 142

```
gatgatagag cctcaggaga aacgaaggcg agtaatactc acgacgatag tttaccaaaa     60
ccagaaacaa ttcaagaggc aaaggcaact attgatgcag ttgaaaaaac tctcagtcaa    120
caaaaagcag aactgacaga gcttgctacc gctctgacaa aaactactgc tgaaatcaac    180
cacttaaaag agcagcaaga taatgaacaa aaagctttaa cctctgcaca agaaatttac    240
actaatactc ttgcaagtag tgaggagacg ctattagccc aaggagccga acatcaaaga    300
gagttaacag ctactgaaac agagcttcat aatgctcaag cagatcaaca ttcaaaagag    360
actgcattgt cagaacaaaa agctagcatt tcagcagaaa ctactcgagc tcaagattta    420
gtggaacaag tcaaaacgtc tgaacaaaat attgctaagc tcaatgctat gattagcaat    480
cctgatgcta tcactaaagc agctcaaacg gctaatgata atacaaaagc attaagctca    540
gaattggaga aggctaaagc tgacttagaa aatcaaaaag ctaaagttaa aaagcaattg    600
actgaagagt tggcagctca gaaagctgct ctagcagaaa aagaggcaga acttagtcgt    660
```

cttaaatcct cagctccgtc tactcaagat agcattgtgg gtaataatac catgaaagca 720
ccgcaaggct atcctcttga agaacttaaa aaattagaag ctagtggtta tattggatca 780
gctagttaca ataattatta caaagagcat gcagatcaaa ttattgccaa agctagtcca 840
ggtaatcaat taaatcaata ccaagatatt ccagcagatc gtaatcgctt tgttgatccc 900
gataatttga caccagaagt gcaaaatgag ctagcgcagt ttgcagctca catgattaat 960
agtgtaagga gacaattagg tctaccacca gttactgtta cagcaggatc acaagaattt 1020
gcaagattac ttagtaccag ctataagaaa actcatggta atacaagacc atcatttgtc 1080
tacggacaac caggggtatc agggcattat ggtgttgggc ctcatgataa aactattatt 1140
gaagactctg ccggagcgtc agggctcatt cgaaatgatg ataacatgta cgagaatatc 1200
ggtgctttta acgatgtgca tactgtgaat ggtattaaac gtggtattta tgacagtatc 1260
aagtatatgc tctttacaga tcatttacac ggaaatacat atggccatgc tattaacttt 1320
ttacgtgtag ataaacgtaa ccctaatgcg cctgtt 1356

<210> SEQ ID NO 143
<211> LENGTH: 1356
<212> TYPE: DNA
<213> ORGANISM: Streptococcus pyogenes

<400> SEQUENCE: 143
gatgatagag cctcaggaga aacgaaggcg agtaatactc acgacgatag tttaccaaaa 60
ccagaaacaa ttcaagaggc aaaggcaact attgaagcag ttgaaaaaac tctcagtcaa 120
caaaaagcag aactgacaga gcttgctacc gctctgacaa aaactactgc tgaaatcaac 180
cacttaaaag agcagcaaga taacgaacaa aaagctttaa cctctgcaca agaaatttac 240
actaatactc ttgcaagtag tgaggagacg ctattagccc aaggagccga acatcaaaga 300
gagttaacag ctactgaaac agagcttcat aatgctcaag cagatcaaca ttcaaaagag 360
actgcattgt cagaacaaaa agctagcatt tcagcagaaa ctactcgagc tcaagattta 420
gtggaacaag tcaaaacgtc tgaacaaaat attgctaagc tcaatgctat gattagcaat 480
cctgatgcta tcactaaagc agctcaaacg gctaatgata atacaaaagc attaagctca 540
gaattggaga aggctaaagc tgacttagaa aatcaaaaag ctaaagttaa aaagcaattg 600
actgaagagt tggcagctca gaaagctgct ctagcagaaa aagaggcaga acttagtcgt 660
cttaaatcct cagctccgtc tactcaagat agcattgtgg gtaataatac catgaaagca 720
ccgcaaggct atcctcttga agaacttaaa aaattagaag ctagtggtta tattggatca 780
gctagttaca ataattatta caaagagcat gcagatcaaa ttattgccaa agctagtcca 840
ggtaatcaat taaatcaata ccaagatatt ccagcagatc gtaatcgctt tgttgatccc 900
gataatttga caccagaagt gcaaaatgag ctagcgcagt ttgcagctca catgattaat 960
agtgtaagaa gacaattagg tctaccacca gttactgtca cagcaggatc acaagaattt 1020
gcaagattac ttagtaccag ctataagaaa actcatggta atacaagacc atcatttgtc 1080
tacggacagc caggggtatc agggcattat ggtgttgggc ctcatgataa aactattatt 1140
gaagactctg ccggagcgtc agggctcatt cgaaatgatg ataacatgta cgagaatatc 1200
ggtgctttta acgatgtgca tactgtgaat ggtattaaac gtggtattta tgacagtatc 1260
aagtatatgc tctttacaga tcatttacac ggaaatacat atggccatgc tattaacttt 1320
ttacgtgtag ataaacgtaa ccctaatgcg cctgtt 1356

-continued

<210> SEQ ID NO 144
<211> LENGTH: 1233
<212> TYPE: DNA
<213> ORGANISM: Streptococcus pyogenes

<400> SEQUENCE: 144
atgatcaaac gattaatttc cctagtggtc atcgccttat tttttgcagc aagcactgtt 60
agcggtgaag agtattcggt aactgctaag catgcgattg ccgttgacct tgaaagtggc 120
aaagttttat acgaaaaaga tgctaaagaa gttgtcccag tcgcctcagt cagtaagctc 180
ttgacaacct atctggttta caaagaagtt tctaagggca agctaaattg ggatagtcct 240
gtaactattt ctaactaccc ttatgaactc actacaaact atactattag taacgttcct 300
cttgataaga gaaaatatac cgttaaagaa cttttaagtg cgttagttgt taataacgcc 360
aatagccccg ctattgcttt agctgaaaaa ataggcggaa ccgaacccaa atttgttgac 420
aaaatgaaaa aacaattaag acaatggggc atttccgatg caaaggtcgt caattcaact 480
ggcttaacta accatttttt aggagctaat acttatccta atacagaacc agatgatgaa 540
aattgttttt gcgccactga tttagctatt attgccaggc atctcttatt agaatttcca 600
gaagtactga aattatctag caaatcctcc actatttttg ctggacaaac catttacagt 660
tataattaca tgcttaaagg catgccttgt tatcgagaag gcgtggatgg tctttttgtt 720
ggttattcta aaaaagccgg tgcttctttt gtagctacta gtgtcgaaaa tcaaatgagg 780
gttattacag tagttttaaa tgctgatcaa agccacgagg atgatttagc tatatttaaa 840
acaaccaatc aattgttgca gtacctttta attaattttc aaaaagtcca gttaattgaa 900
aataataaac cagtaaaaac gttatatgtc ttagacagtc ctgaaaaaac tgtcaaactt 960
gtagcccaaa atagtttatt ttttatcaaa ccaatacata caaagaccaa aaataccgtc 1020
catattacta agaaatcatc cacaatgatc gcacctctat caaagggaca agtcttaggt 1080
agagcaaccc ttcaagataa acatcttatt ggacaaggtt atctggatac tcctccttct 1140
atcaatctta tccttcaaaa aaacatttct aaaagtttct ttttaaaggt ctggtggaac 1200
cgttttgtga ggtatgtcaa tacctcttta tag 1233

<210> SEQ ID NO 145
<211> LENGTH: 486
<212> TYPE: DNA
<213> ORGANISM: Streptococcus pyogenes

<400> SEQUENCE: 145
gaagagtatt cggtaactgc taagcatgcg attgccgttg accttgaaag tggcaaagtt 60
ttatacgaaa aagatgctaa agaagttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgc 486

<210> SEQ ID NO 146
<211> LENGTH: 486
<212> TYPE: DNA
<213> ORGANISM: Streptococcus pyogenes

<400> SEQUENCE: 146
gaagagtatt cggtaactgc taagcatgcg attgccgttg accttgaaag tggcaaagtt 60
ttatacgaaa aagatgctaa agaagttgtc ccagtcgcct cagtcagtaa gctcttgaca 120
acctatctgg tttacaaaga agtttctaag ggcaagctaa attgggatag tcctgtaact 180
atttctaact acccttatga acttactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatacaaagg tcgtcaattc aactggctta 420
actaaccatt ttttaggagc taatacttat cctaatacag aaccagatga tgaaaattgt 480
ttttgc 486

<210> SEQ ID NO 147
<211> LENGTH: 486
<212> TYPE: DNA
<213> ORGANISM: Streptococcus pyogenes

<400> SEQUENCE: 147
gaagagtatt cggtaactgc taagcatgcg attgccgttg accttgaaag tggcaaagtt 60
ttatacgaaa aagatactaa agaagttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taaggcaatg gggcatttcc gatgcaaagg tcgttaattc aactggctta 420
actaaccatt ttttaggagc taatacttat cctaatacag aaccagatga tgaaaattgt 480
ttttgc 486

<210> SEQ ID NO 148
<211> LENGTH: 486
<212> TYPE: DNA
<213> ORGANISM: Streptococcus pyogenes

<400> SEQUENCE: 148
gaagagtatt cggtaactgc taaacatgcg attgccgttg accttgaaag tggcaaagtt 60
ttatacgaaa aagatgctaa agaggttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgc 486

<210> SEQ ID NO 149
<211> LENGTH: 486
<212> TYPE: DNA
<213> ORGANISM: Streptococcus pyogenes

<400> SEQUENCE: 149
gaagagtatt cggtaactgc taagcatgcg attgccgttg accttgaaag tggcaaagtt 60
ttatacgaaa aagatgctaa agaagttgtc cctgtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg ggcatttcc gatgcaaagg tcgtcaattc aactggctta 420
actaaccatt ttttaggagc taatacttat cctaatacag aaccagatga tgaaaattgt 480
ttttgc 486

<210> SEQ ID NO 150
<211> LENGTH: 486
<212> TYPE: DNA
<213> ORGANISM: Streptococcus pyogenes

<400> SEQUENCE: 150
gaagagtatt cggtaactgc taagcatgcg attgccgttg accttgaaag tggcaaagtt 60
ttatacgaaa aagatgctaa agaagttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taaggcaatg gggcatttcc gatgcaaagg tcgttaattc aactggctta 420
actaaccatt ttttaggagc taatacttat cctaatacag aaccagatga tgaaaattgt 480
ttttgc 486

<210> SEQ ID NO 151
<211> LENGTH: 486
<212> TYPE: DNA
<213> ORGANISM: Streptococcus pyogenes

<400> SEQUENCE: 151
gaagagtatt cggtaactgc taagcatgcg attgccgttg accttgaaag tggcaaagtt 60
ttatacgaaa aagatgctaa agaagttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgc 486

<210> SEQ ID NO 152
<211> LENGTH: 486
<212> TYPE: DNA
<213> ORGANISM: Streptococcus pyogenes

<400> SEQUENCE: 152
gaagagtatt cggtaactgc taagcatgcg attgccgttg accttgaaag tggcaaagtt 60
ttatacgaaa aagatgctaa agaggttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgc 486

<210> SEQ ID NO 153
<211> LENGTH: 486
<212> TYPE: DNA
<213> ORGANISM: Streptococcus pyogenes

<400> SEQUENCE: 153
gaagagtatt cggtaactgc taagcatgcg attgccgttg accttgaaag tggcaaagtt 60
ttatacgaaa aagatgctaa agaagttgtc cctgtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgc 486

<210> SEQ ID NO 154
<211> LENGTH: 486
<212> TYPE: DNA
<213> ORGANISM: Streptococcus pyogenes

<400> SEQUENCE: 154
gaagagtatt cggtaactgc taagcatgcg attgccgttg accttgaaag tggcaaagtt 60
ttatacgaaa aagatgctaa agaagttgtc cctgtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgc 486

<210> SEQ ID NO 155
<211> LENGTH: 834
<212> TYPE: DNA
<213> ORGANISM: Streptococcus pyogenes

<400> SEQUENCE: 155
gaagagtatt cggtaactgc taagcatgcg attgccgttg accttgaaag tggcaaagtt 60
ttatacgaaa aagatgctaa agaagttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgcgcca ctgatttagc tattattgcc aggcatctct tattagaatt tccagaagta 540
ctgaaattat ctagcaaatc ctccactatt tttgatggac aaaccattta cagttataat 600
tacatgctta aaggcatgcc ttgttatcga gaaggcgtgg atggtctttt tgttggttat 660
tctaaaaaag ccggtgcttc ttttgtagct actagtgtcg aaaatcaaat gagggttatt 720
acagtagttt taaatgctga tcaaagccac gaggatgatt tagctatatt taaaacaacc 780
aatcaattgt tgcagtacct tttaattaat tttcaaaaag tccagttaat tgaa 834

<210> SEQ ID NO 156
<211> LENGTH: 834
<212> TYPE: DNA
<213> ORGANISM: Streptococcus pyogenes

<400> SEQUENCE: 156
gaagagtatt cggtaactgc taagcatgcg attgccgttg accttgaaag tggcaaagtt 60
ttatacgaaa aagatgctaa agaagttgtc ccagtcgcct cagtcagtaa gctcttgaca 120
acctatctgg tttacaaaga agtttctaag ggcaagctaa attgggatag tcctgtaact 180
atttctaact acccttatga acttactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatacaaagg tcgtcaattc aactggctta 420
actaaccatt ttttaggagc taatacttat cctaatacag aaccagatga tgaaaattgt 480
ttttgcgcca ctgatttagc tattattgcc aggcatctct tattagaatt tccagaagta 540
ctgaaattat ctagcaaatc ctccactatt tttgatggac aaaccattta cagttataat 600
tacatgctta aaggcatgcc ttgttatcga gaaggcgtgg atggtctctt tgtcggttat 660
tctaaaaaag ccggtgcttc ttttgtagct actagtgtcg aaaatcaaat gagggttatt 720
acagtagttt taaatgctga tcaaagccac gaggatgatt tagctatatt taaaacaacc 780
aatcaattgt tgcagtacct tttaattaat tttcaaaaag tccagttaat tgaa 834

<210> SEQ ID NO 157
<211> LENGTH: 834
<212> TYPE: DNA
<213> ORGANISM: Streptococcus pyogenes

<400> SEQUENCE: 157
gaagagtatt cggtaactgc taagcatgcg attgccgttg accttgaaag tggcaaagtt 60
ttatacgaaa aagatactaa agaagttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taaggcaatg gggcatttcc gatgcaaagg tcgttaattc aactggctta 420
actaaccatt ttttaggagc taatacttat cctaatacag aaccagatga tgaaaattgt 480
ttttgcgcca ctgatttagc tattattgcc aggcatctct tattagaatt tccagaagta 540
ctgaaattat ctagcaaatc ctccactatt tttgatggac aaaccattta cagttataat 600
tacatgctta aaggcatgcc ttgttatcga gaaggcgtgg atggtctttt tgttggttat 660
tctaaaaaag ccggtgcttc ttttgtagct actagtgtcg aaaatcaaat gagggttatt 720
acagtagttt taaatgctga tcaaagccac gaggatgatt tagctatatt taaaacaacc 780
aatcaattgt tgcagtacct tttaattaat tttcaaaaag tccagttaat tgaa 834

<210> SEQ ID NO 158
<211> LENGTH: 834
<212> TYPE: DNA
<213> ORGANISM: Streptococcus pyogenes

<400> SEQUENCE: 158
gaagagtatt cggtaactgc taaacatgcg attgccgttg accttgaaag tggcaaagtt 60
ttatacgaaa aagatgctaa agaggttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgcgcca ctgatttagc tattattgcc aggcatctct tattagaatt tccagaagta 540
ctgaaattat ctagcaaatc ctccactatt tttgctggac aaaccattta cagttataat 600
tacatgctta aaggcatgcc ttgttatcga gaaggcgtgg atggtctttt tgttggttat 660
tctaaaaaag ccggtgcttc ttttgtagct actagtgtcg aaaatcaaat gagggttatt 720
acagtagttt taaatgctga tcaaagccac gaggatgatt tagctatatt taaaacaacc 780
aatcaattgt tgcagtacct tttaattaat tttcaaaaag tccagttaat tgaa 834

<210> SEQ ID NO 159
<211> LENGTH: 834
<212> TYPE: DNA
<213> ORGANISM: Streptococcus pyogenes

<400> SEQUENCE: 159
gaagagtatt cggtaactgc taagcatgcg attgccgttg accttgaaag tggcaaagtt 60
ttatacgaaa aagatgctaa agaagttgtc cctgtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgcgcca ctgatttagc tattattgcc aggcatctct tattagaatt tccagaagta 540
ctgaaattat ctagcaaatc ctccactatt tttgatggac aaaccattta cagttataat 600
tacatgctta aaggcatgcc ttgttatcga gaaggcgtgg atggtctttt tgttggttat 660
tctaaaaaag ccggtgcttc ttttgtagct actagtgtcg aaaatcaaat gagggttatt 720
acagtagttt taaatgctga tcaaagccac gaggatgatt tagctatatt taaaacaacc 780
aatcaattgt tgcagtacct tttaattaat tttcaaaaag tccagttaat tgaa 834

<210> SEQ ID NO 160
<211> LENGTH: 834
<212> TYPE: DNA
<213> ORGANISM: Streptococcus pyogenes

<400> SEQUENCE: 160
gaagagtatt cggtaactgc taagcatgcg attgccgttg accttgaaag tggcaaagtt 60
ttatacgaaa aagatgctaa agaagttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taaggcaatg gggcatttcc gatgcaaagg tcgttaattc aactggctta 420
actaaccatt ttttaggagc taatacttat cctaatacag aaccagatga tgaaaattgt 480
ttttgcgcca ctgatttagc tattattgcc aggcatctct tattagaatt tccagaagta 540
ctgaaattat ctagcaaatc ctccactatt tttgatggac aaaccattta cagttataat 600
tacatgctta aaggcatgcc ttgttatcga gaaggcgtgg atggtctttt tattggttat 660
tctaaaaaag ccggtgcttc ttttgtagct actagtgtcg aaaatcaaat gagggttatt 720
acagtagttt taaatgctga tcaaagccac gaggatgatt tagctatatt taaaacaacc 780
aatcaattgt tgcagtacct tttaattaat tttcaaaaag tccagttaat tgaa 834

<210> SEQ ID NO 161
<211> LENGTH: 834
<212> TYPE: DNA
<213> ORGANISM: Streptococcus pyogenes

<400> SEQUENCE: 161
gaagagtatt cggtaactgc taagcatgcg attgccgttg accttgaaag tggcaaagtt 60
ttatacgaaa aagatgctaa agaagttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgcgcca ctgatttagc tattattgcc aggcatctct tattagaatt tccagaagta 540
ctgaaattat ctagcaaatc ctccactatt tttgctggac aaaccattta cagttataat 600
tacatgctta aaggcatgcc ttgttatcga gaaggcgtgg atggtctttt tgttggttat 660
tctaaaaaag ccggtgcttc ttttgtagct actagtgtcg aaaatcaaat gagggttatt 720
acagtagttt taaatgctga tcaaagccac gaggatgatt tagctatatt taaaacaacc 780
aatcaattgt tgcagtacct tttaattaat tttcaaaaag tccagttaat tgaa 834

<210> SEQ ID NO 162
<211> LENGTH: 834
<212> TYPE: DNA
<213> ORGANISM: Streptococcus pyogenes

<400> SEQUENCE: 162
gaagagtatt cggtaactgc taagcatgcg attgccgttg accttgaaag tggcaaagtt 60
ttatacgaaa aagatgctaa agaggttgtc ccagtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgcgcca ctgatttagc tattattgcc aggcatctct tattagaatt tccagaagta 540
ctgaaattat ctagcaaatc ctccactatt tttgatggac aaaccattta cagttataat 600
tacatgctta aaggcatgcc ttgttatcga gaaggcgtgg atggtctttt tgttggttat 660
tctaaaaaag ccggtgcttc ttttgtagct actagtgtcg aaaatcaaat gagggttatt 720
acagtagttt taaatgctga tcaaagccac gaggatgatt tagctatatt taaaacaacc 780
aatcaattgt tgcagtacct tttaattaat tttcaaaaag tccagttaat tgaa 834

<210> SEQ ID NO 163
<211> LENGTH: 834
<212> TYPE: DNA
<213> ORGANISM: Streptococcus pyogenes

<400> SEQUENCE: 163
gaagagtatt cggtaactgc taagcatgcg attgccgttg accttgaaag tggcaaagtt 60
ttatacgaaa aagatgctaa agaagttgtc cctgtcgcct cagtcagtaa gctcttgaca 120
acctatctgg tttacaaaga agtttctaag ggcaagctaa attgggatag tcctgtaact 180
atttctaact acccttatga actcactaca aactatacta ttagtaacgt tcctcttgat 240
aagagaaaat ataccgttaa agaactttta agtgcgttag ttgttaataa cgccaatagc 300
cccgctattg ctttagctga aaaaataggc ggaaccgaac ccaaatttgt tgacaaaatg 360
aaaaaacaat taagacaatg gggcatttcc gatgcaaagg tcgtcaattc aactggctta 420
actaaccatt ttttaggagc taatacttat cctaatacag aaccagatga tgaaaattgt 480
ttttgcgcca ctgatttagc tattattgcc aggcatctct tattagaatt tccagaagta 540
ctgaaattat ctagcaaatc ctccactatt tttgatggac aaaccattta cagttataat 600
tacatgctta aaggcatgcc ttgttatcga gaaggcgtgg atggtctttt tgttggttat 660
tctaaaaaag ccggtgcttc ttttgtagct actagtgtcg aaaatcaaat gagggttatt 720
acagtagtta taaatgctga tcaaagccac gaggatgatt tagctatatt taaaacaacc 780
aatcaattgt tgcagtacct tttaattaat tttcaaaaag tccagttaat tgaa 834

<210> SEQ ID NO 164
<211> LENGTH: 834
<212> TYPE: DNA
<213> ORGANISM: Streptococcus pyogenes

<400> SEQUENCE: 164

```
gaagagtatt cggtaactgc taagcatgcg attgccgttg accttgaaag tggcaaagtt     60
ttatacgaaa aagatgctaa agaagttgtc cctgtcgcct cagtcagtaa gctcttgaca    120
acctatctgg tttacaaaga agtttctaag ggcaagctaa attgggatag tcctgtaact    180
atttctaact acccttatga actcactaca aactatacta ttagtaacgt tcctcttgat    240
aagagaaaat ataccgttaa agaactttta agtgcgttag ttgttaataa cgccaatagc    300
cccgctattg ctttagctga aaaaataggc ggaaccgaac ccaaatttgt tgacaaaatg    360
aaaaaacaat taagacaatg gggcatttcc gatgcaaagg tcgtcaattc aactggctta    420
actaaccatt ttttaggagc taatacttat cctaatacag aaccagatga tgaaaattgt    480
ttttgcgcca ctgatttagc tattattgcc aggcatctct tattagaatt tccagaagta    540
ctgaaattat ctagcaaatc ctccactatt tttgctggac aaaccattta cagttataat    600
tacatgctta aaggcatgcc ttgttatcga gaaggcgtgg atggtctttt tgttggttat    660
tctaaaaaag ccggtgcttc ttttgtagct actagtgtcg aaaatcaaat gagggttatt    720
acagtagttt taaatgctga tcaaagccac gaggatgatt tagctatatt taaaacaacc    780
aatcaattgt tgcagtacct tttaattaat tttcaaaaag tccagttaat tgaa          834
```

<210> SEQ ID NO 165
<211> LENGTH: 2502
<212> TYPE: DNA
<213> ORGANISM: Streptococcus pyogenes

<400> SEQUENCE: 165

```
gcagatgagc taagcacaat gagcgaacca acaatcacga atcacgctca acaacaagcg     60
caacatctca ccaatacaga gttgagctca gctgaatcaa aatctcaaga cacatcacaa    120
atcactctca agacaaatcg tgaaaaagag caatcacaag atctagtctc tgagccaacc    180
acaactgagc tagctgacac agatgcagca tcaatggcta atacaggttc tgatgcgact    240
caaaaaagcg cttctttacc gccagtcaat acagatgttc acgattgggt aaaaaccaaa    300
ggagcttggg acaagggata caaaggacaa ggcaaggttg tcgcagttat tgacacaggg    360
atcgatccgg cccatcaaag catgcgcatc agtgatgtat caactgctaa agtaaaatca    420
aaagaagaca tgctagcacg ccaaaaagcc gccggtatta attatgggag ttggataaat    480
gataaagttg tttttgcaca taattatgtg gaaaatagcg ataatatcaa agaaaatcaa    540
ttcgaggatt ttgatgagga ctgggaaaac tttgagtttg atgcagaggc agagccaaaa    600
gccatcaaaa aacacaagat ctatcgtccc caatcaaccc aggcaccgaa agaaactgtt    660
atcaaaacag aagaaacaga tggttcacat gatattgact ggacacaaac agacgatgac    720
accaaatacg agtcacacgg tatgcatgtg acaggtattg tagccggtaa tagcaaagaa    780
gccgctgcta ctggagaacg ctttttagga attgcaccag aggcccaagt catgttcatg    840
cgtgtttttg ccaacgacat catgggatca gctgaatcac tctttatcaa agctatcgaa    900
gatgccgtgg ctttaggagc agatgtgatc aacctgagtc ttggaaccgc taatggggca    960
cagcttagtg gcagcaagcc tctaatggaa gcaattgaaa aagctaaaaa agccggtgta   1020
tcagttgttg tagcagcagg aaatgagcgc gtctatggat ctgaccatga tgatccattg   1080
gcgacaaatc cagactatgg tttggtcggt tctccctcaa caggtcgaac accaacatca   1140
gtggcagcta taaacagtaa gtgggtgatt caacgtctaa tgacggtcaa agaattagaa   1200
aaccgtgccg atttaaacca tggtaaagcc atctattcag agtctgtcga ctttaaagac   1260
ataaaagata gcctaggtta tgataaatcg catcaatttg cttatgtcaa agagtcaact   1320
```

gatgcgggtt ataacgcaca agacgttaaa ggtaaaattg ctttaattga acgtgatccc 1380
aataaaacct atgacgaaat gattgctttg gctaagaaac atggagctct gggagtactt 1440
atttttaata acaagcctgg tcaatcaaac cgctcaatgc gtctaacagc taatgggatg 1500
gggataccat ctgctttcat atcgcacgaa tttggtaagg ccatgtccca attaaatggc 1560
aatggtacag gaagtttaga gtttgacagt gtggtctcaa aagcaccgag tcaaaaaggc 1620
aatgaaatga atcatttttc aaattggggc ctaacttctg atggctattt aaaacctgac 1680
attactgcac caggtggcga tatctattct acctataacg ataaccacta tggtagccaa 1740
acaggaacaa gtatggcctc tcctcagatt gctggcgcca gccttttggt caaacaatac 1800
ctagaaaaga ctcagccaaa cttgccaaaa gaaaaaattg ctgatatcgt taagaaccta 1860
ttgatgagca atgctcaaat tcatgttaat ccagagacaa aaacgaccac ctcaccgcgt 1920
cagcaagggg caggattact taatattgac ggagctgtca ctagcggcct ttatgtgaca 1980
ggaaaagaca actatggcag tatatcatta ggcaacatca cagatacgat gacgtttgat 2040
gtgactgttc acaacctaag caataaagac aaaacattac gttatgacac agaattgcta 2100
acagatcatg tagacccaca aaagggccgc ttcactttga cttctcactc cttaaaaacg 2160
taccaaggag gagaagttac agtcccagcc aatggaaaag tgactgtaag ggttaccatg 2220
gatgtctcac agttcacaaa agagctaaca aaacagatgc caaatggtta ctatctagaa 2280
ggttttgtcc gctttagaga tagtcaagat gaccaactaa atagagtaaa cattcctttt 2340
gttggtttta aagggcaatt tgaaaactta gcagttgcag aagagtccat ttacagatta 2400
aaatctcaag gcaaaactgg tttttacttt gatgaatcag gtccaaaaga cgatatctat 2460
gtcggtaaac actttacagg acttgtcact cttggttcag ag 2502

<210> SEQ ID NO 166
<211> LENGTH: 1926
<212> TYPE: DNA
<213> ORGANISM: Streptococcus pyogenes

<400> SEQUENCE: 166
gcagatgagc taaccacaac gagtgaacca acaatcacga atcacgctca acaacaagcg 60
caacatctca ccaatacaga gttgagctca gctgaatcac aatccccaga cacatcacaa 120
atcactccca agacaaatcg tgaaaaagag caaccacaag gtctagtctc tgagccaacc 180
acaactgagc tagctgacac agatgcagca tcaatggcta atacaggtcc tgatgcgact 240
caaaaaagcg cttctttacc gccagtcaat acagatgttc acgattgggt aaaaaccaaa 300
ggagcttggg acaagggata caaaggacaa ggcaaggttg tcgcagttat tgacacaggg 360
atcgatccgg cccatcaaag catgcgcatc agtgatgtat caactgctaa agtaaaatca 420
aaagaagaca tgctagcacg ccaaaaagcc gccggtatta attatgggag ttggataaat 480
gataaagttg tttttgcaca taattatgtg gaaaatagcg ataatatcaa agaaaatcaa 540
ttcggggatt ttgatgagga ctgggaaaac tttgagtttg atgcagagcc aaaagccatc 600
aaaaaaaaca agatctatcg tccccaatca acccaggcac cgaaagaaac tgttatcaaa 660
acagaagaaa cagatggttc acatgatatt gactggacac aaacagacga tgacaccaaa 720
tacgagtcac acggtatgca tgtgacaggt attgtagccg gtaatagcaa agaagccgct 780
gctactggag aacgcttttt aggaattgca ccagaggccc aagtcatgtt catgcgtgtt 840
tttgccaacg acgtcatggg atcagctgaa tcactcttta tcaaagctat cgaagatgcc 900
gtggctttag gagcagatgt gatcaacctg agtcttggaa ccgctaatgg ggcacagctt 960
agtggcagca agcctctaat ggaagcaatt gaaaaagcta aaaaagccgg tgtatcagtt 1020
gttgtagcag caggaaatga gcgcgtctat ggatctgacc atgatgatcc attggcaaca 1080
aatccagact atggtttggt cggttctccc tcaacaggtc gaacaccaac atcagtggca 1140
gctataaaca gtaagtgggt gattcaacgt ctaatgacgg ccaaagaatt agaaaaccgt 1200
gccgatttaa accatggtaa agccatctat tcagagtctg tcgactttaa agacataaaa 1260
gatagcctag gttatgataa atcgcatcaa tttgcttatg tcaaagagtc aactgatgcg 1320
ggttataaag cacaagacgt taaagataaa attgctttaa ttgaacgtga tcccaataaa 1380
acctatgacg aaatgattgc tttggctaag aaacatggag ccctgggagt acttattttt 1440
aataacaagc ctggtcaatc aaaccgctca atgcgtctaa cagctaatgg gatgggggata 1500 ccatctgctt tcatatcgca cgaatttggt aaggccatgt cccaattaaa tggcaatggt 1560
acaggaagtt tagagtttga cagtgtggtc tcaaaagcac cgagtcaaaa aggcaatgaa 1620
atgaatcatt tttcaaattg gggcctaact tctgatggct atttaaaacc tgacattact 1680
gcaccaggtg gcgatatcta ctctacctat aacgataacc actatggtag ccaaacagga 1740
acaagtatgg cctctcctca gattgctggc gccagccttt tggtcaaaca atacctagaa 1800
aagactcagc caaacttgcc aaaagaaaaa attgctgata tcgttaagaa cctattgatg 1860
agcaatgctc aaattcatgt taatccagag acaaaaacga ccacctcacc gcgtcagcaa 1920
ggggca 1926

<210> SEQ ID NO 167
<211> LENGTH: 1932
<212> TYPE: DNA
<213> ORGANISM: Streptococcus pyogenes

<400> SEQUENCE: 167
gcagatgagc taaccacaac gagtgaacca acaatcacga atcacactca acaacaagcg 60
caacatctca ccaatacaga gttgagctca gctgaatcaa aacctcaaga cacatcacaa 120
atcactctca agacaaatcg tgaaaaagag caaccacaag gtctagtctc tgagccaacc 180
acaactgagc tagctgacac agatgcagca ccaatggcta atacaggtcc tgatgcgact 240
caaaaaagcg cttctttacc gccagtcaat acagatgttc acgattgggt aaaaaccaaa 300
ggagcttggg acaagggata caaaggacaa ggcaaggttg tcgcagttat tgacacaggg 360
atcgatccgg cccatcaaag catgcgcatc agtgatgtat caactgctaa agtaaaatca 420
aaagaagaca tgctagcacg ccaaaaagcc gccggtatta attatgggag ttggataaat 480
gataaagttg tttttgcaca taattatgtg gaaaatagcg ataatatcaa agaaaatcaa 540
ttcgaggatt ttgatgagga ctgggaaaac tttgagtttg atgcagaggc agagccaaaa 600
gccatcaaaa aacacaagat ctatcgtccc caatcaaccc aggcaccgaa agaaactgtt 660
atcaaaacag aagaaacaga tggttcacat gatattgact ggacacaaac agacgatgac 720
accaaatacg agtcacacgg tatgcatgtg acaggtattg tagccggtaa tagcaaagaa 780
gccgctgcta ctggagaacg ctttttagga attgcaccag aggcccaagt catgttcatg 840
cgtgtttttg ccaacgacgt catgggatca gctgaatcac tctttatcaa agctatcgaa 900
gatgccgtgg ctttaggagc agatgtgatc aacctgagtc ttggaaccgc taatggggca 960
cagcttagtg gcagcaagcc tctaatggaa gcaattgaaa aagctaaaaa agccggtgta 1020
tcagttgttg tagcagcagg aaatgagcgc gtctatggat ctgaccatga tgatccattg 1080
gcaacaaatc cagactatgg tttggtcggt tctccctcaa caggtcgaac accaacatca 1140
gtggcagcta taaacagtaa gtgggtgatt caacgtctaa tgacggtcaa agaattagaa 1200
aaccgtgccg atttaaacca tggtaaagcc atctattcag agtctgtcga ctttaaagac 1260
ataaaagata gcctaggtta tgataaatcg catcaatttg cttatgtcaa agagtcaact 1320
gatgcgggtt ataacgcaca agacgttaaa ggtaaaattg ctttaattga acgtgatccc 1380
aataaaacct atgacgaaat gattgctttg gctaagaaac atggagccct gggagtactt 1440
atttttaata acaagcctgg tcaatcaaac cgctcaatgc gtctaacagc taatgggatg 1500
gggataccat ctgctttcat atcgcacgaa tttggtaagg ccatgtccca attaaatggc 1560
aatggtacag gaagtttaga gtttgacagt gtggtctcaa aagcaccgag tcaaaaaggc 1620
aatgaaatga atcatttttc aaattggggc ctaacttctg atggctattt aaaacctgac 1680
attactgcac caggtggcga tatctactct acctataacg ataaccacta tggtagccaa 1740
acaggaacaa gtatggcctc tcctcagatt gctggcgcca gccttttggt caaacaatac 1800
ctagaaaaga ctcagccaaa cttgccaaaa gaaaaaattg ctgatatcgt taagaaccta 1860
ttgatgagca atgctcaaat tcatgttaat ccagagacaa aaacgaccac ctcaccgcgt 1920
cagcaagggg ca 1932

<210> SEQ ID NO 168
<211> LENGTH: 1932
<212> TYPE: DNA
<213> ORGANISM: Streptococcus pyogenes

<400> SEQUENCE: 168
gcagatgagc taaccacaac gagtgaacca acaatcacga atcacgctca acaacaagcg 60
ccacctctca ccaatacaga gttgagctca gctgaatcac aacctcaaga cacatcacaa 120
gtaactccag agacaaatcg tgaaaaagag caaccacaag gtctagtctc tgagccaaca 180
acaactgagc tagctgacac agatgcagca ccaatggcta atacaggttc tgatgcgact 240
caaaaaagcg cttctttacc gccagtcaat acagatgttc acgattgggt aaaaaccaaa 300
ggagcttggg acaagggata caaaggacaa ggcaaggttg tcgcagttat tgacacaggg 360
atcgatccgg cccatcaaag catgcgcatc agtgatgtat caactgctaa agtaaaatca 420
aaagaagaca tgctagcacg ccaaaaagcc gccggtatta attatgggag ttggataaat 480
gataaagttg tttttgcaca taattatgtg gaaaatagcg ataatatcaa agaaaatcaa 540
ttcgaggatt ttgatgagga ctgggaaaac tttgagtttg atgcagaggc agagccaaaa 600
gccatcaaaa aacacaagat ctatcgtccc caatcaaccc aggcaccgaa agaaactgtt 660
atcaaaacag aagaaacaga tggttcacat gatattgact ggacacaaac agacgatgac 720
accaaatacg agtcacacgg tatgcatgtg acaggtattg tagccggtaa tagcaaagaa 780
gccgctgcta ctggagaacg ctttttagga attgcaccag aggcccaagt catgttcatg 840
cgtgtttttg ccaacgacgt catgggatca gctgaatcac tctttatcaa agctatcgaa 900
gatgccgtgg ccttaggagc agatgtgatc aacctgagtc ttggaaccgc taatggggca 960
cagcttagtg gcagcaagcc tctaatggaa gcaattgaaa aagctaaaaa agccggtgta 1020
tcagttgttg tagcagcagg aaatgagcgc gtctatggat ctgaccatga tgatccattg 1080
gcgacaaatc cagactatgg tttggtcggt tctccctcaa caggtcgaac accaacatca 1140
gtagcagcta taaacagtaa gtgggtgatt caacgtctaa tgacggtcaa agaattggaa 1200
aaccgtgccg atttaaacca tggtaaagcc atctattcag agtctgtcga ctttaaagac 1260
ataaaagata gcctaggtta tgataaatcg catcaatttg cttatgtcaa agagtcaact 1320
gatgcgggtt ataacgcaca aaacgttaaa ggtaaaattg ctttaattga acgtgatccc 1380
aataaaacct atgacgaaat gattgctttg gctaagaaac atggagccct gggagtactt 1440
atttttaata acaagcctgg tcaatcaaac cgctcaatgc gtctaacagc taatgggatg 1500
gggataccat ctgctttcat atcgcacgaa tttggtaagg ccatgtccca attaaatggc 1560
aatggtacag gaagtttaga gtttgacagt gtggtctcaa aagcaccgag tcaaaaaggc 1620
aatgaaatga atcatttttc aaattggggc ctaacctctg atggctattt aaaacctgac 1680
attactgcac caggtggcga tatctactct acctataacg ataaccacta tggtagccaa 1740
acaggaacaa gtatggcctc tcctcagatt gctggcgcca gccttttggt caaacaatac 1800
ctagaaaaga ctcagccaaa tttgccaaaa gaaaaaattg ctgatatcgt taagaaccta 1860
ttgatgagca atgctcaaat tcatgttaat ccagagacaa aaacgaccac ctcaccgcgt 1920
cagcaagggg ca 1932

<210> SEQ ID NO 169
<211> LENGTH: 1926
<212> TYPE: DNA
<213> ORGANISM: Streptococcus pyogenes

<400> SEQUENCE: 169
gcagatgagc taaccacaac gagtgaacca acaatcacga atcacgctca acaacaagcg 60
caacatctca ccaatacaga gttgagctca gctgaatcac aatccccaga cacatcacaa 120
atcactccca agataaatcg tgaaaaagag caaccacaag gtctagtctc tgagccaacc 180
acaactgagc tagctgacac agatgcagca ccaatggcta atacaggtcc tgatgcgact 240
caaaaaagcg cttctttacc gccagtcaat acagatgttc acgattgggt aaaaaccaaa 300
ggagcttggg acaaggggta caaaggacaa ggtaaggttg tcgcagttat tgacacaggg 360
atcgatccgg cccatcaaag catgcgcatc agtgatgtat caactgctaa agtaaaatca 420
aaagaagaca tgctagcacg ccaaaaagcc gccggtatta attatgggag ttggataaat 480
gataaagttg tttttgcaca taattatgtg gaaaatagcg ataatatcaa agaaaatcaa 540
ttcgaggatt ttgatgagga ctgggaaaac tttgagtttg atgcagagcc aaaagccatc 600
aaaaaacaca agatctatcg tccccaatca acccaggcac cgaaagaaac tgttatcaaa 660
acagaagaaa cagatggttc acatgatatt gactggacac aaacagacga tgacaccaaa 720
tacgagtcac acggtatgca tgtgacaggt attgtagccg gtaatagtaa agaagccgct 780
gctactggag aacgcttttt aggaattgca ccagagaccc aagtcatgtt catgcgtgtt 840
tttgccaacg acgtcatggg atcagctgaa tcactcttta tcaaagctat cgaagatgcc 900
gtggccttag gagcagatgt gatcaacctg agtcttggga ccgctaatgg tgcacagctt 960
agtggcagca agcctctaat ggaagcaatt gaaaaagcta aaaaagccgg tgtatcagtt 1020
gttgtagcag caggaaatga gcgcgtctat ggatctgacc atgatgatcc attggcaaca 1080
aatccagact atggtttggt cggttctccc tcaacaggtc gaacaccaac atcagtggca 1140
gctataaaca gtaagtgggt gattcaacgt ctaatgacgg tcaaagaatt agaaaaccgt 1200
gccgatttaa accatggtaa agccatctat tcagagtctg tcgactttaa agacataaaa 1260
gatagcctag gttatgataa atcgcatcaa tttgcttatg tcaaagagtc aactgatgcg 1320
ggttataacg cacaagacgt taaaggtaaa attgctttaa ttgaacgtga tcccaataaa 1380
acctatgacg aaatgattgc tttggctaag aaacatggag ccctgggagt acttattttt 1440
aataacaagc ctggtcaatc aaaccgctca atgcgcctaa cagctaatgg gatggggata 1500
ccatctgctt tcatatcgca cgaatttggt aaggccatgt cccaattaaa tggcaatggt 1560
acaggaagtt tagagtttga cagtgtggtc tcaaaagcac cgagtcaaaa aggcaatgaa 1620
atgaatcatt tttcaaattg ggcctaact tctgatggct atttaaaacc tgacattact 1680
gcaccagggg gtgatatcta ctctacctat aacgataacc actatggtag ccaaacagga 1740
acaagtatgg cctctcctca gattgctggc gccagccttt tggtcaaaca atacctagaa 1800
aagactcagc caaacttgcc aaaagaaaaa attgctgata tcgttaagaa cctattgatg 1860
agcaatgctc aaattcatgt taatccagag acaaaaacga ccacctcacc gcgtcagcaa 1920
ggggca 1926

<210> SEQ ID NO 170
<211> LENGTH: 1932
<212> TYPE: DNA
<213> ORGANISM: Streptococcus pyogenes

<400> SEQUENCE: 170
gcagatgagc taagcacaat gagcgaacca acaatcacga atcacgctca acaacaagcg 60
caacatctca ccaatacaga gttgagctca gctgaatcaa aatctcaaga cacatcacaa 120
atcactctca agacaaatcg tgaaaaagag caatcacaag atctagtctc tgagccaacc 180
acaactgagc tagctgacac agatgcagca tcaatggcta atacaggttc tgatgcgact 240
caaaaaagcg cttctttacc gccagtcaat acagatgttc acgattgggt aaaaaccaaa 300
ggagcttggg acaagggata caaaggacaa ggcaaggttg tcgcagttat tgacacaggg 360
atcgatccgg cccatcaaag catgcgcatc agtgatgtat caactgctaa agtaaaatca 420
aaagaagaca tgctagcacg ccaaaaagcc gccggtatta attatgggag ttggataaat 480
gataaagttg tttttgcaca taattatgtg gaaaatagcg ataatatcaa agaaaatcaa 540
ttcgaggatt ttgatgagga ctgggaaaac tttgagtttg atgcagaggc agagccaaaa 600
gccatcaaaa aacacaagat ctatcgtccc caatcaaccc aggcaccgaa agaaactgtt 660
atcaaaacag aagaaacaga tggttcacat gatattgact ggacacaaac agacgatgac 720
accaaatacg agtcacacgg tatgcatgtg acaggtattg tagccggtaa tagcaaagaa 780
gccgctgcta ctggagaacg ctttttagga attgcaccag aggcccaagt catgttcatg 840
cgtgtttttg ccaacgacat catgggatca gctgaatcac tctttatcaa agctatcgaa 900
gatgccgtgg ctttaggagc agatgtgatc aacctgagtc ttggaaccgc taatggggca 960
cagcttagtg gcagcaagcc tctaatggaa gcaattgaaa aagctaaaaa agccggtgta 1020
tcagttgttg tagcagcagg aaatgagcgc gtctatggat ctgaccatga tgatccattg 1080
gcgacaaatc cagactatgg tttggtcggt tctccctcaa caggtcgaac accaacatca 1140
gtggcagcta taaacagtaa gtgggtgatt caacgtctaa tgacggtcaa agaattagaa 1200
aaccgtgccg atttaaacca tggtaaagcc atctattcag agtctgtcga ctttaaagac 1260
ataaaagata gcctaggtta tgataaatcg catcaatttg cttatgtcaa agagtcaact 1320
gatgcgggtt ataacgcaca agacgttaaa ggtaaaattg ctttaattga acgtgatccc 1380
aataaaacct atgacgaaat gattgctttg gctaagaaac atggagctct gggagtactt 1440
atttttaata acaagcctgg tcaatcaaac cgctcaatgc gtctaacagc taatgggatg 1500
gggataccat ctgctttcat atcgcacgaa tttggtaagg ccatgtccca attaaatggc 1560
aatggtacag gaagtttaga gtttgacagt gtggtctcaa aagcaccgag tcaaaaaggc 1620
aatgaaatga atcatttttc aaattggggc ctaacttctg atggctattt aaaacctgac 1680
attactgcac caggtggcga tatctattct acctataacg ataaccacta tggtagccaa 1740
acaggaacaa gtatggcctc tcctcagatt gctggcgcca gccttttggt caaacaatac 1800
ctagaaaaga ctcagccaaa cttgccaaaa gaaaaaattg ctgatatcgt taagaaccta 1860
ttgatgagca atgctcaaat tcatgttaat ccagagacaa aaacgaccac ctcaccgcgt 1920
cagcaagggg ca 1932

<210> SEQ ID NO 171
<211> LENGTH: 1932
<212> TYPE: DNA
<213> ORGANISM: Streptococcus pyogenes

<400> SEQUENCE: 171
gcagatgagc taaccacaac gagtgaacca acaatcacga atcacgctca acaacaagcg 60
caacctctca ccaatacaga gttgagctca gctgaatcac aatccccaga catatcacaa 120
gtaactccag agacaaatcg tgaaaaagag caaccacaag gtctagtctc tgagccaaca 180
acaactgagc tagctgacac agatgcagca ccaatggcta atacaggtcc tgatgcgact 240
caaaaaagcg cttctttacc gccagtcaat acagatgttc acgattgggt aaaaaccaaa 300
ggagcttggg acaagggata caaaggacaa ggcaaggttg tcgcagttat tgacacaggg 360
atcgatccgg cccatcaaag catgcgcatc agtgatgtat caactgctaa agtaaaatca 420
aaagaagaca tgctagcacg ccaaaaagcc gccggtatta attatgggag ttggataaat 480
gataaagttg tttttgcaca taattatgtg gaaaatagcg ataatatcaa agaaaatcaa 540
ttcgaggatt ttgatgagga ctgggaaaac tttgagtttg atgcagatgc agagccaaaa 600
gccatcaaaa aacacaagat ctatcgtccc caatcaaccc aggcaccgaa agaaactgtt 660
atcaaaacag aagaaacaga tggttcacat gatattgact ggacacaaac agacgatgac 720
accaaatacg agtcacacgg tatgcatgtg acaggtattg tagccggtaa tagcaaagaa 780
gccgctgcta ctggagaacg ctttttagga attgcaccag aggcccaagt catgttcatg 840
cgtgtttttg ccaacgacgt catgggatca gctgaatcac tctttatcaa agctatcgaa 900
gatgccgtgg ctttaggagc agatgtgatc aacctgagtc ttggaaccgc taatggggca 960
cagcttagtg gcagcaagcc tctaatggaa gcaattgaaa aagctaaaaa agccggtgta 1020
tcagttgttg tagcagcagg aaatgagcgc gtctatggat ctgaccatga tgatccattg 1080
gcaacaaatc cagactatgg tttggtcggt tctccctcaa caggtcgaac accaacatca 1140
gtggcagcta taaacagtaa gtgggtgatt caacgtctaa tgacggtcaa aggattagaa 1200
aaccgtgccg atttaaacca tggtaaagcc atctattcag agtctgtcga ctttaaagac 1260
ataaaagata gcctaggtta tgataaatcg catcaatttg cttatgtcaa agagtcaact 1320
gatgcgggtt ataacgcaca agacgttaaa ggtaaaattg ctttaattga acgtgatccc 1380
aataaaacct atgacgaaat gattgctttg gctaagaaac atggagccct gggactactt 1440
atttttaata acaagtctgg tcaatcaaac cgctcaatgc gtctaacagc taatgggatg 1500
gggataccat ctgctttcat atcgcacgaa tttggtaagg ccatgtccca attaaatggc 1560
aatggtacag gaagtttaga gtttgacagt gtggtctcaa aagcaccgag tcaaaaaggc 1620
aatgaaatga atcatttttc aaattggggc ctaacttctg atggctattt aaaacctgac 1680
attactgcac caggtggcga tatctactct acctataacg ataaccacta tggtagccaa 1740
acaggaacaa gtatggcctc tcctcagatt gctggcgcca gccttttggt caaacaatac 1800
ctagaaaaga cccagccaaa cttgccaaaa gaaaaaattg ctgatatcgt taagaaccta 1860
ttgatgagca atgctcaaat tcatgttaat ccagagacaa aaacaaccac ctcaccgcgt 1920
cagcaagggg ca 1932

<210> SEQ ID NO 172
<211> LENGTH: 1932
<212> TYPE: DNA
<213> ORGANISM: Streptococcus pyogenes

<400> SEQUENCE: 172
gcagatgagc taaccacaac gagtgaacca acaatcacga atcacgctca acaacaagcg 60
caacatctca ccaatacaga gttgagctca gctgaatcaa aacctcaaga cacatcacaa 120
atcactccca agacaaatcg tgaaaaagag caatcacaag atctagtctc tgagccaacc 180
acaactgagc tagctgacac agatgcagca tcaatggcta atacaggtcc tgatgcgact 240
caaaaaagcg cttctttacc gccagtcaat acagatgttc acgattgggt aaaaaccaaa 300
ggagcttggg acaagggata caaaggacaa ggcaaggttg tcgcagttat tgacacaggg 360
atcgatccgg cccatcaaag catgcgcatc agtgatgtat caactgctaa agtaaaatca 420
aaagaagaca tgctagcacg ccaaaaagcc gccggtatta attatgggag ttggataaat 480
gataaagttg tttttgcaca taattatgtg gaaaatagcg ataatatcaa agaaaatcaa 540
ttcgaggatt ttgatgagga ctgggaaaac tttgagtttg atgcagaggc agagccaaaa 600
gccatcaaaa aacacaagat ctatcgtccc caatcaaccc aggcaccgaa agaaactgtt 660
atcaaaacag aagaaacaga tggttcacat gatattgact ggacacaaac agacgatgac 720
accaaatacg agtcacacgg tatgcatgtg acaggtattg tagccggtaa tagcaaagaa 780
gccgctgcta ctggagaacg ctttttagga attgcaccag aggcccaagt catgttcatg 840
cgtgtttttg ccaacgacgt catgggatca gctgaatcac tctttatcaa agctatcgaa 900
gatgccgtgg ctttaggagc agatgtgatc aacctgagtc ttggaaccgc taatggggca 960
cagcttagtg gcagcaagcc tctaatggaa gcaattgaaa aagctaaaaa agccggtgta 1020
tcagttgttg tagcagcagg aaatgagcgc gtctatggat ctgaccatga tgatccattg 1080
gcaacaaatc cagactatgg tttggtcggt tctccctcaa caggtcgaac accaacatca 1140
gtggcagcta taaacagtaa gtgggtgatt caacgtctaa tgacggtcaa agaattagaa 1200
aaccgtgccg atttaaacca tggtaaagcc atctattcag agtctgtcga ctttaaaaac 1260
ataaaagata gcctaggtta tgataaatcg catcaatttg cttatgtcaa agagtcaact 1320
gatgcgggtt ataacgcaca agacgttaaa ggtaaaattg ctttaattga acgtgatccc 1380
aataaaacct atgacgaaat gattgctttg gctaagaaac atggagccct gggagtactt 1440
atttttaata acaaacctgg tcaatcaaac cgctcaatgc gcctaacatc taatgggatg 1500
ggaataccat ctgctttcat atcgcacgaa tttggtaagg ccatgtccca attaaatggc 1560
aatggtacag gaagtttaga gtttgacagt gtggtctcaa aagcaccgag tcaaaaaggc 1620
aatgaaatga atcatttttc aaattggggc ctaacttctg atggctattt aaaacctgac 1680
attactgcac caggtggcga tatctactct acctataacg ataaccacta tggtagccaa 1740
acaggaacaa gtatggcctc tcctcagatt gctggcgcca gccttttggt caaacaatac 1800
ctagaaaaga ctcagccaaa cttgccaaaa gaaaaaattg ctgatatcgt taagaaccta 1860
ttgatgagca atgctcaaat tcatgttaat ccagagacaa aaacgaccac ctcaccgcgt 1920
cagcaagggg ca 1932

<210> SEQ ID NO 173
<211> LENGTH: 1932
<212> TYPE: DNA
<213> ORGANISM: Streptococcus pyogenes

<400> SEQUENCE: 173
gcagatgagc taaccacaac gagtgaacca acaatcacga atcacactca acaacaagcg 60
caacatctca ccaatacaga gttgagctca gctgaatcaa aacctcaaga cacatcacaa 120
atcactctca agacaaatcg tgaaaaagag caaccacaag gtctagtctc tgagccaacc 180
acaactgagc tagctgacac agatgcagca ccaatggcta atacaggtcc tgatgcgact 240
caaaaaagcg cttctttacc gccagtcaat acagatgttc acgattgggt aaaaaccaaa 300
ggagcttggg acaagggata caaaggacaa ggcaaggttg tcgcagttat tgacacaggg 360
atcgatccgg cccatcaaag catgcgcatc agtgatgtat caactgctaa agtaaaatca 420
aaagaagaca tgctagcacg ccaaaaagcc gccggtatta attatgggag ttggataaat 480
gataaagttg tttttgcaca taattatgtg gaaaatagcg ataatatcaa agaaaatcaa 540
ttcgaggatt ttgatgagga ctgggaaaac tttgagtttg atgcagaggc agagccaaaa 600
gccatcaaaa aacacaagat ctatcgtccc caatcaaccc aggcaccgaa agaaactgtt 660
atcaaaacag aagaaacaga tggttcacat gatattgact ggacacaaac agacgatgac 720
accaaatacg agtcacacgg tatgcatgtg acaggtattg tagccggtaa tagcaaagaa 780
gccgctgcta ctggagaacg ctttttagga attgcaccag aggcccaagt catgttcatg 840
cgtgtttttg ccaacgacgt catgggatca gctgaatcac tctttatcaa agctatcgaa 900
gatgccgtgg ctttaggagc agatgtgatc aacctgagtc ttggaaccgc taatggggca 960
cagcttagtg gcagcaagcc tctaatggaa gcaattgaaa aagctaaaaa agccggtgta 1020
tcagttgttg tagcagcagg aaatgagcgc gtctatggat ctgaccatga tgatccattg 1080
gcaacaaatc cagactatgg tttggtcggt tctccctcaa caggtcgaac accaacatca 1140
gtggcagcta taaacagtaa gtgggtgatt caacgtctaa tgacggtcaa agaattagaa 1200
aaccgtgccg atttaaacca tggtaaagcc atctattcag agtctgtcga ctttaaaaac 1260
ataaaagata gcctaggtta tgataaatcg catcaatttg cttatgtcaa agagtcaact 1320
gatgcgggtt ataaagcaca agacgttaaa ggtaaaattg ctttaattga acgtgatccc 1380
aataaaacct atgacgaaat gattgctttg gctaagaaac atggagccct gggagtactt 1440
atttttaata acaagcctgg tcaatcaaac cgctcaatgc gtctaacagc taatgggatg 1500
gggataccat ctgctttcat atcgcacgaa tttggtaagg ccatgtccca attaaatggc 1560
aatggtacag gaagtttaga gtttgacagt gtggtctcaa aagcaccgag tcaaaaaggc 1620
aatgaaatga atcatttttc aaattggggc ctaacttctg atggctattt aaaacctgac 1680
attactgcac caggtggcga tatctactct acctataacg ataaccacta tggtagccaa 1740
acaggaacaa gtatggcctc tcctcagatt gctggcgcca gccttttggt caaacaatac 1800
ctagaaaaga ctcagccaaa cttgccaaaa gaaaaaattg ctgatatcgt taagaaccta 1860
ttgatgagca atgctcaaat tcatgttaat ccagagacaa aaacgaccac ctcaccgcgt 1920
cagcaagggg ca 1932

<210> SEQ ID NO 174
<211> LENGTH: 1932
<212> TYPE: DNA
<213> ORGANISM: Streptococcus pyogenes

<400> SEQUENCE: 174

```
gcagatgagc taagcacaat gagtgaacca acaatcacga atcacgctca acaacaagcg     60
caacatctca ccaatacaga gttgagctca gctgaatcaa aatctcaaga cacatcacaa    120
atcactccca agacaaatcg tgaaaaagag caatcacaag atctagtctc tgagccaaca    180
acaactgagc tagctgacac agatgcagca tcaatggcta atacaggttc tgatgcgact    240
caaaaaagcg cttctttacc gccagtcaat acagatgttc acgattgggt aaaaaccaaa    300
ggagcttggg acaagggata caaaggacaa ggcaaggttg tcgcagttat tgacacaggg    360
atcgatccgg cccatcaaag catgcgcatc agtgatgtat caactgctaa agtaaaatca    420
aaagaagaca tgctagcacg ccaaaaagcc gccggtatta attatgggag ttggataaat    480
gataaagttg tttttgcaca taattatgtg gaaaatagcg ataatatcaa agaaaatcaa    540
ttcgaggatt ttgatgagga ctgggaaaac tttgagtttg atgcagatgc agagccaaaa    600
gccatcaaaa aacacaagat ctatcgtccc caatcaaccc aggcaccgaa agaaactgtt    660
atcaaaacag aagaaacaga tggttcacat gatattgact ggacacaaac agacgatgac    720
accaaatacg agtcacacgg tatgcatgtg acaggtattg tagccggtaa tagcaaagaa    780
gccgctgcta ctggagaacg ctttttagga attgcaccag aggcccaagt catgttcatg    840
cgtgtttttg ccaacgacgt catgggatca gctgaatcac tctttatcaa agctatcgaa    900
gatgccgtgg ctttaggagc agatgtgatc aacctgagtc ttggaaccgc taatggggca    960
cagcttagtg gcagcaagcc tctaatggaa gcaattgaaa aagctaaaaa agccggtgta   1020
tcagttgttg tagcagcagg aaatgagcgc gtctatggat ctgaccatga tgacccattg   1080
gcaacaaatc cagactatgg tttggttggt tctccctcaa caggtcgaac accaacatca   1140
gtggcagcta taaacagtaa gtgggtgatt caacgtctaa tgacggtcaa agaattggaa   1200
aaccgtgccg atttaaacca tggtaaagcc atctattcag agtctgtcga ctttaaagac   1260
ataaaagata gcctaggtta tgataaatcg catcaatttg cttatgtcaa agagtcaact   1320
gatgcgggtt ataaagcaca agacgttaaa gataaaattg ctttaattga acgtgatccc   1380
aataaaacct atgacgaaat gattgctttg gctaagaaac atggagccct gggggtactt   1440
atttttaata acaagcctgg tcaatcaaac cgctcaatgc gtctaacagc taatgggatg   1500
gggataccat ctgctttcat atcgcacgaa tttggtaagg ccatgtccca attaaatggc   1560
aatggtacag gaagtttaga gtttgacagt gtggtctcaa aagcaccgag tcaaaaaggc   1620
aatgaaatga atcatttttc aaattggggc ctaacttctg atggctattt aaaacctgac   1680
attactgcac caggcggcga tatctactct acctataacg ataaccacta tggtagccaa   1740
acaggaacaa gtatggcctc tcctcagatt gctggcgcca gccttttggt caaacaatat   1800
ctagaaaaga ctcagccaaa cttgccaaaa gaaaaaattg ctgatatcgt taagaaccta   1860
ttgatgagca atgctcaaat tcatgttaat ccagagacaa aaacgaccac ctcaccgcgt   1920
cagcaagggg ca                                                       1932
```

<210> SEQ ID NO 175
<211> LENGTH: 1926
<212> TYPE: DNA
<213> ORGANISM: Streptococcus pyogenes

<400> SEQUENCE: 175

```
gcagatgagc taaccacaac gagtgaacca acaatcacga atcacgctca acaacaagcg     60
caacatctca ccaatacaga gttgagctca gctgaatcac aatccccaga cacatcacaa    120
atcactccca agacaaatcg tgaaaaagag caaccacaag gtctagtctc tgagccaacc    180
```

-continued

```
acaactgagc tagctgacac agatgcagca tcaatggcta atacaggtcc tgatgcgact    240
caaaaaagcg cttctttacc gccagtcaat acagatgttc acgattgggt aaaaaccaaa    300
ggagcttggg acaagggata caaaggacaa ggcaaggttg tcgcagttat tgacacaggg    360
atcgatccgg cccatcaaag catgcgcatc agtgatgtat caactgctaa agtaaaatca    420
aaagaagaca tgctagcacg ccaaaaagcc gccggtatta attatgggag ttggataaat    480
gataaagttg tttttgcaca taattatgtg gaaaatagcg ataatatcaa agaaaatcaa    540
ttcggggatt ttgatgagga ctgggaaaac tttgagtttg atgcagagcc aaaagccatc    600
aaaaaaaaca agatctatcg tccccaatca acccaggcac cgaaagaaac tgttatcaaa    660
acagaagaaa cagatggttc acatgatatt gactggacac aaacagacga tgacaccaaa    720
tacgagtcac acggtatgca tgtgacaggt attgtagccg gtaatagcaa agaagccgct    780
gctactggag aacgcttttt aggaattgca ccagaggccc aagtcatgtt catgcgtgtt    840
tttgccaacg acgtcatggg atcagctgaa tcactcttta tcaaagctat cgaagatgcc    900
gtggctttag gagcagatgt gatcaacctg agtcttggaa ccgctaatgg ggcacagctt    960
agtggcagca agcctctaat ggaagcaatt gaaaaagcta aaaaagccgg tgtatcagtt   1020
gttgtagcag caggaaatga gcgcgtctat ggatctgacc atgatgatcc attggcaaca   1080
aatccagact atggtttggt cggttctccc tcaacaggtc gaacaccaac atcagtggca   1140
gctataaaca gtaagtgggt gattcaacgt ctaatgacgg ccaaagaatt agaaaaccgt   1200
gccgatttaa accatggtaa agccatctat tcagagtctg tcgactttaa agacataaaa   1260
gatagcctag gttatgataa atcgcatcaa tttgcttatg tcaaagagtc aactgatgcg   1320
ggttataaag cacaagacgt taaagataaa attgctttaa ttgaacgtga tcccaataaa   1380
acctatgacg aaatgattgc tttggctaag aaacatggag ccctgggagt acttattttt   1440
aataacaagc ctggtcaatc aaaccgctca atgcgtctaa cagctaatgg gatggggata   1500
ccatctgctt tcatatcgca cgaatttggt aaggccatgt cccaattaaa tggcaatggt   1560
acaggaagtt tagagtttga cagtgtggtc tcaaaagcac cgagtcaaaa aggcaatgaa   1620
atgaatcatt tttcaaattg ggggcctaact tctgatggct atttaaaacc tgacattact   1680
gcaccaggtg gcgatatcta ctctacctat aacgataacc actatggtag ccaaacagga   1740
acaagtatgg cctctcctca gattgctggc gccagccttt tggtcaaaca atacctagaa   1800
aagactcagc caaacttgcc aaaagaaaaa attgctgata tcgttaagaa cctattgatg   1860
agcaatgctc aaattcatgt taatccagag acaaaaacga ccacctcacc gcgtcagcaa   1920
ggggca                                                              1926
```

<210> SEQ ID NO 176
<211> LENGTH: 927
<212> TYPE: DNA
<213> ORGANISM: Streptococcus pyogenes

<400> SEQUENCE: 176

```
gcagttattg acacagggat cgatccggcc catcaaagca tgcgcatcag tgatgtatca     60
actgctaaag taaaatcaaa agaagacatg ctagcacgcc aaaaagccgc cggtattaat    120
tatgggagtt ggataaatga taaagttgtt tttgcacata attatgtgga aaatagcgat    180
aatatcaaag aaaatcaatt cggggatttt gatgaggact gggaaaactt tgagtttgat    240
gcagagccaa aagccatcaa aaaaaacaag atctatcgtc cccaatcaac ccaggcaccg    300
aaagaaactg ttatcaaaac agaagaaaca gatggttcac atgatattga ctggacacaa    360
```

acagacgatg acaccaaata cgagtcacac ggtatgcatg tgacaggtat tgtagccggt 420
aatagcaaag aagccgctgc tactggagaa cgctttttag gaattgcacc agaggcccaa 480
gtcatgttca tgcgtgtttt tgccaacgac gtcatgggat cagctgaatc actctttatc 540
aaagctatcg aagatgccgt ggctttagga gcagatgtga tcaacctgag tcttggaacc 600
gctaatgggg cacagcttag tggcagcaag cctctaatgg aagcaattga aaaagctaaa 660
aaagccggtg tatcagttgt tgtagcagca ggaaatgagc gcgtctatgg atctgaccat 720
gatgatccat tggcaacaaa tccagactat ggtttggtcg gttctccctc aacaggtcga 780
acaccaacat cagtggcagc tataaacagt aagtgggtga ttcaacgtct aatgacggcc 840
aaagaattag aaaaccgtgc cgatttaaac catggtaaag ccatctattc agagtctgtc 900
gactttaaag acataaaaga tagccta 927

<210> SEQ ID NO 177
<211> LENGTH: 933
<212> TYPE: DNA
<213> ORGANISM: Streptococcus pyogenes

<400> SEQUENCE: 177
gcagttattg acacagggat cgatccggcc catcaaagca tgcgcatcag tgatgtatca 60
actgctaaag taaaatcaaa agaagacatg ctagcacgcc aaaaagccgc cggtattaat 120
tatgggagtt ggataaatga taaagttgtt tttgcacata attatgtgga aaatagcgat 180
aatatcaaag aaaatcaatt cgaggatttt gatgaggact gggaaaactt tgagtttgat 240
gcagaggcag agccaaaagc catcaaaaaa cacaagatct atcgtcccca atcaacccag 300
gcaccgaaag aaactgttat caaaacagaa gaaacagatg gttcacatga tattgactgg 360
acacaaacag acgatgacac caaatacgag tcacacggta tgcatgtgac aggtattgta 420
gccggtaata gcaaagaagc cgctgctact ggagaacgct ttttaggaat tgcaccagag 480
gcccaagtca tgttcatgcg tgtttttgcc aacgacgtca tgggatcagc tgaatcactc 540
tttatcaaag ctatcgaaga tgccgtggct ttaggagcag atgtgatcaa cctgagtctt 600
ggaaccgcta atggggcaca gcttagtggc agcaagcctc taatggaagc aattgaaaaa 660
gctaaaaaag ccggtgtatc agttgttgta gcagcaggaa atgagcgcgt ctatggatct 720
gaccatgatg atccattggc aacaaatcca gactatggtt tggtcggttc tccctcaaca 780
ggtcgaacac caacatcagt ggcagctata aacagtaagt gggtgattca acgtctaatg 840
acggtcaaag aattagaaaa ccgtgccgat ttaaaccatg gtaaagccat ctattcagag 900
tctgtcgact ttaaagacat aaaagatagc cta 933

<210> SEQ ID NO 178
<211> LENGTH: 933
<212> TYPE: DNA
<213> ORGANISM: Streptococcus pyogenes

<400> SEQUENCE: 178
gcagttattg acacagggat cgatccggcc catcaaagca tgcgcatcag tgatgtatca 60
actgctaaag taaaatcaaa agaagacatg ctagcacgcc aaaaagccgc cggtattaat 120
tatgggagtt ggataaatga taaagttgtt tttgcacata attatgtgga aaatagcgat 180
aatatcaaag aaaatcaatt cgaggatttt gatgaggact gggaaaactt tgagtttgat 240
gcagaggcag agccaaaagc catcaaaaaa cacaagatct atcgtcccca atcaacccag 300
gcaccgaaag aaactgttat caaaacagaa gaaacagatg gttcacatga tattgactgg 360

```
acacaaacag acgatgacac caaatacgag tcacacggta tgcatgtgac aggtattgta    420

gccggtaata gcaaagaagc cgctgctact ggagaacgct ttttaggaat tgcaccagag    480

gcccaagtca tgttcatgcg tgtttttgcc aacgacgtca tgggatcagc tgaatcactc    540

tttatcaaag ctatcgaaga tgccgtggcc ttaggagcag atgtgatcaa cctgagtctt    600

ggaaccgcta atggggcaca gcttagtggc agcaagcctc taatggaagc aattgaaaaa    660

gctaaaaaag ccggtgtatc agttgttgta gcagcaggaa atgagcgcgt ctatggatct    720

gaccatgatg atccattggc gacaaatcca gactatggtt tggtcggttc tccctcaaca    780

ggtcgaacac caacatcagt agcagctata aacagtaagt gggtgattca acgtctaatg    840

acggtcaaag aattggaaaa ccgtgccgat ttaaaccatg gtaaagccat ctattcagag    900

tctgtcgact ttaaagacat aaaagatagc cta                                 933
```

<210> SEQ ID NO 179
<211> LENGTH: 927
<212> TYPE: DNA
<213> ORGANISM: Streptococcus pyogenes

<400> SEQUENCE: 179

```
gcagttattg acacagggat cgatccggcc catcaaagca tgcgcatcag tgatgtatca     60

actgctaaag taaaatcaaa agaagacatg ctagcacgcc aaaaagccgc cggtattaat    120

tatgggagtt ggataaatga taaagttgtt tttgcacata attatgtgga aaatagcgat    180

aatatcaaag aaaatcaatt cgaggatttt gatgaggact gggaaaactt tgagtttgat    240

gcagagccaa aagccatcaa aaaacacaag atctatcgtc cccaatcaac ccaggcaccg    300

aaagaaactg ttatcaaaac agaagaaaca gatggttcac atgatattga ctggacacaa    360

acagacgatg acaccaaata cgagtcacac ggtatgcatg tgacaggtat tgtagccggt    420

aatagtaaag aagccgctgc tactggagaa cgctttttag gaattgcacc agagacccaa    480

gtcatgttca tgcgtgtttt tgccaacgac gtcatgggat cagctgaatc actctttatc    540

aaagctatcg aagatgccgt ggccttagga gcagatgtga tcaacctgag tcttgggacc    600

gctaatggtg cacagcttag tggcagcaag cctctaatgg aagcaattga aaaagctaaa    660

aaagccggtg tatcagttgt tgtagcagca ggaaatgagc gcgtctatgg atctgaccat    720

gatgatccat tggcaacaaa tccagactat ggtttggtcg gttctccctc aacaggtcga    780

acaccaacat cagtggcagc tataaacagt aagtgggtga ttcaacgtct aatgacggtc    840

aaagaattag aaaaccgtgc cgatttaaac catggtaaag ccatctattc agagtctgtc    900

gactttaaag acataaaaga tagccta                                        927
```

<210> SEQ ID NO 180
<211> LENGTH: 933
<212> TYPE: DNA
<213> ORGANISM: Streptococcus pyogenes

<400> SEQUENCE: 180

```
gcagttattg acacagggat cgatccggcc catcaaagca tgcgcatcag tgatgtatca     60

actgctaaag taaaatcaaa agaagacatg ctagcacgcc aaaaagccgc cggtattaat    120

tatgggagtt ggataaatga taaagttgtt tttgcacata attatgtgga aaatagcgat    180

aatatcaaag aaaatcaatt cgaggatttt gatgaggact gggaaaactt tgagtttgat    240

gcagaggcag agccaaaagc catcaaaaaa cacaagatct atcgtcccca atcaacccag    300

gcaccgaaag aaactgttat caaaacagaa gaaacagatg gttcacatga tattgactgg    360
```

```
acacaaacag acgatgacac caaatacgag tcacacggta tgcatgtgac aggtattgta    420

gccggtaata gcaaagaagc cgctgctact ggagaacgct ttttaggaat tgcaccagag    480

gcccaagtca tgttcatgcg tgtttttgcc aacgacatca tgggatcagc tgaatcactc    540

tttatcaaag ctatcgaaga tgccgtggct ttaggagcag atgtgatcaa cctgagtctt    600

ggaaccgcta atggggcaca gcttagtggc agcaagcctc taatggaagc aattgaaaaa    660

gctaaaaaag ccggtgtatc agttgttgta gcagcaggaa atgagcgcgt ctatggatct    720

gaccatgatg atccattggc gacaaatcca gactatggtt tggtcggttc tccctcaaca    780

ggtcgaacac caacatcagt ggcagctata aacagtaagt gggtgattca acgtctaatg    840

acggtcaaag aattagaaaa ccgtgccgat ttaaaccatg gtaaagccat ctattcagag    900

tctgtcgact ttaaagacat aaaagatagc cta                                 933
```

<210> SEQ ID NO 181
<211> LENGTH: 933
<212> TYPE: DNA
<213> ORGANISM: Streptococcus pyogenes

<400> SEQUENCE: 181

```
gcagttattg acacagggat cgatccggcc catcaaagca tgcgcatcag tgatgtatca     60

actgctaaag taaaatcaaa agaagacatg ctagcacgcc aaaaagccgc cggtattaat    120

tatgggagtt ggataaatga taaagttgtt tttgcacata attatgtgga aaatagcgat    180

aatatcaaag aaaatcaatt cgaggatttt gatgaggact gggaaaactt tgagtttgat    240

gcagatgcag agccaaaagc catcaaaaaa cacaagatct atcgtcccca atcaacccag    300

gcaccgaaag aaactgttat caaaacagaa gaaacagatg gttcacatga tattgactgg    360

acacaaacag acgatgacac caaatacgag tcacacggta tgcatgtgac aggtattgta    420

gccggtaata gcaaagaagc cgctgctact ggagaacgct ttttaggaat tgcaccagag    480

gcccaagtca tgttcatgcg tgtttttgcc aacgacgtca tgggatcagc tgaatcactc    540

tttatcaaag ctatcgaaga tgccgtggct ttaggagcag atgtgatcaa cctgagtctt    600

ggaaccgcta atggggcaca gcttagtggc agcaagcctc taatggaagc aattgaaaaa    660

gctaaaaaag ccggtgtatc agttgttgta gcagcaggaa atgagcgcgt ctatggatct    720

gaccatgatg atccattggc aacaaatcca gactatggtt tggtcggttc tccctcaaca    780

ggtcgaacac caacatcagt ggcagctata aacagtaagt gggtgattca acgtctaatg    840

acggtcaaag gattagaaaa ccgtgccgat ttaaaccatg gtaaagccat ctattcagag    900

tctgtcgact ttaaagacat aaaagatagc cta                                 933
```

<210> SEQ ID NO 182
<211> LENGTH: 933
<212> TYPE: DNA
<213> ORGANISM: Streptococcus pyogenes

<400> SEQUENCE: 182

```
gcagttattg acacagggat cgatccggcc catcaaagca tgcgcatcag tgatgtatca     60

actgctaaag taaaatcaaa agaagacatg ctagcacgcc aaaaagccgc cggtattaat    120

tatgggagtt ggataaatga taaagttgtt tttgcacata attatgtgga aaatagcgat    180

aatatcaaag aaaatcaatt cgaggatttt gatgaggact gggaaaactt tgagtttgat    240

gcagaggcag agccaaaagc catcaaaaaa cacaagatct atcgtcccca atcaacccag    300

gcaccgaaag aaactgttat caaaacagaa gaaacagatg gttcacatga tattgactgg    360
```

acacaaacag acgatgacac caaatacgag tcacacggta tgcatgtgac aggtattgta 420
gccggtaata gcaaagaagc cgctgctact ggagaacgct ttttaggaat tgcaccagag 480
gcccaagtca tgttcatgcg tgtttttgcc aacgacgtca tgggatcagc tgaatcactc 540
tttatcaaag ctatcgaaga tgccgtggct ttaggagcag atgtgatcaa cctgagtctt 600
ggaaccgcta atggggcaca gcttagtggc agcaagcctc taatggaagc aattgaaaaa 660
gctaaaaaag ccggtgtatc agttgttgta gcagcaggaa atgagcgcgt ctatggatct 720
gaccatgatg atccattggc aacaaatcca gactatggtt tggtcggttc tccctcaaca 780
ggtcgaacac caacatcagt ggcagctata aacagtaagt gggtgattca acgtctaatg 840
acggtcaaag aattagaaaa ccgtgccgat ttaaaccatg gtaaagccat ctattcagag 900
tctgtcgact ttaaaaacat aaaagatagc cta 933

<210> SEQ ID NO 183
<211> LENGTH: 933
<212> TYPE: DNA
<213> ORGANISM: Streptococcus pyogenes

<400> SEQUENCE: 183
gcagttattg acacagggat cgatccggcc catcaaagca tgcgcatcag tgatgtatca 60
actgctaaag taaaatcaaa agaagacatg ctagcacgcc aaaaagccgc cggtattaat 120
tatgggagtt ggataaatga taaagttgtt tttgcacata attatgtgga aaatagcgat 180
aatatcaaag aaaatcaatt cgaggatttt gatgaggact gggaaaactt tgagtttgat 240
gcagaggcag agccaaaagc catcaaaaaa cacaagatct atcgtcccca atcaacccag 300
gcaccgaaag aaactgttat caaaacagaa gaaacagatg gttcacatga tattgactgg 360
acacaaacag acgatgacac caaatacgag tcacacggta tgcatgtgac aggtattgta 420
gccggtaata gcaaagaagc cgctgctact ggagaacgct ttttaggaat tgcaccagag 480
gcccaagtca tgttcatgcg tgtttttgcc aacgacgtca tgggatcagc tgaatcactc 540
tttatcaaag ctatcgaaga tgccgtggct ttaggagcag atgtgatcaa cctgagtctt 600
ggaaccgcta atggggcaca gcttagtggc agcaagcctc taatggaagc aattgaaaaa 660
gctaaaaaag ccggtgtatc agttgttgta gcagcaggaa atgagcgcgt ctatggatct 720
gaccatgatg atccattggc aacaaatcca gactatggtt tggtcggttc tccctcaaca 780
ggtcgaacac caacatcagt ggcagctata aacagtaagt gggtgattca acgtctaatg 840
acggtcaaag aattagaaaa ccgtgccgat ttaaaccatg gtaaagccat ctattcagag 900
tctgtcgact ttaaaaacat aaaagatagc cta 933

<210> SEQ ID NO 184
<211> LENGTH: 933
<212> TYPE: DNA
<213> ORGANISM: Streptococcus pyogenes

<400> SEQUENCE: 184
gcagttattg acacagggat cgatccggcc catcaaagca tgcgcatcag tgatgtatca 60
actgctaaag taaaatcaaa agaagacatg ctagcacgcc aaaaagccgc cggtattaat 120
tatgggagtt ggataaatga taaagttgtt tttgcacata attatgtgga aaatagcgat 180
aatatcaaag aaaatcaatt cgaggatttt gatgaggact gggaaaactt tgagtttgat 240
gcagatgcag agccaaaagc catcaaaaaa cacaagatct atcgtcccca atcaacccag 300
gcaccgaaag aaactgttat caaaacagaa gaaacagatg gttcacatga tattgactgg 360

-continued

```
acacaaacag acgatgacac caaatacgag tcacacggta tgcatgtgac aggtattgta    420

gccggtaata gcaaagaagc cgctgctact ggagaacgct ttttaggaat tgcaccagag    480

gcccaagtca tgttcatgcg tgtttttgcc aacgacgtca tgggatcagc tgaatcactc    540

tttatcaaag ctatcgaaga tgccgtggct ttaggagcag atgtgatcaa cctgagtctt    600

ggaaccgcta atggggcaca gcttagtggc agcaagcctc taatggaagc aattgaaaaa    660

gctaaaaaag ccggtgtatc agttgttgta gcagcaggaa atgagcgcgt ctatggatct    720

gaccatgatg acccattggc aacaaatcca gactatggtt tggttggttc tccctcaaca    780

ggtcgaacac caacatcagt ggcagctata aacagtaagt gggtgattca acgtctaatg    840

acggtcaaag aattggaaaa ccgtgccgat ttaaaccatg gtaaagccat ctattcagag    900

tctgtcgact ttaaagacat aaaagatagc cta                                 933
```

<210> SEQ ID NO 185
<211> LENGTH: 927
<212> TYPE: DNA
<213> ORGANISM: Streptococcus pyogenes

<400> SEQUENCE: 185

```
gcagttattg acacagggat cgatccggcc catcaaagca tgcgcatcag tgatgtatca     60

actgctaaag taaaatcaaa agaagacatg ctagcacgcc aaaaagccgc cggtattaat    120

tatgggagtt ggataaatga taaagttgtt tttgcacata attatgtgga aaatagcgat    180

aatatcaaag aaaatcaatt cggggatttt gatgaggact gggaaaactt tgagtttgat    240

gcagagccaa aagccatcaa aaaaaacaag atctatcgtc cccaatcaac ccaggcaccg    300

aaagaaactg ttatcaaaac agaagaaaca gatggttcac atgatattga ctggacacaa    360

acagacgatg acaccaaata cgagtcacac ggtatgcatg tgacaggtat tgtagccggt    420

aatagcaaag aagccgctgc tactggagaa cgctttttag gaattgcacc agaggcccaa    480

gtcatgttca tgcgtgtttt tgccaacgac gtcatgggat cagctgaatc actctttatc    540

aaagctatcg aagatgccgt ggctttagga gcagatgtga tcaacctgag tcttggaacc    600

gctaatgggg cacagcttag tggcagcaag cctctaatgg aagcaattga aaaagctaaa    660

aaagccggtg tatcagttgt tgtagcagca ggaaatgagc gcgtctatgg atctgaccat    720

gatgatccat tggcaacaaa tccagactat ggtttggtcg gttctccctc aacaggtcga    780

acaccaacat cagtggcagc tataaacagt aagtgggtga ttcaacgtct aatgacggcc    840

aaagaattag aaaaccgtgc cgatttaaac catggtaaag ccatctattc agagtctgtc    900

gactttaaag acataaaaga tagccta                                        927
```

<210> SEQ ID NO 186
<211> LENGTH: 1455
<212> TYPE: DNA
<213> ORGANISM: Streptococcus pyogenes

<400> SEQUENCE: 186

```
tcacaaatca ctcccaagac aaatcgtgaa aaagagcaac cacaaggtct agtctctgag     60

ccaaccacaa ctgagctagc tgacacagat gcagcatcaa tggctaatac aggtcctgat    120

gcgactcaaa aaagcgcttc tttaccgcca gtcaatacag atgttcacga ttgggtaaaa    180

accaaaggag cttgggacaa gggatacaaa ggacaaggca aggttgtcgc agttattgac    240

acagggatcg atccggccca tcaaagcatg cgcatcagtg atgtatcaac tgctaaagta    300

aaatcaaaag aagacatgct agcacgccaa aaagccgccg gtattaatta tgggagttgg    360
```

ataaatgata aagttgtttt tgcacataat tatgtggaaa atagcgataa tatcaaagaa 420
aatcaattcg gggattttga tgaggactgg gaaaactttg agtttgatgc agagccaaaa 480
gccatcaaaa aaaacaagat ctatcgtccc caatcaaccc aggcaccgaa agaaactgtt 540
atcaaaacag aagaaacaga tggttcacat gatattgact ggacacaaac agacgatgac 600
accaaatacg agtcacacgg tatgcatgtg acaggtattg tagccggtaa tagcaaagaa 660
gccgctgcta ctggagaacg ctttttagga attgcaccag aggcccaagt catgttcatg 720
cgtgtttttg ccaacgacgt catgggatca gctgaatcac tctttatcaa agctatcgaa 780
gatgccgtgg ctttaggagc agatgtgatc aacctgagtc ttggaaccgc taatggggca 840
cagcttagtg gcagcaagcc tctaatggaa gcaattgaaa aagctaaaaa agccggtgta 900
tcagttgttg tagcagcagg aaatgagcgc gtctatggat ctgaccatga tgatccattg 960
gcaacaaatc cagactatgg tttggtcggt tctccctcaa caggtcgaac accaacatca 1020
gtggcagcta taaacagtaa gtgggtgatt caacgtctaa tgacggccaa agaattagaa 1080
aaccgtgccg atttaaacca tggtaaagcc atctattcag agtctgtcga ctttaaagac 1140
ataaaagata gcctaggtta tgataaatcg catcaatttg cttatgtcaa agagtcaact 1200
gatgcgggtt ataaagcaca agacgttaaa gataaaattg ctttaattga acgtgatccc 1260
aataaaacct atgacgaaat gattgctttg gctaagaaac atggagccct gggagtactt 1320
atttttaata acaagcctgg tcaatcaaac cgctcaatgc gtctaacagc taatgggatg 1380
gggataccat ctgctttcat atcgcacgaa tttggtaagg ccatgtccca attaaatggc 1440
aatggtacag gaagt 1455

<210> SEQ ID NO 187
<211> LENGTH: 1461
<212> TYPE: DNA
<213> ORGANISM: Streptococcus pyogenes

<400> SEQUENCE: 187
tcacaaatca ctctcaagac aaatcgtgaa aaagagcaac cacaaggtct agtctctgag 60
ccaaccacaa ctgagctagc tgacacagat gcagcaccaa tggctaatac aggtcctgat 120
gcgactcaaa aaagcgcttc tttaccgcca gtcaatacag atgttcacga ttgggtaaaa 180
accaaaggag cttgggacaa gggatacaaa ggacaaggca aggttgtcgc agttattgac 240
acagggatcg atccggccca tcaaagcatg cgcatcagtg atgtatcaac tgctaaagta 300
aaatcaaaag aagacatgct agcacgccaa aaagccgccg gtattaatta tgggagttgg 360
ataaatgata aagttgtttt tgcacataat tatgtggaaa atagcgataa tatcaaagaa 420
aatcaattcg aggattttga tgaggactgg gaaaactttg agtttgatgc agaggcagag 480
ccaaaagcca tcaaaaaaca caagatctat cgtccccaat caacccaggc accgaaagaa 540
actgttatca aaacagaaga aacagatggt tcacatgata ttgactggac acaaacagac 600
gatgacacca aatacgagtc acacggtatg catgtgacag gtattgtagc cggtaatagc 660
aaagaagccg ctgctactgg agaacgcttt ttaggaattg caccagaggc ccaagtcatg 720
ttcatgcgtg tttttgccaa cgacgtcatg ggatcagctg aatcactctt tatcaaagct 780
atcgaagatg ccgtggcttt aggagcagat gtgatcaacc tgagtcttgg aaccgctaat 840
ggggcacagc ttagtggcag caagcctcta atggaagcaa ttgaaaaagc taaaaaagcc 900
ggtgtatcag ttgttgtagc agcaggaaat gagcgcgtct atggatctga ccatgatgat 960
ccattggcaa caaatccaga ctatggtttg gtcggttctc cctcaacagg tcgaacacca 1020
acatcagtgg cagctataaa cagtaagtgg gtgattcaac gtctaatgac ggtcaaagaa 1080
ttagaaaacc gtgccgattt aaaccatggt aaagccatct attcagagtc tgtcgacttt 1140
aaagacataa aagatagcct aggttatgat aaatcgcatc aatttgctta tgtcaaagag 1200
tcaactgatg cgggttataa cgcacaagac gttaaaggta aaattgcttt aattgaacgt 1260
gatcccaata aaacctatga cgaaatgatt gctttggcta agaaacatgg agccctggga 1320
gtacttattt ttaataacaa gcctggtcaa tcaaaccgct caatgcgtct aacagctaat 1380
gggatgggga taccatctgc tttcatatcg cacgaatttg gtaaggccat gtcccaatta 1440
aatggcaatg gtacaggaag t 1461

<210> SEQ ID NO 188
<211> LENGTH: 1461
<212> TYPE: DNA
<213> ORGANISM: Streptococcus pyogenes

<400> SEQUENCE: 188
tcacaagtaa ctccagagac aaatcgtgaa aaagagcaac cacaaggtct agtctctgag 60
ccaacaacaa ctgagctagc tgacacagat gcagcaccaa tggctaatac aggttctgat 120
gcgactcaaa aaagcgcttc tttaccgcca gtcaatacag atgttcacga ttgggtaaaa 180
accaaaggag cttgggacaa gggatacaaa ggacaaggca aggttgtcgc agttattgac 240
acagggatcg atccggccca tcaaagcatg cgcatcagtg atgtatcaac tgctaaagta 300
aaatcaaaag aagacatgct agcacgccaa aaagccgccg gtattaatta tgggagttgg 360
ataaatgata aagttgtttt tgcacataat tatgtggaaa atagcgataa tatcaaagaa 420
aatcaattcg aggattttga tgaggactgg gaaaactttg agtttgatgc agaggcagag 480
ccaaaagcca tcaaaaaaca caagatctat cgtccccaat caacccaggc accgaaagaa 540
actgttatca aaacagaaga aacagatggt tcacatgata ttgactggac acaaacagac 600
gatgacacca aatacgagtc acacggtatg catgtgacag gtattgtagc cggtaatagc 660
aaagaagccg ctgctactgg agaacgcttt ttaggaattg caccagaggc ccaagtcatg 720
ttcatgcgtg tttttgccaa cgacgtcatg ggatcagctg aatcactctt tatcaaagct 780
atcgaagatg ccgtggcctt aggagcagat gtgatcaacc tgagtcttgg aaccgctaat 840
ggggcacagc ttagtggcag caagcctcta atggaagcaa ttgaaaaagc taaaaaagcc 900
ggtgtatcag ttgttgtagc agcaggaaat gagcgcgtct atggatctga ccatgatgat 960
ccattggcga caaatccaga ctatggtttg gtcggttctc cctcaacagg tcgaacacca 1020
acatcagtag cagctataaa cagtaagtgg gtgattcaac gtctaatgac ggtcaaagaa 1080
ttggaaaacc gtgccgattt aaaccatggt aaagccatct attcagagtc tgtcgacttt 1140
aaagacataa aagatagcct aggttatgat aaatcgcatc aatttgctta tgtcaaagag 1200
tcaactgatg cgggttataa cgcacaaaac gttaaaggta aaattgcttt aattgaacgt 1260
gatcccaata aaacctatga cgaaatgatt gctttggcta agaaacatgg agccctggga 1320
gtacttattt ttaataacaa gcctggtcaa tcaaaccgct caatgcgtct aacagctaat 1380
gggatgggga taccatctgc tttcatatcg cacgaatttg gtaaggccat gtcccaatta 1440
aatggcaatg gtacaggaag t 1461

<210> SEQ ID NO 189
<211> LENGTH: 1455
<212> TYPE: DNA
<213> ORGANISM: Streptococcus pyogenes

<400> SEQUENCE: 189

```
tcacaaatca ctcccaagat aaatcgtgaa aaagagcaac cacaaggtct agtctctgag     60
ccaaccacaa ctgagctagc tgacacagat gcagcaccaa tggctaatac aggtcctgat    120
gcgactcaaa aaagcgcttc tttaccgcca gtcaatacag atgttcacga ttgggtaaaa    180
accaaaggag cttgggacaa ggggtacaaa ggacaaggta aggttgtcgc agttattgac    240
acagggatcg atccggccca tcaaagcatg cgcatcagtg atgtatcaac tgctaaagta    300
aaatcaaaag aagacatgct agcacgccaa aaagccgccg gtattaatta tgggagttgg    360
ataaatgata aagttgtttt tgcacataat tatgtggaaa atagcgataa tatcaaagaa    420
aatcaattcg aggattttga tgaggactgg gaaaactttg agtttgatgc agagccaaaa    480
gccatcaaaa aacacaagat ctatcgtccc caatcaaccc aggcaccgaa agaaactgtt    540
atcaaaacag aagaaacaga tggttcacat gatattgact ggacacaaac agacgatgac    600
accaaatacg agtcacacgg tatgcatgtg acaggtattg tagccggtaa tagtaaagaa    660
gccgctgcta ctggagaacg ctttttagga attgcaccag agacccaagt catgttcatg    720
cgtgtttttg ccaacgacgt catgggatca gctgaatcac tctttatcaa agctatcgaa    780
gatgccgtgg ccttaggagc agatgtgatc aacctgagtc ttgggaccgc taatggtgca    840
cagcttagtg gcagcaagcc tctaatggaa gcaattgaaa aagctaaaaa agccggtgta    900
tcagttgttg tagcagcagg aaatgagcgc gtctatggat ctgaccatga tgatccattg    960
gcaacaaatc cagactatgg tttggtcggt tctccctcaa caggtcgaac accaacatca   1020
gtggcagcta taaacagtaa gtgggtgatt caacgtctaa tgacggtcaa agaattagaa   1080
aaccgtgccg atttaaacca tggtaaagcc atctattcag agtctgtcga ctttaaagac   1140
ataaaagata gcctaggtta tgataaatcg catcaatttg cttatgtcaa agagtcaact   1200
gatgcgggtt ataacgcaca agacgttaaa ggtaaaattg ctttaattga acgtgatccc   1260
aataaaacct atgacgaaat gattgctttg gctaagaaac atggagccct gggagtactt   1320
atttttaata acaagcctgg tcaatcaaac cgctcaatgc gcctaacagc taatgggatg   1380
gggataccat ctgctttcat atcgcacgaa tttggtaagg ccatgtccca attaaatggc   1440
aatggtacag gaagt                                                    1455
```

<210> SEQ ID NO 190
<211> LENGTH: 1461
<212> TYPE: DNA
<213> ORGANISM: Streptococcus pyogenes

<400> SEQUENCE: 190

```
tcacaaatca ctctcaagac aaatcgtgaa aaagagcaat cacaagatct agtctctgag     60
ccaaccacaa ctgagctagc tgacacagat gcagcatcaa tggctaatac aggttctgat    120
gcgactcaaa aaagcgcttc tttaccgcca gtcaatacag atgttcacga ttgggtaaaa    180
accaaaggag cttgggacaa gggatacaaa ggacaaggca aggttgtcgc agttattgac    240
acagggatcg atccggccca tcaaagcatg cgcatcagtg atgtatcaac tgctaaagta    300
aaatcaaaag aagacatgct agcacgccaa aaagccgccg gtattaatta tgggagttgg    360
ataaatgata aagttgtttt tgcacataat tatgtggaaa atagcgataa tatcaaagaa    420
aatcaattcg aggattttga tgaggactgg gaaaactttg agtttgatgc agaggcagag    480
ccaaaagcca tcaaaaaaca caagatctat cgtccccaat caacccaggc accgaaagaa    540
actgttatca aaacagaaga aacagatggt tcacatgata ttgactggac acaaacagac    600
```

gatgacacca aatacgagtc acacggtatg catgtgacag gtattgtagc cggtaatagc 660
aaagaagccg ctgctactgg agaacgcttt ttaggaattg caccagaggc ccaagtcatg 720
ttcatgcgtg tttttgccaa cgacatcatg ggatcagctg aatcactctt tatcaaagct 780
atcgaagatg ccgtggcttt aggagcagat gtgatcaacc tgagtcttgg aaccgctaat 840
ggggcacagc ttagtggcag caagcctcta atggaagcaa ttgaaaaagc taaaaaagcc 900
ggtgtatcag ttgttgtagc agcaggaaat gagcgcgtct atggatctga ccatgatgat 960
ccattggcga caaatccaga ctatggtttg gtcggttctc cctcaacagg tcgaacacca 1020
acatcagtgg cagctataaa cagtaagtgg gtgattcaac gtctaatgac ggtcaaagaa 1080
ttagaaaacc gtgccgattt aaaccatggt aaagccatct attcagagtc tgtcgacttt 1140
aaagacataa aagatagcct aggttatgat aaatcgcatc aatttgctta tgtcaaagag 1200
tcaactgatg cgggttataa cgcacaagac gttaaaggta aaattgcttt aattgaacgt 1260
gatcccaata aaacctatga cgaaatgatt gctttggcta agaaacatgg agctctggga 1320
gtacttattt ttaataacaa gcctggtcaa tcaaaccgct caatgcgtct aacagctaat 1380
gggatgggga taccatctgc tttcatatcg cacgaatttg gtaaggccat gtcccaatta 1440
aatggcaatg gtacaggaag t 1461

<210> SEQ ID NO 191
<211> LENGTH: 1461
<212> TYPE: DNA
<213> ORGANISM: Streptococcus pyogenes

<400> SEQUENCE: 191
tcacaagtaa ctccagagac aaatcgtgaa aaagagcaac cacaaggtct agtctctgag 60
ccaacaacaa ctgagctagc tgacacagat gcagcaccaa tggctaatac aggtcctgat 120
gcgactcaaa aaagcgcttc tttaccgcca gtcaatacag atgttcacga ttgggtaaaa 180
accaaaggag cttgggacaa gggatacaaa ggacaaggca aggttgtcgc agttattgac 240
acagggatcg atccggccca tcaaagcatg cgcatcagtg atgtatcaac tgctaaagta 300
aaatcaaaag aagacatgct agcacgccaa aaagccgccg gtattaatta tgggagttgg 360
ataaatgata aagttgtttt tgcacataat tatgtggaaa atagcgataa tatcaaagaa 420
aatcaattcg aggattttga tgaggactgg gaaaactttg agtttgatgc agatgcagag 480
ccaaaagcca tcaaaaaaca caagatctat cgtccccaat caacccaggc accgaaagaa 540
actgttatca aaacagaaga aacagatggt tcacatgata ttgactggac acaaacagac 600
gatgacacca aatacgagtc acacggtatg catgtgacag gtattgtagc cggtaatagc 660
aaagaagccg ctgctactgg agaacgcttt ttaggaattg caccagaggc ccaagtcatg 720
ttcatgcgtg tttttgccaa cgacgtcatg ggatcagctg aatcactctt tatcaaagct 780
atcgaagatg ccgtggcttt aggagcagat gtgatcaacc tgagtcttgg aaccgctaat 840
ggggcacagc ttagtggcag caagcctcta atggaagcaa ttgaaaaagc taaaaaagcc 900
ggtgtatcag ttgttgtagc agcaggaaat gagcgcgtct atggatctga ccatgatgat 960
ccattggcaa caaatccaga ctatggtttg gtcggttctc cctcaacagg tcgaacacca 1020
acatcagtgg cagctataaa cagtaagtgg gtgattcaac gtctaatgac ggtcaaagga 1080
ttagaaaacc gtgccgattt aaaccatggt aaagccatct attcagagtc tgtcgacttt 1140
aaagacataa aagatagcct aggttatgat aaatcgcatc aatttgctta tgtcaaagag 1200
tcaactgatg cgggttataa cgcacaagac gttaaaggta aaattgcttt aattgaacgt 1260
gatcccaata aaacctatga cgaaatgatt gctttggcta agaaacatgg agccctggga 1320
ctacttattt ttaataacaa gtctggtcaa tcaaaccgct caatgcgtct aacagctaat 1380
gggatgggga taccatctgc tttcatatcg cacgaatttg gtaaggccat gtcccaatta 1440
aatggcaatg gtacaggaag t 1461

<210> SEQ ID NO 192
<211> LENGTH: 1461
<212> TYPE: DNA
<213> ORGANISM: Streptococcus pyogenes

<400> SEQUENCE: 192
tcacaaatca ctcccaagac aaatcgtgaa aaagagcaat cacaagatct agtctctgag 60
ccaaccacaa ctgagctagc tgacacagat gcagcatcaa tggctaatac aggtcctgat 120
gcgactcaaa aaagcgcttc tttaccgcca gtcaatacag atgttcacga ttgggtaaaa 180
accaaaggag cttgggacaa gggatacaaa ggacaaggca aggttgtcgc agttattgac 240
acagggatcg atccggccca tcaaagcatg cgcatcagtg atgtatcaac tgctaaagta 300
aaatcaaaag aagacatgct agcacgccaa aaagccgccg gtattaatta tgggagttgg 360
ataaatgata aagttgtttt tgcacataat tatgtggaaa atagcgataa tatcaaagaa 420
aatcaattcg aggattttga tgaggactgg gaaaactttg agtttgatgc agaggcagag 480
ccaaaagcca tcaaaaaaca caagatctat cgtccccaat caacccaggc accgaaagaa 540
actgttatca aaacagaaga aacagatggt tcacatgata ttgactggac acaaacagac 600
gatgacacca aatacgagtc acacggtatg catgtgacag gtattgtagc cggtaatagc 660
aaagaagccg ctgctactgg agaacgcttt ttaggaattg caccagaggc ccaagtcatg 720
ttcatgcgtg tttttgccaa cgacgtcatg ggatcagctg aatcactctt tatcaaagct 780
atcgaagatg ccgtggcttt aggagcagat gtgatcaacc tgagtcttgg aaccgctaat 840
ggggcacagc ttagtggcag caagcctcta atggaagcaa ttgaaaaagc taaaaaagcc 900
ggtgtatcag ttgttgtagc agcaggaaat gagcgcgtct atggatctga ccatgatgat 960
ccattggcaa caaatccaga ctatggtttg gtcggttctc cctcaacagg tcgaacacca 1020
acatcagtgg cagctataaa cagtaagtgg gtgattcaac gtctaatgac ggtcaaagaa 1080
ttagaaaacc gtgccgattt aaaccatggt aaagccatct attcagagtc tgtcgacttt 1140
aaaaacataa aagatagcct aggttatgat aaatcgcatc aatttgctta tgtcaaagag 1200
tcaactgatg cgggttataa cgcacaagac gttaaaggta aaattgcttt aattgaacgt 1260
gatcccaata aaacctatga cgaaatgatt gctttggcta agaaacatgg agccctggga 1320
gtacttattt ttaataacaa acctggtcaa tcaaaccgct caatgcgcct aacatctaat 1380
gggatgggaa taccatctgc tttcatatcg cacgaatttg gtaaggccat gtcccaatta 1440
aatggcaatg gtacaggaag t 1461

<210> SEQ ID NO 193
<211> LENGTH: 1461
<212> TYPE: DNA
<213> ORGANISM: Streptococcus pyogenes

<400> SEQUENCE: 193
tcacaaatca ctctcaagac aaatcgtgaa aaagagcaac cacaaggtct agtctctgag 60
ccaaccacaa ctgagctagc tgacacagat gcagcaccaa tggctaatac aggtcctgat 120
gcgactcaaa aaagcgcttc tttaccgcca gtcaatacag atgttcacga ttgggtaaaa 180
accaaaggag cttgggacaa gggatacaaa ggacaaggca aggttgtcgc agttattgac 240
acagggatcg atccggccca tcaaagcatg cgcatcagtg atgtatcaac tgctaaagta 300
aaatcaaaag aagacatgct agcacgccaa aaagccgccg gtattaatta tgggagttgg 360
ataaatgata aagttgtttt tgcacataat tatgtggaaa atagcgataa tatcaaagaa 420
aatcaattcg aggattttga tgaggactgg gaaaactttg agtttgatgc agaggcagag 480
ccaaaagcca tcaaaaaaca caagatctat cgtccccaat caacccaggc accgaaagaa 540
actgttatca aaacagaaga aacagatggt tcacatgata ttgactggac acaaacagac 600
gatgacacca aatacgagtc acacggtatg catgtgacag gtattgtagc cggtaatagc 660
aaagaagccg ctgctactgg agaacgcttt ttaggaattg caccagaggc ccaagtcatg 720
ttcatgcgtg tttttgccaa cgacgtcatg ggatcagctg aatcactctt tatcaaagct 780
atcgaagatg ccgtggcttt aggagcagat gtgatcaacc tgagtcttgg aaccgctaat 840
ggggcacagc ttagtggcag caagcctcta atggaagcaa ttgaaaaagc taaaaaagcc 900
ggtgtatcag ttgttgtagc agcaggaaat gagcgcgtct atggatctga ccatgatgat 960
ccattggcaa caaatccaga ctatggtttg gtcggttctc cctcaacagg tcgaacacca 1020
acatcagtgg cagctataaa cagtaagtgg gtgattcaac gtctaatgac ggtcaaagaa 1080
ttagaaaacc gtgccgattt aaaccatggt aaagccatct attcagagtc tgtcgacttt 1140
aaaaacataa aagatagcct aggttatgat aaatcgcatc aatttgctta tgtcaaagag 1200
tcaactgatg cgggttataa agcacaagac gttaaaggta aaattgcttt aattgaacgt 1260
gatcccaata aaacctatga cgaaatgatt gctttggcta agaaacatgg agccctggga 1320
gtacttattt ttaataacaa gcctggtcaa tcaaaccgct caatgcgtct aacagctaat 1380
gggatgggga taccatctgc tttcatatcg cacgaatttg gtaaggccat gtcccaatta 1440
aatggcaatg gtacaggaag t 1461

<210> SEQ ID NO 194
<211> LENGTH: 1461
<212> TYPE: DNA
<213> ORGANISM: Streptococcus pyogenes

<400> SEQUENCE: 194
tcacaaatca ctcccaagac aaatcgtgaa aaagagcaat cacaagatct agtctctgag 60
ccaacaacaa ctgagctagc tgacacagat gcagcatcaa tggctaatac aggttctgat 120
gcgactcaaa aaagcgcttc tttaccgcca gtcaatacag atgttcacga ttgggtaaaa 180
accaaaggag cttgggacaa gggatacaaa ggacaaggca aggttgtcgc agttattgac 240
acagggatcg atccggccca tcaaagcatg cgcatcagtg atgtatcaac tgctaaagta 300
aaatcaaaag aagacatgct agcacgccaa aaagccgccg gtattaatta tgggagttgg 360
ataaatgata aagttgtttt tgcacataat tatgtggaaa atagcgataa tatcaaagaa 420
aatcaattcg aggattttga tgaggactgg gaaaactttg agtttgatgc agatgcagag 480
ccaaaagcca tcaaaaaaca caagatctat cgtccccaat caacccaggc accgaaagaa 540
actgttatca aaacagaaga aacagatggt tcacatgata ttgactggac acaaacagac 600
gatgacacca aatacgagtc acacggtatg catgtgacag gtattgtagc cggtaatagc 660
aaagaagccg ctgctactgg agaacgcttt ttaggaattg caccagaggc ccaagtcatg 720
ttcatgcgtg tttttgccaa cgacgtcatg ggatcagctg aatcactctt tatcaaagct 780
atcgaagatg ccgtggcttt aggagcagat gtgatcaacc tgagtcttgg aaccgctaat 840
ggggcacagc ttagtggcag caagcctcta atggaagcaa ttgaaaaagc taaaaaagcc 900
ggtgtatcag ttgttgtagc agcaggaaat gagcgcgtct atggatctga ccatgatgac 960
ccattggcaa caaatccaga ctatggtttg gttggttctc cctcaacagg tcgaacacca 1020
acatcagtgg cagctataaa cagtaagtgg gtgattcaac gtctaatgac ggtcaaagaa 1080
ttggaaaacc gtgccgattt aaaccatggt aaagccatct attcagagtc tgtcgacttt 1140
aaagacataa aagatagcct aggttatgat aaatcgcatc aatttgctta tgtcaaagag 1200
tcaactgatg cgggttataa agcacaagac gttaaagata aaattgcttt aattgaacgt 1260
gatcccaata aaacctatga cgaaatgatt gctttggcta agaaacatgg agccctgggg 1320
gtacttattt ttaataacaa gcctggtcaa tcaaaccgct caatgcgtct aacagctaat 1380
gggatgggga taccatctgc tttcatatcg cacgaatttg gtaaggccat gtcccaatta 1440
aatggcaatg gtacaggaag t 1461

<210> SEQ ID NO 195
<211> LENGTH: 1455
<212> TYPE: DNA
<213> ORGANISM: Streptococcus pyogenes

<400> SEQUENCE: 195
tcacaaatca ctcccaagac aaatcgtgaa aaagagcaac cacaaggtct agtctctgag 60
ccaaccacaa ctgagctagc tgacacagat gcagcatcaa tggctaatac aggtcctgat 120
gcgactcaaa aaagcgcttc tttaccgcca gtcaatacag atgttcacga ttgggtaaaa 180
accaaaggag cttgggacaa gggatacaaa ggacaaggca aggttgtcgc agttattgac 240
acagggatcg atccggccca tcaaagcatg cgcatcagtg atgtatcaac tgctaaagta 300
aaatcaaaag aagacatgct agcacgccaa aaagccgccg gtattaatta tgggagttgg 360
ataaatgata aagttgtttt tgcacataat tatgtggaaa atagcgataa tatcaaagaa 420
aatcaattcg gggattttga tgaggactgg gaaaactttg agtttgatgc agagccaaaa 480
gccatcaaaa aaaacaagat ctatcgtccc caatcaaccc aggcaccgaa agaaactgtt 540
atcaaaacag aagaaacaga tggttcacat gatattgact ggacacaaac agacgatgac 600
accaaatacg agtcacacgg tatgcatgtg acaggtattg tagccggtaa tagcaaagaa 660
gccgctgcta ctggagaacg ctttttagga attgcaccag aggcccaagt catgttcatg 720
cgtgtttttg ccaacgacgt catgggatca gctgaatcac tctttatcaa agctatcgaa 780
gatgccgtgg ctttaggagc agatgtgatc aacctgagtc ttggaaccgc taatggggca 840
cagcttagtg gcagcaagcc tctaatggaa gcaattgaaa aagctaaaaa agccggtgta 900
tcagttgttg tagcagcagg aaatgagcgc gtctatggat ctgaccatga tgatccattg 960
gcaacaaatc cagactatgg tttggtcggt tctccctcaa caggtcgaac accaacatca 1020
gtggcagcta taaacagtaa gtgggtgatt caacgtctaa tgacggccaa agaattagaa 1080
aaccgtgccg atttaaacca tggtaaagcc atctattcag agtctgtcga ctttaaagac 1140
ataaaagata gcctaggtta tgataaatcg catcaatttg cttatgtcaa agagtcaact 1200
gatgcgggtt ataaagcaca agacgttaaa gataaaattg ctttaattga acgtgatccc 1260
aataaaacct atgacgaaat gattgctttg gctaagaaac atggagccct gggagtactt 1320
atttttaata acaagcctgg tcaatcaaac cgctcaatgc gtctaacagc taatgggatg 1380
gggataccat ctgctttcat atcgcacgaa tttggtaagg ccatgtccca attaaatggc 1440
aatggtacag gaagt 1455

<210> SEQ ID NO 196
<211> LENGTH: 1839
<212> TYPE: DNA
<213> ORGANISM: Streptococcus pyogenes

<400> SEQUENCE: 196
gatcaagttg atgtgcaatt ccttggcgtc aatgattttc acggcgctct tgataatacc 60
ggaacagctt acacaccaag tggtaaaata ccaaatgctg ggacggctgc tcaattaggt 120
gcttatatgg atgacgctga gatagacttc aagcaagcaa atcaagacgg aacaagtata 180
cgtgttcaag ctggagatat ggtcggagcc agtcctgcta actctgcact tttacaagat 240
gagcctactg tcaaagtctt taacaaaatg aaatttgaat atggcactct tggtaatcat 300
gaatttgacg aaggactaga tgaatttaac cgtatcatga caggtcaagc gcctgatcct 360
gaatcaacaa ttaatgatat caccaaacaa tatgagcacg aagcttcgca tcaaaccatc 420
gtcattgcta atgttattga taaaaaaacc aaggatatcc cctatggttg gaaaccttat 480
gctataaaag acatagccat taatgacaaa atcgttaaga ttggcttcat tggtgttgtg 540
actacagaga ttccaaatct cgttttaaag caaaactatg aacactatca atttttagat 600
gtagctgaaa ccattgccaa atatgctaaa gaactacaag aacaacatgt tcatgctatt 660
gtggttttag ctcatgttcc tgcaacaagt aaagatggtg ttgttgatca tgaaatggct 720
acggttatgg aaaaagtgaa ccaaatctat cccgaacata gcattgatat tatttttgca 780
ggacataatc atcaatacac taatggaact atcggtaaaa cacgtatcgt tcaagccctc 840
tctcaaggaa aagcttatgc agatgtccgt ggtacgctag atactgatac caatgatttt 900
attaaaactc catcagcaaa tgttgttgct gtagcaccag gtatcaaaac agaaaattca 960
gatatcaaag ctataataaa tcatgctaat gatattgtta aaacagttac tgaacgaaaa 1020
atcggaactg caactaattc ttcaactatt tctaaaacag aaaatattga taaagaatct 1080
cctgtcggta acttagcaac aacggctcag cttactattg ctaagaaaac ttttccaact 1140
gttgactttg ctatgaccaa taatggtggt attcgaagtg acctagttgt caaaaatgac 1200
cggaccatca cctggggagc tgcacaggct gtacaaccat ttggtaatat ccttcaagtc 1260
attcaaatga ctggtcaaca catttacgat gtcctaaatc agcaatacga tgaaaaccag 1320
acctattttc ttcaaatgtc aggtttaaca tacacttata cagataatga tcctaagaac 1380
tctgataccc ccttcaagat agttaaggtt tataaagaca atggtgaaga aattaactta 1440
acaactactt acaccgttgt tgtcaacgac tttctttatg gtggtggtga tggcttttca 1500
gcatttaaaa aagctaaatt aatcggagct attaacacag atactgaagc tttcatcaca 1560
tatatcacaa atttagaagc atcaggtaaa actgttaatg ctactataaa aggggttaaa 1620
aattatgtaa cttcaaacct tgaaagttcg acaaaagtta atagtgctgg taaacacagt 1680
atcattagta aggtttttag aaatcgtgat ggcaatacag tgtctagtga agtcatttca 1740 gacctttga cttctactga aaacactaat aacagccttg gcaaaaaaga aacaacaaca 1800
aacaaaaata ctatctctag ttccactctt ccaataaca 1839

<210> SEQ ID NO 197
<211> LENGTH: 876
<212> TYPE: DNA
<213> ORGANISM: Streptococcus pyogenes

<400> SEQUENCE: 197
gctataataa atcatgctaa tgatattgtt aaaacagtta ctgaacgaaa aatcggaact 60
gcaactaatt cttcaactat ttctaaaaca gaaaatattg ataaagaatc tcctgtcggt 120
aacttagtaa caacggctca gcttactatt gctaagaaaa cttttccaac tgttgacttt 180
gctatgacca ataatggtgg tattcgaagt gacctagttg tcaaaaatga ccggaccatc 240
acctgggaag ctgcacaggc tgtacaacca tttggtaata tccttcaagt cattcaaatg 300
actggtcaac acatttacga tgtcctaaat cagcaatacg atgaaaacca gacctatttt 360
cttcaaatgt caggtttaac atacacttat acagataatg atcctaagaa ctctgatacc 420
cccttcaaga tagttaaggt ttataaagac aatggtgaag aaattaactt aacaactact 480
tacaccgttg ttgtcaacga ctttctttat ggtggtggtg atggcttttc agcatttaaa 540
aaagctaaat taatcggagc tattaacaca gatactgaag ctttcatcac atatatcaca 600
aatttagaag catcaggtaa aactgttaat gctactataa aaggggttaa aaattatgta 660
acttcaaacc ttgaaagttc gacaaaagtt aatagtgctg gtaaacacag tatcattatc 720
attagtaagg tttttagaaa tcgtgatggc aatatagtgt ctagtgaaat catttcagac 780
cttttgactt ctactgaaaa cactaataac agctttggca aaaaagagat aacaacaaac 840
aaaaatacta tctctaattc cactcttcca ataaca 876

<210> SEQ ID NO 198
<211> LENGTH: 870
<212> TYPE: DNA
<213> ORGANISM: Streptococcus pyogenes

<400> SEQUENCE: 198
gctataataa atcatgctaa tgatattgtt aaaacagtta ctgaacgaaa aatcggaact 60
gcaactaatt cttcaactat ttctaaaaca gaaaatattg ataaagaatc tcctgtcggt 120
aacttagtaa caacggctca gcttactatt gctaagaaaa cttttccaac tgttgacttt 180
gctatgacca ataatggtgg tattcgaagt gacctagttg tcaaaaatga ccggaccatc 240
acctggggag ctgcacaggc tgtacaacca tttggtaata tccttcaagt cattcaaatg 300
actggtcaac acatttacga tgtcctaaat cagcaatacg atgaaaacca gacctatttt 360
cttcaaatgt caggtttaac atacacttat acagataatg atcctaagaa ctctgatacc 420
cccttcaaga tagttaaggt ttataaagac aatggtgaag aaattaactt aacaactact 480
tacaccgttg ttgtcaacga ctttctttat ggtggtggtg atggcttttc agcatttaaa 540
aaagctaaat taatcggagc tattaacaca gatactgaag ctttcatcac atatatcaca 600
aatttagaag catcaggtaa aactgttaat gctactataa aaggggttaa aaattatgta 660
acttcaaacc ttgaaagctc gacaaaagtt aatagtgctg gtaaacacag tatcattagt 720
aaggttttta gaaatcgtga tggcaatata gtgtctagtg aaatcatttc agaccttttg 780
acttctactg aaaacactaa taacagcctt ggcaaaaaag aaacaacgac aaacaaaaat 840
actatctcta gttccactct tccaataaca 870

<210> SEQ ID NO 199
<211> LENGTH: 870
<212> TYPE: DNA
<213> ORGANISM: Streptococcus pyogenes

<400> SEQUENCE: 199
gctataataa atcatgctaa tgatattgtt aaaacagtta ctgaacgaaa aatcggaact 60
gcaactaatt cttcaactat ttctaaaaca gaaaatattg ataaagaatc tcctgtcggt 120
aacttagtaa caacggctca gcttactatt gctaagaaaa cttttccaac tgttgacttt 180
gctatgacca ataatggtgg tattcgaagt gacctagttg tcaaaaatga ccggaccatc 240
acctggggag ctgcacaggc tgtacaacca tttggtaata tccttcaagt cattcaaatg 300
actggtcaac acatttacga tgtcctaaat cagcaatacg atgaaaacca gacctatttt 360
cttcaaatgt caggtttaac atacacttat acagataatg atcctaagaa ctctgatatc 420
cccttcaaga tagttaaggt ttataaagac aatggtgaag aaattaactt aacaactact 480
tacaccgttg ttgtcaacga ctttctttat ggtggtggtg atggcttttc agcatttaaa 540
aaagctaaat taatcggagc tattaataca gatactgaag ctttcatcac atatatcaca 600
aatttagaag catcaggtaa aactgttaat gctactataa aaggggttaa aaattatgta 660
acttcaaacc ttgaaagttc gacaaaagtt aatagtgctg gtaaacacag tatcattagt 720
aaggttttta gaaatcgtga tggcaatata gtgtctagtg aagtcatttc agaccttttg 780
acttctactg aaaacactaa taacagcctt ggcaaaaaag aaacaacgac aaacaaaaat 840
actatctcta gttccactct tccaataaca 870

<210> SEQ ID NO 200
<211> LENGTH: 870
<212> TYPE: DNA
<213> ORGANISM: Streptococcus pyogenes

<400> SEQUENCE: 200
gctataataa atcatgctaa tgatattgtt aaaacagtta ctgaacgaaa aatcggaact 60
gcaactaatt cttcaactat ttctaaaaca gaaaatattg ataaagaatc tcctgtcggt 120
aacttagtaa caacagctca gcttactatt gctaagaaaa cttttccaac tgttgacttt 180
gctatgacca ataatggtgg tattcgaagt gacctagttg tcaaaaatga tcggaccatc 240
acctggggag ctgcacaggc tgtacaacca tttggtaata tccttcaagt cattcaaatg 300
actggtcaac acatttacga tgtcctaaat cagcaatacg atgaaaacca gacctatttt 360
cttcaaatgt caggtttaac atacacttat acagataatg atcctaagaa ctctgatacc 420
cccttcaaga tagttaaggt ttataaagac aatggtgaag aaattaactt aacaactact 480
tacaccgttg ttgtcaacga ctttctttat ggtggtggtg atggcttttc agcatttaaa 540
aaagctaaat taattggagc tattaacaca gatactgaag ctttcatcac atatatcaca 600
aatttagaag catcaggtaa aactgttaat gctactataa aaggggttaa aaattatgta 660
acttcaaacc ttgaaagttc gacaaaagtt aatagtgctg gtaaacacag tatcattagt 720
aaggttttta gaaatcgtga tggcaatata gtgtctagtg agatcatttc agaccttttg 780
acttctactg aaaacactaa taacagcctt ggcaaaaaag aaacaacaac aaacaaaaat 840
actatctcta gttccactct tccaataaca 870

<210> SEQ ID NO 201
<211> LENGTH: 870
<212> TYPE: DNA
<213> ORGANISM: Streptococcus pyogenes

<400> SEQUENCE: 201
gctataataa atcatgctaa tgatattgtt aaaacagtta ctgaacgaaa aatcggaact 60
gcaactaatt cttcaactat ttctaaaaca gaaaatattg ataaagaatc tcctgtcggt 120
aacttagcaa caacggctca gcttactatt gctaagaaaa cttttccaac tgttgacttt 180
gctatgacca ataatggtgg tattcgaagt gacctagttg tcaaaaatga ccggaccatc 240
acctggggag ctgcacaggc tgtacaacca tttggtaata tccttcaagt cattcaaatg 300

```
actggtcaac acatttacga tgtcctaaat cagcaatacg atgaaaacca gacctatttt    360

cttcaaatgt caggtttaac atacacttat acagataatg atcctaagaa ctctgatacc    420

cccttcaaga tagttaaggt ttataaagac aatggtgaag aaattaactt aacaactact    480

tacaccgttg ttgtcaacga ctttctttat ggtggtggtg atggcttttc agcatttaaa    540

aaagctaaat taatcggagc tattaacaca gatactgaag ctttcatcac atatatcaca    600

aatttagaag catcaggtaa aactgttaat gctactataa aaggggttaa aaattatgta    660

acttcaaacc ttgaaagttc gacaaaagtt aatagtgctg gtaaacacag tatcattagt    720

aaggttttta gaaatcgtga tggcaataca gtgtctagtg aagtcatttc agaccttttg    780

acttctactg aaaacactaa taacagcctt ggcaaaaaag aaacaacaac aaacaaaaat    840

actatctcta gttccactct tccaataaca                                      870
```

<210> SEQ ID NO 202
<211> LENGTH: 870
<212> TYPE: DNA
<213> ORGANISM: Streptococcus pyogenes

<400> SEQUENCE: 202

```
gctataataa atcatgctaa tgatattgtt aaaacagtta ctgaacgaaa aatcggaact     60

gcaactaatt cttcaactat ttctaaaaca gaaaatattg ataaagaatc tcctgtcggt    120

aacttagtaa caacagctca gcttactatt gctaagaaaa cttttccaac tgttgacttt    180

gctatgacca ataatggtgg tattcgaagt gacctagttg tcaaaaatga tcggaccatc    240

acctggggag ctgcacaggc tgtacaacca tttggtaata tccttcaagt cattcaaatg    300

actggtcaac acatttacga tgtcctaaat cagcaatacg atgaaaacca gacctatttt    360

cttcaaatgt caggtttaac attcacttat acagataatg atcctaagaa ctctgatacc    420

cccttcaaga tagttaaggt ttataaagac aatggtgaag aaattaactt aacaactact    480

tacaccgttg ttgtcaacga ctttctttat ggtggtggtg atggcttttc agcatttaaa    540

aaagctaaat taattggagc tattaacaca gatactgaag ctttcatcac atatatcaca    600

aatttagaag catcaggtaa aactgttaat gctactataa aaggggttaa aaattatgta    660

acttcaaacc ttgaaagctc gacaaaagtt aatagtgctg gtaaacacag tatcattagt    720

aaggttttta gaaatcgtga tggcaatata gtgtctagtg aaataatttc agaccttttg    780

acttctactg aaaacactaa taacagcctt ggcaaaaaag aaacaacgac aaacaaaaat    840

actatctcta gttccactct tccaataaca                                      870
```

<210> SEQ ID NO 203
<211> LENGTH: 870
<212> TYPE: DNA
<213> ORGANISM: Streptococcus pyogenes

<400> SEQUENCE: 203

```
gctataataa atcatgctaa tgatattgtt aaaacagtta ctgaacgaaa aatcggaact     60

gcaactaatt cttcaactat ttctaaaaca gaaaatattg ataaagaatc ccctgtcggt    120

aacttagtaa caacggctca gcttactatt gctaagaaaa cttttccaac tgttgacttt    180

gctatgacca ataatggtgg tattcgaagt gacctagttg tcaaaaatga ccggaccatc    240

acctggggag ctgcacaggc tgtacaacca tttggtaata tccttcaagt cattcaaatg    300

actggtcaac acatttacga tgtcctaaat cagcaatacg atgaaaacca gacctatttt    360

cttcaaatgt caggtttaac atacacttat acagataatg atcctaagaa ctctgatacc    420
```

cccttcaaga tagttaaggt ttataaagac aatggtgaag aaattaactt aacaactact 480
tacaccgttg ttgtcaacga ctttctttat ggtggcggtg atggcttttc agcatttaaa 540
aaagctaaat tagtcggagc tattaacaca gatactgaag ctttcatcac atatatcaca 600
aatttacaag catcaggtaa aactgttaat gctactatca aaggggttaa aaattatgta 660
acttcaaacc ttgaaagatc aacaaaaatt aatagtgctg gcaaacacag tatcattagt 720
aaggttttta gaaatcgtga tggcaatata gtgtctagtg aagtcatttc agaccttttg 780
acttctactg aaaacactaa taacagcttt ggcaaaaaag agacaacaac aaacaaaaat 840
actatctcta attccactct tccaataaca 870

<210> SEQ ID NO 204
<211> LENGTH: 870
<212> TYPE: DNA
<213> ORGANISM: Streptococcus pyogenes

<400> SEQUENCE: 204
gctataataa atcatgctaa tgatattgtt aaaacagtta ctgaacgaaa aatcggaact 60
gcaactaatt cttcaactat ttctaaaaca gaaaatattg ataaagaatc tcctgtcggt 120
aacttagtaa caacggctca gcttactatt gctaagaaaa cttttccaac tgttgacttt 180
gctatgacca ataatggtgg tattcgaagt gacctagttg tcaaaaatga ccggaccatc 240
acctggggag ctgcacaggc tgtacaacca tttggtaata tccttcaagt cattcaaatg 300
actggtcaac acatttacga tgtcctaaat cagcaatacg atgaaaacca gacctatttt 360
cttcaaatgt caggtttaac atacacttat acagataatg atcctaagaa ctctgatacc 420
cccttcaaga tagttaaggt ttataaagac aatggtgaag aaattaactt aacaactact 480
tacaccgttg ttgtcaacga ctttctttat ggtggtggtg atggcttttc agcatttaaa 540
aaagctaaat taatcggagc tattaacaca gatactgaag ctttcatcac atatatcaca 600
aatttagaag catcaggtaa aactgttaat gctactataa aaggggttaa aaattatgta 660
acttcaaacc ttgaaagctc gacaaaagtt aatagtgctg gtaaacacag tatcattagt 720
aaggttttta gaaatcgtga tggcaatata gtgtctagtg aaatcatttc agaccttttg 780
acttctactg aaaacactaa taacagcctt ggcaaaaaag aaacaacgac aaacaaaaat 840
actatctcta gttccactct tccaataaca 870

<210> SEQ ID NO 205
<211> LENGTH: 870
<212> TYPE: DNA
<213> ORGANISM: Streptococcus pyogenes

<400> SEQUENCE: 205
gctataataa atcatgctaa tgatattgtt aaaacagtta ctgaacgaaa aatcggaact 60
gcaactaatt cttcaactat ttctaaaaca gaaaatattg ataaagaatc tcctgtcggt 120
aacttagtaa caacggctca gcttactatt gctaagaaaa cttttccaac tgttgacttt 180
gctatgacca ataatggtgg tattcgaagt gacctagttg tcaaaaatga ccggaccatc 240
acctggggag ctgcacaggc tgtacaacca tttggtaata tccttcaagt cattcaaatg 300
actggtcaac acatttacga tgtcctaaat cagcaatacg atgaaaacca gacctatttt 360
cttcaaatgt caggtttaac atacacttat acagataatg atcctaagaa ctctgatacc 420
cccttcaaga tagttaaggt ttataaagac aatggtgaag aaattaactt aacaactact 480
tacaccgttg ttgtcaacga ctttctttat ggtggtggtg atggcttttc agcatttaaa 540

```
aaaactaaat taatcggagc tattaacaca gatactgaag ctttcatcac atatatcaca    600

aatttagaag catcaggtaa aactgttaat gctactataa aaggggttaa aaattatgta    660

acttcaaacc ttgaaagctc gacaaaagtt aatagtgctg gtaaacacag tatcattagt    720

aaggttttta gaaatcgtga tggcaatata gtgtctagtg aaatcatttc agaccttttg    780

acttctactg aaaacactaa taacagcctt ggcaaaaaag aaacaacgac aaacaaaaat    840

actatctcta gttccactct tccaataaca                                     870
```

<210> SEQ ID NO 206
<211> LENGTH: 876
<212> TYPE: DNA
<213> ORGANISM: Streptococcus pyogenes

<400> SEQUENCE: 206

```
gctataataa atcatgctaa tgatattgtt aaaacagtta ctgaacgaaa aatcggaact     60

gcaactaatt cttcaactat ttctaaaaca gaaaatattg ataaagaatc tcctgtcggt    120

aacttagtaa caacggctca gcttactatt gctaagaaaa cttttccaac tgttgacttt    180

gctatgacca ataatggtgg tattcgaagt gacctagttg tcaaaaatga ccggaccatc    240

acctgggaag ctgcacaggc tgtacaacca tttggtaata tccttcaagt cattcaaatg    300

actggtcaac acatttacga tgtcctaaat cagcaatacg atgaaaacca gacctatttt    360

cttcaaatgt caggtttaac atacacttat acagataatg atcctaagaa ctctgatacc    420

cccttcaaga tagttaaggt ttataaagac aatggtgaag aaattaactt aacaactact    480

tacaccgttg ttgtcaacga ctttctttat ggtggtggtg atggcttttc agcatttaaa    540

aaagctaaat taatcggagc tattaacaca gatactgaag ctttcatcac atatatcaca    600

aatttagaag catcaggtaa aactgttaat gctactataa aaggggttaa aaattatgta    660

acttcaaacc ttgaaagttc gacaaaagtt aatagtgctg gtaaacacag tatcattatc    720

attagtaagg tttttagaaa tcgtgatggc aatatagtgt ctagtgaaat catttcagac    780

cttttgactt ctactgaaaa cactaataac agctttggca aaaaagagat aacaacaaac    840

aaaaatacta tctctaattc cactcttcca ataaca                              876
```

<210> SEQ ID NO 207
<211> LENGTH: 942
<212> TYPE: DNA
<213> ORGANISM: Streptococcus pyogenes

<400> SEQUENCE: 207

```
attgaaatgc ctggaggcgc ttacgatatt cggactgtct tacaagtcaa tggcaaagaa     60

gacaaacgaa aaggagctta ccagtttgtt gcagtgggca ttagtcgtgc cagcctcgct    120

cagctattat atgcttggct gacaccgttt actgaaatta gtacagcaga agatacaaca    180

ggcggataca gcgatgctga tttccttcga attaatcaat tttacatgga aacatcacaa    240

aatgcagcta tttatcaagc tttatcctta gctggaaaac cagttacatt agattataaa    300

ggcgtatatg ttttagacgt aaacaacgaa tctactttta aaggaacgct acacttagca    360

gatactgtaa caggtgtaaa tggtaaacag tttactagtt cagcagaact tattgactat    420

gtttctcacc taaaactagg ggatgaagtt acggttcagt ttacgagtga taataagcct    480

aaaaaaggag ttggccgtat tatcaaactg aaaaatggga aaaatgggat tggcattgcc    540

ttgactgatc atacaagtgt caattcagaa gacacagtga tctttagtac taaaggagta    600

ggaggaccta gtgctggtct aatgtttact cttgatatat atgatcaaat aactaaagaa    660
```

gatttacgca agggccgtac aattgcaggt acaggaacta ttggcaagga tggcgaagta 720
ggagatattg gtggtgcagg tcttaaagta gttgcagcag ctgaagctgg tgcagatata 780
ttttttgttc cgaataatcc tgttgataag gaaattaaaa aagttaatcc aaatgctata 840
agtaattacg aagaagccaa acgggcagcc aaacgactaa agaccaaaat gaagattgtt 900
cctgttacga ctgttcaaga ggcactggtt tatcttcgca aa 942

<210> SEQ ID NO 208
<211> LENGTH: 945
<212> TYPE: DNA
<213> ORGANISM: Streptococcus pyogenes

<400> SEQUENCE: 208
acaaaagaat ttcatcacgt gaccgtactc cttcacgaaa cagtggacat gcttgacata 60
aagcctgatg ggatttatgt tgatgcgacg ctaggtggct caggccactc agcttatttg 120
ttgtccaaac ttggtgaaga agggcacctc tattgttttg accaagacca aaaggctatt 180
gacaatgcac aagttaccct caaatcttat attgacaaag gacaggtaac ttttattaaa 240
gataatttta gacacctcaa agcacgttta acagcgcttg gagttgatga aattgatggt 300
atcttatatg accttggtgt ttccagcccg caattggatg aaagagaacg agggttttct 360
tataaacaag atgctccatt ggatatgcgc atggatcgtc agtcgctctt aacagcttac 420
gaagtggtga atacctatcc attcaatgat ttggttaaga tttttttcaa atatggtgaa 480
gataaattct ccaagcagat cgctcgaaaa attgaacaag caagagctat taagcctatt 540
gagacaacaa cagagttggc agaattgatt aaggcagcaa agccagctaa agagttgaag 600
aaaaaaggcc accctgctaa acagattttt caagctattc gcattgaagt caatgatgaa 660
ttgggagcgg ccgatgaatc tattcaggac gctatggaat tattagccct tgatggtcgt 720
atctcagtta ttaccttcca ttctctggaa gatcgcctaa ccaagcagtt gtttaaagaa 780
gctagtacgg tggatgtgcc aaaagggctt cctctaattc ctgaagatat gaaacctaag 840
tttgaacttg tttcacgtaa gccgatctta cctagtcatt cagagttaac agctaataaa 900
agggcacact cagccaagct acgtgttgcc aaaaaaattc ggaaa 945

<210> SEQ ID NO 209
<211> LENGTH: 21
<212> TYPE: DNA
<213> ORGANISM: Artificial sequence
<220> FEATURE:
<223> OTHER INFORMATION: Primer

<400> SEQUENCE: 209
tgaccttcaa atcattgctg a 21

<210> SEQ ID NO 210
<211> LENGTH: 20
<212> TYPE: DNA
<213> ORGANISM: Artificial sequence
<220> FEATURE:
<223> OTHER INFORMATION: Primer

<400> SEQUENCE: 210
ttttgcactt ctggtgtcaa 20

<210> SEQ ID NO 211
<211> LENGTH: 20
<212> TYPE: DNA
<213> ORGANISM: Artificial sequence
<220> FEATURE:
<223> OTHER INFORMATION: Primer

<400> SEQUENCE: 211
ttgccaaagc tagtccaggt 20

<210> SEQ ID NO 212
<211> LENGTH: 21
<212> TYPE: DNA
<213> ORGANISM: Artificial sequence
<220> FEATURE:
<223> OTHER INFORMATION: Primer

<400> SEQUENCE: 212
agtattatca atgcgctcac g 21

<210> SEQ ID NO 213
<211> LENGTH: 25
<212> TYPE: DNA
<213> ORGANISM: Artificial sequence
<220> FEATURE:
<223> OTHER INFORMATION: Primer

<400> SEQUENCE: 213
aaaagctcat ttgcaatatc taagg 25

<210> SEQ ID NO 214
<211> LENGTH: 22
<212> TYPE: DNA
<213> ORGANISM: Artificial sequence
<220> FEATURE:
<223> OTHER INFORMATION: Primer

<400> SEQUENCE: 214
gctggtgaat ctgatttttc aa 22

<210> SEQ ID NO 215
<211> LENGTH: 26
<212> TYPE: DNA
<213> ORGANISM: Artificial sequence
<220> FEATURE:
<223> OTHER INFORMATION: Primer

<400> SEQUENCE: 215
tcttgtgagg taagtcatta ccttag 26

<210> SEQ ID NO 216
<211> LENGTH: 24
<212> TYPE: DNA
<213> ORGANISM: Artificial sequence
<220> FEATURE:
<223> OTHER INFORMATION: Primer

<400> SEQUENCE: 216
ttcatcatct ggttctgtat tagg 24

<210> SEQ ID NO 217
<211> LENGTH: 19
<212> TYPE: DNA
<213> ORGANISM: Artificial sequence
<220> FEATURE:
<223> OTHER INFORMATION: Primer

<400> SEQUENCE: 217
ggtcgtcaat tcaactggc 19

<210> SEQ ID NO 218
<211> LENGTH: 21
<212> TYPE: DNA
<213> ORGANISM: Artificial sequence
<220> FEATURE:
<223> OTHER INFORMATION: Primer

<400> SEQUENCE: 218
gcgatcattg tggatgattt c 21

<210> SEQ ID NO 219
<211> LENGTH: 21
<212> TYPE: DNA
<213> ORGANISM: Artificial sequence
<220> FEATURE:
<223> OTHER INFORMATION: Primer

<400> SEQUENCE: 219
aaactgtcaa acttgtagcc c 21

<210> SEQ ID NO 220
<211> LENGTH: 21
<212> TYPE: DNA
<213> ORGANISM: Artificial sequence
<220> FEATURE:
<223> OTHER INFORMATION: Primer

<400> SEQUENCE: 220
tgttaggatt ggcctagttt g 21

<210> SEQ ID NO 221
<211> LENGTH: 27
<212> TYPE: DNA
<213> ORGANISM: Artificial sequence
<220> FEATURE:
<223> OTHER INFORMATION: Primer

<400> SEQUENCE: 221
tgagttaatg attaacatta aactggt 27

<210> SEQ ID NO 222
<211> LENGTH: 21
<212> TYPE: DNA
<213> ORGANISM: Artificial sequence
<220> FEATURE:
<223> OTHER INFORMATION: Primer

<400> SEQUENCE: 222
tgacataagc aaattgatgc g 21

<210> SEQ ID NO 223
<211> LENGTH: 23
<212> TYPE: DNA
<213> ORGANISM: Artificial sequence
<220> FEATURE:
<223> OTHER INFORMATION: Primer

<400> SEQUENCE: 223
ccatctattc agagtctgtc gac 23

<210> SEQ ID NO 224
<211> LENGTH: 22
<212> TYPE: DNA
<213> ORGANISM: Artificial sequence
<220> FEATURE:
<223> OTHER INFORMATION: Primer

<400> SEQUENCE: 224
ccttgtcact agcatggtag ac 22

<210> SEQ ID NO 225
<211> LENGTH: 18
<212> TYPE: DNA
<213> ORGANISM: Artificial sequence
<220> FEATURE:
<223> OTHER INFORMATION: Primer

<400> SEQUENCE: 225
ttgcagcctt caaaggtg 18

<210> SEQ ID NO 226
<211> LENGTH: 25
<212> TYPE: DNA
<213> ORGANISM: Artificial sequence
<220> FEATURE:
<223> OTHER INFORMATION: Primer

<400> SEQUENCE: 226
aagacacatt accagctcta tcttc 25

<210> SEQ ID NO 227
<211> LENGTH: 22
<212> TYPE: DNA
<213> ORGANISM: Artificial sequence
<220> FEATURE:
<223> OTHER INFORMATION: Primer

<400> SEQUENCE: 227
cagatggttc ttacaccatt tc 22

<210> SEQ ID NO 228
<211> LENGTH: 23
<212> TYPE: DNA
<213> ORGANISM: Artificial sequence
<220> FEATURE:
<223> OTHER INFORMATION: Primer

<400> SEQUENCE: 228
aatctcaaag aaaggtcaga ctg 23

<210> SEQ ID NO 229
<211> LENGTH: 24
<212> TYPE: DNA
<213> ORGANISM: Artificial sequence
<220> FEATURE:
<223> OTHER INFORMATION: Primer

<400> SEQUENCE: 229
aaagctcgtc attttatatg attt 24

<210> SEQ ID NO 230
<211> LENGTH: 25
<212> TYPE: DNA
<213> ORGANISM: Artificial sequence
<220> FEATURE:
<223> OTHER INFORMATION: Primer

<400> SEQUENCE: 230
tttaatgaga gttgtcattc gttca 25

<210> SEQ ID NO 231
<211> LENGTH: 20
<212> TYPE: DNA
<213> ORGANISM: Artificial sequence
<220> FEATURE:
<223> OTHER INFORMATION: Primer

<400> SEQUENCE: 231
ttttcttgtt caaccgcaag 20

<210> SEQ ID NO 232
<211> LENGTH: 20
<212> TYPE: DNA
<213> ORGANISM: Artificial sequence
<220> FEATURE:
<223> OTHER INFORMATION: Primer

<400> SEQUENCE: 232
gcgctcacag ctacttcaga 20

<210> SEQ ID NO 233
<211> LENGTH: 29
<212> TYPE: DNA
<213> ORGANISM: Artificial sequence
<220> FEATURE:
<223> OTHER INFORMATION: Primer

<400> SEQUENCE: 233
caaaatcata gtaaacttga tctataacg 29

<210> SEQ ID NO 234
<211> LENGTH: 21
<212> TYPE: DNA
<213> ORGANISM: Artificial sequence
<220> FEATURE:
<223> OTHER INFORMATION: Primer

<400> SEQUENCE: 234
gaagaattag ttgcagttcc g 21

<210> SEQ ID NO 235
<211> LENGTH: 21
<212> TYPE: DNA
<213> ORGANISM: Artificial sequence
<220> FEATURE:
<223> OTHER INFORMATION: Primer

<400> SEQUENCE: 235
gttgctgtag caccaggtat c 21

<210> SEQ ID NO 236
<211> LENGTH: 23
<212> TYPE: DNA
<213> ORGANISM: Artificial sequence
<220> FEATURE:
<223> OTHER INFORMATION: Primer

<400> SEQUENCE: 236
ccagcacgaa ttagatcatc tag 23

<210> SEQ ID NO 237
<211> LENGTH: 20
<212> TYPE: DNA
<213> ORGANISM: Artificial sequence
<220> FEATURE:
<223> OTHER INFORMATION: Primer

<400> SEQUENCE: 237
ctgaagagcg ccaaacaact 20

-continued

<210> SEQ ID NO 238
<211> LENGTH: 26
<212> TYPE: DNA
<213> ORGANISM: Artificial sequence
<220> FEATURE:
<223> OTHER INFORMATION: Primer

<400> SEQUENCE: 238
tcgaagaagt aacctttgat taatgt 26

<210> SEQ ID NO 239
<211> LENGTH: 24
<212> TYPE: DNA
<213> ORGANISM: Artificial sequence
<220> FEATURE:
<223> OTHER INFORMATION: Primer

<400> SEQUENCE: 239
gctctagtcg tgtgagagag ctaa 24

<210> SEQ ID NO 240
<211> LENGTH: 23
<212> TYPE: DNA
<213> ORGANISM: Artificial sequence
<220> FEATURE:
<223> OTHER INFORMATION: Primer

<400> SEQUENCE: 240
tgtctatctg gttcaaccgt ttt 23

<210> SEQ ID NO 241
<211> LENGTH: 21
<212> TYPE: DNA
<213> ORGANISM: Artificial sequence
<220> FEATURE:
<223> OTHER INFORMATION: Primer

<400> SEQUENCE: 241
gtggctaagt cagtgcttgc t 21

<210> SEQ ID NO 242
<211> LENGTH: 24
<212> TYPE: DNA
<213> ORGANISM: Artificial sequence
<220> FEATURE:
<223> OTHER INFORMATION: Primer

<400> SEQUENCE: 242
aagtttttat tcgtttttgc aagg 24

<210> SEQ ID NO 243
<211> LENGTH: 27
<212> TYPE: DNA
<213> ORGANISM: Artificial sequence
<220> FEATURE:
<223> OTHER INFORMATION: Primer

<400> SEQUENCE: 243
gatcattgac taagtagcct aaaacaa 27

<210> SEQ ID NO 244
<211> LENGTH: 19
<212> TYPE: DNA
<213> ORGANISM: Artificial sequence -continued

```
<220> FEATURE:
<223> OTHER INFORMATION: Primer

<400> SEQUENCE: 244

ccaaaaacgt catgccaac                                              19
```

SMALL *STREPTOCOCCUS PYOGENES* ANTIGENS AND THEIR USE

CROSS REFERENCE TO RELATED APPLICATIONS

This application is the U.S. National Stage of International Application No. PCT/EP2007/006027, filed Jul. 6, 2007, which claims benefit of European Application No. 06014166.0, filed Jul. 7, 2006, each of which is hereby incorporated by reference.

The present invention relates to a peptide consisting of one antigen of *Streptococcus pyogenes* (*S. pyogenes*) of any of the SEQ ID NOS: 1 to 7 or a functional active variant thereof, optionally further consisting of additional amino acid residue(s); a nucleic acid coding for the same; a pharmaceutical composition, especially a vaccine, comprising said peptide or said nucleic acid; an antibody or functional active fragment thereof specifically binding to the antigen; a hybridoma cell line which produces said antibody; a method for producing said antibody; a pharmaceutical composition comprising said antibody; the use of said peptide or said nucleic acid for the manufacture of a medicament for the immunization or treatment of a subject; the use of said antibody or functional fragment thereof for the manufacture of a medicament for the treatment of an infection; a method of diagnosing a *S. pyogenes* infection; a method for identifying a ligand capable of binding to said peptide; and the use of said peptide for the isolation and/or purification and/or identification of an interaction partner of the peptide.

*Streptococcus pyogenes*, also called group A *streptococcus* (GAS), is an important gram-positive extracellular bacterial pathogen and commonly infects humans. GAS colonizes the throat or skin and is responsible for a number of suppurative infections and non-suppurative sequelae. It is primarily a disease of children and causes a variety of infections including bacterial pharyngitis, scarlet fever, impetigo and sepsis in humans. Decades of epidemiological studies have led to the concept of distinct throat and skin strains, where certain serotypes are often associated with throat or skin infections, respectively (Cunningham, M. (2000). *Clin Microbiol Rev* 13: 470-511). GAS has been discovered responsible for streptococcal toxic shock syndrome associated necrotizing fasciitis which is recently resurgent in the USA (Cone, L., et al. (1987). *New Engl J Med* 317: 146-9; Stevens, D. (1992). *Clin Infect Dis* 14: 2-11) and has been described as the “flesh eating” bacterium which invades skin and soft tissues leading to tissue or limb destruction.

Several post-streptococcal sequelae may occur in humans subsequent to infection, such as acute rheumatic fever, acute glomerulonephritis and reactive arthritis. Acute rheumatic fever and rheumatic heart disease are of these the most serious autoimmune sequelae and have led to disability and death of children worldwide. *S. pyogenes* can also causes severe acute diseases such as scarlet fever and necrotizing fasciitis and has been associated with Tourette’s syndrome, tics and movement and attention disorders.

Group A streptococci are the most common bacterial cause of sore throat and pharyngitis and account for at least 16% of all office calls in a general medical practice, season dependent (Hope-Simpson, R. (1981). *J Hyg* (*Lond*) 87: 109-29). It primarily affects children in school-age between 5 to 15 years of age (Cunningham, supra). All ages are susceptible to spread of the organism under crowded conditions, for example in schools. GAS are not considered normal flora though, but pharyngeal carriage of group A streptococci can occur without clinical symptoms.

Group A streptococci can be distinguished by the Lancefield classification scheme of serologic typing based on their carbohydrate or classified into M protein serotypes based on a surface protein that can be extracted by boiling bacteria with hydrochloric acid. This has led to the identification of more than 80 serotypes, which can also be typed by a molecular approach (emm genes). Molecular typing has identified more than 150 individual emm types. Certain M protein serotypes of *S. pyogenes* are mainly associated with pharyngitis and rheumatic fever, while others mainly seem to cause pyoderma and acute glomerulonephritis (Cunningham, supra).

Also implicated in causing pharyngitis and occasionally toxic shock are group C and G streptococci, which must be distinguished after throat culture (Hope-Simpson, supra; Bisno, A., et al. (1987). *Infect Immun* 55: 753-7).

Currently, streptococcal infections can only be treated by antibiotic therapy. However, 25-30% of those treated with antibiotics show recurrent disease and/or shed the organism in mucosal secretions. There is at present no preventive treatment (vaccine) available to avoid streptococcal infections.

Thus, there remains a need for an effective treatment to prevent or ameliorate streptococcal infections. A vaccine could not only prevent infections by streptococci, but more specifically prevent or ameliorate colonization of host tissues, thereby reducing the incidence of pharyngitis and other suppurative infections. Elimination of non-suppurative sequelae such as rheumatic fever, acute glomerulonephritis, sepsis, toxic shock and necrotizing fasciitis would be a direct consequence of reducing the incidence of acute infection and carriage of the organism. Vaccines capable of showing cross-protection against other streptococci would also be useful to prevent or ameliorate infections caused by all other beta-hemolytic streptococcal species, namely groups A, B, C and G.

A vaccine can contain a whole variety of different antigens. Examples of antigens are whole-killed or attenuated organisms, subfractions of these organisms/tissues, proteins, or, in their most simple form, peptides. Antigens can also be recognized by the immune system in form of glycosylated proteins or peptides and may also be or contain polysaccharides or lipids. Short peptides can be used since for example cytotoxic T-cells (CTL) recognize antigens in form of short usually 8-11 amino acids long peptides in conjunction with major histocompatibility complex (MHC). B-cells can recognize linear epitopes as short as 4-5 amino acids, as well as three-dimensional structures (conformational epitopes).

In some circumstances, adjuvants may be useful for sustaining antigen-specific immune responses. Primarily, adjuvants are acting, but are not restricted in their mode of action, on so-called antigen presenting cells (APCs). These cells usually first encounter the antigen(s) followed by presentation of processed or unmodified antigen to immune effector cells. Intermediate cell types may also be involved. Only effector cells with the appropriate specificity are activated in a productive immune response. The adjuvant may also locally retain antigens and co-injected other factors. In addition the adjuvant may act as a chemoattractant for other immune cells or may act locally and/or systemically as a stimulating agent for the immune system.

Approaches to develop a group A streptococcal vaccine have focused mainly on the cell surface M protein of *S. pyogenes* (Bessen, D., et al. (1988). *Infect Immun* 56: 2666-2672; Bronze, M., et al. (1988). *J Immunol* 141: 2767-2770). Since more than 80 different M serotypes of *S. pyogenes* exist and new serotypes continually arise (Fischetti, V. (1989). *Clin Microbiol Rev* 2: 285-314), inoculation with a limited number of serotype-specific M protein or M protein derived peptides will not likely be effective in protecting against all other M serotypes. Furthermore, it has been shown that the conserved region of the M protein contains an amino acid sequence, which is immunologically cross-reactive with human heart tissue, which is thought to account for heart valve damage associated with rheumatic fever (Fenderson, P., et al. (1989). *J Immunol* 142: 2475-2481).

There are other proteins under consideration for vaccine development, such as the erythrogenic toxins, streptococcal pyrogenic exotoxin A and streptococcal pyrogenic exotoxin B (Lee, P. K. (1989). *J Clin Microbiol* 27: 1890-2). Immunity to these toxins could possibly prevent the deadly symptoms of streptococcal toxic shock, but it may not prevent colonization by group A streptococci.

The use of the above described proteins as antigens for a potential vaccine as well as a number of additional candidates (Ji, Y., et al. (1997). *Infect Immun* 65: 2080-2087; Guzman, C., et al. (1999). *J Infect Dis* 179: 901-6) resulted mainly from a selection based on easiness of identification or chance of availability. There is a demand to identify efficient and relevant antigens for *S. pyogenes.*

WO 2004/078907 describes a method for identification, isolation and production of hyperimmune serum reactive antigens from *Streptococcus pyogenes.*

The antigens described herein focus on regions shown in the present application to be protective. A suitable antigen size to obtain protection varies based on different factors such as the type of protective epitope (e.g., conformational versus linear) and the number of protective epitopes providing a level of protection. Large antigens containing regions not providing useful protection may be disadvantageous in the context of immunization. First, providing of smaller antigens eases production of the protein in recombinant form. It is generally accepted that it is more difficult to produce larger proteins. Smaller proteins may be produced in a more economic manner, thus saving costs, particularly in the health care system. Second, reducing the size of antigenic proteins used for vaccination may lead to safer products. Eliminating extra sequences in antigenic proteins is desirable, since this reduces the probability of inducing antibodies which can cause cross-reactions with human tissues. Third, proteins used for vaccination may contain more than one antigen, the antigens directed either against the same disease or against different diseases, in order to obtain a more effective vaccination or vaccination against several diseases. However, if the single antigens are too large a combination into one protein is not feasible.

Accordingly, one problem underlying the present invention was to provide alternative means for the development of medicaments such as vaccines against *S. pyogenes* infection, particularly smaller proteins.

Surprisingly, the object has been solved by a peptide consisting of one antigen of *S. pyogenes* of the SEQ ID NO: 1, SEQ ID NO: 2, SEQ ID NO: 3, SEQ ID NO: 4, SEQ ID NO: 5, SEQ ID NO: 6 or SEQ ID NO: 7 or a functional active variant of one antigen of *S. pyogenes* of the SEQ ID NO: 1, SEQ ID NO: 2, SEQ ID NO: 3, SEQ ID NO: 4, SEQ ID NO: 5, SEQ ID NO: 6 or SEQ ID NO: 7. These peptides are referred to as antigenic peptides.

The sequences of SEQ ID NOS: 1 to 7 are characterized in table 1 of the present specification. The underlying amino acid sequences are disclosed in the attached sequence data. The peptides of SEQ ID NOS: 1 to 7 have been shown to induce an immune response and/or to show protection against *S. pyogenes* in a sepsis and/or lethality model (see Example 1). Functional active variants are obtained by changing the sequence of the antigen as defined below and are characterized by having a biological activity similar to that displayed by the antigen of any of the sequences of SEQ ID NO: 1 to 7 from which it is derived, including the ability to induce immune responses and/or to show protection against *S. pyogenes* e.g. in a sepsis and/or lethality model.

In some embodiments of the invention the peptide of the invention consists of one antigen of *S. pyogenes* of the SEQ ID NO: 1, SEQ ID NO: 2, SEQ ID NO: 3, SEQ ID NO: 4, SEQ ID NO: 5, SEQ ID NO: 6 or SEQ ID NO: 7 or a functional active variant of one antigen of *S. pyogenes* of the SEQ ID NO: 1, SEQ ID NO: 2, SEQ ID NO: 3, SEQ ID NO: 4, SEQ ID NO: 5, SEQ ID NO: 6 or SEQ ID NO: 7; and a) 1 to 350 additional amino acid residue(s), preferably 1 to 200, more preferably 1 to 150, even more preferably at most 1 to 100, still more preferably at most 1 to 50, most preferably 1, 2, 3, 4, 5, 10, 15, 20 or 25 additional amino acids residue(s) if the antigen is SEQ ID NO: 1; or b) 1 to 200 additional amino acid residue(s), preferably 1 to 150, more preferably 1 to 100, even more preferably at most 1 to 50, still more preferably at most 1 to 25, most preferably 1, 2, 3, 4, 5, 6, 7, 8, 9 or 10 additional amino acids residue(s) if the antigen is SEQ ID NO: 2; or c) 1 to 100 additional amino acid residue(s), preferably 1 to 75, more preferably 1 to 50, even more preferably at most 1 to 25, still more preferably at most 1 to 10, most preferably 1, 2, 3, 4 or 5 additional amino acids residue(s) if the antigen is that of SEQ ID NO: 3; or d) 1 to 150 additional amino acid residue(s), preferably 1 to 100, more preferably 1 to 75, even more preferably at most 1 to 50, still more preferably at most 1 to 25, most preferably 1, 2, 3, 4, 5, 6, 7, 8, 9 or 10 additional amino acids residue(s) if the antigen is that of SEQ ID NO: 4; or e) 1 to 450 additional amino acid residue(s), preferably 1 to 300, more preferably 1 to 150, even more preferably at most 1 to 100, still more preferably at most 1 to 50, most preferably 1, 2, 3, 4, 5, 10, 20, 30 or 40 additional amino acids residue(s) if the antigen is SEQ ID NO: 5; or f) 1 to 250 additional amino acid residue(s), preferably 1 to 200, more preferably 1 to 150, even more preferably at most 1 to 100, still more preferably at most 1 to 50, most preferably 1, 2, 3, 4, 5, 10, 15, 20 or 25 additional amino acids residue(s) if the antigen is SEQ ID NO: 6 or SEQ ID NO: 7.

The antigen of *S. pyogenes* can be any of the antigens as defined above, namely as defined in any of the SEQ ID NOS: 1, 2, 3, 4, 5, 6 or 7, or a functional active variant thereof, wherein the functional active variant is as defined below.

The antigen or the functional active variant thereof may have added at least one additional amino acid residue heterologous or homologous to the peptide. Homologous refers to any amino acid or amino acid sequence which is identical to the amino acid sequence of the *S. pyogenes* protein from which the antigen is derived, wherein the sequences of SEQ ID NO: 1 to 7 are derived from the following proteins:

| Sequence | derived from protein (as disclosed in e.g. WO 2004/078907 or in the attached sequence data) |
|---|---|
| SEQ ID NO: 1 | Spy0269 |
| SEQ ID NO: 2 | Spy0292 |
| SEQ ID NO: 3 | Spy0292 |
| SEQ ID NO: 4 | Spy0416 |
| SEQ ID NO: 5 | Spy0416 |
| SEQ ID NO: 6 | Spy0416 |
| SEQ ID NO: 7 | Spy0872 |

In one embodiment the antigen or the functional active variant thereof having one or more additional amino acid residues (see above, particularly as defined in items (a) to (f)) further encompasses at least one amino acid residue heterologous to the antigen. The feature "heterologous amino acid" or "amino acid heterologous to the antigen or protein" refers to any amino acid which is different from that amino acid located adjacent to the antigen or protein in any naturally occurring protein of *S. pyogenes*, particularly from that of *S. pyogenes* SF370 (serotype MD. Therefore, the protein of the invention encompassing at least one heterologous amino acid refers to a protein which is different from any naturally occurring protein of *S. pyogenes* or fragment thereof, particularly which is different from that of *S. pyogenes* SF370 (serotype M1). The proteins from which the antigens of the invention are derived as well as a reference for their sequences are listed above.

In certain embodiments, the peptide consists of the antigen, optionally the at least one additional amino acid residue as defined above, and at least one additional heterologous amino acid sequence comprising a marker protein.

The additional sequence or amino acid residue(s) as defined above consists of (an) amino acid residue(s), which may be any amino acid, which may be either an L- and/or a D-amino acid, naturally occurring and otherwise. Preferably the amino acid is any naturally occurring amino acid such as alanine, cysteine, aspartic acid, glutamic acid, phenylalanine, glycine, histidine, isoleucine, lysine, leucine, methionine, asparagine, proline, glutamine, arginine, serine, threonine, valine, tryptophan or tyrosine.

However, the amino acid residue(s) may also be (a) modified or unusual amino acid(s). Examples of those are 2-aminoadipic acid, 3-aminoadipic acid, beta-alanine, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, 6-N-Methyllysine, N-methylvaline, norvaline, norleucine or ornithine.

Additionally, the amino acid(s) may be subject to modifications such as posttranslational modifications. Examples of modifications include acetylation, amidation, blocking, formylation, γ-carboxyglutamic acid hydroxylation, glycosilation, methylation, phosphorylation and sulfatation.

If more than one additional or heterologous amino acid residue is present in the peptide, the amino acid residues may be the same or different from one another.

The antigenic peptide may be flanked by the amino acid residue(s) C-terminally, N-terminally, or C- and N-terminally.

In a further embodiment the peptide is as described above in the different embodiments, and contains a region that is essentially identical to any of the antigens of the SEQ ID NO: 1, SEQ ID NO: 2, SEQ ID NO: 3, SEQ ID NO: 4, SEQ ID NO: 5, SEQ ID NO: 6 or SEQ ID NO: 7, but differs from the antigens of any of the of the SEQ ID NO: 1, SEQ ID NO: 2, SEQ ID NO: 3, SEQ ID NO: 4, SEQ ID NO: 5, SEQ ID NO: 6 or SEQ ID NO: 7, in that is it derived from a homologous sequence of a different serotype of *S. pyogenes*, particularly wherein the serotype is M2, M3, M4, M5, M6, M11, M12, M14, M19, M22, M24, M25, M28, M44, M49, M57, M59, M60, M61, M76, M83, M84, M87, M89 or M118, especially *S. pyogenes* SF370.

Accordingly, the present invention also relates to antigens of different *S. pyogenes* isolates. Such homologues may easily be identified and isolated based on the nucleic acid and amino acid sequences disclosed herein. A homologous antigen of a different serotype may be identified by e.g. sequence alignment. The homologous antigen sequence may vary from the antigen of any of the sequences of SEQ ID NO: 1 to 7 by one or more amino acid substitutions, deletions and/or additions. Preferably the homologous antigen sequence has the sequence of any of the homologous variants identified in the attached listing of amino acid sequences.

Examples of homologous sequences of a different serotype are detailed in the attached sequence data. Particularly, sequences homologous to the respective peptide of the invention are those listed below:

| Full length amino acid sequence (SEQ ID NO) | Peptide of the invention (SEQ ID NO) | Homologous amino acid sequences (SEQ ID NOS) |
|---|---|---|
| 57 | 1 | 58 to 67 |
| 68 | 2 | 69 to 78 |
| 68 | 3 | 79 to 88 |
| 89 | 4 | 90 to 99 |
| 89 | 5 | 100 to 109 |
| 89 | 6 | 110 to 119 |
| 120 | 7 | 121 to 130 |

There are more than 150 emm types distinguished to date and the typing is based on the variable region at the 5' end of the emm gene (see e.g. Vitali, L., et al. (2002) *J. Clin. Microbiol.* 40: 679-681). The presence of a homologous antigen can accordingly be determined for every emm type. In addition it is possible to determine the variability of a particular antigen in the various emm types as described for the sic gene (Hoe N., et al. (2001) *J. Inf. Dis.* 183: 633-9). The influence of the various M serotypes on the kind of disease it causes is summarized in a recent review (Cunningham, supra). In particular, two groups of serotypes can be distinguished:
1) Those causing Pharyngitis and Scarlet fever (e.g. M types 1, 3, 5, 6, 14, 18, 19, 24)
2) Those causing Pyoderma and Streptococcal skin infections (e.g. M types 2, 49, 57, 59, 60, 61)

This can serve as the basis to identify the relevance of an antigen for the use as a vaccine or in general as a drug targeting a specific disease.

The information e.g. from the homepage of the Centers for Disease Control and Prevention (CDC) gives a dendrogram showing the relatedness of various emm types. Further relevant references are Vitali et al., supra (molecular emm typing method), Enright et al., Infection and Immunity 69: 2416-2427. (2001) (alternative molecular typing method (MLST)), Hoe et al., supra (example for the variation of one antigen (sic) in many different serotypes) and Cunningham, supra (review on GAS pathogenesis). All emm types are completely listed and are available at publicly available databases (e.g., through the CDC).

In another embodiment of the present invention the variant is a fragment. The fragment is characterized by being derived from the antigen as defined above by one or more amino acid deletions. The deletion(s) may be C-terminally, N-terminally and/or internally. Preferably the fragment is obtained by at most 10, 20, 30, 40, 50, 60, 80, 100, 150 or 200, more preferably by at most 10, 20, 30, 40 or 50, even more preferably at most 5, 10 or 15, still more preferably at most 5 or 10, most preferably 1, 2, 3, 4 or 5 amino acid deletion(s). The functional active fragment of the invention is characterized by having a biological activity similar to that displayed by the complete antigen, including the ability to induce immunization and/or to show protection against *S. pyogenes* e.g. in a sepsis and/or lethality model. The fragment of an antigen is functional active in the context of the present invention, if the activity of the fragment amounts to at least 10%, preferably at least 25%, more preferably at least 50%, even more preferably at least 70%, still more preferably at least 80%, especially at least 90%, particularly at least 95%, most preferably at least 99% of the activity of the antigen without sequence alteration. These fragments may be designed or obtained in any desired length, including as small as about 50 to 80 amino acids in length.

The functional active fragment may be also characterized by other structural features. Accordingly, in one preferred embodiment of the invention the functional active fragments consists of at least 60%, preferably at least 70%, more preferably at least 80%, still more preferably at least 90%, even more preferably at least 95%, most preferably 99% of the amino acids of the antigen of any of the SEQ ID NOS: 1 to 7. The functional active fragment as defined above may be derived from the peptide by one or more amino acid deletions. The deletions may be C-terminally, N-terminally and/or internally.

Another preferred embodiment of the invention relates to a peptide as defined above in the previous embodiments, wherein the antigen is a functional active variant of an antigen of any of the SEQ ID NOS: 1 to 7 and wherein the variant has at least 50% sequence identity to the antigen of any of the SEQ ID NOS: 1 to 7. In a more preferred embodiment the functional active variant has a sequence identity of at least 60%, preferably at least 70%, more preferably at least 80%, still more preferably at least 90%, even more preferably at least 95%, most preferably 99% to the antigen of any of the SEQ ID NOS: 1 to 7.

The percentage of sequence identity can be determined e.g. by sequence alignment. Methods of alignment of sequences for comparison are well known in the art. Various programs and alignment algorithms have been described e.g. in Smith and Waterman, Adv. Appl. Math. 2: 482, 1981 or Pearson and Lipman, Proc. Natl. Acad. Sci. U.S.A. 85: 2444-2448, 1988.

The NCBI Basic Local Alignment Search Tool (BLAST) (Altschul et al., J. Mol. Biol. 215: 403-410, 1990) is available from several sources, including the National Center for Biotechnology Information (NCBI, Bethesda, Md.) and on the Internet, for use in connection with the sequence analysis programs blastp, blastn, blastx, tblastn and tblastx. Variants of an antigen of any of the sequences of SEQ ID NOS: 1 to 7 are typically characterized using the NCBI Blast 2.0, gapped blastp set to default parameters. For comparisons of amino acid sequences of at least 35 amino acids, the Blast 2 sequences function is employed using the default BLOSUM62 matrix set to default parameters, (gap existence cost of 11, and a per residue gap cost of 1). When aligning short peptides (fewer than around 35 amino acids), the alignment is performed using the Blast 2 sequences function, employing the PAM30 matrix set to default parameters (open gap 9, extension gap 1 penalties). Methods for determining sequence identity over such short windows such as 15 amino acids or less are described at the website that is maintained by the National Center for Biotechnology Information in Bethesda, Md.

The functional active variant of an antigen is obtained by sequence alterations in the antigen, wherein the antigen with the sequence alterations retains a function of the unaltered antigen, e.g. having a biological activity similar to that displayed by the complete antigen, including the ability to induce an immune response and/or to show protection against *S. pyogenes* e.g. in a sepsis and/or lethality model. Such sequence alterations can include, but are not limited to, conservative substitutions, deletions, mutations and insertions. These characteristics of the functional active variant can be assessed e.g. as detailed in Example 1. In the context of the present invention a variant specifically has a biological activity similar to that displayed by the antigen without alteration, including the ability to induce an immune response and/or to show protection against *S. pyogenes* e.g. in a sepsis and/or lethality model if the activity of the variant amounts to at least 10%, preferably at least 25%, more preferably at least 50%, even more preferably at least 70%, still more preferably at least 80%, especially at least 90%, particularly at least 95%, most preferably at least 99% of the activity of the antigen without sequence alterations.

The term "functional active variant" includes naturally-occurring allelic variants, as well as mutants or any other non-naturally occurring variants. As is known in the art, an allelic variant is an alternate form of a (poly)peptide that is characterized as having a substitution, deletion, or addition of one or more amino acids that does essentially not alter the biological function of the polypeptide. By "biological function" is meant a function of the polypeptide in the cells in which it naturally occurs, even if the function is not necessary for the growth or survival of the cells. For example, the biological function of a porin is to allow the entry into cells of compounds present in the extracellular medium. The biological function is distinct from the antigenic function. A polypeptide can have more than one biological function.

Within any species of the living world, allelic variation is the rule. For example, any bacterial species, e.g. *S. pyogenes*, is usually represented by a variety of strains (characterized by clonal reproduction) that differ from each other by minor allelic variations. Indeed, a polypeptide that fulfils the same biological function in different strains can have an amino acid sequence that is not identical in each of the strains. Such an allelic variation is equally reflected at the polynucleotide level.

Allelic variation is very common within the *S. pyogenes* species. Such allelic variation is also the basis for the molecular typing of group A streptococcal strains by emm typing as described above (see, e.g. Facklam, R. et al. (1999) Emerg Infect Dis. 5: 247-53 Further, genes such as sic are subject to allelic variation (Hoe N., et al. (2001) J. Inf. Dis. 183: 633-9). However, proteins with large allelic variation are in general not suitable candidates for a vaccine, as immunization would not protect against infection with all strains, or alternative immunization would possibly induce the emergence of new allelic variants not covered by the vaccine.

In a preferred embodiment, the functional active variant or fragment derived from the antigen by amino acid exchanges, deletions or insertions may also conserve, or more preferably improve, the activity (as defined above). Furthermore, these peptides may also cover epitopes, which trigger the same or preferably an improved T cell response. These epitope are referred to as "heteroclitic". They have a similar or preferably greater affinity to MHC/HLA molecules, and the ability to stimulate the T cell receptors (TCR) directed to the original epitope in a similar or preferably stronger manner. Heteroclitic epitopes can be obtained by rational design i.e. taking into account the contribution of individual residues to binding to MHC/HLA as for instance described by (Rammensee, H. et al., 1999, Immunogenetics. 50: 213-219), combined with a systematic exchange of residues potentially interacting with the TCR and testing the resulting sequences with T cells directed against the original epitope. Such a design is possible for a skilled man in the art without much experimentation.

In a still more preferred embodiment of the invention the functional active variant of an antigen of any of the SEQ ID NOS: 1 to 7 having at least 50% sequence identity to the antigen of any of the SEQ ID NOS: 1 to 7, especially at least 60%, preferably at least 70%, more preferably at least 80%, still more preferably at least 90%, even more preferably at least 95%, most preferably 99% to the antigen of any of the SEQ ID NOS: 1 to 7 is derived from the antigen of any of the sequences of SEQ ID NOS: 1 to 7 by conservative substitutions. Conservative substitutions are those that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc. In one embodiment, one conservative substitution is included in the peptide. In another embodiment, two conservative substitutions or less are included in the peptide. In a further embodiment, three conservative substitutions or less are included in the peptide.

Examples of conservative amino acid substitutions include, but are not limited to, those listed below:

| Original Residue | Conservative Substitutions |
|---|---|
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Asn |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Examples of suitable variants of the peptide of the invention obtained by one or more amino acid exchange(s), deletion(s) and/or insertion(s) may be derived from data provided in tables 5 to 7 and 9. Particularly, tables 5 to 7 and 9 list naturally occurring amino acid alterations (substitutions, insertions, deletions) at particular positions in comparison to *S. pyrogenes* SF370.

With respect to a variant of a peptide having (i.e. consisting of or comprising as defined above, particularly as defined in the above items (a) to (f)) SEQ ID NO: 1, the variant of the invention may differ from the peptide having SEQ ID NO: 1 by one or more of the alterations identified in table 5.

With respect to a variant of a peptide having (i.e. consisting of or comprising as defined above, particularly as defined in the above items (a) to (f)) SEQ ID NO: 2, the variant of the invention may differ from the peptide having SEQ ID NO: 2 by one or more of the alterations identified in table 6.

With respect to a variant of a peptide having (i.e. consisting of or comprising as defined above, particularly as defined in the above items (a) to (f)) SEQ ID NO: 3, the variant of the invention may differ from the peptide having SEQ ID NO: 3 by one or more of the alterations identified in table 6.

With respect to a variant of a peptide having (i.e. consisting of or comprising as defined above, particularly as defined in the above items (a) to (f)) SEQ ID NO: 4, the variant of the invention may differ from the peptide having SEQ ID NO: 4 by one or more of the alterations identified in table 7.

With respect to a variant of a peptide having (i.e. consisting of or comprising as defined above, particularly as defined in the above items (a) to (f)) SEQ ID NO: 5, the variant of the invention may differ from the peptide having SEQ ID NO: 5 by one or more of the alterations identified in table 7.

With respect to a variant of a peptide having (i.e. consisting of or comprising as defined above, particularly as defined in the above items (a) to (f)) SEQ ID NO: 6, the variant of the invention may differ from the peptide having SEQ ID NO: 6 by one or more of the alterations identified in table 7.

With respect to a variant of a peptide having (i.e. consisting of or comprising as defined above, particularly as defined in the above items (a) to (f)) SEQ ID NO: 7, the variant of the invention may differ from the peptide having SEQ ID NO: 7 by one or more of the alterations identified in table 9.

It should be understood that variants obtained from a peptide of the invention by one or more sequence alterations in accordance with tables 5 to 7 and 9 are preferred.

A further aspect of the present invention describes a peptide comprising an amino acid sequence with at least 95% sequence identity to at least one of SEQ ID NO: 1, 2, 3, 4, 5, 6 or 7. In different embodiment the peptide comprises, consists, or consists essentially of a region of at least 95%, at least 97% or at least 99% identical to SEQ ID NO: 1, 2, 3, 4, 5, 6 or 7, or differs by 0, 1, 2, 3, 4, 5, 6, 7, 8, 9, 10, 11, 12, 13, 14, 15, 16, 17, 18, 19, or 20 amino acid alteration(s). In one embodiment the term "consist" may be as defined in the above items (a) to (f)). Preferably, the peptide does not contain a full-length naturally occurring Spy0269, Spy0292, Spy0416A (amino acids 33-867), or Spy0872.

SEQ ID NO: 1, 2, 3, 4, 5, 6 or 7 provide core sequences useful for producing a protective immune response. SEQ ID NO: 1 provides an amino acid core from amino acids 37-488 of Spy0269. SEQ ID NO: 2 provides a core region of amino acids 23-184 of Spy0292. SEQ ID NO: 3 provides a core of amino acids 23-300 of Spy0292, which is a longer-length sequence containing the shorter-length core sequence of 23-184 of Spy0292 provided in SEQ ID NO: 2. Surprisingly, the shorter fragment Spy0292-1 (SEQ ID NO: 2) shows even greater protection in the mouse model compared to the longer fragment Spy0292-3 (SEQ ID NO: 3), as depicted in FIG. 1. As described above, smaller peptides are in general advantageous over larger ones, since they may be produced in a more economic manner, they reduce the probability of inducing antibodies which can cause cross-reactions with human tissues, and they facilitate the preparation of combination vaccines comprising more than one antigen. SEQ ID NO: 4, 5, and 6 provide different Spy0416A core sequences of varying activity. SEQ ID NO: 5 provides a common core of amino acids 148-458 of Spy0416A and has the lowest activity. SEQ ID NO: 6 provides a core sequence containing amino acids 72-558 of Spy0416A with greater activity than the shorter core. SEQ ID NO: 4 provides an amino acid core containing amino acids 34-677 of Spy0416, also with activity greater than the 148-458 core.

Based on the guidance provided herein different peptides can be designed taking into account the core sequences provided in SEQ ID NOs: 1-7. Such guidance includes structurally related peptides containing (1) internal alterations; (2) additional amino acid groups at the amino and/or carboxyl terminus; and/or (3) additional modification(s) as described herein.

For structurally related peptides, each amino acid alteration is independently either an addition, substitution, or deletion. In a further embodiment, the amino terminus is methionine. The presence of methionine may be useful for recombinant expression. In some cases, the methionine may be initially present as a result of translation and subsequently cleaved. Additional examples and embodiments, including broader embodiments and some further descriptions applicable for structurally related peptides such as functional variants are provided above, particularly in the description of functional active variants.

In another subject of the invention the peptide as described above comprises or consists of at least 2, preferably at least 3, more preferably at least 4 antigens as defined above. If two ore more peptides derived from the same full length sequence (e.g Spy0292 or Spy0416) are combined into one peptide, these sequences do preferably not overlap. In one embodiment the term "consist" may be as defined in the above items (a) to (f)).

In another embodiment of the invention the peptide as defined above may be modified by one or more of a variety of chemical techniques to produce derivatives having essentially the same activity (as defined above for fragments and variants) as the modified peptides, and optionally having other desirable properties. For example, carboxylic acid groups of the protein, whether C-terminal or side chain, may be provided in the form of a salt of a pharmaceutically-acceptable cation or esterified to form an ester, or converted to an amide. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be converted to an amide. Hydroxyl groups of the peptide side chains may be converted to alkoxy or to an ester using well recognized techniques. Phenyl and phenolic rings of the peptide side chains may be substituted with one or more halogen atoms, such as fluorine, chlorine, bromine or iodine, or with alkyl, alkoxy, carboxylic acids and esters thereof, or amides of such carboxylic acids. Thiols can be protected with any one of a number of well recognized protecting groups, such as acetamide groups.

Peptides of this invention may be in combination with outer surface proteins or other proteins or antigens of other proteins. In such combination, the antigen may be in the form of a fusion protein. The antigen of the invention may be optionally fused to a selected peptide or protein derived from other microorganisms. For example, an antigen or polypeptide of this invention may be fused at its N-terminus or C-terminus to a polypeptide from another pathogen or to more than one polypeptide in sequence. Peptides which may be useful for this purpose include polypeptides identified by the prior art.

In an embodiment of the invention the peptide of the invention is fused to an epitope tag which provides an epitope to which an anti-tag substance can selectively bind. The epitope tag is generally placed at the amino- or carboxyl-terminus of the peptide but may be incorporated as an internal insertion or substitution as the biological activity permits. The presence of such epitope-tagged forms of a peptide can be detected using a substance such as an antibody against the tagged peptide. Also, provision of the epitope tag enables the peptide to be readily purified by affinity purification using an anti-tag antibody or another type of affinity matrix that binds to the epitope tag. Various tag polypeptides and their respective antibodies are well known in the art. Examples include poly-histidine (poly-his), poly-histidine-glycine (poly-his-gly) tags, the HA tag polypeptide, the c-myc tag, the Strep tag and the FLAG tag.

Fusions also may include the peptides or antigens of this invention fused or coupled to moieties other than amino acids, including lipids and carbohydrates. Further, antigens of this invention may be employed in combination with other vaccinal agents described by the prior art, as well as with other species of vaccinal agents derived from other microorganisms. Such proteins are useful in the prevention, treatment and diagnosis of diseases caused by a wide spectrum of *Streptococcus* isolates.

These fusion proteins are constructed for use in the methods and compositions of this invention. These fusion proteins or multimeric proteins may be produced recombinantly, or may be synthesized chemically.

The peptides of the invention may be prepared by any of a number of conventional techniques. Desired peptides may be chemically synthesized. An alternative approach involves generating the fragments of known peptides by enzymatic digestion, e.g., by treating the protein with an enzyme known to cleave proteins at sites defined by particular amino acid residues, or by digesting the DNA with suitable restriction enzymes, expressing the digested DNA and isolating the desired fragment. Yet another suitable technique involves isolating and amplifying a DNA fragment encoding a desired peptide fragment, by polymerase chain reaction (PCR). Oligonucleotides that define the desired termini of the DNA fragment are employed as the 5' and 3' primers in the PCR. Techniques for making mutations, such as deletions, insertions and substitutions, at predetermined sites in DNA, and therefore in proteins, having a known sequence are well known. One of skill in the art using conventional techniques, such as PCR, may readily use the antigens and peptides provided herein to identify and isolate other similar proteins. Such methods are routine and not considered to require undue experimentation, given the information provided herein. For example, variations can be made using oligonucleotide-mediated site-directed mutagenesis (Carter et al., Nucl. Acids Res., 13: 4431 (1985); Zoller et al., Nucl. Acids Res. 10: 6487 (1987)), cassette mutagenesis (Wells et al., Gene, 34: 315 (1985)), restriction selection mutagenesis (Wells et al., Philos. Trans. R. Soc. London SerA, 317: 415 (1986)), PCR mutagenesis, or other known techniques can be performed on the cloned DNA to produce the peptide of the invention.

Another subject of the present invention relates to a nucleic acid encoding a peptide of the invention, i.e. any peptide as defined above, or a nucleic acid complementary thereto. Nucleic acid molecules of the present invention may be in the form of RNA, such as mRNA or cRNA, or in the form of DNA, including, for instance, cDNA and genomic DNA e.g. obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. Nucleic acid molecule as used herein also refers to, among other, single- and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or a mixture of single- and double-stranded regions.

The nucleic acid may be a fragment of a nucleic acid occurring naturally in *S. pyogenes*, especially in *S. pyogenes* serotype M1, M2, M3, M4, M5, M6, M11, M12, M14, M19, M22, M24, M25, M28, M44, M49, M57, M59, M60, M61, M76, M83, M84, M87, M89 or M118, particularly *S. pyogenes* SF370. Preferably the nucleic acid has a sequence as defined in any of the sequences of SEQ ID NOS: 11 to 17 or of any of the homologous variants identified in the attached listing of nucleic acid sequence data. Examples of homologous sequences of a different serotype are those listed below:

| Full length nucleic acid sequence (SEQ ID NO) | Nucleic acid of the invention (SEQ ID NO) | Homologous nucleic acid sequences (SEQ ID NOS) |
|---|---|---|
| 133 | 11 | 134 to 143 |
| 144 | 12 | 145 to 154 |
| 144 | 13 | 155 to 164 |
| 165 | 14 | 166 to 175 |
| 165 | 15 | 176 to 185 |
| 165 | 16 | 186 to 195 |
| 196 | 17 | 197 to 206 |

The nucleic acid also includes sequences that are a result of the degeneration of the genetic code. There are 20 natural amino acids, most of which are specified by more than one codon. Therefore, all nucleotide sequences are included in the invention which result in the peptide as defined above.

Additionally, the nucleic acid may contain one or more modified bases. Such nucleic acids may also contain modifications e.g. in the ribose-phosphate backbone to increase stability and half life of such molecules in physiological environments. Thus, DNAs or RNAs with backbones modified for stability or for other reasons are "nucleic acid molecule" as that feature is intended herein. Moreover, DNAs or RNAs comprising unusual bases, such as inosine, or modified bases, such as tritylated bases, to name just two examples, are nucleic acid molecule within the context of the present invention. It will be appreciated that a great variety of modifications have been made to DNA and RNA that serve many useful purposes known to those of skill in the art. The term nucleic acid molecule as it is employed herein embraces such chemically, enzymatically or metabolically modified forms of nucleic acid molecule, as well as the chemical forms of DNA and RNA characteristic of viruses and cells, including simple and complex cells, inter alia. For example, nucleotide substitutions can be made which do not affect the polypeptide encoded by the nucleic acid, and thus any nucleic acid molecule which encodes an antigen or fragment or functional active variant thereof as defined above is encompassed by the present invention.

Furthermore, any of the nucleic acid molecules encoding an antigen of the invention or fragment or functional active variant thereof can be functionally linked, using standard techniques such as standard cloning techniques, to any desired regulatory sequences, whether a *S. pyogenes* regulatory sequence or a heterologous regulatory sequence, heterologous leader sequence, heterologous marker sequence or a heterologous coding sequence to create a fusion protein.

The nucleic acid of the invention may be originally formed in vitro or in a cell in culture, in general, by the manipulation of nucleic acids by endonucleases and/or exonucleases and/or polymerases and/or ligases and/or recombinases or other methods known to the skilled practitioner to produce the nucleic acids.

In one embodiment of the invention the nucleic acid is located in a vector. A vector may additionally include nucleic acid sequences that permit it to replicate in the host cell, such as an origin of replication, one or more desired genes and/or selectable marker genes and other genetic elements known in the art such as regulatory elements directing transcription, translation and/or secretion of the encoded protein. The vector may be used to transduce, transform or infect a cell, thereby causing the cell to express inserted nucleic acids and/or proteins other than those native to the cell. The vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known (see, e.g. Sambrook et al, Molecular Cloning. A Laboratory Manual, 2" edition, Cold Spring Harbor Laboratory, New York (1989)). In one embodiment, the vector is a viral vector. Viral vectors include, but are not limited to, retroviral and adenoviral vectors.

Suitable host cells or cell lines for transfection by this method include bacterial cells. For example, the various strains of *E. coli* are well-known as host cells in the field of biotechnology. Various strains of *B. subtilis, Pseudomonas, Streptomyces*, and other bacilli and the like may also be employed in this method. Many strains of yeast cells known to those skilled in the art are also available as host cells for expression of the peptides of the present invention. Other fungal cells or insect cells such as *Spodoptera frugipedera* (Sf9) cells may also be employed as expression systems. Alternatively, mammalian cells, such as human 293 cells, Chinese hamster ovary cells (CHO), the monkey COS-1 cell line or murine 3T3 cells derived from Swiss, BALB/c or NIH mice may be used. Still other suitable host cells, as well as methods for transfection, culture, amplification, screening, production, and purification are known in the art.

A peptide of the invention may be produced by expressing a nucleic acid of the invention in a suitable host cell. The host cells can be transfected, e.g. by conventional means such as electroporation with at least one expression vector containing a nucleic acid of the invention under the control of a transcriptional regulatory sequence. The transfected or transformed host cell is then cultured under conditions that allow expression of the protein. The expressed protein is recovered, isolated, and optionally purified from the cell (or from the culture medium, if expressed extracellularly) by appropriate means known to one of skill in the art. For example, the proteins are isolated in soluble form following cell lysis, or extracted using known techniques, e.g. in guanidine chloride. If desired, the peptides or fragments of the invention are produced as a fusion protein. Such fusion proteins are those described above. Alternatively, for example, it may be desirable to produce fusion proteins to enhance expression of the protein in a selected host cell or to improve purification. The molecules comprising the peptides and antigens of this invention may be further purified using any of a variety of conventional methods including, but not limited to: liquid chromatography such as normal or reversed phase, using HPLC, FPLC and the like; affinity chromatography (such as with inorganic ligands or monoclonal antibodies); size to exclusion chromatography; immobilized metal chelate chromatography; gel electro-phoresis; and the like. One of skill in the art may select the most appropriate isolation and purification techniques without departing from the scope of this invention. Such purification provides the antigen in a form substantially free from other proteinaceous and non-proteinaceous materials of the microorganism.

Another subject of the invention is a pharmaceutical composition, especially a vaccine, comprising (i) at least one peptide according to the invention, and/or (ii) at least one peptide comprising or consisting of the sequence of any of the SEQ ID NO: 8, SEQ ID NO: 9, or SEQ ID NO: 10, or a functional active variant thereof, and (iii) optionally a pharmaceutically acceptable carrier or excipient.

The variants of the peptides of (ii) are as defined and may be obtained as the peptides of (i) (see above description of the peptides of the invention). Preferred alterations of the sequences of SEQ ID NO: 8 or 10 are those listed in tables 8 and 9, respectively.

The peptides of (i) and (ii) are referred to as pharmaceutical peptides of the invention.

With respect to the peptide of (ii), these proteins have been shown for the first time to be capable to provide protection against lethal *S. pyogenes* challenge (see Example 1), particularly in a physiologically highly relevant intranasal challenge model. Especially protein Spy0895 (SEQ ID NO: 9) shows particular promise as a vaccine candidate, because it provided protection against group A streptococcal infection in all three models listed in Table 1.

A pharmaceutical peptide of the invention may be used for methods for immunizing or treating humans and/or animals with the disease caused by infection with *S. pyogenes*. Therefore, the pharmaceutical peptide may be used within a pharmaceutical composition. The pharmaceutical composition of the present invention may further encompass pharmaceutically acceptable carriers and/or excipients. The pharmaceutically acceptable carriers and/or excipients useful in this invention are conventional and may include buffers, stabilizers, diluents, preservatives, and solubilizers. Remington's Pharmaceutical Sciences, by E. W. Martin, Mack Publishing Co., Easton, Pa., 15th Edition (1975), describes compositions and formulations suitable for pharmaceutical delivery of the (poly)peptides herein disclosed. In general, the nature of the carrier or excipients will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g. powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In a preferred embodiment the pharmaceutical composition further comprises an immunostimulatory substance such as an adjuvant. The adjuvant can be selected based on the method of administration and may include mineral oil-based adjuvants such as Freund's complete and incomplete adjuvant, Montanide incomplete Seppic adjuvant such as ISA, oil in water emulsion adjuvants such as the Ribi adjuvant system, syntax adjuvant formulation containing muramyl dipeptide, IC31™ (Intercell; a synthetic adjuvant comprising the peptide motif KLK [WO 02/32451] and an oligonucleotide [WO 01/93905]), or aluminum salt adjuvants. Preferably, the adjuvant is a mineral oil-based adjuvant, most preferably ISA206 (SEPPIC, Paris, France).

In other embodiments the immunostimulatory substance is selected from the group comprising polycationic polymers, especially polycationic peptides such as polyarginine, immunostimulatory deoxynucleotides (ODNs), especially Oligo $(dIdC)_{13}$, peptides containing at least two LysLeuLys motifs, especially KLKLLLLLKLK (SEQ ID NO: 55), neuroactive compounds, especially human growth hormone, alum, adjuvants or combinations thereof. In further embodiments, the combination is either a polycationic polymer and immunostimulatory deoxynucleotides or of a peptide containing at least two LysLeuLys motifs and immunostimulatory deoxynucleotides. In a still another embodiment the polycationic polymer is a polycationic peptide.

The term "Oligo$(dIdC)_{13}$" as used in the present invention means a phosphodiester backboned single-stranded DNA molecule containing 13 deoxy (inosine-cytosine) motifs, also defined by the term [oligo-d$(IC)_{13}$]. The exact sequence is 5'-dIdCdIdCdIdCdIdCdIdCdIdCdIdCdIdCdIdCdIdCdIdCdIdCdIdC-3'. Oligo$(dIdC)_{13}$ can also be defined by the terms (oligo-d$IC_{26}$); oligo-d$IC_{26\text{-}mer}$; oligo-deoxy IC, 26-mer; or oligo-dIC, 26-mer, as specified for example in WO 01/93903 and WO 01/93905.

In an embodiment the immunostimulatory substance is at least one immunostimulatory nucleic acid. Immunostimulatory nucleic acids are e.g. neutral or artificial CpG containing nucleic acids, short stretches of nucleic acids derived from non-vertebrates or in form of short oligonucleotides (ODNs) containing non-methylated cytosine-guanine dinucleotides (CpG) in a defined base context (e.g. as described in WO 96/02555). Alternatively, also nucleic acids based on inosine and cytidine as e.g. described in WO 01/93903, or deoxynucleic acids containing deoxy-inosine and/or deoxyuridine residues (described in WO 01/93905 and WO 02/095027) may preferably be used as immunostimulatory nucleic acids in the present invention. Preferably, mixtures of different immunostimulatory nucleic acids are used in the present invention. Additionally, the aforementioned polycationic compounds may be combined with any of the immunostimulatory nucleic acids as aforementioned. Preferably, such combinations are according to the ones described in WO 01/93905, WO 02/32451, WO 01/54720, WO 01/93903, WO 02/13857, WO 02/095027 and WO 03/047602.

In addition or alternatively, such pharmaceutical or vaccine composition may comprise a neuroactive compound. Preferably, the neuroactive compound is human growth factor, e.g. described in WO 01/24822. Also preferably, the neuroactive compound is combined with any of the polycationic compounds and/or immunostimulatory nucleic acids as defined above.

The composition may be used e.g. for immunization or treatment of a subject. The pharmaceutical composition encompasses at least one pharmaceutical peptide of the invention; however, it may also contain a cocktail (i.e., a simple mixture) containing different pharmaceutical peptides (including fragments and other variants) of the invention, optionally mixed with different antigenic proteins or peptides of other pathogens. Such mixtures of these peptides, polypeptides, proteins or fragments or variants thereof are useful e.g. in the generation of desired antibodies to a wide spectrum of Streptococci isolates. The pharmaceutical peptide(s) of the present invention may also be used in the form of a pharmaceutically acceptable salt. Suitable acids and bases which are capable of forming salts with the peptides of the present invention are well known to those of skill in the art, and include inorganic and organic acids and bases.

Still another subject of the invention is a pharmaceutical composition containing a nucleic acid selected from the group consisting of:

(i) a nucleic acid of the invention and/or a nucleic acid complementary thereto, and/or (ii) a nucleic acid coding for the peptide comprising or consisting of the sequence of any of the SEQ ID NO: 8, SEQ ID NO: 9, or SEQ ID NO: 10, particularly a DNA sequence of any of the SEQ ID NO: 18, SEQ ID NO: 19, or SEQ ID NO: 20, or a functional active variant thereof or a nucleic acid complementary thereto or the corresponding RNA sequence, and (iii) optionally a pharmaceutically acceptable carrier or excipient.

The variants of the nucleic acids of (ii) are as defined and may be obtained as the nucleic acids of (i) (see above description of the nucleic acids of the invention). The nucleic acids of (i) and (ii) are referred to as pharmaceutical nucleic acids of the invention.

The pharmaceutical nucleic acid sequences, alone or in combination with other nucleic acid sequences encoding antigens or antibodies or directed to other pathogenic microorganisms, may further be used as components of a pharmaceutical composition. The composition may be used for immunizing or treating humans and/or animals being susceptible to or having a disease caused by infection with *S. pyogenes*, particularly *S. pyogenes* serotype M1, M2, M3, M4, M5, M6, M11, M12, M14, M19, M22, M24, M25, M28, M44, M49, M57, M59, M60, M61, M76, M83, M84, M87, M89 or M118, especially *S. pyogenes* SF370. The pharmaceutically acceptable carrier or excipient may be as defined above.

In another embodiment, the pharmaceutical nucleic acids of this invention, alone or in combination with nucleic acid sequences encoding other antigens or antibodies from other pathogenic microorganisms, may further be used in compositions directed to actively induce a protective immune response in a subject to the pathogen. These components of the present invention are useful in methods for inducing a protective immune response in humans and/or animals against infection with *S. pyogenes*, particularly with *S. pyogenes* serotype M1, M2, M3, M4, M5, M6, M11, M12, M14, M19, M22, M24, M25, M28, M44, M49, M57, M59, M60, M61, M76, M83, M84, M87, M89 or M118, especially *S. pyogenes* SF370.

For use in the preparation of the therapeutic or vaccine compositions, nucleic acid delivery compositions and methods are useful, which are known to those of skill in the art. The pharmaceutical nucleic acid of the invention may be employed in the methods of this invention or in the compositions described herein as DNA sequences, either administered as naked DNA, or associated with a pharmaceutically acceptable carrier and provide for in vivo expression of the antigen, peptide or polypeptide. So-called "naked DNA" may be used to express the antigen, peptide or polypeptide of the invention in vivo in a patient. (See, e.g., J. Cohen, Science, 259: 1691-1692, which describes similar uses of "naked DNA"). For example, "naked DNA" associated with regulatory sequences may be administered therapeutically or as part of the vaccine composition e.g., by injection.

Alternatively, a nucleic acid, especially a pharmaceutical nucleic acid according to the invention, encoding an antigen or peptide of the invention or a nucleic acid complementary thereto may be used within a pharmaceutical composition, e.g. in order to express the antigen or (pharmaceutical) peptide of the invention in vivo, e.g., to induce antibodies.

A preferred embodiment of the invention relates to a pharmaceutical composition, wherein the pharmaceutical nucleic acid according to the invention is comprised in a vector and/or a cell. Vectors and cells suitable in the context of the present invention are described above. Vectors are particularly employed for a DNA vaccine. An appropriate vector for delivery may be readily selected by one of skill in the art. Exemplary vectors for in vivo gene delivery are readily available from a variety of academic and commercial sources, and include, e.g., adeno-associated virus (International patent application No. PCT/US91/03440), adenovirus vectors (M. Kay et al, Proc. Natl. Acad. Sci. USA, 91: 2353 (1994); S. Ishibashi et al, J. Clin. Invest., 92: 883 (1993)), or other viral vectors, e.g., various poxviruses, vaccinia, etc. Recombinant viral vectors, such as retroviruses or adenoviruses, are preferred for integrating the exogenous DNA into the chromosome of the cell.

Another subject of the invention relates to an antibody or functional active fragment thereof which binds specifically to the antigen of the invention. The present invention includes, for example, monoclonal and polyclonal antibodies, chimeric, single chain, and humanized antibodies, as well as Fab fragments, or the product of a Fab expression library.

While *S. pyogenes* infections are primarily a disease of children and cause non-severe diseases such as bacterial pharyngitis and impetigo, GAS are also responsible for streptococcal toxic shock syndrome associated necrotizing fasciitis (Cone, L., et al. (1987). New Engl J Med 317: 146-9; Stevens, D. (1992). Clin Infect Dis 14: 2-11) and several post-streptococcal sequelae such as acute rheumatic fever, acute glomerulonephritis and reactive arthritis. It would be very beneficial to provide monoclonal or polyclonal antibody therapies which target antigenic proteins of *S. pyogenes* and have the potential to support a therapy of an infection or eliminate the pathogen and the disease altogether.

In a preferred embodiment the antibody is a monoclonal, polyclonal, chimeric or humanized antibody or functional active variant thereof. In another preferred embodiment the functional active fragment comprises a Fab fragment.

Antibodies generated against the antigens, fragments or variants thereof of the present invention can be obtained by direct injection of the antigens, fragments or variants thereof into an animal or by administering the antigens, fragments or variants thereof to an animal, preferably a non-human. The antibody so obtained will then bind the antigens, fragments or variants. Such antibodies can then be used to isolate reactive antigens, fragments or variants thereof from tissue expressing those.

For preparation of monoclonal antibodies, any technique known in the art, which provides antibodies produced by continuous cell line cultures, e.g. a hybridoma cell line, can be used.

Techniques described for the production of single chain antibodies (U.S. Pat. No. 4,946,778) can be adapted to produce single chain antibodies to the antigens, fragments or variants thereof according to this invention. Also, transgenic mice or other organisms such as other mammals may be used to express humanized antibodies to antigens, fragments or variants thereof according to this invention.

Still another subject of the invention relates to a hybridoma cell line which produces the antibody of the invention.

Hybridoma cell lines expressing desirable monoclonal antibodies are generated by well-known conventional techniques. The hybridoma cell can be generated by fusing a normal-activated, antibody-producing B cell with a myeloma cell. In the context of the present invention the hybridoma cell is able to produce an antibody specifically binding to the antigen of the invention.

Similarly, desirable high titre antibodies are generated by applying known recombinant techniques to the monoclonal or polyclonal antibodies developed to these antigens (see, e.g., PCT Patent Application No. PCT/GB85/00392; British Patent Application Publication No. GB2188638A; Amit et al., Science, 233: 747-753 (1986); Queen et al., Proc. Natl. Acad. Sci. USA, 86: 10029-10033 (1989); PCT Patent Application No. WO90/07861; Riechmann et al., Nature, 332: 323-327 (1988); Huse et al., Science, 246: 1275-1281 (1988)).

The present invention also provides a method for producing an antibody according to the invention, characterized by the following steps:

(a) administering an effective amount of the peptide according to the invention to an animal; and
(b) isolating the antibody produced by the animal in response to the administration of step (a) from the animal.

Another subject of the invention relates to a method for producing an antibody according to the invention, characterized by the following steps:

(a) contacting a B cell with an effective amount of the peptide according to the invention;
(b) fusing the B cell of step (a) with a myeloma cell to obtain a hybridoma cell; and
(c) isolating the antibody produced by the cultivated hybridoma cell.

More particularly, the antibody may be produced by initiating an immune response in a non-human animal by administrating a peptide of the invention to an animal, removing an antibody containing body fluid from said animal, and producing the antibody by subjecting said antibody containing body fluid to further purification steps. Alternatively, the antibody may be produced by initiating an immune response in a non-human animal by administrating an antigen, fragment or variant thereof, as defined in the present invention, to said animal, removing the spleen or spleen cells from said animal and/or producing hybridoma cells of said spleen or spleen cells, selecting and cloning hybridoma cells specific for said antigen, fragment or variant thereof and producing the antibody by cultivation of said cloned hybridoma cells.

In a preferred embodiment the antibody produced according to a method of the invention is additionally purified. Methods of purification are known to the skilled artisan.

The antibody may be used in methods for preventing or treating an infection. Accordingly, still another subject of the invention relates to a pharmaceutical composition, especially a vaccine, comprising an antibody of the invention. The pharmaceutical composition may encompass further components as detailed above. The composition may further encompass substances increasing their capacity to stimulate T cells. These include T helper cell epitopes, lipids or liposomes or preferred modifications as described in WO01/78767. Another way to increase the T cell stimulating capacity of epitopes is their formulation with immune stimulating substances for instance cytokines or chemokines like interleukin-2, -7, -12, -18, class I and II interferons (IFN), especially IFN-gamma, GM-CSF, TNF-alpha, flt3-ligand and others.

A further subject of the invention relates to a pharmaceutical composition comprising the pharmaceutical peptide of the invention or the pharmaceutical nucleic acid of the invention or an antibody of the invention or functional fragment thereof for the immunization of a subject against an infection or the treatment of a subject having an infection, wherein the infection is preferably a *S. pyogenes* infection. In another aspect of the invention a pharmaceutical peptide of the invention or a pharmaceutical nucleic acid of the invention or an antibody of the invention or functional fragment thereof is used for the manufacture of a medicament for the immunization of a subject against an infection or the treatment of a subject having an infection, wherein the infection is preferably a *S. pyogenes* infection, more preferably an infection with *S. pyogenes* serotype M1, M2, M3, M4, M5, M6, M11, M12, M14, M19, M22, M24, M25, M28, M44, M49, M57, M59, M60, M61, M76, M83, M84, M87, M89 or M118, especially *S. pyogenes* SF370. Alternatively, a pharmaceutical peptide or a pharmaceutical nucleic acid of the invention or an antibody of the invention or functional fragment thereof is used in a method of immunizing or treating a subject in need thereof, wherein an effective amount of the pharmaceutical peptide or the pharmaceutical nucleic acid of the invention or an antibody of the invention or functional fragment thereof is administered to the subject. The subject may be immunized in order to prevent an infection, particularly a *S. pyogenes* infection, or may be treated to ameliorate or cure an infection, particularly a *S. pyogenes* infection. The determination of the effective amount to be administered is within the knowledge of the skilled practitioner. Exemplary amounts are mentioned below.

The pharmaceutical peptides or the pharmaceutical nucleic acids of the invention are generally useful for inducing an immune response in a subject. The vaccine used for immunization may be administered to a subject susceptible to infection by *S. pyogenes*, preferably mammals, and still more preferably humans. Potential modes of administration include oral, intranasal, intramuscular, intra-lymph node, intradermal, intraperitoneal, subcutaneous, and combinations thereof, but most preferably intramuscular injection. The volume of the dose for intramuscular administration is preferably up to about 5 mL, for example, between 0.3 mL and 3 mL, between 1 mL and 3 mL, about 0.5 to 1 mL, or about 2 mL. The amount of protein comprising the antigen in each dose should be enough to confer effective immunity to decrease the risk of developing clinical signs, e.g. resulting from *S. pyogenes* infection. In different embodiments, the unit dose of protein should be up to about 5 μg protein/kg body weight, between about 0.2 to 3 μg, between about 0.3 to 1.5 μg, between about 0.4 to 0.8 μg, or about 0.6 μg. In alternative embodiments unit doses of protein could be up to about 6 μg protein/kg body weight, between about 0.05 to 5 μg, or between about 0.1 to 4 μg. In different embodiments, the dose is administered 1 to 3 times, e.g. with an interval of 1 to 3 weeks. Representative amounts of protein per dose are from approximately 1 μg to approximately 1 mg, more preferably from approximately 5 μg to approximately 500 μg, still more preferably from approximately 10 μg to approximately 250 μg and most preferably from approximately 25 μg to approximately 100 μg.

In still another aspect of the invention the antibody of the invention or functional fragment thereof is used for the manufacture of a medicament for the treatment of an infection, preferably a *S. pyogenes* infection, more preferably an infection with *S. pyogenes* serotype M1, M2, M3, M4, M5, M6, M11, M12, M14, M19, M22, M24, M25, M28, M44, M49, M57, M59, M60, M61, M76, M83, M84, M87, M89 or M118, especially *S. pyogenes* SF370. Alternatively, the antibody of the invention is used in a method of treating a subject in need thereof, wherein an effective amount of the antibody of the invention is administered to the subject. The subject may be treated to ameliorate or cure an infection, particularly a *S. pyogenes* infection. The determination of the effective amount to be administered is within the knowledge of the skilled practitioner.

The treatment involves administering an effective amount of an antibody of the invention to a subject, preferably a mammal, more preferably a human. Thus, antibodies against the antigens, fragments or variants thereof of the present invention may be employed to inhibit and/or treat infections, particularly bacterial infections and especially infections arising from *S. pyogenes*, especially *S. pyogenes* serotype M1, M2, M3, M4, M5, M6, M11, M12, M14, M19, M22, M24, M25, M28, M44, M49, M57, M59, M60, M61, M76, M83, M84, M87, M89 or M118, especially *S. pyogenes* SF370.

An "effective amount" of a pharmaceutical peptide, a pharmaceutical nucleic acid or an antibody of the invention may be calculated as that amount capable of exhibiting an in vivo effect, e.g. preventing or ameliorating a sign or symptom of infection, particularly *S. pyogenes* infection, especially of *S. pyogenes* serotype M1, M2, M3, M4, M5, M6, M11, M12, M14, M19, M22, M24, M25, M28, M44, M49, M57, M59, M60, M61, M76, M83, M84, M87, M89 or M118, especially *S. pyogenes* SF370. Such amounts may be determined by one of skill in the art. Preferably, such a composition is administered parenterally, preferably intramuscularly or subcutaneously. However, it may also be formulated to be administered by any other suitable route, including orally or topically. The selection of the route of delivery and dosage of such therapeutic compositions is within the skill of the art.

Treatment in the context of the present invention refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

Another subject of the invention relates to a method of diagnosing a *S. pyogenes* infection comprising the steps of:

(a) contacting a sample obtained from a subject with the peptide according to the invention; and
(b) detecting the presence of an antibody against *S. pyogenes* in the sample.

The peptides of the invention may be used for the detection of the *S. pyogenes*, particularly *S. pyogenes* serotype M1, M2, M3, M4, M5, M6, M11, M12, M14, M19, M22, M24, M25, M28, M44, M49, M57, M59, M60, M61, M76, M83, M84, M87, M89 or M118, especially *S. pyogenes* SF370. Preferably such detection is for diagnosis, more preferable for the diagnosis of a disease, most preferably for the diagnosis of a *S. pyogenes* infection. The peptides or polypeptides may be used to detect the presence of a *S. pyogenes*-specific antibody or fragment thereof e.g. in a sample obtained from a subject. The sample may be e.g. a blood sample. Alternatively, the presence of a *S. pyogenes*-specific antigen can be detected using an antibody of the invention.

Accordingly, an alternative method of diagnosing a *S. pyogenes* infection comprises the steps of:

(a) contacting a sample obtained from a subject with the antibody according to the invention; and
(b) detecting the presence of an antigen of *S. pyogenes* in the sample.

The present invention also relates to diagnostic assays such as quantitative and diagnostic assays for detecting levels of the peptides or antibodies of the present invention in cells and tissues or body fluids, including determination of normal and abnormal levels. Assay techniques that can be used to determine levels of a peptide or an antibody, in a sample derived from a host are well known to those of skill in the art. Such assay methods include radioimmunoassays, competitive-binding assays, Western Blot analysis and ELISA assays. Among these, ELISAs frequently are preferred. An ELISA assay initially comprises preparing an antibody specific to the peptide, particularly the antigen, preferably a monoclonal antibody. In addition, a reporter antibody generally is prepared which binds to the monoclonal antibody. The reporter antibody is attached to a detectable reagent such as radioactive, fluorescent or enzymatic reagent, such as horseradish peroxidase enzyme.

The peptides or antibodies of the present invention may also be used for the purpose of or in connection with an array. More particularly, at least one of the peptides or antibodies of the present invention may be immobilized on a support. Said support typically comprises a variety of antigens and fragments thereof whereby the variety may be created by using one or several of the peptides or antibodies of the present invention. The characterizing feature of such array as well as of any array in general is the fact that at a distinct or predefined region or position on said support or a surface thereof, a distinct polypeptide is immobilized. Because of this any activity at a distinct position or region of an array can be correlated with a specific polypeptide. The number of different peptides or antibodies of the present invention immobilized on a support may range from as little as 10 to several 1000 different peptides or antibodies of the present invention.

The manufacture of such arrays is known to the one skilled in the art and, for example, described in U.S. Pat. No. 5,744,309. The array preferably comprises a planar, porous or non-porous solid support having at least a first surface. Preferred support materials are, among others, glass or cellulose. It is also within the present invention that the array is used for any of the diagnostic applications described herein. Apart from the peptides or antibodies of the present invention also the nucleic acid molecules according to the present invention to may be used for the generation of an array as described above.

Another aspect of the invention relates to a method for identifying a ligand capable of binding to a peptide according to the invention comprising:

(a) providing a test system comprising the peptide,
(b) contacting the test system with a test compound, and
(c) detecting a signal generated in response to the binding of the test compound to the peptide.

More particularly, the method may be carried out by contacting an isolated or immobilized peptide according to the invention with a candidate ligand under conditions to permit binding of the candidate ligand to the peptide, wherein the test system comprises a component capable of providing a detectable signal in response to the binding of the candidate ligand to said peptide; and detecting the presence or absence of a signal generated in response to the binding of the ligand to the peptide. The ligand may be an agonist or an antagonist.

Test systems for detection binding of a ligand are known to the skilled artisan and include e.g. binding assays with labeled ligand such as radioligands, fluorescence-labeled ligands or enzyme-labeled ligands.

The test compound can be any test compound either naturally occurring or chemically synthesized. Naturally occurring test compounds include in particular antibodies, preferably those showing similarity to the antibodies of the invention. In one preferred embodiment of the invention the test compound is provided in the form of a chemical compound library. Chemical compound libraries include a plurality of chemical compounds and have been assembled from any of multiple sources, including chemically synthesized molecules and natural products, or have been generated by combinatorial chemistry techniques. They are especially suitable for high throughput screening. They may be comprised of chemical compounds of a particular structure or compounds of a particular creature such as a plant.

The method for identifying a ligand may also include the following steps:

(a) providing a peptide according to the invention,
(b) providing an interaction partner to the peptide especially an antibody according to the invention, (c) allowing interaction of the peptide to said interaction partner to form a interaction complex, (d) providing a test compound, (e) allowing a competition reaction to occur between the test compound and the interaction complex, and (f) determining whether the test compound inhibits or reduces the interaction activities of the peptide with the interaction partner.

The ligands identified may be employed, for instance, to inhibit diseases arising from infection with *Streptococcus*, especially *S. pyogenes* and may therefore be formulated in a pharmaceutical composition.

In a last aspect, the peptide according to the invention is used for the isolation and/or purification and/or identification of a ligand of the peptide, wherein the isolation and/or purification and/or identification of the ligand may be carried out as detailed above or as known to the person skilled in the art. In a preferred embodiment of the invention an affinity device may be used. The affinity device may comprise as least a support material and any peptide according to the present invention, which is attached to the support material. Because of the specificity of the peptides according to the present invention for their target cells or target molecules or their interaction partners, the peptides allow a selective removal of their interaction partner(s) from any kind of sample applied to the support material provided that the conditions for binding are met. The sample may be a biological or medical sample, including but not limited to, fermentation broth, cell debris, cell preparation, tissue preparation, organ preparation, blood, urine, lymph liquid, liquor and the like. The peptide may be attached to the matrix in a covalent or non-covalent manner. Suitable support material is known to the one skilled in the art and can be selected from the group comprising cellulose, silicon, glass, aluminium, paramagnetic beads, starch and dextrane.

The present invention is further illustrated by the following figures, examples and the sequence data, from which further features, embodiments and advantages may be taken. It is to be understood that the present examples are given by way of illustration only and not by way of limitation of the disclosure.

Table 1 shows the recombinant proteins of *S. pyogenes* and fragments thereof assessed for protection in murine models of infection.

Table 2 shows the oligonucleotides used for the cloning of genes encoding antigenic proteins and fragments thereof of *S. pyogenes*.

Table 3 shows the *S. pyogenes* strains used for the gene conservation study.

Table 4 shows the oligonucleotides used for PCR and sequencing of the *S. pyogenes* genes.

Table 5 shows the variable amino acid positions of Spy0269 from *S. pyogenes* strains.

Table 6 shows the variable amino acid positions of Spy0292 from *S. pyogenes* strains.

Table 7 shows the variable amino acid positions of Spy0416 from *S. pyogenes* strains.

Table 8 shows the variable amino acid positions of Spy0488 from *S. pyogenes* strains.

Table 9 shows the variable amino acid positions of Spy0872 from *S. pyogenes* strains.

Table 10 shows the variable amino acid positions of Spy0895 from *S. pyogenes* strains.

Table 11 shows the variable amino acid positions of Spy1536 from *S. pyogenes* strains.

Table 12 shows the variable amino acid positions of Spy1666 from *S. pyogenes* strains.

FIGURES

Figure 1:
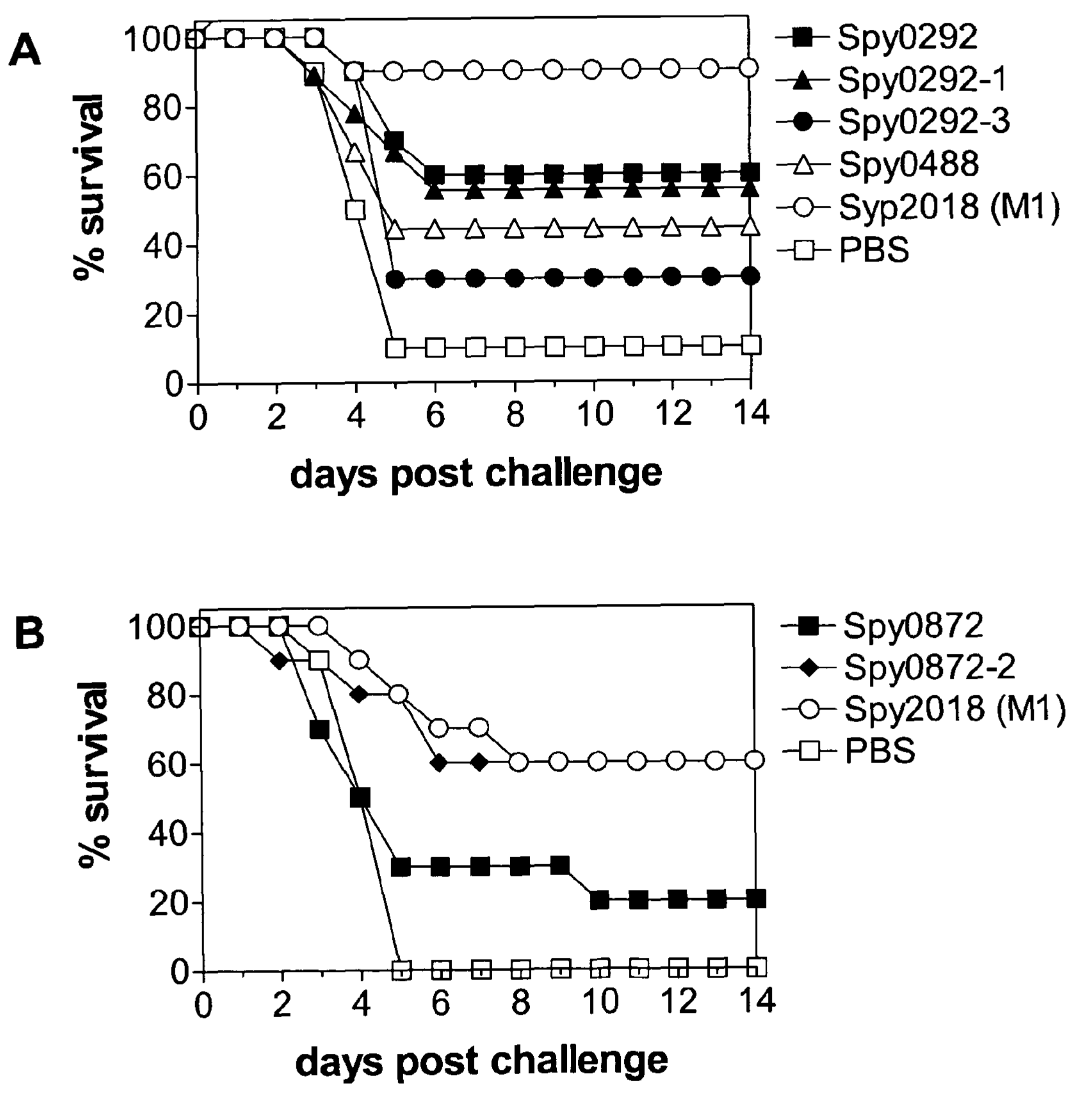
FIG. 1 shows the protection achieved by active immunization with selected *S. pyogenes* antigens and sub-constructs in a mouse lethality model.

FIG. 1: Protection achieved by active immunization with selected *S. pyogenes* antigens and sub-constructs in a mouse lethality model. CD-1 mice (10 mice per group) were immunized subcutaneously with recombinant antigens cloned from an emm type 1 *S. pyogenes* strain (SF370) and challenged with the MA-A20 (emm type 23) strain. Survival was monitored for 14 days post-challenge. Mice were immunized subcutaneously with 50 μg recombinant protein adjuvanted with CFA/IFA. (A) Spy0292, and its sub-constructs Spy0292-1 and Spy0292-3; Spy0488; (B) Spy0872 and its sub-construct Spy0872-2. Anesthetized mice were challenged intranasally with $10^8$ cfu *S. pyogenes* MA-A20. Adjuvant control mice were used as negative controls, while M1 (Spy2018) served as positive control. Numbers of surviving mice are plotted as percentage of total mice.

Figure 2:
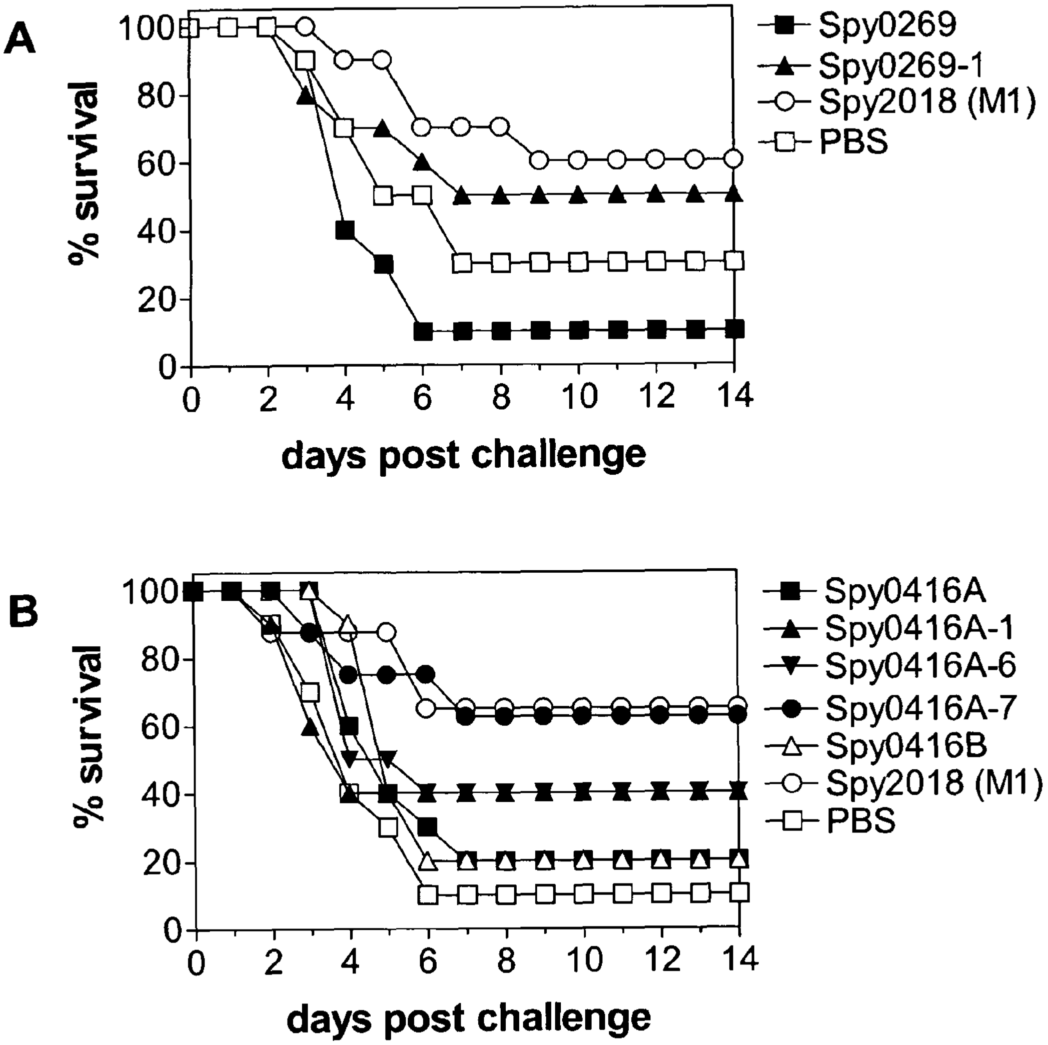
FIG. 2 shows the protection achieved by active immunization with selected *S. pyogenes* antigens and sub-constructs in a mouse lethality model.

FIG. 2: Protection achieved by active immunization with selected *S. pyogenes* antigens and sub-constructs in a mouse lethality model. CD-1 mice (10 mice per group) were immunized subcutaneously with recombinant antigens cloned from an emm type 1 *S. pyogenes* strain (SF370) and challenged with the MA-A20 (emm type 23) strain. Survival was monitored for 14 days post-challenge. Mice were immunized subcutaneously with 50 μg recombinant protein adjuvanted with CFA/IFA. (A) Spy0269 and its sub-construct Spy0269-1; (B) Spy0416A and 3 sub-constructs (Spy0416A-1, Spy0416A-6 and Spy0416A-7) and Spy0416B. Anesthetized mice were challenged intranasally with $10^8$ cfu *S. pyogenes* MA-A20. Adjuvant control mice were used as negative controls, while M1 protein (Spy2018) served as positive control. Numbers of surviving mice are plotted as percentage of total mice.

Figure 3:
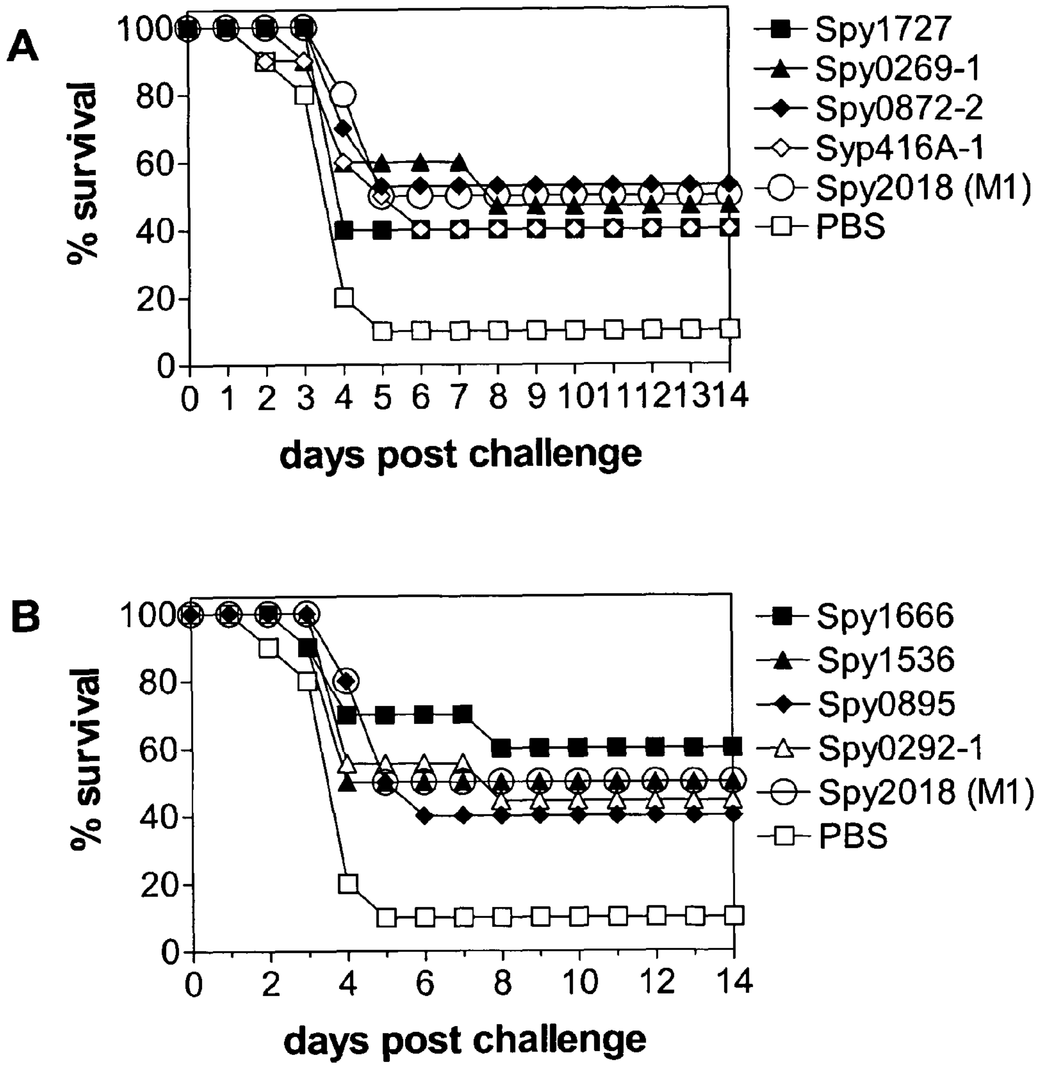
FIG. 3 shows the protection achieved by active immunization with selected *S. pyogenes* antigens and sub-constructs in a mouse lethality model.

FIG. 3: Protection achieved by active immunization with selected *S. pyogenes* antigens or sub-constructs in a mouse lethality model. CD-1 mice (10 mice per group) were immunized subcutaneously with recombinant antigens cloned from an emm type 1 *S. pyogenes* strain (SF370) and challenged with the MA-A20 (emm type 23) strain. Survival was monitored for 14 days post-challenge. Mice were immunized subcutaneously with 50 μg recombinant protein adjuvanted with aluminum hydroxide. (A) Spy1727, Spy0269-1, Spy0872-2, and Spy0416A-1; (B) Spy1666, Spy1536, Spy0895, and Spy0292-1. Anesthetized mice were challenged intranasally with $10^8$ cfu *S. pyogenes* MA-A20. Adjuvant control mice were used as negative controls, while M1 protein (Spy2018) served as positive control. Numbers of surviving mice are plotted as percentage of total mice.

Figure 4:
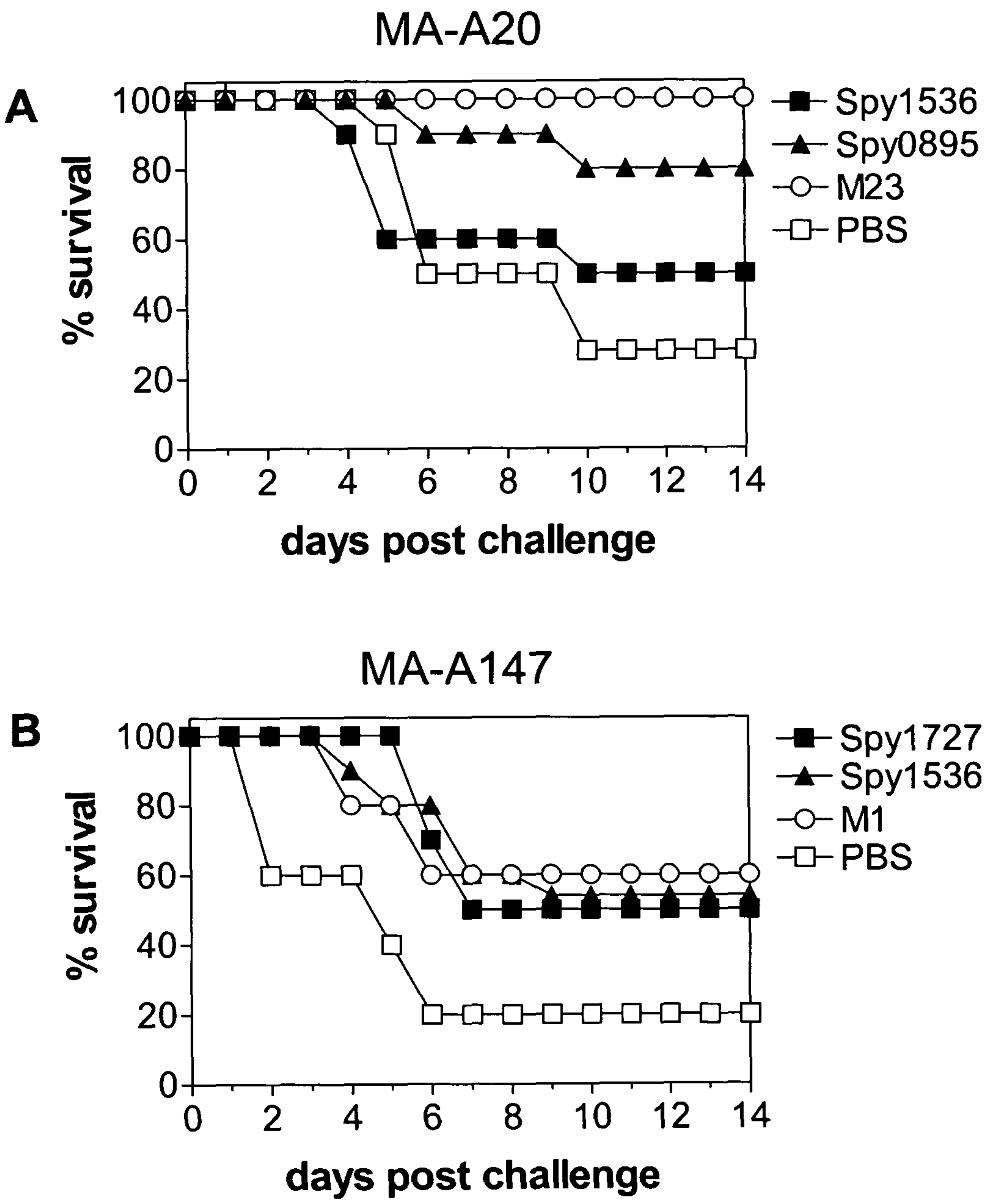
FIG. 4 shows the protection achieved by active immunization with selected *S. pyogenes* antigens in a mouse lethality model.

FIG. 4: Protection achieved by active immunization with selected *S. pyogenes* antigens in a mouse lethality model. BALB/c mice (10 mice per group) were immunized intranasally with recombinant antigens cloned from an emm type 1 *S. pyogenes* strain (SF370) and challenged either with (A)

MA-A20 (emm type 23) strain or with (B) MA-A147 (emm type 11/106) strain. Survival was monitored for 14 days post-challenge. Mice were immunized intranasally with 30-50 μg recombinant protein adjuvanted with IC31™. (A) Spy1536 and Spy0895; (B) Spy1727 and Spy1536. Anesthetized mice were challenged intranasally with $10^6$ cfu *S. pyogenes* MA-A20 or $10^8$ cfu *S. pyogenes* MA-A147. Adjuvant control mice were used as negative controls, while M1 protein (Spy2018) served as positive control. Numbers of surviving mice are plotted as percentage of total mice.

EXAMPLES

Example 1

Group A Streptococcal Antigens and Fragments Thereof Inducing Protective Immune Responses Against Lethal Sepsis in Intranasal Challenge Models Experimental Procedures Cloning and Expression of Recombinant Pneumococcal Proteins Cloning of Genes/DNA Fragments:

The gene/DNA fragment of interest (see Table 1) was amplified from genomic DNA of *Streptococcus pyogenes* SF370 (serotype M1) by PCR using gene specific primers (see Table 2). Apart from the gene specific part, the primers had restriction sites that aided in a directional cloning of the amplified PCR product. The gene annealing (specific) part of the primer ranged between 15-30 bases in length. The PCR products obtained were digested with the appropriate restriction enzymes and cloned into the pET28b (+) vector (Novagen) for His-tagged proteins. The constructs including full length and fragments of the selected antigens are listed in Table 1. Once the recombinant plasmid was confirmed to contain the gene of interest, *E. coli* BL21 Star® cells (Invitrogen) that served as expression host were transformed.

Expression and Purification of Proteins:

*E. coli* BL21 Star® cells harboring the recombinant plasmid were grown into log phase in the required culture volume. Once an $OD_{600nm}$ of 0.6 was reached the culture was induced with 0.5 mM IPTG (isopropyl-beta-D-thiogalactopyranoside) at 37° C. for 3 hours. The cells were harvested by centrifugation, lysed by a combination of the freeze-thaw method followed by disruption of cells with BugBuster® (Novagen). The lysate was separated by centrifugation into soluble (supernatant) and insoluble (pellet) fractions. Depending on the location of the protein different purification strategies were applied.

A) If the His-tagged protein was in the soluble fraction, protein purification was done by binding the supernatant to Ni-Sepharose beads (Ni-Sepharose™ 6 Fast Flow, GE Healthcare). Due to the presence of the hexa Histidine (6×HIS) at the C terminus of the expressed protein, it bound to the Ni-Sepharose while the other contaminating proteins were washed from the column by wash buffer. The protein was eluted by 500 mM Imidazole in 20 mM $NaH_2PO_4$, 0.5 mM NaCl buffer at pH 7.4. The eluate was concentrated, assayed by Bradford for protein concentration and checked by SDS-PAGE and Western blot.

B) If the protein was present in the insoluble fraction the pellet was solubilized in suitable buffer containing 8 M urea and applied onto the Ni-NTA column under denaturing conditions (in buffer containing 8 M urea) using the same materials and procedure as mentioned above. Contaminating proteins were washed from the column by wash buffer without urea. Refolding of the His-tagged protein was performed while the protein was immobilized on the Ni-NTA matrix. After renaturation, proteins were eluted by the addition of 500 mM Imidazole. The eluate was dialyzed to remove traces of urea and concentrated if the volume was large, checked by SDS-PAGE and measured by the Bradford method.

Animal Protection Studies

Animals:

CD-1 or BALB/c female mice (6-8 weeks) were used.

Active Immunization (Subcutaneous Route):

50 μg of recombinant proteins buffered in PBS were injected subcutaneously into CD-1 mice (volume 100 μL), adjuvanted with Complete Freund adjuvant (CFA, final concentration: 50%), aluminium hydroxide (ALUM, final concentration: 1%) or IC31™ (final concentration: 100 nmol L-KLKLLLLLKLK (SEQ ID NO: 55), 4 nmol oligodexoynucleotide ODN 1 a $(dIdC)_{13}$ in PBS) (Intercell AG, Vienna, Austria). Animals were boosted twice with the same amount of protein and adjuvant (except for CFA where Incomplete Freund adjuvant (IFA) was used for the booster immunizations; final concentration: 50%), at days 14 and 28. The published (Dale et al., J. Immunol. 151: 2188 (1993)) protective M1 or M23 protein antigens were used as positive controls, while mice immunized with adjuvant only served as negative controls. Antibody titers were measured at day 35 by ELISA using the respective recombinant proteins.

Active Immunization (Intranasal Route):

30-50 μg of recombinant proteins buffered in PBS were injected intranasally into BALB/c mice (volume 20 μL), adjuvanted with IC31™ (final concentration: 10 nmol L-KLKLLLLLKLK (SEQ ID NO: 55), 0.4 nmol oligodexoynucleotide ODN1a $(dIdC)_{13}$ in PBS) (Intercell AG, Vienna, Austria). Animals were boosted three times with the same amount of protein and adjuvant at days 7, 14 and 28. The published protective M1 or M23 protein antigens were used as positive controls, while mice immunized with adjuvant only served as negative controls. Antibody titers were measured at day 35 by ELISA using the respective recombinant proteins.

Bacterial Challenge:

Freshly grown *S. pyogenes* strains MA-A20 or MA-A147 were used. 1 mL bacterial suspension from an o/n culture of the respective *S. pyogenes* strain was added to 50 mL THY culture medium. Optical density was measured until the bacterial suspension reached an $OD_{600nm}$ between 0.4 and 0.6. Bacterial counts were determined using an individually established growth curve. Bacterial cells were spun down and adjusted with PBS to obtain the desired cfu count. In order to determine the viable cell numbers present in the bacterial inoculum, cfus were determined via plating on blood agar plates. $10^6$-$10^8$ cfus were applied intranasally (20 μL) into individually anesthetized mice. Protection by immunization was measured by a bacteraemia/sepsis model where survival rates were followed for 2 to 3 weeks post-challenge and survival was expressed in percentage of the total number of animals (10 mice/group).

Results

Group A streptococcal antigens and/or their fragments were identified showing protection in an intranasal mouse sepsis/lethality model. As the target indication for a preventive vaccine in humans is pharyngitis, an intranasal challenge model for the evaluation of candidate antigens is believed to be physiologically more relevant than an intravenous or intraperitoneal model, which have been described previously (Guzman et al., J. Inf. Dis. 179: 901 (1999); Stalhammar-Carlemalm et al., Mol. Microbiol. 33: 208 (1999)). Therefore protection was assessed in three distinct models, all applying the bacterial challenge via the intranasal route. Protection was observed for 9 distinct proteins in the intranasal challenge model, some of which were tested as a fragment of the full length recombinant protein.

Since protection against streptococcal challenge is mediated by antibodies, immunizations were first performed using CFA/IFA as adjuvant in order to obtain very high levels of antibodies. Subsequently, experiments were also performed with Alum and IC31™ as adjuvants, as these adjuvants are suited for use in humans and would be a preferred choice for a vaccine to prevent group A streptococcal infections in humans. As can be seen for the experiment depicted in FIG. 1, fragment Spy0292-1 performed as well as full length Spy0292 protein for protection, while Spy0292-3 showed lower levels of protection. This clearly indicates that one region useful for protection lies within the sequence encompassing the Spy0292-1 protein.

Similar results were obtained for the proteins, Spy0269 (good protection also observed with Spy0269-1), Spy0416 (good protection also observed with Spy0416A-1, Spy0416A-6 and Spy0416A-7), and Spy0872 (good protection also observed with Spy0872-2).

For the proteins Spy0488, Spy0895, and Spy1727 full length recombinant proteins were used (Table 1), as these proteins have been shown for the first time to be capable to provide protection against lethal *S. pyogenes* challenge. Especially protein Spy0895 shows promise as a vaccine candidate, because it provided protection against group A streptococcal infection in all three models listed in Table 1.

Spy1536 and Spy1666 have been shown to provide protection in an intravenous challenge model before (WO 2004/078907), but importantly it could now be shown that they also provide protection in the physiologically more relevant intranasal challenge model. Spy1536 was most consistent in providing significant protection in all three models of GAS infection. Besides these two antigens, Spy0895 and Spy1536, several antigens showed protection in at least 2 models: Spy0269-1, Spy0292-1, Spy0416A-1, Spy0872-2, Spy1666 and Spy1727. Importantly, several antigens showed a level of protection that was as high as the level seen for the positive control protein M1 (e.g. Spy0416A-1, Spy0488, Spy0895; Table 1).

These data clearly provide evidence, that the selected proteins are promising candidates for vaccine development. In addition, proteins Spy0269, Spy0292, Spy0416, and Spy0872 have been shown to possess amino acid sequences that are dispensable for protection, since sub-fragments were capable to provide the same or even superior levels of protection than the full length recombinant protein.

TABLE 1

Recombinant proteins of *S. pyogenes* and fragments thereof assessed for protection in murine models of infection.

| ORF/Protein | Length[1] (aa) | Amino acids[1] (from-to) | SEQ ID No | Calculated MW (kDa)[2] | Vector | Base pairs[1] (from-to) | Protection[3] |
|---|---|---|---|---|---|---|---|
| Spy0269 | 837 | 36-873 | 57 | 92.34 | pET28b | 106-2619 | 10% (30%, 60%)[A] |
| Spy0269-1 | 452 | 37-488 | 1 | 50.85 | pET28b | 109-1464 | 50% (10%, 50%)[B,A,C] |
| Spy0292 | 388 | 23-410 | 68 | 44.91 | pET28b | 67-1233 | 60% (10%, 90%)[A,C] |
| Spy0292-1 | 162 | 23-184 | 2 | 19.41 | pET28b | 67-554 | 56% (10%, 90%)[A,B] |
| Spy0292-3 | 278 | 23-300 | 3 | 32.39 | pET28b | 67-900 | 30% (10%, 90%)[A] |
| Spy0416A | 834 | 34-867 | 89 | 95.80 | pET28b | 100-2601 | 20% (10%, 63%)[A] |
| Spy0416A-1 | 644 | 34-677 | 4 | 74.70 | pET28b | 100-2031 | 80% (20%, 80%)[C,A] |
| Spy0416A-6 | 311 | 148-458 | 5 | 38.77 | pET28b | 442-1374 | 40% (10%, 63%)[A] |
| Spy0416A-7 | 487 | 72-558 | 6 | 57.68 | pET28b | 214-1674 | 63% (10%, 63%)[A] |
| Spy0416B | 882 | 736-1617 | 56 | 103.08 | pET28b | 2206-4851 | 20% (10%, 63%)[A] |
| Spy0488 | 331 | 1-331 | 8 | 37.84 | pET28b | 1-993 | 90% (20%, 80)[C,A] |
| Spy0872 | 613 | 28-640 | 120 | 68.38 | pET28b | 82-1920 | 20% (0%, 60%)[A] |
| Spy0872-2 | 290 | 351-640 | 7 | 33.02 | pET28b | 1051-1920 | 60% (0%, 60%)[A,C,B] |
| Spy0895 | 261 | 2-262 | 9 | 32.15 | pET28b | 4-786 | 90% (20%, 80%)[C,A,B] |
| Spy1536 | 314 | 32-345 | 131 | 35.27 | pET28b | 94-1035 | 70% (20%, 80%)[C,A,B] |
| Spy1666 | 315 | 23-337 | 132 | 37.02 | pET28b | 67-1011 | 60% (20%, 80%)[C,B] |
| Spy1727 | 263 | 1-263 | 10 | 32.43 | pET28b | 1-789 | 70% (20%, 80%)[C,B] |

[1]Length, amino acids and base pairs are calculated for the *S. pyogenes* gene specific sequence only.

[2]The calculated molecular weight includes amino acids derived from the vector and the His6-tag.

[3]Protection is based on the animal model as indicated:

[A]s.c. immunization using CFA/IFA as adjuvant, i.n. challenge with *S. pyogenes* A20

[B]s.c. immunization using ALUM as adjuvant and i.n. challenge with *S. pyogenes* A20

[C]intranasal immunization using IC31 ™ or a mucosal adjuvant and intranasal challenge with either *S. pyogenes* A20 or A147.

Brackets show protection in the respective model with the negative (PBS + adjuvant only) and positive control (M protein). If protection was seen in more than one model, the protection data of the model listed first are shown.

TABLE 2

Oligonucleotides used for the cloning of genes encoding antigenic proteins and fragments thereof of *S. pyogenes*.

| ORF-protein | Plasmid name | Primer[1] | Name | Restriction enzyme |
|---|---|---|---|---|
| SPy0269 | pET28b-SPy0269 | TAGTAGCCATGGGC**GATGATAGAGCCTCA GGA** SEQ ID NO: 21 | 210-2129 | NcoI |
| | | TAGTAGGCGGCCGC**CTTAGATTCCTTACG GAACCT** SEQ ID NO: 22 | 210-2196 | NotI |

TABLE 2-continued

Oligonucleotides used for the cloning of genes encoding antigenic proteins and fragments thereof of *S. pyogenes*.

| ORF-protein | Plasmid name | Primer[1] | Name | Restriction enzyme |
|---|---|---|---|---|
| SPy0269-1 | pET28b-SPy0269-1 | TAGTAG<u>CCATGGG</u>CGATGATAGAGCCTCA GGA SEQ ID NO: 23 | 210-2129 | NcoI |
| | | TAGTAG<u>GCGGCCGC</u>AACAGGCGCATTAGG G SEQ ID NO: 24 | 210-2719 | NotI |
| SPy0292 | pET28b-SPy0292 | TAGTAG<u>CCATGGG</u>CGAAGAGTATTCGGTA ACTGC SEQ ID NO: 25 | 210-2131 | NcoI |
| | | TAGTAG<u>GCGGCCGC</u>TAAAGAGGTATTGAC ATACCT SEQ ID NO: 26 | 210-2197 | NotI |
| SPy0292-1 | pET28b-SPy0292-1 | TAGTAG<u>CCATGGG</u>CGAAGAGTATTCGGTA ACTGC SEQ ID NO: 27 | 210-2131 | NcoI |
| | | TAGTAG<u>GCGGCCGC</u>GCAAAAACAATTTTC ATCATC SEQ ID NO: 28 | 210-2954 | NotI |
| SPy0292-3 | pET28b-SPy0292-3 | TAGTAG<u>CCATGGG</u>CGAAGAGTATTCGGTA ACTGC SEQ ID NO: 29 | 210-2131 | NcoI |
| | | TAGTAG<u>GCGGCCGC</u>TTCAATTAACTGGAC TTTTTG SEQ ID NO: 30 | 210-2956 | NotI |
| SPy0416A | pET28b-SPy0416A | TAGTAG<u>GAATTC</u>GGCAGATGAGCTAAGCA CAATG SEQ ID NO: 31 | 210-2246 | EcoRI |
| | | TAGTAG<u>CTCGAG</u>CTCTGAACCAAGAGTGA CAAG SEQ ID NO: 32 | 210-2247 | XhoI |
| SPy0416A-1 | pET28b-SPy0416A-1 | TAGTAG<u>GAATTC</u>GGCAGATGAGCTAAGCA CAATG SEQ ID NO: 33 | 210-2246 | EcoRI |
| | | TAGTAG<u>CTCGAG</u>TGCCCCTTGCTGACGCG GTG SEQ ID NO: 34 | 210-2663 | XhoI |
| SPy0416A-6 | pET28b-SPy0416A-6 | TAGTAG<u>GAATTC</u>GGCAGTTATTGACACAGG G SEQ ID NO: 35 | 210-2715 | EcoRI |
| | | TAGTAG<u>CTCGAG</u>TAGGCTATCTTTTATGTC SEQ ID NO: 36 | 210-2717 | XhoI |
| SPy0416A-7 | pET28b-SPy0416A-7 | TAGTAG<u>GAATTC</u>GTCACAAATCACTCTCAA G SEQ ID NO: 37 | 210-2716 | EcoRI |
| | | TAGTAG<u>CTCGAG</u>ACTTCCTGTACCATTGCC SEQ ID NO: 38 | 210-2718 | XhoI |
| SPy0416B | pET28b-SPy0416B | TAGTAG<u>GAATTC</u>GCATGTAGACCCACAAA AGGGC SEQ ID NO: 39 | 210-2248 | EcoRI |
| | | TAGTAG<u>CTCGAG</u>CGTTGATGGTAGGGCTTT TGC SEQ ID NO: 40 | 210-2249 | XhoI |
| SPy0488 | pET28b-SPy0488 | TAGTAG<u>CCATGGG</u>CTTGCGGCAGATTCAG TCCATT SEQ ID NO: 41 | 210-2139 | NcoI |
| | | TAGTAG<u>GCGGCCGC</u>ACTTTTTAACCTGTCC TCAGC SEQ ID NO: 42 | 210-2199 | NotI |
| SPy0872 | pET28b-SPy0872 | TAGTAG<u>CCATGGG</u>CGATCAAGTTGATGTG CAATTC SEQ ID NO: 43 | 210-2143 | NcoI |
| | | TAGTAG<u>GCGGCCGC</u>TGTTATTGGAAGAGT GGAACT SEQ ID NO: 44 | 210-2144 | NotI |
| SPy0872-2 | pET28b-SPy0872-2 | TAGTAG<u>CCATGGG</u>CGCTATAATAAATCATG CT SEQ ID NO: 45 | 210-2962 | NcoI |
| | | TAGTAG<u>GCGGCCGC</u>TGTTATTGGAAGAGT GGAACT SEQ ID NO: 46 | 210-2144 | NotI |
| SPy0895 | pET28b-SPy0895 | TAGTAG<u>CCATGGG</u>CACTAATAATCAAACA CTA SEQ ID NO: 47 | 210-2145 | NcoI |
| | | TAGTAG<u>GCGGCCGC</u>GACAATAGATTGTCT CCAAAG SEQ ID NO: 48 | 210-2201 | NotI |
| SPy1536 | pET28b-SPy1536 | TAGTAG<u>CCATGGG</u>CATTGAAATGCCTGGA GGCG SEQ ID NO: 49 | 210-2161 | NcoI |
| | | TAGTAG<u>GCGGCCGC</u>TTTGCGAAGATAAAC CAGTGC SEQ ID NO: 50 | 210-2207 | NotI |
| SPy1666 | pET28b-SPy1666 | TAGTAG<u>CCATGGG</u>CACAAAAGAATTTCATC ACGTG SEQ ID NO: 51 | 210-2165 | NcoI |
| | | TAGTAG<u>GCGGCCGC</u>TTTCCGAATTTTTTTG GCAAC SEQ ID NO: 52 | 210-2209 | NotI |

TABLE 2-continued

Oligonucleotides used for the cloning of genes encoding antigenic proteins and fragments thereof of *S. pyogenes*.

| ORF-protein | Plasmid name | Primer[1] | Name | Restriction enzyme |
|---|---|---|---|---|
| SPy1727 | pET28b-SPy1727 | TAGTAGCCATGGGC**GTGACAACGACGGAAACAAG** SEQ ID NO: 53 | 210-2167 | NcoI |
| | | TAGTAGGCGGCCGC**TTTCTTTCTAAATATTTCTCT** SEQ ID NO: 54 | 210-2210 | NotI |

[1]Primer, letters in bold indicate gene-specific sequences, letters underlined indicate the restriction enzyme sites, letters in normal font indicate sequences necessary for cloning, but not present in the final plasmid construct used for expression. The first primer always refers to the sense and the second primer to the anti-sense oligonucleotide in relation to the encoded gene used for amplification.

Example 2

Group A Streptococcal Antigens And Variants Thereof

Experimental Procedures

Preparation of Streptococcal Genomic DNA 5 mL Todd-Hewitt Broth medium were inoculated with the respective strain of *S. pyogenes* (as listed in Table 3) from a frozen stab and grown without shaking at 37° C. overnight. 4 mL of the culture were then harvested by centrifuging at 13,000 rpm in a biofuge fresco (Haereus) for 5 min and the supernatant was removed. DNA was isolated from the bacterial cell pellets following the protocol of Wizard® Genomic DNA Purification Kit (Promega). The DNA pellets were finally dried on air and dissolved in 70 µl dd$H_2O$.

PCR and Sequence Analyses of S. pyogenes Genes

In order to determine the sequence of an antigen from diverse *S. pyogenes* strains, PCR was performed with primers specific for the gene of interest. *S. pyogenes* strains used for these analyses are shown in Table 3. Oligonucleotide sequences as primers for PCR were designed for the selected antigens in order to be able to amplify the full gene. Sequencing was performed with dedicated primers using the PCR products as templates. The sequences of the oligonucleotides are listed in Table 4. Genomic DNA of all *S. pyogenes* strains was prepared as described above. PCR was performed in a reaction volume of 25 µl using Taq polymerase (1 U), 200 nM dNTPs, 10 pMol of each oligonucleotide and the kit according to the manufacturer's instructions (Invitrogen, The Netherlands). As standard, 30 cycles (1×: 5 min. 95° C., 30×: 30 sec. 95° C., 30 sec. 56° C., 120 sec. 72° C., 1×4 min. 72° C.) were performed, unless conditions had to be adapted for individual primer pairs. PCR samples were sequenced with the oligonucleotides as listed in Table 10. Sequencing was performed at Agowa (Germany).

TABLE 3

*S. pyogenes* clinical isolates utilized for the present study.

| No. | Strain | Country of origin | Serotype |
|---|---|---|---|
| 1 | Schmitz 1/94 | Netherlands | 1 |
| 2 | Schmitz 1/12 | Portugal | 1 |
| 3 | Schmitz 1/5 | Portugal | 1 |
| 4 | Schmitz 2/14 | Germany | 1 |
| 5 | Schmitz 1/74 | England | 3 |
| 6 | Schmitz 1/35 | Spain | 3 |
| 7 | Schmitz 1/41 | France | 3 |
| 8 | RDN 78 | unknown | 3.1 |
| 9 | Schmitz 1/17 | Portugal | 4 |

TABLE 3-continued

*S. pyogenes* clinical isolates utilized for the present study.

| No. | Strain | Country of origin | Serotype |
|---|---|---|---|
| 10 | Schmitz 1/156 | Switzerland | 4 |
| 11 | Schmitz 1/22 | Spain | 4 |
| 12 | RDN 60 | unknown | 5 |
| 13 | Schmitz 1/174 | Austria | 6 |
| 14 | Schmitz 1/97 | Belgium | 6 |
| 15 | Schmitz 1/29 | Spain | 9 |
| 16 | Schmitz 1/92 | Netherlands | 11 |
| 17 | Schmitz 1/39 | Spain | 12 |
| 18 | Schmitz 1/248 | Poland | 12 |
| 19 | Schmitz 1/59 | England | 12 |
| 20 | RDN 02 | unknown | 19 |
| 21 | Schmitz 1/76 | England | 22 |
| 22 | Schmitz 1/177 | Austria | 22 |
| 23 | Schmitz 1/43 | France | 22 |
| 24 | Schmitz 2/32 | Germany | 22 |
| 25 | RDN 136 | unknown | 22.2 |
| 26 | Schmitz 1/136 | Germany | 25 |
| 27 | Schmitz 1/56 | France | 28 |
| 28 | Schmitz 1/108 | Belgium | 28 |
| 29 | Schmitz 1/85 | Netherlands | 28 |
| 30 | Schmitz 2/50 | Germany | 28 |
| 31 | Schmitz 1/194 | Italy | 44 |
| 32 | Schmitz 1/234 | Turkey | 44 |
| 33 | Schmitz 1/103 | Belgium | 44 |
| 34 | Schmitz 1/253 | Poland | 49 |
| 35 | Schmitz 1/141 | Germany | 49 |
| 36 | Schmitz 1/123 | Germany | 49 |
| 37 | Schmitz 2/30 | Germany | 66 or 90 |
| 38 | Schmitz 1/144 | Germany | 76 |
| 39 | Schmitz 1/99 | Belgium | 78 |
| 40 | RDN 120 | unknown | 81 |
| 41 | Schmitz 1/142 | Germany | 83 |
| 42 | Schmitz 1/176 | Austria | 83 |
| 43 | Schmitz 1/25 | Spain | 83 |
| 44 | RDN 75 | unknown | 85 |
| 45 | Schmitz 2/46 | Germany | 89 |
| 46 | Schmitz 2/9 | Germany | 90 |
| 47 | Schmitz 2/23 | Germany | 90 |
| 48 | RDN 116 | unknown | 94 |
| 49 | Schmitz 1/55 | France | 118 |
| 50 | Schmitz 1/68 | England | 118 |
| 51 | Schmitz 1/3 | Portugal | 118 |

TABLE 4

Oligonucleotides used for sequence conservation analyses.

| ORF | Primer name | Orientation | Sequence | SEQ ID NO: | Position relative to gene |
|---|---|---|---|---|---|
| Spy0269 | 210-4752 | sense | TGACCTTCAAA*TCATTGCTGA* | 209 | -103 to -82 |
| | 210-4759 | antisense | TTTTGCACTTCTGGTGTCAA | 210 | 1014 to 1034 |
| | 210-4754 | sense | TTGCCAAAGCTA*GTCCAGGT* | 211 | 931 to 951 |
| | 210-4761 | antisense | AGTATTATCAATGCGCTCACG | 212 | 2028 to 2049 |
| | 210-4756 | sense | AAAAGCTCATTTGCAATATCTAAGG | 213 | 1967 to 1992 |
| | 210-4763 | antisense | GCTGGTGAATCTGATTTTTCAA | 214 | 2875 to 2897 |
| Spy0292 | 210-4575 | sense | TCTTGTGAGGTAAGTCATTACCTTAG | 215 | -79 to -53 |
| | 210-4576 | antisense | TTCATCATCTGGTTCTGTATTAGG | 216 | 516 to 540 |
| | 210-4577 | sense | GGTCGTCAATTCAACTGGC | 217 | 464 to 483 |
| | 210-4578 | antisense | GCGATCATTGTGGATGATTTC | 218 | 1031 to 1052 |
| | 210-4579 | sense | AAACTGTCAAACTTGTAGCCC | 219 | 946 to 967 |
| | 210-4580 | antisense | TGTTAGGATTGGCCTAGTTTG | 220 | 1304 to 1325 |
| Spy0416 | 210-4588 | sense | TGAGTTAATGATTAACATTAAACTGGT | 221 | -56 to -29 |
| | 210-4591 | antisense | TGACATAAGCAAATTGATGCG | 222 | 1387 to 1408 |
| | 210-4592 | sense | CCATCTATTCAGAGTCTGTCGAC | 223 | 1327 to 1350 |
| | 210-4595 | antisense | CCTTGTCACTAGCATGGTAGAC | 224 | 2802 to 2824 |
| | 210-4596 | sense | TTGCAGCCTTCAAAGGTG | 225 | 2749 to 2767 |
| | 210-4599 | antisense | AAGACACATTACCAGCTCTATCTTC | 226 | 4128 to 4153 |
| | 210-4600 | sense | CAGATGGTTCTTACACCATTTC | 227 | 4063 to 4085 |
| | 210-4603 | antisense | AATCTCAAAGAAAGGTCAGACTG | 228 | 4982 to 5005 |
| Spy0488 | 210-5497 | sense | AAAGCTCGTCATTTTATATGATTT | 229 | -195 to -171 |
| | 210-4767 | antisense | *TTTAATGAGAGTTGTCATTCGTTCA* | 230 | 497 to 522 |
| | 210-4765 | sense | TTTTCTTGTTCAACCGCAAG | 231 | 404 to 424 |
| | 210-4766 | antisense | GCG*CTCACAGCTACTTCAGA* | 232 | 1052 to 1072 |
| Spy0872 | 210-4581 | sense | CAAAATCATAGTAAACTTGATCTATAACG | 233 | -55 to -26 |
| | 210-4584 | antisense | GAAGAATTAGTTGCAGTTCCG | 234 | 1103 to 1124 |
| | 210-4585 | sense | GTTGCTGTAGCACCAGGTATC | 235 | 1005 to 1026 |
| | 210-4587 | antisense | CCAGCACGAATTAGATCATCTAG | 236 | 2111 to 2134 |
| Spy0985 | 210-4768 | sense | CTGAAGAGCGCCAAACAACT | 237 | -63 to -43 |
| | 210-4771 | antisense | TCGAAGAAGTAACCTTTGATTAATGT | 238 | 864 to 890 |
| Spy1536 | 210-4772 | sense | GCTCTAGTCGTGTGAGAGAGCTAA | 239 | -90 to -66 |
| | 210-4775 | antisense | TGTCTATCTGGTTCAACCGTTTT | 240 | 1089 to 1112 |
| Spy1666 | 210-4780 | sense | GTGGCTAAGTCAGTGCTTGCT | 241 | -80 to-59 |
| | 210-4783 | antisense | AAGTTTTTATTCGTTTTTGCAAGG | 242 | 1055 to 1079 |
| Spy1727 | 210-4776 | sense | GATCATTGACTAAGTAGCCTAAAACAA | 243 | -76 to -49 |
| | 210-4779 | antisense | CCAAAAACGTCATGCCAAC | 244 | 879 to 898 |

Shown are the ORF and primer names, orientation of the primer relative to the gene, the sequence, and the position relative to the gene. Oligonucleotides were used for both PCR amplification of the gene or gene fragment and subsequent sequence analyses.

Results

Gene Conservation Analysis of Selected Streptococcal Antigens

The PCR and sequencing of the 9 selected genes was performed as described under Methods. Table 3 shows the strains used for sequencing, while Table 4 lists the oligonucleotides employed for the PCR and sequencing analyses.

Sequence Analyses of Spy0269

Sequences were obtained from all 51 strains. The level of amino acid sequence identity ranged from 98.7% to 100% as compared to the sequence of Spy0269 from *S. pyogenes* SF370. Table 5 lists all 36 amino acid positions which showed a distinct amino acid as compared to Spy0269 from *S. pyogenes* SF370.

TABLE 5

Gene conservation of Spy0269.

| Position in SF370 gene | Alignment position | Amino acid in SF370 gene | AA change[1] | AA change[2] | Strains with the respective change[1] | Strains with the respective change[2] |
|---|---|---|---|---|---|---|
| 30 | 30 | V | I | | Schm1_142, Schm1_177, Schm1_43, RDN75 | |
| 68 | 68 | D | E | | Schm1_76, Schm1_92, Schm1_142, | |

TABLE 5-continued

| Gene conservation of Spy0269. | | | | | | |
|---|---|---|---|---|---|---|
| Position in SF370 gene | Alignment position | Amino acid in SF370 gene | AA change[1] | AA change[2] | Strains with the respective change[1] | Strains with the respective change[2] |
| | | | | | Schm1_176, Schm1_177, Schm1_25, Schm1_43, Schm2_32, RDN136, RDN75 | |
| 73 | 73 | T | A | | Schm1_142, Schm1_177, Schm1_43 | |
| 80 | 80 | E | K | | Schm1_55, Schm1_68, Schm1_3, Schm2_23, Schm2_30 | |
| 83 | 83 | E | K | | Schm1_17, Schm1_59, Schm1_97 | |
| 94 | 94 | E | K | | Schm1_142, Schm1_177, Schm1_43 | |
| 97 | 97 | H | N | | Schm1_99, Schm2_14, Schm2_46 | |
| 150 | 150 | A | V | | Schm1_74, Schm1_35, Schm1_141, Schm1_174, Schm1_41, Schm2_9, Schm2_50, RDN60, RDN78, RDN75 | |
| 230 | 230 | A | G | | Schm1_35 | |
| 249 | 249 | E | D | | Schm1_103 | |
| 276 | 276 | A | V | | Schm1_56, Schm1_108 | |
| 279 | 279 | G | D | | Schm1_55, Schm1_68, Schm1_3, Schm2_23, Schm2_30 | |
| 307 | 307 | A | G | | Schm1_92 | |
| 482 | 482 | H | R | | Schm1_17, Schm1_56, Schm1_76, Schm1_92, Schm1_142, Schm1_253, Schm1_108, Schm1_141, Schm1_174, Schm1_176, Schm1_177, Schm1_25, Schm1_43, Schm1_59, Schm1_97, Schm1_99, Schm1_123, Schm1_136, Schm2_14, Schm2_32, Schm2_46, Schm2_50, RDN60, RDN02, RDN136, RDN120, RDN116 | |
| 485 | 485 | N | K | | Schm1_39, Schm1_55, Schm1_68, Schm1_156, Schm1_248, | |

TABLE 5-continued

| Gene conservation of Spy0269. | | | | | | |
|---|---|---|---|---|---|---|
| Position in SF370 gene | Alignment position | Amino acid in SF370 gene | AA change[1] | AA change[2] | Strains with the respective change[1] | Strains with the respective change[2] |
| | | | | | Schm1_3, Schm1_22, Schm1_29, Schm2_23, Schm2_30, RDN75 | |
| 537 | 537 | G | S | | Schm1_76, Schm1_92, Schm1_142, Schm1_176, Schm1_177, Schm1_25, Schm1_43, Schm2_32, RDN136 | |
| 577 | 577 | Q | E | | Schm1_39, Schm1_76, Schm1_92, Schm1_142, Schm1_141, Schm1_156, Schm1_174, Schm1_176, Schm1_177, Schm1_248, Schm1_22, Schm1_25, Schm1_29, Schm1_43, Schm2_32, Schm2_50, RDN60, RDN136 | |
| 602 | 602 | G | R | | Schm2_46 | |
| 605 | 605 | R | K | | Schm1_174 | |
| 610 | 610 | A | V | | Schm1_74, Schm1_76, Schm1_35, Schm1_176, Schm1_25, Schm1_41, Schm2_9, Schm2_32, RDN136, RDN78 | |
| 636 | 636 | L | M | | Schm1_74, Schm1_76, Schm1_35, Schm1_176, Schm1_25, Schm1_41, Schm2_9, Schm2_32, RDN136, RDN78 | |
| 640 | 640 | E | K | | Schm1_74, Schm1_76, Schm1_35, Schm1_176, Schm1_25, Schm1_41, Schm2_9, Schm2_32, RDN136, RDN78 | |
| 641 | 641 | A | V | | Schm1_56, Schm1_108 | |
| 650 | 650 | V | E | | Schm2_9 | |
| 666 | 666 | F | L | | Schm1_22 | |
| 700 | 700 | A | T | | Schm1_17, Schm1_39, | |

TABLE 5-continued

| Gene conservation of Spy0269. | | | | | | |
|---|---|---|---|---|---|---|
| Position in SF370 gene | Alignment position | Amino acid in SF370 gene | AA change[1] | AA change[2] | Strains with the respective change[1] | Strains with the respective change[2] |
| | | | | | Schm1_55, Schm1_56, Schm1_253, Schm1_68, Schm1_108, Schm1_156, Schm1_248, Schm1_3, Schm1_22, Schm1_29, Schm1_59, Schm1_97, Schm1_123, Schm1_136, Schm2_23, Schm2_30, RDN02, RDN120, RDN116 | |
| 703 | 703 | A | V | | Schm2_50, RDN60 | |
| 710 | 710 | S | G | | Schm1_17, Schm1_59, Schm1_97 | |
| 733 | 733 | E | G | | Schm1_56, Schm1_108 | |
| 750 | 750 | A | P | | Schm1_22 | |
| 752 | 752 | P | S | | Schm1_55, Schm1_74, Schm1_76, Schm1_92, Schm1_142, Schm1_144, Schm1_194, Schm1_35, Schm1_68, Schm1_176, Schm1_177, Schm1_234, Schm1_3, Schm1_25, Schm1_41, Schm1_43, Schm1_99, Schm1_103, Schm2_9, Schm2_14, Schm2_23, Schm2_30, Schm2_32, Schm2_46, RDN136, RDN78 | |
| 758 | 758 | P | L | | Schm1_92 | |
| 764 | 764 | I | V | | Schm1_74, Schm1_76, Schm1_92, Schm1_142, Schm1_144, Schm1_194, Schm1_35, Schm1_176, Schm1_177, Schm1_234, Schm1_25, Schm1_41, Schm1_43, Schm1_99, Schm1_103, Schm2_9, | |

TABLE 5-continued

| Gene conservation of Spy0269. | | | | | | |
|---|---|---|---|---|---|---|
| Position in SF370 gene | Alignment position | Amino acid in SF370 gene | AA change[1] | AA change[2] | Strains with the respective change[1] | Strains with the respective change[2] |
| | | | | | Schm2__14, Schm2__32, Schm2__46, RDN136, RDN78 | |
| 765 | 765 | D | E | | Schm1__74, Schm1__76, Schm1__92, Schm1__142, Schm1__144, Schm1__194, Schm1__35, Schm1__176, Schm1__177, Schm1__234, Schm1__25, Schm1__41, Schm1__43, Schm1__99, Schm1__103, Schm2__9, Schm2__14, Schm2__32, Schm2__46, RDN136, RDN78 | |
| 794 | 794 | L | F | H | Schm1__22 | Schm2__23, Schm2__30 |
| 873 | 873 | K | R | | Schm1__55, Schm1__74, Schm1__76, Schm1__92, Schm1__142, Schm1__144, Schm1__194, Schm1__35, Schm1__68, Schm1__141, Schm1__174, Schm1__176, Schm1__177, Schm1__234, Schm1__3, Schm1__25, Schm1__41, Schm1__43, Schm1__99, Schm1__103, Schm2__9, Schm2__14, Schm2__23, Schm2__30, Schm2__32, Schm2__46, Schm2__50, RDN60, RDN136, RDN78, RDN75 | |

[1]observed amino acid at respective position in any of the sequenced genes of the respective *S. pyogenes* strains.

Sequence Analyses of Spy0292

Sequences were obtained from all 51 strains. The level of amino acid sequence identity ranged from 97.3% to 100% as compared to the sequence of Spy0292 from *S. pyogenes* SF370. Table 6 lists all 36 amino acid positions which showed a distinct amino acid as compared to Spy0292 from *S. pyogenes* SF370.

TABLE 6

Gene conservation of Spy0292.

| Position in SF370 gene | Alignment position | Amino acid in SF370 gene | AA change[1] | AA change[2] | AA change[3] | Strains with respective change[1] | Strains with respective change[2] | Strains with respective change[3] |
|---|---|---|---|---|---|---|---|---|
| 21 | 21 | S | N | | | Schm1_136 | | |
| 32 | 32 | A | V | | | RDN02 | | |
| 45 | 45 | E | K | | | RDN60 | | |
| 48 | 48 | A | T | | | Schm1_56, Schm1_108, Schm1_85 | | |
| 50 | 50 | E | K | | | RDN75 | | |
| 57 | 57 | V | I | | | Schm2_50 | | |
| 58 | 58 | S | T | | | Schm2_50 | | |
| 65 | 65 | L | M | | | Schm1_141, Schm1_156, Schm1_174 | | |
| 68 | 68 | K | Q | N | | Schm2_30 | Schm2_50 | |
| 88 | 88 | Y | D | | | Schm2_30 | | |
| 89 | 89 | E | D | | | Schm2_30 | | |
| 93 | 93 | N | Y | | | Schm2_50 | | |
| 95 | 95 | T | S | | | Schm2_30 | | |
| 96 | 96 | I | M | | | Schm2_30 | | |
| 101 | 101 | L | P | | | Schm2_30 | | |
| 121 | 121 | N | I | | | Schm2_50 | | |
| 122 | 122 | S | T | | | Schm2_50 | | |
| 128 | 128 | A | P | S | | RDN60 | RDN60 | |
| 137 | 137 | K | N | | | Schm2_30 | | |
| 141 | 141 | K | E | Q | | Schm1_17 | Schm2_50 | |
| 147 | 147 | R | L | W | I | Schm1_17 | Schm2_50 | RDN60 |
| 148 | 148 | Q | L | | | Schm2_30, RDN60 | | |
| 152 | 152 | S | F | | | RDN120 | | |
| 154 | 154 | A | T | | | Schm1_55, Schm1_68, Schm1_3, Schm1_29, Schm2_23, Schm2_30 | | |
| 165 | 165 | H | L | | | RDN60 | | |
| 188 | 188 | L | F | | | Schm1_174 | | |
| 189 | 189 | A | P | | | Schm1_174 | | |
| 190 | 190 | I | V | | | Schm1_253, Schm1_123 | | |
| 214 | 214 | A | D | | | Schm1_39, Schm1_55, Schm1_56, Schm1_76, Schm1_92, Schm1_142, Schm1_144, Schm1_108, Schm1_141, Schm1_156, Schm1_174, Schm1_176, Schm1_177, Schm1_234, Schm1_248, Schm1_25, Schm1_43, Schm1_59, Schm1_85, Schm1_99, Schm1_103, Schm2_32, Schm2_46, Schm2_50, RDN60, RDN02, RDN136, RDN120 | | |
| 240 | 240 | V | I | | | Schm1_92, RDN120 | | |
| 266 | 266 | L | I | | | Schm1_144, Schm1_234, Schm1_103 | | |

TABLE 6-continued

Gene conservation of Spy0292.

| Position in SF370 gene | Alignment position | Amino acid in SF370 gene | AA change[1] | AA change[2] | AA change[3] | Strains with respective change[1] | Strains with respective change[2] | Strains with respective change[3] |
|---|---|---|---|---|---|---|---|---|
| 309 | 309 | Y | S | | | Schm1_17, Schm1_39, Schm1_55, Schm1_56, Schm1_74, Schm1_76, Schm1_92, Schm1_142, Schm1_144, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_136, Schm2_9, Schm2_23, Schm2_30, Schm2_32, Schm2_46, Schm2_50, RDN60, RDN02, RDN136, RDN78, RDN120, RDN75, RDN116 | | |
| 314 | 314 | P | S | | | Schm1_17, Schm1_22, Schm1_97 | | |
| 351 | 351 | A | P | | | Schm1_177 | | |
| 371 | 371 | G | A | | | Schm1_234 | | |
| 386 | 386 | Q | H | | | Schm1_234 | | |

[1]observed amino acid at respective position in any of the sequenced genes of the respective *S. pyogenes* strains.
[2]second possible amino acid observed at the respective position.
[3]third possible amino acid observed at the respective position.

Sequence Analyses of Spy0416

Sequences were obtained from all 50 strains excluding strain Schmitz 1/74. The level of amino acid sequence identity ranged from 98.1% to 100% as compared to the sequence of Spy0416 from *S. pyogenes* SF370. Table 7 lists all 103 amino acid positions which showed a distinct amino acid as compared to Spy0416 from *S. pyogenes* SF370. The gene showed in addition an insertion of 2 amino acids after position 31, as well as several deletions of amino acids at the indicated positions (e.g. strains Schmitz 1/17 and Schmitz 1/39).

TABLE 7

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| 21 | 21 | I | V | | Schm1__99, Schm2__46 | |
| 27 | 27 | V | M | | Schm1__17, Schm1__39, Schm1__55, Schm1__56, Schm1__76, Schm1__142, Schm1__253, Schm1__35, Schm1__68, Schm1__108, Schm1__141, Schm1__156, Schm1__174, Schm1__176, Schm1__177, Schm1__248, Schm1__3, Schm1__22, Schm1__25, Schm1__29, Schm1__41, Schm1__43, Schm1__59, Schm1__85, Schm1__97, Schm1__99, Schm1__123, Schm1__136, Schm2__9, Schm2__14, Schm2__23, Schm2__30, Schm2__32, Schm2__46, Schm2__50, RDN60, RDN136, RDN78, RDN120, RDN75, RDN116 | |
| 29 | 29 | T | M | | Schm1__17, Schm1__39, Schm1__76, Schm1__142, Schm1__35, Schm1__141, Schm1__156, Schm1__174, Schm1__176, Schm1__177, Schm1__248, Schm1__22, Schm1__25, Schm1__41, Schm1__43, Schm1__59, Schm1__97, Schm1__136, Schm2__9, Schm2__14, RDN136, RDN78, RDN75 | |
| Insertion | 32 | — | T | | Schm1__17, Schm1__39, Schm1__76, Schm1__142, Schm1__35, Schm1__141, Schm1__156, Schm1__174, | |

TABLE 7-continued

Gene conservation of Spy0416.

| Position in SF370 gene | Alignment position | Amino acid in SF370 gene | AA change[1] | AA change[2] | Strains with respective change[1] | Strains with respective change[2] |
|---|---|---|---|---|---|---|
| | | | | | Schm1_176, Schm1_177, Schm1_248, Schm1_22, Schm1_25, Schm1_41, Schm1_43, Schm1_59, Schm1_97, Schm1_136, Schm2_9, Schm2_14, RDN136, RDN78 | |
| Insertion | 33 | — | T | | Schm1_17, Schm1_22, Schm1_97 | |
| 38 | 40 | S | T | | Schm1_17, Schm1_39, Schm1_55, Schm1_56, Schm1_76, Schm1_142, Schm1_253, Schm1_35, Schm1_68, Schm1_108, Schm1_141, Schm1_156, Schm1_174, Schm1_176, Schm1_177, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_14, Schm2_23, Schm2_30, Schm2_32, Schm2_46, Schm2_50, RDN136, RDN78, RDN116 | |
| 40 | 42 | M | T | | Schm1_17, Schm1_39, Schm1_55, Schm1_56, Schm1_76, Schm1_142, Schm1_253, Schm1_35, Schm1_68, Schm1_108, Schm1_141, Schm1_156, Schm1_174, Schm1_176, Schm1_177, Schm1_248, Schm1_3, | |

TABLE 7-continued

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__14, Schm2__23, Schm2__30, Schm2__32, Schm2__46, Schm2__50, RDN136, RDN78, RDN116 | |
| 49 | 51 | A | T | | Schm1__39, Schm1__76, Schm1__142, Schm1__35, Schm1__176, Schm1__177, Schm1__248, Schm1__25, Schm1__41, Schm1__43, Schm1__59, Schm2__9, Schm2__14, Schm2__32, RDN60, RDN136, RDN78 | |
| 54 | 56 | Q | P | | Schm1__55, Schm1__68, Schm1__3, Schm1__29, Schm2__23, Schm2__30 | |
| 55 | 57 | H | P | | Schm1__55, Schm1__253, Schm1__68, Schm1__3, Schm1__29, Schm1__99, Schm1__123, Schm2__23, Schm2__30, Schm2__32, Schm2__46, RDN116 | |
| 67 | 69 | K | Q | | Schm1__17, Schm1__55, Schm1__56, Schm1__253, Schm1__68, Schm1__108, Schm1__3, Schm1__22, Schm1__29, Schm1__85, Schm1__97, Schm1__99, Schm1__123, Schm1__136, Schm2__23, Schm2__30, | |

TABLE 7-continued

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm2__32, Schm2__46, Schm2__50, RDN120, RDN116 | |
| 68 | 70 | S | P | T | Schm1__39, Schm1__55, Schm1__76, Schm1__142, Schm1__35, Schm1__68, Schm1__141, Schm1__156, Schm1__174, Schm1__176, Schm1__177, Schm1__248, Schm1__3, Schm1__25, Schm1__29, Schm1__41, Schm1__43, Schm1__59, Schm2__9, Schm2__14, Schm2__23, Schm2__30, RDN136, RDN78, RDN75 | Schm1__92 |
| 69 | 71 | Q | P | | Schm1__17, Schm1__56, Schm1__253, Schm1__108, Schm1__22, Schm1__85, Schm1__97, Schm1__99, Schm1__123, Schm1__136, Schm2__32, Schm2__46, Schm2__50, RDN120, RDN116 | |
| 71 | 73 | T | I | | Schm1__253, Schm1__123, Schm2__32 | |
| 74 | 76 | I | V | | Schm1__55, Schm1__253, Schm1__68, Schm1__3, Schm1__29, Schm1__99, Schm1__123, Schm1__136, Schm2__23, Schm2__30, Schm2__46 | |
| 76 | 78 | L | P | | Schm1__17, Schm1__55, Schm1__56, Schm1__92, Schm1__144, Schm1__194, Schm1__253, Schm1__68, Schm1__108, Schm1__141, Schm1__156, Schm1__174, Schm1__234, Schm1__3, Schm1__22, | |

TABLE 7-continued

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1_29, Schm1_85, Schm1_97, Schm1_99, Schm1_123, Schm1_136, Schm2_23, Schm2_30, Schm2_46, Schm2_50, RDN60, RDN02, RDN116 | |
| 77 | 79 | K | E | | Schm1_55, Schm1_253, Schm1_68, Schm1_3, Schm1_29, Schm1_99, Schm1_123, Schm1_136, Schm2_23, Schm2_30, Schm2_46 | |
| 78 | 80 | T | I | | Schm1_56, Schm1_108, Schm1_85, Schm2_50 | |
| 85 | 87 | S | P | | Schm1_17, Schm1_39, Schm1_55, Schm1_56, Schm1_76, Schm1_92, Schm1_142, Schm1_253, Schm1_35, Schm1_68, Schm1_108, Schm1_176, Schm1_177, Schm1_248, Schm1_3, Schm1_22, Schm1_25, Schm1_29, Schm1_41, Schm1_43, Schm1_59, Schm1_85, Schm1_97, Schm1_103, Schm1_123, Schm1_136, Schm2_9, Schm2_14, Schm2_23, Schm2_30, Schm2_50, RDN60, RDN136, RDN78 | |
| 87 | 89 | D | G | | Schm1_17, Schm1_39, Schm1_55, Schm1_56, Schm1_76, Schm1_92, Schm1_142, Schm1_253, Schm1_35, Schm1_68, Schm1_108, | |

TABLE 7-continued

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1_176, Schm1_177, Schm1_248, Schm1_3, Schm1_22, Schm1_25, Schm1_29, Schm1_41, Schm1_43, Schm1_59, Schm1_85, Schm1_97, Schm1_103, Schm1_123, Schm1_136, Schm2_9, Schm2_14, Schm2_23, Schm2_30, Schm2_50, RDN60, RDN136, RDN78 | |
| 91 | 93 | E | K | | Schm1_99, Schm2_46, RDN116 | |
| 93 | 95 | T | Deletion | | RDN60 | |
| 102 | 104 | A | S | | RDN120, RDN75, RDN116 | |
| 104 | 106 | S | P | | Schm1_39, Schm1_55, Schm1_56, Schm1_76, Schm1_142, Schm1_253, Schm1_35, Schm1_68, Schm1_108, Schm1_176, Schm1_177, Schm1_248, Schm1_3, Schm1_25, Schm1_29, Schm1_41, Schm1_43, Schm1_59, Schm1_85, Schm1_99, Schm1_123, Schm1_136, Schm2_9, Schm2_14, Schm2_23, Schm2_30, Schm2_32, Schm2_46, Schm2_50, RDN60, RDN136, RDN78, RDN120, RDN75, RDN116 | |
| 107 | 109 | N | Deletion | | Schm1_92 | |
| 110 | 112 | S | P | | Schm1_17, Schm1_39, Schm1_56, Schm1_76, Schm1_92, Schm1_142, Schm1_253, | |

TABLE 7-continued

Gene conservation of Spy0416.

| Position in SF370 gene | Alignment position | Amino acid in SF370 gene | AA change[1] | AA change[2] | Strains with respective change[1] | Strains with respective change[2] |
|---|---|---|---|---|---|---|
| | | | | | Schm1_35, Schm1_108, Schm1_141, Schm1_156, Schm1_174, Schm1_176, Schm1_177, Schm1_248, Schm1_22, Schm1_25, Schm1_41, Schm1_43, Schm1_59, Schm1_85, Schm1_97, Schm1_99, Schm1_103, Schm1_123, Schm1_136, Schm2_9, Schm2_14, Schm2_32, Schm2_46, Schm2_50, RDN60, RDN136, RDN78, RDN120, RDN75, RDN116 | |
| 183 | 185 | A | V | | RDN75 | |
| 215 | 217 | E | G | | Schm1_17, Schm1_92, Schm1_22, Schm1_97, Schm1_99, Schm2_46, RDN116 | |
| 228 | 230 | A | Deletion | | Schm1_17, Schm1_56, Schm1_92, Schm1_108, Schm1_22, Schm1_85, Schm1_97, Schm2_50, RDN120 | |
| 229 | 231 | E | Deletion | D | Schm1_17, Schm1_56, Schm1_92, Schm1_108, Schm1_22, Schm1_85, Schm1_97, Schm2_50, RDN120, RDN116 | Schm1_144, Schm1_194, Schm1_253, Schm1_234, Schm1_99, Schm1_123, Schm1_136, Schm2_46, RDN02 |
| 230 | 232 | A | Deletion | | RDN116 | |
| 238 | 240 | H | N | | Schm1_17, Schm1_92, Schm1_22, Schm1_97 | |
| 273 | 275 | D | E | | Schm1_92, Schm1_99, Schm2_46, RDN120, RDN116 | |
| 308 | 310 | A | T | | Schm1_56, Schm1_108, Schm1_85, Schm2_50 | |
| 320 | 322 | I | V | | Schm1_17, Schm1_39, | |

TABLE 7-continued

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1_55, Schm1_56, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_14, Schm2_23, Schm2_30, Schm2_32, Schm2_46, Schm2_50, RDN02, RDN136, RDN78, RDN120, RDN75, RDN116 | |
| 428 | 430 | T | A | | Schm1_142 | |
| 429 | 431 | V | A | | Schm1_17, Schm1_22, Schm1_97 | |
| 431 | 433 | E | G | | Schm1_253, Schm1_123 | |
| 434 | 436 | N | S | | RDN116 | |
| 449 | 451 | V | F | | Schm1_177 | |
| 453 | 455 | D | N | | Schm1_142, Schm1_35, Schm1_141, Schm1_174, Schm1_176, Schm1_177, Schm1_248, Schm1_25, Schm1_41, Schm1_43, Schm1_59, Schm1_97, Schm1_123, Schm1_136, Schm2_9, RDN136 | |
| 463 | 465 | S | T | | Schm1_177, RDN136 | |
| 478 | 480 | N | K | | Schm1_17, Schm1_76, Schm1_92, | |

TABLE 7-continued

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1__142, Schm1__144, Schm1__194, Schm1__176, Schm1__177, Schm1__234, Schm1__22, Schm1__25, Schm1__43, Schm1__97, RDN60, RDN02, RDN136, RDN120, RDN116 | |
| 481 | 483 | D | N | | Schm1__55, Schm1__68, Schm1__3, Schm1__29, Schm1__136, Schm2__23, Schm2__30 | |
| 484 | 486 | G | D | | Schm1__17, Schm1__92, Schm1__144, Schm1__194, Schm1__234, Schm1__22, Schm1__97, RDN02 | |
| 493 | 495 | P | L | | RDN120 | |
| 512 | 514 | V | L | | Schm1__253, Schm1__123 | |
| 519 | 521 | P | S | | Schm1__253, Schm1__123 | |
| 530 | 532 | A | S | | Schm1__141, Schm1__156, Schm1__174 | |
| 535 | 537 | I | V | | RDN120 | |
| 547 | 549 | A | V | | Schm1__35, Schm1__41, Schm2__9 | |
| 553 | 555 | G | T | | RDN116 | |
| 560 | 562 | E | V | | RDN02, RDN116 | |
| 630 | 632 | V | I | | RDN75 | |
| 668 | 670 | T | M | | RDN116 | |
| 689 | 691 | G | D | | Schm1__39, Schm1__248, Schm1__59, Schm2__14 | |
| 706 | 708 | I | V | | RDN02 | |
| 723 | 725 | D | A | | Schm1__39, Schm1__55, Schm1__56, Schm1__92, Schm1__144, Schm1__194, Schm1__253, Schm1__35, Schm1__68, Schm1__108, Schm1__141, Schm1__156, Schm1__174, Schm1__234, Schm1__248, Schm1__3, Schm1__29, Schm1__41, Schm1__59, Schm1__85, Schm1__103, | |

TABLE 7-continued

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1_123, Schm1_136, Schm2_9, Schm2_23, Schm2_30, Schm2_50, RDN60, RDN02, RDN78, RDN120, RDN116 | |
| 734 | 736 | T | A | | RDN02 | |
| 743 | 745 | R | H | | RDN116 | |
| 749 | 751 | H | R | | Schm1_17, Schm1_39, Schm1_55, Schm1_56, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_14, Schm2_23, Schm2_30, Schm2_32, Schm2_46, RDN60, RDN02, RDN136, RDN78, RDN120, RDN75, RDN116 | |
| 770 | 772 | R | K | | RDN60, RDN120 | |
| 804 | 806 | D | A | | Schm1_55, Schm1_68, Schm1_248, Schm1_3, Schm1_29, Schm2_23, Schm2_30, RDN02, RDN120, RDN75 | |
| 874 | 876 | T | M | | Schm1_35, Schm1_41, | |

TABLE 7-continued

Gene conservation of Spy0416.

| Position in SF370 gene | Alignment position | Amino acid in SF370 gene | AA change[1] | AA change[2] | Strains with respective change[1] | Strains with respective change[2] |
|---|---|---|---|---|---|---|
| | | | | | Schm1_103, Schm1_136, Schm2_9, RDN78 | |
| 876 | 878 | S | C | | Schm1_94 | |
| 913 | 915 | N | S | | RDN60 | |
| 951 | 953 | P | S | | Schm1_76, Schm1_177, Schm1_43 | |
| 991 | 993 | H | Y | | Schm1_17, Schm1_39, Schm1_55, Schm1_56, Schm1_142, Schm1_144, Schm1_194, Schm1_35, Schm1_68, Schm1_108, Schm1_141, Schm1_156, Schm1_174, Schm1_176, Schm1_234, Schm1_248, Schm1_3, Schm1_22, Schm1_25, Schm1_29, Schm1_41, Schm1_59, Schm1_85, Schm1_97, Schm1_99, Schm1_136, Schm2_9, Schm2_14, Schm2_23, Schm2_30, Schm2_46, Schm2_50, RDN60, RDN02, RDN78, RDN120, RDN116 | |
| 1053 | 1055 | V | A | | Schm1_94, Schm1_12X, Schm1_5 | |
| 1078 | 1080 | E | A | | Schm1_92, Schm1_142, Schm1_176, Schm1_25, Schm1_99, Schm2_23, Schm2_30, Schm2_46 | |
| 1080 | 1082 | N | S | | Schm1_35, Schm1_41, Schm2_9, RDN78 | |
| 1227 | 1229 | T | I | | Schm1_76 | |
| 1238 | 1240 | V | A | | Schm1_17, Schm1_39, Schm1_55, Schm1_56, Schm1_76, Schm1_92, Schm1_142, Schm1_144, Schm1_194, Schm1_253, Schm1_35, | |

TABLE 7-continued

Gene conservation of Spy0416.

| Position in SF370 gene | Alignment position | Amino acid in SF370 gene | AA change[1] | AA change[2] | Strains with respective change[1] | Strains with respective change[2] |
|---|---|---|---|---|---|---|
| | | | | | Schm1_68, | |
| | | | | | Schm1_108, | |
| | | | | | Schm1_141, | |
| | | | | | Schm1_156, | |
| | | | | | Schm1_174, | |
| | | | | | Schm1_176, | |
| | | | | | Schm1_177, | |
| | | | | | Schm1_234, | |
| | | | | | Schm1_248, | |
| | | | | | Schm1_3, | |
| | | | | | Schm1_22, | |
| | | | | | Schm1_25, | |
| | | | | | Schm1_29, | |
| | | | | | Schm1_41, | |
| | | | | | Schm1_43, | |
| | | | | | Schm1_59, | |
| | | | | | Schm1_85, | |
| | | | | | Schm1_97, | |
| | | | | | Schm1_99, | |
| | | | | | Schm1_103, | |
| | | | | | Schm1_123, | |
| | | | | | Schm1_136, | |
| | | | | | Schm2_9, | |
| | | | | | Schm2_14, | |
| | | | | | Schm2_23, | |
| | | | | | Schm2_30, | |
| | | | | | Schm2_32, | |
| | | | | | Schm2_46, | |
| | | | | | Schm2_50, | |
| | | | | | RDN60, | |
| | | | | | RDN02, | |
| | | | | | RDN136, | |
| | | | | | RDN78, | |
| | | | | | RDN120, | |
| | | | | | RDN75, | |
| | | | | | RDN116 | |
| 1241 | 1243 | I | V | | Schm1_253, | |
| | | | | | Schm1_123 | |
| 1302 | 1304 | D | G | | Schm1_253, | |
| | | | | | Schm1_123 | |
| 1313 | 1315 | D | G | | Schm1_17, | |
| | | | | | Schm1_39, | |
| | | | | | Schm1_55, | |
| | | | | | Schm1_56, | |
| | | | | | Schm1_76, | |
| | | | | | Schm1_92, | |
| | | | | | Schm1_94, | |
| | | | | | Schm1_142, | |
| | | | | | Schm1_144, | |
| | | | | | Schm1_253, | |
| | | | | | Schm1_12X, | |
| | | | | | Schm1_35, | |
| | | | | | Schm1_68, | |
| | | | | | Schm1_108, | |
| | | | | | Schm1_141, | |
| | | | | | Schm1_156, | |
| | | | | | Schm1_174, | |
| | | | | | Schm1_176, | |
| | | | | | Schm1_177, | |
| | | | | | Schm1_234, | |
| | | | | | Schm1_248, | |
| | | | | | Schm1_3, | |
| | | | | | Schm1_5, | |
| | | | | | Schm1_22, | |
| | | | | | Schm1_25, | |
| | | | | | Schm1_29, | |
| | | | | | Schm1_41, | |
| | | | | | Schm1_43, | |
| | | | | | Schm1_59, | |
| | | | | | Schm1_85, | |
| | | | | | Schm1_97, | |
| | | | | | Schm1_99, | |
| | | | | | Schm1_103, | |

TABLE 7-continued

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1_123, Schm1_136, Schm2_9, Schm2_14, Schm2_23, Schm2_30, Schm2_32, Schm2_46, Schm2_50, RDN60, RDN02, RDN136, RDN78, RDN120, RDN75, RDN116 | |
| 1322 | 1324 | V | I | | RDN120 | |
| 1349 | 1351 | V | M | | RDN02 | |
| 1355 | 1357 | P | S | | Schm1_234, Schm1_136, RDN75 | |
| 1364 | 1366 | R | E | | Schm1_156 | |
| 1365 | 1367 | D | I | | Schm1_156 | |
| 1393 | 1395 | A | V | | Schm1_35, Schm1_41, Schm2_9, RDN78 | |
| 1425 | 1427 | A | V | | RDN02 | |
| 1479 | 1481 | N | K | | RDN60 | |
| 1483 | 1485 | V | I | | Schm1_141, Schm1_156, Schm1_174 | |
| 1487 | 1489 | I | M | | Schm1_17, Schm1_39, Schm1_55, Schm1_56, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_14, Schm2_23, Schm2_30, Schm2_32, Schm2_46, Schm2_50, RDN60, | |

TABLE 7-continued

Gene conservation of Spy0416.

| Position in SF370 gene | Alignment position | Amino acid in SF370 gene | AA change[1] | AA change[2] | Strains with respective change[1] | Strains with respective change[2] |
|---|---|---|---|---|---|---|
| | | | | | RDN02, RDN136, RDN78, RDN120, RDN75, RDN116 | |
| 1505 | 1507 | E | K | | Schm2_50 | |
| 1516 | 1518 | D | G | | Schm1_17, Schm1_39, Schm1_55, Schm1_56, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_14, Schm2_23, Schm2_30, Schm2_32, Schm2_46, Schm2_50, RDN60, RDN02, RDN136, RDN78, RDN120, RDN75, RDN116 | |
| 1522 | 1524 | E | G | | Schm1_99, Schm2_32, Schm2_46 | |
| 1538 | 1540 | G | D | | Schm1_17, Schm1_22, Schm1_97 | |
| 1545 | 1547 | S | T | | Schm2_50 | |
| 1555 | 1557 | N | D | | Schm1_35, Schm1_41, Schm2_9, RDN78 | |
| 1560 | 1562 | T | A | | Schm1_17, Schm1_144, Schm1_194, Schm1_35, Schm1_234, Schm1_22, Schm1_41, Schm1_97, | |

TABLE 7-continued

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1_99, Schm1_103, Schm1_136, Schm2_9, Schm2_32, Schm2_46, RDN78 | |
| 1576 | 1578 | G | R | | Schm2_50 | |
| 1580 | 1582 | D | G | | Schm1_144, Schm1_194, Schm1_234, Schm1_136 | |
| 1587 | 1589 | V | A | | Schm1_142, Schm1_176, Schm1_25 | |
| 1591 | 1593 | N | S | | RDN75 | |
| 1598 | 1600 | A | V | | Schm1_17, Schm1_22, Schm1_97 | |
| 1605 | 1607 | S | T | | Schm1_17, Schm1_39, Schm1_55, Schm1_56, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_14, Schm2_23, Schm2_30, Schm2_32, Schm2_46, Schm2_50, RDN60, RDN02, RDN136, RDN78, RDN120, RDN75, RDN116 | |
| 1608 | 1610 | S | P | | Schm1_144, Schm1_194, Schm1_234, Schm1_136 | |
| 1609 | 1611 | A | Deletion | | Schm1_142, Schm1_176, Schm1_25, | |

TABLE 7-continued

| Gene conservation of Spy0416. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | RDN120 | |
| 1610 | 1612 | T | Deletion | | Schm1_142, Schm1_176, Schm1_25, RDN120 | |
| 1617 | 1619 | T | A | | Schm1_17, Schm1_39, Schm1_56, Schm1_92, Schm1_35, Schm1_108, Schm1_141, Schm1_156, Schm1_174, Schm1_248, Schm1_22, Schm1_41, Schm1_59, Schm1_85, Schm1_97, Schm1_99, Schm2_9, Schm2_14, Schm2_23, Schm2_30, Schm2_46, Schm2_50, RDN60, RDN78, RDN116 | |
| 1622 | 1624 | G | S | | Schm1_142, Schm1_176, Schm1_25, RDN120 | |
| 1642 | 1644 | K | T | | Schm1_144 | |

[1]observed amino acid at respective position in any of the sequenced genes of the respective *S. pyogenes* strains.
[2]second possible amino acid observed at the respective position.
Deletion or insertion refers to a missing or additional amino acid relative to Spy0416 of *S. pyogenes* SF370.

Sequence Analyses of Spy0488

Sequences were obtained from all 51 strains. The level of amino acid sequence identity ranged from 85.4% to 100% as compared to the sequence of Spy0488 from *S. pyogenes SF*370. Table 8 lists all 49 amino acid positions which showed a distinct amino acid as compared to Spy0488 from *S. pyogenes* SF370. The genes from several strains (e.g. Schmitz 1/55) possessed furthermore a different N terminus, with an addition of 25 amino acids and a frame-shift for the first 16 amino acids relative to Spy0488 from *S. pyogenes* SF370.

TABLE 8

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| Insertion | 1 | — | M | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, | |

TABLE 8-continued

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| Insertion | 2 | — | M | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| Insertion | 3 | — | M | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, | |

TABLE 8-continued

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| Insertion | 4 | — | L | | Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 Schm1_39 Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174 Schm1_176, Schm1_177, Schm1_234, Schm1_248, Schm1_3, Schm1_22, | |
| Insertion | 5 | — | R | | Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, | |
| Insertion | 6 | — | D | | Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, | |
| | | | | | Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, | |

TABLE 8-continued

Gene conservation of Spy0488.

| Position in SF370 gene | Alignment position | Amino acid in SF370 gene | AA change[1] | AA change[2] | Strains with respective change[1] | Strains with respective change[2] |
|---|---|---|---|---|---|---|
| | | | | | Schm2_32, Schm2_46, Schm2_50, RDN60, RDN02, RDN136, RDN78, RDN120, RDN75, RDN116 | |
| Insertion | 7 | — | V | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| Insertion | 8 | — | K | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| Insertion | 9 | — | V | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| Insertion | 10 | — | K | | Schm1_39, Schm1_55, Schm1_56, Schm1_74, Schm1_76, Schm1_92, | |

TABLE 8-continued

Gene conservation of Spy0488.

| Position in SF370 gene | Alignment position | Amino acid in SF370 gene | AA change[1] | AA change[2] | Strains with respective change[1] | Strains with respective change[2] |
|---|---|---|---|---|---|---|
| | | | | | Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| Insertion | 11 | — | M | T | Schm1__39, Schm1__55, Schm1__74, Schm1__76, Schm1__92, Schm1__142, Schm1__144, Schm1__194, Schm1__253, Schm1__35, Schm1__68, Schm1__141, Schm1__156, Schm1__174, Schm1__176, Schm1__177, Schm1__234, Schm1__248, Schm1__3, Schm1__25, Schm1__29, Schm1__41, Schm1__43, Schm1__59, Schm1__99, Schm1__103, Schm1__123, Schm1__136, Schm2__9, Schm2__23, Schm2__30, Schm2__32, Schm2__46, RDN60, RDN136, RDN78, RDN120, RDN75 | Schm1__56, Schm1__108, Schm1__22, Schm1__85, Schm1__97, Schm2__50, RDN02, RDN116 |
| Insertion | 12 | — | S | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| Insertion | 13 | — | S | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, | |

TABLE 8-continued

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| Insertion | 14 | — | L | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| Insertion | 15 | — | L | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| Insertion | 16 | — | V | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, | |

TABLE 8-continued

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| Insertion | 17 | — | G | | RDN02, RDN136, RDN78, RDN120, RDN75, RDN116 Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, | |
| Insertion | 18 | — | C | | RDN02, RDN136, RDN78, RDN120, RDN75, RDN116 Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, | |
| Insertion | 19 | — | A | | RDN02, RDN136, RDN78, RDN120, RDN75, RDN116 Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, | |
| Insertion | 20 | — | A | | RDN02, RDN136, RDN78, RDN120, RDN75, RDN116 Schm1__39, Schm1__55, Schm1__56, Schm1__74, Schm1__76, Schm1__92, Schm1__142, Schm1__144, Schm1__194, Schm1__253, | |

TABLE 8-continued

Gene conservation of Spy0488.

| Position in SF370 gene | Alignment position | Amino acid in SF370 gene | AA change[1] | AA change[2] | Strains with respective change[1] | Strains with respective change[2] |
|---|---|---|---|---|---|---|
| | | | | | Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| Insertion | 21 | — | T | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| Insertion | 22 | — | L | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| Insertion | 23 | — | L | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, | |

TABLE 8-continued

Gene conservation of Spy0488.

| Position in SF370 gene | Alignment position | Amino acid in SF370 gene | AA change[1] | AA change[2] | Strains with respective change[1] | Strains with respective change[2] |
|---|---|---|---|---|---|---|
| | | | | | Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| Insertion | 24 | — | V | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| Insertion | 25 | — | S | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| 2 | 27 | R | S | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, | |

TABLE 8-continued

Gene conservation of Spy0488.

| Position in SF370 gene | Alignment position | Amino acid in SF370 gene | AA change[1] | AA change[2] | Strains with respective change[1] | Strains with respective change[2] |
|---|---|---|---|---|---|---|
| | | | | | Schm2_50, RDN60, RDN02, RDN136, RDN78, RDN120, RDN75, RDN116 | |
| 3 | 28 | Q | S | G | Schm1_39, Schm1_55, Schm1_56, Schm1_76, Schm1_142, Schm1_253, Schm1_68, Schm1_108, Schm1_141, Schm1_156, Schm1_174, Schm1_176, Schm1_177, Schm1_248, Schm1_3, Schm1_22, Schm1_25, Schm1_29, Schm1_43, Schm1_59, Schm1_85, Schm1_97, Schm1_99, Schm1_123, Schm1_136, Schm2_23, Schm2_30, Schm2_32, Schm2_46, Schm2_50, RDN60, RDN02, RDN136, RDN120, RDN75, RDN116 | Schm1_74, Schm1_92, Schm1_144, Schm1_194, Schm1_35, Schm1_234, Schm1_41, Schm1_103, Schm2_9, RDN78 |
| 4 | 29 | I | T | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| 5 | 30 | Q | V | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| 6 | 31 | S | A | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, | |

TABLE 8-continued

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| 7 | 32 | I | A | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| 8 | 33 | R | D | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| 9 | 34 | L | S | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, | |

TABLE 8-continued

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1_136, Schm2_9, Schm2_23, Schm2_30, Schm2_32, Schm2_46, Schm2_50, RDN60, RDN02, RDN136, RDN78, RDN120, RDN75, RDN116 | |
| 10 | 35 | I | V | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| 11 | 36 | D | H | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |
| 12 | 37 | V | S | | Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_23, Schm2_30, Schm2_32, Schm2_46, Schm2_50, RDN60, RDN02, RDN136, RDN78, RDN120, RDN75, RDN116 | |

TABLE 8-continued

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| 13 | 38 | L | S | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN120, RDN75, RDN116 | RDN78 |
| 14 | 39 | E | D | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| 15 | 40 | L | R | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| 16 | 41 | A | R | | Schm1__39, Schm1__55, Schm1__56, Schm1__74, Schm1__76, Schm1__92, Schm1__142, Schm1__144, Schm1__194, Schm1__253, Schm1__35, Schm1__68, Schm1__108, Schm1__141, | |

TABLE 8-continued

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm1__156, Schm1__174, Schm1__176, Schm1__177, Schm1__234, Schm1__248, Schm1__3, Schm1__22, Schm1__25, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| 30 | 55 | S | F | | Schm1__99, Schm1__136, Schm2__46 | |
| 35 | 60 | S | Y | | RDN75 | |
| 50 | 75 | A | T | | Schm1__39, Schm1__55, Schm1__56, Schm1__74, Schm1__76, Schm1__92, Schm1__144, Schm1__194, Schm1__253, Schm1__35, Schm1__68, Schm1__108, Schm1__141, Schm1__156, Schm1__174, Schm1__177, Schm1__234, Schm1__248, Schm1__3, Schm1__22, Schm1__29, Schm1__41, Schm1__43, Schm1__59, Schm1__85, Schm1__97, Schm1__99, Schm1__103, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| 53 | 78 | N | D | | Schm1__253, Schm1__99, Schm1__123, Schm1__136, Schm2__46, RDN120 | |
| 56 | 81 | S | Y | | Schm1__39, Schm1__55, Schm1__56, Schm1__76, Schm1__92, Schm1__144, Schm1__194, Schm1__68, Schm1__108, Schm1__141, Schm1__156, Schm1__174, Schm1__177, Schm1__234, Schm1__248, Schm1__3, Schm1__22, Schm1__29, Schm1__43, Schm1__59, Schm1__85, Schm1__97, Schm1__99, Schm1__103, Schm1__136, Schm2__23, Schm2__30, Schm2__32, Schm2__46, Schm2__50, RDN60, RDN02, RDN136, RDN120, RDN75, RDN116 | |
| 60 | 85 | D | G | | Schm1__248, Schm1__59 | |
| 69 | 94 | D | G | | Schm1__39, Schm1__55, Schm1__56, Schm1__76, Schm1__92, Schm1__253, Schm1__68, Schm1__108, Schm1__141, Schm1__156, Schm1__174, Schm1__177, Schm1__248, Schm1__3, Schm1__22, Schm1__29, Schm1__43, Schm1__59, Schm1__85, Schm1__97, Schm1__99, Schm1__123, Schm1__136, Schm2__23, Schm2__30, Schm2__32, | |

TABLE 8-continued

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm2__46, Schm2__50, RDN60, RDN02, RDN136, RDN120 | |
| 75 | 100 | Q | H | | Schm2__32 | |
| 76 | 101 | I | T | | Schm1__39, Schm1__55, Schm1__56, Schm1__76, Schm1__144, Schm1__194, Schm1__253, Schm1__68, Schm1__108, Schm1__141, Schm1__156, Schm1__174, Schm1__177, Schm1__234, Schm1__248, Schm1__3, Schm1__22, Schm1__29, Schm1__43, Schm1__59, Schm1__85, Schm1__97, Schm1__99, Schm1__103, Schm1__123, Schm1__136, Schm2__23, Schm2__30, Schm2__32, Schm2__46, Schm2__50, RDN60, RDN02, RDN136, RDN120 | |
| 87 | 112 | F | L | | Schm1__253, Schm1__123 | |
| 93 | 118 | G | E | | Schm1__99, Schm2__46 | |
| 112 | 137 | V | A | | Schm1__253, Schm1__123 | |
| 117 | 142 | I | T | | Schm1__39, Schm1__55, Schm1__56, Schm1__74, Schm1__76, Schm1__92, Schm1__253, Schm1__35, Schm1__68, Schm1__108, Schm1__141, Schm1__156, Schm1__174, Schm1__177, Schm1__248, Schm1__3, Schm1__22, Schm1__29, Schm1__41, Schm1__43, Schm1__59, Schm1__85, Schm1__97, Schm1__99, Schm1__123, Schm1__136, Schm2__9, Schm2__23, Schm2__30, Schm2__32, Schm2__46, Schm2__50, RDN60, RDN02, RDN136, RDN78, RDN120, RDN75, RDN116 | |
| 127 | 152 | H | Y | | Schm1__39 | |
| 157 | 182 | D | G | | RDN75 | |
| 163 | 188 | V | L | | RDN75 | |
| 174 | 199 | K | T | | Schm1__55, Schm1__68, Schm1__3, Schm1__29, Schm2__23, Schm2__30 | |
| 183 | 208 | G | R | | RDN75 | |
| 184 | 209 | G | S | | Schm1__56, Schm1__108, Schm1__85, Schm2__50, RDN02 | |
| 188 | 213 | F | L | | Schm1__92, Schm1__144, Schm1__194, Schm1__253, Schm1__35, Schm1__234, Schm1__41, Schm1__99, Schm1__103, Schm1__123, Schm1__136, Schm2__9, Schm2__46, RDN78 | |
| 198 | 223 | P | S | | Schm1__92 | |
| 199 | 224 | K | R | | Schm1__56, Schm1__108, Schm1__85, Schm2__50, RDN02 | |
| 201 | 226 | R | G | | Schm1__56, Schm1__74, Schm1__76, Schm1__92, Schm1__144, Schm1__194, Schm1__253, Schm1__35, Schm1__108, Schm1__177, Schm1__234, Schm1__41, Schm1__43, Schm1__85, Schm1__99, Schm1__103, Schm1__123, Schm1__136, | |

TABLE 8-continued

| Gene conservation of Spy0488. | | | | | | |
|---|---|---|---|---|---|---|
| Position in SF370 gene | Alignment position | Amino acid in SF370 gene | AA change[1] | AA change[2] | Strains with respective change[1] | Strains with respective change[2] |
| | | | | | Schm2_9, Schm2_32, Schm2_46, Schm2_50, RDN02, RDN136, RDN78, RDN120 | |
| 202 | 227 | Q | L | | Schm1_144, Schm1_194, Schm1_35, Schm1_234, Schm1_41, Schm1_99, Schm1_103, Schm1_136, Schm2_9, Schm2_46, RDN78 | |
| 206 | 231 | T | I | | Schm1_56, Schm1_108, Schm1_85, Schm2_50, RDN02 | |
| 209 | 234 | D | A | | Schm1_92, Schm1_144, Schm1_194, Schm1_35, Schm1_234, Schm1_41, Schm1_99, Schm1_103, Schm1_136, Schm2_9, Schm2_46, RDN78 | |
| 217 | 242 | P | S | | Schm1_56, Schm1_108, Schm1_85, Schm2_50, RDN02 | |
| 221 | 246 | W | C | | Schm1_76, Schm1_177, Schm1_43, RDN136 | |
| 222 | 247 | K | E | | Schm1_56, Schm1_108, Schm1_85, Schm2_50, RDN02 | |
| 232 | 257 | A | T | | Schm1_39, Schm1_22, Schm1_97 | |
| 235 | 260 | S | F | | Schm1_253, Schm1_123 | |
| 238 | 263 | T | I | | Schm1_248, Schm1_59 | |
| 258 | 283 | A | V | | Schm1_92 | |
| 291 | 316 | E | Q | | Schm1_55, Schm1_68, Schm1_3, Schm1_29, Schm2_23, Schm2_30 | |

[1]observed amino acid at respective position in any of the sequenced genes of the respective *S. pyogenes* strains.
[2]second possible amino acid observed at the respective position.
Insertion refers to an additional amino acid relative to Spy0488 of *S. pyogenes* SF370.

Sequence Analyses of Spy0872

Sequences were obtained from all 51 strains. The level of amino acid sequence identity ranged from 98.2% to 100% as compared to the sequence of Spy0872 from *S. pyogenes* SF370. Table 9 lists all 34 acid positions which showed a distinct amino acid as compared to Spy0872 from *S. pyogenes* SF370. The gene from strain Schmitz 1/22 showed in addition an insertion of 2 amino acids after position 587.

TABLE 9

| Gene conservation of Spy0872. | | | | |
|---|---|---|---|---|
| Position in SF370 gene | Alignment position | Amino acid in SF370 gene | AA change[1] | Strains with respective change[1] |
| 67 | 67 | G | C | Schm1_136 |
| 74 | 74 | E | D | Schm1_76, Schm1_177, Schm1_43, RDN136 |
| 178 | 178 | K | N | Schm1_7, Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_14, Schm2_32, Schm2_46, Schm2_50, RDN60, RDN02, RDN136, RDN78, RDN120, RDN75, RDN116 |
| 181 | 181 | P | S | RDN60 |
| 222 | 222 | H | Y | RDN120 |
| 228 | 228 | V | A | Schm1_56, Schm1_108, Schm1_85, Schm2_50 |

TABLE 9-continued

Gene conservation of Spy0872.

| Position in SF370 gene | Alignment position | Amino acid in SF370 gene | AA change[1] | Strains with respective change[1] |
|---|---|---|---|---|
| 253 | 253 | V | I | Schm1_7, Schm1_39, Schm1_55, Schm1_56, Schm1_76, Schm1_142, Schm1_144, Schm1_194, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_43, Schm1_59, Schm1_85, Schm1_97, Schm1_99, Schm1_103, Schm2_14, Schm2_32, Schm2_46, Schm2_50, RDN60, RDN136, RDN120 |
| 328 | 328 | I | M | Schm1_55, Schm1_56, Schm1_92, Schm1_68, Schm1_108, Schm1_3, Schm1_29, Schm1_85, Schm1_136, Schm2_23, Schm2_30, Schm2_50, RDN75 |
| 329 | 329 | K | T | Schm1_55, Schm1_56, Schm1_92, Schm1_68, Schm1_108, Schm1_3, Schm1_29, Schm1_85, Schm1_136, Schm2_23, Schm2_30, Schm2_50, RDN75 |
| 336 | 336 | V | I | Schm1_56, Schm1_108, Schm1_85, Schm2_50 |
| 337 | 337 | A | T | Schm1_136, RDN75 |
| 340 | 340 | P | L | RDN120 |
| 393 | 393 | A | V | Schm1_7, Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_14, Schm2_23, Schm2_30, Schm2_32, Schm2_46, Schm2_50, RDN60, RDN02, RDN136, RDN78, RDN120, RDN75, RDN116 |
| 412 | 412 | M | I | RDN120 |
| 427 | 427 | D | Y | Schm2_46 |
| 433 | 433 | G | E | Schm1_7, Schm1_22, Schm1_97 |
| 444 | 444 | I | T | RDN75 |
| 478 | 478 | Y | F | Schm1_253, Schm1_123 |
| 490 | 490 | T | I | Schm1_55, Schm1_68, Schm1_3, Schm1_29, Schm2_23, Schm2_30 |
| 492 | 492 | F | C | RDN02 |
| 532 | 532 | A | T | Schm1_144, Schm1_194, Schm1_234, Schm1_103 |
| 535 | 535 | I | V | Schm1_142, Schm1_176, Schm1_25, Schm2_46, RDN116 |
| 553 | 553 | E | Q | Schm1_142, Schm1_176, Schm1_25, Schm1_99, Schm2_32, Schm2_46, RDN116 |
| 576 | 576 | S | R | Schm1_142, Schm1_176, Schm1_25, Schm1_99, Schm2_46, RDN116 |
| 580 | 580 | V | I | Schm1_142, Schm1_176, Schm1_25, Schm1_99, Schm2_46, RDN116 |
| Insertion | 588 | — | I | Schm1_7, Schm1_22, Schm1_97 |
| Insertion | 589 | — | I | Schm1_7, Schm1_22, Schm1_97 |
| 588 | 590 | I | T | RDN78 |
| 598 | 600 | G | D | Schm1_92 |
| 600 | 602 | T | I | Schm1_7, Schm1_39, Schm1_55, Schm1_56, Schm1_74, Schm1_76, Schm1_92, Schm1_142, Schm1_144, Schm1_194, Schm1_253, Schm1_35, Schm1_68, Schm1_108, Schm1_141, Schm1_156, Schm1_174, Schm1_176, Schm1_177, Schm1_234, Schm1_248, Schm1_3, Schm1_22, Schm1_25, Schm1_29, Schm1_41, Schm1_43, Schm1_59, Schm1_85, Schm1_97, Schm1_99, Schm1_103, Schm1_123, Schm1_136, Schm2_9, Schm2_14, Schm2_23, Schm2_30, Schm2_32, Schm2_46, Schm2_50, RDN60, RDN02, RDN136, RDN78, RDN120, RDN75, RDN116 |
| 605 | 607 | V | I | Schm1_7, Schm1_39, Schm1_56, Schm1_76, Schm1_144, Schm1_194, Schm1_253, Schm1_108, Schm1_141, Schm1_156, Schm1_174, Schm1_177, Schm1_234, Schm1_248, Schm1_22, Schm1_43, Schm1_59, Schm1_85, Schm1_97, Schm1_103, Schm1_123, Schm2_14, Schm2_50, RDN60, RDN02, RDN136, RDN78, RDN120 |
| 620 | 622 | L | F | Schm1_7, Schm1_142, Schm1_176, Schm1_22, Schm1_25, Schm1_97, Schm1_99, Schm2_32, Schm2_46, RDN116 |

TABLE 9-continued

Gene conservation of Spy0872.

| Position in SF370 gene | Alignment position | Amino acid in SF370 gene | AA change[1] | Strains with respective change[1] |
|---|---|---|---|---|
| 625 | 627 | T | I | Schm1_7, Schm1_22, Schm1_97 |
| 634 | 636 | S | N | Schm1_7, Schm1_142, Schm1_176, Schm1_22, Schm1_25, Schm1_97, Schm1_99, Schm2_46, RDN116 |
| 659 | 661 | G | C | Schm1_253, Schm1_123 |
| 667 | 669 | K | E | Schm1_144, Schm1_194, Schm1_234, Schm1_103, RDN120 |

[1]observed amino acid at respective position in any of the sequenced genes of the respective *S. pyogenes* strains. Insertion refers to an additional amino acid relative to Spy0872 of *S. pyogenes* SF370.

Sequence Analyses of Spy0895

Sequences were obtained from all 51 strains. The level of amino acid sequence identity ranged from 98.9% to 100% as compared to the sequence of Spy0895 from *S. pyogenes* SF370. Table 10 lists all 13 amino acid positions which showed a distinct amino acid as compared to Spy0895 from *S. pyogenes* SF370.

TABLE 10

Gene conservation of Spy0895.

| Position in SF370 gene | Alignment position | Amino acid in SF370 gene | AA change[1] | Strains with respective change[1] |
|---|---|---|---|---|
| 19 | 19 | A | V | Schm1_17, Schm1_22, Schm1_97 |
| 33 | 33 | A | V | Schm1_17, Schm1_141, Schm1_156, Schm1_174, Schm1_22, Schm1_97, RDN02 |
| 50 | 50 | F | V | Schm1_253, Schm1_123 |
| 52 | 52 | A | V | Schm1_17, Schm1_55, Schm1_68, Schm1_141, Schm1_156, Schm1_174, Schm1_3, Schm1_22, Schm1_29, Schm1_97, Schm2_30 |
| 60 | 60 | T | I | Schm1_56, Schm1_108, Schm1_85, Schm2_50 |
| 71 | 71 | L | I | Schm1_92, Schm1_144, Schm1_194, Schm1_234, Schm1_103 |
| 138 | 138 | H | Q | Schm1_92, Schm1_144, Schm1_194, Schm1_234, Schm1_103 |
| 188 | 188 | R | P | Schm1_174 |
| 238 | 238 | R | C | Schm1_55, Schm1_76, Schm1_68, Schm1_177, Schm1_3, Schm1_29, Schm1_43, Schm2_30, RDN136 |
| 242 | 242 | Y | C | Schm1_136 |
| 252 | 252 | K | T | Schm1_56, Schm1_108, Schm1_85, Schm2_50 |
| 255 | 255 | S | G | Schm1_56, Schm1_108, Schm1_85, Schm2_50 |
| 256 | 256 | L | F | RDN60 |

[1]observed amino acid at respective position in any of the sequenced genes of the respective *S. pyogenes* strains.

Sequence Analyses of Spy1536

Sequences were obtained from all 51 strains. The level of amino acid sequence identity ranged from 99.1% to 100% as compared to the sequence of Spy1536 from *S. pyogenes* SF370. Table 11 lists all 8 amino acid positions which showed a distinct amino acid as compared to Spy1536 from *S. pyogenes* SF370. The gene from strain Schmitz 2/14 showed in addition an insertion of 3 amino acids after position 207.

TABLE 11

| Position in SF370 gene | Alignment position | Amino acid in SF370 gene | AA change[1] | Strains with respective change[1] |
|---|---|---|---|---|
| Gene conservation of Spy1536. | | | | |
| 5 | 5 | K | N | Schm1_12, Schm2_9, Schm1_136 |
| 92 | 92 | G | R | Schm1_142 |
| 97 | 97 | A | T | Schm1_5, Schm1_74 |
| 125 | 125 | P | S | Schm1_123 |
| 126 | 126 | V | A | Schm1_142 |
| 183 | 183 | V | I | Schm1_94, RDN78, Schm1_97, Schm1_59, Schm1_76, RDN136, Schm1_177, Schm2_32, Schm1_141, Schm1_144, RDN120, Schm1_25, Schm1_176, RDN75_85, Schm2_46, Schm2_23, Schm1_55 |
| Insertion | 208 | — | K | Schm2_14 |
| Insertion | 209 | — | N | Schm2_14 |
| Insertion | 210 | — | G | Schm2_14 |

TABLE 11-continued

| Position in SF370 gene | Alignment position | Amino acid in SF370 gene | AA change[1] | Strains with respective change[1] |
|---|---|---|---|---|
| Gene conservation of Spy1536. | | | | |
| 333 | 336 | V | I | Schm1_12, Schm1_35, Schm2_9, Schm1_174, Schm1_136, Schm1_234, Schm1_68 |
| 337 | 340 | Q | E | Schm1_43, Schm1_108 |

[1]observed amino acid at respective position in any of the sequenced genes of the respective *S. pyogenes* strains. Insertion refers to an additional amino acid relative to Spy1536 of *S. pyogenes* SF370.

Sequence Analyses of Spy1666

Sequences were obtained from 50 strains. The sequence from strain RDN120 was not determined. The level of amino acid sequence identity ranged from 98.2 to 100% as compared to the sequence of Spy1666 from *S. pyogenes* SF370. Table 12 lists all 18 amino acid positions which showed a distinct amino acid as compared to Spy1666 from *S. pyogenes* SF370.

TABLE 12

| Position in SF370 gene | Alignment position | Amino acid in SF370 gene | AA change[1] | Strains with respective change[1] |
|---|---|---|---|---|
| Gene conservation of Spy1666. | | | | |
| 3 | 3 | S | P | Schm1_17, Schm1_22, Schm1_97, Schm1_136, Schm1_17, Schm1_22, Schm1_97, Schm1_136 |
| 11 | 11 | L | V | Schm1_17, Schm1_22, Schm1_97, Schm1_136, Schm1_17, Schm1_22, Schm1_97, Schm1_136 |
| 45 | 45 | D | N | Schm1_17, Schm1_22, Schm1_97, Schm1_136, Schm1_17, Schm1_22, Schm1_97, Schm1_136 |
| 67 | 67 | G | S | Schm1_17, Schm1_22, Schm1_97, Schm1_136, Schm1_17, Schm1_22, Schm1_97, Schm1_136 |
| 69 | 69 | E | Q | Schm1_17, Schm1_22, Schm1_97, Schm1_136, Schm1_17, Schm1_22, Schm1_97, Schm1_136 |
| 90 | 90 | K | Q | Schm1_142, Schm1_176, Schm1_25, Schm2_46, Schm1_142, Schm1_176, Schm1_25, Schm2_46 |
| 106 | 106 | R | I | RDN136, RDN78, RDN136, RDN78 |
| 120 | 120 | I | F | Schm1_136, Schm1_136 |
| 149 | 149 | L | S | RDN78, RDN78 |
| 167 | 167 | T | N | RDN75, RDN75 |
| 204 | 204 | T | A | Schm1_253, Schm1_103, Schm1_123, Schm1_253, Schm1_103, Schm1_123 |
| 217 | 217 | P | S | Schm1_39, Schm1_248, Schm1_59, Schm1_39, Schm1_248, Schm1_59 |
| 251 | 251 | Q | H | Schm1_97, Schm1_97 |
| 252 | 252 | D | E | Schm1_76, Schm1_141, Schm1_156, Schm1_174, Schm1_177, Schm1_43, Schm2_32, RDN136, Schm1_76, Schm1_141, Schm1_156, Schm1_174, Schm1_177, Schm1_43, Schm2_32, RDN136 |
| 259 | 259 | L | F | Schm1_92, RDN75, Schm1_92, RDN75 |
| 292 | 292 | L | F | RDN116, RDN116 |
| 302 | 302 | K | T | Schm1_17, Schm1_142, Schm1_176, Schm1_22, Schm1_25, Schm1_97, Schm2_46, Schm1_17, Schm1_142, Schm1_176, Schm1_22, Schm1_25, Schm1_97, Schm2_46 |
| 319 | 319 | T | A | Schm1_76, Schm1_141, Schm1_156, Schm1_174, Schm1_177, Schm1_43, Schm2_32, RDN136, Schm1_76, Schm1_141, Schm1_156, Schm1_174, Schm1_177, Schm1_43, Schm2_32, RDN136 |

[1]observed amino acid at respective position in any of the sequenced genes of the respective *S. pyogenes* strains.

Sequence Analyses of Spy1727

No sequence variation was observed on the amino acid sequence level in any of the analyzed 51 gene sequences obtained from the listed *S. pyogenes* strains.

SEQUENCE DATA FOR AMINO ACID SEQUENCES

1. Spy0269
1.1 Full length Spy0269
> Spy0269/SF370 (serotype 1); SEQ ID NO: 57
MDLEQTKPNQVKQKIALTSTIALLSASVGVSHQVKADDRASGETKASNTHDDSLPKPETIQEAKATIDAVEKT

LSQQKAELTELATALTKTTAEINHLKEQQDNEQKALTSAQEIYTNTLASSEETLLAQGAEHQRELTATETELH

NAQADQHSKETALSEQKASISAETTRAQDLVEQVKTSEQNIAKLNAMISNPDAITKAAQTANDNTKALSSELE

KAKADLENQKAKVKKQLTEELAAQKAALAEKEAELSRLKSSAPSTQDSIVGNNTMKAPQGYPLEELKKLEASG

YIGSASYNNYYKEHADQIIAKASPGNQLNQYQDIPADRNRFVDPDNLTPEVQNELAQFAAHMINSVRRQLGLP

PVTVTAGSQEFARLLSTSYKKTHGNTRPSFVYGQPGVSGHYGVGPHDKTIIEDSAGASGLIRNDDNMYENIGA

FNDVHTVNGIKRGIYDSIKYMLFTDHLHGNTYGHAINFLRVDKHNPNAPVYLGFSTSNVGSLNEHFVMFPESN

IANHQRFNKTPIKAVGSTKDYAQRVGTVSDTIAAIKGKVSSLENRLSAIHQEADIMAAQAKVSQLQGKLASTL

KQSDSLNLQVRQLNDTKGSLRTELLAAKAKQAQLEATRDQSLAKLASLKAALHQTEALAEQAAARVTALVAKK

AHLQYLRDFKLNPNRLQVIRERIDNTKQDLAKTTSSLLNAQEALAALQAKQSSLEATIATTEHQLTLLKTLAN

EKEYRHLDEDIATVPDLQVAPPLTGVKPLSYSKIDTTPLVQEMVKETKQLLEASARLAAENTSLVAEALVGQT

SEMVASNAIVSKITSSITQPSSKTSYGSGSSTTSNLISDVDESTQRALKAGVVMLAAVGLTGFRFRKESK 1.2 Antigenic fragment Spy0269-1
> Spy0269-1/SF370 (serotype 1); SEQ ID NO: 1
DDRASGETKASNTHDDSLPKPETIQEAKATIDAVEKTLSQQKAELTELATALTKTTAEINHLKEQQDNEQKAL

TSAQEIYTNTLASSEETLLAQGAEHQRELTATETELHNAQADQHSKETALSEQKASISAETTRAQDLVEQVKT

SEQNIAKLNAMISNPDAITKAAQTANDNTKALSSELEKAKADLENQKAKVKKQLTEELAAQKAALAEKEAELS

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKHNPNAPV 1.3 Homologous sequences of other *S. pyogenes* isolates and/or serotypes
> Spy0269-1/Schmitz 2/14 (serotype 1); SEQ ID NO: 58
DDRASGETKASNTHDDSLPKPETIQEAKATIDAVEKTLSQQKAELTELATALTKTTAEINNLKEQQDNEQKAL

TSAQEIYTNTLASSEETLLAQGAEHQRELTATETELHNAQADQHSKETALSEQKASISAETTRAQDLVEQVKT

SEQNIAKLNAMISNPDAITKAAQTANDNTKALSSELEKAKADLENQKAKVKKQLTEELAAQKAALAEKEAELS

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKRNPNAPV

> Spy0269-1/Schmitz 1/156 (serotype 4); SEQ ID NO: 59
DDRASGETKASNTHDDSLPKPETIQEAKATIDAVEKTLSQQKAELTELATALTKTTAEINHLKEQQDNEQKAL

TSAQEIYTNTLASSEETLLAQGAEHQRELTATETELHNAQADQHSKETALSEQKASISAETTRAQDLVEQVKT

SEQNIAKLNAMISNPDAITKAAQTANDNTKALSSELEKAKADLENQKAKVKKQLTEELAAQKAALAEKEAELS

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKHNPKAPV

> Spy0269-1/Schmitz 1/59 (serotype 12); SEQ ID NO: 60
DDRASGETKASNTHDDSLPKPETIQEAKATIDAVEKTLSQQKAELTKLATALTKTTAEINHLKEQQDNEQKAL

TSAQEIYTNTLASSEETLLAQGAEHQRELTATETELHNAQADQHSKETALSEQKASISAETTRAQDLVEQVKT

-continued

SEQUENCE DATA FOR AMINO ACID SEQUENCES

SEQNIAKLNAMISNPDAITKAAQTANDNTKALSSELEKAKADLENQKAKVKKQLTEELAAQKAALAEKEAELS

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKRNPNAPV

> Spy0269-1/Schmitz 1/177 (serotype 22); SEQ ID NO: 61
DDRASGETKASNTHDDSLPKPETIQEAKATIEAVEKALSQQKAELTELATALTKTTAKINHLKEQQDNEQKAL

TSAQEIYTNTLASSEETLLAQGAEHQRELTATETELHNAQADQHSKETALSEQKASISAETTRAQDLVEQVKT

SEQNIAKLNAMISNPDAITKAAQTANDNTKALSSELEKAKADLENQKAKVKKQLTEELAAQKAALAEKEAELS

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKRNPNAPV

> Spy0269-1/Schmitz 1/43 (serotype 22); SEQ ID NO: 62
DDRASGETKASNTHDDSLPKPETIQEAKATIEAVEKALSQQKAELTELATALTKTTAKINHLKEQQDNEQKAL

TSAQEIYTNTLASSEETLLAQGAEHQRELTATETELHNAQADQHSKETALSEQKASISAETTRAQDLVEQVKT

SEQNIAKLNAMISNPDAITKAAQTANDNTKALSSELEKAKADLENQKAKVKKQLTEELAAQKAALAEKEAELS

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKRNPNAPV

> Spy0269-1/Schmitz 1/136 (serotype 25); SEQ ID NO: 63
DDRASGETKASNTHDDSLPKPETIQEAKATIDAVEKTLSQQKAELTELATALTKTTAEINHLKEQQDNEQKAL

TSAQEIYTNTLASSEETLLAQGAEHQRELTATETELHNAQADQHSKETALSEQKASISAETTRAQDLVEQVKT

SEQNIAKLNAMISNPDAITKAAQTANDNTKALSSELEKAKADLENQKAKVKKQLTEELAAQKAALAEKEAELS

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKRNPNAPV

> Spy0269-1/Schmitz 1/85 (serotype 28); SEQ ID NO: 64
DDRASGETKASNTHDDSLPKPETIQEAKATIDAVEKTLSQQKAELTELATALTKTTAEINHLKEQQDNEQKAL

TSAQEIYTNTLASSEETLLAQGAEHQRELTATETELHNAQADQHSKETALSEQKASISAETTRAQDLVEQVKT

SEQNIAKLNAMISNPDAITKAAQTANDNTKALSSELEKAKADLENQKAKVKKQLTEELAAQKAALAEKEAELS

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKHNPNAPV

> Spy0269-1/Schmitz 2/50 (serotype 28); SEQ ID NO: 65
DDRASGETKASNTHDDSLPKPETIQEAKATIDAVEKTLSQQKAELTELATALTKTTAEINHLKEQQDNEQKAL

TSAQEIYTNTLASSEETLLAQGAEHQRELTATETELHNAQVDQHSKETALSEQKASISAETTRAQDLVEQVKT

SEQNIAKLNAMISNPDAITKAAQTANDNTKALSSELEKAKADLENQKAKVKKQLTEELAAQKAALAEKEAELS

-continued

SEQUENCE DATA FOR AMINO ACID SEQUENCES

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKRNPNAPV

> Spy0269-1/Schmitz 1/123 (serotype 49); SEQ ID NO: 66
DDRASGETKASNTHDDSLPKPETIQEAKATIDAVEKTLSQQKAELTELATALTKTTAEINHLKEQQDNEQKAL

TSAQEIYTNTLASSEETLLAQGAEHQRELTATETELHNAQADQHSKETALSEQKASISAETTRAQDLVEQVKT

SEQNIAKLNAMISNPDAITKAAQTANDNTKALSSELEKAKADLENQKAKVKKQLTEELAAQKAALAEKEAELS

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKRNPNAPV

> Spy0269-1/Schmitz 1/176 (serotype 83); SEQ ID NO: 67
DDRASGETKASNTHDDSLPKPETIQEAKATIEAVEKTLSQQKAELTELATALTKTTAEINHLKEQQDNEQKAL

TSAQEIYTNTLASSEETLLAQGAEHQRELTATETELHNAQADQHSKETALSEQKASISAETTRAQDLVEQVKT

SEQNIAKLNAMISNPDAITKAAQTANDNTKALSSELEKAKADLENQKAKVKKQLTEELAAQKAALAEKEAELS

RLKSSAPSTQDSIVGNNTMKAPQGYPLEELKKLEASGYIGSASYNNYYKEHADQIIAKASPGNQLNQYQDIPA

DRNRFVDPDNLTPEVQNELAQFAAHMINSVRRQLGLPPVTVTAGSQEFARLLSTSYKKTHGNTRPSFVYGQPG

VSGHYGVGPHDKTIIEDSAGASGLIRNDDNMYENIGAFNDVHTVNGIKRGIYDSIKYMLFTDHLHGNTYGHAI

NFLRVDKRNPNAPV

2. Spy0292
2.1 Full length Spy0292
> Spy0292/SF370 (serotype 1); SEQ ID NO: 68
MIKRLISLVVIALFFAASTVSGEEYSVTAKHAIAVDLESGKVLYEKDAKEVVPVASVSKLLTTYLVYKEVSKG

KLNWDSPVTISNYPYELTTNYTISNVPLDKRKYTVKELLSALVVNNANSPAIALAEKIGGTEPKFVDKMKKQL

RQWGISDAKVVNSTGLTNHFLGANTYPNTEPDDENCFCATDLAIIARHLLLEFPEVLKLSSKSSTIFAGQTIY

SYNYMLKGMPCYREGVDGLFVGYSKKAGASFVATSVENQMRVITVVLNADQSHEDDLAIFKTTNQLLQYLLIN

FQKVQLIENNKPVKTLYVLDSPEKTVKLVAQNSLFFIKPIHTKTKNTVHITKKSSTMIAPLSKGQVLGRATLQ

DKHLIGQGYLDTPPSINLILQKNISKSFFLKVWWNRFVRYVNTSL 2.2 Antigenic fragment Spy0292-1
> Spy0292-1/SF370 (serotype 1); SEQ ID NO: 2
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFC 2.3 Homologous sequences of other *S. pyogenes* isolates and/or serotypes
> Spy0292-1/Schmitz 1/39 (serotype 12); SEQ ID NO: 69
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFC

> Spy0292-1/Schmitz 1/55 (serotype 118); SEQ ID NO: 70
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDTKVVNSTGLTNHFLG

ANTYPNTEPDDENCFC

> Spy0292-1/Schmitz 1/56 (serotype 28); SEQ ID NO: 71
EEYSVTAKHAIAVDLESGKVLYEKDTKEVVPVASVSKLLTTYLVYKEVSKGKLNWDSPVTISNYPYELTTNYT -continued

| SEQUENCE DATA FOR AMINO ACID SEQUENCES |
|---|

ISNVPLDKRKYTVKELLSALVVNNANSPAIALAEKIGGTEPKFVDKMKKQLRQWGISDAKVVNSTGLTNHFLG

ANTYPNTEPDDENCFC

> Spy0292-1/Schmitz 1/74 (serotype 3); SEQ ID NO: 72
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFC

> Spy0292-1/Schmitz 1/76 (serotype 22); SEQ ID NO: 73
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFC

> Spy0292-1/Schmitz 1/92 (serotype 11); SEQ ID NO: 74
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFC

> Spy0292-1/Schmitz 1/94 (serotype 1); SEQ ID NO: 75
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFC

> Spy0292-1/Schmitz 1/142 (serotype 83); SEQ ID NO: 76
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFC

> Spy0292-1/Schmitz 1/144 (serotype 76); SEQ ID NO: 77
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFC

> Spy0292-1/Schmitz 1/194 (serotype 44); SEQ ID NO: 78
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFC 2.4 Antigenic fragment Spy0292-3
> Spy0292-3/SF370 (serotype 1); SEQ ID NO: 3
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFCATDLAIIARHLLLEFPEVLKLSSKSSTIFAGQTIYSYNYMLKGMPCYREGVDGLFVG

YSKKAGASFVATSVENQMRVITVVLNADQSHEDDLAIFKTTNQLLQYLLINFQKVQLIE 2.5 Homologous sequences of other *S. pyogenes* isolates and/or serotypes
> Spy0292-3/Schmitz 1/39 (serotype 12); SEQ ID NO: 79
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDAKVVNSTGLTNHFLG

ANTYPNTEPDDENCFCATDLAIIARHLLLEFPEVLKLSSKSSTIFDGQTIYSYNYMLKGMPCYREGVDGLFVG

YSKKAGASFVATSVENQMRVITVVLNADQSHEDDLAIFKTTNQLLQYLLINFQKVQLIE

> Spy0292-3/Schmitz 1/55 (serotype 118); SEQ ID NO: 80
EEYSVTAKHAIAVDLESGKVLYEKDAKEVVPVASVSKLLTTYLVYKEVSKGKLNWDSPVTISNYPYELTTNYT

ISNVPLDKRKYTVKELLSALVVNNANSPAIALAEKIGGTEPKFVDKMKKQLRQWGISDTKVVNSTGLTNHFLG

-continued

| SEQUENCE DATA FOR AMINO ACID SEQUENCES |
| --- |
| ANTYPNTEPDDENCFCATDLAIIARHLLLEFPEVLKLSSKSSTIFDGQTIYSYNYMLKGMPCYREGVDGLFVG<br><br>YSKKAGASFVATSVENQMRVITVVLNADQSHEDDLAIFKTTNQLLQYLLINFQKVQLIE |
| > Spy0292-3/Schmitz 1/56 (serotype 28); SEQ ID NO: 81<br>EEYSVTAKHAIAVDLESGKVLYEKDTKEVVPVASVSKLLTTYLVYKEVSKGKLNWDSPVTISNYPYELTTNYT<br><br>ISNVPLDKRKYTVKELLSALVVNNANSPAIALAEKIGGTEPKFVDKMKKQLRQWGISDAKVVNSTGLTNHFLG<br><br>ANTYPNTEPDDENCFCATDLAIIARHLLLEFPEVLKLSSKSSTIFDGQTIYSYNYMLKGMPCYREGVDGLFVG<br><br>YSKKAGASFVATSVENQMRVITVVLNADQSHEDDLAIFKTTNQLLQYLLINFQKVQLIE |
| > Spy0292-3/Schmitz 1/74 (serotype 3); SEQ ID NO: 82<br>EEYSVTAKHAIAVDLESGKVLYEKDAKEVVPVASVSKLLTTYLVYKEVSKGKLNWDSPVTISNYPYELTTNYT<br><br>ISNVPLDKRKYTVKELLSALVVNNANSPAIALAEKIGGTEPKFVDKMKKQLRQWGISDAKVVNSTGLTNHFLG<br><br>ANTYPNTEPDDENCFCATDLAIIARHLLLEFPEVLKLSSKSSTIFAGQTIYSYNYMLKGMPCYREGVDGLFVG<br><br>YSKKAGASFVATSVENQMRVITVVLNADQSHEDDLAIFKTTNQLLQYLLINFQKVQLIE |
| > Spy0292-3/Schmitz 1/76 (serotype 22); SEQ ID NO: 83<br>EEYSVTAKHAIAVDLESGKVLYEKDAKEVVPVASVSKLLTTYLVYKEVSKGKLNWDSPVTISNYPYELTTNYT<br><br>ISNVPLDKRKYTVKELLSALVVNNANSPAIALAEKIGGTEPKFVDKMKKQLRQWGISDAKVVNSTGLTNHFLG<br><br>ANTYPNTEPDDENCFCATDLAIIARHLLLEFPEVLKLSSKSSTIFDGQTIYSYNYMLKGMPCYREGVDGLFVG<br><br>YSKKAGASFVATSVENQMRVITVVLNADQSHEDDLAIFKTTNQLLQYLLINFQKVQLIE |
| > Spy0292-3/Schmitz 1/92 (serotype 11); SEQ ID NO: 84<br>EEYSVTAKHAIAVDLESGKVLYEKDAKEVVPVASVSKLLTTYLVYKEVSKGKLNWDSPVTISNYPYELTTNYT<br><br>ISNVPLDKRKYTVKELLSALVVNNANSPAIALAEKIGGTEPKFVDKMKKQLRQWGISDAKVVNSTGLTNHFLG<br><br>ANTYPNTEPDDENCFCATDLAIIARHLLLEFPEVLKLSSKSSTIFDGQTIYSYNYMLKGMPCYREGVDGLFIG<br><br>YSKKAGASFVATSVENQMRVITVVLNADQSHEDDLAIFKTTNQLLQYLLINFQKVQLIE |
| > Spy0292-3/Schmitz 1/94 (serotype 1); SEQ ID NO: 85<br>EEYSVTAKHAIAVDLESGKVLYEKDAKEVVPVASVSKLLTTYLVYKEVSKGKLNWDSPVTISNYPYELTTNYT<br><br>ISNVPLDKRKYTVKELLSALVVNNANSPAIALAEKIGGTEPKFVDKMKKQLRQWGISDAKVVNSTGLTNHFLG<br><br>ANTYPNTEPDDENCFCATDLAIIARHLLLEFPEVLKLSSKSSTIFAGQTIYSYNYMLKGMPCYREGVDGLFVG<br><br>YSKKAGASFVATSVENQMRVITVVLNADQSHEDDLAIFKTTNQLLQYLLINFQKVQLIE |
| > Spy0292-3/Schmitz 1/142 (serotype 83); SEQ ID NO: 86<br>EEYSVTAKHAIAVDLESGKVLYEKDAKEVVPVASVSKLLTTYLVYKEVSKGKLNWDSPVTISNYPYELTTNYT<br><br>ISNVPLDKRKYTVKELLSALVVNNANSPAIALAEKIGGTEPKFVDKMKKQLRQWGISDAKVVNSTGLTNHFLG<br><br>ANTYPNTEPDDENCFCATDLAIIARHLLLEFPEVLKLSSKSSTIFDGQTIYSYNYMLKGMPCYREGVDGLFVG<br><br>YSKKAGASFVATSVENQMRVITVVLNADQSHEDDLAIFKTTNQLLQYLLINFQKVQLIE |
| > Spy0292-3/Schmitz 1/144 (serotype 76); SEQ ID NO: 87<br>EEYSVTAKHAIAVDLESGKVLYEKDAKEVVPVASVSKLLTTYLVYKEVSKGKLNWDSPVTISNYPYELTTNYT<br><br>ISNVPLDKRKYTVKELLSALVVNNANSPAIALAEKIGGTEPKFVDKMKKQLRQWGISDAKVVNSTGLTNHFLG<br><br>ANTYPNTEPDDENCFCATDLAIIARHLLLEFPEVLKLSSKSSTIFDGQTIYSYNYMLKGMPCYREGVDGLFVG<br><br>YSKKAGASFVATSVENQMRVITVVINADQSHEDDLAIFKTTNQLLQYLLINFQKVQLIE |
| > Spy0292-3/Schmitz 1/194 (serotype 44); SEQ ID NO: 88<br>EEYSVTAKHAIAVDLESGKVLYEKDAKEVVPVASVSKLLTTYLVYKEVSKGKLNWDSPVTISNYPYELTTNYT<br><br>ISNVPLDKRKYTVKELLSALVVNNANSPAIALAEKIGGTEPKFVDKMKKQLRQWGISDAKVVNSTGLTNHFLG<br><br>ANTYPNTEPDDENCFCATDLAIIARHLLLEFPEVLKLSSKSSTIFAGQTIYSYNYMLKGMPCYREGVDGLFVG<br><br>YSKKAGASFVATSVENQMRVITVVLNADQSHEDDLAIFKTTNQLLQYLLINFQKVQLIE |
| 3. Spy0416A |

-continued

SEQUENCE DATA FOR AMINO ACID SEQUENCES 3.1 Full length Spy0416A
> Spy0416A/SF370 (serotype 1); SEQ ID NO: 89
ADELSTMSEPTITNHAQQQAQHLTNTELSSAESKSQDTSQITLKTNREKEQSQDLVSEPTTTELADTDAASMA

NTGSDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFEDFDEDWENFEFDAEAEPKAIKKHKIYRPQSTQAPKET

VIKTEETDGSHDIDWTQTDDDTKYESHGMHVTGIVAGNSKEAAATGERFLGIAPEAQVMFMRVFANDIMGSAE

SLFIKAIEDAVALGADVINLSLGTANGAQLSGSKPLMEAIEKAKKAGVSVVVAAGNERVYGSDHDDPLATNPD

YGLVGSPSTGRTPTSVAAINSKWVIQRLMTVKELENRADLNHGKAIYSESVDFKDIKDSLGYDKSHQFAYVKE

STDAGYNAQDVKGKIALIERDPNKTYDEMIALAKKHGALGVLIFNNKPGQSNRSMRLTANGMGIPSAFISHEF

GKAMSQLNGNGTGSLEFDSVVSKAPSQKGNEMNHFSNWGLTSDGYLKPDITAPGGDIYSTYNDNHYGSQTGTS

MASPQIAGASLLVKQYLEKTQPNLPKEKIADIVKNLLMSNAQIHVNPETKTTTSPRQQGAGLLNIDGAVTSGL

YVTGKDNYGSISLGNITDTMTFDVTVHNLSNKDKTLRYDTELLTDHVDPQKGRFTLTSHSLKTYQGGEVTVPA

NGKVTVRVTMDVSQFTKELTKQMPNGYYLEGFVRFRDSQDDQLNRVNIPFVGFKGQFENLAVAEESIYRLKSQ

GKTGFYFDESGPKDDIYVGKHFTGLVTLGSE 3.2 Antigenic fragment Spy0416A-1
> Spy0416A-1/SF370 (serotype 1); SEQ ID NO: 4
ADELSTMSEPTITNHAQQQAQHLTNTELSSAESKSQDTSQITLKTNREKEQSQDLVSEPTTTELADTDAASMA

NTGSDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFEDFDEDWENFEFDAEAEPKAIKKHKIYRPQSTQAPKET

VIKTEETDGSHDIDWTQTDDDTKYESHGMHVTGIVAGNSKEAAATGERFLGIAPEAQVMFMRVFANDIMGSAE

SLFIKAIEDAVALGADVINLSLGTANGAQLSGSKPLMEAIEKAKKAGVSVVVAAGNERVYGSDHDDPLATNPD

YGLVGSPSTGRTPTSVAAINSKWVIQRLMTVKELENRADLNHGKAIYSESVDFKDIKDSLGYDKSHQFAYVKE

STDAGYNAQDVKGKIALIERDPNKTYDEMIALAKKHGALGVLIFNNKPGQSNRSMRLTANGMGIPSAFISHEF

GKAMSQLNGNGTGSLEFDSVVSKAPSQKGNEMNHFSNWGLTSDGYLKPDITAPGGDIYSTYNDNHYGSQTGTS

MASPQIAGASLLVKQYLEKTQPNLPKEKIADIVKNLLMSNAQIHVNPETKTTTSPRQQGA 3.3 Homologous sequences of other *S. pyogenes* isolates and/or serotypes
> Spy0416A-1/Schmitz 1/7 (serotype 4); SEQ ID NO: 90
ADELTTTSEPTITNHAQQQAQHLTNTELSSAESQSPDTSQITPKTNREKEQPQGLVSEPTTTELADTDAASMA

NTGPDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFGDFDEDWENFEFDAEPKAIKKNKIYRPQSTQAPKETVI

KTEETDGSHDIDWTQTDDDTKYESHGMHVTGIVAGNSKEAAATGERFLGIAPEAQVMFMRVFANDVMGSAESL

FIKAIEDAVALGADVINLSLGTANGAQLSGSKPLMEAIEKAKKAGVSVVVAAGNERVYGSDHDDPLATNPDYG

LVGSPSTGRTPTSVAAINSKWVIQRLMTAKELENRADLNHGKAIYSESVDFKDIKDSLGYDKSHQFAYVKEST

DAGYKAQDVKDKIALIERDPNKTYDEMIALAKKHGALGVLIFNNKPGQSNRSMRLTANGMGIPSAFISHEFGK

AMSQLNGNGTGSLEFDSVVSKAPSQKGNEMNHFSNWGLTSDGYLKPDITAPGGDIYSTYNDNHYGSQTGTSMA

SPQIAGASLLVKQYLEKTQPNLPKEKIADIVKNLLMSNAQIHVNPETKTTTSPRQQGA

> Spy0416A-1/Schmitz 1/39 (serotype 12); SEQ ID NO: 91
ADELTTTSEPTITNHTQQQAQHLTNTELSSAESKPQDTSQITLKTNREKEQPQGLVSEPTTTELADTDAAPMA

NTGPDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFEDFDEDWENFEFDAEAEPKAIKKHKIYRPQSTQAPKET

VIKTEETDGSHDIDWTQTDDDTKYESHGMHVTGIVAGNSKEAAATGERFLGIAPEAQVMFMRVFANDVMGSAE

SLFIKAIEDAVALGADVINLSLGTANGAQLSGSKPLMEAIEKAKKAGVSVVVAAGNERVYGSDHDDPLATNPD

YGLVGSPSTGRTPTSVAAINSKWVIQRLMTVKELENRADLNHGKAIYSESVDFKDIKDSLGYDKSHQFAYVKE

-continued

| SEQUENCE DATA FOR AMINO ACID SEQUENCES |
| --- |

STDAGYNAQDVKGKIALIERDPNKTYDEMIALAKKHGALGVLIFNNKPGQSNRSMRLTANGMGIPSAFISHEF

GKAMSQLNGNGTGSLEFDSVVSKAPSQKGNEMNHFSNWGLTSDGYLKPDITAPGGDIYSTYNDNHYGSQTGTS

MASPQIAGASLLVKQYLEKTQPNLPKEKIADIVKNLLMSNAQIHVNPETKTTTSPRQQGA

> Spy0416A-1/Schmitz 1/55 (serotype 118); SEQ ID NO: 92
ADELTTTSEPTITNHAQQQAPPLTNTELSSAESQPQDTSQVTPETNREKEQPQGLVSEPTTTELADTDAAPMA

NTGSDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFEDFDEDWENFEFDAEAEPKAIKKHKIYRPQSTQAPKET

VIKTEETDGSHDIDWTQTDDDTKYESHGMHVTGIVAGNSKEAAATGERFLGIAPEAQVMFMRVFANDVMGSAE

SLFIKAIEDAVALGADVINLSLGTANGAQLSGSKPLMEAIEKAKKAGVSVVVAAGNERVYGSDHDDPLATNPD

YGLVGSPSTGRTPTSVAAINSKWVIQRLMTVKELENRADLNHGKAIYSESVDFKDIKDSLGYDKSHQFAYVKE

STDAGYNAQNVKGKIALIERDPNKTYDEMIALAKKHGALGVLIFNNKPGQSNRSMRLTANGMGIPSAFISHEF

GKAMSQLNGNGTGSLEFDSVVSKAPSQKGNEMNHFSNWGLTSDGYLKPDITAPGGDIYSTYNDNHYGSQTGTS

MASPQIAGASLLVKQYLEKTQPNLPKEKIADIVKNLLMSNAQIHVNPETKTTTSPRQQGA

> Spy0416A-1/Schmitz 1/56 (serotype 28); SEQ ID NO: 93
ADELTTTSEPTITNHAQQQAPPLTNTELSSAESQPQDTSQVTPETNREKEQPQGLVSEPTTTELADTDAAPMA

NTGSDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFEDFDEDWENFEFDAEAEPKAIKKHKIYRPQSTQAPKET

VIKTEETDGSHDIDWTQTDDDTKYESHGMHVTGIVAGNSKEAAATGERFLGIAPEAQVMFMRVFANDVMGSAE

SLFIKAIEDAVALGADVINLSLGTANGAQLSGSKPLMEAIEKAKKAGVSVVVAAGNERVYGSDHDDPLATNPD

YGLVGSPSTGRTPTSVAAINSKWVIQRLMTVKELENRADLNHGKAIYSESVDFKDIKDSLGYDKSHQFAYVKE

STDAGYNAQNVKGKIALIERDPNKTYDEMIALAKKHGALGVLIFNNKPGQSNRSMRLTANGMGIPSAFISHEF

GKAMSQLNGNGTGSLEFDSVVSKAPSQKGNEMNHFSNWGLTSDGYLKPDITAPGGDIYSTYNDNHYGSQTGTS

MASPQIAGASLLVKQYLEKTQPNLPKEKIADIVKNLLMSNAQIHVNPETKTTTSPRQQGA

> Spy0416A-1/Schmitz 1/94 (serotype 1); SEQ ID NO: 94
ADELSTMSEPTITNHAQQQAQHLTNTELSSAESKSQDTSQITLKTNREKEQSQDLVSEPTTTELADTDAASMA

NTGSDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFEDFDEDWENFEFDAEAEPKAIKKHKIYRPQSTQAPKET

VIKTEETDGSHDIDWTQTDDDTKYESHGMHVTGIVAGNSKEAAATGERFLGIAPEAQVMFMRVFANDIMGSAE

SLFIKAIEDAVALGADVINLSLGTANGAQLSGSKPLMEAIEKAKKAGVSVVVAAGNERVYGSDHDDPLATNPD

YGLVGSPSTGRTPTSVAAINSKWVIQRLMTVKELENRADLNHGKAIYSESVDFKDIKDSLGYDKSHQFAYVKE

STDAGYNAQDVKGKIALIERDPNKTYDEMIALAKKHGALGVLIFNNKPGQSNRSMRLTANGMGIPSAFISHEF

GKAMSQLNGNGTGSLEFDSVVSKAPSQKGNEMNHFSNWGLTSDGYLKPDITAPGGDIYSTYNDNHYGSQTGTS

MASPQIAGASLLVKQYLEKTQPNLPKEKIADIVKNLLMSNAQIHVNPETKTTTSPRQQGA

> Spy0416A-1/Schmitz 1/253 (serotype 49); SEQ ID NO: 95
ADELTTTSEPTITNHAQQQAQPLTNTELSSAESQSPDISQVTPETNREKEQPQGLVSEPTTTELADTDAAPMA

NTGPDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFEDFDEDWENFEFDADAEPKAIKKHKIYRPQSTQAPKET

VIKTEETDGSHDIDWTQTDDDTKYESHGMHVTGIVAGNSKEAAATGERFLGIAPEAQVMFMRVFANDVMGSAE

SLFIKAIEDAVALGADVINLSLGTANGAQLSGSKPLMEAIEKAKKAGVSVVVAAGNERVYGSDHDDPLATNPD

YGLVGSPSTGRTPTSVAAINSKWVIQRLMTVKGLENRADLNHGKAIYSESVDFKDIKDSLGYDKSHQFAYVKE

STDAGYNAQDVKGKIALIERDPNKTYDEMIALAKKHGALGLLIFNNKSGQSNRSMRLTANGMGIPSAFISHEF

-continued

SEQUENCE DATA FOR AMINO ACID SEQUENCES

GKAMSQLNGNGTGSLEFDSVVSKAPSQKGNEMNHFSNWGLTSDGYLKPDITAPGGDIYSTYNDNHYGSQTGTS

MASPQIAGASLLVKQYLEKTQPNLPKEKIADIVKNLLMSNAQIHVNPETKTTTSPRQQGA

> Spy0416A-1/Schmitz 1/174 (serotype 6); SEQ ID NO: 96
ADELTTTSEPTITNHAQQQAQHLTNTELSSAESKPQDTSQITPKTNREKEQSQDLVSEPTTTELADTDAASMA

NTGPDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFEDFDEDWENFEFDAEAEPKAIKKHKIYRPQSTQAPKET

VIKTEETDGSHDIDWTQTDDDTKYESHGMHVTGIVAGNSKEAAATGERFLGIAPEAQVMFMRVFANDVMGSAE

SLFIKAIEDAVALGADVINLSLGTANGAQLSGSKPLMEAIEKAKKAGVSVVVAAGNERVYGSDHDDPLATNPD

YGLVGSPSTGRTPTSVAAINSKWVIQRLMTVKELENRADLNHGKAIYSESVDFKNIKDSLGYDKSHQFAYVKE

STDAGYNAQDVKGKIALIERDPNKTYDEMIALAKKHGALGVLIFNNKPGQSNRSMRLTSNGMGIPSAFISHEF

GKAMSQLNGNGTGSLEFDSVVSKAPSQKGNEMNHFSNWGLTSDGYLKPDITAPGGDIYSTYNDNHYGSQTGTS

MASPQIAGASLLVKQYLEKTQPNLPKEKIADIVKNLLMSNAQIHVNPETKTTTSPRQQGA

> Spy0416A-1/Schmitz 1/176 (serotype 83); SEQ ID NO: 97
ADELTTTSEPTITNHTQQQAQHLTNTELSSAESKPQDTSQITLKTNREKEQPQGLVSEPTTTELADTDAAPMA

NTGPDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFEDFDEDWENFEFDAEAEPKAIKKHKIYRPQSTQAPKET

VIKTEETDGSHDIDWTQTDDDTKYESHGMHVTGIVAGNSKEAAATGERFLGIAPEAQVMFMRVFANDVMGSAE

SLFIKAIEDAVALGADVINLSLGTANGAQLSGSKPLMEAIEKAKKAGVSVVVAAGNERVYGSDHDDPLATNPD

YGLVGSPSTGRTPTSVAAINSKWVIQRLMTVKELENRADLNHGKAIYSESVDFKNIKDSLGYDKSHQFAYVKE

STDAGYKAQDVKGKIALIERDPNKTYDEMIALAKKHGALGVLIFNNKPGQSNRSMRLTANGMGIPSAFISHEF

GKAMSQLNGNGTGSLEFDSVVSKAPSQKGNEMNHFSNWGLTSDGYLKPDITAPGGDIYSTYNDNHYGSQTGTS

MASPQIAGASLLVKQYLEKTQPNLPKEKIADIVKNLLMSNAQIHVNPETKTTTSPRQQGA

> Spy0416A-1/Schmitz 1/234 (serotype 44); SEQ ID NO: 98
ADELSTMSEPTITNHAQQQAQHLTNTELSSAESKSQDTSQITPKTNREKEQSQDLVSEPTTTELADTDAASMA

NTGSDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFEDFDEDWENFEFDADAEPKAIKKHKIYRPQSTQAPKET

VIKTEETDGSHDIDWTQTDDDTKYESHGMHVTGIVAGNSKEAAATGERFLGIAPEAQVMFMRVFANDVMGSAE

SLFIKAIEDAVALGADVINLSLGTANGAQLSGSKPLMEAIEKAKKAGVSVVVAAGNERVYGSDHDDPLATNPD

YGLVGSPSTGRTPTSVAAINSKWVIQRLMTVKELENRADLNHGKAIYSESVDFKDIKDSLGYDKSHQFAYVKE

STDAGYKAQDVKDKIALIERDPNKTYDEMIALAKKHGALGVLIFNNKPGQSNRSMRLTANGMGIPSAFISHEF

GKAMSQLNGNGTGSLEFDSVVSKAPSQKGNEMNHFSNWGLTSDGYLKPDITAPGGDIYSTYNDNHYGSQTGTS

MASPQIAGASLLVKQYLEKTQPNLPKEKIADIVKNLLMSNAQIHVNPETKTTTSPRQQGA

> Spy0416A-1/Schmitz 1/22 (serotype 4); SEQ ID NO: 99
ADELTTTSEPTITNHAQQQAQHLTNTELSSAESQSPDTSQITPKTNREKEQPQGLVSEPTTTELADTDAASMA

NTGPDATQKSASLPPVNTDVHDWVKTKGAWDKGYKGQGKVVAVIDTGIDPAHQSMRISDVSTAKVKSKEDMLA

RQKAAGINYGSWINDKVVFAHNYVENSDNIKENQFGDFDEDWENFEFDAEPKAIKKNKIYRPQSTQAPKETVI

KTEETDGSHDIDWTQTDDDTKYESHGMHVTGIVAGNSKEAAATGERFLGIAPEAQVMFMRVFANDVMGSAESL

FIKAIEDAVALGADVINLSLGTANGAQLSGSKPLMEAIEKAKKAGVSVVVAAGNERVYGSDHDDPLATNPDYG

LVGSPSTGRTPTSVAAINSKWVIQRLMTAKELENRADLNHGKAIYSESVDFKDIKDSLGYDKSHQFAYVKEST

DAGYKAQDVKDKIALIERDPNKTYDEMIALAKKHGALGVLIFNNKPGQSNRSMRLTANGMGIPSAFISHEFGK

AMSQLNGNGTGSLEFDSVVSKAPSQKGNEMNHFSNWGLTSDGYLKPDITAPGGDIYSTYNDNHYGSQTGTSMA

-continued

| SEQUENCE DATA FOR AMINO ACID SEQUENCES |
|---|

SPQIAGASLLVKQYLEKTQPNLPKEKIADIVKNLLMSNAQIHVNPETKTTTSPRQQGA 3.4 Antigenic fragment Spy0416A-6
> Spy0416A-6/SF370 (serotype 1); SEQ ID NO: 5
AVIDTGIDPAHQSMRISDVSTAKVKSKEDMLARQKAAGINYGSWINDKVVFAHNYVENSDNIKENQFEDFDED

WENFEFDAEAEPKAIKKHKIYRPQSTQAPKETVIKTEETDGSHDIDWTQTDDDTKYESHGMHVTGIVAGNSKE

AAATGERFLGIAPEAQVMFMRVFANDIMGSAESLFIKAIEDAVALGADVINLSLGTANGAQLSGSKPLMEAIE

KAKKAGVSVVVAAGNERVYGSDHDDPLATNPDYGLVGSPSTGRTPTSVAAINSKWVIQRLMTVKELENRADLN

HGKAIYSESVDFKDIKDSL 3.5 Homologous sequences of other *S. pyogenes* isolates and/or serotypes
> Spy0416A-6/Schmitz 1/7 (serotype 4); SEQ ID NO: 100
AVIDTGIDPAHQSMRISDVSTAKVKSKEDMLARQKAAGINYGSWINDKVVFAHNYVENSDNIKENQFGDFDED

WENFEFDAEPKAIKKNKIYRPQSTQAPKETVIKTEETDGSHDIDWTQTDDDTKYESHGMHVTGIVAGNSKEAA

ATGERFLGIAPEAQVMFMRVFANDVMGSAESLFIKAIEDAVALGADVINLSLGTANGAQLSGSKPLMEAIEKA

KKAGVSVVVAAGNERVYGSDHDDPLATNPDYGLVGSPSTGRTPTSVAAINSKWVIQRLMTAKELENRADLNHG

KAIYSESVDFKDIKDSL

> Spy0416A-6/Schmitz 1/39 (serotype 12); SEQ ID NO: 101
AVIDTGIDPAHQSMRISDVSTAKVKSKEDMLARQKAAGINYGSWINDKVVFAHNYVENSDNIKENQFEDFDED

WENFEFDAEAEPKAIKKHKIYRPQSTQAPKETVIKTEETDGSHDIDWTQTDDDTKYESHGMHVTGIVAGNSKE

AAATGERFLGIAPEAQVMFMRVFANDVMGSAESLFIKAIEDAVALGADVINLSLGTANGAQLSGSKPLMEAIE

KAKKAGVSVVVAAGNERVYGSDHDDPLATNPDYGLVGSPSTGRTPTSVAAINSKWVIQRLMTVKELENRADLN

HGKAIYSESVDFKDIKDSL

> Spy0416A-6/Schmitz 1/55 (serotype 118); SEQ ID NO: 102
AVIDTGIDPAHQSMRISDVSTAKVKSKEDMLARQKAAGINYGSWINDKVVFAHNYVENSDNIKENQFEDFDED

WENFEFDAEAEPKAIKKHKIYRPQSTQAPKETVIKTEETDGSHDIDWTQTDDDTKYESHGMHVTGIVAGNSKE

AAATGERFLGIAPEAQVMFMRVFANDVMGSAESLFIKAIEDAVALGADVINLSLGTANGAQLSGSKPLMEAIE

KAKKAGVSVVVAAGNERVYGSDHDDPLATNPDYGLVGSPSTGRTPTSVAAINSKWVIQRLMTVKELENRADLN

HGKAIYSESVDFKDIKDSL

> Spy0416A-6/Schmitz 1/56 (serotype 28); SEQ ID NO: 103
AVIDTGIDPAHQSMRISDVSTAKVKSKEDMLARQKAAGINYGSWINDKVVFAHNYVENSDNIKENQFEDFDED

WENFEFDAEPKAIKKHKIYRPQSTQAPKETVIKTEETDGSHDIDWTQTDDDTKYESHGMHVTGIVAGNSKEAA

ATGERFLGIAPETQVMFMRVFANDVMGSAESLFIKAIEDAVALGADVINLSLGTANGAQLSGSKPLMEAIEKA

KKAGVSVVVAAGNERVYGSDHDDPLATNPDYGLVGSPSTGRTPTSVAAINSKWVIQRLMTVKELENRADLNHG

KAIYSESVDFKDIKDSL

> Spy0416A-6/Schmitz 1/94 (serotype 1); SEQ ID NO: 104
AVIDTGIDPAHQSMRISDVSTAKVKSKEDMLARQKAAGINYGSWINDKVVFAHNYVENSDNIKENQFEDFDED

WENFEFDAEAEPKAIKKHKIYRPQSTQAPKETVIKTEETDGSHDIDWTQTDDDTKYESHGMHVTGIVAGNSKE

AAATGERFLGIAPEAQVMFMRVFANDIMGSAESLFIKAIEDAVALGADVINLSLGTANGAQLSGSKPLMEAIE

KAKKAGVSVVVAAGNERVYGSDHDDPLATNPDYGLVGSPSTGRTPTSVAAINSKWVIQRLMTVKELENRADLN

HGKAIYSESVDFKDIKDSL

> Spy0416A-6/Schmitz 1/253 (serotype 49); SEQ ID NO: 105
AVIDTGIDPAHQSMRISDVSTAKVKSKEDMLARQKAAGINYGSWINDKVVFAHNYVENSDNIKENQFEDFDED

WENFEFDADAEPKAIKKHKIYRPQSTQAPKETVIKTEETDGSHDIDWTQTDDDTKYESHGMHVTGIVAGNSKE

AAATGERFLGIAPEAQVMFMRVFANDVMGSAESLFIKAIEDAVALGADVINLSLGTANGAQLSGSKPLMEAIE

-continued

| SEQUENCE DATA FOR AMINO ACID SEQUENCES |
|---|
| KAKKAGVSVVVAAGNERVYGSDHDDPLATNPDYGLVGSPSTGRTPTSVAAINSKWVIQRLMTVKGLENRADLN |
| HGKAIYSESVDFKDIKDSL |
| > Spy0416A-6/Schmitz 1/174 (serotype 6); SEQ ID NO: 106 |
| AVIDTGIDPAHQSMRISDVSTAKVKSKEDMLARQKAAGINYGSWINDKVVFAHNYVENSDNIKENQFEDFDED |
| WENFEFDAEAEPKAIKKHKIYRPQSTQAPKETVIKTEETDGSHDIDWTQTDDDTKYESHGMHVTGIVAGNSKE |
| AAATGERFLGIAPEAQVMFMRVFANDVMGSAESLFIKAIEDAVALGADVINLSLGTANGAQLSGSKPLMEAIE |
| KAKKAGVSVVVAAGNERVYGSDHDDPLATNPDYGLVGSPSTGRTPTSVAAINSKWVIQRLMTVKELENRADLN |
| HGKAIYSESVDFKNIKDSL |
| > Spy0416A-6/Schmitz 1/176 (serotype 83); SEQ ID NO: 107 |
| AVIDTGIDPAHQSMRISDVSTAKVKSKEDMLARQKAAGINYGSWINDKVVFAHNYVENSDNIKENQFEDFDED |
| WENFEFDAEAEPKAIKKHKIYRPQSTQAPKETVIKTEETDGSHDIDWTQTDDDTKYESHGMHVTGIVAGNSKE |
| AAATGERFLGIAPEAQVMFMRVFANDVMGSAESLFIKAIEDAVALGADVINLSLGTANGAQLSGSKPLMEAIE |
| KAKKAGVSVVVAAGNERVYGSDHDDPLATNPDYGLVGSPSTGRTPTSVAAINSKWVIQRLMTVKELENRADLN |
| HGKAIYSESVDFKNIKDSL |
| > Spy0416A-6/Schmitz 1/234 (serotype 44); SEQ ID NO: 108 |
| AVIDTGIDPAHQSMRISDVSTAKVKSKEDMLARQKAAGINYGSWINDKVVFAHNYVENSDNIKENQFEDFDED |
| WENFEFDADAEPKAIKKHKIYRPQSTQAPKETVIKTEETDGSHDIDWTQTDDDTKYESHGMHVTGIVAGNSKE |
| AAATGERFLGIAPEAQVMFMRVFANDVMGSAESLFIKAIEDAVALGADVINLSLGTANGAQLSGSKPLMEAIE |
| KAKKAGVSVVVAAGNERVYGSDHDDPLATNPDYGLVGSPSTGRTPTSVAAINSKWVIQRLMTVKELENRADLN |
| HGKAIYSESVDFKDIKDSL |
| > Spy0416A-6/Schmitz 1/22 (serotype 4); SEQ ID NO: 109 |
| AVIDTGIDPAHQSMRISDVSTAKVKSKEDMLARQKAAGINYGSWINDKVVFAHNYVENSDNIKENQFGDFDED |
| WENFEFDAEPKAIKKNKIYRPQSTQAPKETVIKTEETDGSHDIDWTQTDDDTKYESHGMHVTGIVAGNSKEAA |
| ATGERFLGIAPEAQVMFMRVFANDVMGSAESLFIKAIEDAVALGADVINLSLGTANGAQLSGSKPLMEAIEKA |
| KKAGVSVVVAAGNERVYGSDHDDPLATNPDYGLVGSPSTGRTPTSVAAINSKWVIQRLMTAKELENRADLNHG |
| KAIYSESVDFKDIKDSL |
| 3.6 Antigenic fragment Spy0416A-7 |
| > Spy0416A-7/SF370 (serotype 1); SEQ ID NO: 6 |
| SQITLKTNREKEQSQDLVSEPTTTELADTDAASMANTGSDATQKSASLPPVNTDVHDWVKTKGAWDKGYKGQG |
| KVVAVIDTGIDPAHQSMRISDVSTAKVKSKEDMLARQKAAGINYGSWINDKVVFAHNYVENSDNIKENQFEDF |
| DEDWENFEFDAEAEPKAIKKHKIYRPQSTQAPKETVIKTEETDGSHDIDWTQTDDDTKYESHGMHVTGIVAGN |
| SKEAAATGERFLGIAPEAQVMFMRVFANDIMGSAESLFIKAIEDAVALGADVINLSLGTANGAQLSGSKPLME |
| AIEKAKKAGVSVVVAAGNERVYGSDHDDPLATNPDYGLVGSPSTGRTPTSVAAINSKWVIQRLMTVKELENRA |
| DLNHGKAIYSESVDFKDIKDSLGYDKSHQFAYVKESTDAGYNAQDVKGKIALIERDPNKTYDEMIALAKKHGA |
| LGVLIFNNKPGQSNRSMRLTANGMGIPSAFISHEFGKAMSQLNGNGTGS |
| 3.7 Homologous sequences of other *S. pyogenes* isolates and/or serotypes |
| > Spy0416A-7/Schmitz 1/7 (serotype 4); SEQ ID NO: 110 |
| SQITPKTNREKEQPQGLVSEPTTTELADTDAASMANTGPDATQKSASLPPVNTDVHDWVKTKGAWDKGYKGQG |
| KVVAVIDTGIDPAHQSMRISDVSTAKVKSKEDMLARQKAAGINYGSWINDKVVFAHNYVENSDNIKENQFGDF |
| DEDWENFEFDAEPKAIKKNKIYRPQSTQAPKETVIKTEETDGSHDIDWTQTDDDTKYESHGMHVTGIVAGNSK |
| EAAATGERFLGIAPEAQVMFMRVFANDVMGSAESLFIKAIEDAVALGADVINLSLGTANGAQLSGSKPLMEAI |
| EKAKKAGVSVVVAAGNERVYGSDHDDPLATNPDYGLVGSPSTGRTPTSVAAINSKWVIQRLMTAKELENRADL |
| NHGKAIYSESVDFKDIKDSLGYDKSHQFAYVKESTDAGYKAQDVKDKIALIERDPNKTYDEMIALAKKHGALG |

-continued

| SEQUENCE DATA FOR AMINO ACID SEQUENCES |
|---|
| VLIFNNKPGQSNRSMRLTANGMGIPSAFISHEFGKAMSQLNGNGTGS |
| > Spy0416A-7/Schmitz 1/39 (serotype 12); SEQ ID NO: 111<br>SQITLKTNREKEQPQGLVSEPTTTELADTDAAPMANTGPDATQKSASLPPVNTDVHDWVKTKGAWDKGYKGQG |
| KVVAVIDTGIDPAHQSMRISDVSTAKVKSKEDMLARQKAAGINYGSWINDKVVFAHNYVENSDNIKENQFEDF |
| DEDWENFEFDAEAEPKAIKKHKIYRPQSTQAPKETVIKTEETDGSHDIDWTQTDDDTKYESHGMHVTGIVAGN |
| SKEAAATGERFLGIAPEAQVMFMRVFANDVMGSAESLFIKAIEDAVALGADVINLSLGTANGAQLSGSKPLME |
| AIEKAKKAGVSVVVAAGNERVYGSDHDDPLATNPDYGLVGSPSTGRTPTSVAAINSKWVIQRLMTVKELENRA |
| DLNHGKAIYSESVDFKDIKDSLGYDKSHQFAYVKESTDAGYNAQDVKGKIALIERDPNKTYDEMIALAKKHGA |
| LGVLIFNNKPGQSNRSMRLTANGMGIPSAFISHEFGKAMSQLNGNGTGS |
| > Spy0416A-7/Schmitz 1/55 (serotype 118); SEQ ID NO: 112<br>SQVTPETNREKEQPQGLVSEPTTTELADTDAAPMANTGSDATQKSASLPPVNTDVHDWVKTKGAWDKGYKGQG |
| KVVAVIDTGIDPAHQSMRISDVSTAKVKSKEDMLARQKAAGINYGSWINDKVVFAHNYVENSDNIKENQFEDF |
| DEDWENFEFDAEAEPKAIKKHKIYRPQSTQAPKETVIKTEETDGSHDIDWTQTDDDTKYESHGMHVTGIVAGN |
| SKEAAATGERFLGIAPEAQVMFMRVFANDVMGSAESLFIKAIEDAVALGADVINLSLGTANGAQLSGSKPLME |
| AIEKAKKAGVSVVVAAGNERVYGSDHDDPLATNPDYGLVGSPSTGRTPTSVAAINSKWVIQRLMTVKELENRA |
| DLNHGKAIYSESVDFKDIKDSLGYDKSHQFAYVKESTDAGYNAQNVKGKIALIERDPNKTYDEMIALAKKHGA |
| LGVLIFNNKPGQSNRSMRLTANGMGIPSAFISHEFGKAMSQLNGNGTGS |
| > Spy0416A-7/Schmitz 1/56 (serotype 28); SEQ ID NO: 113<br>SQITPKINREKEQPQGLVSEPTTTELADTDAAPMANTGPDATQKSASLPPVNTDVHDWVKTKGAWDKGYKGQG |
| KVVAVIDTGIDPAHQSMRISDVSTAKVKSKEDMLARQKAAGINYGSWINDKVVFAHNYVENSDNIKENQFEDF |
| DEDWENFEFDAEPKAIKKHKIYRPQSTQAPKETVIKTEETDGSHDIDWTQTDDDTKYESHGMHVTGIVAGNSK |
| EAAATGERFLGIAPETQVMFMRVFANDVMGSAESLFIKAIEDAVALGADVINLSLGTANGAQLSGSKPLMEAI |
| EKAKKAGVSVVVAAGNERVYGSDHDDPLATNPDYGLVGSPSTGRTPTSVAAINSKWVIQRLMTVKELENRADL |
| NHGKAIYSESVDFKDIKDSLGYDKSHQFAYVKESTDAGYNAQDVKGKIALIERDPNKTYDEMIALAKKHGALG |
| VLIFNNKPGQSNRSMRLTANGMGIPSAFISHEFGKAMSQLNGNGTGS |
| > Spy0416A-7/Schmitz 1/94 (serotype 1); SEQ ID NO: 114<br>SQITLKTNREKEQSQDLVSEPTTTELADTDAASMANTGSDATQKSASLPPVNTDVHDWVKTKGAWDKGYKGQG |
| KVVAVIDTGIDPAHQSMRISDVSTAKVKSKEDMLARQKAAGINYGSWINDKVVFAHNYVENSDNIKENQFEDF |
| DEDWENFEFDAEAEPKAIKKHKIYRPQSTQAPKETVIKTEETDGSHDIDWTQTDDDTKYESHGMHVTGIVAGN |
| SKEAAATGERFLGIAPEAQVMFMRVFANDIMGSAESLFIKAIEDAVALGADVINLSLGTANGAQLSGSKPLME |
| AIEKAKKAGVSVVVAAGNERVYGSDHDDPLATNPDYGLVGSPSTGRTPTSVAAINSKWVIQRLMTVKELENRA |
| DLNHGKAIYSESVDFKDIKDSLGYDKSHQFAYVKESTDAGYNAQDVKGKIALIERDPNKTYDEMIALAKKHGA |
| LGVLIFNNKPGQSNRSMRLTANGMGIPSAFISHEFGKAMSQLNGNGTGS |
| > Spy0416A-7/Schmitz 1/253 (serotype 49); SEQ ID NO: 115<br>SQVTPETNREKEQPQGLVSEPTTTELADTDAAPMANTGPDATQKSASLPPVNTDVHDWVKTKGAWDKGYKGQG |
| KVVAVIDTGIDPAHQSMRISDVSTAKVKSKEDMLARQKAAGINYGSWINDKVVFAHNYVENSDNIKENQFEDF |
| DEDWENFEFDADAEPKAIKKHKIYRPQSTQAPKETVIKTEETDGSHDIDWTQTDDDTKYESHGMHVTGIVAGN |
| SKEAAATGERFLGIAPEAQVMFMRVFANDVMGSAESLFIKAIEDAVALGADVINLSLGTANGAQLSGSKPLME |
| AIEKAKKAGVSVVVAAGNERVYGSDHDDPLATNPDYGLVGSPSTGRTPTSVAAINSKWVIQRLMTVKGLENRA |
| DLNHGKAIYSESVDFKDIKDSLGYDKSHQFAYVKESTDAGYNAQDVKGKIALIERDPNKTYDEMIALAKKHGA |
| LGLLIFNNKSGQSNRSMRLTANGMGIPSAFISHEFGKAMSQLNGNGTGS |
| > Spy0416A-7/Schmitz 1/174 (serotype 6); SEQ ID NO: 116 |

-continued

SEQUENCE DATA FOR AMINO ACID SEQUENCES

SQITPKTNREKEQSQDLVSEPTTTELADTDAASMANTGPDATQKSASLPPVNTDVHDWVKTKGAWDKGYKGQG

KVVAVIDTGIDPAHQSMRISDVSTAKVKSKEDMLARQKAAGINYGSWINDKVVFAHNYVENSDNIKENQFEDF

DEDWENFEFDAEAEPKAIKKHKIYRPQSTQAPKETVIKTEETDGSHDIDWTQTDDDTKYESHGMHVTGIVAGN

SKEAAATGERFLGIAPEAQVMFMRVFANDVMGSAESLFIKAIEDAVALGADVINLSLGTANGAQLSGSKPLME

AIEKAKKAGVSVVVAAGNERVYGSDHDDPLATNPDYGLVGSPSTGRTPTSVAAINSKWVIQRLMTVKELENRA

DLNHGKAIYSESVDFKNIKDSLGYDKSHQFAYVKESTDAGYNAQDVKGKIALIERDPNKTYDEMIALAKKHGA

LGVLIFNNKPGQSNRSMRLTSNGMGIPSAFISHEFGKAMSQLNGNGTGS

> Spy0416A-7/Schmitz 1/176 (serotype 83); SEQ ID NO: 117
SQITLKTNREKEQPQGLVSEPTTTELADTDAAPMANTGPDATQKSASLPPVNTDVHDWVKTKGAWDKGYKGQG

KVVAVIDTGIDPAHQSMRISDVSTAKVKSKEDMLARQKAAGINYGSWINDKVVFAHNYVENSDNIKENQFEDF

DEDWENFEFDAEAEPKAIKKHKIYRPQSTQAPKETVIKTEETDGSHDIDWTQTDDDTKYESHGMHVTGIVAGN

SKEAAATGERFLGIAPEAQVMFMRVFANDVMGSAESLFIKAIEDAVALGADVINLSLGTANGAQLSGSKPLME

AIEKAKKAGVSVVVAAGNERVYGSDHDDPLATNPDYGLVGSPSTGRTPTSVAAINSKWVIQRLMTVKELENRA

DLNHGKAIYSESVDFKNIKDSLGYDKSHQFAYVKESTDAGYKAQDVKGKIALIERDPNKTYDEMIALAKKHGA

LGVLIFNNKPGQSNRSMRLTANGMGIPSAFISHEFGKAMSQLNGNGTGS

> Spy0416A-7/Schmitz 1/234 (serotype 44); SEQ ID NO: 118
SQITPKTNREKEQSQDLVSEPTTTELADTDAASMANTGSDATQKSASLPPVNTDVHDWVKTKGAWDKGYKGQG

KVVAVIDTGIDPAHQSMRISDVSTAKVKSKEDMLARQKAAGINYGSWINDKVVFAHNYVENSDNIKENQFEDF

DEDWENFEFDADAEPKAIKKHKIYRPQSTQAPKETVIKTEETDGSHDIDWTQTDDDTKYESHGMHVTGIVAGN

SKEAAATGERFLGIAPEAQVMFMRVFANDVMGSAESLFIKAIEDAVALGADVINLSLGTANGAQLSGSKPLME

AIEKAKKAGVSVVVAAGNERVYGSDHDDPLATNPDYGLVGSPSTGRTPTSVAAINSKWVIQRLMTVKELENRA

DLNHGKAIYSESVDFKDIKDSLGYDKSHQFAYVKESTDAGYKAQDVKDKIALIERDPNKTYDEMIALAKKHGA

LGVLIFNNKPGQSNRSMRLTANGMGIPSAFISHEFGKAMSQLNGNGTGS

> Spy0416A-7/Schmitz 1/22 (serotype 4); SEQ ID NO: 119
SQITPKTNREKEQPQGLVSEPTTTELADTDAASMANTGPDATQKSASLPPVNTDVHDWVKTKGAWDKGYKGQG

KVVAVIDTGIDPAHQSMRISDVSTAKVKSKEDMLARQKAAGINYGSWINDKVVFAHNYVENSDNIKENQFGDF

DEDWENFEFDAEPKAIKKNKIYRPQSTQAPKETVIKTEETDGSHDIDWTQTDDDTKYESHGMHVTGIVAGNSK

EAAATGERFLGIAPEAQVMFMRVFANDVMGSAESLFIKAIEDAVALGADVINLSLGTANGAQLSGSKPLMEAI

EKAKKAGVSVVVAAGNERVYGSDHDDPLATNPDYGLVGSPSTGRTPTSVAAINSKWVIQRLMTAKELENRADL

NHGKAIYSESVDFKDIKDSLGYDKSHQFAYVKESTDAGYKAQDVKDKIALIERDPNKTYDEMIALAKKHGALG

VLIFNNKPGQSNRSMRLTANGMGIPSAFISHEFGKAMSQLNGNGTGS 3.8 Full length Spy0416B
> Spy0416B/SF370 (serotype 1); SEQ ID NO: 56
HVDPQKGRFTLTSHSLKTYQGGEVTVPANGKVTVRVTMDVSQFTKELTKQMPNGYYLEGFVRFRDSQDDQLNR

VNIPFVGFKGQFENLAVAEESIYRLKSQGKTGFYEDESGPKDDIYVGKHFTGLVTLGSETNVSTKTISDNGLH

TLGTFKNADGKFILEKNAQGNPVLAISPNGDNNQDFAAFKGVFLRKYQGLKASVYHASDKEHKNPLWVSPESF

KGDKNFNSDIRFAKSTTLLGTAFSGKSLTGAELPDGHYHYVVSYYPDVVGAKRQEMTFDMILDRQKPVLSQAT

FDPETNRFKPEPLKDRGLAGVRKDSVFYLERKDNKPYTVTINDSYKYVSVEDNKTFVERQADGSFILPLDKAK

LGDFYYMVEDFAGNVAIAKLGDHLPQTLGKTPIKLKLTDGNYQTKETLKDNLEMTQSDTGLVTNQAQLAVVHR

NQPQSQLTKMNQDFFISPNEDGNKDFVAFKGLKNNVYNDLTVNVYAKDDHQKQTPIWSSQAGASVSAIESTAW

YGITARGSKVMPGDYQYVVTYRDEHGKEHQKQYTISVNDKKPMITQGRFDTINGVDHFTPDKTKALDSSGIVR

EEVFYLAKKNGRKFDVTEGKDGITVSDNKVYIPKNPDGSYTISKRDGVTLSDYYYLVEDRAGNVSFATLRDLK

-continued

SEQUENCE DATA FOR AMINO ACID SEQUENCES

AVGKDKAVVNFGLDLPVPEDKQIVNFTYLVRDADGKPIENLEYYNNSGNSLILPYGKYTVELLTYDTNAAKLE

SDKIVSFTLSADNNFQQVTFKITMLATSQITAHFDHLLPEGSRVSLKTAQDQLIPLEQSLYVPKAYGKTVQEG

TYEVVVSLPKGYRIEGNTKVNTLPNEVHELSLRLVKVGDASDSTGDHKVMSKNNSQALTASATPTKSTTSATA

KALPST

4. Spy0872
4.1 Full length Spy0872
> Spy0872/SF370 (serotype 1); SEQ ID NO: 120
DQVDVQFLGVNDFHGALDNTGTAYTPSGKIPNAGTAAQLGAYMDDAEIDFKQANQDGTSIRVQAGDMVGASPA

NSALLQDEPTVKVFNKMKFEYGTLGNHEFDEGLDEFNRIMTGQAPDPESTINDITKQYEHEASHQTIVIANVI

DKKTKDIPYGWKPYAIKDIAINDKIVKIGFIGVVTTEIPNLVLKQNYEHYQFLDVAETIAKYAKELQEQHVHA

IVVLAHVPATSKDGVVDHEMATVMEKVNQIYPEHSIDIIFAGHNHQYTNGTIGKTRIVQALSQGKAYADVRGT

LDTDTNDFIKTPSANVVAVAPGIKTENSDIKAIINHANDIVKTVTERKIGTATNSSTISKTENIDKESPVGNL

ATTAQLTIAKKTFPTVDFAMTNNGGIRSDLVVKNDRTITWGAAQAVQPFGNILQVIQMTGQHIYDVLNQQYDE

NQTYFLQMSGLTYTYTDNDPKNSDTPFKIVKVYKDNGEEINLTTTYTVVVNDFLYGGGDGFSAFKKAKLIGAI

NTDTEAFITYITNLEASGKTVNATIKGVKNYVTSNLESSTKVNSAGKHSIISKVFRNRDGNTVSSEVISDLLT

STENTNNSLGKKETTTNKNTISSSTLPIT 4.2 Antigenic fragment Spy0872-2
> Spy0872-2/SF370 (serotype 1); SEQ ID NO: 7
AIINHANDIVKTVTERKIGTATNSSTISKTENIDKESPVGNLATTAQLTIAKKTFPTVDFAMTNNGGIRSDLV

VKNDRTITWGAAQAVQPFGNILQVIQMTGQHIYDVLNQQYDENQTYFLQMSGLTYTYTDNDPKNSDTPFKIVK

VYKDNGEEINLTTTYTVVVNDFLYGGGDGFSAFKKAKLIGAINTDTEAFITYITNLEASGKTVNATIKGVKNY

VTSNLESSTKVNSAGKHSIISKVFRNRDGNTVSSEVISDLLTSTENTNNSLGKKETTTNKNTISSSTLPIT 4.3 Homologous sequences of other *S. pyogenes* isolates and/or serotypes
> Spy0872-2/Schmitz 1/7 (serotype 4); SEQ ID NO: 121
AIINHANDIVKTVTERKIGTATNSSTISKTENIDKESPVGNLVTTAQLTIAKKTFPTVDFAMTNNGGIRSDLV

VKNDRTITWEAAQAVQPFGNILQVIQMTGQHIYDVLNQQYDENQTYFLQMSGLTYTYTDNDPKNSDTPFKIVK

VYKDNGEEINLTTTYTVVVNDFLYGGGDGFSAFKKAKLIGAINTDTEAFITYITNLEASGKTVNATIKGVKNY

VTSNLESSTKVNSAGKHSIIIIISKVFRNRDGNIVSSEIISDLLTSTENTNNSFGKKEITTNKNTISNSTLPIT

> Spy0872-2/Schmitz 1/39 (serotype 12); SEQ ID NO: 122
AIINHANDIVKTVTERKIGTATNSSTISKTENIDKESPVGNLVTTAQLTIAKKTFPTVDFAMTNNGGIRSDLV

VKNDRTITWGAAQAVQPFGNILQVIQMTGQHIYDVLNQQYDENQTYFLQMSGLTYTYTDNDPKNSDTPFKIVK

VYKDNGEEINLTTTYTVVVNDFLYGGGDGFSAFKKAKLIGAINTDTEAFITYITNLEASGKTVNATIKGVKNY

VTSNLESSTKVNSAGKHSIISKVFRNRDGNIVSSEIISDLLTSTENTNNSLGKKETTTNKNTISSSTLPIT

> Spy0872-2/Schmitz 1/55 (serotype 118); SEQ ID NO: 123
AIINHANDIVKTVTERKIGTATNSSTISKTENIDKESPVGNLVTTAQLTIAKKTFPTVDFAMTNNGGIRSDLV

VKNDRTITWGAAQAVQPFGNILQVIQMTGQHIYDVLNQQYDENQTYFLQMSGLTYTYTDNDPKNSDIPFKIVK

VYKDNGEEINLTTTYTVVVNDFLYGGGDGFSAFKKAKLIGAINTDTEAFITYITNLEASGKTVNATIKGVKNY

VTSNLESSTKVNSAGKHSIISKVFRNRDGNIVSSEVISDLLTSTENTNNSLGKKETTTNKNTISSSTLPIT

> Spy0872-2/Schmitz 1/56 (serotype 28); SEQ ID NO: 124
AIINHANDIVKTVTERKIGTATNSSTISKTENIDKESPVGNLVTTAQLTIAKKTFPTVDFAMTNNGGIRSDLV

VKNDRTITWGAAQAVQPFGNILQVIQMTGQHIYDVLNQQYDENQTYFLQMSGLTYTYTDNDPKNSDTPFKIVK

VYKDNGEEINLTTTYTVVVNDFLYGGGDGFSAFKKAKLIGAINTDTEAFITYITNLEASGKTVNATIKGVKNY

VTSNLESSTKVNSAGKHSIISKVFRNRDGNIVSSEIISDLLTSTENTNNSLGKKETTTNKNTISSSTLPIT

> Spy0872-2/Schmitz 1/94 (serotype 1); SEQ ID NO: 125

-continued

SEQUENCE DATA FOR AMINO ACID SEQUENCES

AIINHANDIVKTVTERKIGTATNSSTISKTENIDKESPVGNLATTAQLTIAKKTFPTVDFAMTNNGGIRSDLV

VKNDRTITWGAAQAVQPFGNILQVIQMTGQHIYDVLNQQYDENQTYFLQMSGLTYTYTDNDPKNSDTPFKIVK

VYKDNGEEINLTTTYTVVVNDFLYGGGDGFSAFKKAKLIGAINTDTEAFITYITNLEASGKTVNATIKGVKNY

VTSNLESSTKVNSAGKHSIISKVFRNRDGNTVSSEVISDLLTSTENTNNSLGKKETTTNKNTISSSTLPIT

> Spy0872-2/Schmitz 1/253 (serotype 49); SEQ ID NO: 126
AIINHANDIVKTVTERKIGTATNSSTISKTENIDKESPVGNLVTTAQLTIAKKTFPTVDFAMTNNGGIRSDLV

VKNDRTITWGAAQAVQPFGNILQVIQMTGQHIYDVLNQQYDENQTYFLQMSGLTFTYTDNDPKNSDTPFKIVK

VYKDNGEEINLTTTYTVVVNDFLYGGGDGFSAFKKAKLIGAINTDTEAFITYITNLEASGKTVNATIKGVKNY

VTSNLESSTKVNSAGKHSIISKVFRNRDGNIVSSEIISDLLTSTENTNNSLGKKETTTNKNTISSSTLPIT

> Spy0872-2/Schmitz 1/176 (serotype 83); SEQ ID NO: 127
AIINHANDIVKTVTERKIGTATNSSTISKTENIDKESPVGNLVTTAQLTIAKKTFPTVDFAMTNNGGIRSDLV

VKNDRTITWGAAQAVQPFGNILQVIQMTGQHIYDVLNQQYDENQTYFLQMSGLTYTYTDNDPKNSDTPFKIVK

VYKDNGEEINLTTTYTVVVNDFLYGGGDGFSAFKKAKLVGAINTDTEAFITYITNLQASGKTVNATIKGVKNY

VTSNLERSTKINSAGKHSIISKVFRNRDGNIVSSEVISDLLTSTENTNNSFGKKETTTNKNTISNSTLPIT

> Spy0872-2/Schmitz 1/177 (serotype 22); SEQ ID NO: 128
AIINHANDIVKTVTERKIGTATNSSTISKTENIDKESPVGNLVTTAQLTIAKKTFPTVDFAMTNNGGIRSDLV

VKNDRTITWGAAQAVQPFGNILQVIQMTGQHIYDVLNQQYDENQTYFLQMSGLTYTYTDNDPKNSDTPFKIVK

VYKDNGEEINLTTTYTVVVNDFLYGGGDGFSAFKKAKLIGAINTDTEAFITYITNLEASGKTVNATIKGVKNY

VTSNLESSTKVNSAGKHSIISKVFRNRDGNIVSSEIISDLLTSTENTNNSLGKKETTTNKNTISSSTLPIT

> Spy0872-2/Schmitz 1/234 (serotype 44); SEQ ID NO: 129
AIINHANDIVKTVTERKIGTATNSSTISKTENIDKESPVGNLVTTAQLTIAKKTFPTVDFAMTNNGGIRSDLV

VKNDRTITWGAAQAVQPFGNILQVIQMTGQHIYDVLNQQYDENQTYFLQMSGLTYTYTDNDPKNSDTPFKIVK

VYKDNGEEINLTTTYTVVVNDFLYGGGDGFSAFKKAKLIGAINTDTEAFITYITNLEASGKTVNATIKGVKNY

VTSNLESSTKVNSAGKHSIISKVFRNRDGNIVSSEIISDLLTSTENTNNSLGKKETTTNKNTISSSTLPIT

> Spy0872-2/Schmitz 1/22 (serotype 4); SEQ ID NO: 130
AIINHANDIVKTVTERKIGTATNSSTISKTENIDKESPVGNLVTTAQLTIAKKTFPTVDFAMTNNGGIRSDLV

VKNDRTITWEAAQAVQPFGNILQVIQMTGQHIYDVLNQQYDENQTYFLQMSGLTYTYTDNDPKNSDTPFKIVK

VYKDNGEEINLTTTYTVVVNDFLYGGGDGFSAFKKAKLIGAINTDTEAFITYITNLEASGKTVNATIKGVKNY

VTSNLESSTKVNSAGKHSIIIISKVFRNRDGNIVSSEIISDLLTSTENTNNSFGKKEITTNKNTISNSTLPIT

5. Further Sequences
> Spy0488/SF370 (serotype 1); SEQ ID NO: 8
LRQIQSIRLIDVLELAFGVGYKEETTSQFSSDQPSQVVLYRGEANTVRFAYTNQMSLMKDIRIALDGSDKSLT

AQIVPGMGHVYEGFQTSARGIFTMSGVPESTVPVANPNVQTKYIRYFKVIDDMHNTMYKGTVFLVQPQAWKYT

MKSVDQLPVDDLNHIGVAGIERMTTLIKNAGALLTTGGSGAFPDNIKVSINPKGRQATITYGDGSTDIIPPAV

LWKKGSVKEPTEADQSVGTPTPGIPGKFKRDQSLNEHEAMVNVEPLSHVVKDNIKVIDEKSTGRFEPFRPNED

EKEKPASDVKVRPAEVGSWLEPATALPSVEMSAEDRLKS

> Spy0895/SF370 (serotype 1); SEQ ID NO: 9
TNNQTLDILLDVYAYNHAFRIAKALPNIPKTALYLLEMLKERRELNLAFLAEHAAENRTIEDQYHCSLWLNQS

LEDEQIANYILDLEVKVKNGAIIDFVRSVSPILYRLFLRLITSEIPNFKAYIFDTKNDQYDTWHFQAMLESDH

EVFKAYLSQKQSRNVTTKSLADMLTLTSLPQEIKDLVFLLRHFEKAVRNPLAHLIKPFDEEELHRTTHFSSQA

FLENIITLATFSGVIYRREPFYFDDMNAIIKKELSLWRQSIV

> Spy1536/SF370 (serotype 1); SEQ ID NO: 131
IEMPGGAYDIRTVLQVNGKEDKRKGAYQFVAVGISRASLAQLLYAWLTPFTEISTAEDTTGGYSDADFLRINQ

FYMETSQNAAIYQALSLAGKPVTLDYKGVYVLDVNNESTFKGTLHLADTVTGVNGKQFTSSAELIDYVSHLKL

-continued

| SEQUENCE DATA FOR AMINO ACID SEQUENCES |
|---|
| GDEVTVQFTSDNKPKKGVGRIIKLKNGKNGIGIALTDHTSVNSEDTVIFSTKGVGGPSAGLMFTLDIYDQITK |
| EDLRKGRTIAGTGTIGKDGEVGDIGGAGLKVVAAAEAGADIFFVPNNPVDKEIKKVNPNAISNYEEAKRAAKR |
| LKTKMKIVPVTTVQEALVYLRK |
| > Spy1666/SF370 (serotype 1); SEQ ID NO: 132<br>TKEFHHVTVLLHETVDMLDIKPDGIYVDATLGGSGHSAYLLSKLGEEGHLYCFDQDQKAIDNAQVTLKSYIDK |
| GQVTFIKDNFRHLKARLTALGVDEIDGILYDLGVSSPQLDERERGFSYKQDAPLDMRMDRQSLLTAYEVVNTY |
| PFNDLVKIFFKYGEDKFSKQIARKIEQARAIKPIETTTELAELIKAAKPAKELKKKGHPAKQIFQAIRIEVND |
| ELGAADESIQDAMELLALDGRISVITFHSLEDRLTKQLFKEASTVDVPKGLPLIPEDMKPKFELVSRKPILPS |
| HSELTANKRAHSAKLRVAKKIRK |
| > Spy1727/SF370 (serotype 1); SEQ ID NO: 10<br>VTTTEQELTLTPLRGKSGKAYKGTYPNGECVFIKLNTTPILPALAKEQIAPQLLWAKRMGNGDMMSAQEWLNG |
| RTLTKEDMNSKQIIHILLRLHKSKKLVNQLLQLNYKIENPYDLLVDFEQNAPLQIQQNSYLQAIVKELKRSLP |
| EFKSEVATIVHGDIKHSNWVITTSGMIFLVDWDSVRLTDRMYDVAYLLSHYIPRSRWSEWLSYYGYKNNDKVM |
| QKIIWYGQFSHLTQILKCFDKRDMEHVNQEIYALRKFREIFRKK |

| SEQUENCE DATA FOR DNA SEQUENCES |
|---|
| 1. Spy0269<br>1.1 Full length Spy0269<br>> Spy0269/SF370 (serotype 1); SEQ ID NO: 133<br>ATGGACTTAGAACAAACGAAGCCAAACCAAGTTAAGCAGAAAATTGCTTTAACCTCAACAATTGCTTTATTGA |
| GTGCCAGTGTAGGCGTATCTCACCAAGTCAAAGCAGATGATAGAGCCTCAGGAGAAACGAAGGCGAGTAATAC |
| TCACGACGATAGTTTACCAAAACCAGAAACAATTCAAGAGGCAAAGGCAACTATTGATGCAGTTGAAAAAACT |
| CTCAGTCAACAAAAAGCAGAACTGACAGAGCTTGCTACCGCTCTGACAAAAACTACTGCTGAAATCAACCACT |
| TAAAAGAGCAGCAAGATAATGAACAAAAAGCTTTAACCTCTGCACAAGAAATTTACACTAATACTCTTGCAAG |
| TAGTGAGGAGACGCTATTAGCCCAAGGAGCCGAACATCAAAGAGAGTTAACAGCTACTGAAACAGAGCTTCAT |
| AATGCTCAAGCAGATCAACATTCAAAAGAGACTGCATTGTCAGAACAAAAAGCTAGCATTTCAGCAGAAACTA |
| CTCGAGCTCAAGATTTAGTGGAACAAGTCAAAACGTCTGAACAAAATATTGCTAAGCTCAATGCTATGATTAG |
| CAATCCTGATGCTATCACTAAAGCAGCTCAAACGGCTAATGATAATACAAAAGCATTAAGCTCAGAATTGGAG |
| AAGGCTAAAGCTGACTTAGAAAATCAAAAAGCTAAAGTTAAAAAGCAATTGACTGAAGAGTTGGCAGCTCAGA |
| AAGCTGCTCTAGCAGAAAAAGAGGCAGAACTTAGTCGTCTTAAATCCTCAGCTCCGTCTACTCAAGATAGCAT |
| TGTGGGTAATAATACCATGAAAGCACCGCAAGGCTATCCTCTTGAAGAACTTAAAAAATTAGAAGCTAGTGGT |
| TATATTGGATCAGCTAGTTACAATAATTATTACAAAGAGCATGCAGATCAAATTATTGCCAAAGCTAGTCCAG |
| GTAATCAATTAAATCAATACCAAGATATTCCAGCAGATCGTAATCGCTTTGTTGATCCCGATAATTTGACACC |
| AGAAGTGCAAAATGAGCTAGCGCAGTTTGCAGCTCACATGATTAATAGTGTAAGAAGACAATTAGGTCTACCA |
| CCAGTTACTGTTACAGCAGGATCACAAGAATTTGCAAGATTACTTAGTACCAGCTATAAGAAAACTCATGGTA |
| ATACAAGACCATCATTTGTCTACGGACAGCCAGGGGTATCAGGGCATTATGGTGTTGGGCCTCATGATAAAAC |
| TATTATTGAAGACTCTGCCGGAGCGTCAGGGCTCATTCGAAATGATGATAACATGTACGAGAATATCGGTGCT |
| TTTAACGATGTGCATACTGTGAATGGTATTAAACGTGGTATTTATGACAGTATCAAGTATATGCTCTTTACAG |
| ATCATTTACACGGAAATACATACGGCCATGCTATTAACTTTTTACGTGTAGATAAACATAACCCTAATGCGCC |
| TGTTTACCTTGGATTTTCAACCAGCAATGTAGGATCTTTGAATGAACACTTTGTAATGTTTCCAGAGTCTAAC |

-continued

| SEQUENCE DATA FOR DNA SEQUENCES |
|---|
| ATTGCTAACCATCAACGCTTTAATAAGACCCCTATAAAAGCCGTTGGAAGTACAAAAGATTATGCCCAAAGAG |
| TAGGCACTGTATCTGATACTATTGCAGCGATCAAAGGAAAAGTAAGCTCATTAGAAAATCGTTTGTCGGCTAT |
| TCATCAAGAAGCTGATATTATGGCAGCCCAAGCTAAAGTAAGTCAACTTCAAGGTAAATTAGCAAGCACACTT |
| AAGCAGTCAGACAGCTTAAATCTCCAAGTGAGACAATTAAATGATACTAAAGGTTCTTTGAGAACAGAATTAC |
| TAGCAGCTAAAGCAAAACAAGCACAACTCGAAGCTACTCGTGATCAATCATTAGCTAAGCTAGCATCGTTGAA |
| AGCCGCACTGCACCAGACAGAAGCCTTAGCAGAGCAAGCCGCAGCCAGAGTGACAGCACTGGTGGCTAAAAAA |
| GCTCATTTGCAATATCTAAGGGACTTTAAATTGAATCCTAACCGCCTTCAAGTGATACGTGAGCGCATTGATA |
| ATACTAAGCAAGATTTGGCTAAAACTACCTCATCTTTGTTAAATGCACAAGAAGCTTTAGCAGCCTTACAAGC |
| TAAACAAAGCAGTCTAGAAGCTACTATTGCTACCACAGAACACCAGTTGACTTTGCTTAAAACCTTAGCTAAC |
| GAAAAGGAATATCGCCACTTAGACGAAGATATAGCTACTGTGCCTGATTTGCAAGTAGCTCCACCTCTTACGG |
| GCGTAAAACCGCTATCATATAGTAAGATAGATACTACTCCGCTTGTTCAAGAAATGGTTAAAGAAACGAAACA |
| ACTATTAGAAGCTTCAGCAAGATTAGCTGCTGAAAATACAAGTCTTGTAGCAGAAGCGCTTGTTGGCCAAACC |
| TCTGAAATGGTAGCAAGTAATGCCATTGTGTCTAAAATCACATCTTCGATTACTCAGCCCTCATCTAAGACAT |
| CTTATGGCTCAGGATCTTCTACAACGAGCAATCTCATTTCTGATGTTGATGAAAGTACTCAAAGAGCTCTTAA |
| AGCAGGAGTCGTCATGTTGGCAGCTGTCGGCCTCACAGGATTTAGGTTCCGTAAGGAATCTAAGTGA |
| 1.2 Antigenic fragment Spy0269-1<br>> Spy0269-1/SF370 (serotype 1); SEQ ID NO: 11<br>GATGATAGAGCCTCAGGAGAAACGAAGGCGAGTAATACTCACGACGATAGTTTACCAAAACCAGAAACAATTC |
| AAGAGGCAAAGGCAACTATTGATGCAGTTGAAAAAACTCTCAGTCAACAAAAAGCAGAACTGACAGAGCTTGC |
| TACCGCTCTGACAAAAACTACTGCTGAAATCAACCACTTAAAAGAGCAGCAAGATAATGAACAAAAAGCTTTA |
| ACCTCTGCACAAGAAATTTACACTAATACTCTTGCAAGTAGTGAGGAGACGCTATTAGCCCAAGGAGCCGAAC |
| ATCAAAGAGAGTTAACAGCTACTGAAACAGAGCTTCATAATGCTCAAGCAGATCAACATTCAAAAGAGACTGC |
| ATTGTCAGAACAAAAAGCTAGCATTTCAGCAGAAACTAGTCGAGCTCAAGATTTAGTGGAACAAGTCAAAACG |
| TCTGAAGAAAATATTGCTAAGCTCAATGCTATGATTAGCAATCCTGATGCTATCACTAAAGCAGCTCAAACGG |
| CTAATGATAATACAAAAGCATTAAGCTCAGAATTGGAGAAGGCTAAAGCTGACTTAGAAAATCAAAAAGCTAA |
| AGTTAAAAAGCAATTGACTGAAGAGTTGGCAGCTCAGAAAGCTGCTCTAGCAGAAAAAGAGGCAGAACTTAGT |
| CGTCTTAAATCCTCAGCTCCGTCTACTCAAGATAGCATTGTGGGTAATAATACCATGAAAGCACCGCAAGGCT |
| ATCCTCTTGAAGAACTTAAAAAATTAGAAGCTAGTGGTTATATTGGATCAGCTAGTTACAATAATTATTACAA |
| AGAGCATGCAGATCAAATTATTGCCAAAGCTAGTCCAGGTAATCAATTAAATCAATACCAAGATATTCCAGCA |
| GATCGTAATCGCTTTGTTGATCCCGATAATTTGACACCAGAAGTGCAAAATGAGCTAGCGCAGTTTGCAGCTC |
| ACATGATTAATAGTGTAAGAAGACAATTAGGTCTACCACCAGTTACTGTTACAGCAGGATCACAAGAATTTGC |
| AAGATTACTTAGTACCAGCTATAAGAAAACTCATGGTAATACAAGACCATCATTTGTCTACGGACAGCCAGGG |
| GTATCAGGGCATTATGGTGTTGGGCCTCATGATAAAACTATTATTGAAGACTCTGCCGGAGCGTCAGGGCTCA |
| TTCGAAATGATGATAACATGTACGAGAATATCGGTGCTTTTAACGATGTGCATACTGTGAATGGTATTAAACG |
| TGGTATTTATGACAGTATCAAGTATATGCTCTTTACAGATCATTTACACGGAAATACATACGGCCATGCTATT |
| AACTTTTTACGTGTAGATAAACATAACCCTAATGCGCCTGTT |
| 1.3 Homologous sequences of other *S. pyogenes* isolates and/or serotypes<br>> Spy0269-1/Schmitz 2/14 (serotype 1); SEQ ID NO: 134<br>GATGATAGAGCCTCAGGAGAAACGAAGGCGAGTAATACTCACGACGATAGTTTACCAAAACCAGAAACAATTC |
| AAGAGGCAAAGGCAACTATTGATGCAGTTGAAAAAACTCTCAGTCAACAAAAAGCAGAACTGACAGAGCTTGC |
| TACCGCTCTGACAAAAACTACTGCTGAAATCAACAACTTAAAAGAGCAGCAAGATAATGAACAAAAAGCTTTA |

-continued

SEQUENCE DATA FOR DNA SEQUENCES

ACCTCTGCACAAGAAATTTACACTAATACTCTTGCAAGTAGTGAGGAGACGCTATTAGCCCAAGGAGCCGAAC

ATCAAAGAGAGTTAACAGCTACTGAAACAGAGCTTCATAATGCTCAAGCAGATCAACATTCAAAAGAGACTGC

ATTGTCAGAACAAAAAGCTAGCATTTCAGCAGAAACTACTCGAGCTCAAGATTTAGTGGAACAAGTCAAAACG

TCTGAACAAAATATTGCTAAGCTCAATGCTATGATTAGCAATCCTGATGCTATCACTAAAGCAGCTCAAACGG

CTAATGATAATACAAAAGCATTAAGCTCAGAATTGGAGAAGGCTAAAGCTGACTTAGAAAATCAAAAAGCTAA

AGTTAAAAAGCAATTGACTGAAGAGTTGGCAGCTCAGAAAGCTGCTCTAGCAGAAAAAGAGGCAGAACTTAGT

CGTCTTAAATCCTCAGCTCCGTCTACTCAAGATAGCATTGTGGGTAATAATACCATGAAAGCACCGCAAGGCT

ATCCTCTTGAAGAACTTAAAAAATTAGAAGCTAGTGGTTATATTGGATCAGCTAGTTACAATAATTATTACAA

AGAGCATGCAGATCAAATTATTGCCAAAGCTAGTCCAGGTAATCAATTAAATCAATACCAAGATATTCCAGCA

GATCGTAATCGCTTTGTTGATCCCGATAATTTGACACCAGAAGTGCAAAATGAGCTAGCGCAGTTTGCAGCTC

ACATGATTAATAGTGTAAGAAGACAATTAGGTCTACCACCAGTTACTGTTACAGCAGGATCACAAGAATTTGC

AAGATTACTTAGTACCAGCTATAAGAAAACTCATGGTAATACAAGACCATCATTTGTCTACGGACAGCCAGGG

GTATCAGGGCATTATGGTGTTGGGCCTCATGATAAAACTATTATTGAAGACTCTGCCGGAGCGTCAGGGCTCA

TTCGAAATGATGATAACATGTACGAGAATATCGGTGCTTTTAACGATGTGCATACTGTGAATGGTATTAAACG

TGGTATTTATGACAGTATCAAGTATATGCTCTTTACAGATCATTTACACGGAAATACATACGGCCATGCTATT

AACTTTTTACGTGTAGATAAACGTAACCCTAATGCCCCTGTT

> Spy0269-1/Schmitz 1/156 (serotype 4); SEQ ID NO: 135
GATGATAGAGCCTCAGGAGAAACGAAGGCGAGTAATACTCACGACGATAGTTTACCAAAACCAGAAACAATTC

AAGAGGCAAAGGCAACTATTGATGCAGTTGAAAAAACTCTCAGTCAACAAAAAGCAGAACTGACAGAGCTTGC

TACCGCTCTGACAAAAACTACTGCTGAAATCAACCACTTAAAAGAGCAGCAAGATAATGAACAAAAAGCTTTA

ACCTCTGCACAAGAAATTTACACTAATACTCTTGCAAGTAGTGAGGACACGCTATTAGCCCAAGGAGCCGAAC

ATCAAAGAGAGTTAACAGCTACTGAAACAGAGCTTCATAATGCTCAAGCAGATCAACATTCAAAAGAGACTGC

ATTGTCAGAACAAAAAGCTAGCATTTCAGCAGAAACTACTCGAGCTCAAGATTTAGTGGAACAAGTCAAAACG

TCTGAACAAAATATTGCTAAGCTCAATGCTATGATTAGCAATCCTGATGCTATCACTAAAGCAGCTCAAACGG

CTAATGATAATACAAAAGCATTAAGCTCAGAATTGGAGAAGGCTAAAGCTGACTTAGAAAATCAAAAAGCTAA

AGTTAAAAAGCAATTGACTGAAGAGTTGGCAGCTCAGAAAGCTGCTCTAGCAGAAAAAGAGGCAGAACTTAGT

CGTCTTAAATCCTCAGCTCCGTCTACTCAAGATAGCATTGTGGGTAATAATACCATGAAAGCACCGCAAGGCT

ATCCTCTTGAAGAACTTAAAAAATTAGAAGCTAGTGGTTATATTGGATCAGCTAGTTACAATAATTATTACAA

AGAGCATGCAGATCAAATTATTGCCAAAGCTAGTCCAGGTAATCAATTAAATCAATACCAAGATATTCCAGCA

GATCGTAATCGCTTTGTTGATCCCGATAATTTGACACCAGAAGTGCAAAATGAGCTAGCGCAGTTTGCAGCTC

ACATGATTAATAGTGTAAGGAGACAATTAGGTCTACCACCAGTTACTGTCACAGCAGGATCACAAGAATTTGC

AAGATTACTTAGTACCAGCTATAAGAAAACTCATGGTAATACAAGACCATCATTTGTCTACGGACAGCCAGGG

GTATCAGGGCATTATGGTGTTGGGCCTCATGATAAAACTATTATTGAAGACTCTGCCGGAGCGTCAGGGCTCA

TTCGAAATGATGATAACATGTACGAGAATATCGGTGCTTTTAACGATGTGCATACTGTGAATGGTATTAAACG

TGGTATTTATGACAGTATCAAGTATATGCTCTTTACAGATCATTTACACGGAAATACATATGGTCATGCTATT

AACTTTTTACGTGTAGATAAACATAACCCTAAGGCGCCTGTT

> Spy0269-1/Schmitz 1/59 (serotype 12); SEQ ID NO: 136
GATGATAGAGCCTCAGGAGAAACGAAGGCGAGTAATACTCACGACGATAGTTTACCAAAACCAGAAACAATTC

AAGAGGCAAAGGCAACTATTGATGGAGTTGAAAAAACTCTCAGTCAACAAAAAGCAGAACTGACAAAGCTTGC

TACCGCTCTGACAAAAACTACTGCTGAAATCAACCACTTAAAAGAGCAGCAAGATAATGAACAAAAAGCTTTA

-continued

SEQUENCE DATA FOR DNA SEQUENCES

ACCTCTGCACAAGAAATTTACACTAATACTCTTGCAAGTAGTGAGGAGACGCTATTAGCCCAAGGAGCCGAAC

ATCAAAGAGAGTTAACAGCTACTGAAACAGAGCTTCATAATGCTCAAGCAGATCAACATTCAAAAGAGACTGC

ATTGTCAGAACAAAAAGCTAGCATTTCAGCAGAAACTACTCGAGCTCAAGATTTAGTGGAACAAGTCAAAACG

TCTGAACAAAATATTGCTAAGCTCAATGCTATGATTAGCAATCCTGATGCTATCACTAAAGCAGCTCAAACGG

CTAATGATAATACAAAAGCATTAAGCTCAGAATTGGAGAAGGCTAAAGCTGACTTAGAAAATCAAAAAGCTAA

AGTTAAAAAGCAATTGACTGAAGAGTTGGCAGCTCAGAAAGCTGCTCTAGCAGAAAAAGAGGCAGAACTTAGT

CGTCTTAAATCCTCAGCTCCGTCTACTCAAGATAGCATTGTGGGTAATAATACCATGAAAGCACCGCAAGGCT

ATCCTCTTGAAGAACTTAAAAAATTAGAAGCTAGTGGTTATATTGGATCAGGTAGTTACAATAATTATTACAA

AGAGCATGCAGATCAAATTATTGCCAAAGCTAGTCCAGGTAATCAATTAAATCAATACCAAGATATTCGAGCA

GATCGTAATCGCTTTGTTGATCCCGATAATTTGACACCAGAAGTGCAAAATGAGCTAGCGCAGTTTGCAGCTC

ACATGATTAATAGTGTAAGAAGACAATTAGGTCTACCACCAGTTACTGTTACAGCAGGATCACAAGAATTTGC

AAGATTACTTAGTACCAGCTATAAGAAAACTCATGGTAATACAAGACCATCATTTGTCTACGGACAGCCAGGG

GTATCAGGGCATTATGGTGTTGGGCCTCATGATAAAACTATTATTGAAGACTCTGCCGGAGCGTCAGGGCTCA

TTCGAAATGATGATAACATGTACGAGAATATCGGTGCTTTTAACGATGTGCATACTGTGAATGGTATTAAACG

TGGTATTTATGACAGTATCAAGTATATGCTCTTTACAGATCATTTACACGGAAATACATACGGCCATGCTATT

AACTTTTTACGTGTAGATAAACGTAACCCTAATGCGCCTGTT

> Spy0269-1/Schmitz 1/177 (serotype 22); SEQ ID NO: 137
GATGATAGAGCCTCAGGAGAAACGAAGGCGAGTAATACTCACGACGATAGTTTACCAAAACCAGAAACAATTC

AAGAGGCAAAGGCAACTATTGAAGCAGTTGAAAAAGCTCTCAGTCAACAAAAAGCAGAACTGACAGAGCTTGC

TACCGCTCTGACAAAAACTACTGCTAAAATCAACCACTTAAAACAGCAGCAAGATAATGAACAAAAAGCTTTA

ACCTCTGCACAAGAAATTTACACTAATACTCTTGCAAGTAGTGAGGAGACGCTATTAGCCCAAGGAGCCGAAC

ATCAAAGAGAGTTAACAGCTACTGAAACAGAGCTTCATAATGCTCAAGCAGATCAACATTCAAAAGAGACTGC

ATTGTCAGAACAAAAAGCTAGCATTTCAGCAGAAACTACTCGAGCTCAAGATTTAGTGGAACAAGTCAAAACG

TCTGAACAAAATATTGCTAAGCTCAATGCTATGATTAGTAATCCTGATGCTATCACTAAAGCAGCTCAAACGG

CTAATGATAATACAAAAGCATTAAGCTCAGAATTGGAGAAGGCTAAAGCTGACTTAGAAAATCAAAAAGCTAA

AGTTAAAAAGCAATTGACTGAAGAGTTGGCAGCTCAGAAAGCTGCTCTAGCAGAAAAAGAGGCAGAACTTAGT

CGTCTTAAATCCTCAGCTCCGTCTACTCAAGATAGCATTGTGGGTAATAATACCATGAAAGCACCGCAAGGCT

ATCCTCTTGAAGAACTTAAAAAATTAGAAGCTAGTGGTTATATTGGATCAGCTAGTTACAATAATTATTACAA

AGAGCATGCAGATCAAATTATTGCCAAAGCTAGTCCAGGTAATCAATTAAATCAATACCAAGATATTCCAGCA

GATCGTAATCGCTTTGTTGATCCCGATAATTTGACACCAGAAGTGCAAAATGAGCTAGCGCAGTTTGCAGCTC

ACATGATTAATAGTGTAAGAAGACAATTAGGTCTACCACCAGTTACTGTCACAGCAGGATCACAAGAATTTGC

AAGATTACTTAGTACCAGCTATAAGAAAACTCATGGTAATACAAGACCATCATTTGTCTACGGACAGCCAGGG

GTATCAGGGCATTATGGTGTTGGGCCTCATGATAAAACTATTATTGAAGACTCTGCCGGAGCGTCAGGGCTCA

TTCGAAATGATGATAACATGTACGAGAATATCGGTGCTTTTAACGATGTGCATACTGTGAATGGTATTAAACG

TGGTATTTATGACAGTATCAAGTATATGCTCTTTACAGATCATTTACACGGAAATACATATGGCCATGCTATT

AACTTTTTACGTGTAGATAAACGTAACCCTAATGCGCCTGTT

> Spy0269-1/Schmitz 1/43 (serotype 22); SEQ ID NO: 138
GATGATAGAGCCTCAGGAGAAACGAAGGCGAGTAATACTCACGACGATAGTTTACCAAAACCAGAAACAATTC

AAGAGGCAAAGGCAACTATTGAAGCAGTTGAAAAAGCTCTCAGTCAACAAAAAGCAGAACTGACAGAGCTTGC

TACCGCTCTGACAAAAACTACTGCTAAAATCAACCACTTAAAAGAGCAGCAAGATAATGAACAAAAAGCTTTA

-continued

SEQUENCE DATA FOR DNA SEQUENCES

ACCTCTGCACAAGAAATTTACAGTAATACTCTTGCAAGTAGTGAGGAGACGCTATTAGCCCAAGGAGCCGAAC

ATCAAAGAGAGTTAACAGCTACTGAAACAGAGCTTCATAATGCTCAAGCAGATCAACATTCAAAAGAGACTGC

ATTGTCAGAACAAAAAGCTAGCATTTCAGCAGAAACTACTCGAGCTCAAGATTTAGTGGAACAAGTCAAAACG

TCTGAACAAAATATTGCTAAGCTCAATGCTATGATTAGTAATCCTGATGCTATCACTAAAGCAGCTCAAACGG

CTAATGATAATACAAAAGCATTAAGCTCAGAATTGGAGAAGGCTAAAGCTGACTTAGAAAATCAAAAAGCTAA

AGTTAAAAAGCAATTGACTGAAGAGTTGGCAGCTCAGAAAGCTGCTCTAGCAGAAAAAGAGGCAGAACTTAGT

CGTCTTAAATCCTCAGCTCCGTCTACTCAAGATAGCATTGTGGGTAATAATACCATGAAAGCACCGCAAGGCT

ATCCTCTTGAAGAACTTAAAAAATTAGAAGCTAGTGGTTATATTGGATCAGCTAGTTACAATAATTATTACAA

AGAGCATGCAGATCAAATTATTGCCAAAGCTAGTCCAGGTAATCAATTAAATCAATACCAAGATATTCCAGCA

GATCGTAATCGCTTTGTTGATCCGGATAATTTGACACCAGAAGTGCAAAATGAGCTAGCGCAGTTTGCAGCTC

ACATGATTAATAGTGTAAGAAGACAATTAGGTCTACCACCAGTTACTGTCACAGCAGGATCACAAGAATTTGC

AAGATTACTTAGTACCAGCTATAAGAAAACTCATGGTAATACAAGACCATCATTTGTCTACGGACAGCCAGGG

GTATCAGGGCATTATGGTGTTGGGCCTCATGATAAAACTATTATTGAAGACTCTGCCGGAGCGTCAGGGCTCA

TTCGAAATGATGATAACATGTACGAGAATATCGGTGCTTTTAACGATGTGCATACTGTGAATGGTATTAAACG

TGGTATTTATGACAGTATCAAGTATATGCTCTTTACAGATCATTTACACGGAAATACATATGGCCATGCTATT

AACTTTTTACGTGTAGATAAACGTAACCCTAATGCGCCTGTT

> Spy0269-1/Schmitz 1/136 (serotype 25); SEQ ID NO: 139
GATGATAGAGCCTCAGGAGAAACGAAGGCGAGTAATACTCACGACGATAGTTTACCAAAACCAGAAACAATTC

AAGAGGCAAAGGCAACTATTGATGCAGTTGAAAAAACTCTCAGTCAACAAAAAGCAGAACTGACAGAGCTTGC

TACCGCTCTGACAAAAACTACTGCTGAAATCAACCACTTAAAAGAGCAGCAAGATAATGAACAAAAAGCTTTA

ACCTCTGCACAAGAAATTTACACTAATACTCTTGCAAGTAGTGAGGAGACGCTATTAGCCCAAGGAGCCGAAC

ATCAAAGAGAGTTAACAGCTACTGAAACAGAGCTTCATAATGCTCAAGCAGATCAACATTCAAAAGAGACTGC

ATTGTCAGAACAAAAAGCTAGCATTTCAGCAGAAACTACTCGAGCTCAAGATTTAGTGGAACAAGTCAAAACG

TCTGAACAAAATATTGCTAAGCTCAATGCTATGATTAGCAATCCTGATGCTATCACTAAAGCAGCTCAAACGG

CTAATGATAATACAAAAGCATTAAGCTCAGAATTGGAGAAGGCTAAAGCTGACTTAGAAAATCAAAAAGCTAA

AGTTAAAAAGCAATTGACTGAAGAGTTGGCAGCTCAGAAAGCTGCTCTAGCAGAAAAAGAGGCAGAACTTAGT

CGTCTTAAATCCTCAGCTCCGTCTACTCAAGATAGCATTGTGGGTAATAATACCATGAAAGCACCGCAAGGCT

ATCCTCTTGAAGAACTTAAAAAATTAGAAGCTAGTGGTTATATTGGATCAGCTAGTTACAATAATTATTACAA

AGAGCATGCAGATCAAATTATTGCCAAAGCTAGTCCAGGTAATCAATTAAATCAATACCAAGATATTCCAGCA

GATCGTAATCGCTTTGTTGATCCCGATAATTTGACACCAGAAGTGCAAAATGAGCTAGCGCAGTTTGCAGCTC

ACATGATTAATAGTGTAAGAAGACAATTAGGTCTACCACCAGTTACTGTTACAGCAGGATCACAAGAATTTGC

AAGATTACTTAGTACCAGCTATAAGAAAACTCATGGTAATACAAGACCATCATTTGTCTACGGACAGCCAGGG

GTATCAGGGCATTATGGTGTTGGGCCTCATGATAAAACTATTATTGAAGACTCTGCCGGAGCGTCAGGGCTCA

TTCGAAATGATGATAACATGTACGAGAATATCGGTGCTTTTAACGATGTGCATACTGTGAATGGTATTAAACG

TGGTATTTATGACAGTATCAAGTATATGCTCTTTACAGATCATTTACACGGAAATACATACGGCCATGCTATT

AACTTTTTACGTGTAGATAAACGTAACCCTAATGCGCCTGTT

> Spy0269-1/Schmitz 1/85 (serotype 28); SEQ ID NO: 140
GATGATAGAGCCTCAGGAGAAACGAAGGCGAGTAATACTCACGACGATAGTTTACCAAAACCAGAAACAATTC

AAGAGGCAAAGGCAACTATTGATGCAGTTGAAAAAACTCTCAGTCAACAAAAAGCAGAACTGACAGAGCTTGC

TACCGCTCTGACAAAAACTACTGCTGAAATCAACCACTTAAAAGAGCAGCAAGATAATGAACAAAAAGCTTTA

-continued

SEQUENCE DATA FOR DNA SEQUENCES

ACCTCTGCACAAGAAATTTACACTAATACTCTTGCAAGTAGTGAGGAGACGCTATTAGCCCAAGGAGCCGAAC

ATCAAAGAGAGTTAACAGCTACTGAAACAGAGCTTCATAATGCTCAAGCAGATCAACATTCAAAAGAGACTGC

ATTGTCAGAACAAAAAGCTAGCATTTCAGCAGAAACTACTCGAGCTCAAGATTTAGTGGAACAAGTCAAAACG

TCTGAACAAAATATTGCTAAGCTCAATGCTATGATTAGCAATCCTGATGCTATCACTAAAGCAGCTCAAACGG

CTAATGATAATACAAAAGCATTAAGCTCAGAATTGGAGAAGGCTAAAGCTGACTTAGAAAATCAAAAAGCTAA

AGTTAAAAAGCAATTGACTGAAGAGTTGGCAGCTCAGAAAGCTGCTCTAGCAGAAAAAGAGGCAGAACTTAGT

CGTCTTAAATCCTCAGCTCCGTCTACTCAAGATAGCATTGTGGGTAATAATACCATGAAAGCACCGCAAGGCT

ATCCTCTTGAAGAACTTAAAAAATTAGAAGCTAGTGGTTATATTGGATCAGCTAGTTACAATAATTATTACAA

AGAGCATGCAGATCAAATTATTGCCAAAGCTAGTCCAGGTAATCAATtAAATCAATACCAAGatattccagca gatcgtaatcgctttGTTGATCCCGATAATTTGACACCAGAAGTGCAAAATGAGCTAGCGCAGTTTGCAGCTC ACATGATTAATAGTGTAAGAAGACAATTAGGTCTACCACCAGTTACTGTTACAGCAGGATCACaagaatttgc aagattacttagtaccagctataagaaaactcatggtaatacaagaccatcatttgtctACGGACAGCCAGGG

GTATCAGGGCATTATGGTGTTGGGCCTCATGATAAAACTATTATTGAAGACTCTGCCGGAGCGTCAGGGCTCA

TTCGAAATGATGATAACATGTACGAGAATATCGGTGCTTTTAACGATGTGCATACTGTGAATGGTATTAAACG

TGCTATTTATGACAGTATCAAGTATATGCTCTTTACAGATCATTTACACGGAAATACATACGGCCATGCTATT

AACTTTTTACGTGTAGATAAACATAACCCTAATGCGCCTGTT

> Spy0269-1/Schmitz 2/50 (serotype 28); SEQ ID NO: 141
GATGATAGAGCCTCAGGAGAAACGAAGGCGAGTAATACTCACGACGATAGTTTACCAAAACCAGAAACAATTC

AAGAGGCAAAGGCAACTATTGATGCAGTTGAAAAAACTCTCAGTCAACAAAAAGCAGAACTGACAGAGCTTGC

TACCGCTCTGACAAAAACTACTGCTGAAATCAACCACTTAAAAGAGCAGCAAGATAATGAACAAAAAGCTTTA

ACCTCTGCACAAGAAATTTACACTAATACTCTTGCAAGTAGTGAGGAGACGCTATTAGCCCAAGGAGCCGAAC

ATCAAAGAGAGTTAACAGCTACTGAAACAGAGCTTCATAATGCTCAAGTAGATCAACATTCAAAAGAGACTGC

ATTGTCAGAACAAAAAGCTAGCATTTCAGCAGAAACTACTCGAGCTCAAGATTTAGTGGAACAAGTCAAAACG

TCTGAACAAAATATTGCTAAGCTCAATGCTATGATTAGCAATCCTGATGCTATCACTAAAGCAGCTCAAACGG

CTAATGATAATACAAAAGCATTAAGCTCAGAATTGGAGAAGGCTAAAGCTGACTTAGAAAATCAAAAAGCTAA

AGTTAAAAAGCAATTGACTGAAGAGTTGGCAGCTCAGAAAGCTGCTCTAGCAGAAAAAGAGGCAGAACTTAGT

CGTCTTAAATCCTCAGCTCCGTCTACTCAAGATAGCATTGTGGGTAATAATACCATGAAAGCACCGCAAGGCT

ATCCTCTTGAAGAACTTAAAAAATTAGAAGCTAGTGGTTATATTGGATCAGCTAGTTACAATAATTATTACAA

AGAGCATGCAGATCAAATTATTGCCAAAGCTAGTCCAGGTAATCAATTAAATCAATACCAAGATATtCCAGCA

GATCGTAATCGCTTTGTTGATCCCGATAATTTGACACCAGAAGTGCAAaATGAGCTAGCGCAGTTTGCAGCTC

ACATGATTAATAGTGTAAGAAGACAATTAGGTCTACCACCAGTTACTGTTACAGCAGGATCACAAGAATTTGC

AAGATTACTTAGTACCAGCTATAAGAAGACTCATGGTAATACAAGACCATCATTTGTCTACGGACAGCCAGGG

GTATCAGGGCATTATGGTGTTGGGCCTCATGATAAAACTATTATTGAAGACTCTGGCGGAGCGTCAGGGCTCA

TTCGAAATGATGATAACATGTACGAGAATATCGGTGCTTTTAACGATGTGCATACTGTGAATGGTATTAAACG

TGGTATTTATGACAGTATCAAGTATATGCTCTTTACAGATCATTTACACGGAAATACATACGGCCATGCTATT

AACTTTTTACGTGTAGATAAACGTAACCCTAATGCGCCTGTT

> Spy0269-1/Schmitz 1/123 (serotype 49); SEQ ID NO: 142
GATGATAGAGCCTCAGGAGAAACGAAGGCGAGTAATACTCACGACGATAGTTTACCAAAACCAGAAACAATTC

AAGAGGCAAAGGCAACTATTGATGCAGTTGAAAAAACTCTCAGTCAACAAAAAGCAGAACTGACAGAGCTTGC

TACCGCTCTGACAAAAACTACTGCTGAAATCAACCACTTAAAAGAGCAGCAAGATAATGAACAAAAAGCTTTA

-continued

| SEQUENCE DATA FOR DNA SEQUENCES |
| --- |

ACCTCTGCACAAGAAATTTACACTAATACTCTTGCAAGTAGTGAGGAGACGCTATTAGCCCAAGGAGCCGAAC

ATCAAAGAGAGTTAACAGCTACTGAAACAGAGCTTCATAATGCTCAAGCAGATCAACATTCAAAAGAGACTGC

ATTGTCAGAACAAAAAGCTAGCATTTCAGCAGAAACTACTCGAGCTCAAGATTTAGTGGAACAAGTCAAAACG

TCTGAACAAAATATTGCTAAGCTCAATGCTATGATTAGCAATCCTGATGCTATCACTAAAGCAGCTCAAACGG

CTAATGATAATACAAAAGCATTAAGCTCAGAATTGGAGAAGGCTAAAGCTGACTTAGAAAATCAAAAAGCTAA

AGTTAAAAAGCAATTGACTGAAGAGTTGGCAGCTCAGAAAGCTGCTCTAGCAGAAAAAGAGGCAGAACTTAGT

CGTCTTAAATCCTCAGCTCCGTCTACTCAAGATAGCATTGTGGGTAATAATACCATGAAAGCACCGCAAGGCT

ATCCTCTTGAAGAACTTAAAAAATTAGAAGCTAGTGGTTATATTGGATCAGCTAGTTACAATAATTATTACAA

AGAGCATGCAGATCAAATTATTGCCAAAGCTAGTCCAGGTAATCAATTAAATCAATACCAAGATATtCCAGCA

GAtcgtaatcgctttGTTGATCCCGATAATTTGACACCAGAAGTGCAAAATGAGCTAGCGCAGTTTGCAGCTC

ACATGATTAATAGTGTAAGGAGACAATTAGGTCTACCACCAGTTACTGTTACAGCAGGATCACAAGAATTTGC

AAGATTACTTAGTACCAGCTATAAGAAAACTCATGGTAATACAAGACCATCATTTGTCTACGGACAACCAGGG

GTATCAGGGCATTATGGTGTTGGGCCTCATGATAAAACTATTATTGAAGACTCTGCCGGAGCGTCAGGGCTCA

TTCGAAATGATGATAACATGTACGAGAATATCGGTGCTTTTAACGATGTGCATACTGTGAATGGTATTAAACG

TGGTATTTATGACAGTATCAAGTATATGCTCTTTACAGATCATTTACACGGAAATACATATGGCCATGCTATT

AACTTTTTACGTGTAGATAAACGTAACCCTAATGCGCCTGTT

> Spy0269-1/Schmitz 1/176 (serotype 83); SEQ ID NO: 143
GATGATAGAGCCTCAGGAGAAACGAAGGCGAGTAATACTCACGACGATAGTTTACCAAAACCAGAAACAATTC

AAGAGGCAAAGGCAACTATTGAAGCAGTTGAAAAAACTCTCAGTCAACAAAAAGCAGAACTGACAGAGCTTGC

TACCGCTCTGACAAAAACTACTGCTGAAATCAACCACTTAAAAGAGCAGCAAGATAACGAACAAAAAGCTTTA

ACCTCTGCACAAGAAATTTACACTAATACTCTTGCAAGTAGTGAGGAGACGCTATTAGCCCAAGGAGCCGAAC

ATCAAAGAGAGTTAACAGCTACTGAAACAGAGCTTCATAATGCTCAAGCAGATCAACATTCAAAAGAGACTGC

ATTGTCAGAACAAAAAGCTAGCATTTCAGCAGAAACTACTCGAGCTCAAGATTTAGTGGAACAAGTCAAAACG

TCTGAACAAAATATTGCTAAGCTCAATGCTATGATTAGCAATCCTGATGCTATCACTAAAGCAGCTCAAACGG

CTAATGATAATACAAAAGCATTAAGCTCAGAATTGGAGAAGGCTAAAGCTGACTTAGAAAATCAAAAAGCTAA

AGTTAAAAAGCAATTGACTGAAGAGTTGGCAGCTCAGAAAGCTGCTCTAGCAGAAAAAGAGGCAGAACTTAGT

CGTCTTAAATCCTCAGCTCCGTCTACTCAAGATAGCATTGTGGGTAATAATACCATGAAAGCACCGCAAGGCT

ATCCTCTTGAAGAACTTAAAAAATTAGAAGCTAGTGGTTATATTGGATCAGCTAGTTACAATAATTATTACAA

AGAGCATGCAGATCAAATTATTGCCAAAGCTAGTCCAGGTAATCAATtAAATCAATACCAAGatATTCCAGCA

GatcgtaatcgctttGTTGATCCCGATAATTTGACACCAGAAGTGCAAAATGAGCTAGCGCAGTTTGCAGCTC

ACATGATTAATAGTGTAAGAAGACAATTAGGTCTACCACCAGTTACTGTCACAGCAGGATCACAAGAATTTGC

AAGATTACTTAGTACCAGCTATAAGAAAACTCATGGTAATACAAGACCATCATTTGTCTACGGACAGCCAGGG

GTATCAGGGCATTATGGTGTTGGGCCTCATGATAAAACTATTATTGAAGACTCTGCCGGAGCGTCAGGGCTCA

TTCGAAATGATGATAACATGTACGAGAATATCGGTGCTTTTAACGATGTGCATACTGTGAATGGTATTAAACG

TGGTATTTATGACAGTATCAAGTATATGCTCTTTACAGATCATTTACACGGAAATACATATGGCCATGCTATT

AACTTTTTACGTGTAGATAAACGTAACCCTAATGCGCCTGTT

2. Spy0292
2.1 Full length Spy0292
> Spy0292/SF370 (serotype 1); SEQ ID NO: 144
ATGATCAAACGATTAATTTCCCTAGTGGTCATCGCCTTATTTTTTGCAGCAAGCACTGTTAGCGGTGAAGAGT

ATTCGGTAACTGCTAAGCATGCGATTGCCGTTGACCTTGAAAGTGGCAAAGTTTTATACGAAAAAGATGCTAA

-continued

| SEQUENCE DATA FOR DNA SEQUENCES |
|---|

AGAAGTTGTCCCAGTCGCCTCAGTCAGTAAGCTCTTGACAACCTATCTGGTTTACAAAGAAGTTTCTAAGGGC

AAGCTAAATTGGGATAGTCCTGTAACTATTTCTAACTACCCTTATGAACTCACTACAAACTATACTATTAGTA

ACGTTCCTCTTGATAAGAGAAAATATACCGTTAAAGAACTTTTAAGTGCGTTAGTTGTTAATAACGCCAATAG

CCCCGCTATTGCTTTAGCTGAAAAAATAGGCGGAACCGAACCCAAATTTGTTGACAAAATGAAAAAACAATTA

AGACAATGGGGCATTTCCGATGCAAAGGTCGTCAATTCAACTGGCTTAACTAACCATTTTTTAGGAGCTAATA

CTTATCCTAATACAGAACCAGATGATGAAAATTGTTTTTGCGCCACTGATTTAGCTATTATTGCCAGGCATCT

CTTATTAGAATTTCCAGAAGTACTGAAATTATCTAGCAAATCCTCCACTATTTTTGCTGGACAAACCATTTAC

AGTTATAATTACATGCTTAAAGGCATGCCTTGTTATCGAGAAGGCGTGGATGGTCTTTTTGTTGGTTATTCTA

AAAAAGCCGGTGCTTCTTTTGTAGCTACTAGTGTCGAAAATCAAATGAGGGTTATTACAGTAGTTTTAAATGC

TGATCAAAGCCACGAGGATGATTTAGCTATATTTAAAACAACCAATCAATTGTTGCAGTACCTTTTAATTAAT

TTTCAAAAAGTCCAGTTAATTGAAAATAATAAACCAGTAAAAACGTTATATGTCTTAGACAGTCCTGAAAAAA

CTGTCAAACTTGTAGCCCAAAATAGTTTATTTTTTATCAAACCAATACATACAAAGACCAAAAATACCGTCCA

TATTACTAAGAAATCATCCACAATGATCGCACCTCTATCAAAGGGACAAGTCTTAGGTAGAGCAACCCCTTCAA

GATAAACATCTTATTGGACAAGGTTATCTGGATACTCCTCCTTCTATCAATCTTATCCTTCAAAAAAACATTT

CTAAAAGTTTCTTTTTAAAGGTCTGGTGGAACCGTTTTGTGAGGTATGTCAATACCTCTTTATAG 2.2 Antigenic fragment Spy0292-1
> Spy0292-1/SF370 (serotype 1); SEQ ID NO: 12
GAAGAGTATTCGGTAACTGCTAAGCATGCGATTGCCGTTGACCTTGAAAGTGGCAAAGTTTTATACGAAAAAG

ATGCTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAACCAGATGATGAAAATTGTTTTTGC 2.3 Homologous sequences of other *S. pyogenes* isolates and/or serotypes
> Spy0292-1/Schmitz 1/39 (serotype 12); SEQ ID NO: 145
GAAGAGTATTCGGTAACTGCTAAGCATGCGATTGCCGTTGACCTTGAAAGTGGCAAAGTTTTATACGAAAAAG

ATGCTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAACcagaTGATGAAAATTGTTTTTGC

> Spy0292-1/Schmitz 1/55 (serotype 118); SEQ ID NO: 146
GAAGAGTATTCGGTAACTGCTAAGCATGCGATTGCCGTTGACCTTGAAAGTGGCAAAGTTTTATACGAAAAAG

ATGCTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTTACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATACAAAGGTCGTCAATTCAACTGGCTTAACTAACCATTTTTTAGGA

GCTAATACTTATCCTAATACAGAACCAGATGATGAAAATTGTTTTTGC

-continued

| SEQUENCE DATA FOR DNA SEQUENCES |
|---|

> Spy0292-1/Schmitz 1/56 (serotype 28); SEQ ID NO: 147
GAAGAGTATTCGGTAACTGCTAAGCATGCGATTGCCGTTGACCTTGAAAGTGGCAAAGTTTTATACGAAAAAG

ATACTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGGCAATGGGGCATTTCCGATGCAAAGGTCGTTAATTCAACTGGCTTAACTAACCATTTTTTAGGA

GCTAATACTTATCCTAATACAGAACCAGATGATGAAAATTGTTTTTGC

> Spy0292-1/Schmitz 1/74 (serotype 3); SEQ ID NO: 148
GAAGAGTATTCGGTAACTGCTAAACATGCGATTGCCGTTGACCTTGAAAGTGGCAAAGTTTTATACGAAAAAG

ATGCTAAAGAGGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGcTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAACCAGATGATGAAAATTGTTTTTGC

> Spy0292-1/Schmitz 1/76 (serotype 22); SEQ ID NO: 149
GAAGAGTATTCGGTAACTGCTAAGCATGCGATTGCCGTTGACCTTGAAAGTGGCAAAGTTTTATACGAAAAAG

ATGCTAAAGAAGTTGTCCCTGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTACGGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAAccagATGATGAAAATTGTTTTTGC

> Spy0292-1/Schmitz 1/92 (serotype 11); SEQ ID NO: 150
GAAGAGTATTCGGTAACTGCTAAGCATGCGATTGCCGTTGACCTTGAAAGTGGCAAAGTTTTATACGAAAAAG

ATGCTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGGCAATGGGGCATTTCCGATGCAAAGGTCGTTAATTCAACTGGCTTAACTAACCATTTTTTAGGA

GCTAATACTTATCCTAATACAGAACCAGATGATGaaaATTGTTTTTGC

> Spy0292-1/Schmitz 1/94 (serotype 1); SEQ ID NO: 151
GAAGAGTATTCGGTAACTGCTAAGCATGCGATTGCCGTTGACCTTGAAAGTGGCAAAGTTTTATACGAAAAAG

ATGCTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAACCAGATGATGAAAATTGTTTTTGC

> Spy0292-1/Schmitz 1/142 (serotype 83); SEQ ID NO: 152
GAAGAGTATTCGGTAACTGCTAAGCATGCGATTGCCGTTGACCTTGAAAGTGGCAAAGTTTTATACGAAAAAG -continued

SEQUENCE DATA FOR DNA SEQUENCES

ATGCTAAAGAGGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAAccagaTGATGAAAATTGTTTTTGC

> Spy0292-1/Schmitz 1/144 (serotype 76); SEQ ID NO: 153
GAAGAGTATTCGGTAACTGCTAAGCATGCGATTGCCGTTGACCTTGAAAGTGGCAAAGTTTTATACGAAAAAG

ATGCTAAAGAAGTTGTCCCTGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAaccagaTGATGAAAATTGTTTTTGC

> Spy0292-1/Schmitz 1/194 (serotype 44); SEQ ID NO: 154
GAAGAGTATTCGGTAACTGCTAAGCATGCGATTGCCGTTGACCTTGAAAGTGGCAAAGTTTTATACGAAAAAG

ATGCTAAAGAAGTTGTCCCTGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAACCAGATGATGAAAATTGTTTTTGC 2.4 Antigenic fragment Spy0292-3
> Spy0292-3/SF370 (serotype 1); SEQ ID NO: 13
GAAGAGTATTCGGTAACTGCTAAGCATGCGATTGCCGTTGACCTTGAAAGTGGCAAAGTTTTATACGAAAAAG

ATGCTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAACCAGATGATGAAAATTGTTTTTGCGCCACTGATTTAGCTATTATTGCCA

GGCATCTCTTATTAGAATTTCCAGAAGTACTGAAATTATCTAGCAAATCCTCCACTATTTTTGCTGGACAAAC

CATTTACAGTTATAATTACATGCTTAAAGGCATGCCTTGTTATCGAGAAGGCGTGGATGGTCTTTTTGTTGGT

TATTCTAAAAAAGCCGGTGCTTCTTTTGTAGCTACTAGTGTCGAAAATCAAATGAGGGTTATTACAGTAGTTT

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA 2.5 Homologous sequences of other *S. pyogenes* isolates and/or serotypes
> Spy0292-3/Schmitz 1/39 (serotype 12); SEQ ID NO: 155
GAAGAGTATTCGGTAACTGCTAAGCATGCGATTGCCGTTGACCTTGAAAGTGGCAAAGTTTTATACGAAAAAG

ATGCTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

-continued

SEQUENCE DATA FOR DNA SEQUENCES

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAACcagaTGATGAAAATTGTTTTTGCGCCACTGATTTAGCTATTATTGCCA

GGCATCTCTTATTAGAATTTCCAGAAGTACTGAAATTATCTAGCAAATCCTCCACTATTTTTGATGGACAAAC

CATTTACAGTTATAATTACATGCTTAAAGGCATGCCTTGTTATCGAGAAGGCGTGGATGGTCTTTTTGTTGGT

TATTCTAAAAAAGCCGGTGCTTCTTTTGTAGCTACTAGTGTCGAAAATCAAATGAGGGTTATTACAGTAGTTT

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA

> Spy0292-3/Schmitz 1/55 (serotype 118); SEQ ID NO: 156
GAAGAGTATTCGGTAACTGCTAAGCATGCGATTGCCGTTGACCTTGAAAGTGGCAAAGTTTTATACGAAAAAG

ATGCTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTTACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATACAAAGGTCGTCAATTCAACTGGCTTAACTAACCATTTTTTAGGA

GCTAATACTTATCCTAATACAGAACCAGATGATGAAAATTGTTTTTGCGCCACTGATTTAGCTATTATTGCCA

GGCATCTCTTATTAGAATTTCCAGAAGTACTGAAATTATCTAGCAAATCCTCCACTATTTTTGATGGACAAAC

CATTTACAGTTATAATTACATGCTTAAAGGCATGCCTTGTTATCGAGAAGGCGTGGATGGTCTCTTTGTCGGT

TATTCTAAAAAAGCCGGTGCTTCTTTTGTAGCTACTAGTGTCGAAAATCAAATGAGGGTTATTACAGTAGTTT

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA

> Spy0292-3/Schmitz 1/56 (serotype 28); SEQ ID NO: 157
GAAGAGTATTCGGTAACTGCTAAGCATGCGATTGCCGTTGACCTTGAAAGTGGCAAAGTTTTATACGAAAAAG

ATACTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGGCAATGGGGCATTTCCGATGCAAAGGTCGTTAATTCAACTGGCTTAACTAACCATTTTTTAGGA

GCTAATACTTATCCTAATACAGAACCAGATGATGAAAATTGTTTTTGCGCCACTGATTTAGCTATTATTGCCA

GGCATCTCTTATTAGAATTTCCAGAAGTACTGAAATTATCTAGCAAATCCTCCACTATTTTTGATGGACAAAC

CATTTACAGTTATAATTACATGCTTAAAGGCATGCCTTGTTATCGAGAAGGCGTGGATGGTCTTTTTGTTGGT

TATTCTAAAAAAGCCGGTGCTTCTTTTGTAGCTACTAGTGTCGAAAATCAAATGAGGGTTATTACAGTAGTTT

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA

> Spy0292-3/Schmitz 1/74 (serotype 3); SEQ ID NO: 158
GAAGAGTATTCGGTAACTGCTAAACATGCGATTGCCGTTGACCTTGAAAGTGGCAAAGTTTTATACGAAAAAG

ATGCTAAAGAGGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGcTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

-continued

SEQUENCE DATA FOR DNA SEQUENCES

GCTAATACTTATCCTAATACAGAACCAGATGATGAAAATTGTTTTTGCGCCACTGATTTAGCTATTATTGCCA

GGCATCTCTTATTAGAATTTCCAGAAGTACTGAAATTATCTAGCAAATCCTCCACTATTTTTGCTGGACAAAC

CATTTACAGTTATAATTACATGCTTAAAGGCATGCCTTGTTATCGAGAAGGCGTGGATGGTCTTTTTGTTGGT

TATTCTAAAAAAGCCGGTGCTTCTTTTGTAGCTACTAGTGTCGAAAATCAAATGAGGGTTATTACAGTAGTTT

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA

> Spy0292-3/Schmitz 1/76 (serotype 22); SEQ ID NO: 159
GAAGAGTATTCGGTAACTGCTAAGCATGCGATTGCCGTTGACCTTGAAAGTGGCAAAGTTTTATACGAAAAAG

ATGCTAAAGAAGTTGTCCCTGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAAccagATGATGAAAATTGTTTTTGCGCCACTGATTTAGCTATTATTGCCA

GGCATCTCTTATTAGAATTTCCAGAAGTACTGAAATTATCTAGCAAATCCTCCACTATTTTTGATGGACAAAC

CATTTACAGTTATAATTACATGCTTAAAGGCATGCCTTGTTATCGAGAAGGCGTGGATGGTCTTTTTGTTGGT

TATTCTAAAAAAGCCGGTGCTTCTTTTGTAGCTACTAGTGTCGAAAATCAAATGAGGGTTATTACAGTAGTTT

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA

> Spy0292-3/Schmitz 1/92 (serotype 11); SEQ ID NO: 160
GAAGAGTATTCGGTAACTGCTAAGCATGCGATTGCCGTTGACCTTGAAAGTGGCAAAGTTTTATACGAAAAAG

ATGCTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGGCAATGGGGCATTTCCGATGCAAAGGTCGTTAATTCAACTGGCTTAACTAACCATTTTTTAGGA

GCTAATACTTATCCTAATACAGAACCAGATGATGaaaATTGTTTTTGCGCCACTGATTTAGCTATTATTGCCA

GGCATCTCTTATTAGAATTTCCAGAAGTACTGAAATTATCTAGCAAATCCTCCACTATTTTTGATGGACAAAC

CATTTACAGTTATAATTACATGCTTAAAGGCATGCCTTGTTATCGAGAAGGCGTGGATGGTCTTTTTATTGGT

TATTCTAAAAAAGCCGGTGCTTCTTTTGTAGCTACTAGTGTCGAAAATCAAATGAGGGTTATTACAGTAGTTT

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA

> Spy0292-3/Schmitz 1/94 (serotype 1); SEQ ID NO: 161
GAAGAGTATTCGGTAACTGCTAAGCATGCGATTGCCGTTGACCTTGAAAGTGGCAAAGTTTTATACGAAAAAG

ATGCTAAAGAAGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTTAATTCAACTGGCTTAACTAACCATTTTTTAGGA

GCTAATACTTATCCTAATACAGAACCAGATGATGAAAATTGTTTTTGCGCCACTGATTTAGCTATTATTGCCA

-continued

SEQUENCE DATA FOR DNA SEQUENCES

GGCATCTCTTATTAGAATTTCCAGAAGTACTGAAATTATCTAGCAAATCCTCCACTATTTTTGCTGGACAAAC

CATTTACAGTTATAATTACATGCTTAAAGGCATGCCTTGTTATCGAGAAGGCGTGGATGGTCTTTTTGTTGGT

TATTCTAAAAAAGCCGGTGCTTCTTTTGTAGCTACTAGTGTCGAAAATCAAATGAGGGTTATTACAGTAGTTT

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA

> Spy0292-3/Schmitz 1/142 (serotype 83); SEQ ID NO: 162
GAAGAGTATTCGGTAACTGCTAAGCATGCGATTGCCGTTGACCTTGAAAGTGGCAAAGTTTTATACGAAAAAG

ATGCTAAAGAGGTTGTCCCAGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTTAATTCAACTGGCTTAACTAACCATTTTTTAGGA

GCTAATACTTATCCTAATACAGAAccagaTGATGAAAATTGTTTTTGCGCCACTGATTTAGCTATTATTGCCA

GGCATCTCTTATTAGAATTTCCAGAAGTACTGAAATTATCTAGCAAATCCTCCACTATTTTTGATGGACAAAC

CATTTACAGTTATAATTACATGCTTAAAGGCATGCCTTGTTATCGAGAAGGCGTGGATGGTCTTTTTGTTGGT

TATTCTAAAAAAGCCGGTGCTTCTTTTGTAGCTACTAGTGTCGAAAATCAAATGAGGGTTATTACAGTAGTTT

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA

> Spy0292-3/Schmitz 1/144 (serotype 76); SEQ ID NO: 163
GAAGAGTATTCGGTAACTGCTAAGCATGCGATTGCCGTTGACCTTGAAAGTGGCAAAGTTTTATACGAAAAAG

ATGCTAAAGAAGTTGTCCCTGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAaccagaTGATGAAAATTGTTTTTGCGCCACTGATTTAGCTATTATTGCCA

GGCATCTCTTATTAGAATTTCCAGAAGTACTGAAATTATCTAGCAAATCCTCCACTATTTTTGATGGACAAAC

CATTTACAGTTATAATTACATGCTTAAAGGCATGCCTTGTTATCGAGAAGGCGTGGATGGTCTTTTTGTTGGT

TATTCTAAAAAAGCCGGTGCTTCTTTTGTAGCTACTAGTGTCGAAAATCAAATGAGGGTTATTACAGTAGTTA

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA

> Spy0292-3/Schmitz 1/194 (serotype 44); SEQ ID NO: 164
GAAGAGTATTCGGTAACTGCTAAGCATGCGATTGCCGTTGACCTTGAAAGTGGCAAAGTTTTATACGAAAAAG

ATGCTAAAGAAGTTGTCCCTGTCGCCTCAGTCAGTAAGCTCTTGACAACCTATCTGGTTTACAAAGAAGTTTC

TAAGGGCAAGCTAAATTGGGATAGTCCTGTAACTATTTCTAACTACCCTTATGAACTCACTACAAACTATACT

ATTAGTAACGTTCCTCTTGATAAGAGAAAATATACCGTTAAAGAACTTTTAAGTGCGTTAGTTGTTAATAACG

CCAATAGCCCCGCTATTGCTTTAGCTGAAAAAATAGGCGGAACCGAACCCAAATTTGTTGACAAAATGAAAAA

ACAATTAAGACAATGGGGCATTTCCGATGCAAAGGTCGTCAATTCAACTGGCTTAACTAACCATTTTTTAGGA

GCTAATACTTATCCTAATACAGAACCAGATGATGAAAATTGTTTTTGCGCCACTGATTTAGCTATTATTGCCA

GGCATCTCTTATTAGAATTTCCAGAAGTACTGAAATTATCTAGCAAATCCTCCACTATTTTTGCTGGACAAAC

CATTTACAGTTATAATTACATGCTTAAAGGCATGCCTTGTTATCGAGAAGGCGTGGATGGTCTTTTTGTTGGT

-continued

SEQUENCE DATA FOR DNA SEQUENCES

TATTCTAAAAAAGCCGGTGCTTCTTTTGTAGCTACTAGTGTCGAAAATCAAATGAGGGTTATTACAGTAGTTT

TAAATGCTGATCAAAGCCACGAGGATGATTTAGCTATATTTAAAACAACCAATCAATTGTTGCAGTACCTTTT

AATTAATTTTCAAAAAGTCCAGTTAATTGAA

3. Spy0416A
3.1 Full length Spy0416A
> Spy0416A/SF370 (serotype 1); SEQ ID NO: 165
GCAGATGAGCTAAGCACAATGAGCGAACCAACAATCACGAATCACGCTCAACAACAAGCGCAACATCTCACCA

ATACAGAGTTGAGCTCAGCTGAATCAAAATCTCAAGACACATCACAAATCACTCTCAAGACAAATCGTGAAAA

AGAGCAATCACAAGATCTAGTCTCTGAGCCAACCACAACTGAGCTAGCTGACACAGATGCAGCATCAATGGCT

AATACAGGTTCTGATGCGACTCAAAAAAGCGCTTCTTTACCGCCAGTCAATACAGATGTTCACGATTGGGTAA

AAACCAAAGGAGCTTGGGACAAGGGATACAAAGGACAAGGCAAGGTTGTCGCAGTTATTGACACAGGGATCGA

TCCGGCCCATCAAAGCATGCGCATCAGTGATGTATCAACTGCTAAAGTAAAATCAAAAGAAGACATGCTAGCA

CGCCAAAAAGCCGCCGGTATTAATTATGGGAGTTGGATAAATGATAAAGTTGTTTTTGCACATAATTATGTGG

AAAATAGCGATAATATCAAAGAAAATCAATTCGAGGATTTTGATGAGGACTGGGAAAACTTTGAGTTTGATGC

AGAGGCAGAGCCAAAAGCCATCAAAAAACACAAGATCTATCGTCCCCAATCAACCCAGGCACCGAAAGAAACT

GTTATCAAAACAGAAGAAACAGATGGTTCACATGATATTGACTGGACACAAACAGACGATGACACCAAATACG

AGTCACACGGTATGCATGTGACAGGTATTGTAGCCGGTAATAGCAAAGAAGCCGCTGCTACTGGAGAACGCTT

TTTAGGAATTGCACCAGAGGCCCAAGTCATGTTCATGCGTGTTTTTGCCAACGACATCATGGGATCAGCTGAA

TCACTCTTTATCAAAGCTATCGAAGATGCCGTGGCTTTAGGAGCAGATGTGATCAACCTGAGTCTTGGAACCG

CTAATGGGGCACAGCTTAGTGGCAGCAAGCCTCTAATGGAAGCAATTGAAAAAGCTAAAAAAGCCGGTGTATC

AGTTGTTGTAGCAGCAGGAAATGAGCGCGTCTATGGATCTGACCATGATGATCCATTGGCGACAAATCCAGAC

TATGGTTTGGTCGGTTCTCCCTCAACAGGTCGAACACCAACATCAGTGGCAGCTATAAACAGTAAGTGGGTGA

TTCAACGTCTAATGACGGTCAAAGAATTAGAAAACCGTGCCGATTTAAACCATGGTAAAGCCATCTATTCAGA

GTCTGTCGACTTTAAAGACATAAAAGATAGCCTAGGTTATGATAAATCGCATCAATTTGCTTATGTCAAAGAG

TCAACTGATGCGGGTTATAACGCACAAGACGTTAAAGGTAAAATTGCTTTAATTGAACGTGATCCCAATAAAA

CCTATGACGAAATGATTGCTTTGGCTAAGAAACATGGAGCTCTGGGAGTACTTATTTTTAATAACAAGCCTGG

TCAATCAAACCGCTCAATGCGTCTAACAGCTAATGGGATGGGGATACCATCTGCTTTCATATCGCACGAATTT

GGTAAGGCCATGTCCCAATTAAATGGCAATGGTACAGGAAGTTTAGAGTTTGACAGTGTGGTCTCAAAAGCAC

CGAGTCAAAAAGGCAATGAAATGAATCATTTTTCAAATTGGGGCCTAACTTCTGATGGCTATTTAAAACCTGA

CATTACTGCACCAGGTGGCGATATCTATTCTACCTATAACGATAACCACTATGGTAGCCAAACAGGAACAAGT

ATGGCCTCTCCTCAGATTGCTGGCGCCAGCCTTTTGGTCAAACAATACCTAGAAAAGACTCAGCCAAACTTGC

CAAAAGAAAAAATTGCTGATATCGTTAAGAACCTATTGATGAGCAATGCTCAAATTCATGTTAATCCAGAGAC

AAAAACGACGACCTCACCGCGTGAGCAAGGGGCAGGATTACTTAATATTGACGGAGCTGTCACTAGCGGCCTT

TATGTGACAGGAAAAGACAACTATGGCAGTATATCATTAGGCAACATCACAGATACGATGACGTTTGATGTGA

CTGTTCACAACCTAAGCAATAAAGACAAAACATTACGTTATGACACAGAATTGCTAACAGATCATGTAGACCC

ACAAAAGGGCCGCTTCACTTTGACTTCTCACTCCTTAAAAACGTACCAAGGAGGAGAAGTTACAGTCCCAGCC

AATGGAAAAGTGACTGTAAGGGTTACCATGGATGTCTCACAGTTCACAAAAGAGCTAACAAAACAGATGCCAA

ATGGTTACTATCTAGAAGGTTTTGTCCGCTTTAGAGATAGTCAAGATGACCAACTAAATAGAGTAAACATTCC

TTTTGTTGGTTTTAAAGGGCAATTTGAAAACTTAGCAGTTGCAGAAGAGTCCATTTACAGATTAAAATCTCAA

GGCAAAACTGGTTTTTACTTTGATGAATCAGGTCCAAAAGACGATATCTATGTCGGTAAACACTTTACAGGAC

-continued

SEQUENCE DATA FOR DNA SEQUENCES

TTGTCACTCTTGGTTCAGAG 3.2 Antigenic fragment Spy0416A-1
> Spy0416A-1/SF370 (serotype 1); SEQ ID NO: 14
GCAGATGAGCTAAGCACAATGAGCGAACCAACAATCACGAATCACGCTCAACAACAAGCGCAACATCTCACCA

ATACAGAGTTGAGCTCAGCTGAATCAAAATCTCAAGACACATCACAAATCACTCTCAAGACAAATCGTGAAAA

AGAGCAATCACAAGATCTAGTCTCTGAGCCAACCACAACTGAGCTAGCTGACACAGATGCAGCATCAATGGCT

AATACAGGTTCTGATGCGACTCAAAAAAGCGCTTCTTTACCGCCAGTCAATACAGATGTTCACGATTGGGTAA

AAACCAAAGGAGCTTGGGACAAGGGATACAAAGGACAAGGCAAGGTTGTCGCAGTTATTGACACAGGGATCGA

TCCGGCCCATCAAAGCATGCGCATCAGTGATGTATCAACTGCTAAAGTAAAATCAAAAGAAGACATGCTAGCA

CGCCAAAAAGCCGCCGGTATTAATTATGGGAGTTGGATAAATGATAAAGTTGTTTTTGCACATAATTATGTGG

AAAATAGCGATAATATCAAAGAAAATCAATTCGAGGATTTTGATGAGGACTGGGAAAACTTTGAGTTTGATGC

AGAGGCAGAGCCAAAAGCCATCAAAAAACACAAGATCTATCGTCCCCAATCAACCCAGGCACCGAAAGAAACT

GTTATCAAAACAGAAGAAACAGATGGTTCACATGATATTGACTGGACACAAACAGACGATGACACCAAATACG

AGTCACACGGTATGCATGTGACAGGTATTGTAGCCGGTAATAGCAAAGAAGCCGCTGCTACTGGAGAACGCTT

TTTAGGAATTGCACCAGAGGCCCAAGTCATGTTCATGCGTGTTTTTGCCAACGACATCATGGGATCAGCTGAA

TCACTCTTTATCAAAGCTATCGAAGATGCCGTGGCTTTAGGAGCAGATGTGATCAACCTGAGTCTTGGAACCG

CTAATGGGGCACAGCTTAGTGGCAGCAAGCCTCTAATGGAAGCAATTGAAAAAGCTAAAAAAGCCGGTGTATC

AGTTGTTGTAGCAGCAGGAAATGAGCGCGTCTATGGATCTGACCATGATGATCCATTGGCGACAAATCCAGAC

TATGGTTTGGTCGGTTCTCCCTCAACAGGTCGAACACCAACATCAGTGGCAGCTATAAACAGTAAGTGGGTGA

TTCAACGTCTAATGACGGTCAAAGAATTAGAAAACCGTGCCGATTTAAACCATGGTAAAGCCATCTATTCAGA

GTCTGTCGACTTTAAAGACATAAAAGATAGCCTAGGTTATGATAAATCGCATCAATTTGCTTATGTCAAAGAG

TCAACTGATGCGGGTTATAACGCACAAGACGTTAAAGGTAAAATTGCTTTAATTGAACGTGATCCCAATAAAA

CCTATGACGAAATGATTGCTTTGGCTAAGAAACATGGAGCTCTGGGAGTACTTATTTTTAATAACAAGCCTGG

TCAATCAAACCGCTCAATGCGTCTAACAGCTAATGGGATGGGGATACCATCTGCTTTCATATCGCACGAATTT

GGTAAGGCCATGTCCCAATTAAATGGCAATGGTACAGGAAGTTTAGAGTTTGACAGTGTGGTCTCAAAAGCAC

CGAGTCAAAAAGGCAATGAAATGAATCATTTTTCAAATTGGGGCCTAACTTCTGATGGCTATTTAAAACCTGA

CATTACTGCACCAGGTGGCGATATCTATTCTACCTATAACGATAACCACTATGGTAGCCAAACAGGAACAAGT

ATGGCCTCTCCTCAGATTGCTGGCGCCAGCCTTTTGGTCAAACAATACCTAGAAAAGACTCAGCCAAACTTGC

CAAAAGAAAAAATTGCTGATATCGTTAAGAACCTATTGATGAGCAATGCTCAAATTCATGTTAATCCAGAGAC

AAAAACGACCACCTCACCGCGTCAGCAAGGGGCA 3.3 Homologous sequences of other *S. pyogenes* isolates and/or serotypes
> Spy0416A-1/Schmitz 1/7 (serotype 4); SEQ ID NO: 166
GCAGATGAGCTAACCACAACGAGTGAACCAACAATCACGAATCACGCTCAACAACAAGCGCAACATCTCACCA

ATACAGAGTTGAGCTCAGCTGAATCACAATCCCCAGACACATCACAAATCACTCCCAAGACAAATCGTGAAAA

AGAGCAACCACAAGGTCTAGTCTCTGAGCCAACCACAACTGAGCTAGCTGACACAGATGCAGCATCAATGGCT

AATACAGGTCCTGATGCGACTCAAAAAAGCGCTTCTTTACCGCCAGTCAATACAGATGTTCACGATTGGGTAA

AAACCAAAGGAGCTTGGGACAAGGGATACAAAGGACAAGGCAAGGTTGTCGCAGTTATTGACACAGGGATCGA

TCCGGCCCATCAAAGCATGCGCATCAGTGATGTATCAACTGCTAAAGTAAAATCAAAAGAAGACATGCTAGCA

CGCCAAAAAGCCGCCGGTATTAATTATGGGAGTTGGATAAATGATAAAGTTGTTTTTGCACATAATTATGTGG

AAAATAGCGATAATATCAAAGAAAATCAATTCGGGGATTTTGATGAGGACTGGGAAAACTTTGAGTTTGATGC

AGAGCCAAAAGCCATCAAAAAAAACAAGATCTATCGTCCCCAATCAACCCAGGCACCGAAAGAAACTGTTATC

-continued

| SEQUENCE DATA FOR DNA SEQUENCES |
|---|
| AAAACAGAAGAAACAGATGGTTCACATGATATTGACTGGACACAAACAGACGATGACACCAAATACGAGTCAC |
| ACGGTATGCATGTGACAGGTATTGTAGCCGGTAATAGCAAAGAAGCCGCTGCTACTGGAGAACGCTTTTTAGG |
| AATTGCACCAGAGGCCCAAGTCATGTTCATGCGTGTTTTTGCCAACGACGTCATGGGATCAGCTGAATCACTC |
| TTTATCAAAGCTATCGAAGATGCCGTGGCTTTAGGAGCAGATGTGATCAACCTGAGTCTTGGAACCGCTAATG |
| GGGCACAGCTTAGTGGCAGCAAGCCTCTAATGGAAGCAATTGAAAAAGCTAAAAAAGCCGGTGTATCAGTTGT |
| TGTAGCAGCAGGAAATGAGCGCGTCTATGGATCTGACCATGATGATCCATTGGCAACAAATCCAGACTATGGT |
| TTGGTCGGTTCTCCCTCAACAGGTCGAACACCAACATCAGTGGCAGCTATAAACAGTAAGTGGGTGATTCAAC |
| GTCTAATGAGGGCCAAAGAATTAGAAAACCGTGCCGATTTAAACCATGGTAAAGCCATCTATTCAGAGTCTGT |
| CGActttaaagacataaaagatagcctaggttatgataaATCGCATCAATTTGCTTATGTCAAaGAGTCAACT |
| GATGCGGGTTATAAAGCACAAGACGTTAAAGATAAAATTGCTTTAATTGAACGTGATCCCAATAAAACCTATG |
| ACGAAATGATTGCTTTGGCTAAGAAACATGGAGCCCTGGGAGTACTTATTTTTAATAACAAGCCTGGTCAATC |
| AAACCGCTCAATGCGTCTAACAGCTAATGGGATGGGGATACCATCTGCTTTCATATCGCACGAATTTGGTAAG |
| GCCATGTCCGAATTAAATGGCAATGGTACAGGAAGTTTAGAGTTTGACAGTGTGGTCTCAAAAGCACCGAGTC |
| AAAAAGGCAATGAAATGAATCATTTTTCAAATTGGGGCCTAACTTCTGATGGCTATTTAAAACCTGACATTAC |
| TGCACCAGGTGGCGATATCTACTCTACCTATAACGATAACCACTATGGTAGCCAAACAGGAACAAGTATGGCC |
| TCTCCTCAGATTGCTGGCGCCAGCCTTTTGGTCAAACAATACCTAGAAAAGACTCAGCCAAACTTGCCAAAAG |
| AAAAAATTGCTGATATCGTTAAGAACCTATTGATGAGCAATGCTCAAATTCATGTTAATCCAGAGACAAAAAC |
| GACCACCTCACCGCGTCAGCAAGGGGCA |
| > Spy0416A-1/Schmitz 1/39 (serotype 12); SEQ ID NO: 167<br>GCAGATGAGCTAACCACAACGAGTGAACCAACAATCACGAATCACACTCAACAACAAGCGCAACATCTCACCA |
| ATACAGAGTTGAGCTCAGCTGAATCAAAACCTCAAGACACATCACAAATCACTCTCAAGACAAATCGTGAAAA |
| AGAGCAACCACAAGGTCTAGTCTCTGAGCCAACCACAACTGAGCTAGCTGACACAGATGCAGCACCAATGGCT |
| AATACAGGTCCTGATGCGACTCAAAAAAGCGCTTCTTTACCGCCAGTCAATACAGATGTTCACGATTGGGTAA |
| AAACCAAAGGAGCTTGGGACAAGGGATACAAAGGACAAGGCAAGGTTGTCGCAGTTATTGACACAGGGATCGA |
| TCCGGCCCATCAAAGCATGCGCATCAGTGATGTATCAACTGCTAAAGTAAAATCAAAAGAAGACATGCTAGCA |
| CGCCAAAAAGCCGCCGGTATTAATTATGGGAGTTGGATAAATGATAAAGTTGTTTTTGCACATAATTATGTGG |
| AAAATAGCGATAATATCAAAGAAAATCAATTCGAGGATTTTGATGAGGACTGGGAAAACTTTGAGTTTGATGC |
| AGAGGCAGAGCCAAAAGCCATCAAAAAACACAAGATCTATCGTCCCCAATCAACCCAGGCACCGAAAGAAACT |
| GTTATCAAAACAGAAGAAACAGATGGTTCACATGATATTGACTGGACACAAACAGACGATGACACCAAATACG |
| AGTCACACGGTATGCATGTGACAGGTATTGTAGCCGGTAATAGCAAAGAAGCCGCTGCTACTGGAGAACGCTT |
| TTTAGGAATTGCACCAGAGGCCCAAGTCATGTTCATGCGTGTTTTTGCCAACGACGTCATGGGATCAGCTGAA |
| TCACTCTTTATCAAAGCTATCGAAGATGCCGTGGCTTTAGGAGCAGATGTGATCAACCTGAGTCTTGGAACCG |
| CTAATGGGGCACAGCTTAGTGGCAGCAAGCCTCTAATGGAAGCAATTGAAAAAGCTAAAAAAGCCGGTGTATC |
| AGTTGTTGTAGCAGCAGGAAATGAGCGCGTCTATGGATCTGACCATGATGATCCATTGGCAACAAATCCAGAC |
| TATGGTTTGGTCGGTTCTCCCTCAACAGGTCGAACACCAACATCAGTGGCAGCTATAAACAGTAAGTGGGTGA |
| TTCAACGTCTAATGACGGTCAAAGAATTAGAAAACCGTGCCGATTTAAACCATGGTAAAGCCATCTaTTCAGA |
| GTCTGTCGActttaaaGACATAAAAGATAGCCTAGGTTATGATAAATCGCATCAATTTGCTTATGTCaAAGAG |
| TCAACTGATGCGGGTTATAACGCACAAGACGTTAAAGGTAAAATTGCTTTAATTGAACGTGATCCCAATAAAA |
| CCTATGACGAAATGATTGCTTTGGCTAAGAAACATGGAGCCCTGGGAGTACTTATTTTTAATAACAAGCCTGG |
| TCAATCAAACCGCTCAATGCGTCTAACAGCTAATGGGATGGGGATACCATCTGCTTTCATATCGCACGAATTT |

-continued

SEQUENCE DATA FOR DNA SEQUENCES

GGTAAGGCCATGTCCCAATTAAATGGCAATGGTACAGGAAGTTTAGAGTTTGACAGTGTGGTCTCAAAAGCAC

CGAGTCAAAAAGGCAATGAAATGAATCATTTTTCAAATTGGGGCCTAACTTCTGATGGCTATTTAAAACCTGA

CATTACTGCACCAGGTGGCGATATCTACTCTACCTATAACGATAACCACTATGGTAGCCAAACAGGAACAAGT

ATGGCCTCTCCTCAGATTGCTGGCGCCAGCCTTTTGGTCAAACAATACCTAGAAAAGACTCAGCCAAACTTGC

CAAAAGAAAAAATTGCTGATATCGTTAAGAACCTATTGATGAGCAATGCTCAAATTCATGTTAATCCAGAGAC

AAAAACGACCACCTCACCGCGTCAGCAAGGGGCA

> Spy0416A-1/Schmitz 1/55 (serotype 118); SEQ ID NO: 168
GCAGATGAGCTAACCACAACGAGTGAACCAACAATCACGAATCACGCTCAACAACAAGCGCCACCTCTCACCA

ATACAGAGTTGAGCTCAGCTGAATCACAACCTCAAGACACATCACAAGTAACTCCAGAGACAAATCGTGAAAA

AGAGCAACCACAAGGTCTAGTCTCTGAGCCAACAACAACTGAGCTAGCTGACACAGATGCAGCACCAATGGCT

AATACAGGTTCTGATGCGACTCAAAAAAGCGCTTCTTTACCGCCAGTCAATACAGATGTTCACGATTGGGTAA

AAACCAAAGGAGCTTGGGACAAGGGATACAAAGGACAAGGCAAGGTTGTCGCAGTTATTGACACAGGGATCGA

TCCGGCCCATCAAAGCATGCGCATCAGTGATGTATCAACTGCTAAAGTAAAATCAAAAGAAGACATGCTAGCA

CGCCAAAAAGCCGCCGGTATTAATTATGGGAGTTGGATAAATGATAAAGTTGTTTTTGCACATAATTATGTGG

AAAATAGCGATAATATCAAAGAAAATCAATTCGAGGATTTTGATGAGGACTGGGAAAACTTTGAGTTTGATGC

AGAGGCAGAGCCAAAAGCCATCAAAAAACACAAGATCTATCGTCCCCAATCAACCCAGGCACCGAAAGAAACT

GTTATCAAAACAGAAGAAACAGATGGTTCACATGATATTGACTGGACACAAACAGACGATGACACCAAATACG

AGTCACACGGTATGCATGTGACAGGTATTGTAGCCGGTAATAGCAAAGAAGCCGCTGCTACTGGAGAACGCTT

TTTAGGAATTGCACCAGAGGCCCAAGTCATGTTCATGCGTGTTTTTGCCAACGACGTCATGGGATCAGCTGAA

TCACTCTTTATCAAAGCTATCGAAGATGCCGTGGCCTTAGGAGCAGATGTGATCAACCTGAGTCTTGGAACCG

CTAATGGGGCACAGCTTAGTGGCAGCAAGCCTCTAATGGAAGCAATTGAAAAAGCTAAAAAAGCCGGTGTATC

AGTTGTTGTAGCAGCAGGAAATGAGCGCGTCTATGGATCTGACCATGATGATCCATTGGCGACAAATCCAGAC

TATGGTTTGGTCGGTTCTCCCTCAACAGGTCGAACACCAACATCAGTAGCAGCTATAAACAGTAAGTGGGTGA

TTCAACGTCTAATGACGGTCAAAGAATTGGAAAACCGTGCCGATTTAAACCATGGTAAAGCCATCTaTTCAGA

GTCTGTCGACTTTAAAGACATAAAAGATAGCCTAGGTTATGATAAATCGCATCAATTTGCTTATGTCAaAGAG

TCAACTGATGCGGGTTATAACGCACAAAACGTTAAAGGTAAAATTGCTTTAATTGAACGTGATCCCAATAAAA

CCTATGACGAAATGATTGCTTTGGCTAAGAAACATGGAGCCCTGGGAGTACTTATTTTTAATAACAAGCCTGG

TGAATCAAACCGCTCAATGCGTCTAACAGCTAATGGGATGGGGATACCATCTGCTTTCATATGGCACGAATTT

GGTAAGGCCATGTCCCAATTAAATGGCAATGGTACAGGAAGTTTAGAGTTTGACAGTGTGGTCTCAAAAGCAC

CGAGTCAAAAAGGCAATGAAATGAATCATTTTTCAAATTGGGGCCTAACCTCTGATGGCTATTTAAAACCTGA

CATTACTGCACCAGGTGGCGATATCTACTCTACCTATAACGATAACCACTATGGTAGCCAAACAGGAACAAGT

ATGGCCTCTCCTCAGATTGCTGGCGCCAGCCTTTTGGTCAAACAATACCTAGAAAAGACTCAGCCAAATTTGC

CAAAAGAAAAAATTGCTGATATCGTTAAGAACCTATTGATGAGCAATGCTCAAATTCATGTTAATCCAGAGAC

AAAAACGACCACCTCACCGCGTCAGCAAGGGGCA

> Spy0416A-1/Schmitz 1/56 (serotype 28); SEQ ID NO: 169
GCAGATGAGCTAACCACAACGAGTGAACCAACAATCACGAATCACGCTCAACAACAAGCGCAACATCTCACCA

ATACAGAGTTGAGCTCAGCTGAATCACAATCCCCAGACACATCACAAATCACTCCCAAGATAAATCGTGAAAA

AGAGCAACCACAAGGTCTAGTCTCTGAGCCAACCACAACTGAGCTAGCTGACACAGATGCAGCACCAATGGCT

AATACAGGTCCTGATGCGACTCAAAAAAGCGCTTCTTTACCGCCAGTCAATACAGATGTTCACGATTGGGTAA

AAACCAAAGGAGCTTGGGACAAGGGGTACAAAGGACAAGGTAAGGTTGTCGCAGTTATTGACACAGGGATCGA

-continued

| SEQUENCE DATA FOR DNA SEQUENCES |
|---|

TCCGGCCCATCAAAGCATGCGCATCAGTGATGTATCAACTGCTAAAGTAAAATCAAAAGAAGACATGCTAGCA

CGCCAAAAAGCCGCCGGTATTAATTATGGGAGTTGGATAAATGATAAAGTTGTTTTTGCACATAATTATGTGG

AAAATAGCGATAATATCAAAGAAAATCAATTCGAGGATTTTGATGAGGACTGGGAAAACTTTGAGTTTGATGC

AGAGCCAAAAGCCATCAAAAAACACAAGATCTATCGTCCCCAATCAACCCAGGCACCGAAAGAAACTGTTATC

AAAACAGAAGAAACAGATGGTTCACATGATATTGACTGGACACAAACAGACGATGACACCAAATACGAGTCAC

ACGGTATGCATGTGACAGGTATTGTAGCCGGTAATAGTAAAGAAGCCGCTGCTACTGGAGAACGCTTTTTAGG

AATTGCACCAGAGACCCAAGTCATGTTCATGCGTGTTTTTGCCAACGACGTCATGGGATCAGCTGAATCACTC

TTTATCAAAGCTATCGAAGATGCCGTGGCCTTAGGAGCAGATGTGATCAACCTGAGTCTTGGGACCGCTAATG

GTGCACAGCTTAGTGGCAGCAAGCCTCTAATGGAAGCAATTGAAAAAGCTAAAAAAGCCGGTGTATCAGTTGT

TGTAGCAGCAGGAAATGAGCGCGTCTATGGATCTGACCATGATGATCCATTGGCAACAAATCCAGACTATGGT

TTGGTCGGTTCTCCCTCAACAGGTCGAACACCAACATCAGTGGCAGCTATAAACAGTAAGTGGGTGATTCAAC

GTCTAATGACGGTCAAAGAATTAGAAAACCGTGCCGATTTAAACCATGGTAAAGCCATCTaTTCAGAGTCTGT

CGACTTtAAAGACATAAAAGATAGCCTAGGTTATGATAAATCGCATCAATTTGCTTATGTCAAAGAGTCAACT

GATGCGGGTTATAACGCACAAGACGTTAAAGGTAAAATTGCTTTAATTGAACGTGATCCCAATAAAACCTATG

ACGAAATGATTGCTTTGGCTAAGAAACATGGAGCCCTGGGAGTACTTATTTTTAATAACAAGCCTGGTCAATC

AAACCGCTCAATGCGCCTAACAGCTAATGGGATGGGGATACCATCTGCTTTCATATCGCACGAATTTGGTAAG

GCCATGTCCCAATTAAATGGCAATGGTACAGGAAGTTTAGAGTTTGACAGTGTGGTCTCAAAAGCACCGAGTC

AAAAAGGCAATGAAATGAATCATTTTTCAAATTGGGGCCTAACTTCTGATGGCTATTTAAAACCTGACATTAC

TGCACCAGGGGGTGATATCTACTCTACCTATAACGATAACCACTATGGTAGCCAAACAGGAACAAGTATGGCC

TCTCCTCAGATTGCTGGCGCCAGCCTTTTGGTCAAACAATACCTAGAAAAGACTCAGCCAAAACTTGCCAAAAG

AAAAAATTGCTGATATCGTTAAGAACCTATTGATGAGCAATGCTCAAATTCATGTTAATCCAGAGACAAAAAC

GACCACCTCACCGCGTCAGCAAGGGGCA

> Spy0416A-1/Schmitz 1/94 (serotype 1); SEQ ID NO: 170
GCAGATGAGCTAAGCACAATGAGCGAACCAACAATCACGAATCACGCTCAACAACAAGCGCAACATCTCACCA

ATACAGAGTTGAGCTCAGCTGAATCAAAATCTCAAGACACATCACAAATCACTCTCAAGACAAATCGTGAAAA

AGAGCAATCACAAGATCTAGTCTCTGAGCCAACCACAACTGAGCTAGCTGACACAGATGCAGCATCAATGGCT

AATACAGGTTCTGATGCGACTCAAAAAAGCGCTTCTTTACCGCCAGTCAATACAGATGTTCACGATTGGGTAA

AAACCAAAGGAGCTTGGGACAAGGGATACAAAGGACAAGGCAAGGTTGTCGCAGTTATTGACACAGGGATCGA

TCCGGCCCATCAAAGCATGCGCATCAGTGATGTATCAACTGCTAAAGTAAAATCAAAAGAAGACATGCTAGCA

CGCCAAAAAGCCGCCGGTATTAATTATGGGAGTTGGATAAATGATAAAGTTGTTTTTGCACATAATTATGTGG

AAAATAGCGATAATATCAAAGAAAATCAATTCGAGGATTTTGATGAGGACTGGGAAAACTTTGAGTTTGATGC

AGAGGCAGAGCCAAAAGCCATGAAAAAACACAAGATCTATCGTCCCCAATCAACCCAGGCACCGAAAGAAACT

GTTATCAAAACAGAAGAAACAGATGGTTCACATGATATTGACTGGACACAAACAGACGATGACACCAAATACG

AGTCACACGGTATGCATGTGACAGGTATTGTAGCCGGTAATAGCAAAGAAGCCGCTGCTACTGGAGAACGCTT

TTTAGGAATTGCACCAGAGGCCCAAGTCATGTTCATGCGTGTTTTTGCCAACGACATCATGGGATCAGCTGAA

TCACTCTTTATCAAAGCTATCGAAGATGCCGTGGCTTTAGGAGCAGATGTGATCAACCTGAGTCTTGGAACCG

CTAATGGGGCACAGCTTAGTGGCAGCAAGCCTCTAATGGAAGCAATTGAAAAAGCTAAAAAAGCCGGTGTATC

AGTTGTTGTAGCAGCAGGAAATGAGCGCGTCTATGGATCTGACCATGATGATCCATTGGCGACAAATCCAGAC

TATGGTTTGGTCGGTTCTCCCTCAACAGGTCGAACACCAACATCAGTGGCAGCTATAAACAGTAACTGGGTGA

-continued

SEQUENCE DATA FOR DNA SEQUENCES

TTCAACGTCTAATGACGGTCAAAGAATTAGAAAACCGTGCCGATTTAAACCATGGTAAAGCCATCTATTCAGA

GTCTGTCGACTTTAAAGACATAAAAGATAGCCTAGGTTATGATAAATCGCATCAATTTGCTTATGTCaAAGAG

TCAACTGATGCGGGTTATAACGCACAAGACGTTAAAGGTAAAATTGCTTTAATTGAACGTGATCCCAATAAAA

CCTATGACGAAATGATTGCTTTGGCTAAGAAACATGGAGCTCTGGGAGTACTTATTTTTAATAACAAGCCTGG

TCAATCAAACCGCTCAATGCGTCTAACAGCTAATGGGATGGGGATACCATCTGCTTTCATATCGCACGAATTT

GGTAAGGCCATGTCCCAATTAAATGGCAATGGTACAGGAAGTTTAGAGTTTGACAGTGTGGTCTCAAAAGCAC

CGAGTCAAAAAGGCAATGAAATGAATCATTTTTCAAATTGGGGCCTAACTTCTGATGGCTATTTAAAACCTGA

CATTACTGCACCAGGTGGCGATATCTATTCTACCTATAACGATAACCACTATGGTAGCCAAACAGGAACAAGT

ATGGCCTCTCCTCAGATTGCTGGCGCCAGCCTTTTGGTCAAACAATACCTAGAAAAGACTCAGCCAAACTTGC

CAAAAGAAAAAATTGCTGATATCGTTAAGAACCTATTGATGAGCAATGCTCAAATTCATGTTAATCCAGAGAC

AAAAACGACCACCTCACCGCGTCAGCAAGGGGCA

> Spy0416A-1/Schmitz 1/253 (serotype 49); SEQ ID NO: 171
GCAGATGAGCTAACCACAACGAGTGAACCAACAATCACGAATCACGCTCAACAACAAGCGCAACCTCTCACCA

ATACAGAGTTGAGCTCAGCTGAATCACAATCCCCAGACATATCACAAGTAACTCCAGAGACAAATCGTGAAAA

AGAGCAACCACAAGGTCTAGTCTCTGAGCCAACAACAACTGAGCTAGCTGACACAGATGCAGCACCAATGGCT

AATACAGGTCCTGATGCGACTCAAAAAAGCGCTTCTTTACCGCCAGTCAATACAGATGTTCACGATTGGGTAA

AAACCAAAGGAGCTTGGGACAAGGGATACAAAGGACAAGGCAAGCTTGTCGCAGTTATTGACACAGGGATCGA

TCCGGCCCATCAAAGCATGCGCATCAGTGATGTATCAACTGCTAAAGTAAAATCAAAAGAAGACATGCTAGCA

CGCCAAAAAGCCGCCGGTATTAATTATGGGAGTTGGATAAATGATAAAGTTGTTTTTGCACATAATTATGTGG

AAAATAGCGATAATATCAAAGAAAATCAATTCGAGGATTTTGATGAGGACTGGGAAAACTTTGAGTTTGATGC

AGATGCAGAGCCAAAAGCCATCAAAAAACACAAGATCTATCGTCCCCAATCAACCCAGGCACCGAAAGAAACT

GTTATCAAAACAGAAGAAACAGATGGTTCACATGATATTGACTGGACACAAACAGACGATGACACCAAATACG

AGTCACACGGTATGCATGTGACAGGTATTGTAGCCGGTAATAGCAAAGAAGCCGCTGCTACTGGAGAACGCTT

TTTAGGAATTGCACCAGAGGCCCAAGTCATGTTCATGCGTGTTTTTGCCAACGACGTCATGCGATCAGCTGAA

TCACTCTTTATCAAAGCTATCGAAGATGCCGTGGCTTTAGGAGCAGATGTGATCAACCTGAGTCTTGGAACCG

CTAATGGGGCACAGCTTAGTGGCAGCAAGCCTCTAATGGAAGCAATTGAAAAAGCTAAAAAAGCCGGTGTATC

AGTTGTTGTAGCAGCAGGAAATGAGCGCGTCTATGGATCTCACCATGATGATCCATTGGCAACAAATCCAGAC

TATGGTTTGGTCGGTTCTCCCTCAACAGGTCGAACACCAACATCAGTGGCAGCTATAAACAGTAAGTGGGTGA

TTCAACGTCTAATGACGGTCAAAGGATTAGAAAACCGTGCCGATTTAaACCATGGTAAAGCCATCTATTCAGA

GTCTGTCGACTTTAAAGACATAAAAGATAGCCTAGGTTATGATAAATCGCATCAATTTGCTTATGTCAAaGAG

TCAACTGATGCGGGTTATAACGCACAAGACGTTAAACGTAAAATTGCTTTAATTGAACGTGATCCCAATAAAA

CCTATGACGAAATGATTGCTTTGGCTAAGAAACATGCAGCCCTGGGACTACTTATTTTTAATAACAAGTCTGG

TCAATCAAACCGCTCAATGCGTCTAACAGCTAATGGGATGGGGATACCATCTGCTTTCATATCGCACGAATTT

GGTAAGGCCATGTCCCAATTAAATGGCAATGGTACAGGAAGTTTAGAGTTTGACAGTGTGGTCTCAAAAGCAC

CGAGTCAAAAAGGCAATGAAATGAATCATTTTTCAAATTGGGGCCTAACTTCTGATGGCTATTTAAAACCTGA

CATTACTGCACCAGGTGGCGATATCTACTCTACCTATAACGATAACCACTATGGTAGCCAAACAGGAACAAGT

ATGGCCTCTCCTCAGATTGCTGGCGCCAGCCTTTTGGTCAAACAATACCTAGAAAAGACCCAGCCAAACTTGC

CAAAAGAAAAAATTGCTGATATCGTTAAGAACCTATTGATGAGCAATGCTCAAATTCATGTTAATCCAGAGAC

AAAAACAACCACCTCACCGCGTCAGCAAGGGGCA

> Spy0416A-1/Schmitz 1/174 (serotype 6); SEQ ID NO: 172

-continued

SEQUENCE DATA FOR DNA SEQUENCES

GCAGATGAGCTAACCACAACGAGTGAACCAACAATCACGAATCACGCTCAACAACAAGCGCAACATCTCACCA

ATACAGAGTTGAGCTCAGCTGAATCAAAACCTCAAGACACATCACAAATCACTCCCAAGACAAATCGTGAAAA

AGAGCAATCACAAGATCTAGTCTCTGAGCCAACCACAACTGAGCTAGCTGACACAGATGCAGCATCAATGGCT

AATACAGGTCCTGATGCGACTCAAAAAAGCGCTTCTTTACCGCCAGTCAATACAGATGTTCACGATTGGGTAA

AAACCAAAGGAGCTTGGGACAAGGGATACAAAGGACAAGGCAAGGTTGTCGCAGTTATTGACACAGGGATCGA

TCCGGCCCATCAAAGCATGCGCATCAGTGATGTATCAACTGCTAAAGTAAAATCAAAAGAAGACATGCTAGCA

CGCCAAAAAGCCGCCGGTATTAATTATGGGAGTTGGATAAATGATAAAGTTGTTTTTGCACATAATTATGTGG

AAAATAGCGATAATATCAAAGAAAATCAATTCGAGGATTTTGATGAGGACTGGGAAAACTTTGAGTTTGATGC

AGAGGCAGAGCCAAAAGCCATCAAAAAACACAAGATCTATCGTCCCCAATCAACCCAGGCACCGAAAGAAACT

GTTATCAAAACAGAAGAAACAGATGCTTCACATGATATTGACTGGACACAAACAGACGATGACACCAAATACG

AGTCACACGGTATGCATGTGACAGGTATTGTAGCCGGTAATAGCAAAGAAGCCGCTGCTACTGGAGAACGCTT

TTTAGGAATTGCACCAGAGGCCCAAGTCATGTTCATGCGTGTTTTTGCCAACGACGTCATGGGATCAGCTGAA

TCACTCTTTATCAAAGCTATCGAAGATGCCGTGGCTTTAGGAGCAGATGTGATCAACCTGAGTCTTGGAACCG

CTAATGGGGCACAGCTTAGTGGCAGCAAGCCTCTAATGGAAGCAATTGAAAAAGCTAAAAAAGCCGGTGTATC

AGTTGTTGTAGCAGCAGGAAATGAGCGCGTCTATGGATCTGACCATGATGATCCATTGGCAACAAATCCAGAC

TATGGTTTGGTCGGTTCTCCCTCAACAGGTCGAACACCAACATCAGTGGCAGCTATAAACAGTAAGTGGGTGA

TTCAACGTCTAATGACGGTCAAAGAATTAGAAAACCGTGCCGATTTAAACCATGGTAAAGCCATCTaTTCAGA

GTCTGTCGACTTTAAAaACATAAAAGATAGCCTAGGTTATGATAAATCGCATCAATTTGCTTATGTCAAaGAG

TCAACTGATGCGGGTTATAACGCAGAAGACGTTAAAGGTAAAATTGCTTTAATTGAACGTGATCCCAATAAAA

CCTATGACGAAATGATTGCTTTGGCTAAGAAACATGGAGCCCTGGGAGTACTTATTTTTAATAACAAACCTGG

TCAATCAAACCGCTCAATGCGCCTAACATCTAATGGGATGGGAATACCATCTGCTTTCATATCGCACGAATTT

GGTAAGGCCATGTCCCAATTAAATGGCAATGGTACAGGAAGTTTAGAGTTTGACAGTGTGGTCTCAAAAGCAC

CGAGTCAAAAAGGCAATGAAATGAATCATTTTTCAAATTGGGGCCTAACTTCTGATGGCTATTTAAAACCTGA

CATTACTGCACCAGGTGGCGATATCTACTCTACCTATAACGATAACCACTATGGTAGCCAAACAGGAACAAGT

ATGGCCTCTCCTCAGATTGCTGGCGCCAGCCTTTTGGTCAAACAATACCTAGAAAAGACTCAGCCAAACTTGC

CAAAAGAAAAAATTGCTGATATCGTTAAGAACCTATTGATGAGCAATGCTCAAATTCATGTTAATCCAGAGAC

AAAAACGACCACCTCACCGCGTCAGCAAGGGGCA

> Spy0416A-1/Schmitz 1/176 (serotype 83); SEQ ID NO: 173
GCAGATGAGCTAACCACAACGAGTGAACCAACAATCACGAATCACACTCAACAACAAGCGCAACATCTCACCA

ATACAGAGTTGAGCTCAGCTGAATCAAAACCTCAAGACACATCACAAATCACTCTCAAGACAAATCGTGAAAA

AGAGCAACCACAAGGTCTAGTCTCTGAGCCAACCACAACTGAGCTAGCTGACACAGATGCAGCACCAATGGCT

AATACAGGTCCTGATGCGACTCAAAAAAGCGCTTCTTTACCGCCAGTCAATACAGATGTTCACGATTGGGTAA

AAACCAAAGGAGCTTGGGACAAGGGATACAAAGGACAAGGCAAGGTTGTCGCAGTTATTGACACAGGGATCGA

TCCGGCCCATCAAAGCATGCGCATCAGTGATGTATCAACTGCTAAAGTAAAATCAAAAGAAGACATGCTAGCA

CGCCAAAAAGCCGCCGGTATTAATTATGGGAGTTGGATAAATGATAAAGTTGTTTTTGCACATAATTATGTGG

AAAATAGCGATAATATCAAAGAAAATCAATTCGAGGATTTTGATGAGGACTGGGAAAACTTTGAGTTTGATGC

AGAGGCAGAGCCAAAAGCCATCAAAAAACACAAGATCTATCGTCCCCAATCAACCCAGGCACCGAAAGAAACT

GTTATCAAAACAGAAGAAACAGATGGTTCACATGATATTGACTGGACACAAACAGACGATGACACCAAATACG

AGTCACACGGTATGCATGTGACAGGTATTGTAGCCGGTAATAGCAAAGAAGCCGCTGCTACTGGAGAACGCTT

TTTAGGAATTGCACCAGAGGCCCAAGTCATGTTCATGCGTGTTTTTGCCAACGACGTCATGGGATCAGCTGAA

-continued

| SEQUENCE DATA FOR DNA SEQUENCES |
|---|

TCACTCTTTATCAAAGCTATCGAAGATGCCGTGGCTTTAGGAGCAGATGTGATCAACCTGAGTCTTGGAACCG

CTAATGGGGCACAGCTTAGTGGCAGCAAGCCTCTAATGGAAGCAATTGAAAAAGCTAAAAAAGCCGGTGTATC

AGTTGTTGTAGCAGCAGGAAATGAGCGCGTCTATGGATCTGACCATGATGATCCATTGGCAACAAATCCAGAC

TATGGTTTGGTCGGTTCTCCCTCAACAGGTCGAACACCAACATCAGTGGCAGCTATAAACAGTAAGTGGGTGA

TTCAACGTCTAATGACGGTCAAAGAATTAGAAAACCGTGCCGATTTAAACCATGGTAAAGCCATCTATTCAGA

GTCTGTCGACTTTAAAAACATAAAAGATAGCCTAGGTTATGATAAATCGCATCAATTTGCTTATGTCAAAGAG

TCAACTGATGCGGGTTATAAAGCACAAGACGTTAAAGGTAAAATTGCTTTAATTGAACGTGATCCCAATAAAA

CCTATGACGAAATGATTGCTTTGGCTAAGAAACATGGAGCCCTGGGAGTACTTATTTTTAATAACAAGCCTGG

TCAATCAAACCGCTCAATGCGTCTAACAGCTAATGGGATGGGGATACCATCTGCTTTCATATCGCACGAATTT

GGTAAGGCCATGTCCCAATTAAATGGCAATGGTACAGGAAGTTTAGAGTTTGACAGTGTGGTCTCAAAAGCAC

CGAGTCAAAAAGGCAATGAAATGAATCATTTTTCAAATTGGGGCCTAACTTCTGATGGCTATTTAAAACCTGA

CATTACTGCACCAGGTGGCGATATCTACTCTACCTATAACGATAACCACTATGGTAGCCAAACAGGAACAAGT

ATGGCCTCTCCTCAGATTGCTGGCGCCAGCCTTTTGGTCAAACAATACCTAGAAAAGACTCAGCCAAACTTGC

CAAAAGAAAAAATTGCTGATATCGTTAAGAACCTATTGATGAGCAATGCTCAAATTCATGTTAATCCAGAGAC

AAAAACGACCACCTCACCGCGTCAGCAAGGGGCA

> Spy0416A-1/Schmitz 1/234 (serotype 44); SEQ ID NO: 174
GCAGATGAGCTAAGCACAATGAGTGAACCAACAATCACGAATCACGCTCAACAACAAGCGCAACATCTCACCA

ATACAGAGTTGAGCTCAGCTGAATCAAAATCTCAAGACACATCACAAATCACTCCCAAGACAAATCGTGAAAA

AGAGCAATCACAAGATCTAGTCTCTGAGCCAACAACAACTGAGCTAGCTGACACAGATGCAGCATCAATGGCT

AATACAGGTTCTGATGCGACTCAAAAAAGCGCTTCTTTACCGCCAGTCAATACAGATGTTCACGATTGGGTAA

AAACCAAAGGAGCTTGGGACAAGGGATACAAAGGACAAGGCAAGGTTGTCGCAGTTATTGACACAGGGATCGA

TCCGGCCCATCAAAGCATGCGCATCAGTGATGTATCAACTGCTAAAGTAAAATCAAAAGAAGACATGCTAGCA

CGCCAAAAAGCCGCCGGTATTAATTATGGGAGTTGGATAAATGATAAAGTTGTTTTTGCACATAATTATGTGG

AAAATAGCGATAATATCAAAGAAAATCAATTCGAGGATTTTGATGAGGACTGGGAAAACTTTGAGTTTGATGC

AGATGCAGAGCCAAAAGCCATCAAAAAACACAAGATCTATCGTCCCCAATCAACCCAGGCACCGAAAGAAACT

GTTATCAAAACAGAAGAAACAGATGGTTCACATGATATTGACTGGACACAAACAGACGATGACACCAAATACG

AGTCACACGGTATGCATGTGACAGGTATTGTAGCCGGTAATAGCAAAGAAGCCGCTGCTACTGGAGAACGCTT

TTTAGGAATTGCACCAGAGGCCCAAGTCATGTTCATGCGTGTTTTTGCCAACGACGTCATGGGATCAGCTGAA

TCACTCTTTATCAAAGCTATCGAAGATGCCGTGGCTTTAGGAGCAGATGTGATCAACCTGAGTCTTGGAACCG

CTAATGGGGCACAGCTTAGTGGCAGCAAGCCTCTAATGGAAGCAATTGAAAAAGCTAAAAAAGCCGGTGTATC

AGTTGTTGTAGCAGCAGGAAATGAGCGCGTCTATGGATCTGACCATGATGACCCATTGGCAACAAATCCAGAC

TATGGTTTGGTTGGTTCTCCCTCAACAGGTCGAACACCAACATCAGTGGCAGCTATAAACAGTAAGTGGGTGA

TTCAACGTCTAATGACGGTCAAAGAATTGGAAAACCGTGCCGATTTAAACCATGGTAAAGCCATCTaTTCAGA

GTCTGTCGACTTtAAAGACATAAAAGATAGCCTAGGTTATGATAAATCGCATCAATTTGCTTATGTCAAAGAG

TCAACTGATGCGGGTTATAAAGCACAAGACGTTAAAGATAAAATTGCTTTAATTGAACGTGATCCCAATAAAA

CCTATGACGAAATGATTGCTTTGGCTAAGAAACATGGAGCCCTGGGGGTACTTATTTTTAATAACAAGCCTGG

TCAATCAAACCGCTCAATGCGTCTAACAGCTAATGGGATGGGGATACCATCTGCTTTCATATCGCACGAATTT

GGTAAGGCCATGTCCCAATTAAATGGCAATGGTACAGGAAGTTTAGAGTTTGACAGTGTGGTCTCAAAAGCAC

CGAGTCAAAAAGGCAATGAAATGAATCATTTTTCAAATTGGGGCCTAACTTCTGATGGCTATTTAAAACCTGA

-continued

| SEQUENCE DATA FOR DNA SEQUENCES |
|---|
| CATTACTGCACGAGGCGGCGATATCTACTCTACCTATAACGATAACCACTATGGTAGCCAAACAGGAACAAGT |
| ATGGCCTCTCCTCAGATTGCTGGCGCCAGCCTTTTGGTCAAACAATATCTAGAAAAGACTCAGCCAAACTTGC |
| CAAAAGAAAAAATTGCTGATATCGTTAAGAACCTATTGATGAGCAATGCTCAAATTCATGTTAATCCAGAGAC |
| AAAAACGACCACCTCACCGCGTCAGCAAGGGGCA |
| > Spy0416A-1/Schmitz 1/22 (serotype 4); SEQ ID NO: 175<br>GCAGATGAGCTAACCACAACGAGTGAACCAACAATCACGAATCACGCTCAACAACAAGCGCAACATCTCACCA |
| ATACAGAGTTGAGCTCAGCTGAATCACAATCCCCAGACACATCACAAATCACTCCCAAGACAAATCGTGAAAA |
| AGAGCAACCACAAGGTCTAGTCTCTGAGCCAACCACAACTGAGCTAGCTGACACAGATGCAGCATCAATGGCT |
| AATACAGGTCCTGATGCGACTCAAAAAAGCGCTTCTTTACCGCCAGTCAATACAGATGTTCACGATTGGGTAA |
| AAACCAAAGGAGCTTGGGACAAGGGATACAAAGGACAAGGCAAGGTTGTCGCAGTTATTGACACAGGGATCGA |
| TCCGGCCCATCAAAGCATGCGCATCAGTGATGTATCAACTGCTAAAGTAAAATCAAAAGAAGACATGCTAGCA |
| CGCCAAAAAGCCGCCGGTATTAATTATGGGAGTTGGATAAATGATAAAGTTGTTTTTGCACATAATTATGTGG |
| AAAATAGCGATAATATCAAAGAAAATCAATTCGGGGATTTTGATGAGGACTGGGAAAACTTTGAGTTTGATGC |
| AGAGCCAAAAGCCATCAAAAAAAACAAGATCTATCGTCCCCAATCAACCCAGGCACCGAAAGAAACTGTTATC |
| AAAACAGAAGAAACAGATGGTTCACATGATATTGACTGGACACAAACAGACGATGACACCAAATACGAGTCAC |
| ACGGTATGCATGTGACAGGTATTGTAGCCGGTAATAGCAAAGAAGCCGCTGCTACTGGAGAACGCTTTTTAGG |
| AATTGCACCAGAGGCCCAAGTCATGTTCATGCGTGTTTTTGCCAACGACGTCATGGGATCAGCTGAATCACTC |
| TTTATCAAAGCTATCGAAGATGCCGTGGCTTTAGGAGCAGATGTGATCAACCTGAGTCTTGGAACCGCTAATG |
| GGGCACAGCTTAGTGGCAGCAAGCCTCTAATGGAAGCAATTGAAAAAGCTAAAAAAGCCGGTGTATCAGTTGT |
| TGTAGCAGCAGGAAATGAGCGCGTCTATGGATCTGACCATGATGATCCATTGGCAACAAATCCAGACTATGGT |
| TTGGTCGGTTCTCCCTCAACAGGTCGAACACCAACATCAGTGGCAGCTATAAACAGTAAGTGGGTGATTCAAC |
| GTCTAATGACGGCCAAAGAATTAGAAAACCGTGCCGATTTAAACCATGGTAAAGCCATCTATTCAGAGTCTGT |
| CGACTTTAAAGACATAAAAGATAGCCTAGGTTATGATAAATCGCATCAATTTGCTTATGTCAAAGAGTCAACT |
| GATGCGGGTTATAAAGCACAAGACGTTAAAGATAAAATTGCTTTAATTGAACGTGATCCCAATAAAACCTATG |
| ACGAAATGATTGCTTTGGCTAAGAAACATGGAGCCCTGGGAGTACTTATTTTTAATAACAAGCCTGGTCAATC |
| AAACCGCTCAATGCGTCTAACAGCTAATGGGATGGGGATACCATCTGCTTTCATATCGCACGAATTTGGTAAG |
| GCCATGTCCCAATTAAATGGCAATGGTACAGGAAGTTTAGAGTTTGACAGTGTGGTCTCAAAAGCACCGAGTC |
| AAAAAGGCAATGAAATGAATCATTTTTCAAATTGGGGCCTAACTTCTGATGGCTATTTAAAACCTGACATTAC |
| TGCACCAGGTGGCGATATCTACTCTACCTATAACGATAACCACTATGGTAGCCAAACAGGAACAAGTATGGCC |
| TCTCCTCAGATTGCTGGCGCCAGCCTTTTGGTCAAACAATACCTAGAAAAGACTCAGCCAAACTTGCCAAAAG |
| AAAAAATTGCTGATATCGTTAAGAACCTATTGATGAGCAATGCTCAAATTCATGTTAATCCAGAGACAAAAAC |
| GACCACCTCACCGCGTCAGCAAGGGGCA |
| 3.4 Antigenic fragment Spy0416A-6<br>> Spy0416A-6/SF370 (serotype 1); SEQ ID NO: 15<br>GCAGTTATTGACACAGGGATCGATCCGGCCCATCAAAGCATGCGCATCAGTGATGTATCAACTGCTAAAGTAA |
| AATCAAAAGAAGACATGCTAGCACGCCAAAAAGCCGCCGGTATTAATTATGGGAGTTGGATAAATGATAAAGT |
| TGTTTTTGCACATAATTATGTGGAAAATAGCGATAATATCAAAGAAAATCAATTCGAGGATTTTGATGAGGAC |
| TGGGAAAACTTTGAGTTTGATGCAGAGGCAGAGCCAAAAGCCATCAAAAAAACACAAGATCTATCGTCCCCAAT |
| CAACCCAGGCACCGAAAGAAACTGTTATCAAAACAGAAGAAACAGATGGTTCACATGATATTGACTGGACACA |
| AACAGACGATGACACCAAATACGAGTCACACGGTATGCATGTGACAGGTATTGTAGCCGGTAATAGCAAAGAA |
| GCCGCTGCTACTGGAGAACGCTTTTTAGGAATTGCACCAGAGGCCCAAGTCATGTTCATGCGTGTTTTTGCCA |

-continued

SEQUENCE DATA FOR DNA SEQUENCES

ACGACATCATGGGATCAGCTGAATCACTCTTTATCAAAGCTATCGAAGATGCCGTGGCTTTAGGAGCAGATGT

GATCAACCTGAGTCTTGGAACCGCTAATGGGGCACAGCTTAGTGGCAGCAAGCCTCTAATGGAAGCAATTGAA

AAAGCTAAAAAAGCCGGTGTATCAGTTGTTGTAGCAGCAGGAAATGAGCGCGTCTATGGATCTGACCATGATG

ATCCATTGGCGACAAATCCAGACTATGGTTTGGTCGGTTCTCCCTCAACAGGTCGAACACCAACATCAGTGGC

AGCTATAAACAGTAAGTGGGTGATTCAACGTCTAATGACGGTCAAAGAATTAGAAAACCGTGCCGATTTAAAC

CATGGTAAAGCCATCTATTCAGAGTCTGTCGACTTTAAAGACATAAAAGATAGCCTA 3.5 Homologous sequences of other *S. pyogenes* isolates and/or serotypes
> Spy0416A-6/Schmitz 1/7 (serotype 4); SEQ ID NO: 176
GCAGTTATTGACACAGGGATCGATCCGGCCCATCAAAGCATGCGCATCAGTGATGTATCAACTGCTAAAGTAA

AATCAAAAGAAGACATGCTAGCACGCCAAAAAGCCGCCGGTATTAATTATGGGAGTTGGATAAATGATAAAGT

TGTTTTTGCACATAATTATGTGGAAAATAGCGATAATATCAAAGAAAATCAATTCGGGGATTTTGATGAGGAC

TGGGAAAACTTTGAGTTTGATGCAGAGCCAAAAGCCATCAAAAAAAACAAGATCTATCGTCCCCAATCAACCC

AGGCACCGAAAGAAACTGTTATCAAAACAGAAGAAACAGATGGTTCACATGATATTGACTGGACACAAACAGA

CGATGACACCAAATACGAGTCACACGGTATGCATGTGACAGGTATTGTAGCCGGTAATAGCAAAGAAGCCGCT

GCTACTGGAGAACGCTTTTTAGGAATTGCACCAGAGGCCCAAGTCATGTTCATGCGTGTTTTTGCCAACGACG

TCATGGGATCAGCTGAATCACTCTTTATCAAAGCTATCGAAGATGCCGTGGCTTTAGGAGCAGATGTGATCAA

CCTGAGTCTTGGAACCGCTAATGGGGCACAGCTTAGTGGCAGCAAGCCTCTAATGGAAGCAATTGAAAAAGCT

AAAAAAGCCGGTGTATCAGTTGTTGTAGCAGCAGGAAATGAGCGCGTCTATGGATCTGACCATGATGATCCAT

TGGCAACAAATCCAGACTATGGTTTGGTCGGTTCTCCCTCAACAGGTCGAACACCAACATCAGTGGCAGCTAT

AAACAGTAAGTGGGTGATTCAACGTCTAATGACGGCCAAAGAATTAGAAAACCGTGCCGATTTAAACCATGGT

AAAGCCATCTATTCAGAGTCTGTCGActttaaagacataaaagatagccta

> Spy0416A-6/Schmitz 1/39 (serotype 12); SEQ ID NO: 177
GCAGTTATTGACACAGGGATCGATCCGGCCCATCAAAGCATGCGCATCAGTGATGTATCAACTGCTAAAGTAA

AATCAAAAGAAGACATGCTAGCACGCCAAAAAGCCGCCGGTATTAATTATGGGAGTTGGATAAATGATAAAGT

TGTTTTTGCACATAATTATGTGGAAAATAGCGATAATATCAAAGAAAATCAATTCGAGGATTTTGATGAGGAC

TGGGAAAACTTTGAGTTTGATGCAGAGGCAGAGCCAAAAGCCATCAAAAAACACAAGATCTATCGTCCCCAAT

CAACCCAGGCACCGAAAGAAACTGTTATCAAAACAGAAGAAACAGATGGTTCACATGATATTGACTGGACACA

AACAGACGATGACACCAAATACGAGTCACACGGTATGCATGTGACAGGTATTGTAGCCGGTAATAGCAAAGAA

GCCGCTGCTACTGGAGAACGCTTTTTAGGAATTGCACCAGAGGCCCAAGTCATGTTCATGCGTGTTTTTGCCA

ACGACGTCATGGGATCAGCTGAATCACTCTTTATCAAAGCTATCGAAGATGCCGTGGCTTTAGGAGCAGATGT

GATCAACCTGAGTCTTGGAACCGCTAATGGGGCACAGCTTAGTGGCAGCAAGCCTCTAATGGAAGCAATTGAA

AAAGCTAAAAAAGCCGGTGTATCAGTTGTTGTAGCAGCAGGAAATGAGCGCGTCTATGGATCTGACCATGATG

ATCCATTGGCAACAAATCCAGACTATGGTTTGGTCGGTTCTCCCTCAACAGGTCGAACACCAACATCAGTGGC

AGCTATAAACAGTAAGTGGGTGATTCAACGTCTAATGACGGTCAAAGAATTAGAAAACCGTGCCGATTTAAAC

CATGGTAAAGCCATCTaTTCAGAGTCTGTCGActttaaaGACATAAAAGATAGCCTA

> Spy0416A-6/Schmitz 1/55 (serotype 118); SEQ ID NO: 178
GCAGTTATTGACACAGGGATCGATCCGGCCCATCAAAGCATGCGCATCAGTGATGTATCAACTGCTAAAGTAA

AATCAAAAGAAGACATGCTAGCACGCCAAAAAGCCGCCGGTATTAATTATGGGAGTTGGATAAATGATAAAGT

TGTTTTTGCACATAATTATGTGGAAAATAGCGATAATATCAAAGAAAATCAATTCGAGGATTTTGATGAGGAC

TGGGAAAACTTTGAGTTTGATGCAGAGGCAGAGCCAAAAGCCATCAAAAAACACAAGATCTATCGTCCCCAAT

CAACCCAGGCACCGAAAGAAACTGTTATCAAAACAGAAGAAACAGATGGTTCACATGATATTGACTGGACACA

-continued

SEQUENCE DATA FOR DNA SEQUENCES

AACAGACGATGACACCAAATACGAGTCACACGGTATGCATGTGACAGGTATTGTAGCCGGTAATAGCAAAGAA

GCCGCTGCTACTGGAGAACGCTTTTTAGGAATTGCACCAGAGGCCCAAGTCATGTTCATGCGTGTTTTTGCCA

ACGACGTCATGGGATCAGCTGAATCACTCTTTATCAAAGCTATCGAAGATGCCGTGGCCTTAGGAGCAGATGT

GATCAACCTGAGTCTTGGAACCGCTAATGGGGCACAGCTTAGTGGCAGCAAGCCTCTAATGGAAGCAATTGAA

AAAGCTAAAAAAGCCGGTGTATCAGTTGTTGTAGCAGCAGGAAATGAGCGCGTCTATGGATCTGACCATGATG

ATCCATTGGCGACAAATCCAGACTATGGTTTGGTCGGTTCTCCCTCAACAGGTCGAACACCAACATCAGTAGC

AGCTATAAACAGTAAGTGGGTGATTCAACGTCTAATGACGGTCAAAGAATTGGAAAACCGTGCCGATTTAAAC

CATGGTAAAGCCATCTaTTCAGAGTCTGTCGACTTTAAAGACATAAAAGATAGCCTA

> Spy0416A-6/Schmitz 1/56 (serotype 28); SEQ ID NO: 179
GCAGTTATTGACACAGGGATCGATCCGGCCCATCAAAGCATGCGCATCAGTGATGTATCAACTGCTAAAGTAA

AATCAAAAGAAGACATGCTAGCACGCCAAAAAGCCGCCGGTATTAATTATGGGAGTTGGATAAATGATAAAGT

TGTTTTTGCACATAATTATGTGGAAAATAGCGATAATATCAAAGAAAATCAATTCGAGGATTTTGATGAGGAC

TGGGAAAACTTTGAGTTTGATGCAGAGCCAAAAGCCATCAAAAAACACAAGATCTATCGTCCCCAATCAACCC

AGGCACCGAAAGAAACTGTTATCAAAACAGAAGAAACAGATGGTTCACATGATATTGACTGGACACAAACAGA

CGATGACACCAAATACGAGTCACACGGTATGCATGTGACAGGTATTGTAGCCGGTAATAGTAAAGAAGCCGCT

GCTACTGGAGAACGCTTTTTAGGAATTGCACCAGAGACCCAAGTCATGTTCATGCGTGTTTTTGCCAACGACG

TCATGGGATCAGCTGAATCACTCTTTATCAAAGCTATCGAAGATGCCGTGGCCTTAGGAGCAGATGTGATCAA

CCTGAGTCTTGGGACCGCTAATGGTGCACAGCTTAGTGGCAGCAAGCCTCTAATGGAAGCAATTGAAAAAGCT

AAAAAAGCCGGTGTATCAGTTGTTGTAGCAGCAGGAAATGAGCGCGTCTATGGATCTGACCATGATGATCCAT

TGGCAACAAATCCAGACTATGGTTTGGTCGGTTCTCCCTCAACAGGTCGAACACCAACATCAGTGGCAGCTAT

AAACAGTAAGTGGGTGATTCAACGTCTAATGACGGTCAAAGAATTAGAAAACCGTGCCGATTTAAACCATGGT

AAAGCCATCTaTTCAGAGTCTGTCGACTTtAAAGACATAAAAGATAGCCTA

> Spy0416A-6/Schmitz 1/94 (serotype 1); SEQ ID NO: 180
GCAGTTATTGACACAGGGATCGATCCGGCCCATCAAAGCATGCGCATCAGTGATGTATCAACTGCTAAAGTAA

AATCAAAAGAAGACATGCTAGCACGCCAAAAAGCCGCCGGTATTAATTATGGGAGTTGGATAAATGATAAAGT

TGTTTTTGCACATAATTATGTGGAAAATAGCGATAATATCAAAGAAAATCAATTCGAGGATTTTGATGAGGAC

TGGGAAAACTTTGAGTTTGATGCAGAGGCAGAGCCAAAAGCCATCAAAAAACACAAGATCTATCGTCCCCAAT

CAACCCAGGCACCGAAAGAAACTGTTATCAAAACAGAAGAAACAGATGGTTCACATGATATTGACTGGACACA

AACAGACGATGACACCAAATACGAGTCACACGGTATGCATGTGACAGGTATTGTAGCCGGTAATAGCAAAGAA

GCCGCTGCTACTGGAGAACGCTTTTTAGGAATTGCACCAGAGGCCCAAGTCATGTTCATGCGTGTTTTTGCCA

ACGACATCATGGGATCAGCTGAATCACTCTTTATCAAAGCTATCGAAGATGCCGTGGCTTTAGGAGCAGATGT

GATCAACCTGAGTCTTGGAACCGCTAATGGGGCACAGCTTAGTGGCAGCAAGCCTCTAATGGAAGCAATTGAA

AAAGCTAAAAAAGCCGGTGTATCAGTTGTTGTAGCAGCAGGAAATGAGCGCGTCTATGGATCTGACCATGATG

ATCCATTGGCGACAAATCCAGACTATGGTTTGGTCGGTTCTCCCTCAACAGGTCGAACACCAACATCAGTGGC

AGCTATAAACAGTAAGTGGGTGATTCAACGTCTAATGACGGTCAAAGAATTAGAAAACCGTGCCGATTTAAAC

CATGGTAAAGCCATCTATTCAGAGTCTGTCGACTttAAAGACATAAAAGATAGCCTA

> Spy0416A-6/Schmitz 1/253 (serotype 49); SEQ ID NO: 181
GCAGTTATTGACACAGGGATCGATCCGGCCCATCAAAGCATGCGCATCAGTGATGTATCAACTGCTAAAGTAA

AATCAAAAGAAGACATGCTAGCACGCCAAAAAGCCGCCGGTATTAATTATGGGAGTTGGATAAATGATAAAGT

TGTTTTTGCACATAATTATGTGGAAAATAGCGATAATATCAAAGAAAATGAATTCGAGGATTTTGATGAGGAC

-continued

| SEQUENCE DATA FOR DNA SEQUENCES |
| --- |

TGGGAAAACTTTGAGTTTGATGCAGATGCAGAGCCAAAAGCCATCAAAAAACACAAGATCTATCGTCCCCAAT

CAACCCAGGCACCGAAAGAAACTGTTATCAAAACAGAAGAAACAGATGGTTCACATGATATTGACTGGACACA

AACAGACGATGACACCAAATACGAGTCACACGGTATGCATGTGACAGGTATTGTAGCCGGTAATAGCAAAGAA

GCCGCTGCTACTGGAGAACGCTTTTTAGGAATTGCACCAGAGGCCCAAGTCATGTTCATGCGTGTTTTTGCCA

ACGACGTCATGGGATCAGCTGAATCACTCTTTATCAAAGCTATCGAAGATGCCGTGGCTTTAGGAGCAGATGT

GATCAACCTGAGTCTTGGAACCGCTAATGGGGCACAGCTTAGTGGCAGCAAGCCTCTAATGGAAGCAATTGAA

AAAGCTAAAAAAGCCGGTGTATCAGTTGTTGTAGCAGCAGGAAATGAGCGCGTCTATGGATCTGACCATGATG

ATCCATTGGCAACAAATCCAGACTATGGTTTGGTCGGTTCTCCCTCAACAGGTCGAACACCAACATCAGTGGC

AGCTATAAACAGTAAGTGGGTGATTCAACGTCTAATGACGGTCAAAGGATTAGAAAACCGTGCCGATTTAaAC

CATGGTAAAGCCATCTATTCAGAGTCTGTCGACTTTAAAGACATAAAAGATAGCCTA

> Spy0416A-6/Schmitz 1/174 (serotype 6); SEQ ID NO: 182
GCAGTTATTGACACAGGGATCGATCCGGCCCATCAAAGCATGCGCATCAGTGATGTATCAACTGCTAAAGTAA

AATCAAAAGAAGACATGCTAGCACGCCAAAAAGCCGCCGGTATTAATTATGGGAGTTGGATAAATGATAAAGT

TGTTTTTGCACATAATTATGTGGAAAATAGCGATAATATCAAAGAAAATCAATTCGAGGATTTTGATGAGGAC

TGGGAAAACTTTGAGTTTGATGCAGAGGCAGAGCCAAAAGCCATCAAAAAACACAAGATCTATCGTCCCCAAT

CAACCCAGGCACCGAAAGAAACTGTTATCAAAACAGAAGAAACAGATGGTTCACATGATATTGACTGGACACA

AACAGACGATGACACCAAATACGAGTCACACGGTATGCATGTGACAGGTATTGTAGCCGGTAATAGCAAAGAA

GCCGCTGCTACTGGAGAACGCTTTTTAGGAATTGCACCAGAGGCCCAAGTCATGTTCATGCGTGTTTTTGCCA

ACGACGTCATGGGATCAGCTGAATCACTCTTTATCAAAGCTATCGAAGATGCCGTGGCTTTAGGAGCAGATGT

GATCAACCTGAGTCTTGGAACCGCTAATGGGGCACAGCTTAGTGGCAGCAAGCCTCTAATGGAAGCAATTGAA

AAAGCTAAAAAAGCCGGTGTATCAGTTGTTGTAGCAGCAGGAAATGAGCGCGTCTATGGATCTGACCATGATG

ATCCATTGGCAACAAATCCAGACTATGGTTTGGTCGGTTCTCCCTCAACAGGTCGAACACCAACATCAGTGGC

AGCTATAAACAGTAAGTGGGTGATTCAACGTCTAATGACGGTCAAAGAATTAGAAAACCGTGCCGATTTAAAC

CATGGTAAAGCCATCTaTTCAGAGTCTGTCGACTTTAAAaACATAAAAGATAGCCTA

> Spy0416A-6/Schmitz 1/176 (serotype 83); SEQ ID NO: 183
GCAGTTATTGACACAGGGATCGATCCGGCCCATCAAAGCATGCGCATCAGTGATGTATCAACTGCTAAAGTAA

AATCAAAAGAAGACATGCTAGCACGCCAAAAAGCCGCCGGTATTAATTATGGGAGTTGGATAAATGATAAAGT

TGTTTTTGCACATAATTATGTGGAAAATAGCGATAATATCAAAGAAAATCAATTCGAGGATTTTGATGAGGAC

TGGGAAAACTTTGAGTTTGATGCAGAGGCAGAGCCAAAAGCCATCAAAAAACACAAGATCTATCGTCCCCAAT

CAACCCAGGCACCGAAAGAAACTGTTATCAAAACAGAAGAAACAGATGGTTCACATGATATTGACTGGACACA

AACAGACGATGACACCAAATACGAGTCACACGGTATGCATGTGACAGGTATTGTAGCCGGTAATAGCAAAGAA

GCCGCTGCTACTGGAGAACGCTTTTTAGGAATTGCACCAGAGGCCCAAGTCATGTTCATGCGTGTTTTTGCCA

ACGACGTCATGGGATCAGCTGAATCACTCTTTATCAAAGCTATCGAAGATGCCGTGGCTTTAGGAGCAGATGT

GATCAACCTGAGTCTTGGAACCGCTAATGGGGCACAGCTTAGTGGCAGCAAGCCTCTAATGGAAGCAATTGAA

AAAGCTAAAAAAGCCGGTGTATCAGTTGTTGTAGCAGCAGGAAATGAGCGCGTCTATGGATCTGACCATGATG

ATCCATTGGCAACAAATCCAGACTATGGTTTGGTCGGTTCTCCCTCAACAGGTCGAACACCAACATCAGTGGC

AGCTATAAACAGTAAGTGGGTGATTCAACGTCTAATGACGGTCAAAGAATTAGAAAACCGTGCCGATTTAAAC

CATGGTAAAGCCATCTATTCAGAGTCTGTCGACTTTAAAAACATAAAAGATAGCCTA

> Spy0416A-6/Schmitz 1/234 (serotype 44); SEQ ID NO: 184
GCAGTTATTGACACAGGGATCGATCCGGCCCATCAAAGCATGCGCATCAGTGATGTATCAACTGCTAAAGTAA

AATCAAAAGAAGACATGCTAGCACGCCAAAAAGCCGCCGGTATTAATTATGGGAGTTGGATAAATGATAAAGT

-continued

SEQUENCE DATA FOR DNA SEQUENCES

TGTTTTTGCACATAATTATGTGGAAAATAGCGATAATATCAAAGAAAATCAATTCGAGGATTTTGATGAGGAC

TGGGAAAACTTTGAGTTTGATGCAGATGCAGAGCCAAAAGCCATCAAAAAACACAAGATCTATCGTCCCCAAT

CAACCCAGGCACCGAAAGAAACTGTTATCAAAACAGAAGAAACAGATGGTTCACATGATATTGACTGGACACA

AACAGACGATGACACCAAATACGAGTCACACGGTATGCATGTGACAGGTATTGTAGCCGGTAATAGCAAAGAA

GCCGCTGCTACTGGAGAACGCTTTTTAGGAATTGCACCAGAGGCCCAAGTCATGTTCATGCGTGTTTTTGCCA

ACGACGTCATGGGATCAGCTGAATCACTCTTTATCAAAGCTATCGAAGATGCCGTGGCTTTAGGAGCAGATGT

GATCAACCTGAGTCTTGGAACCGCTAATGGGGCACAGCTTAGTGGCAGCAAGCCTCTAATGGAAGCAATTGAA

AAAGCTAAAAAAGCCGGTGTATCAGTTGTTGTAGCAGCAGGAAATGAGCGCGTCTATGGATCTGACCATGATG

ACCCATTGGCAACAAATCCAGACTATGGTTTGGTTGGTTCTCCCTCAACAGGTCGAACACCAACATCAGTGGC

AGCTATAAACAGTAAGTGGGTGATTCAACGTCTAATGACGGTCAAAGAATTGGAAAACCGTGCCGATTTAAAC

CATGGTAAAGCCATCTaTTCAGAGTCTGTCGACTTtAAAGACATAAAAGATAGCCTA

> Spy0416A-6/Schmitz 1/22 (serotype 4); SEQ ID NO: 185
GCAGTTATTGACACAGGGATCGATCCGGCCCATCAAAGCATGCGCATCAGTGATGTATCAACTGCTAAAGTAA

AATCAAAAGAAGACATGCTAGCACGCCAAAAAGCCGCCGGTATTAATTATGGGAGTTGGATAAATGATAAAGT

TGTTTTTGCACATAATTATGTGGAAAATAGCGATAATATCAAAGAAAATCAATTCGGGGATTTTGATGAGGAC

TGGGAAAACTTTGAGTTTGATGCAGAGCCAAAAGCCATCAAAAAAAACAAGATCTATCGTCCCCAATCAACCC

AGGCACCGAAAGAAACTGTTATCAAAACAGAAGAAACAGATGGTTCACATGATATTGACTGGACACAAACAGA

CGATGACACCAAATACGAGTCACACGGTATGCATGTGACAGGTATTGTAGCCGGTAATAGCAAAGAAGCCGCT

GCTACTGGAGAACGCTTTTTAGGAATTGCACCAGAGGCCCAAGTCATGTTCATGCGTGTTTTTGCCAACGACG

TCATGGGATCAGCTGAATCACTCTTTATCAAAGCTATCGAAGATGCCGTGGCTTTAGGAGCAGATGTGATCAA

CCTGAGTCTTGGAACCGCTAATGGGGCACAGCTTAGTGGCAGCAAGCCTCTAATGGAAGCAATTGAAAAAGCT

AAAAAAGCCGGTGTATCAGTTGTTGTAGCAGCAGGAAATGAGCGCGTCTATGGATCTGACCATGATGATCCAT

TGGCAACAAATCCAGACTATGGTTTGGTCGGTTCTCCCTCAACAGGTCGAACACCAACATCAGTGGCAGCTAT

AAACAGTAAGTGGGTGATTCAACGTCTAATGACGGCCAAAGAATTAGAAAACCGTGCCGATTTAAACCATGGT

AAAGCCATCTATTCAGAGTCTGTCGACTTTAAAGACATAAAAGATAGCCTA 3.6 Antigenic fragment Spy0416A-7
> Spy0416A-7/SF370 (serotype 1); SEQ ID NO: 16
TCACAAATCACTCTCAAGACAAATCGTGAAAAAGAGCAATCACAAGATCTAGTCTCTGAGCCAACCACAACTG

AGCTAGCTGACACAGATGCAGCATCAATGGCTAATACAGGTTCTGATGCGACTCAAAAAAGCGCTTCTTTACC

GCCAGTCAATACAGATGTTCACGATTGGGTAAAAACCAAAGGAGCTTGGGACAAGGGATACAAAGGACAAGGC

AAGGTTGTCGCAGTTATTGACACAGGGATCGATCCGGCCCATCAAAGCATGCGCATCAGTGATGTATCAACTG

CTAAAGTAAAATCAAAAGAAGACATCCTAGCACGCCAAAAAGCCGCCGGTATTAATTATGGGAGTTGGATAAA

TGATAAAGTTGTTTTTGCACATAATTATGTGGAAAATAGCGATAATATCAAAGAAAATCAATTCGAGGATTTT

GATGAGGACTGGGAAAACTTTGAGTTTGATGCAGAGGCAGAGCCAAAAGCCATCAAAAAACACAAGATCTATC

GTCCCCAATCAACCCAGGCACCGAAAGAAACTGTTATCAAAACAGAAGAAACAGATGGTTCACATGATATTGA

CTGGACACAAACAGACGATGACACCAAATACGAGTCACACGGTATGCATGTGACAGGTATTGTAGCCGGTAAT

AGCAAAGAAGCCGCTGCTACTGGAGAACGCTTTTTAGGAATTGCACCAGAGGCCCAAGTCATGTTCATGCGTG

TTTTTGCCAACGACATCATGGGATCAGCTGAATCACTCTTTATCAAAGCTATCGAAGATGCCGTGGCTTTAGG

AGCAGATGTGATCAACCTGAGTCTTGGAACCGCTAATGGGGCACAGCTTAGTGGCAGCAAGCCTCTAATGGAA

GCAATTGAAAAAGCTAAAAAAGCCGGTGTATCAGTTGTTGTAGCAGCAGGAAATGAGCGCGTCTATGGATCTG

| SEQUENCE DATA FOR DNA SEQUENCES |
| --- |
| ACCATGATGATCCATTGGCGACAAATCCAGACTATGGTTTGGTCGGTTCTCCCTCAACAGGTCGAACACCAAC |
| ATCAGTGGCAGCTATAAACAGTAAGTGGGTGATTCAACGTCTAATGACGGTCAAAGAATTAGAAAACCGTGCC |
| GATTTAAACCATGGTAAAGCCATCTATTCAGAGTCTGTCGACTTTAAAGACATAAAAGATAGCCTAGGTTATG |
| ATAAATCGCATCAATTTGCTTATGTCAAAGAGTCAACTGATGCGGGTTATAACGCACAAGACGTTAAAGGTAA |
| AATTGCTTTAATTGAACGTGATCCCAATAAAACCTATGACGAAATGATTGCTTTGGCTAAGAAACATGGAGCT |
| CTGGGAGTACTTATTTTTAATAACAAGCCTGGTCAATCAAACCGCTCAATGCGTCTAACAGCTAATGGGATGG |
| GGATACCATCTGCTTTCATATCGCACGAATTTGGTAAGGCCATGTCCCAATTAAATGGCAATGGTACAGGAAG |
| T |

3.7 Homologous sequences of other *S. pyogenes* isolates and/or serotypes
> Spy0416A-7/Schmitz 1/7 (serotype 4); SEQ ID NO: 186
TCACAAATCACTCCCAAGACAAATCGTGAAAAAGAGCAACCACAAGGTCTAGTCTCTGAGCCAACCACAACTG

AGCTAGCTGACACAGATGCAGCATCAATGGCTAATACAGGTCCTGATGCGACTCAAAAAAGCGCTTCTTTACC

GCCAGTCAATACAGATGTTCACGATTGGGTAAAAACCAAAGGAGCTTGGGACAAGGGATACAAAGGACAAGGC

AAGGTTGTCGCAGTTATTGACACAGGGATCGATCCGGCCCATCAAAGCATGCGCATCAGTGATGTATCAACTG

CTAAAGTAAAATCAAAAGAAGACATGCTAGCACGCCAAAAAGCCGCCGGTATTAATTATGGGAGTTGGATAAA

TGATAAAGTTGTTTTTGCACATAATTATGTGGAAAATAGCGATAATATCAAAGAAAATCAATTCGGGGATTTT

GATGAGGACTGGGAAAACTTTGAGTTTGATGCAGAGCCAAAAGCCATCAAAAAAAACAAGATCTATCGTCCCC

AATCAACCCAGGCACCGAAAGAAACTGTTATCAAAACAGAAGAAACAGATGGTTCACATGATATTGACTGGAC

ACAAACAGACGATGACACCAAATACGAGTCACACGGTATGCATGTGACAGGTATTGTAGCCGGTAATAGCAAA

GAAGCCGCTGCTACTGGAGAACGCTTTTTAGGAATTGCACCAGAGGCCCAAGTCATGTTCATGCGTGTTTTTG

CCAACGACGTCATGGGATCAGCTGAATCACTCTTTATCAAAGCTATCGAAGATGCCGTGGCTTTAGGAGCAGA

TGTGATCAACCTGAGTCTTGGAACCGCTAATGGGGCACAGCTTAGTGGCAGCAAGCCTCTAATGGAAGCAATT

GAAAAAGCTAAAAAAGCCGGTGTATCAGTTGTTGTAGCAGCAGGAAATGAGCGCGTCTATGGATCTGACCATG

ATGATCCATTGGCAACAAATCCAGACTATGGTTTGGTCGGTTCTCCCTCAACAGGTCGAACACCAACATCAGT

GGCAGCTATAAACAGTAAGTGGGTGATTCAACGTCTAATGACGGCCAAAGAATTAGAAAACCGTGCCGATTTA

AACCATGGTAAAGCCATCTATTCACAGTCTGTCGActttaaagacataaaagatagcctaggttatgataaAT

CGCATCAATTTGCTTATGTCAAaGAGTCAACTGATGCGGGTTATAAAGCACAAGACGTTAAAGATAAAATTGC

TTTAATTGAACGTGATCCCAATAAACCTATGACGAAAATGATTGCTTTGGCTAAGAAACATGGAGCCCTGGGA

GTACTTATTTTTAATAACAAGCCTGGTCAATCAAACCGCTCAATGCGTCTAACAGCTAATGGGATGGGGATAC

CATCTGCTTTCATATCGCACGAATTTGGTAAGGCCATGTCCCAATTAAATGGCAATGGTACAGGAAGT

> Spy0416A-7/Schmitz 1/39 (serotype 12); SEQ ID NO: 187
TCACAAATCACTCTCAAGACAAATCGTGAAAAAGAGCAACCACAAGGTCTAGTCTCTGAGCCAACCACAACTG

AGCTAGCTGACACAGATGCAGCACCAATGGCTAATACAGGTCCTGATGCGACTCAAAAAAGCGCTTCTTTACC

GCCAGTCAATACAGATGTTCACGATTGGGTAAAAACCAAAGGAGCTTGGGACAAGGGATACAAAGGACAAGGC

AAGGTTGTCGCAGTTATTGACACAGGGATCGATCCGGCCCATCAAAGCATGCGCATCAGTGATGTATCAACTG

CTAAAGTAAAATCAAAAGAAGACATGCTAGCACGCCAAAAAGCCGCCGGTATTAATTATGGGAGTTGGATAAA

TGATAAAGTTGTTTTTGCACATAATTATGTGGAAAATAGCGATAATATCAAAGAAAATCAATTCGAGGATTTT

GATGAGGACTGGGAAAACTTTGAGTTTGATGCAGAGGCAGAGCCAAAAGCCATCAAAAAACACAAGATCTATC

GTCCCCAATCAACCCAGGCACCGAAAGAAACTGTTATCAAAACAGAAGAAACAGATGGTTCACATGATATTGA

CTGGACACAAACAGACGATGACACCAAATACGAGTCACACGGTATGCATGTGACAGGTATTGTAGCCGGTAAT

AGCAAAGAAGCCGCTGCTACTGGAGAACGCTTTTTAGGAATTGCACCAGAGGCCCAAGTCATGTTCATGCGTG

-continued

SEQUENCE DATA FOR DNA SEQUENCES

TTTTTGCCAACGACGTCATGGGATCAGCTGAATCACTCTTTATCAAAGCTATCGAAGATGCCGTGGCTTTAGG

AGCAGATGTGATCAACCTGAGTCTTGGAACCGCTAATGGGGCACAGCTTAGTGGCAGCAAGCCTCTAATGGAA

GCAATTGAAAAAGCTAAAAAAGCCGGTGTATCAGTTGTTGTAGCAGCAGGAAATGAGCGCGTCTATGGATCTG

ACCATGATGATCCATTGGCAACAAATCCAGACTATGGTTTGGTCGGTTCTCCCTCAACAGGTCGAACACCAAC

ATCAGTGGCAGCTATAAACAGTAAGTGGGTGATTCAACGTCTAATGACGGTCAAAGAATTAGAAAACCGTGCC

GATTTAAACCATGGTAAAGCCATCTaTTCAGAGTCTGTCGActttaaaGACATAAAAGATAGCCTAGGTTATG

ATAAATCGCATCAATTTGCTTATGTCaAGAGTCAACTGATGCGGGTTATAACGCACAAGACGTTAAAGGTAA

AATTGCTTTAATTGAACGTGATCCCAATAAAACCTATGACGAAATGATTGCTTTGGCTAAGAAACATGGAGCC

CTGGGAGTACTTATTTTTAATAACAAGCCTGGTCAATCAAACCGCTCAATGCGTCTAACAGCTAATGGGATGG

GGATACCATCTGCTTTCATATCGCACGAATTTGGTAAGGCCATGTCCCAATTAAATGGCAATGGTACAGGAAG

T

> Spy0416A-7/Schmitz 1/55 (serotype 118); SEQ ID NO: 188
TCACAAGTAACTCCAGAGACAAATCGTGAAAAAGAGCAACCACAAGGTCTAGTCTCTGAGCCAACAACAACTG

AGCTAGCTGACACAGATGCAGCACCAATGGCTAATACAGGTTCTGATGCGACTCAAAAAAGCGCTTCTTTACC

GCCAGTCAATACAGATGTTCACGATTGGGTAAAAACCAAAGGAGCTTGGGACAAGGGATACAAAGGACAAGGC

AAGGTTGTCGCAGTTATTGACACAGGGATCGATCCGGCCCATCAAAGCATGCGCATCAGTGATGTATCAACTG

CTAAAGTAAAATCAAAAGAAGACATGCTAGCACGCCAAAAAGCCGCCGGTATTAATTATGGGAGTTGGATAAA

TGATAAAGTTGTTTTTGCACATAATTATGTGGAAAATAGCGATAATATCAAAGAAAATCAATTCGAGGATTTT

GATGAGGACTGGGAAAACTTTGAGTTTGATGCAGAGGCAGAGCCAAAAGCCATCAAAAAACACAAGATCTATC

GTCCCCAATCAACCCAGGCACCGAAAGAAACTGTTATCAAAACAGAAGAAACAGATGGTTCACATGATATTGA

CTGGACACAAACAGACGATGACACCAAATACGAGTCACACGGTATGCATGTGACAGGTATTGTAGCCGGTAAT

AGCAAAGAAGCCGCTGCTACTGGAGAACGCTTTTTAGGAATTGCACCAGAGGCCCAAGTCATGTTCATGCGTG

TTTTTGCCAACGACGTCATGGGATCAGCTGAATCACTCTTTATCAAAGCTATCGAAGATGCCGTGGCCTTAGG

AGCAGATGTGATCAACCTGAGTCTTGGAACCGCTAATGGGGCACAGCTTAGTGGCAGCAAGCCTCTAATGGAA

GCAATTGAAAAAGCTAAAAAAGCCGGTGTATCAGTTGTTGTAGCAGCAGGAAATGAGCGCGTCTATGGATCTG

ACCATGATGATCCATTGGCGACAAATCCAGACTATGGTTTGGTCGGTTCTCCCTCAACAGGTCGAACACCAC

ATCAGTAGCAGCTATAAACAGTAAGTGGGTGATTCAACGTCTAATGACGGTCAAAGAATTGGAAACCGTGCC

GATTTAAACCATGGTAAAGCCATCTaTTCAGAGTCTGTCGACTTTAAAGACATAAAAGATAGCCTAGGTTATG

ATAAATCGCATCAATTTGCTTATGTCAaGAGTCAACTGATGCGGGTTATAACGCACAAAACGTTAAGGTAA

AATTGCTTTAATTGAACGTGATCCCAATAAAACCTATGACGAAATGATTGCTTTGGCTAAGAAACATGGAGCC

CTGGGAGTACTTATTTTTAATAACAAGCCTGGTCAATCAAACCGCTCAATGCGTCTAACAGCTAATGGGATGG

GGATACCATCTGCTTTCATATCGCACGAATTTGGTAAGGCCATGTCCCAATTAAATGGCAATGGTACAGGAG

T

> Spy0416A-7/Schmitz 1/56 (serotype 28); SEQ ID NO: 189
TCACAAATCACTCCCAAGATAAATCGTGAAAAAGAGCAACCACAAGGTCTAGTCTCTGAGCCAACCACAACTG

AGCTAGCTGACACAGATGCAGCACCAATGGCTAATACAGGTCCTGATGCGACTCAAAAAAGCGCTTCTTTACC

GCCAGTCAATACAGATGTTCACGATTGGGTAAAAACCAAAGGAGCTTGGGACAGGGGTACAAAGGACAAGGT

AAGGTTGTCGCAGTTATTGACACAGGGATCGATCCGGCCCATCAAAGCATGCGCATCAGTGATGTATCAACTG

CTAAAGTAAAATCAAAAGAAGACATGCTAGCACGCCAAAAAGCCGCCGGTATTATTATGGGAGTTGGATAAA

TGATAAAGTTGTTTTTGCACATAATTATGTGGAAATAGCGATAATATCAAAGAAAATCAATTCGAGGATTTT

-continued

SEQUENCE DATA FOR DNA SEQUENCES

GATGAGGACTGGGAAAACTTTGAGTTTGATGCAGAGCCAAAAGCCATCAAAAAACACAAGATCTATCGTCCCC

AATCAACCCAGGCACCGAAAGAAACTGTTATCAAAACAGAAGAAACAGATGGTTCACATGATATTGACTGGAC

ACAAACAGACGATGACACCAAATACGAGTCACACGGTATGCATGTGACAGGTATTGTAGCCGGTAATAGTAAA

GAAGCCGCTGCTACTGGAGAACGCTTTTTAGGAATTGCACCAGAGACCCAAGTCATGTTCATGCGTGTTTTTG

CCAACGACGTCATGGGATCAGCTGAATCACTCTTTATCAAAGCTATCGAAGATGCCGTGGCCTTAGGAGCAGA

TGTGATCAACCTGAGTCTTGGGACCGCTAATGGTGCACAGCTTAGTGGCAGCAAGCCTCTAATGGAAGCAATT

GAAAAAGCTAAAAAAGCCGGTGTATCAGTTGTTGTAGCAGCAGGAAATGAGCGCGTCTATGGATCTGACCATG

ATGATCCATTGGCAACAAATCCAGACTATGGTTTGGTCGGTTCTCCCTCAACAGGTCGAACACCAACATCAGT

GGCAGCTATAAACAGTAAGTGGTGATTCAACGTCTAATGACGGTCAAAGAATTAGAAAACCGTGCCGATTTA

AACCATGGTAAAGCCATCTaTTCAGAGTCTGTCGACTTtAAAGACATAAAAGATAGCCTAGGTTATGATAAAT

CGCATCAATTTGCTTATGTCAAAGAGTCAACTGATGCGGGTTATAACGCACAAGACGTTAAAGGTAAAATTGC

TTTAATTGAACGTGATCCCAATAAAACCTATGACGAAATGATTGCTTTGGCTAAGAAACATGGAGCCCTGGGA

GTACTTATTTTTAATAACAAGCCTGGTCAATCAAACCGCTCAATGCGCCTAACAGCTAATGGGATGGGGATAC

CATCTGCTTTCATATCGCACGAATTTGGTAAGGCCATGTCCCAATTAAATGGCAATGGTACAGGAAGT

> Spy0416A-7/Schmitz 1/94 (serotype 1); SEQ ID NO: 190
TCACAAATCACTCTCAAGACAAATCGTGAAAAAGAGCAATCACAAGATCTAGTCTCTGAGCCAACCACAACTG

AGCTAGCTGACACAGATGCAGCATCAATGGCTAATACAGGTTCTGATGCGACTCAAAAAAGCGCTTCTTTACC

GCCAGTCAATACAGATGTTCACGATTGGGTAAAAACCAAAGGAGCTTGGGACAAGGGATACAAAGGACAAGGC

AAGGTTGTCGCAGTTATTGACACAGGGATCGATCCGGCCCATCAAAGCATGCGCATCAGTGATGTATCAACTG

CTAAAGTAAAATCAAAAGAAGACATGCTAGCACGCCAAAAAGCCGCCGGTATTAATTATGGGAGTTGGATAAA

TGATAAAGTTGTTTTTGCACATAATTATGTGGAAAATAGCGATAATATCAAAGAAAATCAATTCGAGGATTTT

GATGAGGACTGGGAAAACTTTGAGTTTGATGCAGAGGCAGAGCCAAAAGCCATCAAAAAACACAAGATCTATC

GTCCCCAATCAACCCAGGCACCGAAAGAAACTGTTATCAAAACAGAAGAAACAGATGGTTCACATGATATTGA

CTGGACACAAACAGACGATGACACCAAATACGAGTCACACGGTATGCATGTGACAGGTATTGTAGCCGGTAAT

AGCAAAGAAGCCGCTGCTACTGGAGAACGCTTTTTAGGAATTGCACCAGAGGCCCAAGTCATGTTCATGCGTG

TTTTTGCCAACGACATCATGGGATCAGCTGAATCACTCTTTATCAAAGCTATCGAAGATGCCGTGGCTTTAGG

AGCAGATGTGATCAACCTGAGTCTTGGAACCGCTAATGGGGCACAGCTTAGTGGCAGCAAGCCTCTAATGGAA

GCAATTGAAAAAGCTAAAAAAGCCGGTGTATCAGTTGTTGTAGCAGCAGGAAATGAGCGCGTCTATGGATCTG

ACCATGATGATCCATTGGCGACAAATCCAGACTATGGTTTGGTCGGTTCTCCCTCAACAGGTCGAACACCAAC

ATCAGTGGCAGCTATAAACAGTAAGTGGGTGATTCAACGTCTAATGACGGTCAAAGAATTAGAAAACCGTGCC

GATTTAAACCATGGTAAAGCCATCTATTCAGAGTCTGTCGACTttAAAGACATAAAAGATAGCCTAGGTTATG

ATAAATCGCATCAATTTGCTTATGTCaAAGAGTCAACTGATGCGGGTTATAACGCACAAGACGTTAAAGGTAA

AATTGCTTTAATTGAACGTGATCCCAATAAAACCTATGACGAAATGATTGCTTTGGCTAAGAAACATGGAGCT

CTGGGAGTACTTATTTTTAATAACAAGCCTGGTCAATCAAACCGCTCAATGCGTCTAACAGCTAATGGGATGG

GGATACCATCTGCTTTCATATCGCACGAATTTGGTAAGGCCATGTCCCAATTAAATGGCAATGGTACAGGAAG

T

> Spy0416A-7/Schmitz 1/253 (serotype 49); SEQ ID NO: 191
TCACAAGTAACTCCAGAGACAAATCGTGAAAAGAGCAACCACAAGGTCTAGTCTCTGAGCCAACAACAACTG

AGCTAGCTGACACAGATGCAGCACCAATGGCTAATACAGGTCCTGATGCGACTCAAAAAAGCGCTTCTTTACC

GCCAGTCAATACAGATGTTCACGATTGGGTAAAAACCAAAGGAGCTTGGGACAAGGGATACAAAGGACAAGGC

-continued

SEQUENCE DATA FOR DNA SEQUENCES

AAGGTTGTCGCAGTTATTGACACAGGGATCGATCCGGCCCATCAAAGCATGCGCATCAGTGATGTATCAACTG

CTAAAGTAAAATCAAAAGAAGACATGCTAGCACGCCAAAAAGCCGCCGGTATTATTATGGGAGTTGGATAAA

TGATAAAGTTGTTTTTGCACATAATTATGTGGAAAATAGCGATAATATCAAAGAAAATCAATTCGAGGATTTT

GATGAGGACTGGGAAAACTTTGAGTTTGATGCAGATGCAGAGCCAAAAGCCATCAAAAAACACAAGATCTATC

GTCCCCAATCAACCCAGGCACCGAAAGAAACTGTTATCAAAACAGAAGAAACAGATGGTTCACATGATATTGA

CTGGACACAAACAGACGATGACACCAAATACGAGTCACACGGTATGCATGTGACAGGTATTGTAGCCGGTAAT

AGCAAAGAAGCCGCTGCTACTGGAGAACGCTTTTTAGGAATTGCACCAGAGGCCCAAGTCATGTTCATGCGTG

TTTTTGCCAACGACGTCATGGGATCAGCTGAATCACTCTTTATCAAAGCTATCGAAGATGCCGTGGCTTTAGG

AGCAGATGTGATCAACCTGAGTCTTGGAACCGCTAATGGGGCACAGCTTAGTGGCAGCAAGCCTCTAATGGAA

GCAATTGAAAAAGCTAAAAAAGCCGGTGTATCAGTTGTTGTAGCAGCAGGAAATGAGCGCGTCTATGGATCTG

ACCATGATGATCCATTGGCAACAAATCCAGACTATGGTTTGGTCGGTTCTCCCTCAACAGGTCGAACACCAAC

ATCAGTGGCAGCTATAAACAGTAAGTGGGTGATTCAACGTCTAATGACGGTCAAAGGATTAGAAAACCGTGCC

GATTTAaACCATGGTAAAGCCATCTATTCAGAGTCTGTCGACTTTAAAGACATAAAAGATAGCCTAGGTTATG

ATAAATCGCATCAATTTGCTTATGTCAAaGAGTCAACTGATGCGGGTTATAACGCACAAGACGTTAAAGGTAA

AATTGCTTTAATTGAACGTGATCCCAATAAAACCTATGACGAAATGATTGCTTTGGCTAAGAAACATGGAGCC

CTGGGACTACTTATTTTTAATAACAAGTCTGGTCAATCAAACCGCTCAATGCGTCTAACAGCTAATGGGATGG

GGATACCATCTGCTTTCATATCGCACGATTTGGTAAGGCCATGTCCCAATTAAATGGCAATGGTACAGGAAG

T

> Spy0416A-7/Schmitz 1/174 (serotype 6); SEQ ID NO: 192
TCACAATCACTCCGAAGACAAATCGTGAAAAAGAGCAATCACAAGATCTAGTCTCTGAGCCAACCACAACTG

AGCTAGCTGACACAGATGCAGCATCAATGGCTAATACAGGTCCTGATGCGACTCAAAAAAGCGCTTCTTTACC

GCCAGTCAATACAGATGTTCACGATTGGGTAAAAACCAAAGGAGCTTGGGACAAGGGATACAAAGGACAAGGC

AAGGTTGTCGCAGTTATTGACACAGGGATCGATCCGGCCCATCAAAGCATGCGCATCAGTGATGTATCACTG

CTAAAGTAAAATCAAAAGAAGACATGCTAGCACGCCAAAAAGCCGCCGGTATTAATTATGGGAGTTGGATAAA

TGATAAAGTTGTTTTTGCACATAATTATGTGGAAAATAGCGATAATATCAAAGAAAATCAATTCGAGGATTTT

GATGAGGACTGGGAAAACTTTGAGTTTGATGCAGAGGCAGAGCCAAAAGCCATCAAAAAACACAAGATCTATC

GTCCCCAATCAACCCAGGCACCGAAAGAAACTGTTATCAAAACAGAAGAAACAGATGGTTCACATGATATTGA

CTGGACACAAACAGACGATGACACCAAATACGAGTCACACGGTATGCATGTGACAGGTATTGTAGCCGGTAAT

AGCAAAGAAGCCGCTGCTACTGGAGAACGCTTTTTAGGAATTGCACCAGAGGCCCAAGTCATGTTCATGCGTG

TTTTTGCCAACGACGTCATGGGATCAGCTGAATCACTCTTTATCAAAGCTATCGAAGATGCCGTGGCTTTAGG

AGCAGATGTGATCAACCTGAGTCTTGGAACCGCTAATGGGGCACAGCTTAGTGGCAGCAAGCCTCTAATGGAA

GCAATTGAAAAAGCTAAAAAAGCCGGTGTATCAGTTGTTGTAGCAGCAGGAAATGAGCGCGTCTATGGATCTG

ACCATGATGATCCATTGGCAACAAATCCAGACTATGGTTTGGTCGGTTCTCCCTCAACAGGTCGAACACCAAC

ATCAGTGGCAGCTATAAACAGTAAGTGGGTGATTCAACGTCTAATGACGGTCAAAGAATTAGAAAACCGTGCC

GATTTAAACCATGGTAAAGCCATCTaTTCAGAGTCTGTCGACTTTAAAaACATAAAAGATAGCCTAGGTTATG

ATAAATCGCATCAATTTGCTTATGTCAAaGAGTCAACTGATGCGGGTTATAACGCACAAGACGTTAAAGGTAA

AATTGCTTTAATTGAACGTGATCCCAATAAAACCTATGACGAAATGATTGCTTTGGCTAAGAAAACATGGAGCC

CTGGGAGTACTTATTTTTAATAACAAACCTGGTCAATCAAACCGCTCAATGCGCCTAACATCTAATGGGATGG

GAATACCATCTGCTTTCATATCGCACGAATTTGGTAAGGCCATGTCCCAATTAAATGGCAATGGTACAGGAG

-continued

| SEQUENCE DATA FOR DNA SEQUENCES |
| --- |

T

> Spy0416A-7/Schmitz 1/176 (serotype 83); SEQ ID NO: 193
TCACAAATCACTCTCAAGACAAATCGTGAAAAAGAGCAACCACAAGGTCTAGTCTCTGAGCCAACCACAACTG

AGCTAGCTGACACAGATGCAGCACCAATGGCTAATACAGGTCCTGATGCGACTCAAAAAAGCGCTTCTTTACC

GCCAGTCAATACAGATGTTCACGATTGGGTAAAAACCAAAGGAGCTTGGGACAAGGGATACAAAGGACAAGGC

AAGGTTGTCGCAGTTATTGACACAGGGATCGATCCGGCCCATCAAAGCATGCGCATCAGTGATGTATCAACTG

CTAAAGTAAAATCAAAAGAAGACATGCTAGCACGCCAAAAAGCCGCCGGTATTAATTATGGGAGTTGGATAAA

TGATAAAGTTGTTTTTGCACATAATTATGTGGAAAATAGCGATAATATCAAAGAAAATCAATTCGAGGATTTT

GATGAGGACTGGGAAAACTTTGAGTTTGATGCAGAGGCAGAGCCAAAAGCCATCAAAAAACACAAGATCTATC

GTCCCCAATCAACCCAGGCACCGAAAGAAACTGTTATCAAAACAGAAGAAACAGATGGTTCACATGATATTGA

CTGGACACAAACAGACGATGACACCAAATACGAGTCACACGGTATGCATGTGACAGGTATTGTAGCCGGTAAT

AGCAAAGAAGCCGCTGCTACTGGAGAACGCTTTTTAGGAATTGCACCAGAGGCCCAAGTCATGTTCATGCGTG

TTTTTGCCAACGACGTCATGGGATCAGCTGAATCACTCTTTATCAAAGCTATCGAAGATGCCGTGGCTTTAGG

AGCAGATGTGATCAACCTGAGTCTTGGAACCGCTAATGGGGCACAGCTTAGTGGCAGCAAGCCTCTAATGGAA

GCAATTGAAAAAGCTAAAAAAGCCGGTGTATCAGTTGTTGTAGCAGCAGGAAATGAGCGCGTCTATGGATCTG

ACCATGATGATCCATTGGCAACAATCCAGACTATGGTTTGGTCGGTTCTCCCTCAACAGGTCGAACACCAAC

ATCAGTGGCAGCTATAAACAGTAAGTGGGTGATTCAACGTCTAATGACGGTCAAAGAATTAGAAAACCGTGCC

GATTTAAACCATGGTAAAGCCATCTATTCAGAGTCTGTCGACTTTAAAAACATAAAAGATAGCCTAGGTTATG

ATAAATCGCATCAATTTGCTTATGTCAAAGAGTCAACTGATGCGGGTTATAAAGCACAAGACGTTAAAGGTAA

AATTGCTTTAATTGAACGTGATCCCAATAAAACCTATGACGAAATGATTGCTTTGGCTAAGAAACATGGAGCC

CTGGGAGTACTTATTTTTAATAACAAGCCTGGTCAATCAAACCGCTCAATGCGTCTAACAGCTAATGGGATGG

GGATACCATCTGCTTTCATATCGCACGAATTTGGTAAGGCCATGTCCCAATTAAATGGCAATGGTACAGGAAG

T

> Spy0416A-7/Schmitz 1/234 (serotype 44); SEQ ID NO: 194
TCACAAATCACTCCCAAGACAAATCGTGAAAAAGAGCAATCACAAGATCTAGTCTCTGAGCCAACAACAACTG

AGCTAGCTGACACAGATGCAGCATCAATGGCTAATACAGGTTCTGATGCGACTCAAAAAGCGCTTCTTTACC

GCCAGTCAATACAGATGTTCACGATTGGGTAAAAACCAAAGGAGCTTGGGACAAGGGATACAAAGGACAAGGC

AAGGTTGTCGCAGTTATTGACACAGGGATCGATCCGGCCCATCAAAGCATGCGCATCAGTGATGTATCAACTG

CTAAAGTAAAATCAAAAGAAGACATGCTAGCACGCCAAAAAGCCGCCGGTATTAATTATGGGAGTTGGATAAA

TGATAAAGTTCTTTTTGCACATAATTATGTGGAAAATAGCGATAATATCAAAGAAAATCAATTCGAGGATTTT

GATGAGGACTGGGAAAACTTTGAGTTTGATGCAGATGCAGAGCCAAAAGCCATCAAAAAACACAAGATCTATC

GTCCCCAATCAACCCAGGCACCGAAAGAAACTGTTATCAAACAGAGAAACAGATGGTTCACATGATATTGA

CTGGACACAAACAGACGATGACACCAAATACGAGTCACACGGTATGCATGTGACAGGTATTGTAGCCGGTAAT

AGCAAAGAAGCCGCTGCTACTGGAGAACGCTTTTTAGGAATTGCACCAGAGGCCCAAGTCATGTTCATGCGTG

TTTTTGCCAACGACGTCATGGGATCAGCTGAATCACTCTTTATCAAAGCTATCGAAGATGCCGTGGCTTTAGG

AGCAGATGTGATCAACCTGAGTCTTGGAACCGCTAATGGGGCACAGCTTAGTGGCAGCAAGCCTCTAATGGAA

GCAATTGAAAAAGCTAAAAAAGCCGGTGTATCAGTTGTTGTAGCAGCAGGAAATGAGCGCGTCTATGGATCTG

ACCATGATGACCCATTGGCAACAATCCAGACTATGGTTTGGTTGGTTCTCCCTCAACAGGTCGAACACCAAC

ATCAGTGGCAGCTATAAACAGTAAGTGGGTGATTCAACGTCTAATGACGGTCAAAGAATTGGAAAACCGTGCC

GATTTAAACCATGGTAAAGCCATCTaTTCAGAGTCTGTCGACTTtAAAGACATAAAAGATAGCCTAGGTTATG

-continued

SEQUENCE DATA FOR DNA SEQUENCES

ATAAATCGCATCAATTTGCTTATGTCAAAGAGTCAACTGATGCGGGTTATAAAGCACAAGACGTTAAAGATAA

AATTGCTTTAATTGAACGTGATCCCAATAAAACCTATGACGAAATGATTGCTTTGGCTAAGAAACATGGAGCC

CTGGGGGTACTTATTTTTAATAACAAGCCTGGTCAATCAAACCGCTCAATGCGTCTAACAGCTAATGGGATGG

GGATACCATCTGCTTTCATATCGCACGAATTTGGTAAGGCCATGTCCCAATTAAATGGCAATGGTACAGGAAG

T

> Spy0416A-7/Schmitz 1/22 (serotype 4); SEQ ID NO: 195
TCACAAATCACTCCCAAGACAAATCGTGAAAAAGAGCAACCACAAGGTCTAGTCTCTGAGCCAACCACAACTG

AGCTAGCTGACACAGATGCAGCATCAATGGCTAATACAGGTCCTGATGCGACTCAAAAAAGCGCTTCTTTACC

GCCAGTCAATACAGATGTTCACGATTGGGTAAAAACCAAAGGAGCTTGGGACAAGGGATACAAAGGACAAGGC

AAGGTTGTCGCAGTTATTGACACAGGGATCGATCCGGCCCATCAAAGCATGCGCATCAGTGATGTATCAACTG

CTAAAGTAAAATCAAAAGAAGACATGCTAGCACGCCAAAAAGCCGCCGGTATTAATTATGGGAGTTGGATAAA

TGATAAAGTTGTTTTTGCACATAATTATGTGGAAAATAGCGATAATATCAAAAGAAAATCAATTCGGGGATTTT

GATGAGGACTGGGAAAACTTTGAGTTTGATGCAGAGCCAAAAGCCATCAAAAAAAACAAGATCTATCGTCCCC

AATCAACCCAGGCACCGAAAGAAACTGTTATCAAAACAGAAGAAACAGATGGTTCACATGATATTGACTGGAC

ACAAACAGACGATGACACCAAATACGAGTCACACGGTATGCATGTGACAGGTATTGTAGCCGGTAATAGCAAA

GAAGCCGCTGCTACTGGAGAACGCTTTTTAGGAATTGCACCAGAGGCCCAAGTCATGTTCATGCGTGTTTTTG

CCAACGACGTCATGGGATCAGCTGAATCACTCTTTATCAAAGCTATCGAAGATGCCGTGGCTTTAGGAGCAGA

TGTGATCAACCTGAGTCTTGGAACCGCTAATGGGGCACAGCTTAGTGGCAGCAAGCCTCTAATGGAAGCAATT

GAAAAAGCTAAAAAAGCCGGTGTATCAGTTGTTGTAGCAGCAGGAAATGAGCGCGTCTATGGATCTGACCATG

ATGATCCATTGGCAACAAATCCAGACTATGGTTTGGTCGGTTCTCCCTCAACAGGTCGAACACCAACATCAGT

GGCAGCTATAAACAGTAAGTGGGTGATTCAACGTCTAATGACGGCCAAAGAATTAGAAAACCGTGCCGATTTA

AACCATGGTAAAGCCATCTATTCAGAGTCTGTCGACTTTAAAGACATAAAAGATAGCCTAGGTTATGATAAAT

CGCATCAATTTGCTTATGTCAAAGAGTCAACTGATGCGGGTTATAAAGCACAAGACGTTAAAGATAAAATTGC

TTTAATTGAACGTGATCCCAATAAAACCTATGACGAAATGATTGCTTTGGCTAAGAAACATGGAGCCCTGGGA

GTACTTATTTTTAATAACAAGCCTGGTCAATCAAACCGCTCAATGCGTCTAACAGCTAATGGGATGGGGATAC

CATCTGCTTTCATATCGCACGAATTTGGTAAGGCCATGTCCCAATTAAATGGCAATGGTACAGGAAGT

4. Spy0872
4.1 Full length Spy0872
> Spy0872/SF370 (serotype 1); SEQ ID NO: 196
GATCAAGTTGATGTGCAATTCCTTGGCGTCAATGATTTTCACGGCGCTCTTGATAATACCGGAACAGCTTACA

CACCAAGTGGTAAAATACCAAATGCTGGGACGGCTGCTCAATTAGGTGCTTATATGGATGACGCTGAGATAGA

CTTCAAGCAAGCAAATCAAGACGGAACAAGTATACGTGTTCAAGCTGGAGATATGGTCGGAGCCAGTCCTGCT

AACTCTGCACTTTTACAAGATGAGCCTACTGTCAAAGTCTTTAACAAAATGAAATTTGAATATGGCACTCTTG

GTAATCATGAATTTGACGAAGGACTAGATGAATTTAACCGTATCATGACAGGTCAAGCGCCTGATCCTGAATC

AACAATTAATGATATCACCAAACAATATGAGCACGAAGCTTCGCATCAAACCATCGTCATTGCTAATGTTATT

GATAAAAAAACCAAGGATATCCCCTATGGTTGGAAACCTTATGCTATAAAAGACATAGCCATTAATGACAAAA

TCGTTAAGATTGGCTTCATTGGTGTTGTGACTACAGAGATTCCAAATCTCGTTTTAAAGCAAAACTATGAACA

CTATCAATTTTTAGATGTAGCTGAAACCATTGCCAAATATGCTAAAGAACTACAAGAACAACATGTTCATGCT

ATTGTGGTTTTAGCTCATGTTCCTGCAACAAGTAAAGATGGTGTTGTTGATCATGAAATGGCTACGGTTATGG

AAAAAGTGAACCAAATCTATCCCGAACATAGCATTGATATTATTTTTGCAGGACATAATCATCAATACACTAA

TGGAACTATCGGTAAAACACGTATCGTTCAAGCCCTCTCTCAAGGAAAAGCTTATGCAGATGTCCGTGGTACG

-continued

| SEQUENCE DATA FOR DNA SEQUENCES |
|---|
| CTAGATACTGATACCAATGATTTTATTAAAACTCCATCAGCAAATGTTGTTGCTGTAGCACCAGGTATCAAAA |
| CAGAAAATTCAGATATCAAAGCTATAATAAATCATGCTAATGATATTGTTAAAACAGTTACTGAACGAAAAAT |
| CGGAACTGCAACTAATTCTTCAACTATTTCTAAAACAGAAAATATTGATAAAGAATCTCCTGTCGGTAACTTA |
| GCAACAACGGCTCAGCTTACTATTGCTAAGAAAACTTTTCCAACTGTTGACTTTGCTATGACCAATAATGGTG |
| GTATTCGAAGTGACCTAGTTGTCAAAAATGACCGGACCATCACCTGGGGAGCTGCACAGGCTGTACAACCATT |
| TGGTAATATCCTTCAAGTCATTCAAATGACTGGTCAACACATTTACGATGTCCTAAATCAGCAATACGATGAA |
| AACCAGACCTATTTTCTTCAATGTCAGGTTTAACATACACTTATACAGATAATGATCCTAAGAACTCTGATA |
| CCCCCTTCAAGATAGTTAAGGTTTATAAAGACAATGGTGAAGAAATTAACTTAACAACTACTTACACCGTTGT |
| TGTCAAGGACTTTCTTTATGGTGGTGGTGATGGCTTTTCAGCATTTAAAAAAGCTAAATTATCGGAGCTATT |
| AACACAGATACTGAAGCTTTCATCACATATATCACAAATTTAGAAGCATCAGGTAAAACTGTTAATGCTACTA |
| TAAAAGGGGTTAAAAATTATGTAACTTCAAACCTTGAAAGTTCGACAAAAGTTAATAGTGCTGGTAAACACAG |
| TATCATTAGTAAGGTTTTTAGAAATCGTGATGGCAATACAGTGTCTAGTGAAGTCATTTCAGACCTTTTGACT |
| TCTACTGAAAACACTAATAACAGCCTTGGCAAAAAAGAAACAACAACAAACAAAAATACTATCTCTAGTTCCA |
| CTCTTCCAATAACA |
| 4.2 Antigenic fragment Spy0872-2<br>> Spy0872-2/SF370 (serotype 1); SEQ ID NO: 17<br>GCTATAATAAATCATGCTAATGATATTGTTAAAACAGTTACTGAACGAAAAATCGGAACTGCACTAATTCTT |
| CAACTATTTCTAAAACAGAAAATATTGATAAAGAATCTCCTGTCGGTAACTTAGCAACAACGGCTCAGCTTAC |
| TATTGCTAAGAAAACTTTTCCAACTGTTGACTTTGCTATGACCAATAATGGTGGTATTCGAAGTGACCTAGTT |
| GTCAAAAATGACCGGACCATCACCTGGGGAGCTGCACAGGCTGTACAACCATTTGGTAATATCCTTCAAGTCA |
| TTCAAATGACTGGTCAACACATTTACGATGTCCTAAATCAGCAATACGATGAAAACCAGACCTATTTTCTTCA |
| AATGTCAGGTTTAACATACACTTATACAGATAATGATCCTAAGAACTCTGATACCCCCTTCAAGATAGTTAAG |
| GTTTATAAAGACAATGGTGAAGAAATTAACTTAACAACTACTTACACCGTTGTTGTCAACGACTTTCTTTATG |
| GTGGTGGTGATGGCTTTTCAGCATTTAAAAAAGCTAAATTAATCGGAGCTATTAACACAGATACTGAAGCTTT |
| CATCACATATATCACAAATTTAGAAGCATCAGGTAAAACTGTTAATGCTACTATAAAAGGGGTTAAAAATTAT |
| GTAACTTCAAACCTTGAAAGTTCGACAAAAGTTAATAGTGCTGGTAAACACAGTATCATTAGTAAGGTTTTTA |
| GAAATCGTGATGGCAATACAGTGTCTAGTGAAGTCATTTCAGACCTTTTGACTTCTACTGAAAACACTAATAA |
| CAGCCTTGGCAAAAAAGAAACAACAACAAACAAAAATACTATCTCTAGTTCCACTCTTCCAATAACA |
| 4.3 Homologous sequences of other *S. pyogenes* isolates and/or serotypes<br>> Spy0872-2/Schmitz 1/7 (serotype 4); SEQ ID NO: 197<br>GCTATAATAAATCATGCTAATGATATTGTTAAAACAGTTACTGAACGAAAAATCGGAACTGCAACTAATTCTT |
| CAACTATTTCTAAAACAGAAAATATTGATAAAGAATCTCCTGTCGGTAACTTAGTAACAACGGCTCAGCTTAC |
| TATTGCTAAGAAAACTTTTCCAACTGTTGACTTTGCTATGACCAATAATGGTGGTATTCGAAGTGACCTAGTT |
| GTCAAAAATGACCGGACCATCACCTGGGAAGCTGCACAGGCTGTACAACCATTTGGTAATATCCTTCAAGTCA |
| TTCAAATGACTGGTCAACACATTTACGATGTCCTAAATCAGCAATACGATGAAAACCAGACCTATTTTCTTCA |
| AATGTCAGGTTTAACATACACTTATACAGATAATGATCCTAAGAACTCTGATACCCCCTTCAAGATAGTTAAG |
| GTTTATAAAGACAATGGTGAAGAAATTAACTTAACAACTACTTACACCGTTGTTGTCAACGACTTTCTTTATG |
| GTGGTGGTGATGGCTTTTCAGCATTTAAAAAAGCTAAATTAATCGGAGCTATTAACACAGATACTGAAGCTTT |
| CATCACATATATCACAAATTTAGAAGCATCAGGTAAAACTGTTAATGCTACTATAAAAGGGGTTAAAAATTAT |
| GTAACTTCAAACCTTGAAAGTTCGACAAAAGTTAATAGTGCTGGTAAACACAGTATCATTATCATTAGTAAGG |
| TTTTTAGAAATCGTGATGGCAATATAGTGTCTAGTGAAATCATTTCAGACCTTTTGACTTCTACTGAAAACAC |

-continued

SEQUENCE DATA FOR DNA SEQUENCES

TAATAACAGCTTTGGCAAAAAAGAGATAACAACAAAcaAAAATACTATCTCTAATTCCACTCTTCCAATAACA

> Spy0872-2/Schmitz 1/39 (serotype 12); SEQ ID NO: 198
GCTATAATAAATCATGCTAATGATATTGTTAAAaCAGTTACTGAACGAAAAATCGGAACTGCAACTAATTCTT

CAACTATTTCTAAAACAGAAAATATTGATAAAGAATCTCCTGTCGGTAACTTAGTAACAACGGCTCAGCTTAC

TATTGCTAAGAAAACTTTTCCAACTGTTGACTTTGCTATGACCAATAATGGTGGTATTCGAAGTGACCTAGTT

GTCAAAAATGACCGGACCATCACCTGGGGAGCTGCACAGGCTGTACAACCATTTGGTAATATCCTTCAAGTCA

TTCAAATGACTGGTCAACACATTTACGATGTCCTAAATCAGCAATACGATGAAAACCAGACCTATTTTCTTCA

AATGTCAGGTTTAACATACACTTATACAGATAATGATCCTAAGAACTCTGATACCCCCATTCAAGATAGTTAAG

GTTTATAAAGACAATGGTGAAGAAATTAACTTAACAACTACTTACACCGTTGTTGTCAACGACTTTCTTTATG

GTGGTGGTGATGGCTTTTCAGCATTTAAAAAAGCTAAATTAATCGGAGCTATTAACACAGATACTGAAGCTTT

CATCACATATATCACAAATTTAGAAGCATCAGGTAAAACTGTTAATGCTACTATAAAAGGGGTTAAAAATTAT

GTAACTTCAAACCTTGAAAGCTCGACAAAAGTTAATAGTGCTGGTAAACACAGTATCATTAGTAAGGTTTTTA

GAATCGTGATGGCAATATAGTGTCTAGTGAAATCATTTCAGACCTTTTGACTTCTACTGAAAACACTAATAA

CAGCCTTGGCAAAAAAGAAACAACGACAAACAAAAATACTATCTCTAGTTCCACTCTTCCAATAACA

> Spy0872-2/Schmitz 1/55 (serotype 118); SEQ ID NO: 199
GCTATAATAAaTCATGCTAATGATATTGTTAAAACAGTTACTGAACGAAAAATCGGACTGCAACTAATTCTT

CAACTATTTCTAAAACAGAAAATATTGATAAAGAATCTCCTGTCGGTAACTTAGTAACAACGGCTCAGCTTAC

TATTGCTAAGAAAACTTTTCCAACTGTTGACTTTGCTATGACCAATAATGGTGGTATTCGAAGTGACCTAGTT

GTCAAAAATGACCGGACCATCACCTGGGGAGCTGCACAGGCTGTACAACCATTTGGTAATATCCTTCAAGTCA

TTCAAATGACTGGTCAACACATTTACGATGTCCTAAATCAGCAATACGATGAAAACCAGACCTATTTTCTTCA

AATGTCAGGTTTAACATACACTTATACAGATAATGATCCTAAGAACTCTGATATCCCCTTCAAGATAGTTAAG

GTTTATAAAGACAATGGTGAAGAAATTAACTTAACAACTACTTACACCGTTGTTGTCAACGACTTTCTTTATG

GTGGTGGTGATGGCTTTTCAGCATTTAAAAAAGCTAAATTAATCGGAGCTATTAATACAGATACTGAAGCTTT

CATCACATATATCACAAATTTAGAAGCATCAGGTAAAACTGTTAATGCTACTATAAAAGGGGTTAAAAATTAT

GTAACTTCAAACCTTGAAAGTTCGACAAAAGTTAATAGTGCTGGTAAACACAGTATCATTAGTAAGGTTTTTA

GAAATCGTGATGGCAATATAGTGTCTAGTGAAGTCATTTCAGACCTTTTGACTTCTACTGAAAACACTAATAA

CAGCCTTGGCAAAAAAGAAACAaCGACAAACAAAAATACTATCTCTAGTTCCACTCTTCCAATAACA

> Spy0872-2/Schmitz 1/56 (serotype 28); SEQ ID NO: 200
GCTATAATAAATCATGCTAATGATATTGTTAAAACAGTTACTGAACGAAAAATCGGAACTGCAACTAATTCTT

CAACTATTTCTAAAACAGAAAATATTGATAAAGAATCTCCTGTCGGTAACTTAGTAACAACAGCTCAGCTTAC

TATTGCTAAGAAAACTTTTCCAACTGTTGACTTTGCTATGACCAATAATGGTGGTATTCGAAGTGACCTAGTT

GTCAAAAATGATCGGACCATCACCTGGGGAGCTGCACAGGCTGTACAACCATTTGGTAATATCCTTCAAGTCA

TTCAAATGACTGGTCAACACATTTACGATGTCCTAAATCAGCAATACGATGAAAACCAGACCTATTTTCTTCA

AATGTCAGGTTTAACATACACTTATACAGATAATGATCCTAAGAACTCTGATACCCCCTTCAAGATAGTTAAG

GTTTATAAAGACAATGGTGAAGAAATTAACTTAACAACTACTTACACCGTTGTTGTCAACGACTTTCTTTATG

GTGGTGGTGATGGCTTTTCAGCATTTAAAAAAGCTAAATTAATTGGAGCTATTAACACAGATACTGAAGCTTT

CATCACATATATCACAAATTTAGAAGCATCAGGTAAAACTGTTAATGCTACTATAAAAGGGGTTAAAAATTAT

GTAACTTCAAACCTTGAAAGTTCGACAAAAGTTAATAGTGCTGGTAAACACAGTATCATTAGTAAGGTTTTTA

GAAATCGTGATGGCAATATAGTGTCTAGTGAGATCATTTCAGACCTTTTGACTTCTACTGAAAACACTAATAA

CAGCCTTGGCAAAAAAGAAACAACAACAAACAAAAATACTATCTCTAGTTCCACTCTTCCAATAACA

> Spy0872-2/Schmitz 1/94 (serotype 1); SEQ ID NO: 201

-continued

SEQUENCE DATA FOR DNA SEQUENCES

GCTATAATAAATCATGCTAATGATATTGTTAAAACAGTTACTGAACGAAAAATCGGAACTGCAACTAATTCTT

CAACTATTTCTAAAACAGAAAATATTGATAAAGAATCTCCTGTCGGTAACTTAGCAACAACGGCTCAGCTTAC

TATTGCTAAGAAAACTTTTCCAACTGTTGACTTTGCTATGACCAATAATGGTGGTATTCGAAGTGACCTAGTT

GTCAAAAATGACCGGACCATCACCTGGGGAGCTGCACAGGCTGTACAACCATTTGGTAATATCCTTCAAGTCA

TTCAAATGACTGGTCAACACATTTACGATGTCCTAAATCAGCAATACGATGAAAACCAGACCTATTTTCTTCA

AATGTCAGGTTTAACATACACTTATACAGATAATGATCCTAAGAACTCTGATACCCCCTTCAAGATAGTTAAG

GTTTATAAAGACAATGGTGAAGAAATTAACTTAACAACTACTTACACCGTTGTTGTCAACGACTTTCTTTATG

GTGGTGGTGATGGCTTTTCAGCATTTAAAAAAGCTAAATTAATCGGAGCTATTAACACAGATACTGAAGCTTT

CATCACATATATCACAAATTTAGAAGCATCAGGTAAAACTGTTAATGCTACTATAAAAGGGGTTAAAAATTAT

GTAACTTCAAACCTTGAAAGTTCGACAAAAGTTAATAGTGCTGGTAAACACAGTATCATTAGTAAGGTTTTTA

GAAATCGTGATGGCAATACAGTGTCTAGTGAAGTCATTTCAGACCTTTTGACTTCTACTGAAAACACTAATAA

CAGCCTTGGCAAAAAAGAAACAACAACAAACAAAAATACTATCTCTAGTTCCACTCTTCCAATAACA

> Spy0872-2/Schmitz 1/253 (serotype 49); SEQ ID NO: 202
GCTATAATAAATCATGCTAATGATATTGTTAAAaCAGTTACTGAACGAAAAATCGGAACTGCAACTAATTCTT

CAACTATTTCTAAAACAGAAAATATTGATAAAGAATCTCCTGTCGGTAACTTAGTAACAACAGCTCAGCTTAC

TATTGCTAAGAAAACTTTTCCAACTGTTGACTTTGCTATGACCAATAATGGTGGTATTCGAAGTGACCTAGTT

GTCAAAAATGATCGGACCATCACCTGGGGAGCTGCACAGGCTGTACAACCATTTGGTAATATCCTTCAAGTCA

TTCAAATGACTGGTCAACACATTTACGATGTCCTAAATCAGCAATACGATGAAAACCAGACCTATTTTCTTCA

AATGTCAGGTTTAACATTCACTTATACAGATAATGATCCTAAGAACTCTGATACCCCCTTCAAGATAGTTAAG

GTTTATAAAGACAATGGTGAAGAAATTAACTTAACAACTACTTACACCGTTGTTGTCAACGACTTTCTTTATG

GTGGTGGTGATGGCTTTTCAGCATTTAAAAAAGCTAAATTAATTGGAGCTATTAACACAGATACTGAAGCTTT

CATCACATATATCACAAATTTAGAAGCATCAGGTAAAACTGTTAATGCTACTATAAAAGGGGTTAAAAATTAT

GTAACTTCAAACCTTGAAAGCTCGACAAAAGTTAATAGTGCTGGTAAACACAGTATCATTAGTAAGGTTTTTA

GAAATCGTGATGGCAATATAGTGTCTAGTGAAATAATTTCAGACCTTTTGACTTCTACTGAAAACACTAATAA

CAGCCTTGGCAAAAAAGAAACAACGACaAACAAAAATACTATCTCTAGTTCCACTCTTCCAATAACA

> Spy0872-2/Schmitz 1/176 (serotype 83); SEQ ID NO: 203
GCTATAATAAATCATGCTAATGATATTGTTAAAACAGTTACTGAACGAAAAATCGGAACTGCAACTAATTCTT

CAACTATTTCTAAAACAGAAAATATTGATAAAGAATCCCCTGTCGGTAACTTAGTAACAACGGCTCAGCTTAC

TATTGCTAAGAAAACTTTTCCAACTGTTGACTTTGCTATGACCAATAATGGTGGTATTCGAAGTGACCTAGTT

GTCAAAAATGACCGGACCATCACCTGGGGAGCTGCACAGGCTGTACAACCATTTGGTAATATCCTTCAAGTCA

TTCAAATGACTGGTCAACACATTTACGATGTCCTAAATCAGCAATACGATGAAAACCAGACCTATTTTCTTCA

AATGTCAGGTTTAACATACACTTATACAGATAATGATCCTAAGAACTCTGATACCCCCTTCAAGATAGTTAAG

GTTTATAAAGACAATGGTGAAGAAATTAACTTAACAACTACTTACACCGTTGTTGTCAACGACTTTCTTTATG

GTGGCGGTGATGGCTTTTCAGCATTTAAAAAAGCTAAATTAGTCGGAGCTATTAACACAGATACTGAAGCTTT

CATCACATATATCACAAATTTACAAGCATCAGGTAAAACTGTTAATGCTACTATCAAAGGGGTTAAAAATTAT

GTAACTTCAAACCTTGAAAGATCAACAAAAATTAATAGTGCTGGCAAACACAGTATCATTAGTAAGGTTTTTA

GAAATCGTGATGGCAATATAGTGTCTAGTGAAGTCATTTCAGACCTTTTGACTTCTACTGAAAACACTAATAA

CAGCTTTGGCAAAaAAGAGACAACAACAAACAAAAATACTATCTCTAATTCCACTCTTCCAATAACA

> Spy0872-2/Schmitz 1/177 (serotype 22); SEQ ID NO: 204
GCTATAATAAATCATGCTAATGATATTGTTAAAACAGTTACTGAACGAAAAATCGGAACTGCAACTAATTCTT

CAACTATTTCTAAAACAGAAAATATTGATAAAGAATCTCCTGTCGGTAACTTAGTAACAACGGCTCAGCTTAC

-continued

SEQUENCE DATA FOR DNA SEQUENCES

TATTGCTAAGAAAACTTTTCCAACTGTTGACTTTGCTATGACCAATAATGGTGGTATTCGAAGTGACCTAGTT

GTCAAAAATGACCGGACCATCACGTGGGGAGCTGCACAGGCTGTACAACCATTTGGTAATATCCTTCAAGTCA

TTCAAATGACTGGTCAACACATTTACGATGTCCTAAATCAGCAATACGATGAAAACCAGACCTATTTTCTTCA

AATGTCAGGTTTAACATACACTTATACAGATAATGATCCTAAGAACTCTGATACCCCCTTCAAGATAGTTAAG

GTTTATAAAGACAATGGTGAAGAAATTAACTTAACAACTACTTACACCGTTGTTGTCAACGACTTTCTTTATG

GTGGTGGTGATGGCTTTTCAGCATTTAAAAAAGCTAAATTAATCGGAGCTATTAACACAGATACTGAAGCTTT

CATCACATATATCACAAATTTAGAAGCATCAGGTAAAACTGTTAATGCTACTATAAAAGGGGTTAAAAATTAT

GTAACTTCAAACCTTGAAAGCTCGACAAAAGTTAATAGTGCTGGTAAACACAGTATCATTAGTAAGGTTTTTA

GAAATCGTGATGGCAATATAGTGTCTAGTGAAATCATTTCAGACCTTTTGACTTCTACTGAAAACACTAATAA

CAGCCTTGGCAAAAAAGAAACaACGACAAACAAAAATACTATCTCTAGTTCCACTCTTCCAATAACA

> Spy0872-2/Schmitz 1/234 (serotype 44); SEQ ID NO: 205
GCTATAATAAATCATGCTAATGATATTGTTAAAACAGTTACTGAACGAAAAATCGGAACTGCAACTAATTCTT

CAACTATTTCTAAAACAGAAAATATTGATAAAGAATCTCCTGTCGGTAACTTAGTAACAACGGCTCAGCTTAC

TATTGCTAAGAAAACTTTTCCAACTGTTGACTTTGCTATGACCAATAATGGTGGTATTCGAAGTGACCTAGTT

GTCAAAAATGACCGGACCATCACCTGGGGAGCTGCACAGGCTGTACAACCATTTGGTAATATCCTTCAAGTCA

TTCAAATGACTGGTCAACACATTTACGATGTCCTAAATCAGCAATACGATGAAAACCAGACCTATTTTCTTCA

AATGTCAGGTTTAACATACACTTATACAGATAATGATCCTAAGAACTCTGATACCCCCTTCAAGATAGTTAAG

GTTTATAAAGACAATGGTGAAGAAATTAACTTAACAACTACTTACACCGTTGTTGTCAACGACTTTCTTTATG

GTGGTGGTGATGGCTTTTCAGCATTTAAAAAAACTAAATTAATCGGAGCTATTAACACAGATACTGAAGCTTT

CATCACATATATCACAAATTTAGAAGCATCAGGTAAAACTGTTAATGCTACTATAAAAGGGGTTAAAAATTAT

GTAACTTCAAACCTTGAAAGCTCGACAAAAGTTAATAGTGCTGGTAAACACAGTATCATTAGTAAGGTTTTTA

GAAATCGTGATGGCAATATAGTGTCTAGTGAAATCATTTCAGACCTTTTGACTTCTACTGAAAACACTAATAA

CAGCCTTGGCAAAAAAGAAACAACGACaAACAAAAATACTATCTCTAGTTCCACTCTTCCAATAACA

> Spy0872-2/Schmitz 1/22 (serotype 4); SEQ ID NO: 206
GCTATAATAAATCATGCTAATGATATTGTTAAAACAGTTACTGAACGAAAAATCGGAACTGCAACTAATTCTT

CAACTATTTCTAAAACAGAAAATATTGATAAAGAATCTCCTGTCGGTAACTTAGTAACAACGGCTCAGCTTAC

TATTGCTAAGAAAACTTTTCCAACTGTTGACTTTGCTATGACCAATAATGGTGGTATTCGAAGTGACCTAGTT

GTCAAAAATGACCGGACCATCACCTGGGAAGCTGCACAGGCTGTACAACCATTTGGTAATATCCTTCAAGTCA

TTCAAATGACTGGTCAACACATTTACGATGTCCTAAATCAGCAATACGATGAAAACCAGACCTATTTTCTTCA

AATGTCAGGTTTAACATACACTTATACAGATAATGATCCTAAGAACTCTGATACCCCCTTCAAGATAGTTAAG

GTTTATAAAGACAATGGTGAAGAAATTAACTTAACAACTACTTACACCGTTGTTGTCAACGACTTTCTTTATG

GTGGTGGTGATGGCTTTTCAGCATTTAAAAAAGCTAAATTAATCGGAGCTATTAACACAGATACTGAAGCTTT

CATCACATATATCACAAATTTAGAAGCATCAGGTAAAACTGTTAATGCTACTATAAAAGGGGTTAAAAATTAT

GTAACTTCAAACCTTGAAAGTTCGACAAAAGTTAATAGTGCTGGTAAACACAGTATCATTATCATTAGTAAGG

TTTTTAGAAATCGTGATGGCAATATAGTGTCTAGTGAAATCATTTCAGACCTTTTGACTTCTACTGAAAACAC

TAATAACAGCTTTGGCAAAAAAGAGATAACAACAAACAAAAATACTATCTCTAATTCCACTCTTCCAATAACA

5. Further Sequences
> Spy0488/SF370 (serotype 1); SEQ ID NO: 18
TTGCGGCAGATTCAGTCCATTCGTCTGATAGACGTTTTGGAGTTGGCTTTTGGAGTTGGCTATAAGGAAGAAA

CAACCTCTCAGTTTTCTTCGGATCAGCCCTCCCAAGTGGTTTTGTATCGAGGTGAGGCTAACACGGTTAGGTT

TGCCTATACCAATCAGATGTCTCTGATGAAAGATATTCGCATTGCTTTGGATGGTTCTGATAAGTCTTTGACC

-continued

SEQUENCE DATA FOR DNA SEQUENCES

GCTCAGATTGTTCCTGGTATGGGTCATGTTTATGAGGGCTTTCAAACTTCTGCTAGAGGGATTTTTACGATGT

CAGGAGTTCCTGAAAGCACTGTTCCCGTTGCTAACCCTAATGTACAAACCAAATATATAAGGTATTTCAAAGT

CATTGATGATATGCATAACACAATGTATAAAGGAACTGTTTTTCTTGTTCAACCGCAAGCTTGGAAATACACC

ATGAAATCTGTTGATCAGTTACCAGTAGATGACTTGAACCATATTGGCGTTGCTGGTATTGAACGAATGACAA

CTCTCATTAAAAATGCGGGTGCCCTTTTAACCACAGGAGGTAGTGGGGCTTTCCCAGACAATATTAAAGTATC

TATTAATCCAAAGGGGAGGCAGGCCACGATTACTTATGGGGACGGCTCTACGGATATTATTCCTCCAGCAGTT

TTATGGAAAAAAGGCTCCGTAAAAGAGCCTACTGAAGCCGATCAATCTGTCGGAACACCGACTCCTGGTATTC

CTGGTAAATTCAAACGAGACCAGAGCCTTAACGAGCATGAAGCTATGGTAAATGTCGAACCACTGTCTCATGT

AGTAAAAGACAATATAAAGGTCATAGATGAAAAATCAACAGGGCGGTTTGAGCCTTTTAGACCTAATGAAGAT

GAGAAGGAGAAGCCTGCCAGCGATGTTAAGGTAAGACCAGCAGAAGTTGGTAGCTGGCTAGAACCAGCGACAG

CTCTTCCTAGTGTTGAAATGAGCGCTGAGGACAGGTTAAAAAGT

> Spy0895/SF370 (serotype 1); SEQ ID NO: 19
ACTAATAATCAAACACTAGACATCCTTTTGGATGTCTATGCTTATAATCACGCCTTTAGAATTGCTAAAGCCT

TGCCAAATATCCCTAAAAGTGCCCTCTATTTACTAGAGATGTTAAAAGAGCGCAGAGAATTGAACCTTGCCTT

TCTAGCGGAACATGCAGCAGAGAATCGGACCATTGAAGACCAGTATCACTGTTCATTATGGCTTAACCAATCG

CTTGAAGATGAGCAGATTGCCAATTACATTTTGGATTTAGAAGTTAAAGTAAAAAACGGTGCTATTATTGATT

TCGTCAGGTCAGTGTCGCCTATTCTTTACCGACTTTTTCTCAGACTAATCACGTCAGAAATTCCAAACTTCAA

GGCTTATATTTTTGATACAAAGAATGACCAATATGATACCTGGCATTTTCAGGCCATGTTGGAATCTGATCAC

GAGGTTTTCAAGGCTTACCTGTCTCAAAAGCAGTCTCGCAATGTGACGACCAAAAGCTTAGCAGACATGTTGA

CGTTGACCTCCTTACCTCAGGAAATCAAGGACTTGGTTTTTTTGTTACGACATTTTGAAAAGGCTGTCCGTAA

TCCTCTGGCTCATTTGATTAAGCCTTTTGATGAAGAGGAACTGCATCGCACCACTCATTTTTCTTCTCAGGCT

TTTTTGGAAAACATTATCACCTTGGCGACTTTTTCTGGTGTAATCTACCGACGTGAGCCTTTTTACTTTGATG

ACATGAATGCCATTATTAAAAAGGAGTTGAGCCTTTGGAGACAATCTATTGTC

> Spy1536/SF370 (serotype 1); SEQ ID NO: 207
ATTGAAATGCCTGGAGGCGCTTACGATATTCGGACTGTCTTACAAGTCAATGGCAAAGAAGACAAACGAAAAG

GAGCTTACCAGTTTGTTGCAGTGGGCATTAGTCGTGCCAGCCTCGCTCAGCTATTATATGCTTGGCTGACACC

GTTTACTGAAATTAGTACAGCAGAAGATACAACAGGCGGATACAGCGATGCTGATTTCCTTCGAATTAATCAA

TTTTACATGGAAACATCACAAAATGCAGCTATTTATCAAGCTTTATCCTTAGCTGGAAAACCAGTTACATTAG

ATTATAAAGGCGTATATGTTTTAGACGTAAACAACGAATCTACTTTTAAAGGAACGCTACACTTAGCAGATAC

TGTAACAGGTGTAAATGGTAAACAGTTTACTAGTTCAGCAGAACTTATTGACTATGTTTCTCACCTAAAACTA

GGGGATGAAGTTACGGTTCAGTTTACGAGTGATAATAAGCCTAAAAAAGGAGTTGGCCGTATTATCAAACTGA

AAAATGGGAAAAATGGGATTGGCATTGCCTTGACTGATCATACAAGTGTCAATTCAGAAGACACAGTGATCTT

TAGTACTAAAGGAGTAGGAGGACCTAGTGCTGGTCTAATGTTTACTCTTGATATATATGATCAAATAACTAAA

GAAGATTTACGCAAGGGCCGTACAATTGCAGGTACAGGAACTATTGGCAAGGATGGCGAAGTAGGAGATATTG

GTGGTGCAGGTCTTAAAGTAGTTGCAGCAGCTGAAGCTGGTGCAGATATATTTTTTGTTCCGAATAATCCTGT

TGATAAGGAAATTAAAAAAGTTAATCCAAATGCTATAAGTAATTACGAAGAAGCCAAACGGGCAGCCAAACGA

CTAAAGACCAAAATGAAGATTGTTCCTGTTACGACTGTTCAAGAGGCACTGGTTTATCTTCGCAAA

> Spy1666/SF370 (serotype 1); SEQ ID NO: 208
ACAAAAGAATTTCATCACGTGACCGTACTCCTTCACGAAACAGTGGACATGCTTGACATAAAGCCTGATGGGA

TTTATGTTGATGCGACGCTAGGTGGCTCAGGCCACTCAGCTTATTTGTTGTCCAAACTTGGTGAAGAAGGGCA

-continued

SEQUENCE DATA FOR DNA SEQUENCES

CCTCTATTGTTTTGACCAAGACCAAAAGGCTATTGACAATGCACAAGTTACCCTCAAATCTTATATTGACAAA

GGACAGGTAACTTTTATTAAAGATAATTTTAGACACCTCAAAGCACGTTTAACAGCGCTTGGAGTTGATGAAA

TTGATGGTATCTTATATGACCTTGGTGTTTCCAGCCCGCAATTGGATGAAAGAGAACGAGGGTTTTCTTATAA

ACAAGATGCTCCATTGGATATGCGCATGGATCGTCAGTCGCTCTTAACAGCTTACGAAGTGGTGAATACCTAT

CCATTCAATGATTTGGTTAAGATTTTTTTCAAATATGGTGAAGATAAATTCTCCAAGCAGATCGCTCGAAAAA

TTGAACAAGCAAGAGCTATTAAGCCTATTGAGACAACAACAGAGTTGGCAGAATTGATTAAGGCAGCAAAGCC

AGCTAAAGAGTTGAAGAAAAAAGGCCACCCTGCTAAACAGATTTTTCAAGCTATTCGCATTGAAGTCAATGAT

GAATTGGGAGCGGCCGATGAATCTATTCAGGACGCTATGGAATTATTAGCCCTTGATGGTCGTATCTCAGTTA

TTACCTTCCATTCTCTGGAAGATCGCCTAACCAAGCAGTTGTTTAAAGAAGCTAGTACGGTGGATGTGCCAAA

AGGGCTTCCTCTAATTCCTGAAGATATGAAACCTAAGTTTGAACTTGTTTCACGTAAGCCGATCTTACCTAGT

CATTCAGAGTTAACAGCTAATAAAAGGGCACACTCAGCCAAGCTACGTGTTGCCAAAAAAATTCGGAAA

> Spy1727/SF370 (serotype 1); SEQ ID NO: 20
GTGACAACGACGGAACAAGAACTTACCTTGACTCCCTTACGTGGGAAAAGTGGCAAAGCTTATAAAGGCACTT

ATCCAAATGGGGAATGTGTCTTTATAAAATTAAATACGACCCCTATTCTACCTGCCTTAGCAAAAGAACAGAT

TGCGCCACAGTTACTTTGGGCCAAACGCATGGGCAATGGTGATATGATGAGTGCCCAAGAATGGCTTAACGGC

CGTACATTGACCAAAGAAGATATGAACAGTAAGCAAATCATTCATATTCTATTGCGCCTTCACAAATCTAAAA

AATTAGTCAATCAACTGCTTCAGCTCAATTATAAGATTGAAAACCCATACGATTTATTGGTTGATTTTGAGCA

AAATGCACCCTTGCAAATTCAGCAAAATTCATACTTACAAGCTATCGTTAAAGAATTAAAACGGAGCTTACCA

GAGTTCAAATCAGAAGTAGCAACGATTGTGCATGGAGATATTAAACATAGCAATTGGGTGATTACTACTAGTG

GTATGATTTTTTTAGTAGATTGGGATTCTGTTCGTCTAACTGATCGGATGTATGATGTTGCTTACCTGTTGAG

CCACTATATTCCACGGTCTCGTTGGTCAGAATGGCTGTCTTATTATGGCTATAAAAATAATGACAAGGTTATG

CAAAAAATTATTTGGTATGGTCAATTTTCTCACCTGACACAAATTCTCAAGTGTTTTGACAAGCGTGACATGG

AGCATGTGAATCAGGAGATTTATGCCCTCAGAAAATTTAGAGAAATATTTAGAAAGAAA

The invention claimed is:

1. An isolated protein consisting of a) the amino acid sequence of SEQ ID NO: 4, b) a fragment of SEQ ID NO: 4, wherein the fragment is at least 50 consecutive amino acids from SEQ ID NO: 4, or c) an amino acid sequence with at least 95% sequence identity to the full length of the sequence of SEQ ID NO: 4.

2. The isolated protein of claim 1, wherein the amino acid sequence is from a serotype of *S. pyogenes* selected from the group consisting of M2, M3, M4, M5, M6, M11, M12, M14, M19, M22, M24, M25, M28, M44, M49, M57, M59, M60, M61, M76, M83, M84, M87, M89 and M118.

3. The isolated protein of claim 1, wherein the fragment consists of at least 95% of the amino acid sequence of SEQ ID NO:4.

4. The isolated protein of claim 1, wherein the amino acid sequence has at least 97% sequence identity to the sequence of SEQ ID NO:4.

5. The isolated protein of claim 1, wherein the amino acid sequence is selected from SEQ ID NOs: 90, 91, 92, 95, 96, 97 and 98.

6. The isolated protein of claim 1, wherein the fragment consists of SEQ ID NO: 5 or SEQ ID NO: 6.

7. A fusion protein comprising the isolated protein of claim 1, further comprising additional amino acid residue(s) from a heterologous amino acid sequence.

8. The fusion protein of claim 7, wherein the additional amino acid residue(s) is/are flanking the antigen C-terminally, N-terminally, or C- and N-terminally.

9. A fusion protein comprising at least two isolated proteins of claim 1.

10. The fusion protein of claim 7, wherein the amino acid sequence of said isolated protein is from a serotype of *S. pyogenes* selected from the group consisting of M2, M3, M4, M5, M6, M11, M12, M14, M19, M22, M24, M25, M28, M44, M49, M57, M59, M60, M61, M76, M83, M84, M87, M89 and M118.

11. The fusion protein of claim 7, wherein the fragment consists of at least 95% of the amino acid sequence of SEQ ID NO:4.

12. The fusion protein of claim 7, wherein the isolated protein has at least 97% sequence identity to the sequence of SEQ ID NO:4.

13. The fusion protein of claim 12, wherein the amino acid sequence differs from the sequence of SEQ ID NO:4 by at least one conservative amino acid substitution.

14. The fusion protein of claim 7, wherein said isolated protein is selected from SEQ ID NOs: 90, 91, 92, 95, 96, 97 and 98.

15. The fusion protein of claim 7, wherein said isolated protein consists of SEQ ID NO: 5 or SEQ ID NO: 6.

16. An immunogenic composition comprising at least one isolated protein according to claim 1 and a pharmaceutically acceptable carrier or excipient.

17. An immunogenic composition comprising at least one fusion protein according to claim 7 and a pharmaceutically acceptable carrier or excipient.

18. Method of inducing an immune response in a subject, the method comprising administering to the subject an effective amount of the protein of claim 1.

* * * * *

UNITED STATES PATENT AND TRADEMARK OFFICE

CERTIFICATE OF CORRECTION

| | |
|---|---|
| PATENT NO. | : 8,529,911 B2 |
| APPLICATION NO. | : 12/304981 |
| DATED | : September 10, 2013 |
| INVENTOR(S) | : Meineke et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 476 days.

Signed and Sealed this
Twenty-seventh Day of January, 2015

Michelle K. Lee

*Deputy Director of the United States Patent and Trademark Office*